US012324447B2

(12) United States Patent
Liu et al.

(10) Patent No.: US 12,324,447 B2
(45) Date of Patent: Jun. 10, 2025

(54) ANIMAL FEED COMPOSITIONS AND USES THEREOF

(71) Applicant: Novozymes A/S, Bagsvaerd (DK)

(72) Inventors: Ye Liu, Beijing (CN); Kirk Matthew Schnorr, Holte (DK); Lars Kiemer, Ballerup (DK); Lars Kobberoee Skov, Ballerup (DK); Dorthe Hoej Sandvang, Slangerup (DK); Marianne Thorup Cohn, Copenhagen (DK); Ming Li, Beijing (CN)

(73) Assignee: Novozymes A/S, Bagsvaerd (DK)

( * ) Notice: Subject to any disclaimer, the term of this patent is extended or adjusted under 35 U.S.C. 154(b) by 982 days.

(21) Appl. No.: 17/153,096

(22) Filed: Jan. 20, 2021

(65) Prior Publication Data
US 2021/0153523 A1 May 27, 2021

Related U.S. Application Data

(62) Division of application No. 15/579,769, filed as application No. PCT/CN2016/088362 on Jul. 4, 2016, now Pat. No. 10,945,449.

(30) Foreign Application Priority Data

Jul. 2, 2015 (EP) .................................. 15175030

(51) Int. Cl.
| A23K 20/189 | (2016.01) |
| A23K 20/147 | (2016.01) |
| A23K 20/174 | (2016.01) |
| A23K 20/28 | (2016.01) |
| A23K 50/30 | (2016.01) |
| A23K 50/60 | (2016.01) |
| A23K 50/75 | (2016.01) |
| A23K 50/80 | (2016.01) |
| A61K 38/47 | (2006.01) |
| C12N 9/36 | (2006.01) |

(52) U.S. Cl.
CPC .......... *A23K 20/189* (2016.05); *A23K 20/147* (2016.05); *A23K 20/174* (2016.05); *A23K 20/28* (2016.05); *A23K 50/30* (2016.05); *A23K 50/60* (2016.05); *A23K 50/75* (2016.05); *A23K 50/80* (2016.05); *A61K 38/47* (2013.01); *C12N 9/2462* (2013.01); *C12Y 302/01017* (2013.01)

(58) Field of Classification Search
CPC .. A23K 20/189; A23K 20/147; A23K 20/174; A23K 20/28; A61K 38/47; C12N 9/2462; C12Y 302/01017
See application file for complete search history.

(56) References Cited

U.S. PATENT DOCUMENTS

| 2008/0227147 A1 | 9/2008 | Wu |
| 2012/0288490 A1 | 11/2012 | De Maria |
| 2014/0325711 A1 | 10/2014 | Schnorr |
| 2015/0023945 A1 | 11/2015 | Klausen |
| 2019/0297917 A1 | 10/2019 | Liu |

FOREIGN PATENT DOCUMENTS

| CN | 101912048 A | 12/2010 |
| CN | 103385366 A | 11/2013 |
| GB | 2002780 A | 2/1979 |
| WO | 2005/080559 A1 | 9/2005 |
| WO | 2011/104339 A1 | 9/2011 |
| WO | 2012/035103 A1 | 3/2012 |
| WO | 2013/076253 A2 | 5/2013 |
| WO | 2013/076259 A1 | 5/2013 |
| WO | WO 2013076259 A2 * | 5/2013 |
| WO | WO 2015109405 A1 * | 7/2015 |
| WO | 2017/001703 A1 | 1/2017 |
| WO | 2017/064092 A1 | 4/2017 |

OTHER PUBLICATIONS

Whisstock et al. Quaterly Reviews of Biophysics, 2003, "Prediction of protein function from protein sequence and structure", 36(3):307-340. (Year: 2003).*
Witkowski et al. Conversion of a beta-ketoacyl synthase to a malonyl decarboxylase by replacement of the active-site cysteine with glutamine, Biochemistry. Sep. 7, 1999;38(36):11643-50. (Year: 1999).*
Kisselev L., Polypeptide release factors in prokaryotes and eukaryotes: same function, different structure. Structure, 2002, vol. 10: 8-9. (Year: 2002).*
Aureli et al., EBI Accession No. BDM61069 (2017).
Brahmbhatt et al., Biochem. Cell. Arch., vol. 12, No. 1, pp. 51-55 (2012).
Brahmbhatt et al., Database Biosis Accession No. PREV201200528164 (2012).
Coleman et al., EBI Accession No. C7Z8W0 (2009).
Cuomo et al., EBI Accession No. Q2GND9 (2006).
Hu et al., EBI Accession No. A0A0B4FYT8 (2015).
Kuo et al., UniProt Accession No. A0A024S3W9 (2014).
Leushkin et al., EBI Accession No. A0A094DN53 (2014).
Liao et al., Derwent Accession No. 2014-B11670 (2014).
Masschalck et al., Journal of Food Protection, vol. 65, No. 12, pp. 1916-1923 (2002).
Qi et al., Derwent Accession No. 2011-A34726 (2011).
Spang et al., UniProt Accession No. A0A0F9Z1Q6 (2015).
Traeger et al., UniProt Accession No. U4LG64 (2013).
Verlhac, EBI Accession No. BDV60965 (2017).

* cited by examiner

*Primary Examiner* — Iqbal H Chowdhury
(74) *Attorney, Agent, or Firm* — Adam Rucker

(57) ABSTRACT

The present invention relates animal feed or animal feed additives comprising one or more polypeptides having lysozyme activity. The invention also relates to polypeptides having lysozyme activity, polynucleotides encoding the polypeptides nucleic acid constructs, vectors, and host cells comprising the polynucleotides as well as methods of producing and using the polypeptides.

7 Claims, No Drawings

Specification includes a Sequence Listing.

SEQUENCE LISTING

<160> NUMBER OF SEQ ID NOS: 306

<210> SEQ ID NO 1
<211> LENGTH: 157
<212> TYPE: PRT
<213> ORGANISM: Ajellomyces capsulatus

<400> SEQUENCE: 1

```
Pro His Val Asn Lys Ala Thr Leu Ala Leu Ile Lys Glu Phe Glu Gly
1               5                   10                  15

Phe Val Pro Arg Pro Glu Pro Asp Pro Ile Gly Leu Pro Thr Val Gly
            20                  25                  30

Tyr Gly His Leu Cys Lys Thr Lys Gly Cys Lys Glu Val Lys Phe Pro
        35                  40                  45

Leu Ser Lys Gly Thr Ala Thr Thr Leu Leu Lys Lys Asp Leu Arg Ser
    50                  55                  60

Phe Gln Gln Ala Ile Thr Leu Ser Thr Lys Thr Ala Val Lys Leu Asn
65                  70                  75                  80

Ala Asn Gln Tyr Gly Ala Leu Val Ser Trp Ala Tyr Asn Val Gly Pro
                85                  90                  95

Asn Ala Ala Arg Ser Ser Ser Leu Ile Ser Arg Leu Asn Gln Gly Glu
            100                 105                 110

Asp Pro Asn Gln Val Ile Ala Gln Glu Leu Pro Lys Trp Arg Leu Ala
        115                 120                 125

Gly Gly Lys Val Phe Glu Gly Leu Val Arg Arg Arg Lys Ala Glu Val
    130                 135                 140

Lys Leu Ala Lys Thr Pro Thr Lys Ser Lys Ala Leu Pro
145                 150                 155
```

<210> SEQ ID NO 2
<211> LENGTH: 159
<212> TYPE: PRT
<213> ORGANISM: Coprinopsis cinerea

<400> SEQUENCE: 2

```
Ile Asn Lys Lys Thr Leu Asp Leu Leu Lys Glu Phe Glu Gly Trp Ala
1               5                   10                  15

Ala Ser Pro Tyr Lys Asp Val Ala Gly Tyr Pro Thr Val Gly Tyr Gly
            20                  25                  30

His Lys Cys Ser Lys Asn Asp Cys Ser Glu Leu Gly Tyr Lys Phe Pro
        35                  40                  45

Met Thr Lys Ala Gln Gly Glu Glu Leu Leu Ala Lys Asp Val Lys Gly
    50                  55                  60

Phe Glu Lys Cys Ile Ser Asp Tyr Ile Asn Asp Thr Ile Lys Leu Asn
65                  70                  75                  80

Asp Asn Gln Tyr Gly Ala Leu Val Ser Trp Ser Phe Asn Val Gly Cys
                85                  90                  95

Gly Ala Ala Lys Asp Ser Thr Leu Ile Ser Arg Leu Asn Lys Gly Asp
            100                 105                 110

Ser Pro Asn Thr Val Ala Gly Glu Glu Leu Pro Arg Trp Asn Lys Ala
        115                 120                 125

Gly Gly Lys Val Val Asp Gly Leu Thr Asn Arg Arg Lys Lys Glu Val
    130                 135                 140

Glu Leu Phe Lys Thr Ser Ser Thr Val Ile Ala His Pro Pro Cys
145                 150                 155
```

```
<210> SEQ ID NO 3
<211> LENGTH: 154
<212> TYPE: PRT
<213> ORGANISM: Aspergillus terreus

<400> SEQUENCE: 3
```

Gly Lys Leu Leu Arg Arg Gly Ile Ser Asp Ala Val Glu Leu Ile
1               5                   10                  15

Gly Ser Leu Glu Gly Phe Arg Pro Asp Phe Tyr Tyr Ile Asn Gly His
            20                  25                  30

Lys Thr Val Gly Tyr Gly His Asp Cys Val Ala Lys Gln Asp Cys Asp
        35                  40                  45

Ser Ile Asp Thr Pro Leu Thr Lys Glu Glu Gly Ala Ala Leu Leu Lys
50                  55                  60

Lys Asp Leu Ala Gly Tyr Glu Asn Cys Val Cys Glu Met Asp Asn Ala
65                  70                  75                  80

Lys Tyr Leu Asn Ala Asn Gln Tyr Gly Ala Leu Val Ser Phe Ala Tyr
                85                  90                  95

Asn Ser Gly Cys Gly Gly Val Gln Ser Trp Trp His Gly Ala Met Glu
            100                 105                 110

Gln Lys Asn Phe Lys Gly Ile Cys Ser Ala Leu Pro Asn Thr Asn Thr
        115                 120                 125

Leu Gly Gly Glu Leu Ser Ser Arg Arg Ala Lys Glu Gly Ala Phe Cys
130                 135                 140

Ala Lys Pro Thr Asn Gln Thr Ser Gly Cys
145                 150

```
<210> SEQ ID NO 4
<211> LENGTH: 166
<212> TYPE: PRT
<213> ORGANISM: Aspergillus terreus

<400> SEQUENCE: 4
```

Ala Cys Ser Gly Pro Asn Val Asn Glu Ala Thr Ile Lys Leu Met Lys
1               5                   10                  15

Gly Tyr Glu Ser Trp Glu Ala Asp Val Tyr Asp Asp Gly Tyr Gly Asn
            20                  25                  30

Pro Thr Val Gly Tyr Gly His Leu Cys Asp Asp Trp Ser Cys Ser Asp
        35                  40                  45

Val Ser Tyr Asp Ile Pro Leu Ser Glu Ser Asp Gly Glu Lys Leu Phe
50                  55                  60

Ala Glu Asp Ile Val Ala Tyr Gln Asn Gly Val Val Ala Ala Leu Ser
65                  70                  75                  80

Asp Asp Val Thr Leu Asn Asp Asn Gln Tyr Gly Ala Leu Val Ser Trp
                85                  90                  95

Cys Phe Asn Val Gly Thr Gly Ala Val Ala Glu Ser Thr Leu Ala Lys
            100                 105                 110

Arg Leu Asn Asn Gly Glu Asp Pro Asp Thr Val Ala Glu Glu Glu Leu
        115                 120                 125

Pro Lys Trp Val Tyr Ala Asn Gly Ala Pro Ser Glu Gly Leu Lys Asn
130                 135                 140

Arg Arg Ala Ala Glu Leu Lys Leu Phe Thr Thr Ser Ser Asp Thr Glu
145                 150                 155                 160

Ala Leu Pro Val Asp Cys
            165

```
<210> SEQ ID NO 5
<211> LENGTH: 154
<212> TYPE: PRT
<213> ORGANISM: Aspergillus oryzae

<400> SEQUENCE: 5

Ala Thr Val Val Arg Arg Gly Ala Ser Ala Thr Val Ser Leu Ile
1               5                   10                  15

Gly Glu Val Glu Gly Phe Arg Ala Asp Phe Tyr Asp Met Met Gly His
            20                  25                  30

Lys Thr Ile Gly Tyr Gly His Asp Cys Val Ala Lys Gln Asp Cys Asp
        35                  40                  45

Ser Ile Lys Ala Pro Ile Ser Asn Ala Gln Gly Asp Glu Ile Leu Gln
    50                  55                  60

Lys Asp Leu Ala Gly Phe Glu Gln Cys Val Cys Ala Leu Pro Asn Ala
65                  70                  75                  80

Lys Ala Leu Asn Ala Asn Gln Tyr Gly Ala Leu Val Ser Tyr Ala Phe
                85                  90                  95

Asn Thr Gly Cys Gly Gly Leu Gln Gln Ala Trp Thr Ala Ala Met Thr
            100                 105                 110

Ser Lys Asn Phe Asp Ser Ile Cys Ala Asp Leu Pro His Thr Asn Thr
        115                 120                 125

Leu Asn Gly Val Leu Asp Asn Arg Arg Lys Lys Glu Ala Ala Leu Cys
    130                 135                 140

Ser Thr Pro Thr Thr Gln Met Cys Gly Cys
145                 150

<210> SEQ ID NO 6
<211> LENGTH: 163
<212> TYPE: PRT
<213> ORGANISM: Aspergillus oryzae

<400> SEQUENCE: 6

Gly Pro Pro Val Asn Gln Asn Gly Leu Asn Leu Ile Lys Ser Phe Glu
1               5                   10                  15

Ser Phe Gln Pro Ser Val Tyr Asp Asp Gly Phe Gly Asn Pro Thr Ile
            20                  25                  30

Gly Tyr Gly His Leu Cys Gly Asp Ala Thr Cys Ser Glu Val Thr Tyr
        35                  40                  45

Pro Lys Pro Leu Ser Glu Ala Asp Ala Ser Arg Leu Leu Ala Asp Asp
    50                  55                  60

Leu Val Ser Tyr Gln Asp Ala Leu Thr Asn Ala Leu Ala Asp Pro Val
65                  70                  75                  80

Thr Leu Asn Asp Asn Gln Tyr Ala Ala Leu Val Ser Trp Thr Phe Asn
                85                  90                  95

Ile Gly Asn Gly Asn Met Gln Lys Ser Asp Leu Val Ala Arg Met Asn
            100                 105                 110

Lys Gly Glu Asn Val Ala Thr Val Ala His Asp Glu Leu Pro Gln Trp
        115                 120                 125

Asn Lys Ala Asn Gly Gln Val Val Asn Gly Leu Thr Arg Arg Arg Lys
    130                 135                 140

Ala Glu Leu Asp Leu Phe Asp Ala Pro Ala Ile Tyr Gly Ala Leu Pro
145                 150                 155                 160

Val Pro Cys

<210> SEQ ID NO 7
```

<211> LENGTH: 162
<212> TYPE: PRT
<213> ORGANISM: Emericella nidulans

<400> SEQUENCE: 7

```
Pro Asp Val Asn Thr Ala Thr Thr Asp Leu Met Lys Ala Phe Glu Ser
1               5                   10                  15

Trp Glu Pro Asp Val Tyr Asp Gly Tyr Gly Asn Pro Thr Ile Gly
            20                  25                  30

Tyr Gly His Leu Cys Ser Asp Trp Ser Cys Ser Asp Val Ala Tyr Asp
            35                  40                  45

Ile Pro Leu Ser Glu Glu Asp Gly Val Lys Leu Phe Ala Glu Asp Ile
50                  55                  60

Ala Val Tyr Gln Asp Gly Val Val Ser Ala Leu Asp Ser Ser Val Thr
65                  70                  75                  80

Leu Asn Asp Asn Gln Tyr Gly Ala Leu Val Ser Trp Cys Tyr Asn Val
                85                  90                  95

Gly Ala Gly Ala Val Ala Glu Ser Thr Leu Ala Ala Arg Leu Asn Ala
            100                 105                 110

Gly Glu Asp Pro Asn Thr Val Ala Glu Glu Leu Ile Lys Trp Val
            115                 120                 125

Tyr Ala Asn Gly Glu Val Ser Glu Gly Leu Lys Arg Arg Arg Asn Ala
130                 135                 140

Glu Ile Glu Leu Phe Gln Thr Ser Ser Asp Gly Glu Ala Leu Pro Val
145                 150                 155                 160

Ser Cys
```

<210> SEQ ID NO 8
<211> LENGTH: 159
<212> TYPE: PRT
<213> ORGANISM: Laccaria bicolor

<400> SEQUENCE: 8

```
Ile Ser Ser Ala Thr Val Asn Leu Ile Lys Gly Ser Glu Ser Leu Val
1               5                   10                  15

Pro Ile Pro Ser Pro Asp Pro Ile Gly Leu Leu Thr Val Gly Tyr Gly
            20                  25                  30

His Lys Cys Leu Lys Pro Gln Cys Ser Glu Val Thr Phe Pro Phe Pro
            35                  40                  45

Leu Ser Ser Ser Thr Ala Ser Gln Leu Phe Ala Gln Asp Met Thr Gln
50                  55                  60

Tyr Ile Asn Cys Leu His Arg Ser Ile Ser Lys Ser Val Val Leu Asn
65                  70                  75                  80

Asp Asn Gln Phe Gly Ala Leu Val Ser Trp Thr Tyr Asn Ala Gly Cys
                85                  90                  95

Glu Gly Met Gly Thr Ser Thr Leu Val Lys Arg Leu Asn Asn Gly Glu
            100                 105                 110

Asp Pro Asn Thr Val Val Ala Gln Glu Leu Pro Lys Trp Asn Ile Ala
            115                 120                 125

Lys Lys Lys Ile Ser Lys Gly Leu Val Asn Arg Arg Asn Arg Glu Ile
130                 135                 140

Ser Phe Phe Gln Thr Pro Ser Asn Val Ala His Pro Leu Cys
145                 150                 155
```

<210> SEQ ID NO 9
<211> LENGTH: 160

```
<212> TYPE: PRT
<213> ORGANISM: Laccaria bicolor

<400> SEQUENCE: 9

Pro Pro Ala Asn Ala Asp Thr Ile Asn Leu Ile Glu Arg Phe Glu Gly
1               5                   10                  15

Phe Val Pro Ser Pro Arg Pro Asp Pro Ile Gly Leu Pro Thr Val Gly
                20                  25                  30

Tyr Gly His Leu Cys Lys Thr Lys Gly Cys Ser Glu Val Pro Phe Lys
            35                  40                  45

Phe Pro Val Thr Lys Ala Asn Ala Val Thr Leu Leu His Ser Asp Leu
        50                  55                  60

Thr Thr Phe Gln Asn Cys Val Asn Ser Asp Ile Lys Arg Ser Val His
65                  70                  75                  80

Leu Asn Asp Asn Gln Tyr Gly Ala Leu Val Ser Trp Ala Tyr Asn Val
                85                  90                  95

Gly Cys Gly Asn Ile Lys Thr Ser Ser Leu Val Arg Arg Leu Asn Ala
            100                 105                 110

Gly Glu Asp Pro Asn Thr Val Ala Ala Gln Glu Leu Pro Gln Trp Asn
        115                 120                 125

Lys Gly Gly Lys Val Leu Pro Gly Leu Val Arg Arg Ala Glu
    130                 135                 140

Glu Val Lys Leu Phe Lys Thr Pro Ser Ser Val Ser Ala His Pro Cys
145                 150                 155                 160

<210> SEQ ID NO 10
<211> LENGTH: 162
<212> TYPE: PRT
<213> ORGANISM: Laccaria bicolor

<400> SEQUENCE: 10

Pro Ala Val Asn Ala Ala Thr Ile Ala Leu Ile Lys Lys Phe Glu Gly
1               5                   10                  15

Phe Val Ala Ser Pro Ser Pro Asp Pro Ile Gly Leu Pro Thr Val Gly
                20                  25                  30

Tyr Gly His Leu Cys Gln Thr Lys Asn Cys Ala Glu Val Pro Phe Ser
            35                  40                  45

Phe Pro Leu Thr Glu Ala Glu Ala Ser Thr Leu Leu Asn Ser Asp Leu
        50                  55                  60

Lys Thr Tyr Glu Ala Cys Ile Thr Lys Asp Ile Val Ser Ser Val Arg
65                  70                  75                  80

Leu Asn Asp Asn Gln Tyr Gly Ala Leu Cys Ser Trp Ala Phe Asn Glu
                85                  90                  95

Gly Cys Gly Ala Ala Gly Ser Ser Thr Leu Ile Ala Arg Leu Asn Ala
            100                 105                 110

Gly Gln Asp Pro Asp Ala Val Ala Ala Gln Glu Leu Pro Lys Trp Asp
        115                 120                 125

Ile Ala Gly Gly Lys Val Leu Gln Gly Leu Val Asn Arg Arg Ala Ala
130                 135                 140

Glu Val Ala Leu Phe Lys Thr Pro Ser Ser Val Ile Ala His Pro Pro
145                 150                 155                 160

His Cys

<210> SEQ ID NO 11
<211> LENGTH: 163
<212> TYPE: PRT
```

<213> ORGANISM: Aspergillus flavus

<400> SEQUENCE: 11

Gly Pro Pro Val Asn Gln Asn Gly Leu Asn Leu Ile Lys Ser Phe Glu
1               5                   10                  15

Ser Phe Gln Pro Ser Val Tyr Asp Asp Gly Phe Gly Asn Pro Thr Ile
            20                  25                  30

Gly Tyr Gly His Leu Cys Gly Asp Ala Thr Cys Ser Glu Val Thr Tyr
        35                  40                  45

Pro Lys Pro Leu Ser Glu Ala Asp Ala Ser Arg Leu Leu Ala Asp Asp
    50                  55                  60

Leu Val Ser Tyr Gln Asp Ala Leu Thr Asn Ala Leu Ala Asp Pro Val
65                  70                  75                  80

Thr Leu Asn Asp Asn Gln Tyr Ala Ala Leu Val Ser Trp Thr Phe Asn
                85                  90                  95

Ile Gly Asn Gly Asn Met Gln Lys Ser Asp Leu Val Ala Arg Met Asn
            100                 105                 110

Lys Gly Glu Asn Val Ala Thr Val Ala His Asp Glu Leu Pro Gln Trp
        115                 120                 125

Asn Lys Ala Asn Gly Gln Val Val Asn Gly Leu Thr Arg Arg Arg Lys
    130                 135                 140

Ala Glu Leu Asp Leu Phe Asp Ala Pro Ala Ile Tyr Gly Ala Leu Pro
145                 150                 155                 160

Val Pro Cys

<210> SEQ ID NO 12
<211> LENGTH: 154
<212> TYPE: PRT
<213> ORGANISM: Aspergillus flavus

<400> SEQUENCE: 12

Ala Thr Val Val Arg Arg Gly Ala Ser Ala Thr Val Ser Leu Ile
1               5                   10                  15

Gly Glu Val Glu Gly Phe Arg Ala Asp Phe Tyr Asp Met Met Gly His
            20                  25                  30

Lys Thr Ile Gly Tyr Gly His Asp Cys Val Ala Lys Gln Asp Cys Asp
        35                  40                  45

Ser Ile Lys Ala Pro Ile Ser Asn Ala Gln Gly Asp Glu Ile Leu Gln
    50                  55                  60

Lys Asp Leu Ala Gly Phe Glu Gln Cys Val Cys Ala Leu Pro Asn Ala
65                  70                  75                  80

Lys Ala Leu Asn Ala Asn Gln Tyr Gly Ala Leu Val Ser Tyr Ala Phe
                85                  90                  95

Asn Thr Gly Cys Gly Gly Leu Gln Gln Ala Trp Thr Ala Ala Met Thr
            100                 105                 110

Ser Lys Asn Phe Asp Ser Ile Cys Ala Asp Leu Pro His Thr Asn Thr
        115                 120                 125

Leu Asn Gly Val Leu Asp Asn Arg Arg Lys Lys Glu Ala Ala Leu Cys
    130                 135                 140

Ala Thr Pro Thr Thr Gln Met Cys Gly Cys
145                 150

<210> SEQ ID NO 13
<211> LENGTH: 157
<212> TYPE: PRT
<213> ORGANISM: Ajellomyces capsulatus

```
<400> SEQUENCE: 13

Pro Asn Val Asn Lys Ala Thr Leu Asp Leu Ile Lys Glu Phe Glu Gly
1               5                   10                  15

Phe Val Pro Arg Pro Glu Pro Asp Pro Ile Gly Leu Pro Thr Val Gly
            20                  25                  30

Tyr Gly His Leu Cys Lys Thr Lys Gly Cys Lys Glu Val Lys Phe Pro
                35                  40                  45

Leu Ser Lys Glu Thr Ala Thr Thr Leu Leu Lys Lys Asp Leu Arg Ser
    50                  55                  60

Phe Gln Gln Ala Ile Thr Leu Ser Thr Lys Thr Ala Val Lys Leu Asn
65                  70                  75                  80

Ala Asn Gln Tyr Gly Ala Leu Val Ser Trp Ala Tyr Asn Val Gly Pro
                85                  90                  95

Asn Ala Ala Arg Ser Ser Ser Leu Ile Ser Arg Leu Asn Lys Gly Glu
            100                 105                 110

Asp Pro Asn Lys Val Ile Ala Gln Glu Leu Pro Lys Trp Arg Leu Ala
        115                 120                 125

Gly Gly Lys Val Phe Lys Gly Leu Val Arg Arg Lys Ala Glu Val
130                 135                 140

Lys Leu Ala Lys Thr Pro Thr Lys Ser Lys Ala Leu Pro
145                 150                 155

<210> SEQ ID NO 14
<211> LENGTH: 162
<212> TYPE: PRT
<213> ORGANISM: Arthroderma otae

<400> SEQUENCE: 14

Pro Asp Val Asn Asp Glu Thr Ile Ala Leu Ile Lys His Phe Glu Gly
1               5                   10                  15

Phe Val Pro Arg Pro Ala Pro Asp Pro Ile Gly Leu Pro Thr Val Gly
            20                  25                  30

Tyr Gly His Leu Cys Arg Thr Lys Gly Cys Gly Glu Val Pro Phe Pro
                35                  40                  45

Phe Pro Leu Thr Glu Glu Ser Ala Thr Glu Leu Leu His Gln Asp Val
    50                  55                  60

Lys Ser Pro Gln Gln Ser Ile Thr Leu Ser Thr Ala Asp Ser Val Val
65                  70                  75                  80

Leu Asn Ala Asn Gln Tyr Gly Ala Leu Val Ser Trp Ala Phe Asn Val
                85                  90                  95

Gly Gly Gly Ala Ala Lys Lys Ser Ser Leu Ile Lys Arg Leu Asn Gln
            100                 105                 110

Gly Gln Asp Val Asp Thr Val Ile Arg Glu Glu Leu Pro Leu Trp Asn
        115                 120                 125

Lys Ala Gly Gly His Val Leu Pro Gly Leu Val Arg Arg Arg Lys Ala
130                 135                 140

Glu Val Glu Leu Ala Met Glu His Thr Asp Asp Gly Ala Leu Pro Val
145                 150                 155                 160

Asp Cys

<210> SEQ ID NO 15
<211> LENGTH: 162
<212> TYPE: PRT
<213> ORGANISM: Arthroderma otae
```

```
<400> SEQUENCE: 15

Pro Asp Val Asn Ala Thr Ile Ser Leu Val Lys Glu Phe Glu Arg
1               5                   10                  15

Phe Val Pro Ser Pro Ser Pro Asp Pro Ile Gly Leu Pro Thr Val Gly
            20                  25                  30

Tyr Gly His Leu Cys Gln Ser Lys Asn Cys Gly Val Gly Phe Pro
            35                  40                  45

Phe Pro Leu Thr Glu Asp Thr Ala Thr Gln Leu Leu Ala Gln Asp Ile
 50                      55                  60

Lys Ala Pro Gln Gln Thr Ile Thr Leu Lys Thr Val Asn Gly Val His
 65                 70                  75                  80

Leu Asn Glu Asn Gln Tyr Gly Ala Leu Val Ser Trp Thr Phe Asn Val
                85                  90                  95

Gly Pro Gly Asn Val Ala Thr Ser Ser Leu Leu Lys Arg Leu Asn Ala
                100                 105                 110

Leu Glu Asp Val Asn Thr Val Leu Arg Glu Leu Pro Lys Trp Lys
            115                 120                 125

Tyr Ala Gly Gly Lys Val Leu Pro Gly Leu Val Arg Arg Ala Ala
 130                 135                 140

Glu Val Ala Leu Gly Glu Thr Pro Ser Asn Val Gly Ala Leu Pro Val
145                 150                 155                 160

Asp Cys

<210> SEQ ID NO 16
<211> LENGTH: 160
<212> TYPE: PRT
<213> ORGANISM: Ajellomyces dermatitidis

<400> SEQUENCE: 16

Pro Asn Val Asn Lys Ala Thr Leu Ala Leu Ile Lys Glu Phe Glu Gly
1               5                   10                  15

Phe Val Pro Arg Pro Ala Pro Asp Pro Ile Gly Leu Pro Thr Val Gly
            20                  25                  30

Tyr Gly His Leu Cys Lys Thr Lys Gly Cys Lys Glu Val Lys Phe Pro
            35                  40                  45

Leu Thr Lys Lys Thr Ala Thr Ala Leu Leu Lys Asp Leu Arg Ser
 50                      55                  60

Phe Gln Gln Ala Ile Thr Leu Ser Thr Lys Lys Ala Val Lys Leu Asn
 65                 70                  75                  80

Ala Asn Gln Tyr Gly Ala Leu Val Ser Trp Ala Tyr Asn Val Gly Pro
                85                  90                  95

Asn Ala Ala Arg Ser Ser Ser Leu Ile Arg Arg Leu Asn Arg Gly Glu
                100                 105                 110

Asn Pro Asn Lys Val Ile Ala Gln Glu Leu Pro Lys Trp Arg Leu Ala
            115                 120                 125

Gly Gly Lys Val Phe Lys Gly Leu Val Arg Arg Lys Ala Glu Val
 130                 135                 140

Lys Leu Ala Lys Thr Pro Thr Lys Lys Lys Ala Leu Pro Val Lys Cys
145                 150                 155                 160

<210> SEQ ID NO 17
<211> LENGTH: 157
<212> TYPE: PRT
<213> ORGANISM: Ajellomyces capsulatus

<400> SEQUENCE: 17
```

```
Pro Asn Val Asn Lys Ala Thr Leu Ala Leu Ile Lys Glu Phe Glu Gly
1               5                   10                  15

Phe Val Pro Arg Pro Glu Pro Asp Pro Ile Gly Leu Pro Thr Val Gly
                20                  25                  30

Tyr Gly His Leu Cys Lys Thr Lys Gly Cys Lys Glu Val Lys Phe Pro
            35                  40                  45

Leu Ser Lys Gly Thr Ala Thr Thr Leu Leu Lys Asp Leu Arg Ser
50                      55                  60

Phe Gln Gln Ala Ile Thr Leu Ser Thr Lys Thr Ala Val Lys Leu Asn
65                  70                  75                  80

Ala Asn Gln Tyr Gly Ala Leu Val Ser Trp Ala Tyr Asn Val Gly Pro
                85                  90                  95

Asn Ala Ala Arg Ser Ser Ser Leu Ile Ser Arg Leu Asn Lys Gly Glu
                100                 105                 110

Asp Pro Asn Lys Val Ile Ala Gln Glu Leu Pro Lys Trp Arg Leu Ala
            115                 120                 125

Gly Gly Lys Val Phe Lys Gly Leu Val Arg Arg Lys Ala Glu Val
130                 135                 140

Lys Leu Ala Lys Thr Pro Thr Lys Ser Lys Ala Leu Pro
145                 150                 155
```

<210> SEQ ID NO 18
<211> LENGTH: 163
<212> TYPE: PRT
<213> ORGANISM: Hypocrea jecorina

<400> SEQUENCE: 18

```
Lys Thr Ile Asn Gly Ala Gly Val Asp Leu Ile Ala Lys Trp Glu Gly
1               5                   10                  15

Phe Val Ala Ser Pro Lys Pro Asp Pro Ile Gly Leu Pro Thr Val Gly
                20                  25                  30

Tyr Gly His Leu Cys Gln Gln Lys Asn Cys Ala Glu Val Lys Tyr Lys
            35                  40                  45

Phe Pro Leu Thr Lys Thr Thr Ala Lys Glu Leu Leu Leu Asp Asp Leu
50                  55                  60

Pro Lys Tyr Thr Lys Cys Leu Ala Asp Val Leu Asn Ser Lys Pro Lys
65                  70                  75                  80

Leu Asn Ala Asn Gln Trp Ala Ala Leu Ser Ser Trp Val Phe Asn Val
                85                  90                  95

Gly Cys Gly Asn Ala Lys Thr Ser Thr Leu Val Lys Arg Leu Asn Asn
                100                 105                 110

Gly Glu Ala Pro Asn Thr Val Ala Ala Gln Glu Leu Pro Lys Trp Arg
            115                 120                 125

Met Ala Gly Gly Lys Val Met Pro Gly Leu Glu Ala Arg Arg Lys Asp
130                 135                 140

Glu Val Lys Leu Phe Lys Thr Ala Ser Ser Lys Glu Ala Tyr Pro Lys
145                 150                 155                 160

Cys Gln Ala
```

<210> SEQ ID NO 19
<211> LENGTH: 162
<212> TYPE: PRT
<213> ORGANISM: Arthroderma benhamiae

<400> SEQUENCE: 19

```
Pro Asp Val Asn Pro Ala Thr Ile Ala Leu Ile Lys Glu Phe Glu Gly
1               5                   10                  15

Phe Val Pro Ala Pro Ala Pro Asp Pro Val Gly Leu Pro Thr Val Gly
            20                  25                  30

Tyr Gly His Leu Cys Gln Ser Lys Asn Cys Gly Glu Val Gly Phe Pro
            35                  40                  45

Phe Pro Leu Thr Glu Asp Thr Ala Thr Gln Leu Leu Ile Gln Asp Val
        50                  55                  60

Lys Ala Pro Gln Gln Thr Ile Thr Leu Lys Thr Ala Asp Gly Val His
65                  70                  75                  80

Leu Asn Glu Asn Gln Tyr Gly Ala Leu Val Ser Trp Thr Phe Asn Val
                85                  90                  95

Gly Pro Gly Asn Val Ala Thr Ser Ser Leu Leu Gln Arg Leu Asn Ala
                100                 105                 110

Leu Glu Asp Val Asn Thr Val Leu Arg Glu Glu Leu Pro Gln Trp Lys
                115                 120                 125

Tyr Gly Gly Gly Lys Val Leu Pro Gly Leu Val Arg Arg Arg Ala Ala
            130                 135                 140

Glu Val Ala Leu Gly Glu Thr Ala Ser Asp Val Pro Ala Leu Pro Val
145                 150                 155                 160

Ala Cys

<210> SEQ ID NO 20
<211> LENGTH: 162
<212> TYPE: PRT
<213> ORGANISM: Trichophyton verrucosum

<400> SEQUENCE: 20

Pro Asp Val Asn Pro Ala Thr Ile Ala Leu Ile Lys Glu Phe Glu Gly
1               5                   10                  15

Phe Val Pro Ala Pro Ala Pro Asp Pro Val Gly Leu Pro Thr Val Gly
            20                  25                  30

Tyr Gly His Leu Cys Gln Ser Lys Asn Cys Gly Glu Val Gly Phe Pro
            35                  40                  45

Phe Pro Leu Thr Glu Asp Thr Ala Thr Gln Leu Leu Ile Gln Asp Val
        50                  55                  60

Lys Ala Pro Gln Gln Thr Ile Thr Leu Lys Thr Ala Asp Gly Val His
65                  70                  75                  80

Leu Asn Glu Asn Gln Tyr Gly Ala Leu Val Ser Trp Thr Phe Asn Val
                85                  90                  95

Gly Pro Gly Asn Val Ala Thr Ser Ser Leu Leu Gln Arg Leu Asn Ala
                100                 105                 110

Leu Glu Asp Val Asn Thr Val Leu Arg Glu Glu Leu Pro Gln Trp Lys
                115                 120                 125

Tyr Gly Gly Gly Lys Val Leu Pro Gly Leu Val Arg Arg Arg Ala Ala
            130                 135                 140

Glu Val Ala Leu Gly Glu Thr Ala Ser Asp Val Pro Ala Leu Pro Val
145                 150                 155                 160

Ala Cys

<210> SEQ ID NO 21
<211> LENGTH: 162
<212> TYPE: PRT
<213> ORGANISM: Trichophyton verrucosum

<400> SEQUENCE: 21
```

```
Pro Asp Val Asn Asp Glu Thr Ile Ala Leu Ile Lys His Phe Glu Gly
1               5                   10                  15

Phe Val Pro Arg Pro Ala Pro Asp Pro Ile Gly Leu Pro Thr Val Gly
            20                  25                  30

Tyr Gly His Leu Cys Arg Thr Asn Gly Cys Ser Glu Val Pro Phe Ser
            35                  40                  45

Phe Pro Leu Thr Glu Glu Thr Ala Thr Glu Leu Leu Met Gln Asp Val
        50                  55                  60

Lys Ser Pro Gln Gln Ser Ile Thr Leu Ser Thr Thr Asp Gln Val Val
65                      70                  75                  80

Leu Asn Ala Asn Gln Tyr Gly Ala Leu Val Ser Trp Ala Tyr Asn Val
                85                  90                  95

Gly Gly Asp Ala Ala Lys Lys Ser Ser Leu Ile Ser Arg Leu Asn Gln
                100                 105                 110

Gly Gln Asp Val Asp Val Val Ile Arg Glu Glu Leu Pro Leu Trp Asn
            115                 120                 125

Lys Ala Gly Gly His Val Leu Pro Gly Leu Val Arg Arg Arg Ala Ala
130                 135                 140

Glu Val Glu Leu Ala Ser Glu Asn Thr Asp Gln Pro Ala Leu Pro Val
145                 150                 155                 160

Asp Cys

<210> SEQ ID NO 22
<211> LENGTH: 161
<212> TYPE: PRT
<213> ORGANISM: Coprinopsis cinerea

<400> SEQUENCE: 22

Asn Thr Ala Thr Val Asn Leu Ile Gln Glu Phe Glu Gly Phe Val Ala
1               5                   10                  15

Ser Pro Glu Pro Asp Pro Ile Gly Leu Pro Thr Val Gly Phe Gly His
            20                  25                  30

Leu Cys Arg Gln Pro Asn Cys Ala Glu Val Thr Ala Gln Gly Leu Ser
            35                  40                  45

Phe Pro Leu Ser Arg Ala Gln Ala Glu Gln Leu Leu Gln Ser Asp Val
        50                  55                  60

Gln Thr Phe Thr Asn Cys Leu Ala Arg Phe Ile Asp Asp Ser Val Val
65                      70                  75                  80

Leu Asn Glu Asn Gln Phe Gly Ala Leu Thr Ser Trp Ala Phe Asn Val
                85                  90                  95

Gly Cys Gly Asn Val Gln Arg Ser Thr Leu Arg Arg Arg Leu Asn Ala
                100                 105                 110

Gly Gln Asp Pro Asn Thr Val Ala Ala Gln Glu Leu Pro Arg Phe Asn
            115                 120                 125

Arg Ala Gly Gly Arg Val Leu Asn Gly Leu Thr Arg Arg Arg Asn Ala
130                 135                 140

Glu Val Ala Leu Phe Gln Thr Pro Ser Asn Thr Val Ala Leu Pro Val
145                 150                 155                 160

Cys

<210> SEQ ID NO 23
<211> LENGTH: 162
<212> TYPE: PRT
<213> ORGANISM: Arthroderma gypseum
```

```
<400> SEQUENCE: 23

Pro Asp Val Asn Ala Ala Thr Ile Ala Leu Val Lys Glu Phe Glu Gly
1               5                   10                  15

Phe Val Pro Ser Pro Ala Pro Asp Pro Ile Gly Leu Pro Thr Val Gly
            20                  25                  30

Tyr Gly His Leu Cys Gln Ser Lys Asn Cys Gly Val Gly Phe Pro
        35                  40                  45

Phe Pro Leu Thr Glu Asp Thr Ala Thr Gln Leu Leu Ser Gln Asp Ile
    50                  55                  60

Lys Ala Pro Gln Gln Thr Ile Thr Leu Lys Thr Ala Asp Gly Val His
65                  70                  75                  80

Leu Asn Glu Asn Gln Tyr Gly Ala Leu Val Ser Trp Thr Phe Asn Val
                85                  90                  95

Gly Pro Gly Asn Val Ala Thr Ser Ser Leu Leu Lys Arg Leu Asn Ala
                100                 105                 110

Leu Glu Asp Val Asn Thr Val Leu Arg Glu Glu Leu Pro Lys Trp Lys
            115                 120                 125

Tyr Ala Gly Gly Lys Val Leu Pro Gly Leu Val Arg Arg Ala Ala
        130                 135                 140

Glu Val Ala Leu Gly Glu Thr Pro Ser Asp Val Pro Ala Leu Pro Val
145                 150                 155                 160

Asp Cys

<210> SEQ ID NO 24
<211> LENGTH: 162
<212> TYPE: PRT
<213> ORGANISM: Arthroderma gypseum

<400> SEQUENCE: 24

Pro Asp Val Asn Glu Ala Thr Ile Ser Leu Ile Lys His Phe Glu Gly
1               5                   10                  15

Phe Val Pro Arg Pro Ala Pro Asp Pro Ile Gly Leu Pro Thr Val Gly
            20                  25                  30

Tyr Gly His Ala Cys Arg Thr Lys Gly Cys Ala Glu Val Pro Phe Pro
        35                  40                  45

Phe Pro Leu Thr Glu Asp Thr Ala Thr Glu Leu Leu Met Gln Asp Val
    50                  55                  60

Lys Ser Phe Gln Gln Ser Ile Thr Leu Ser Thr Asp Glu Val Val
65                  70                  75                  80

Leu Asn Ala Asn Glu Tyr Gly Ala Leu Val Ser Trp Ala Phe Asn Ile
                85                  90                  95

Gly Gly Gly Ala Ala Lys Lys Ser Ser Leu Ile Arg Arg Leu Asn Gln
                100                 105                 110

Gly Gln Asp Val Asn Thr Val Leu Arg Glu Glu Leu Pro Leu Trp Asn
            115                 120                 125

Lys Ala Gly Gly Lys Val Leu Pro Gly Leu Val Arg Arg Ala Ala
        130                 135                 140

Glu Val Glu Leu Ala Ser Glu His Thr Asp Glu Pro Ala Leu Pro Val
145                 150                 155                 160

Asp Cys

<210> SEQ ID NO 25
<211> LENGTH: 162
<212> TYPE: PRT
<213> ORGANISM: Hypocrea virens
```

<400> SEQUENCE: 25

```
Lys Thr Ile Asn Gly Ala Gly Val Asp Leu Ile Ala Lys Trp Glu Gly
1               5                   10                  15

Phe Val Ala Ser Pro Lys Pro Asp Pro Ile Gly Leu Pro Thr Val Gly
            20                  25                  30

Tyr Gly His Leu Cys Gln Gln Lys Asn Cys Arg Glu Val Lys Tyr Lys
        35                  40                  45

Phe Pro Leu Thr Lys Thr Thr Ala Lys Glu Leu Leu Asp Asp Leu
    50                  55                  60

Pro Lys Tyr Thr Lys Cys Leu Ala Asp Tyr Leu Asn Thr Lys Pro Lys
65                  70                  75                  80

Leu Asn Asp Asn Gln Trp Ala Ala Leu Thr Ser Trp Val Phe Asn Val
                85                  90                  95

Gly Cys Gly Asn Ala Lys Thr Ser Thr Leu Val Lys Arg Leu Asn Asn
            100                 105                 110

Gly Glu Ala Ala Asn Thr Val Ala Ala Glu Glu Leu Pro Lys Trp Arg
        115                 120                 125

Met Ala Gly Gly Lys Val Leu Pro Gly Leu Glu Ala Arg Arg Lys Asp
    130                 135                 140

Glu Val Lys Leu Phe Lys Thr Ala Ser Ser Lys Gln Ala Tyr Pro Lys
145                 150                 155                 160

Cys Gln
```

<210> SEQ ID NO 26
<211> LENGTH: 162
<212> TYPE: PRT
<213> ORGANISM: Agaricus bisporus

<400> SEQUENCE: 26

```
Pro Arg Val Asn Ser Ala Thr Ile Ser Leu Ile Lys Glu Phe Glu Gly
1               5                   10                  15

Phe Val Lys Ser Pro Ser Pro Asp Pro Ile Gly Leu Pro Thr Val Gly
            20                  25                  30

Phe Gly His Leu Cys Lys Ser Lys Gly Cys Ala Glu Val Pro Tyr Lys
        35                  40                  45

Phe Pro Leu Thr Glu Ala Asn Ala Gly Lys Leu Leu Gln Thr Asp Ile
    50                  55                  60

Lys Ser Phe Thr Lys Cys Val Ser Asp Asn Ile Lys Asp Ala Val Lys
65                  70                  75                  80

Leu Asn Ala Asn Gln Phe Gly Ala Leu Ser Ser Trp Ala Phe Asn Val
                85                  90                  95

Gly Cys Gly Asn Val Lys Ala Ser Ala Leu Val Ala Arg Leu Asn Arg
            100                 105                 110

Gly Glu Lys Pro Asn Thr Val Ala Ala Glu Glu Leu Pro Lys Trp Arg
        115                 120                 125

Leu Ala Gly Gly Lys Val Leu Lys Gly Leu Val Arg Arg Arg Ala Ala
    130                 135                 140

Glu Val Lys Leu Phe Lys Thr Ala Ser Lys Ala Ile Ala His Pro Pro
145                 150                 155                 160

Lys Cys
```

<210> SEQ ID NO 27
<211> LENGTH: 163
<212> TYPE: PRT

<213> ORGANISM: Metarhizium robertsii

<400> SEQUENCE: 27

Lys Thr Leu Asn Lys Ala Gly Thr Asp Leu Ile Thr Arg Trp Glu Gly
1               5                   10                  15

Phe Val Asp Arg Pro Lys Pro Asp Pro Ile Gly Leu Pro Thr Val Gly
            20                  25                  30

Tyr Gly His Leu Cys Gln Lys Lys Ser Cys Ala Glu Val Lys Tyr Thr
        35                  40                  45

Phe Pro Leu Thr Lys Ala Thr Ala Leu Gln Leu Leu Asn Asp Asp Leu
50                  55                  60

Pro Ser Tyr Thr Lys Cys Leu Gly Lys Val Leu Asp Ala Gly Lys Val
65                  70                  75                  80

Lys Leu Asn Glu Asn Gln Trp Ala Ala Leu Thr Ser Trp Val Phe Asn
                85                  90                  95

Val Gly Cys Gly Ala Ala Gln Ser Ser Ser Leu Val Lys Arg Leu Asn
            100                 105                 110

Arg Gly Glu Asn Ala Asn Thr Val Ala Ser Glu Leu Pro Lys Trp
        115                 120                 125

Lys Met Gly Gly Gly Arg Val Leu Pro Gly Leu Val Lys Arg Arg Ala
130                 135                 140

Asp Glu Val Ala Leu Phe Lys Ile Ala Ser Ser Arg Ser Ala Phe Pro
145                 150                 155                 160

Gln Cys Gln

<210> SEQ ID NO 28
<211> LENGTH: 157
<212> TYPE: PRT
<213> ORGANISM: Ajellomyces capsulatus

<400> SEQUENCE: 28

Pro Asn Val Asn Lys Ala Thr Leu Ala Leu Ile Lys Glu Phe Glu Gly
1               5                   10                  15

Phe Val Pro Arg Pro Glu Pro Asp Pro Ile Gly Leu Pro Thr Val Gly
            20                  25                  30

Tyr Gly His Leu Cys Lys Thr Lys Gly Cys Lys Glu Val Lys Phe Pro
        35                  40                  45

Leu Ser Lys Gly Thr Ala Thr Leu Leu Lys Lys Asp Leu Arg Ser
50                  55                  60

Phe Gln Gln Ala Ile Thr Leu Ser Thr Lys Thr Ala Val Lys Leu Asn
65                  70                  75                  80

Ala Asn Gln Tyr Gly Ala Leu Val Ser Trp Ala Tyr Asn Val Gly Pro
                85                  90                  95

Asn Ala Ala Arg Ser Ser Ser Leu Ile Ser Arg Leu Asn Lys Gly Glu
            100                 105                 110

Asp Pro Asn Lys Val Ile Ala Gln Glu Leu Pro Lys Trp Arg Leu Ala
        115                 120                 125

Ser Gly Lys Val Phe Lys Gly Leu Val Arg Arg Lys Ala Glu Val
130                 135                 140

Lys Leu Ala Lys Thr Pro Thr Lys Ser Lys Ala Leu Pro
145                 150                 155

<210> SEQ ID NO 29
<211> LENGTH: 162
<212> TYPE: PRT
<213> ORGANISM: Trichophyton tonsurans

```
<400> SEQUENCE: 29

Pro Asp Val Asn Asp Glu Thr Ile Ala Leu Ile Lys His Phe Glu Gly
1               5                   10                  15

Phe Val Pro Arg Pro Ala Pro Asp Pro Ile Gly Leu Pro Thr Val Gly
            20                  25                  30

Tyr Gly His Leu Cys Arg Thr Lys Gly Cys Ser Glu Val Pro Phe Pro
        35                  40                  45

Phe Pro Leu Thr Glu Glu Thr Ala Thr Glu Leu Leu Met Gln Asp Val
    50                  55                  60

Lys Ser Pro Gln Gln Ser Ile Thr Leu Ser Thr Thr Asp Gln Val Val
65                  70                  75                  80

Leu Asn Ala Asn Gln Tyr Gly Ala Leu Val Ser Trp Ala Tyr Asn Val
                85                  90                  95

Gly Gly Ser Ala Ala Lys Lys Ser Ser Leu Ile Ser Arg Leu Asn Gln
            100                 105                 110

Gly Gln Asp Val Asp Ala Val Ile Arg Glu Leu Pro Leu Trp Asn
        115                 120                 125

Lys Ala Gly Gly His Val Leu Ser Gly Leu Val Arg Arg Ala Ala
130                 135                 140

Glu Val Glu Leu Ala Ser Glu His Thr Asp Gln Pro Ala Leu Pro Val
145                 150                 155                 160

Asp Cys

<210> SEQ ID NO 30
<211> LENGTH: 159
<212> TYPE: PRT
<213> ORGANISM: Trichophyton equinum

<400> SEQUENCE: 30

Pro Asp Val Asn Pro Ala Thr Ile Ala Leu Ile Lys Glu Phe Glu Gly
1               5                   10                  15

Phe Val Pro Ser Pro Ala Pro Asp Pro Val Gly Leu Pro Thr Val Gly
            20                  25                  30

Tyr Gly His Leu Cys Gln Ser Lys Asn Cys Gly Glu Val Gly Phe Pro
        35                  40                  45

Phe Pro Leu Thr Glu Asp Thr Ala Thr Gln Leu Leu Leu Gln Asp Val
    50                  55                  60

Lys Ala Pro Gln Gln Thr Ile Thr Leu Lys Thr Ala Asp Gly Val His
65                  70                  75                  80

Leu Asn Glu Asn Gln Tyr Gly Ala Leu Val Ser Trp Thr Phe Asn Val
                85                  90                  95

Gly Pro Gly Asn Val Ala Thr Ser Ser Leu Leu Gln Arg Leu Asn Ala
            100                 105                 110

Leu Glu Asp Val Asn Thr Val Leu Arg Glu Glu Leu Pro Gln Trp Lys
        115                 120                 125

Tyr Gly Gly Gly Lys Val Leu Pro Gly Leu Val Arg Arg Arg Ala Ala
130                 135                 140

Glu Val Ala Leu Gly Glu Thr Pro Ser Asn Val Ala Ala Leu Pro
145                 150                 155

<210> SEQ ID NO 31
<211> LENGTH: 162
<212> TYPE: PRT
<213> ORGANISM: Trichophyton rubrum
```

<400> SEQUENCE: 31

Pro Asp Val Asn Pro Ala Thr Ile Ala Leu Ile Lys Glu Phe Glu Gly
1               5                   10                  15

Phe Val Pro Ala Pro Ala Pro Asp Pro Val Gly Leu Pro Thr Val Gly
                20                  25                  30

Tyr Gly His Leu Cys Gln Ser Lys Asn Cys Gly Val Gly Phe Pro
            35                  40                  45

Phe Pro Leu Thr Glu Asp Thr Ala Thr Gln Leu Leu Ile Gln Asp Val
    50                  55                  60

Lys Ala Pro Gln Gln Thr Ile Thr Leu Lys Thr Ala Asp Gly Val His
65                  70                  75                  80

Leu Asn Glu Asn Gln Tyr Gly Ala Leu Val Ser Trp Thr Phe Asn Val
                85                  90                  95

Gly Pro Gly Asn Val Ala Thr Ser Ser Leu Leu Gln Arg Leu Asn Ala
                100                 105                 110

Leu Glu Asp Val Asn Thr Val Leu Arg Glu Glu Leu Pro Gln Trp Lys
                115                 120                 125

Tyr Gly Gly Gly Lys Val Leu Pro Gly Leu Val Arg Arg Ala Ala
                130                 135                 140

Glu Val Ala Leu Gly Glu Thr Ala Ser Asp Val Pro Ala Leu Pro Val
145                 150                 155                 160

Ala Cys

<210> SEQ ID NO 32
<211> LENGTH: 161
<212> TYPE: PRT
<213> ORGANISM: Trichophyton rubrum

<400> SEQUENCE: 32

Asn Val Asn Asp Glu Thr Ile Gly Leu Ile Lys His Phe Glu Gly Phe
1               5                   10                  15

Val Leu Arg Pro Ala Pro Asp Pro Ile Gly Leu Pro Thr Val Gly Tyr
                20                  25                  30

Gly His Leu Cys Arg Thr Lys Gly Cys Ser Glu Val Ser Phe Pro Phe
            35                  40                  45

Phe Leu Thr Glu Glu Thr Ala Thr Glu Leu Leu Ile Gln Asp Val Lys
    50                  55                  60

Ser Ser Gln Gln Ser Ile Thr Leu Ser Thr Thr Asp Gln Val Val Phe
65                  70                  75                  80

Asn Ala Asn Gln Ser Gly Ala Leu Val Ser Trp Ala Tyr Thr Val Gly
                85                  90                  95

Gly Ala Thr Ala Lys Lys Ser Ser Leu Ile Ser Arg Leu Asn Arg Glu
                100                 105                 110

Gln Asp Val Asp Ala Val Ile Arg Glu Glu Leu Pro Leu Trp Asn Lys
                115                 120                 125

Ala Gly Arg His Val Leu Pro Gly Gln Val Arg Arg Ala Ala Glu
                130                 135                 140

Val Glu Leu Ala Ser Gly His Thr Asp Gln Pro Pro Leu Leu Val Asp
145                 150                 155                 160

Cys

<210> SEQ ID NO 33
<211> LENGTH: 150
<212> TYPE: PRT
<213> ORGANISM: Pleurotus ostreatus

<400> SEQUENCE: 33

Met Ile Lys Ser Phe Glu Ser Phe Val Pro Ser Pro Ala Pro Asp Pro
1               5                   10                  15

Val Gly Lys Leu Thr Val Gly Tyr Gly His Lys Cys Ile Gln Pro Gly
                20                  25                  30

Cys Ser Glu Ala Gly Pro Phe Pro Leu Thr Glu Ala Gly Ala Val Ala
                35                  40                  45

Leu Met His Arg Asp Leu Arg Ile Ala Thr Thr Cys Leu Ser Pro Ala
        50                  55                  60

Ile Ser Ser Thr Val Arg Leu Asn Asp Asn Gln Phe Gly Ala Leu Ala
65                  70                  75                  80

Asp Trp Ala Phe Asn Val Gly Cys Gly Ala Met Arg Arg Ser Thr Leu
                85                  90                  95

Val Ser Arg Leu Asn Ser Gly Glu Asn Pro Asn Thr Val Ala Ala Gln
                100                 105                 110

Glu Leu Pro Lys Trp Asn Val Ala Glu Gly His Val Ser Asn Gly Leu
                115                 120                 125

Ile Arg Arg Arg Ala Ala Glu Val Ala Leu Phe Gln Thr Ala Ser Ser
        130                 135                 140

Val Ile Ala His Pro Cys
145             150

<210> SEQ ID NO 34
<211> LENGTH: 150
<212> TYPE: PRT
<213> ORGANISM: Pleurotus ostreatus

<400> SEQUENCE: 34

Leu Ile Lys Glu Phe Glu Gly Phe Val Ala Arg Pro Ala Pro Asp Pro
1               5                   10                  15

Ile Gly Leu Pro Thr Val Gly Tyr Gly His Leu Cys Gln Thr Thr Ser
                20                  25                  30

Cys Ser Glu Ala Gly Ala Phe Pro Leu Thr Glu Ala Arg Ala Thr Thr
                35                  40                  45

Leu Leu Leu Ser Asp Ser Arg Val Ala Thr Ser Cys Leu Asn Thr Ala
        50                  55                  60

Ile Ser Arg Asn Val Arg Leu Asn Ala Asn Gln Phe Gly Ala Leu Thr
65                  70                  75                  80

Ser Trp Thr Phe Asn Val Gly Cys Gly Asn Met Arg Ser Ser Ser Leu
                85                  90                  95

Leu Ser Arg Leu Asn Ala Gly Glu Ala Pro Asn Thr Val Ala Ala Gln
                100                 105                 110

Glu Leu Pro Lys Trp Asn Lys Ala Gly Gly Gln Val Leu Ala Gly Leu
                115                 120                 125

Thr Arg Arg Arg Ala Ala Glu Val Val Leu Phe Gln Thr Ala Ser Ser
        130                 135                 140

Val Ile Ala His Pro Cys
145             150

<210> SEQ ID NO 35
<211> LENGTH: 150
<212> TYPE: PRT
<213> ORGANISM: Pleurotus ostreatus

<400> SEQUENCE: 35

Leu Ile Lys Ser Ser Glu Gly Phe Val Pro Ser Ala Pro Asp Pro
1               5                   10                  15

Ile Gly Leu Pro Thr Val Gly Tyr Gly His Leu Cys Gln Thr Ser Ser
            20                  25                  30

Cys Ser Glu Ala Gly Pro Phe Pro Leu Thr Glu Ala Arg Ala Thr Thr
            35                  40                  45

Leu Leu Leu Ala Asp Ser Arg Thr Ala Thr Ser Cys Leu Asn Thr Ala
50                  55                  60

Ile Ser Ser Ser Val Arg Leu Asn Asp Asn Gln Phe Gly Ala Leu Thr
65                  70                  75                  80

Ser Trp Thr Phe Asn Val Gly Cys Ala Asn Met Arg Ser Ser Thr Leu
                85                  90                  95

Val Ser Arg Leu Asn Ala Gly Glu Thr Pro Asn Thr Val Ala Ala Gln
            100                 105                 110

Glu Leu Pro Arg Trp Asn Leu Ala Gly Gly Val Val Gln Pro Gly Leu
            115                 120                 125

Val Thr Arg Arg Ala Asn Glu Val Lys Leu Phe Gln Thr Ala Ser Ser
            130                 135                 140

Val Val Ala His Pro Cys
145                 150

<210> SEQ ID NO 36
<211> LENGTH: 146
<212> TYPE: PRT
<213> ORGANISM: Serratia marcescens

<400> SEQUENCE: 36

Glu Leu Gln Thr Ser Glu Ala Gly Leu Arg Leu Ile Ala Asp Leu Glu
1               5                   10                  15

Gly Cys Arg Leu Ser Pro Tyr Gln Cys Ser Ala Gly Val Trp Thr Gln
            20                  25                  30

Gly Ile Gly His Thr Ala Gly Val Ile Pro Gly Lys Ala Ile Asp Glu
            35                  40                  45

His Lys Ala Ala Met Asp Leu Val Asp Asp Val Arg Arg Thr Glu Arg
50                  55                  60

Gly Met Ala Ala Cys Leu Pro Asp Thr Leu Ser Gln Gln Thr Tyr Asp
65                  70                  75                  80

Ala Ala Ile Ala Phe Ala Phe Asn Val Gly Val Ser Ala Ala Cys His
                85                  90                  95

Ser Thr Leu Val Ala Leu Leu Gln Gln Arg Gln Trp Arg Gln Ala Cys
            100                 105                 110

Asp Gln Leu Pro Arg Trp Val Tyr Val Asn Gly Lys Lys Asn Lys Gly
            115                 120                 125

Leu Glu Gln Arg Arg Ala Met Glu Arg Ala Leu Cys Leu Gln Gly Ile
            130                 135                 140

Ala Ser
145

<210> SEQ ID NO 37
<211> LENGTH: 162
<212> TYPE: PRT
<213> ORGANISM: Galerina marginata

<400> SEQUENCE: 37

Pro Glu Val Asn Ala Ala Thr Ile Ser Leu Ile Lys Lys Phe Glu Gly
1               5                   10                  15

Phe Val Ser Lys Pro Ala Pro Asp Pro Ile Gly Leu Pro Thr Val Gly
                20                  25                  30

Tyr Gly His Leu Cys Lys Thr Thr Gly Cys Ala Glu Val Pro Phe Ser
            35                  40                  45

Phe Pro Leu Thr Glu Ala Glu Ala Thr Thr Leu Leu Asn Thr Asp Leu
        50                  55                  60

Lys Thr Phe Thr Ala Cys Ile Thr Lys Asp Ile Ser Ser Lys Ile Lys
65                  70                  75                  80

Leu Asn Asp Asn Gln Tyr Gly Ala Leu Ser Ser Trp Ala Phe Asn Glu
                85                  90                  95

Gly Cys Gly Asn Val Gly Ser Ser Thr Leu Ile Ala Arg Leu Asn Ala
            100                 105                 110

Gly Asp Asn Pro Asn Thr Val Ala Ala Gln Glu Leu Pro Lys Trp Asp
        115                 120                 125

Ile Ala Gly Gly Met Val Leu Gln Gly Leu Val Asn Arg Arg Val Ala
    130                 135                 140

Glu Val Lys Leu Phe Gln Thr Pro Ser Ser Val Ile Ala His Pro Pro
145                 150                 155                 160

Gln Cys

<210> SEQ ID NO 38
<211> LENGTH: 161
<212> TYPE: PRT
<213> ORGANISM: Galerina marginata

<400> SEQUENCE: 38

Thr Pro Pro Asn Ala Ala Thr Val Ser Leu Ile Lys Ser Phe Glu Gly
1               5                   10                  15

Phe Val Ala Ser Pro Lys Pro Asp Pro Ile Gly Leu Pro Thr Ala Gly
                20                  25                  30

Phe Gly His Lys Cys Val Lys Ala Asn Cys Ala Glu Val Pro Phe Ser
            35                  40                  45

Phe Pro Leu Ser Gln Asp Thr Ala Thr Gln Leu Leu Gln Ser Asp Ala
        50                  55                  60

Gln Lys Phe Val Thr Cys Leu His Gly Leu Ile Ser Lys Lys Val Thr
65                  70                  75                  80

Leu Asn Asp Asn Gln Phe Gly Ala Leu Thr Ser Phe Ala Phe Asn Leu
                85                  90                  95

Gly Cys Gly Ala Val Gln Ser Ser Thr Leu Leu Lys Arg Leu Asn Asn
            100                 105                 110

Gly Glu Asp Pro Asn Thr Val Ala Ala Ala Glu Ile Pro Arg Phe Asn
        115                 120                 125

Lys Ala Gly Gly Lys Val Ser Ser Gly Leu Ala Arg Arg Arg Ala Ala
    130                 135                 140

Glu Val Gln Leu Phe Gln Thr Pro Ser Ser Thr Thr Ala Gln Pro Leu
145                 150                 155                 160

Cys

<210> SEQ ID NO 39
<211> LENGTH: 163
<212> TYPE: PRT
<213> ORGANISM: Agaricus bisporus

<400> SEQUENCE: 39

Pro Arg Val Asn Ser Ala Thr Ile Ser Leu Ile Lys Glu Phe Glu Gly
1               5                   10                  15

```
Phe Val Lys Ser Pro Ser Pro Asp Pro Ile Gly Leu Pro Thr Val Gly
             20                  25                  30

Phe Gly His Leu Cys Lys Ser Lys Gly Cys Ala Glu Val Pro Tyr Lys
         35                  40                  45

Phe Pro Leu Thr Glu Ala Asn Ala Gly Lys Leu Leu Gln Thr Asp Ile
     50                  55                  60

Lys Ser Phe Thr Lys Cys Val Ser Asp Asn Ile Lys Asp Ala Val Lys
65                  70                  75                  80

Leu Asn Ala Asn Gln Phe Gly Ala Leu Ser Ser Trp Ala Phe Asn Val
                 85                  90                  95

Gly Cys Gly Asn Val Lys Ala Ser Ala Leu Val Ala Arg Leu Asn Arg
                100                 105                 110

Gly Glu Lys Pro Asn Thr Val Ala Ala Glu Leu Pro Lys Trp Arg
            115                 120                 125

Leu Ala Gly Gly Lys Val Leu Lys Gly Leu Val Arg Arg Ala Ala
    130                 135                 140

Glu Val Lys Leu Phe Lys Thr Ala Ser Ser Ala Ile Ala His Pro Pro
145                 150                 155                 160

Lys Cys Ser

<210> SEQ ID NO 40
<211> LENGTH: 167
<212> TYPE: PRT
<213> ORGANISM: Trichosporon asahii

<400> SEQUENCE: 40

Val Asn Ala Asp Gly Ile Ala Leu Ile Gln Glu Phe Glu Ser Phe Gln
1               5                   10                  15

Pro Arg Pro Tyr Lys Asp Pro Lys Gly Leu Trp Thr Val Gly Tyr Gly
            20                  25                  30

His Leu Cys Ala Asn Gly Gly Lys Asp Ser Thr Cys Ser Gly Thr Gly
        35                  40                  45

Phe Lys Tyr Pro Leu Thr Leu Ala Thr Ala Gly Glu Leu Leu Lys Lys
    50                  55                  60

Asp Ile Pro Arg Tyr Thr Lys Cys Leu Arg Asp Asn Leu Asn Glu Asp
65                  70                  75                  80

Lys Val Lys Leu Asn Lys Asn Gln Trp Ala Ala Leu Ser Ser Phe Val
                85                  90                  95

Phe Asn Leu Gly Cys Gly Asn Phe Gln Arg Ser Asp Leu Met Ala Arg
                100                 105                 110

Leu Asn Lys Gly Glu Asp Val Asn Thr Val Ile Ala Ala Glu Phe Pro
            115                 120                 125

Arg Trp Asn Lys Ala Asp Gly Ala Val Leu Thr Gly Leu Val Arg Arg
        130                 135                 140

Arg Ala Glu Val Ala Leu Ala Lys Lys Thr Ser His Gly Thr Ser
145                 150                 155                 160

Lys Ala Phe Pro Thr Cys Thr
            165

<210> SEQ ID NO 41
<211> LENGTH: 164
<212> TYPE: PRT
<213> ORGANISM: Trichosporon asahii

<400> SEQUENCE: 41
```

```
Cys Pro Ser Ile Asn Asp Ala Gly Ile Ala Leu Ile Lys Glu Phe Glu
1               5                   10                  15

Gly Phe Phe Lys Asn Pro Tyr Lys Asp Pro Val Gly Leu Trp Thr Val
                20                  25                  30

Gly Tyr Gly His Leu Cys Ala Asn Gly Gly Lys Asp Ser Ser Cys Ser
            35                  40                  45

Gly Thr Gly Phe Lys Tyr Pro Leu Thr Glu Ala Thr Ala Thr Glu Leu
        50                  55                  60

Leu Lys Lys Asp Leu Pro Ser Tyr Thr Ser Cys Phe Pro Lys Tyr Leu
65                  70                  75                  80

Thr Ser Gly Ala Lys Leu Asn Lys Asn Gln Tyr Ala Ala Leu Thr Ser
                85                  90                  95

Phe Thr Phe Asn Leu Gly Cys Gly Val Leu Lys Asp Phe Ala Gly Arg
                100                 105                 110

Leu Asn Lys Gly Glu Asp Ala Ser Thr Val Phe Ala Gln Glu Phe Pro
            115                 120                 125

Lys Tyr Val His Ala Gly Gly Asn Val Leu Gln Gly Leu Val Arg Arg
130                 135                 140

Arg Asn Ala Glu Val Ala Leu Ala Lys Lys Ala Gly Ser Thr Glu Ala
145                 150                 155                 160

Trp Pro Lys Cys

<210> SEQ ID NO 42
<211> LENGTH: 160
<212> TYPE: PRT
<213> ORGANISM: Trichosporon asahii

<400> SEQUENCE: 42

Ile Asn Asp Ala Gly Val Glu Leu Ile Lys Ser Phe Glu Gly Cys Val
1               5                   10                  15

Ala Asn Pro Tyr Gln Asp Ala Gly Gly Lys Trp Thr Val Gly Tyr Gly
                20                  25                  30

His Leu Cys Ser Gly Gly Asp Asp Ser Thr Cys Ser Asp Thr Gly Phe
            35                  40                  45

Ser Tyr Pro Leu Thr Glu Glu Thr Ala Thr Glu Leu Phe Lys Arg Asp
        50                  55                  60

Leu Pro Asn Tyr Val Ser Cys Met Pro Gln Tyr Leu Thr Asp Gly Ala
65                  70                  75                  80

Lys Leu Asn Lys Asn Gln Trp Ala Ala Leu Thr Ser Phe Cys Tyr Asn
                85                  90                  95

Leu Gly Cys Gly Ile Leu Ser Asp Phe Ala Gly Arg Leu Asn Ala Gly
                100                 105                 110

Glu Asp Ala Asn Val Val Ile Gly Glu Phe Pro Lys Tyr Thr Leu
            115                 120                 125

Ala Glu Gly Val Glu Leu Glu Gly Thr Gly Ala Gly Gly Asp Glu Glu
        130                 135                 140

Val Ala Leu Ala Gln Ser Pro Gly Ser Thr Glu Ala Trp Pro Asn Cys
145                 150                 155                 160

<210> SEQ ID NO 43
<211> LENGTH: 168
<212> TYPE: PRT
<213> ORGANISM: Trichosporon asahii

<400> SEQUENCE: 43

Val Asn Ala Asp Gly Ile Ala Leu Ile Gln Glu Phe Glu Ser Phe Gln
```

```
            1               5                  10                 15
        Pro Arg Pro Tyr Lys Asp Pro Lys Gly Leu Trp Thr Val Gly Tyr Gly
                        20                 25                 30

His Leu Cys Ala Asn Gly Gly Lys Asp Ser Thr Cys Ser Gly Thr Gly
                        35                 40                 45

Phe Lys Tyr Pro Leu Thr Leu Ala Thr Ala Gly Glu Leu Leu Lys Lys
                        50                 55                 60

Asp Ile Pro Arg Tyr Thr Lys Cys Leu Arg Asp Asn Leu Asn Glu Asp
        65                         70                 75                 80

Lys Val Lys Leu Asn Lys Asn Gln Trp Ala Ala Leu Ser Ser Phe Val
                        85                 90                 95

Phe Asn Leu Gly Cys Gly Asn Phe Gln Arg Ser Asp Leu Met Ala Arg
                       100                105                110

Leu Asn Lys Gly Glu Asp Val Asn Thr Val Ile Ala Ala Glu Phe Pro
                       115                120                125

Arg Trp Asn Lys Ala Asp Gly Ala Val Leu Thr Gly Leu Val Arg Arg
                       130                135                140

Arg Ala Glu Val Ala Leu Ala Lys Lys Thr Ser His Gly Thr Ser
        145                      150                155                160

Lys Ala Phe Pro Thr Ala Pro Lys
                       165
```

```
<210> SEQ ID NO 44
<211> LENGTH: 131
<212> TYPE: PRT
<213> ORGANISM: Rhizophagus irregularis

<400> SEQUENCE: 44

1               5                  10                 15
        Met Ser Leu Phe Lys Glu Asn Phe Tyr Asp Asp Pro Val Gly Ile Thr

Thr Ile Gly Tyr Gly His Asn Cys Lys Ala Asn Lys Asp Ser Asp Lys
                        20                 25                 30

Ile Lys Ala Pro Ile Ser Ile Lys Glu Ala Glu Leu Leu Arg Lys
                        35                 40                 45

Asp Leu Val Lys Phe Glu Asp Tyr Val Asn Lys Gln Val Pro Glu Leu
                        50                 55                 60

Asn Ser Asn Gln Phe Ser Ala Val Val Ser Phe Ala Tyr Asn Leu Gly
        65                         70                 75                 80

Cys Asp Lys Leu Arg Thr Ser Ile Leu Leu Lys Lys Leu Lys Ala Gly
                        85                 90                 95

Asp Thr Gln Gly Ala Ser Glu Glu Phe Gly Arg Trp Val His Ala Lys
                       100                105                110

Arg Lys Arg Leu Pro Gly Leu Val Arg Arg Arg Glu Asp Glu Arg Gln
                       115                120                125

Leu Phe Leu
                       130
```

```
<210> SEQ ID NO 45
<211> LENGTH: 141
<212> TYPE: PRT
<213> ORGANISM: Rhizophagus irregularis

<400> SEQUENCE: 45

1               5                  10                 15
        Val Asn Lys Glu Gly Leu Asp Leu Ile Glu Gly Phe Glu Gly Phe Tyr

Pro Asn Phe Tyr Lys Asp Pro Val Gly Ile Lys Thr Ile Gly Tyr Gly
```

-continued

```
                20                  25                  30
His Ala Cys His Val His Asp Cys Ser Lys Ile Gln Ala Pro Ile Ser
            35                  40                  45
Leu Ala Glu Gly Glu Thr Leu Leu Lys Ser Asp Leu Ala Val Phe Glu
        50                  55                  60
Ser Cys Val Glu Ser Leu Thr Arg Thr Asn Leu Asn Pro Asp Gln Phe
65                  70                  75                  80
Ser Ala Leu Val Ser Phe Thr Phe Asn Leu Gly Cys Gly Ala Tyr Gln
                85                  90                  95
Lys Ser Thr Leu Arg Arg Lys Leu Asn Ala Gly Asp Thr Lys Gly Ala
            100                 105                 110
Ser Leu Glu Phe Ala Lys Trp Val Tyr Gly Gly Lys Lys Leu Pro
        115                 120                 125
Gly Leu Val Arg Arg Asn Ala Glu Arg Asp Leu Phe
    130                 135                 140

<210> SEQ ID NO 46
<211> LENGTH: 105
<212> TYPE: PRT
<213> ORGANISM: Rhizophagus irregularis

<400> SEQUENCE: 46

Ile Asn Lys Ala Gly Leu Lys Leu Ile Lys Phe Glu Gly Phe Arg
1               5                   10                  15

Ser Arg Phe Tyr Val Asp Lys Gly Ile Ile Thr Ile Gly Tyr Gly His
                20                  25                  30

Ala Cys His Val Tyr Asp Cys Ser Lys Ile His Pro Pro Ile Ser Arg
            35                  40                  45

Ala Lys Gly Glu Ala Leu Leu Lys Lys Asp Leu Val Val Phe Glu Lys
        50                  55                  60

Cys Val Asp Ser Leu Thr Gln Ile Lys Leu Asn Ser Asn Gln Phe Ser
65                  70                  75                  80

Ala Leu Val Ser Phe Thr Tyr Asn Leu Cys Cys Glu Ala Tyr Arg Arg
                85                  90                  95

Ser Thr Leu Arg Arg Lys Leu Asn Ala
            100                 105

<210> SEQ ID NO 47
<211> LENGTH: 155
<212> TYPE: PRT
<213> ORGANISM: Coniosporium apollinis

<400> SEQUENCE: 47

Pro Thr Val Asn Asp Gly Thr Ile Ile Met Leu Lys Glu Leu Glu Gly
1               5                   10                  15

Phe Ser Ala Thr Pro Tyr Leu Asp Val Asn Lys Ala Ala Ile Gly Tyr
                20                  25                  30

Gly His Gln Cys Asn Glu Pro Glu Cys Ala Gly Leu Ser Pro Pro Ile
            35                  40                  45

Thr Glu Val Glu Ala Thr Glu Leu Met Leu Gln Asp Leu Arg Thr Tyr
        50                  55                  60

Arg Asp Cys Leu Thr Ala Lys Leu Gly Ser Val Thr Leu Asn Glu Asn
65                  70                  75                  80

Gln Tyr Gly Ala Leu Ala Ser Trp Thr Phe Asn Val Gly Cys Gly Asn
                85                  90                  95

Met Arg Gly Ser Thr Leu Val Ile Arg Leu Leu Ala Gly Glu Asp Pro
```

```
            100                 105                 110

Asn Thr Val Ala Ala Asp Glu Leu Pro Lys Trp Arg Leu Val Asn Gly
            115                 120                 125

Gln Val Ser Gln Ala Leu Val Arg Arg Arg Glu Lys Glu Ile Ala Leu
        130                 135                 140

Phe Lys Thr Glu Ser Gly Val Gln Val Leu Pro
145                 150                 155

<210> SEQ ID NO 48
<211> LENGTH: 114
<212> TYPE: PRT
<213> ORGANISM: Rhizophagus irregularis

<400> SEQUENCE: 48

Thr Ile Gly Tyr Gly His Asn Cys Glu Ala Asn Asn Asp Gly Asp Lys
1               5                   10                  15

Ile Asn Ala Pro Ile Ser Ile Ala Gln Ala Glu Asp Leu Leu Arg Arg
            20                  25                  30

Asp Leu Ser Met Tyr Glu Asn Tyr Val Asn Ser Gln Val Pro Gly Leu
        35                  40                  45

Asn Ser Asn Gln Phe Ser Ala Leu Val Ser Phe Thr Phe Asn Val Gly
    50                  55                  60

Cys Gly Asn Leu Gly Ser Ser Thr Leu Leu Lys Lys Leu Lys Ala Gly
65                  70                  75                  80

Asp Thr Gln Gly Ala Ala Asn Glu Phe Gly Arg Trp Val Tyr Ala Asn
                85                  90                  95

Lys Lys Lys Leu Pro Gly Leu Ile Arg Arg Arg Glu Ala Glu Lys Arg
            100                 105                 110

Leu Phe

<210> SEQ ID NO 49
<211> LENGTH: 163
<212> TYPE: PRT
<213> ORGANISM: Penicillium roqueforti

<400> SEQUENCE: 49

Gly Pro Ala Val Asn Thr Asn Gly Leu Asp Leu Ile Lys Ser Phe Glu
1               5                   10                  15

Ser Phe Gln Ala Asn Val Tyr Asp Asp Gly Tyr Gly Asn Pro Thr Ile
            20                  25                  30

Gly Tyr Gly His Leu Cys Ser Asp Ser Thr Cys Ser Glu Val Thr Phe
        35                  40                  45

Ser Lys Pro Leu Thr Glu Asp Thr Ala Ser Gln Leu Leu Ala Lys Asp
    50                  55                  60

Leu Val Thr Tyr Gln Asn Gly Val Thr Asn Ala Leu Ala Thr Ala Val
65                  70                  75                  80

Thr Leu Asn Asp Asn Gln Tyr Ala Ala Leu Val Ser Trp Thr Phe Asn
                85                  90                  95

Val Gly Val Gly Asn Met Gln Ser Ser Ser Leu Val Ser Arg Met Asn
            100                 105                 110

Ala Gly Glu Asn Val Glu Thr Val Ala Ser Glu Leu Pro Lys Trp
            115                 120                 125

Asn Lys Ala Asn Gly Ala Val Val Ala Gly Leu Thr Arg Arg Arg Ala
        130                 135                 140

Asp Glu Val Lys Leu Phe Glu Glu Ala Ser Gln Thr Lys Ala Leu Pro
145                 150                 155                 160
```

Val Gly Cys

<210> SEQ ID NO 50
<211> LENGTH: 163
<212> TYPE: PRT
<213> ORGANISM: Aspergillus ruber

<400> SEQUENCE: 50

```
Gly Pro Pro Ala Asn Ile Pro Thr Leu Asp Leu Leu Lys Gly Phe Glu
1               5                   10                  15

Thr Met Gln Pro Asp Pro Tyr Asp Asp Gly Phe Gly Asn Pro Thr Ile
            20                  25                  30

Gly Tyr Gly His Leu Cys Thr Asn Lys Ala Cys Ser Asp Val Pro Phe
        35                  40                  45

Ser Lys Pro Leu Ser Glu Asp Ser Ala Thr Arg Leu Leu Gln Gly Asp
50                  55                  60

Leu Thr Ser Ala Gln Asp Ala Val Thr Asn Ala Leu Ala Asp Pro Val
65                  70                  75                  80

Thr Leu Asn Asp Asn Gln Tyr Gly Ala Leu Ile Ser Trp Thr Phe Asn
                85                  90                  95

Val Gly Asn Gly Asn Met Lys Ser Ser Asp Leu Val Arg Leu Met Asn
            100                 105                 110

Ala Gly Glu Glu Ile Val Ala Val Ala Asn Asn Glu Leu Pro Leu Trp
        115                 120                 125

Asn Lys Ala Asn Gly Lys Val Val Asn Gly Leu Val Arg Arg Arg Lys
130                 135                 140

Ala Glu Val Asp Leu Phe Asn Thr Pro Ser Asn Phe Gly Ala Leu Pro
145                 150                 155                 160

Val Pro Cys
```

<210> SEQ ID NO 51
<211> LENGTH: 162
<212> TYPE: PRT
<213> ORGANISM: Pyronema omphalodes

<400> SEQUENCE: 51

```
Ile Asn Ala Ala Thr Ile Ser Leu Ile Lys Ser Phe Glu Gly Phe Val
1               5                   10                  15

Pro Ser Pro Lys Pro Asp Pro Ile Gly Leu Pro Thr Val Gly Tyr Gly
            20                  25                  30

His Leu Cys Lys Lys Gly Cys Ala Glu Val Lys Tyr Lys Phe Pro
        35                  40                  45

Leu Thr Glu Ala Thr Ala Ala Gln Leu Leu Gln Asp Asp Ala Tyr Thr
50                  55                  60

Phe Arg Lys Cys Val Ala Ala Ile Lys Asp Ser Val Thr Leu Thr
65                  70                  75                  80

Asp Asn Gln Tyr Gly Ala Leu Val Ser Trp Ala Phe Asn Val Gly Cys
                85                  90                  95

Gly Gly Val Gln Thr Ser Thr Leu Val Lys Arg Leu Asn Arg Gly Glu
            100                 105                 110

Asn Lys Asn Ile Val Ala Ser Gln Glu Leu Ile Lys Trp Asn Lys Ala
        115                 120                 125

Gly Asn Pro Pro Lys Pro Met Asn Gly Leu Thr Arg Arg Arg Asn Ala
130                 135                 140

Glu Ile Ala Leu Phe Lys Lys Ala Ser Ser Val Gln Ala His Pro Pro
```

```
                          145                 150                 155                 160
Lys Cys

<210> SEQ ID NO 52
<211> LENGTH: 161
<212> TYPE: PRT
<213> ORGANISM: Pyronema omphalodes

<400> SEQUENCE: 52

Pro Pro Val Asn Thr Ala Thr Val Asn Leu Ile Lys Glu Phe Glu Gly
1               5                   10                  15

Phe Val Pro Ser Pro Ala Pro Asp Pro Ile Gly Leu Pro Thr Val Gly
            20                  25                  30

Tyr Gly His Leu Cys Lys Gln Thr Asn Cys Ala Glu Val Pro Tyr Pro
        35                  40                  45

Phe Pro Leu Thr Thr Thr Ala Ala Ala Leu Leu Gln Thr Asp Leu
    50                  55                  60

Lys Thr Tyr Thr Lys Cys Ile Ser Asp Tyr Ile Val Asp Ser Val Arg
65                  70                  75                  80

Leu Asn Asp Asn Gln Tyr Gly Ala Leu Ser Ser Trp Ala Phe Asn Val
                85                  90                  95

Gly Cys Gly Asn Ala Lys Thr Ser Thr Leu Ile Ser Arg Leu Asn Ala
            100                 105                 110

Gly Gln Asn Pro Asn Thr Val Ala Ser Glu Glu Leu Pro Lys Trp Asn
        115                 120                 125

Lys Ala Gly Gly Ser Val Leu Pro Gly Leu Thr Arg Arg Ala Ala
    130                 135                 140

Glu Val Thr Leu Phe Lys Thr Ala Ser Thr Lys Ile Ala His Pro Ala
145                 150                 155                 160

Cys

<210> SEQ ID NO 53
<211> LENGTH: 144
<212> TYPE: PRT
<213> ORGANISM: Trichophyton interdigitale

<400> SEQUENCE: 53

Pro Asp Val Asn Asp Glu Thr Ile Ala Leu Ile Lys His Phe Glu Gly
1               5                   10                  15

Phe Val Pro Arg Pro Ala Pro Asp Pro Ile Gly Leu Pro Thr Val Gly
            20                  25                  30

Tyr Gly His Leu Cys Arg Thr Lys Gly Cys Ser Glu Val Pro Phe Pro
        35                  40                  45

Phe Pro Leu Thr Glu Glu Thr Ala Thr Glu Leu Leu Met Gln Asp Val
    50                  55                  60

Lys Ser Pro Gln Gln Ser Ile Thr Leu Ser Thr Thr Asp Gln Val Val
65                  70                  75                  80

Leu Asn Ala Asn Gln Tyr Gly Ala Leu Val Ser Trp Ala Tyr Asn Val
                85                  90                  95

Gly Gly Ser Ala Ala Lys Lys Ser Ser Leu Ile Ser Arg Leu Asn Gln
            100                 105                 110

Gly Gln Asp Val Asp Ala Val Ile Arg Glu Glu Leu Pro Leu Trp Asn
        115                 120                 125

Lys Ala Gly Gly His Val Leu Pro Gly Leu Val Arg Arg Ala Ala
    130                 135                 140
```

<210> SEQ ID NO 54
<211> LENGTH: 134
<212> TYPE: PRT
<213> ORGANISM: Rhizophagus irregularis

<400> SEQUENCE: 54

Ile Asn Lys Glu Gly Leu Ala Leu Ile Glu Arg Phe Glu Gly Phe Ser
1               5                   10                  15

Pro Asn Phe Tyr Lys Asp Pro Val Gly Ile Lys Thr Ile Gly Tyr Gly
                20                  25                  30

His Ala Tyr His Val Asn Asp Cys Ser Lys Ile Arg Pro Pro Ile Ser
            35                  40                  45

Arg Ala Glu Gly Glu Ala Leu Leu Lys Lys Asp Leu Ala Arg Phe Glu
        50                  55                  60

Lys Cys Val Glu Ser Leu Thr Arg Val Lys Leu Asn Ser Asn Gln Phe
65                  70                  75                  80

Ser Ala Leu Cys Ser Phe Thr Phe Asn Ile Gly Cys Gly Ala Tyr Gln
                85                  90                  95

Lys Ser Thr Leu Arg Arg Lys Leu Asn Ala Gly Asp Thr Lys Gly Ala
            100                 105                 110

Ser Leu Glu Tyr Arg Lys Trp Val Tyr Gly Gly Lys Pro Leu Pro
        115                 120                 125

Gly Leu Val Lys Arg Arg
    130

<210> SEQ ID NO 55
<211> LENGTH: 141
<212> TYPE: PRT
<213> ORGANISM: Rhizophagus irregularis

<400> SEQUENCE: 55

Val Asn Lys Glu Gly Leu Asp Leu Ile Glu Gly Phe Glu Gly Phe Tyr
1               5                   10                  15

Pro Asn Phe Tyr Lys Asp Pro Val Gly Ile Lys Thr Ile Gly Tyr Gly
                20                  25                  30

His Ala Cys His Val His Asp Cys Ser Lys Ile Gln Ala Pro Ile Ser
            35                  40                  45

Leu Ala Glu Gly Glu Thr Leu Leu Lys Ser Asp Leu Ala Val Phe Glu
        50                  55                  60

Ser Cys Val Glu Ser Leu Thr Arg Thr Asn Leu Asn Pro Asp Gln Phe
65                  70                  75                  80

Ser Ala Leu Val Ser Phe Thr Phe Asn Leu Gly Cys Gly Ala Tyr Gln
                85                  90                  95

Lys Ser Thr Leu Arg Arg Lys Leu Asn Ala Gly Asp Thr Lys Gly Ala
            100                 105                 110

Ser Leu Glu Phe Ala Lys Trp Val Tyr Gly Gly Lys Lys Leu Pro
        115                 120                 125

Gly Leu Val Arg Arg Arg Asn Ala Glu Arg Asp Leu Phe
    130                 135                 140

<210> SEQ ID NO 56
<211> LENGTH: 163
<212> TYPE: PRT
<213> ORGANISM: Metarhizium anisopliae

<400> SEQUENCE: 56

Lys Thr Leu Asn Lys Ala Gly Thr Asp Leu Ile Thr Arg Trp Glu Gly

-continued

```
1               5                   10                  15

Phe Val Asp Arg Pro Gln Pro Asp Pro Ile Gly Leu Pro Thr Val Gly
            20                  25                  30

Tyr Gly His Leu Cys Gln Lys Lys Ser Cys Ala Glu Val Lys Tyr Thr
        35                  40                  45

Phe Pro Leu Thr Lys Ala Thr Ala Leu Gln Leu Leu Asn Asp Asp Leu
    50                  55                  60

Pro Ser Tyr Thr Lys Cys Leu Gly Lys Val Leu Asp Ala Gly Lys Val
65                  70                  75                  80

Lys Leu Asn Glu Asn Gln Trp Ala Ala Leu Thr Ser Trp Val Phe Asn
                85                  90                  95

Val Gly Cys Gly Ala Ala Gln Ser Ser Ser Leu Val Lys Arg Leu Asn
            100                 105                 110

Arg Gly Glu Asn Ala Asn Thr Val Ala Ser Glu Glu Leu Pro Lys Trp
        115                 120                 125

Lys Met Gly Gly Gly Arg Val Leu Pro Gly Leu Val Lys Arg Arg Ala
    130                 135                 140

Asp Glu Val Ala Leu Phe Lys Met Ala Ser Ser Arg Ser Ala Phe Pro
145                 150                 155                 160

Gln Cys Gln

<210> SEQ ID NO 57
<211> LENGTH: 132
<212> TYPE: PRT
<213> ORGANISM: Beauveria bassiana

<400> SEQUENCE: 57

Met Leu Thr Asp Leu Glu Gly Val Arg Tyr Thr Pro Tyr Tyr Asp Val
1               5                   10                  15

Ala Gly Val Leu Thr Val Cys Tyr Gly His Thr Gly Ala Asp Ile Ile
            20                  25                  30

Lys Thr Lys Thr Tyr Ser Ala Thr Glu Cys Gln Ala Met Leu Asp Lys
        35                  40                  45

Asp Leu Val Pro Phe Ala Arg Ser Val Glu Arg Ser Val Lys Val Pro
    50                  55                  60

Thr Thr Glu Tyr Gln Lys Ala Ala Leu Ile Ser Phe Ser Tyr Asn Val
65                  70                  75                  80

Gly Val Thr Ala Phe Glu Arg Ser Ser Leu Leu Arg Gln Leu Asn Ala
                85                  90                  95

Gly Asn Tyr Gln Ala Ala Cys Asp Gly Leu Arg Gln Trp Thr Tyr Ala
            100                 105                 110

Gly Gly Lys Gln Trp Lys Gly Leu Met Asn Arg Arg Asp Ile Glu Arg
        115                 120                 125

Glu Val Cys Met
    130

<210> SEQ ID NO 58
<211> LENGTH: 137
<212> TYPE: PRT
<213> ORGANISM: Beauveria bassiana

<400> SEQUENCE: 58

Gly Val Asp Leu Ile Lys Ser Phe Glu Gly Leu Arg Leu Ala Lys Tyr
1               5                   10                  15

Lys Asp Ala Val Gly Lys Trp Thr Ile Gly Tyr Gly His Leu Ile Leu
            20                  25                  30
```

```
Ala Thr Glu Asn Tyr Asp Arg Pro Leu Thr Glu Gln Glu Ala Glu Asn
            35                  40                  45

Leu Leu Arg Ser Asp Leu Ala Leu Thr Glu Arg Gly Val Tyr Arg Gln
 50                  55                  60

Val Ser Met Ala Leu Asn Gln Asn Gln Phe Asp Ala Leu Val Ala Phe
 65                  70                  75                  80

Ala Phe Asn Val Gly Leu Gly Asn Leu Gln Asn Ser Thr Leu Leu Arg
                 85                  90                  95

Leu Leu Asn Gln Gly Asn Tyr Ser Ala Ala Asp Glu Phe Leu Arg
            100                 105                 110

Trp Asn Lys Ala Gly Gly Asn Val Leu Ala Gly Leu Thr Arg Arg Arg
            115                 120                 125

Glu Ala Glu Arg Lys Leu Phe Leu Ser
130                 135

<210> SEQ ID NO 59
<211> LENGTH: 138
<212> TYPE: PRT
<213> ORGANISM: Beauveria bassiana

<400> SEQUENCE: 59

Leu Leu Pro Glu Leu Glu Gly Val Ser Tyr Thr Pro Tyr Tyr Asp Val
1               5                   10                  15

Ala Gly Val Leu Thr Val Cys Tyr Gly His Thr Gly Gln Asp Ile Ile
                 20                  25                  30

Pro Asp Lys Thr Tyr Thr Leu Ser Glu Cys Arg Arg Trp Leu Asp Gln
            35                  40                  45

Asp Leu Arg Pro Ala Ala Gln Val Val Ser Arg Ala Val Thr Val Pro
 50                  55                  60

Val Ser Glu Tyr Gln Arg Ala Ala Leu Ile Ser Phe Thr Tyr Asn Val
 65                  70                  75                  80

Gly Thr Ala Ala Phe Leu Arg Ser Ser Val Leu Arg Thr Leu Asn Ala
                 85                  90                  95

Gly Asp Tyr Glu Gln Ala Cys Ala Gly Leu Lys Lys Trp Ile Trp Ala
            100                 105                 110

Gly Gly Lys Pro Trp Gln Gly Leu Ile Asn Arg Arg Glu Val Glu Tyr
            115                 120                 125

Gln Leu Cys Thr Trp Pro Glu Pro Glu Lys
            130                 135

<210> SEQ ID NO 60
<211> LENGTH: 163
<212> TYPE: PRT
<213> ORGANISM: Metarhizium guizhouense

<400> SEQUENCE: 60

Lys Thr Leu Asn Lys Ala Gly Thr Asp Leu Val Thr Arg Trp Glu Gly
1               5                   10                  15

Phe Val Asp Arg Pro Lys Pro Asp Pro Ile Gly Leu Pro Thr Val Gly
                 20                  25                  30

Tyr Gly His Leu Cys Gln Lys Lys Ser Cys Ala Glu Val Lys Tyr Thr
            35                  40                  45

Phe Pro Leu Thr Lys Thr Thr Ala Leu Gln Leu Leu Asn Asp Asp Leu
 50                  55                  60

Pro Ser Tyr Thr Lys Cys Leu Gly Glu Val Leu Asp Ala Ser Lys Val
 65                  70                  75                  80
```

```
Lys Leu Asn Glu Asn Gln Trp Ala Ala Leu Thr Ser Trp Val Phe Asn
                85                  90                  95

Val Gly Cys Gly Ala Ala Gln Ser Ser Ser Leu Val Lys Arg Leu Asn
            100                 105                 110

His Gly Glu Asn Ala Asn Thr Val Ala Ser Glu Glu Leu Pro Lys Trp
        115                 120                 125

Lys Met Gly Gly Gly Arg Val Leu Pro Gly Leu Val Lys Arg Ala
    130                 135                 140

Asp Glu Val Ala Leu Phe Lys Ile Ala Ser Ser Arg Ser Ala Phe Pro
145                 150                 155                 160

Gln Cys Gln

<210> SEQ ID NO 61
<211> LENGTH: 163
<212> TYPE: PRT
<213> ORGANISM: Metarhizium majus

<400> SEQUENCE: 61

Lys Thr Leu Asn Lys Ala Gly Thr Asp Leu Val Thr Arg Trp Glu Gly
1               5                   10                  15

Phe Val Asp Arg Pro Lys Pro Asp Pro Ile Gly Leu Pro Thr Val Gly
            20                  25                  30

Tyr Gly His Leu Cys Gln Lys Lys Ser Cys Ala Glu Val Lys Tyr Thr
        35                  40                  45

Phe Pro Leu Thr Lys Ala Thr Ala Leu Gln Leu Leu Asn Asp Asp Leu
    50                  55                  60

Pro Asn Tyr Thr Lys Cys Leu Gly Glu Val Leu Asp Ala Ser Lys Val
65              70                  75                  80

Lys Leu Asn Glu Asn Gln Trp Ala Ala Leu Thr Ser Trp Val Phe Asn
                85                  90                  95

Val Gly Cys Gly Ala Ala Lys Ser Ser Ser Leu Val Lys Arg Leu Asn
            100                 105                 110

His Gly Glu Asn Ala Asn Thr Val Ala Ser Glu Glu Leu Pro Lys Trp
        115                 120                 125

Arg Met Gly Gly Gly Lys Val Leu Pro Gly Leu Val Lys Arg Ala
    130                 135                 140

Asp Glu Val Ala Leu Phe Lys Ile Ala Ser Ser Arg Ser Ala Phe Pro
145                 150                 155                 160

Gln Cys Gln

<210> SEQ ID NO 62
<211> LENGTH: 163
<212> TYPE: PRT
<213> ORGANISM: Metarhizium brunneum

<400> SEQUENCE: 62

Lys Thr Leu Asn Lys Ala Gly Thr Asp Leu Ile Thr Arg Trp Glu Gly
1               5                   10                  15

Phe Val Asp Arg Pro Lys Pro Asp Pro Ile Gly Leu Pro Thr Val Gly
            20                  25                  30

Tyr Gly His Leu Cys Gln Lys Lys Gly Cys Ala Glu Val Lys Tyr Thr
        35                  40                  45

Phe Pro Leu Thr Lys Ala Thr Ala Leu Gln Leu Leu Asn Asp Asp Leu
    50                  55                  60

Pro Ser Tyr Thr Lys Cys Leu Gly Arg Ala Leu Asp Ala Gly Lys Val
```

```
                65                  70                  75                  80
Lys Leu Asn Glu Asn Gln Trp Ala Ala Leu Thr Ser Trp Val Phe Asn
                    85                  90                  95

Val Gly Cys Gly Ala Ala Gln Ser Ser Ser Leu Val Lys Arg Leu Asn
                100                 105                 110

Arg Gly Glu Asn Ala Asn Thr Val Ala Ser Glu Leu Pro Lys Trp
                115                 120                 125

Lys Met Gly Gly Arg Val Leu Pro Gly Leu Val Lys Arg Ala
130                 135                 140

Asp Glu Val Gly Leu Phe Lys Ile Ala Ser Ser Arg Ser Ala Phe Pro
145                 150                 155                 160

Gln Cys Gln

<210> SEQ ID NO 63
<211> LENGTH: 163
<212> TYPE: PRT
<213> ORGANISM: Magnaporthe oryzae

<400> SEQUENCE: 63

Pro Lys Leu Asn Gln Ala Ser Leu Asp Leu Val Lys Glu Phe Glu Gly
1               5                   10                  15

Trp Phe Pro Asp Ile Tyr Leu Asp Pro Val Gly Leu Pro Thr Val Gly
                20                  25                  30

Tyr Gly His Leu Cys Ser Asn Pro Thr Cys Ser Glu Val Pro Tyr Pro
            35                  40                  45

Ile Pro Leu Ser Val Ala Asn Gly Glu Ala Leu Leu Gln Ser Asp Leu
50                  55                  60

Gly Ile Ala Arg Arg Cys Leu Ser Ala Asp Leu Val Asp Ser Val Val
65                  70                  75                  80

Leu Asn Pro Asn Gln Tyr Gly Ala Leu Val Ser Trp Val Phe Asn Met
                85                  90                  95

Gly Cys Gly Ala Gln Lys Ser Ser Thr Leu Thr Ala Arg Leu Asn Ala
                100                 105                 110

Gly Glu Asp Lys Ser Val Val Ala Arg Gln Glu Leu Pro Arg Trp Val
                115                 120                 125

Tyr Ala Gly Gly Gln Val Leu Asn Gly Leu Val Arg Arg Ala Ala
                130                 135                 140

Glu Val Ala Leu Phe Asp Thr Pro Ala Glu Gly Val Ala His Pro Pro
145                 150                 155                 160

Arg Pro Cys

<210> SEQ ID NO 64
<211> LENGTH: 162
<212> TYPE: PRT
<213> ORGANISM: Coprinopsis cinerea

<400> SEQUENCE: 64

Thr Thr Val Asn Ala Arg Thr Val Arg Glu Ile Lys Ser Ser Glu Gly
1               5                   10                  15

Phe Val Lys Ser Pro Ala Pro Asp Pro Ile Gly Leu Pro Thr Val Gly
                20                  25                  30

Tyr Gly His Leu Cys Lys Thr Lys Gly Cys Ala Glu Val Pro Tyr Lys
            35                  40                  45

Phe Pro Leu Thr Asp Ala Gln Ala Thr Ser Leu Leu Lys Ser Asp Leu
50                  55                  60
```

```
Lys Thr Phe Gln Asn Cys Ile Ser Lys Asp Leu Arg Asp Thr Val Arg
 65                  70                  75                  80

Leu Asn Glu Asn Gln Tyr Gly Ala Leu Val Ser Trp Ala Phe Asn Val
             85                  90                  95

Gly Cys Arg Ala Thr Gly Ser Ser Thr Leu Ile Ala Arg Leu Asn Arg
            100                 105                 110

Gly Asp Asn Pro Ala Lys Val Ala Glu Glu Leu Pro Lys Trp Asn
            115                 120                 125

Lys Ala Asn Gly Lys Val Leu Gln Gly Leu Val Asn Arg Arg Lys Arg
            130                 135                 140

Glu Ile Ala Met Phe Lys Thr Pro Ser Lys Val Ile His His Pro Pro
145                 150                 155                 160

Lys Cys
```

<210> SEQ ID NO 65
<211> LENGTH: 162
<212> TYPE: PRT
<213> ORGANISM: Coprinopsis cinerea

<400> SEQUENCE: 65

```
Thr Asn Val Asn Ser Lys Thr Val Glu His Ile Lys Gln Trp Glu Gly
  1               5                  10                  15

Phe Val Lys Ser Pro Ala Pro Asp Pro Ile Gly Leu Pro Thr Val Gly
             20                  25                  30

Tyr Gly His Leu Cys Lys Thr Lys Gly Cys Ser Glu Val Pro Tyr Lys
             35                  40                  45

Phe Pro Leu Thr Glu Ala Gln Ala Thr Ser Leu Leu Lys Thr Asp Leu
 50                  55                  60

Lys Thr Phe Gln Asn Cys Ile Ser Ser Gln Leu Lys Asp Ser Val Arg
 65                  70                  75                  80

Leu Asn Ala Asn Gln Tyr Gly Ala Leu Val Ser Trp Ala Phe Asn Val
             85                  90                  95

Gly Cys Gly Asn Thr Ser Gly Ser Ala Leu Ile Ser Arg Leu Asn Lys
            100                 105                 110

Gly Glu Ser Pro Asn Thr Val Ala Ser Gln Glu Leu Pro Lys Trp Asn
            115                 120                 125

Lys Ala Gly Gly Lys Val Leu Gln Gly Leu Val Asn Arg Arg Lys Ala
            130                 135                 140

Glu Val Thr Leu Phe Lys Thr Ser Ser Val Ile His His Pro Pro
145                 150                 155                 160

Thr Cys
```

<210> SEQ ID NO 66
<211> LENGTH: 162
<212> TYPE: PRT
<213> ORGANISM: Coprinopsis cinerea

<400> SEQUENCE: 66

```
Ser Pro Val Asn Ser Arg Thr Val Gln Glu Ile Lys Asn Ser Glu Gly
  1               5                  10                  15

Phe Val Arg Ser Pro Ala Pro Asp Pro Ile Gly Leu Pro Thr Val Gly
             20                  25                  30

Tyr Gly His Leu Cys Lys Asn Lys Gly Cys Ser Glu Val Pro Tyr Ser
             35                  40                  45

Phe Pro Leu Thr Glu Ala Gln Ala Thr Ser Leu Leu Met Thr Asp Leu
 50                  55                  60
```

```
Lys Thr Phe Gln Lys Cys Ile Ser Asp Gln Ile Asn Asp Ser Ile Arg
 65                  70                  75                  80

Leu Asn Glu Asn Gln Tyr Gly Ala Leu Val Ser Trp Ala Phe Asn Val
             85                  90                  95

Gly Cys Gly Asn Thr Ala Ser Ser Ala Leu Ile Ser Arg Leu Asn Lys
            100                 105                 110

Gly Glu Ser Pro Asn Lys Val Ala Glu Glu Leu Pro Arg Trp Lys
            115                 120                 125

Tyr Ala Gly Gly Gln Val Leu Pro Gly Leu Val Ala Arg Asn Arg
        130                 135                 140

Glu Ile Ala Leu Phe Lys Thr Ala Ser Ser Val Val Gly His Pro Pro
145                 150                 155                 160

Arg Cys

<210> SEQ ID NO 67
<211> LENGTH: 162
<212> TYPE: PRT
<213> ORGANISM: Chaetomium globosum

<400> SEQUENCE: 67

Pro Lys Ser Asn Ser Ala Thr Val Asp Leu Ile Ala Lys Ser Glu Gly
  1               5                  10                  15

Phe Arg Ala Asn Val Tyr Asn Asp Pro Ala Gly His Pro Thr Val Gly
             20                  25                  30

Tyr Gly His Leu Cys Thr Lys Ala Lys Cys Ala Glu Ile Lys Tyr Lys
         35                  40                  45

Ile Pro Leu Ser Thr Thr Asp Gly Lys Lys Leu Leu Ala Asp Asp Met
 50                  55                  60

Lys Lys Phe Glu Lys Cys Ile Thr Ala Met Leu Asn Ser Lys Ala Lys
 65                  70                  75                  80

Leu Asn Leu Asn Gln Tyr Gly Ala Leu Val Ser Trp Ser Phe Asn Val
             85                  90                  95

Gly Cys Gly Ala Ala Gln Gly Ser Gln Leu Val Lys Arg Leu Asn Lys
            100                 105                 110

Gly Glu Asn Val Asn Thr Val Leu Ser Asn Glu Leu Pro Lys Trp Val
            115                 120                 125

Asn Ala Gly Gly Lys Lys Leu Pro Gly Leu Val Thr Arg Arg Asn Asn
        130                 135                 140

Glu Ile Ala Leu Ala Lys Lys Ser Gly Ser Gly Ala Ala Leu Pro Val
145                 150                 155                 160

Lys Cys

<210> SEQ ID NO 68
<211> LENGTH: 162
<212> TYPE: PRT
<213> ORGANISM: Nectria haematococca

<400> SEQUENCE: 68

Pro Lys Ser Asn Gln Ala Thr Val Asn Leu Ile Ala Ser Phe Glu Gly
  1               5                  10                  15

Phe Arg Ala Asn Ile Tyr Lys Asp Ala Ala Gly Tyr Pro Thr Val Gly
             20                  25                  30

Tyr Gly His Leu Cys Ser Asn Ser Lys Cys Thr Asp Val Lys Tyr Ser
         35                  40                  45

Ile Pro Leu Ser Gln Ala Asn Gly Lys Lys Leu Leu Ala Ser Asp Met
```

```
            50                  55                  60
Ala Lys Phe Glu Lys Cys Ile Thr Ala Met Val Lys Ser Asn Val Lys
 65                  70                  75                  80

Leu Asn Lys Asn Gln Tyr Gly Ala Leu Val Ser Trp Ser Phe Asn Asn
                 85                  90                  95

Gly Cys Gly Ala Ala Lys Thr Ser Thr Leu Ile Lys Arg Leu Asn Lys
             100                 105                 110

Gly Glu Ala Pro Asn Thr Val Ile Ser Gln Glu Leu Pro Lys Trp Val
         115                 120                 125

Tyr Ala Gly Gly Lys Lys Leu Asn Gly Leu Val Arg Arg Lys Ala
     130                 135                 140

Glu Val Ala Leu Ala Lys Lys Ala Thr Thr Glu Lys Ala Leu Pro Lys
145                 150                 155                 160

Ser Cys

<210> SEQ ID NO 69
<211> LENGTH: 162
<212> TYPE: PRT
<213> ORGANISM: Nectria haematococca

<400> SEQUENCE: 69

Pro Pro Val Asn Gln Ala Thr Leu Ser Leu Val Glu Glu Phe Glu Gly
 1               5                  10                  15

Phe Arg Ala Asp Val Tyr Ile Asp Ala Thr Gly Asn Pro Thr Val Gly
             20                  25                  30

Tyr Gly His Leu Cys Lys Gln Ser Gly Cys Ser Glu Ile Pro Tyr Pro
         35                  40                  45

Ile Pro Leu Ser Gln Ala Asp Gly Gln Lys Leu Leu Gln Asp Asp Ile
     50                  55                  60

Lys Val Ala Gln Gln Cys Ile Thr Leu Asp Thr Thr Ser Ala Val Val
 65                  70                  75                  80

Leu Asn Ala Asn Gln Tyr Gly Ala Leu Val Ser Trp Ala Phe Asn Val
                 85                  90                  95

Gly Cys Gly Ala Ser Gly Asp Ser Thr Leu Ile Arg Arg Leu Asn Asn
             100                 105                 110

Gly Glu Asp Ala Asn Thr Val Ala Ser Glu Glu Leu Pro Lys Trp Asn
         115                 120                 125

Lys Gly Asn Gly Gln Pro Ile Ala Gly Leu Thr Arg Arg Arg Ala Ala
     130                 135                 140

Glu Val Glu Leu Phe Lys Ala Pro Thr Asp Val Gly Ala Leu Pro Val
145                 150                 155                 160

Gly Cys

<210> SEQ ID NO 70
<211> LENGTH: 162
<212> TYPE: PRT
<213> ORGANISM: Nectria haematococca

<400> SEQUENCE: 70

Pro Ser Ser Asn Gln Ala Thr Val Asp Leu Ile Gly Glu Phe Glu Gly
 1               5                  10                  15

Phe Val Pro His Ile Tyr Lys Asp Ala Ala Gly Tyr Pro Thr Val Gly
             20                  25                  30

Tyr Gly His Leu Cys Ser Asn Ser Lys Cys Thr Asp Val Lys Tyr Pro
         35                  40                  45
```

```
Ile Pro Leu Ser Lys Thr Asn Gly Lys Lys Leu Leu Ala Asp Asp Met
 50                  55                  60

Arg Lys Phe Glu Lys Cys Ile Ala Lys Met Val Ser Ser Lys Val Thr
 65                  70                  75                  80

Leu Asn Lys Asn Glu Phe Gly Ala Leu Val Ser Trp Ser Phe Asn Val
                 85                  90                  95

Gly Cys Gly Ala Ala Glu Gly Ser Gln Leu Ile Lys Arg Leu Asn Lys
                100                 105                 110

Gly Glu Lys Pro Asn Thr Val Ile Ser Gly Leu Pro Lys Trp Val
            115                 120                 125

Tyr Ala Gly Lys Arg Lys Leu Pro Gly Leu Val Arg Arg Asn Ala
130                 135                 140

Glu Ile Ala Leu Ala Lys Lys Ala Thr Ser Glu Lys Ala Leu Pro Val
145                 150                 155                 160

Lys Cys

<210> SEQ ID NO 71
<211> LENGTH: 155
<212> TYPE: PRT
<213> ORGANISM: Verticillium alfalfae

<400> SEQUENCE: 71

Pro Asn Val Asn Ala Thr Ile Ser Leu Ile Thr Glu Phe Glu Gly
 1               5                  10                  15

Trp Tyr Pro Asn Ile Tyr Ile Asp Pro Val Gly Leu Pro Thr Val Gly
                 20                  25                  30

Tyr Gly His Leu Cys Ala Asp Ser Ser Cys Ser Asp Val Arg Tyr Pro
             35                  40                  45

Ile Pro Leu Ser Arg Ala Asn Gly Glu Gln Leu Leu Arg Asp Asp Ile
 50                  55                  60

Ala Gly Phe Gln Asn Cys Ile Thr Leu Gln Thr Ala Ser Ser Val Val
 65                  70                  75                  80

Leu Asn Ala Asn Gln Tyr Gly Ala Leu Val Ser Trp Ala Phe Asn Val
                 85                  90                  95

Gly Cys Gly Ala Thr Lys Thr Ser Thr Leu Ile Gln Arg Leu Asn Ala
                100                 105                 110

Gly Gly Asn Pro Asn Thr Val Ala Ala Glu Leu Pro Lys Trp Asn
            115                 120                 125

Arg Gly Gly Gly Gln Val Leu Pro Gly Leu Thr Arg Arg Ala Ala
130                 135                 140

Glu Val Ala Leu His Arg Thr Ala Thr Ser Ala
145                 150                 155

<210> SEQ ID NO 72
<211> LENGTH: 162
<212> TYPE: PRT
<213> ORGANISM: Thielavia terrestris

<400> SEQUENCE: 72

Pro Lys Ser Asn Gln Ala Thr Val Asn Leu Ile Ala Glu Tyr Glu Gly
 1               5                  10                  15

Phe Val Asp His Val Tyr Thr Asp Ala Thr Gly His Pro Thr Val Gly
                 20                  25                  30

Tyr Gly His Leu Cys Ser Asn Ser Lys Cys Ser Asp Val Pro Tyr His
             35                  40                  45

Ile Pro Leu Ser Gln Ala Asp Gly Lys Lys Leu Leu Ala Asp Asp Met
```

```
                    50                  55                  60

Lys Lys Tyr Glu Lys Cys Ile Thr Ala Met Leu Thr Ser Lys Ala Val
65                  70                  75                  80

Val Asn Leu Asn Gln Tyr Gly Ala Leu Val Ser Trp Ala Phe Asn Met
                85                  90                  95

Gly Cys Gly Ala Ala Glu Ser Ser Thr Leu Val Lys Arg Leu Asn Ala
            100                 105                 110

Gly Glu Asn Val Asn Thr Val Leu Ser Gln Glu Leu Pro Lys Trp Val
        115                 120                 125

His Gly Asp Gly Lys Val Leu Pro Gly Leu Val Arg Arg Asn Ala
    130                 135                 140

Glu Ile Ala Leu Ala Lys Thr Pro Thr Ser Asp Lys Ala Leu Pro Val
145                 150                 155                 160

Lys Cys

<210> SEQ ID NO 73
<211> LENGTH: 162
<212> TYPE: PRT
<213> ORGANISM: Thielavia heterothallica

<400> SEQUENCE: 73

Pro Lys Ser Asn Ser Ala Thr Val Asp Leu Ile Ala Lys Ser Glu Gly
1               5                   10                  15

Phe Arg Ser Lys Ile Tyr Thr Asp Ala Thr Gly His Ala Thr Val Gly
                20                  25                  30

Tyr Gly His Met Cys Thr Lys Pro Lys Cys Ala Glu Val Lys Tyr Lys
            35                  40                  45

Ile Pro Leu Ser Thr Ala Asp Gly Lys Lys Leu Leu Ala Glu Asp Met
        50                  55                  60

Arg Lys Phe Glu Lys Cys Ile Thr Asn Met Leu Asn Ser Lys Ala Val
65                  70                  75                  80

Leu Asn Tyr Asn Gln Phe Gly Ala Leu Val Ser Trp Ser Phe Asn Val
                85                  90                  95

Gly Cys Gly Ala Ala Gln Ser Ser Gln Leu Val Lys Arg Leu Asn Lys
            100                 105                 110

Gly Glu Asn Val Asn Lys Val Leu Ser Glu Glu Leu Pro Lys Trp Val
        115                 120                 125

His Gly Gly Gly Lys Val Leu Pro Gly Leu Val Thr Arg Arg Lys Asn
    130                 135                 140

Glu Val Ala Leu Ala Lys Lys Pro Gly Ser Ser Lys Ala Leu Pro Val
145                 150                 155                 160

Lys Cys

<210> SEQ ID NO 74
<211> LENGTH: 162
<212> TYPE: PRT
<213> ORGANISM: Coprinopsis cinerea

<400> SEQUENCE: 74

Pro Asn Val Asn Thr Arg Thr Leu Asp Leu Ile Lys Leu Ser Glu Gly
1               5                   10                  15

Phe Val Ala Ser Pro Glu Pro Asp Pro Ile Gly Leu Pro Thr Val Gly
                20                  25                  30

Tyr Gly His Leu Cys Gln Arg Thr Gly Cys Thr Glu Val Pro Tyr Ser
            35                  40                  45
```

```
Phe Pro Leu Thr Gln Ala Gln Ala His Ala Leu Leu Ile Ser Asp Leu
        50                  55                  60

Arg Thr Tyr Gln Asn Cys Ile Ala Arg Asp Ile Val Asp Ser Val Arg
 65                  70                  75                  80

Leu Asn Asp Asn Gln Tyr Gly Ala Leu Val Ser Trp Ala Phe Asn Val
                85                  90                  95

Gly Cys Thr Asn Thr Ala Ser Ser Thr Leu Ile Arg Arg Leu Asn Ala
                100                 105                 110

Gly Glu Asn Pro Asn Thr Val Ala Glu Gln Leu Pro Arg Trp Asn
                115                 120                 125

Met Ala Gly Gly Gln Val Leu Pro Gly Leu Val Thr Arg Arg Ala Arg
130                 135                 140

Glu Val Thr Leu Phe Lys Thr Ala Ser Ser Val Ile Ala His Pro Pro
145                 150                 155                 160

Pro Cys

<210> SEQ ID NO 75
<211> LENGTH: 162
<212> TYPE: PRT
<213> ORGANISM: Fusarium oxysporum

<400> SEQUENCE: 75

Pro Ser Ser Asn Gln Ala Thr Val Asp Leu Ile Gly Glu Phe Glu Gly
1               5                   10                  15

Phe Val Pro His Ile Tyr Lys Asp Ala Ala Gly Tyr Pro Thr Val Gly
                20                  25                  30

Tyr Gly His Leu Cys Ser Asn Ser Lys Cys Thr Asp Val Lys Tyr Ala
                35                  40                  45

Ile Pro Leu Ser Lys Ala Asn Gly Lys Lys Leu Leu Ala Asp Asp Met
        50                  55                  60

Arg Lys Phe Glu Lys Cys Ile Ala Lys Met Val Ser Ser Lys Val Thr
 65                  70                  75                  80

Leu Asn Lys Asn Gln Phe Gly Ala Leu Val Ser Trp Ser Phe Asn Leu
                85                  90                  95

Gly Cys Gly Ala Ala Glu Gly Ser Gln Leu Leu Lys Arg Leu Asn Lys
                100                 105                 110

Gly Glu Lys Pro Asn Thr Val Ile Ser Gln Glu Leu Pro Lys Trp Val
                115                 120                 125

Tyr Ala Gly Gly Arg Lys Leu Pro Gly Leu Val Arg Arg Arg Asn Ala
130                 135                 140

Glu Val Ala Leu Ala Lys Lys Ala Thr Ser Glu Lys Ala Leu Pro Val
145                 150                 155                 160

Lys Cys

<210> SEQ ID NO 76
<211> LENGTH: 162
<212> TYPE: PRT
<213> ORGANISM: Metarhizium acridum

<400> SEQUENCE: 76

Pro Lys Ala Asn Glu Asp Thr Val Lys Phe Ile Ser Gly Phe Glu Gly
1               5                   10                  15

Trp Ser Asp His Val Tyr Arg Asp Pro Gly Pro Gln His Leu Glu Thr
                20                  25                  30

Leu Gly Tyr Gly His Leu Cys Lys Lys Pro Asn Cys Ala Glu Val Lys
                35                  40                  45
```

-continued

```
Tyr Pro Phe Pro Pro Leu Ser Lys Ala Asp Gly Leu Lys Leu Leu Ser
         50                  55                  60

Asp Asp Met Ser Val Ala Glu Asn Cys Ile Tyr Lys Asp Val Asn Pro
 65                  70                  75                  80

Lys Val Ala Leu Asn Ala Asn Gln Tyr Gly Ala Leu Val Ser Trp Ala
                 85                  90                  95

Phe Asn Val Gly Cys Gly Asn Val Ala Ser Ser Arg Leu Ile Arg Arg
                100                 105                 110

Leu Asn Ala Gly Glu Asp Pro Asn Thr Val Ala Ala Gln Glu Leu Pro
            115                 120                 125

Gln Trp Asn Lys Ala Gly Gly Lys Val Leu Pro Gly Leu Thr Arg Arg
    130                 135                 140

Arg Asn Ala Glu Val Glu Leu Phe Lys Thr Pro Thr Asn Asp Pro Ala
145                 150                 155                 160

Leu Pro

<210> SEQ ID NO 77
<211> LENGTH: 162
<212> TYPE: PRT
<213> ORGANISM: Metarhizium robertsii

<400> SEQUENCE: 77

Pro Lys Ala Asn Glu Ala Thr Val Lys Phe Ile Ser Thr Phe Glu Gly
 1               5                  10                  15

Trp Tyr Asp His Val Tyr Pro Asp Pro Gly Pro Gln His Leu Glu Thr
                20                  25                  30

Leu Gly Tyr Gly His Leu Cys Lys Lys Pro Asn Cys Ala Glu Val Lys
            35                  40                  45

Tyr Pro Phe Pro Pro Leu Ser Lys Ala Asp Gly Leu Lys Leu Leu Ser
         50                  55                  60

Asp Asp Met Ser Val Ala Glu Asn Cys Ile Tyr Gln Asp Thr Ser Ala
 65                  70                  75                  80

Lys Val Thr Leu Asn Ala Asn Gln Tyr Gly Ala Leu Val Ser Trp Ala
                 85                  90                  95

Phe Asn Val Gly Cys Gly Asn Val Ala Ser Ser Arg Leu Ile Arg Arg
                100                 105                 110

Leu Asn Ala Gly Glu Asp Pro Asn Thr Val Ala Ala Gln Glu Leu Pro
            115                 120                 125

Gln Trp Asn Arg Ala Gly Gly Lys Val Leu Pro Gly Leu Thr Arg Arg
    130                 135                 140

Arg Asn Ala Glu Val Glu Leu Phe Lys Thr Pro Thr Asn Asp Pro Ala
145                 150                 155                 160

Leu Pro

<210> SEQ ID NO 78
<211> LENGTH: 162
<212> TYPE: PRT
<213> ORGANISM: Fusarium oxysporum

<400> SEQUENCE: 78

Pro Ser Ser Asn Gln Ala Thr Val Asp Leu Ile Gly Glu Phe Glu Gly
 1               5                  10                  15

Phe Val Pro His Ile Tyr Lys Asp Ala Ala Gly Tyr Pro Thr Val Gly
                20                  25                  30

Tyr Gly His Leu Cys Ser Asn Ser Lys Cys Thr Asp Val Lys Tyr Pro
```

-continued

```
                35                  40                  45

Ile Pro Leu Ser Lys Ala Asn Gly Lys Lys Leu Leu Ala Asp Asp Met
 50                  55                  60

Arg Lys Phe Glu Lys Cys Ile Ala Lys Met Val Ser Ser Lys Val Thr
 65                  70                  75                  80

Leu Asn Lys Asn Gln Phe Gly Ala Leu Val Ser Trp Ser Phe Asn Leu
                 85                  90                  95

Gly Cys Gly Ala Ala Glu Gly Ser Gln Leu Leu Lys Arg Leu Asn Lys
                100                 105                 110

Gly Glu Lys Pro Asn Thr Val Ile Ser Gln Glu Leu Pro Lys Trp Val
                115                 120                 125

Tyr Ala Gly Gly Arg Lys Leu Pro Gly Leu Val Arg Arg Arg Asn Ala
                130                 135                 140

Glu Val Ala Leu Ala Lys Lys Ala Thr Ser Glu Lys Ala Leu Pro Val
145                 150                 155                 160

Lys Cys
```

<210> SEQ ID NO 79
<211> LENGTH: 161
<212> TYPE: PRT
<213> ORGANISM: Fusarium oxysporum

<400> SEQUENCE: 79

```
Pro Lys Ser Asn Ala Ala Thr Val Lys Leu Ile Ser Ser Phe Glu Gly
 1                   5                  10                  15

Phe Arg Pro Asp Val Tyr Asn Asp Pro Thr Gly Asn Pro Thr Val Gly
                 20                  25                  30

Tyr Gly His Leu Cys Asp Ala Pro Gln Cys Ser Glu Val Lys Tyr Pro
                 35                  40                  45

Val Pro Leu Ser Val Ala Asn Gly Lys Lys Leu Leu Ala Asp Asp Met
 50                  55                  60

Lys Glu Phe Glu Val Cys Ile Thr Ala Met Leu Asn Ser Lys Ala Arg
 65                  70                  75                  80

Leu Asn Arg Asn Gln Tyr Gly Ala Leu Ile Ser Trp Ala Phe Asn Met
                 85                  90                  95

Gly Cys Gly Asn Ala Glu Ser Thr Leu Val Gly Arg Leu Asn Asn Gly
                100                 105                 110

Glu Asp Pro Asn Thr Val Ile Ser Gln Glu Leu Pro Gln Trp Val Tyr
                115                 120                 125

Ala Ser Gly Gln Arg Leu Pro Gly Leu Val His Arg Arg Asn Ala Glu
                130                 135                 140

Ile Glu Leu Ala Gln Lys Pro Thr Arg Arg Ser Ala Leu Pro Lys Arg
145                 150                 155                 160

Cys
```

<210> SEQ ID NO 80
<211> LENGTH: 162
<212> TYPE: PRT
<213> ORGANISM: Chaetomium thermophilum

<400> SEQUENCE: 80

```
Pro Lys Ser Asn Gln Ala Thr Val Asp Leu Ile Ala Glu Phe Glu Gly
 1                   5                  10                  15

Phe Arg Ala Asn Ile Tyr Thr Asp Ala Ala Gly Tyr Ala Thr Val Gly
                 20                  25                  30
```

```
Tyr Gly His Lys Cys Gln Lys Ala Lys Cys Ala Glu Val Lys Tyr Lys
             35                  40                  45

Ile Pro Leu Ser Lys Ala Asp Gly Lys Lys Leu Leu Ala Asp Asp Met
 50                  55                  60

Arg Ser Phe Glu Val Cys Ile Thr Asn Met Leu Asn Ser Lys Ala Lys
 65                  70                  75                  80

Leu Asn Tyr Asn Gln Phe Gly Ala Leu Val Ser Trp Ser Phe Asn Val
             85                  90                  95

Gly Cys Gly Ala Ala Lys Ser Ser Thr Leu Ile Lys Arg Leu Asn Asn
            100                 105                 110

Gly Glu Asn Val Asn Lys Val Leu Ser Glu Leu Pro Lys Trp Asn
            115                 120                 125

Lys Ala Gly Gly Lys Val Leu Gln Gly Leu Val Arg Arg Ala Ala
130                 135                 140

Glu Val Ala Leu Ala Lys Lys Ser Gly Ser Ser Gln Ala Leu Pro Val
145                 150                 155                 160

Lys Cys

<210> SEQ ID NO 81
<211> LENGTH: 154
<212> TYPE: PRT
<213> ORGANISM: Verticillium dahliae

<400> SEQUENCE: 81

Pro Asn Val Asn Ala Ala Thr Ile Ser Leu Ile Thr Glu Phe Glu Gly
 1               5                  10                  15

Trp Tyr Pro Asn Ile Tyr Ile Asp Pro Val Gly Leu Pro Thr Val Gly
             20                  25                  30

Tyr Gly His Leu Cys Ala Asp Ser Ser Cys Ser Asp Val Arg Tyr Pro
             35                  40                  45

Ile Pro Leu Ser Arg Ala Asn Gly Glu Gln Leu Leu Arg Asp Asp Ile
 50                  55                  60

Ala Gly Phe Gln Asn Cys Ile Thr Leu Gln Thr Ala Ser Ser Val Val
 65                  70                  75                  80

Leu Asn Ala Asn Gln Tyr Gly Ala Leu Val Ser Trp Ala Phe Asn Val
             85                  90                  95

Gly Cys Gly Ala Thr Arg Thr Ser Thr Leu Ile Gln Arg Leu Asn Ala
            100                 105                 110

Gly Gly Asp Pro Asn Thr Val Ala Ala Glu Leu Pro Lys Trp Asn
            115                 120                 125

Arg Gly Gly Gly Gln Val Leu Pro Gly Leu Thr Arg Arg Arg Ala Ala
130                 135                 140

Glu Val Ala Leu His Arg Thr Ala Thr Ser
145                 150

<210> SEQ ID NO 82
<211> LENGTH: 162
<212> TYPE: PRT
<213> ORGANISM: Fusarium oxysporum

<400> SEQUENCE: 82

Pro Ser Ser Asn Gln Ala Thr Val Asp Leu Ile Gly Glu Phe Glu Gly
 1               5                  10                  15

Phe Val Pro His Ile Tyr Lys Asp Ala Ala Gly Tyr Pro Thr Val Gly
             20                  25                  30

Tyr Gly His Leu Cys Ser Asn Ser Lys Cys Thr Asp Val Lys Tyr Pro
```

```
            35                  40                  45
Ile Pro Leu Ser Lys Ala Asn Gly Lys Lys Leu Leu Ala Asp Asp Met
 50                  55                  60
Arg Lys Phe Glu Lys Cys Ile Ala Lys Met Ile Ser Ser Lys Val Thr
 65                  70                  75                  80
Leu Asn Lys Asn Gln Phe Gly Ala Leu Val Ser Trp Ser Phe Asn Leu
                 85                  90                  95
Gly Cys Gly Ala Ala Glu Gly Ser Gln Leu Leu Lys Arg Leu Asn Lys
                100                 105                 110
Gly Glu Lys Pro Asn Thr Val Ile Ser Gln Glu Leu Pro Lys Trp Val
                115                 120                 125
Tyr Ala Gly Gly Arg Lys Leu Pro Gly Leu Val Arg Arg Asn Ala
            130                 135                 140
Glu Val Ala Leu Ala Lys Lys Ala Thr Ser Glu Lys Ala Leu Pro Val
145                 150                 155                 160
Lys Cys

<210> SEQ ID NO 83
<211> LENGTH: 162
<212> TYPE: PRT
<213> ORGANISM: Fusarium oxysporum

<400> SEQUENCE: 83

Pro Ser Ser Asn Lys Ala Thr Val Asp Leu Ile Gly Glu Phe Glu Gly
 1                   5                  10                  15
Phe Val Pro His Ile Tyr Lys Asp Ala Ala Gly Tyr Pro Thr Val Gly
                 20                  25                  30
Tyr Gly His Leu Cys Ser Asn Ser Lys Cys Thr Asp Val Lys Tyr Ala
            35                  40                  45
Ile Pro Leu Ser Lys Ala Asn Gly Lys Lys Leu Leu Ala Asp Asp Met
 50                  55                  60
Arg Lys Phe Glu Lys Cys Ile Ala Lys Met Val Ser Ser Lys Val Thr
 65                  70                  75                  80
Leu Asn Lys Asn Gln Phe Gly Ala Leu Val Ser Trp Ser Phe Asn Leu
                 85                  90                  95
Gly Cys Gly Ala Ala Glu Gly Ser Gln Leu Leu Lys Arg Leu Asn Lys
                100                 105                 110
Gly Glu Lys Pro Asn Thr Val Ile Ser Gln Glu Leu Pro Lys Trp Val
                115                 120                 125
Tyr Ala Gly Gly Arg Lys Leu Pro Gly Leu Val Arg Arg Asn Ala
            130                 135                 140
Glu Val Ala Leu Ala Lys Lys Ala Thr Ser Glu Lys Ala Leu Pro Val
145                 150                 155                 160
Lys Cys

<210> SEQ ID NO 84
<211> LENGTH: 162
<212> TYPE: PRT
<213> ORGANISM: Fusarium oxysporum

<400> SEQUENCE: 84

Pro Lys Ser Asn Ala Ala Thr Val Asn Leu Ile Ala Ser Phe Lys Gly
 1                   5                  10                  15
Phe Arg Pro Asp Val Tyr Asn Asp Pro Thr Gly Asn Pro Thr Val Gly
                 20                  25                  30
```

```
Tyr Gly His Leu Cys Asp Ala Pro Gln Cys Ser Glu Ala Lys Tyr Pro
            35                  40                  45

Ile Pro Leu Ser Ile Val Asn Gly Lys Lys Leu Leu Ala Asp Gly Met
 50                  55                  60

Lys Glu Phe Glu Ile Cys Ile Thr Ala Met Leu Asn Ser Lys Ala Asn
 65                  70                  75                  80

Leu Asn Arg Asn Gln Tyr Gly Ala Leu Ile Ser Trp Ala Phe Asn Met
                85                  90                  95

Gly Cys Gly Asn Ala Asp Ser Ser Thr Leu Val Gly Arg Leu Asn Asn
                100                 105                 110

Gly Glu Asp Pro Asn Thr Val Ile Ser Gln Glu Leu Pro Gln Trp Val
            115                 120                 125

Asn Val Ser Gly Gln Arg Leu Pro Gly Leu Val Arg Arg Asn Ala
130                 135                 140

Glu Ile Glu Leu Ala Gln Lys Pro Thr Arg Arg Ala Leu Pro Lys
145                 150                 155                 160

Arg Cys
```

<210> SEQ ID NO 85
<211> LENGTH: 162
<212> TYPE: PRT
<213> ORGANISM: Fusarium oxysporum

<400> SEQUENCE: 85

```
Pro Ser Ser Asn Gln Ala Thr Val Asp Leu Ile Gly Glu Phe Glu Gly
 1               5                  10                  15

Phe Val Pro His Ile Tyr Lys Asp Ala Ala Gly Tyr Pro Thr Val Gly
            20                  25                  30

Tyr Gly His Leu Cys Ser Asn Ser Lys Cys Thr Asp Val Lys Tyr Ala
            35                  40                  45

Ile Pro Leu Ser Lys Ala Asn Gly Lys Lys Leu Leu Ala Asp Asp Met
 50                  55                  60

Arg Lys Phe Glu Lys Cys Ile Ala Lys Met Val Ser Ser Lys Val Thr
 65                  70                  75                  80

Leu Asn Lys Asn Gln Phe Gly Ala Leu Val Ser Trp Ser Phe Asn Leu
                85                  90                  95

Gly Cys Gly Ala Ala Glu Gly Ser Gln Leu Leu Lys Arg Leu Asn Lys
                100                 105                 110

Gly Glu Lys Pro Asn Thr Val Ile Ser Gln Glu Leu Pro Lys Trp Val
            115                 120                 125

Tyr Ala Gly Gly Arg Lys Leu Pro Gly Leu Val Arg Arg Asn Ala
130                 135                 140

Glu Val Ala Leu Ala Lys Lys Thr Ser Glu Lys Ala Leu Pro Val
145                 150                 155                 160

Lys Cys
```

<210> SEQ ID NO 86
<211> LENGTH: 162
<212> TYPE: PRT
<213> ORGANISM: Fusarium oxysporum

<400> SEQUENCE: 86

```
Pro Lys Ser Asn Ala Ala Thr Val Asn Leu Ile Ala Ser Phe Glu Gly
 1               5                  10                  15

Phe Arg Pro Asp Val Tyr Asn Asp Pro Thr Gly Asn Pro Thr Val Gly
            20                  25                  30
```

```
Tyr Gly His Leu Cys Asp Ala Pro Gln Cys Ser Glu Val Lys Tyr Pro
            35                  40                  45

Val Pro Leu Ser Val Ala Asn Gly Lys Lys Leu Leu Ala Asp Asp Met
 50                  55                  60

Lys Glu Phe Glu Val Cys Ile Thr Ala Met Leu Asn Ser Lys Ala Arg
 65                  70                  75                  80

Leu Asn Arg Asn Gln Tyr Gly Ala Leu Ile Ser Trp Ala Phe Asn Met
                 85                  90                  95

Gly Cys Gly Asn Ala Glu Ser Ser Ile Leu Val Gly Arg Leu Asn Asn
                100                 105                 110

Gly Glu Asp Pro Asn Ser Val Ile Ser Gln Leu Pro Gln Trp Val
                115                 120                 125

Tyr Ala Ser Gly Gln Arg Leu Pro Gly Leu Val Leu Arg Arg Asn Ala
                130                 135                 140

Glu Ile Glu Leu Ala Gln Lys Pro Thr Arg Arg Ala Leu Pro Lys
145                 150                 155                 160

Arg Cys
```

<210> SEQ ID NO 87
<211> LENGTH: 162
<212> TYPE: PRT
<213> ORGANISM: Fusarium oxysporum

<400> SEQUENCE: 87

```
Pro Ser Ser Asn Gln Ala Thr Val Asp Leu Ile Gly Glu Phe Glu Gly
 1               5                  10                  15

Phe Val Pro His Ile Tyr Lys Asp Ala Ala Gly Tyr Pro Thr Val Gly
                 20                  25                  30

Tyr Gly His Leu Cys Ser Asn Ser Lys Cys Thr Asp Val Lys Tyr Ala
            35                  40                  45

Ile Pro Leu Ser Lys Ala Asn Gly Lys Lys Leu Leu Ala Asp Asp Met
 50                  55                  60

Arg Lys Phe Glu Lys Cys Ile Ala Lys Met Val Ser Ser Lys Val Thr
 65                  70                  75                  80

Leu Asn Lys Asn Gln Phe Gly Ala Leu Val Ser Trp Ser Phe Asn Leu
                 85                  90                  95

Gly Cys Gly Ala Ala Glu Gly Ser Gln Leu Leu Lys Arg Leu Asn Lys
                100                 105                 110

Gly Glu Lys Pro Asn Thr Val Ile Ser Gln Glu Leu Pro Lys Trp Val
                115                 120                 125

Tyr Ala Gly Gly Arg Lys Leu Pro Gly Leu Val Arg Arg Arg Asn Ala
                130                 135                 140

Glu Val Ala Leu Ala Lys Lys Ala Thr Ser Glu Lys Ala Leu Pro Val
145                 150                 155                 160

Lys Cys
```

<210> SEQ ID NO 88
<211> LENGTH: 162
<212> TYPE: PRT
<213> ORGANISM: Fusarium oxysporum

<400> SEQUENCE: 88

```
Pro Ser Ser Asn Gln Ala Thr Val Asp Leu Ile Gly Glu Phe Glu Gly
 1               5                  10                  15

Phe Val Pro His Ile Tyr Lys Asp Ala Ala Gly Tyr Pro Thr Val Gly
```

```
              20                  25                  30

Tyr Gly His Leu Cys Ser Asn Ser Lys Cys Thr Asp Val Lys Tyr Ala
             35                  40                  45

Ile Pro Leu Ser Lys Ala Asn Gly Lys Lys Leu Leu Ala Asp Asp Met
 50                  55                  60

Arg Lys Phe Glu Lys Cys Ile Ala Gln Met Val Ser Ser Lys Val Thr
 65                  70                  75                  80

Leu Asn Lys Asn Gln Phe Gly Ala Leu Val Ser Trp Ser Phe Asn Leu
                 85                  90                  95

Gly Cys Gly Ala Ala Glu Gly Ser Gln Leu Leu Lys Arg Leu Asn Lys
                100                 105                 110

Gly Glu Lys Pro Asn Thr Val Ile Ser Gln Glu Leu Pro Lys Trp Val
                115                 120                 125

Tyr Ala Gly Gly Arg Lys Leu Pro Gly Leu Val Arg Arg Asn Ala
                130                 135                 140

Glu Val Ala Leu Ala Lys Lys Ala Thr Ser Glu Lys Ala Leu Pro Val
145                 150                 155                 160

Lys Cys

<210> SEQ ID NO 89
<211> LENGTH: 126
<212> TYPE: PRT
<213> ORGANISM: Fusarium oxysporum

<400> SEQUENCE: 89

Pro Lys Ser Asn Ala Ala Thr Ile Asn Leu Ile Ala Ser Phe Glu Gly
 1               5                  10                  15

Phe Arg Pro Asp Val Tyr Asn Asp Pro Thr Gly Asn Pro Thr Val Gly
                 20                  25                  30

Tyr Gly His Leu Cys Asp Ala Pro Gln Cys Ser Glu Val Lys Tyr Pro
             35                  40                  45

Ile Pro Leu Ser Ile Val Asn Gly Lys Lys Leu Leu Ala Asp Gly Met
 50                  55                  60

Lys Glu Phe Glu Ile Cys Ile Thr Ala Met Leu Asn Ser Lys Ala Asn
65                  70                  75                  80

Leu Asn Arg Asn Gln Tyr Gly Ala Leu Ile Ser Trp Ala Phe Asn Met
                 85                  90                  95

Gly Cys Gly Asn Ala Asp Ser Ser Thr Leu Val Gly Arg Leu Asn Asn
                100                 105                 110

Gly Glu Asp Pro Asn Ile Val Ile Ser Gln Glu Leu Pro Gln
                115                 120                 125

<210> SEQ ID NO 90
<211> LENGTH: 162
<212> TYPE: PRT
<213> ORGANISM: Gibberella moniliformis

<400> SEQUENCE: 90

Pro Lys Ser Asn Ala Ala Thr Val Asn Leu Ile Ala Ser Phe Glu Gly
 1               5                  10                  15

Phe Arg Pro Asp Val Tyr Asn Asp Pro Thr Gly Asn Pro Thr Val Gly
                 20                  25                  30

Tyr Gly His Leu Cys Asp Ala Pro Gln Cys Ser Glu Val Lys Tyr Pro
             35                  40                  45

Ile Pro Leu Ser Val Val Asn Gly Lys Lys Leu Leu Ala Asp Asp Met
 50                  55                  60
```

Lys Glu Phe Glu Val Cys Ile Thr Ala Met Leu Asn Ser Lys Ala Lys
65                  70                  75                  80

Leu Asn Arg Asn Gln Tyr Gly Ala Leu Ile Ser Trp Ala Phe Asn Met
            85                  90                  95

Gly Cys Gly Asn Ala Glu Ser Thr Leu Ile Gly Arg Leu Asn Asn
            100                 105                 110

Cys Glu Asp Pro Asn Thr Val Ile Ser Gln Glu Leu Pro Gln Trp Glu
            115                 120                 125

Tyr Ala Ser Gly Gln Arg Leu Pro Gly Leu Leu Arg Arg Asn Ala
        130                 135                 140

Glu Ile Glu Leu Ala Gln Lys Pro Thr Arg Arg Arg Ala Leu Pro Lys
145                 150                 155                 160

Arg Cys

<210> SEQ ID NO 91
<211> LENGTH: 162
<212> TYPE: PRT
<213> ORGANISM: Fusarium oxysporum

<400> SEQUENCE: 91

Pro Ser Ser Asn Gln Ala Thr Val Asp Leu Ile Gly Glu Phe Glu Gly
1               5                   10                  15

Phe Val Pro His Ile Tyr Lys Asp Ala Ala Gly Tyr Pro Thr Val Gly
                20                  25                  30

Tyr Gly His Leu Cys Ser Asn Ser Lys Cys Thr Asp Val Lys Tyr Pro
            35                  40                  45

Ile Pro Leu Ser Lys Ala Asn Gly Lys Lys Leu Leu Ala Asp Asp Met
50                  55                  60

Arg Lys Phe Glu Lys Cys Ile Ala Lys Met Val Ser Ser Lys Val Thr
65                  70                  75                  80

Leu Asn Lys Asn Gln Phe Gly Ala Leu Val Ser Trp Ser Phe Asn Leu
            85                  90                  95

Gly Cys Gly Ala Ala Glu Gly Ser Gln Leu Leu Lys Arg Leu Asn Lys
            100                 105                 110

Gly Glu Lys Pro Asn Thr Val Ile Ser Gln Glu Leu Pro Lys Trp Val
        115                 120                 125

Tyr Ala Gly Gly Arg Lys Leu Pro Gly Leu Val Arg Arg Arg Asn Ala
        130                 135                 140

Glu Val Ala Leu Ala Lys Lys Ala Thr Ser Glu Lys Ala Leu Pro Val
145                 150                 155                 160

Lys Cys

<210> SEQ ID NO 92
<211> LENGTH: 162
<212> TYPE: PRT
<213> ORGANISM: Fusarium oxysporum

<400> SEQUENCE: 92

Pro Lys Ser Asn Ala Ala Thr Val Asn Leu Ile Ala Ser Phe Glu Gly
1               5                   10                  15

Phe Arg Pro Asp Val Tyr Asn Asp Pro Thr Gly Asn Pro Thr Val Gly
                20                  25                  30

Tyr Gly His Gln Cys Asp Ala Pro Gln Cys Ser Glu Val Lys Tyr Pro
            35                  40                  45

Val Pro Leu Ser Val Ala Asn Gly Lys Lys Leu Leu Ala Asp Asp Met

```
            50                  55                  60
Lys Glu Phe Glu Val Cys Ile Thr Ala Met Leu Asn Ser Lys Ala Arg
 65                  70                  75                  80

Leu Asn Arg Asn Gln Tyr Gly Ala Leu Ile Ser Trp Ala Phe Asn Met
                 85                  90                  95

Gly Cys Gly Asn Gly Glu Ser Ser Thr Leu Val Gly Arg Leu Lys Asn
                100                 105                 110

Gly Glu Asp Pro Asn Thr Val Ile Ser Gln Glu Leu Pro Gln Trp Val
            115                 120                 125

Tyr Ala Ser Gly Gln Arg Leu Pro Gly Leu Val His Arg Arg Asn Ala
        130                 135                 140

Glu Ile Glu Leu Ala Gln Lys Pro Thr Arg Arg Ala Leu Pro Lys
145                 150                 155                 160

Arg Cys

<210> SEQ ID NO 93
<211> LENGTH: 161
<212> TYPE: PRT
<213> ORGANISM: Fusarium oxysporum

<400> SEQUENCE: 93

Pro Lys Ser Asn Ala Ala Thr Val Lys Leu Ile Ser Phe Glu Gly
 1               5                  10                  15

Phe Arg Pro Asp Val Tyr Asn Asp Pro Thr Gly Asn Pro Thr Val Gly
                 20                  25                  30

Tyr Gly His Leu Cys Asp Ala Pro Gln Cys Ser Glu Val Lys Tyr Pro
             35                  40                  45

Val Pro Leu Ser Val Ala Asn Gly Lys Lys Leu Leu Ala Asp Asp Met
 50                  55                  60

Lys Glu Phe Glu Val Cys Ile Thr Ala Met Leu Asn Ser Lys Ala Arg
 65                  70                  75                  80

Leu Asn Arg Asn Gln Tyr Gly Ala Leu Ile Ser Trp Ala Phe Asn Met
                 85                  90                  95

Gly Cys Gly Asn Ala Glu Ser Thr Leu Val Gly Arg Leu Asn Asn Gly
                100                 105                 110

Glu Asp Pro Asn Thr Val Ile Ser Gln Glu Leu Pro Gln Trp Val Tyr
            115                 120                 125

Ala Ser Gly Gln Arg Leu Pro Gly Leu Val His Arg Arg Asn Ala Glu
        130                 135                 140

Ile Glu Leu Ala Gln Lys Pro Thr Arg Arg Ser Ala Leu Pro Lys Arg
145                 150                 155                 160

Cys

<210> SEQ ID NO 94
<211> LENGTH: 139
<212> TYPE: PRT
<213> ORGANISM: Fusarium oxysporum

<400> SEQUENCE: 94

Pro Lys Ser Asn Val Ala Thr Ile Asn Leu Ile Ala Ser Phe Glu Gly
 1               5                  10                  15

Phe Arg Pro Asp Phe Tyr Asn Asp Pro Thr Gly Asn Pro Thr Val Gly
                 20                  25                  30

Tyr Gly His Leu Cys Asp Ala Pro Gln Cys Ser Glu Val Lys Tyr Pro
             35                  40                  45
```

```
Ile Pro Leu Ser Ile Val Asn Gly Lys Lys Leu Leu Ala Asp Gly Met
        50                  55                  60

Lys Glu Phe Glu Ile Cys Ile Thr Ala Met Leu Asn Ser Lys Ala Asn
 65                  70                  75                  80

Leu Asn Arg Asn Gln Tyr Gly Ala Leu Ile Ser Trp Ala Phe Asn Met
                85                  90                  95

Gly Cys Gly Asn Ala Asn Ser Ser Thr Leu Val Gly Arg Leu Asn Asn
            100                 105                 110

Glu Glu Asp Pro Asn Thr Val Ile Ser Gln Leu Pro Gln Trp Val
                115                 120                 125

Asn Val Ser Gly Gln Arg Leu Pro Gly Leu Val
        130                 135
```

<210> SEQ ID NO 95
<211> LENGTH: 162
<212> TYPE: PRT
<213> ORGANISM: Fusarium oxysporum

<400> SEQUENCE: 95

```
Pro Lys Ser Asn Ala Ala Thr Val Asn Leu Val Ala Ser Phe Glu Gly
 1               5                  10                  15

Phe Lys Pro Asp Val Tyr Asn Asp Pro Thr Gly Asn Pro Thr Val Gly
                20                  25                  30

Tyr Gly His Leu Cys Asp Ala Pro Gln Cys Ser Glu Val Arg Tyr Pro
            35                  40                  45

Val Pro Leu Ser Val Ala Asn Gly Lys Lys Leu Leu Ala Asp Asp Met
        50                  55                  60

Lys Gly Phe Ala Val Cys Ile Ser Ala Met Leu Asn Ser Lys Ala Arg
 65                  70                  75                  80

Leu Asn Arg Asn Gln Tyr Gly Ala Leu Ile Ser Trp Ala Phe Asn Met
                85                  90                  95

Gly Cys Gly Asn Ala Glu Ser Ser Thr Leu Ile Gly Arg Leu Asn Asn
            100                 105                 110

Trp Glu Asp Pro Asn Thr Val Ile Ser Gln Glu Leu Pro Arg Trp Val
                115                 120                 125

Tyr Ala Ser Gly Lys Arg Leu Pro Gly Leu Val Arg Arg Asn Ala
        130                 135                 140

Glu Ile Glu Leu Ala Gln Lys Pro Thr Arg Arg Ala Leu Pro Lys
145                 150                 155                 160

Arg Cys
```

<210> SEQ ID NO 96
<211> LENGTH: 162
<212> TYPE: PRT
<213> ORGANISM: Gibberella fujikuroi

<400> SEQUENCE: 96

```
Pro Lys Ser Asn Ala Ala Thr Val Asn Leu Ile Ala Ser Phe Glu Gly
 1               5                  10                  15

Phe Arg Pro Asp Val Tyr Ser Asp Pro Thr Gly Asn Pro Thr Val Gly
                20                  25                  30

Tyr Gly His Leu Cys Asp Ala Pro Gln Cys Ser Glu Val Lys Tyr Pro
            35                  40                  45

Ile Pro Leu Ser Val Ala Asn Gly Lys Lys Leu Leu Val Asp Asp Met
        50                  55                  60

Lys Asp Phe Glu Val Cys Leu Thr Ala Met Leu Asn Ser Lys Ala Lys
```

```
                65                  70                  75                  80
Leu Asn Arg Asn Gln Tyr Gly Ala Leu Ile Ser Trp Ala Phe Asn Met
                    85                  90                  95
Gly Cys Gly Asn Ala Gln Ser Ser Thr Leu Val Gly Arg Leu Asn Asn
                    100                 105                 110
Gly Glu Asp Pro Asn Thr Val Ile Ser Gln Glu Leu Pro His Trp Val
                    115                 120                 125
Tyr Ala Ser Gly Gln Arg Leu Pro Gly Leu Val Arg Arg Asn Ala
                130                 135                 140
Glu Ile Glu Leu Ala Gln Lys Pro Thr Arg Arg Ala Leu Pro Lys
145                 150                 155                 160
Arg Cys

<210> SEQ ID NO 97
<211> LENGTH: 145
<212> TYPE: PRT
<213> ORGANISM: Glarea lozoyensis

<400> SEQUENCE: 97

Pro Lys Val Asn Thr Ala Thr Leu Lys Leu Ile Glu Gly Phe Glu Gly
1               5                   10                  15
Trp Ser Ala Thr Ala Tyr Lys Asp Pro Asp Gly Asn Pro Thr Ile Gly
                20                  25                  30
Tyr Gly His Leu Cys Ser Ser Ala Ser Cys Lys Glu Ile Lys Tyr Ser
                35                  40                  45
Ile Pro Leu Ser Arg Ala Glu Gly Asp Ser Leu Ile Gln Asp Asp Leu
                50                  55                  60
Ala Val Ala Arg Lys Cys Ile Ala Lys Gln Ile Lys Asp Ser Ile Lys
65                  70                  75                  80
Leu Asn Ala Asn Gln Phe Gly Ala Leu Val Ser Trp Ala Phe Asn Val
                    85                  90                  95
Gly Cys Gly Asn Ser Gly Asp Ser Thr Leu Ile Arg Arg Leu Asn Ala
                    100                 105                 110
Gly Glu Ala Pro Asn Thr Val Ala Gly Gln Glu Leu Pro Lys Trp Asn
                    115                 120                 125
Arg Gly Lys Asn Gly Val Leu Pro Gly Leu Thr Arg Arg Asn Ala
                130                 135                 140
Glu
145

<210> SEQ ID NO 98
<211> LENGTH: 160
<212> TYPE: PRT
<213> ORGANISM: Coniosporium apollinis

<400> SEQUENCE: 98

Pro Asp Val Asn Ala Ala Thr Val Ala Leu Ile Lys Glu Phe Glu Gly
1               5                   10                  15
Phe Val Arg Ser Pro Ala Pro Asp Pro Ile Gly Leu Pro Thr Val Gly
                20                  25                  30
Phe Gly His Leu Cys Lys Thr Ala Gly Cys Ala Glu Val Pro Tyr Lys
                35                  40                  45
Phe Pro Leu Thr Glu Ala Gln Ala Ala Ala Leu Leu Gln Thr Asp Leu
                50                  55                  60
Lys Thr Tyr Glu Lys Cys Leu Ala Asp Lys Val Ala Asp Ser Val Arg
65                  70                  75                  80
```

```
Leu Asn Asp Asn Gln Tyr Gly Ala Leu Val Ser Trp Thr Phe Asn Val
                85                  90                  95

Gly Cys Gly Asn Met Gly Ser Ser Thr Leu Val Arg Arg Leu Asn Ala
           100                 105                 110

Gly Glu Ala Pro Asn Thr Val Ala Ala Gln Glu Leu Pro Lys Trp Asn
       115                 120                 125

Lys Ala Gly Gly Asn Val Leu Ala Gly Leu Thr Arg Arg Ala Ala
       130                 135                 140

Glu Val Arg Leu Phe Gln Thr Ala Ser Gly Thr Gln Ala Leu Pro Ser
145                 150                 155                 160

<210> SEQ ID NO 99
<211> LENGTH: 162
<212> TYPE: PRT
<213> ORGANISM: Endocarpon pusillum

<400> SEQUENCE: 99

Pro Asp Val Asn Ala Ala Thr Val Ala Leu Ile Lys Glu Phe Glu Gly
1               5                  10                  15

Phe Val Lys Ser Pro Ala Pro Asp Pro Ile Gly Leu Pro Thr Val Gly
            20                  25                  30

Tyr Gly His Leu Cys Lys Thr Asn Gly Cys Ser Glu Val Pro Tyr Pro
        35                  40                  45

Phe Pro Leu Ser Glu Ala Gln Ala Ala Ala Leu Leu Gln Thr Asp Leu
    50                  55                  60

Lys Ser Tyr Glu Lys Cys Leu Ala Asp Lys Val Ser Asp Ser Val Lys
65                  70                  75                  80

Leu Ser Asp Asn Gln Tyr Gly Ala Leu Val Ser Trp Thr Phe Asn Val
                85                  90                  95

Gly Cys Gly Asn Met Gly Gly Ser Thr Leu Val Thr Arg Leu Asn Asn
           100                 105                 110

Gly Glu Ser Pro Asn Thr Val Ala Ala Gln Glu Leu Pro Lys Trp Asn
       115                 120                 125

Lys Ala Gly Gly Ser Ala Leu Ala Gly Leu Thr Arg Arg Arg Ala Ala
       130                 135                 140

Glu Val Gln Leu Phe Gln Thr Ala Ser Gly Thr Gln Ala Leu Pro Ala
145                 150                 155                 160

Lys Cys

<210> SEQ ID NO 100
<211> LENGTH: 105
<212> TYPE: PRT
<213> ORGANISM: Fusarium oxysporum

<400> SEQUENCE: 100

Asp Pro Thr Gly Asn Pro Thr Val Gly Tyr Gly His Leu Cys Asp Ala
1               5                  10                  15

Ala Gln Cys Ser Glu Val Lys Tyr Pro Ile Pro Leu Ser Ile Val Asn
            20                  25                  30

Gly Lys Lys Leu Leu Ala Asp Gly Met Lys Glu Phe Glu Ile Cys Asn
        35                  40                  45

Pro Ala Met Leu Asn Ser Lys Ala Asn Leu Asn Arg Asn Gln Tyr Gly
    50                  55                  60

Ala Leu Ile Ser Trp Ala Phe Asn Met Gly Arg Gly Asn Ala Asp Ser
65                  70                  75                  80
```

```
Ser Thr Leu Val Gly Arg Leu Asn Asn Gly Glu Asp Pro Asn Thr Val
            85                  90                  95

Ile Ser Gln Glu Leu Pro Gln Trp Val
            100                 105

<210> SEQ ID NO 101
<211> LENGTH: 150
<212> TYPE: PRT
<213> ORGANISM: Stachybotrys chartarum

<400> SEQUENCE: 101

Pro Thr Thr Asn Ser Ala Thr Val Ser Leu Ile Gln Glu Phe Glu Gly
1               5                   10                  15

Trp Ser Pro Thr Ile Tyr Leu Asp Pro Ser Gly Tyr Pro Thr Val Gly
            20                  25                  30

Tyr Gly His Leu Cys Ala Asn Ser Arg Cys Thr Asp Val Pro Tyr Pro
            35                  40                  45

Ile Pro Leu Ser Thr Ala Asn Gly Asn Leu Leu Gln Ser Asp Met
    50                  55                  60

Leu Val Ala Arg Arg Cys Ile Ala Gln Asp Val Asn Val Arg Leu Asn
65                  70                  75                  80

Ala Asn Gln Tyr Gly Ala Leu Val Ser Trp Ala Phe Asn Val Gly Cys
                85                  90                  95

Gly Ala Ser Gly Ser Ser Thr Leu Val Arg Arg Leu Asn Ala Gly Glu
            100                 105                 110

Asn Pro Asn Thr Val Ala Ala Glu Glu Leu Pro Arg Trp Val Asn Ser
            115                 120                 125

Gly Gly Val Gln Leu Pro Gly Leu Val Arg Arg Asn Ala Glu Val
            130                 135                 140

Ala Leu Phe Arg Thr Ala
145                 150

<210> SEQ ID NO 102
<211> LENGTH: 160
<212> TYPE: PRT
<213> ORGANISM: Acremonium chrysogenum

<400> SEQUENCE: 102

Pro Lys Ser Asn Lys Ala Thr Val Asp Leu Ile Ser Glu Phe Glu Gly
1               5                   10                  15

Phe Arg Ala Asp Ile Tyr Ile Asp Ala Thr Gly His Pro Thr Val Gly
            20                  25                  30

Tyr Gly His Leu Cys Ser Asp Lys Cys Ser Asp Val Ser Tyr Pro
            35                  40                  45

Ile Pro Leu Ser Lys Ala Asn Gly Lys Lys Leu Leu Ala Lys Asp Met
    50                  55                  60

Arg Arg Phe Glu Lys Cys Ile Thr Asn Met Val Asp Ala Lys Val Asn
65                  70                  75                  80

Lys Asn Gln Tyr Gly Ala Leu Val Ser Trp Ser Phe Asn Val Gly Cys
                85                  90                  95

Gly Ala Ala Gln Gly Ser Gln Leu Val Lys Arg Leu Asn Lys Gly Gln
            100                 105                 110

Lys Val Asn Lys Val Leu Ser Glu Glu Leu Pro Lys Trp Val His Gly
            115                 120                 125

Gly Gly Gln Val Leu Pro Gly Leu Val Arg Arg Lys Ala Glu Ile
            130                 135                 140
```

```
Ala Leu Ala Lys Lys Thr Asp Ala Lys Ala Leu Pro Pro Thr Cys
145                 150                 155                 160

<210> SEQ ID NO 103
<211> LENGTH: 150
<212> TYPE: PRT
<213> ORGANISM: Acremonium chrysogenum

<400> SEQUENCE: 103

Pro Glu Val Asn Gln Pro Ala Leu Asn Leu Val Gln Gln Phe Glu Asp
1               5                   10                  15

Phe Arg Ala Thr Ile Tyr Lys Asp Pro Ala Gly His Pro Ala Val Gly
                20                  25                  30

Tyr Gly His Leu Cys Ser Asp Ser Ala Cys Ser Asp Val Pro Tyr Thr
            35                  40                  45

Ile Pro Leu Ser Tyr Thr Asp Ala Glu Arg Leu Leu Arg Asp Asp Leu
50                  55                  60

Ala Asp Cys Ile Thr Asn Asp Thr Gly Asn Asn Val Val Leu Asn Ala
65                  70                  75                  80

Asn Gln Tyr Gly Ala Leu Val Ser Trp Ala Phe Asn Val Gly Cys Glu
                85                  90                  95

Asn Ser Gly Phe Ser Ala Leu Ile Glu Arg Leu Asn Met Gly Glu Asp
            100                 105                 110

Pro Thr Ser Val Ala Thr Asp Glu Leu Pro Arg Trp Asn Met Ile Gly
        115                 120                 125

Asp Glu Val Val Pro Ala Phe Glu Arg Arg Ala Ala Glu Val Asp
130                 135                 140

Leu Phe Leu Ala Pro Ser
145                 150

<210> SEQ ID NO 104
<211> LENGTH: 155
<212> TYPE: PRT
<213> ORGANISM: Acremonium chrysogenum

<400> SEQUENCE: 104

Pro Ala Ala Asn Ala Ala Thr Val Ser Leu Val Ala Glu Phe Glu Gly
1               5                   10                  15

Phe Ser Pro Asp Ile Tyr Asp Asp Pro Ser Gly Tyr Pro Thr Val Gly
                20                  25                  30

Tyr Gly His Leu Cys Gly Asp Pro Ser Cys Ser Glu Val Pro Tyr Pro
            35                  40                  45

Ile Pro Leu Ser Glu Glu Asp Gly Arg Lys Leu Leu Ala Ser Asp Met
50                  55                  60

Ala Val Ala Gln Asn Cys Ile Thr Met Gln Thr Ala Glu Ser Val Val
65                  70                  75                  80

Leu Asn Asp Asn Gln Tyr Gly Ala Leu Val Ser Trp Ala Phe Asn Val
                85                  90                  95

Gly Cys Gly Asn Ser Gly Ser Ser Thr Leu Ile Ser Arg Leu Asn Ala
            100                 105                 110

Gly Glu Asp Pro Asn Thr Val Ala Ala Glu Leu Pro Lys Trp Lys
        115                 120                 125

Tyr Ser Gly Gly Val Glu Leu Pro Gly Leu Val Arg Arg Arg Ala Ala
        130                 135                 140

Glu Val Asp Leu His Lys Thr Pro Ser Asp Val
145                 150                 155
```

<210> SEQ ID NO 105
<211> LENGTH: 157
<212> TYPE: PRT
<213> ORGANISM: Metarhizium anisopliae

<400> SEQUENCE: 105

```
Pro Lys Ala Asn Glu Ala Thr Val Lys Phe Ile Ser Thr Phe Glu Gly
1               5                   10                  15

Trp Tyr Asp His Val Tyr Pro Asp Pro Gly Pro Gln His Leu Glu Thr
            20                  25                  30

Leu Gly Tyr Gly His Leu Cys Lys Lys Pro Asn Cys Ala Glu Val Lys
        35                  40                  45

Tyr Pro Phe Pro Pro Leu Ser Lys Ala Asp Gly Leu Lys Leu Leu Ser
    50                  55                  60

Asp Asp Met Ser Val Ala Glu Asn Cys Ile Tyr Gln Asp Thr Ser Ala
65                  70                  75                  80

Lys Val Thr Leu Asn Ala Asn Gln Tyr Gly Ala Leu Val Ser Trp Ala
                85                  90                  95

Phe Asn Val Gly Cys Gly Asn Val Ala Ser Ser Arg Leu Ile Arg Arg
            100                 105                 110

Leu Asn Ala Gly Glu Asp Pro Asp Thr Val Ala Ala Gln Glu Leu Pro
        115                 120                 125

Gln Trp Asn Arg Ala Gly Gly Lys Val Leu Pro Gly Leu Thr Arg Arg
    130                 135                 140

Arg Asn Ala Glu Val Glu Leu Phe Lys Thr Pro Thr Asn
145                 150                 155
```

<210> SEQ ID NO 106
<211> LENGTH: 150
<212> TYPE: PRT
<213> ORGANISM: Stachybotrys chlorohalonata

<400> SEQUENCE: 106

```
Pro Thr Thr Asn Ser Ala Thr Val Ser Leu Ile Gln Glu Phe Glu Gly
1               5                   10                  15

Trp Ser Ser Thr Ile Tyr Leu Asp Pro Ser Gly Tyr Pro Thr Val Gly
            20                  25                  30

Tyr Gly His Leu Cys Ala Asn Ser Arg Cys Thr Asp Val Pro Tyr Pro
        35                  40                  45

Ile Pro Leu Ser Thr Ala Asn Gly Asn Leu Leu Gln Ser Asp Met
    50                  55                  60

Leu Val Ala Arg Arg Cys Ile Ala Gln Asp Val Asn Val Arg Leu Asn
65                  70                  75                  80

Ala Asn Gln Tyr Gly Ala Leu Val Ser Trp Ala Phe Asn Val Gly Cys
                85                  90                  95

Gly Ala Ser Gly Ser Ser Thr Leu Val Arg Arg Leu Asn Ala Gly Glu
            100                 105                 110

Asn Pro Asn Thr Val Ala Ala Glu Glu Leu Pro Arg Trp Val Asn Ser
        115                 120                 125

Gly Gly Val Gln Leu Pro Gly Leu Val Arg Arg Asn Ala Glu Val
    130                 135                 140

Ala Leu Phe Arg Thr Ala
145                 150
```

<210> SEQ ID NO 107
<211> LENGTH: 158

```
<212> TYPE: PRT
<213> ORGANISM: Pseudogymnoascus pannorum

<400> SEQUENCE: 107

Pro Lys Ser Asn Gly Ala Thr Val Asp Leu Ile Ala Glu Phe Glu Gly
1               5                   10                  15

Phe Val Pro Asn Val Tyr Thr Asp Ala Thr Gly His Ala Thr Val Gly
            20                  25                  30

Tyr Gly His Leu Cys Gln Lys Ser Lys Cys Ser Glu Val Pro Tyr His
        35                  40                  45

Ile Pro Leu Thr Lys Ala Asn Gly Lys Leu Leu Ala Ser Asp Ile
    50                  55                  60

Gly Val Tyr Glu Lys Cys Val Thr Ala Met Leu Asn Ser Lys Ala Lys
65              70                  75                  80

Val Asn Leu Asn Gln Tyr Gly Ala Leu Val Ser Leu Thr Phe Asn Met
                85                  90                  95

Gly Cys Gly Ala Ile Lys Ser Ser Ala Ile Val Thr Arg Leu Asn Lys
            100                 105                 110

Gly Glu Lys Ala Thr Thr Val Ile Ser Ser Glu Phe Pro Lys Trp Val
        115                 120                 125

His Gly Gly Gly Lys Val Leu Pro Gly Leu Val Arg Arg Lys Ala
    130                 135                 140

Glu Val Ala Leu Ala Lys Lys Thr Ala Gly Lys Ala Leu Pro
145                 150                 155

<210> SEQ ID NO 108
<211> LENGTH: 158
<212> TYPE: PRT
<213> ORGANISM: Pseudogymnoascus pannorum

<400> SEQUENCE: 108

Pro Lys Ser Asn Ala Ala Thr Val Asn Leu Ile Ala Glu Phe Glu Gly
1               5                   10                  15

Phe Val Pro His Val Tyr Thr Asp Ala Thr Gly His Pro Thr Val Gly
            20                  25                  30

Tyr Gly His Leu Cys Ser Asn Ser Lys Cys Ser Asp Ala Gly Tyr Pro
        35                  40                  45

Ile Pro Ile Ser Lys Ala Asn Gly Lys Lys Leu Leu Ala Lys Asp Met
    50                  55                  60

Gly Lys Ala Glu Lys Cys Ile Thr Ala Met Val Asn Ser Lys Val Thr
65              70                  75                  80

Leu Asn Ala Asn Gln Tyr Gly Ala Leu Val Ser Leu Ala Phe Asn Val
                85                  90                  95

Gly Cys Gly Ala Met Lys Ser Ser Thr Leu Val Lys Arg Leu Asn Asn
            100                 105                 110

Gly Glu Lys Ala Ser Val Val Tyr Pro Lys Glu Phe Pro Lys Trp Val
        115                 120                 125

His Gly Asn Gly Lys Val Leu Pro Gly Leu Val Arg Arg Arg Lys Ala
    130                 135                 140

Glu Val Ala Leu Ser Lys Lys Ala Ala Gly Lys Ala Leu Pro
145                 150                 155

<210> SEQ ID NO 109
<211> LENGTH: 158
<212> TYPE: PRT
<213> ORGANISM: Pseudogymnoascus pannorum
```

<400> SEQUENCE: 109

Pro Lys Ser Asn Ala Ala Thr Val Asp Leu Ile Ala Glu Phe Glu Gly
1               5                   10                  15

Phe Val Pro Lys Val Tyr Thr Asp Ala Thr Gly His Pro Thr Val Gly
            20                  25                  30

Tyr Gly His Leu Cys Ser Asn Ser Lys Cys Ser Asp Ala Gly Tyr Pro
        35                  40                  45

Ile Pro Leu Ser Lys Ala Asn Gly Lys Lys Leu Leu Ala Lys Asp Met
    50                  55                  60

Gly Lys Ala Glu Lys Cys Val Thr Ala Met Val Asn Ser Lys Val Thr
65                  70                  75                  80

Leu Asn Ala Asn Glu Tyr Gly Ala Leu Val Ser Leu Ala Phe Asn Val
                85                  90                  95

Gly Cys Gly Ala Met Gln Ser Ser Leu Val Lys Arg Leu Asn Asn
            100                 105                 110

Gly Glu Lys Ala Ser Val Val Tyr Pro Val Glu Phe Pro Lys Trp Val
        115                 120                 125

His Gly Asn Gly Lys Val Leu Pro Gly Leu Val Arg Arg Arg Lys Ala
    130                 135                 140

Glu Val Ala Leu Ser Lys Lys Ala Ala Gly Lys Ala Leu Pro
145                 150                 155

<210> SEQ ID NO 110
<211> LENGTH: 158
<212> TYPE: PRT
<213> ORGANISM: Pseudogymnoascus pannorum

<400> SEQUENCE: 110

Pro His Ser Asn Thr Ala Thr Val Asn Leu Ile Ala Glu Phe Glu Gly
1               5                   10                  15

Phe Val Pro Asn Val Tyr Thr Asp Ala Thr Gly His Pro Thr Val Gly
            20                  25                  30

Tyr Gly His Leu Cys Ser Asn Ser Lys Cys Ser Gly Ile Gly Tyr Pro
        35                  40                  45

Ile Pro Leu Ser Val Ala Asn Gly Lys Lys Leu Leu Ala Lys Asp Met
    50                  55                  60

Gly Val Ala Glu Arg Cys Ile Thr Ala Met Thr Asn Ser Lys Ala Val
65                  70                  75                  80

Leu Asn Ala Asn Gln Tyr Gly Ala Leu Val Ser Leu Thr Phe Asn Met
                85                  90                  95

Gly Cys Gly Ala Ile Gln Ser Ser Ala Ile Lys Arg Ile Asn Asn
            100                 105                 110

Gly Glu Lys Ala Ser Val Val Phe Pro Asn Glu Phe Pro Lys Trp Val
        115                 120                 125

His Gly Gly Gly Val Val Leu Pro Gly Leu Val Arg Arg Arg Asn Ala
    130                 135                 140

Glu Ile Ala Leu Ser Lys Lys Ala Ala Asp Lys Val Leu Pro
145                 150                 155

<210> SEQ ID NO 111
<211> LENGTH: 158
<212> TYPE: PRT
<213> ORGANISM: Pseudogymnoascus pannorum

<400> SEQUENCE: 111

Pro His Ser Asn Thr Ala Thr Val Asn Leu Ile Ala Glu Phe Glu Gly

```
            1               5                  10                 15
       Phe Val Pro Asn Val Tyr Thr Asp Ala Thr Gly His Pro Thr Val Gly
                       20                  25                 30

Tyr Gly His Leu Cys Ser Asn Ser Lys Cys Ser Gly Ile Gly Tyr Pro
                       35                  40                 45

Ile Pro Leu Ser Val Ala Asn Gly Lys Lys Leu Leu Ala Lys Asp Met
                       50                  55                 60

Gly Val Ala Glu Lys Cys Ile Thr Ala Met Thr Asn Ser Lys Ala Val
        65                  70                  75                 80

Leu Asn Ala Asn Gln Tyr Gly Ala Leu Val Ser Leu Thr Phe Asn Met
                           85                  90                 95

Gly Cys Gly Ala Ile Gln Ser Ser Asp Ile Ile Lys Arg Ile Asn Lys
                          100                 105                110

Gly Glu Lys Ala Ser Val Val Phe Pro Ser Glu Phe Pro Lys Trp Val
                          115                 120                125

His Gly Gly Gly Val Val Leu Pro Gly Leu Val Arg Arg Arg Asn Ala
                          130                 135                140

Glu Ile Ala Leu Ser Lys Lys Ala Ala Asp Lys Val Leu Pro
       145                 150                 155

<210> SEQ ID NO 112
<211> LENGTH: 162
<212> TYPE: PRT
<213> ORGANISM: Torrubiella hemipterigena

<400> SEQUENCE: 112

Pro Ala Val Asn Gln Ala Thr Val Asn Leu Val Ala Glu Phe Glu Gly
        1               5                  10                 15

Phe Arg Ala Ser Glu Tyr Thr Asp Ala Thr Gly His Pro Thr Ile Gly
                       20                  25                 30

Tyr Gly His Leu Cys Thr Ala Lys Gly Cys Ala Asp Val Ala Tyr Pro
                       35                  40                 45

Lys Pro Leu Ser Glu Ala Asp Gly Lys Lys Gln Leu Ala Lys Asp Leu
                       50                  55                 60

Ala Val Ala Gln Asn Cys Ile Thr Thr Met Thr Ala Asn Pro Val Thr
        65                  70                  75                 80

Leu Asn Ala Asn Gln Tyr Gly Ala Leu Val Ser Trp Ala Phe Asn Val
                           85                  90                 95

Gly Cys Gly Ala Ala Lys Ser Ser Thr Leu Ile Lys Glu Leu Asn Ala
                          100                 105                110

Gly Lys Asp Ala Arg Thr Val Ile Asp Thr Glu Leu Pro Lys Trp Asn
                          115                 120                125

Lys Gly Asn Gly Lys Pro Ile Ala Gly Leu Thr Arg Arg Arg Lys Ala
                          130                 135                140

Glu Val Asp Leu Ser His Val Ala Thr Ser Gln Gly Ala Leu Pro Ala
       145                 150                 155                160

Lys Cys

<210> SEQ ID NO 113
<211> LENGTH: 164
<212> TYPE: PRT
<213> ORGANISM: Torrubiella hemipterigena

<400> SEQUENCE: 113

Pro Val Ala Asn Ala Ala Thr Val Glu Phe Val Ser Gly Phe Glu Gly
        1               5                  10                 15
```

```
Trp Arg Asp Tyr Val Tyr Arg Asp Pro Gly Asn Gly Phe Gln Thr Leu
             20                  25                  30

Gly Tyr Gly His Leu Cys Lys Lys Pro Asn Cys Ala Glu Val Pro Tyr
         35                  40                  45

Lys Phe Pro Pro Leu Ser Lys Ala Asp Gly Leu Lys Leu Leu Ser Ser
 50                  55                  60

Asp Met Ala Ile Ala Glu Asn Cys Val Thr Lys Ile Lys Asp Lys
 65                  70                  75                  80

Ile Val Leu Asn Ala Asn Gln Tyr Gly Ala Leu Val Ser Trp Ala Phe
                 85                  90                  95

Asn Val Gly Cys Gly Asn Val Ala Ser Ser Leu Ile Arg Arg Leu
             100                 105                 110

Asn Ala Gly Glu Asn Pro Asn Val Val Ala Ala Ser Glu Leu Pro Lys
             115                 120                 125

Trp Asn Lys Asp Ala Lys Gly His Val Leu Pro Gly Leu Thr Arg Arg
130                 135                 140

Arg Ala Ala Glu Val Lys Leu Phe Gln Thr Pro Thr Ser Glu His Ala
145                 150                 155                 160

Leu Pro Ala Cys

<210> SEQ ID NO 114
<211> LENGTH: 158
<212> TYPE: PRT
<213> ORGANISM: Pseudogymnoascus pannorum

<400> SEQUENCE: 114

Pro His Ser Asn Thr Ala Thr Val Asn Leu Ile Ala Glu Phe Glu Gly
1               5                  10                  15

Phe Val Pro Asn Val Tyr Thr Asp Ala Thr Gly His Pro Thr Val Gly
             20                  25                  30

Tyr Gly His Leu Cys Ser Asn Ser Lys Cys Ser Gly Ile Gly Tyr Pro
         35                  40                  45

Ile Pro Leu Ser Val Ala Asn Gly Lys Leu Leu Ala Lys Asp Met
 50                  55                  60

Gly Val Ala Glu Arg Cys Ile Thr Ala Met Thr Asn Ser Lys Ala Val
 65                  70                  75                  80

Leu Asn Ala Asn Gln Tyr Gly Ala Leu Val Ser Leu Thr Phe Asn Met
                 85                  90                  95

Gly Cys Gly Ala Ile Gln Ser Ser Asp Ile Ile Lys Arg Ile Asn Asn
             100                 105                 110

Gly Glu Lys Ala Ser Val Val Phe Pro Lys Glu Phe Pro Arg Trp Val
             115                 120                 125

His Gly Gly Gly Val Val Leu Pro Gly Leu Val Arg Arg Arg Asn Ala
             130                 135                 140

Glu Ile Ala Leu Ser Lys Lys Ala Ala Asp Lys Val Leu Pro
145                 150                 155

<210> SEQ ID NO 115
<211> LENGTH: 158
<212> TYPE: PRT
<213> ORGANISM: Pseudogymnoascus pannorum

<400> SEQUENCE: 115

Pro Lys Ser Asn Ala Ala Thr Val Asp Leu Ile Ala Glu Phe Glu Gly
1               5                  10                  15
```

Phe Val Pro Lys Val Tyr Thr Asp Ala Thr Gly His Pro Thr Val Gly
                20                  25                  30

Tyr Gly His Leu Cys Ser Asn Ser Lys Cys Ser Asp Ala Gly Tyr Pro
            35                  40                  45

Ile Pro Leu Ser Lys Ala Asn Gly Lys Lys Leu Leu Ala Lys Asp Met
50                  55                  60

Gly Lys Ala Glu Lys Cys Val Thr Ala Met Val Asn Ser Lys Val Thr
65                  70                  75                  80

Leu Asn Ala Asn Glu Tyr Gly Ala Leu Val Ser Leu Ala Phe Asn Val
                85                  90                  95

Gly Cys Gly Ala Met Gln Ser Ser Leu Val Lys Arg Leu Asn Asn
            100                 105                 110

Gly Glu Lys Ala Ser Val Val Tyr Pro Val Glu Phe Pro Lys Trp Val
            115                 120                 125

His Gly Asn Gly Lys Val Leu Pro Gly Leu Val Arg Arg Lys Ala
            130                 135                 140

Glu Val Ala Leu Ser Lys Lys Ala Ala Gly Lys Ala Leu Pro
145                 150                 155

<210> SEQ ID NO 116
<211> LENGTH: 158
<212> TYPE: PRT
<213> ORGANISM: Pseudogymnoascus pannorum

<400> SEQUENCE: 116

Pro Lys Ser Asn Ala Ala Thr Val Asp Leu Ile Ala Glu Phe Glu Gly
1               5                   10                  15

Phe Val Ala Lys Val Tyr Ile Asp Ala Thr Gly His Pro Thr Val Gly
                20                  25                  30

Tyr Gly His Leu Cys Thr Lys Ser Lys Cys Ala Glu Val Gly Tyr Pro
            35                  40                  45

Ile Pro Leu Ser Lys Ala Asn Gly Lys Lys Leu Leu Ala Thr Asp Met
50                  55                  60

Ala Lys Ala Glu Lys Cys Val Thr Ala Met Leu Asn Ser Lys Ala Val
65                  70                  75                  80

Leu Asn Ala Asn Gln Tyr Gly Ala Leu Val Ser Leu Ala Phe Asn Val
                85                  90                  95

Gly Cys Gly Ala Val Gln Ser Ser Ile Val Thr Arg Leu Asn Lys
            100                 105                 110

Gly Glu Lys Ala Ala Thr Val Tyr Pro Gln Glu Phe Pro Lys Trp Val
            115                 120                 125

His Gly Gly Gly Lys Val Leu Pro Gly Leu Val Arg Arg Asn Ala
            130                 135                 140

Glu Val Ala Leu Ala Lys Lys Ala Ala Gly Lys Ala Leu Pro
145                 150                 155

<210> SEQ ID NO 117
<211> LENGTH: 158
<212> TYPE: PRT
<213> ORGANISM: Pseudogymnoascus pannorum

<400> SEQUENCE: 117

Pro Lys Ser Asn Ala Ala Thr Val Asp Leu Ile Ala Glu Phe Glu Gly
1               5                   10                  15

Phe Val Ala Lys Val Tyr Ile Asp Ala Thr Gly His Pro Thr Val Gly
                20                  25                  30

Tyr Gly His Leu Cys Thr Lys Ser Lys Cys Ala Glu Val Gly Tyr Pro
                35                  40                  45

Ile Pro Leu Ser Lys Ala Asn Gly Lys Lys Leu Leu Ala Thr Asp Met
 50                  55                  60

Ala Lys Ala Glu Lys Cys Val Thr Ala Met Leu Asn Ser Lys Ala Val
 65                  70                  75                  80

Leu Asn Ala Asn Gln Tyr Gly Ala Leu Val Ser Leu Ala Phe Asn Val
                 85                  90                  95

Gly Cys Gly Ala Val Gln Ser Ser Ile Val Thr Arg Leu Asn Lys
                100                 105                 110

Gly Glu Lys Ala Ala Thr Val Tyr Pro Gln Glu Phe Pro Lys Trp Val
                115                 120                 125

His Gly Gly Gly Lys Val Leu Pro Gly Leu Val Arg Arg Arg Asn Ala
            130                 135                 140

Glu Val Ala Leu Ala Lys Lys Ala Ala Gly Lys Ala Leu Pro
145                 150                 155

<210> SEQ ID NO 118
<211> LENGTH: 158
<212> TYPE: PRT
<213> ORGANISM: Pseudogymnoascus pannorum

<400> SEQUENCE: 118

Pro Lys Ser Asn Ala Ala Thr Val Asp Leu Ile Ala Glu Phe Glu Gly
  1               5                  10                  15

Phe Val Pro Asn Val Tyr Thr Asp Ala Thr Gly His Ala Thr Val Gly
                 20                  25                  30

Tyr Gly His Leu Cys Gln Lys Ser Lys Cys Ser Glu Val Pro Tyr His
                35                  40                  45

Ile Pro Leu Thr Lys Ala Asn Gly Lys Lys Leu Leu Ala Ser Asp Ile
 50                  55                  60

Gly Val Tyr Glu Lys Cys Val Thr Ala Met Leu Asn Ser Lys Ala Lys
 65                  70                  75                  80

Leu Asn Leu Asn Gln Tyr Gly Ala Leu Val Ser Leu Thr Phe Asn Met
                 85                  90                  95

Gly Cys Gly Ala Ile Lys Ser Ser Ala Ile Val Thr Arg Leu Asn Lys
                100                 105                 110

Gly Glu Lys Ala Thr Thr Val Ile Ser Gly Glu Phe Pro Lys Trp Val
                115                 120                 125

His Gly Gly Gly Lys Val Leu Pro Gly Leu Val Arg Arg Arg Lys Ala
            130                 135                 140

Glu Val Ala Leu Ala Lys Lys Thr Ala Gly Lys Ala Leu Pro
145                 150                 155

<210> SEQ ID NO 119
<211> LENGTH: 158
<212> TYPE: PRT
<213> ORGANISM: Pseudogymnoascus pannorum

<400> SEQUENCE: 119

Pro Lys Ser Asn Ala Ala Thr Val Asp Leu Ile Ala Glu Phe Glu Gly
  1               5                  10                  15

Phe Val Pro Asn Val Tyr Ile Asp Ala Thr Gly His Pro Thr Val Gly
                 20                  25                  30

Tyr Gly His Leu Cys Thr Lys Ser Lys Cys Ala Glu Ile Gly Tyr Pro
                35                  40                  45

```
Ile Pro Leu Ser Lys Ala Asn Gly Lys Lys Leu Leu Ala Lys Asp Ile
    50                  55                  60

Ala Lys Phe Glu Lys Cys Val Thr Ala Met Leu Lys Ser Lys Ala Val
 65                  70                  75                  80

Leu Asn Leu Asn Gln Tyr Gly Ala Leu Val Ser Leu Ala Phe Asn Val
                 85                  90                  95

Gly Cys Gly Ala Val Gln Ser Ser Ile Val Thr Arg Leu Asn Lys
                100                 105                 110

Gly Glu Lys Ala Ala Thr Val Phe Pro Gln Phe Pro Lys Trp Val
            115                 120                 125

His Gly Asn Gly Lys Val Leu Pro Gly Leu Val Arg Arg Lys Ala
    130                 135                 140

Glu Val Ala Leu Ala Lys Lys Ala Ala Gly Lys Ala Leu Pro
145                 150                 155
```

<210> SEQ ID NO 120
<211> LENGTH: 162
<212> TYPE: PRT
<213> ORGANISM: Pseudogymnoascus pannorum

<400> SEQUENCE: 120

```
Pro Ala Ser Asn Gln Ala Thr Ile Asp Leu Ile Ala Gly Ser Glu Gly
  1               5                  10                  15

Phe Ser Gly Asp Val Tyr Thr Asp Pro Thr Gly Asn Pro Thr Val Gly
                 20                  25                  30

Tyr Gly His Leu Cys Gln Asp Ser Thr Cys Ala Asp Thr Gly Phe Pro
                 35                  40                  45

Ile Pro Leu Ser Glu Glu Asp Gly Lys Lys Leu Leu Ala Gly Asp Met
 50                  55                  60

Lys Gln Phe Glu Ser Cys Ile Thr Thr Met Thr Gly Asp Ala Val Thr
 65                  70                  75                  80

Leu Asn Leu Asn Gln Phe Gly Ala Leu Val Ser Trp Ser Phe Asn Asn
                 85                  90                  95

Gly Cys Gly Ala Ala Gln Ser Ser Thr Leu Ile Ser Arg Leu Asn Asn
                100                 105                 110

Gly Glu Asp Pro Asn Thr Val Ile Glu Gln Leu Pro Gln Trp Val
            115                 120                 125

Tyr Gly Asn Gly Gln Ile Leu Asp Gly Leu Val Lys Arg Arg Gln Ala
                130                 135                 140

Glu Ile Asp Leu Ala Lys Thr Pro Thr Ser Asp Gly Ala Leu Pro Ala
145                 150                 155                 160

Pro Cys
```

<210> SEQ ID NO 121
<211> LENGTH: 162
<212> TYPE: PRT
<213> ORGANISM: Metarhizium majus

<400> SEQUENCE: 121

```
Pro Lys Ala Asn Glu Ala Thr Val Lys Phe Ile Ser Thr Phe Glu Gly
  1               5                  10                  15

Trp Tyr Asp His Val Tyr Pro Asp Pro Gly Pro Gln His Leu Glu Thr
                 20                  25                  30

Leu Gly Tyr Gly His Leu Cys Lys Lys Pro Asn Cys Ala Glu Val Lys
                 35                  40                  45

Tyr Pro Phe Pro Pro Leu Ser Lys Ala Asp Gly Leu Lys Leu Leu Ser
```

```
                50                  55                  60
Asp Asp Met Ser Val Ala Glu Asn Cys Ile Tyr Gln Asp Thr Asn Ala
 65                  70                  75                  80

Lys Val Thr Leu Asn Ala Asn Gln Tyr Gly Ala Leu Val Ser Trp Ala
                 85                  90                  95

Phe Asn Val Gly Cys Gly Asn Val Ala Ser Ser Arg Leu Ile Arg Arg
                100                 105                 110

Leu Asn Ala Gly Glu Asp Pro Asn Met Val Ala Ala Gln Glu Leu Pro
                115                 120                 125

Gln Trp Asn Arg Ala Asp Gly Lys Val Leu Pro Gly Leu Thr Arg Arg
                130                 135                 140

Arg Asn Ala Glu Val Glu Leu Phe Lys Thr Pro Thr Asn Asp Pro Ala
145                 150                 155                 160

Leu Pro

<210> SEQ ID NO 122
<211> LENGTH: 162
<212> TYPE: PRT
<213> ORGANISM: Metarhizium guizhouense

<400> SEQUENCE: 122

Pro Lys Ala Asn Glu Ala Thr Val Lys Phe Ile Ser Thr Phe Glu Gly
  1               5                  10                  15

Trp Tyr Asp His Val Tyr Pro Asp Pro Gly Pro Gln His Leu Glu Thr
                 20                  25                  30

Leu Gly Tyr Gly His Leu Cys Lys Lys Pro Asn Cys Ala Glu Val Lys
                 35                  40                  45

Tyr Pro Phe Pro Pro Leu Ser Lys Ala Asp Gly Leu Lys Leu Leu Ser
 50                  55                  60

Asp Asp Met Ser Val Ala Glu Asn Cys Ile Tyr Gln Asp Thr Asn Ala
 65                  70                  75                  80

Lys Val Thr Leu Asn Ala Asn Gln Tyr Gly Ala Leu Val Ser Trp Ala
                 85                  90                  95

Phe Asn Val Gly Cys Gly Asn Val Ala Ser Ser Arg Leu Ile Arg Arg
                100                 105                 110

Leu Asn Ala Gly Glu Asp Pro Asn Thr Val Ala Ala Gln Glu Leu Pro
                115                 120                 125

Gln Trp Asn Arg Ala Asp Gly Lys Val Leu Pro Gly Leu Thr Arg Arg
                130                 135                 140

Arg Asn Ala Glu Val Glu Leu Phe Lys Thr Pro Thr Asn Asp Pro Ala
145                 150                 155                 160

Leu Pro

<210> SEQ ID NO 123
<211> LENGTH: 74
<212> TYPE: PRT
<213> ORGANISM: Podospora anserina

<400> SEQUENCE: 123

Tyr Pro Ile Thr Gly Asp Val Val Asn Cys Arg Ser Gly Pro Gly Thr
  1               5                  10                  15

Ser Tyr Ser Val Val Lys Gln Tyr Thr Gln Gly Gln Asp Val Thr Ile
                 20                  25                  30

Thr Cys Gln Thr Glu Gly Thr Asn Val Asn Gly Val Thr Ile Trp Asp
                 35                  40                  45
```

```
Lys Thr Ala Asp Gly Asn Cys Tyr Val Ser Asp Tyr Tyr Val Gln Thr
 50                  55                  60

Gly Val Asn Gly Tyr Val Thr Glu Arg Cys
 65                  70
```

<210> SEQ ID NO 124
<211> LENGTH: 73
<212> TYPE: PRT
<213> ORGANISM: Penicillium chrysogenum

<400> SEQUENCE: 124

```
Tyr Pro Ile Thr Gly Asp Gly Val Asn Cys Arg Ser Gly Pro Gly Thr
 1               5                  10                  15

Ser Tyr Ser Val Val Lys Ser Tyr Lys Gln Gly Ala Asp Val Ala Ile
                 20                  25                  30

Thr Cys Gln Thr Ala Gly Thr Ser Val Asn Gly Asn Glu Ile Trp Asp
             35                  40                  45

Lys Thr Glu Asp Gly Cys Tyr Ile Thr Asp Tyr Ile Arg Thr Gly
         50                  55                  60

Ser Ser Ser Tyr Val Thr Lys Lys Cys
 65                  70
```

<210> SEQ ID NO 125
<211> LENGTH: 73
<212> TYPE: PRT
<213> ORGANISM: Nectria haematococca

<400> SEQUENCE: 125

```
Tyr Pro Val Thr Ser Asp Asn Leu Asn Cys Arg Ser Gly Pro Gly Thr
 1               5                  10                  15

Ala Phe Ala Ile Lys Lys Ser Tyr Lys Asn Gly Gln Asp Val Thr Ile
                 20                  25                  30

Thr Cys Gln Thr Glu Gly Asp Asn Ile Glu Gly Asn Ser Ile Trp Asp
             35                  40                  45

Lys Thr Ser Asp Gly Cys Tyr Val Ala Asp Lys Tyr Val Lys Thr Gly
         50                  55                  60

Lys Asp Gly Tyr Val Lys Gly Lys Cys
 65                  70
```

<210> SEQ ID NO 126
<211> LENGTH: 61
<212> TYPE: PRT
<213> ORGANISM: Metarhizium acridum

<400> SEQUENCE: 126

```
Tyr Pro Ile Thr Gly Thr Thr Val Asn Cys Arg Ala Gly Pro Ala Thr
 1               5                  10                  15

Asp Pro Ala Ile Val Arg Ala Tyr Lys Lys Asp Lys Val Ser Ile
                 20                  25                  30

Ala Arg Gln Thr Gln Gly Pro Asp Ile Asn Gly Thr Ile Trp Asp
             35                  40                  45

Lys Thr Ala Asp Gly Cys Tyr Val Ser Asp Tyr Phe Val
         50                  55                  60
```

<210> SEQ ID NO 127
<211> LENGTH: 73
<212> TYPE: PRT
<213> ORGANISM: Metarhizium robertsii

<400> SEQUENCE: 127

```
Phe Pro Val Thr Ala Asp Ser Leu Asn Cys Arg Ala Glu Pro Asn Thr
1               5                   10                  15

Ser Ser Ala Val Lys Lys Thr Tyr Lys Thr Asp Val Lys Ile
            20                  25                  30

Ser Cys Gln Thr Glu Gly Pro Ser Ile Asn Gly Asn Ser Ile Trp Asp
            35                  40                  45

Lys Thr Gln Asp Gly Cys Tyr Val Ala Asp Tyr Tyr Ile Lys Thr Gly
        50                  55                  60

Ser Ser Gly Tyr Val Thr Gly Lys Cys
65              70
```

<210> SEQ ID NO 128
<211> LENGTH: 73
<212> TYPE: PRT
<213> ORGANISM: Metarhizium robertsii

<400> SEQUENCE: 128

```
Tyr Ala Ile Glu Ala Asp Gly Val Asn Cys Arg Ser Gly Pro Ser Thr
1               5                   10                  15

Ser Asp Lys Val Val Arg Thr Tyr Asn Lys Gly Asn Asp Val Lys Leu
            20                  25                  30

Glu Cys Gln Thr Ala Gly Gln Ala Ile His Gly Asp Ser Leu Trp Asp
            35                  40                  45

Lys Thr Thr Asp Gly Cys Tyr Val Ala Asp Tyr Tyr Val Lys Thr Gly
        50                  55                  60

Thr Thr Asn Met Val Thr Gly Gln Cys
65              70
```

<210> SEQ ID NO 129
<211> LENGTH: 73
<212> TYPE: PRT
<213> ORGANISM: Fusarium oxysporum

<400> SEQUENCE: 129

```
Tyr Pro Val Thr Ser Asp Asn Leu Asn Cys Arg Ser Gly Pro Gly Thr
1               5                   10                  15

Ala Phe Ala Ile Lys Lys Ser Tyr Lys Lys Gly Gln Asp Val Thr Ile
            20                  25                  30

Thr Cys Gln Thr Gln Gly Asp Asn Val Glu Gly Asn Ser Ile Trp Asp
            35                  40                  45

Lys Thr Ser Asp Gly Cys Tyr Val Ala Asp Lys Tyr Val Lys Thr Gly
        50                  55                  60

Lys Asp Gly Tyr Val Lys Gly Lys Cys
65              70
```

<210> SEQ ID NO 130
<211> LENGTH: 69
<212> TYPE: PRT
<213> ORGANISM: Fusarium oxysporum

<400> SEQUENCE: 130

```
Asp Glu Gly Val Arg Cys Arg Ser Gly Pro Thr Thr Ser His Ala Ile
1               5                   10                  15

Gln Arg Gln Phe Thr Lys Gly Thr Asp Val Thr Ile Thr Cys Gln Ile
            20                  25                  30

Glu Gly Thr Asn Ile Glu Gly Asn Ala Leu Trp Asp Lys Thr Thr Phe
            35                  40                  45
```

Gly Cys Tyr Val Ser Asp Tyr Val Ala Thr Gly Ser Ser Gly Tyr
            50                  55                  60

Val Thr Ser Lys Cys
65

<210> SEQ ID NO 131
<211> LENGTH: 73
<212> TYPE: PRT
<213> ORGANISM: Thielavia terrestris

<400> SEQUENCE: 131

Tyr Pro Val Lys Ala Asp Thr Leu Asn Cys Arg Ser Gly Pro Gly Thr
1               5                   10                  15

Ser Tyr Lys Val Ile Lys Thr Tyr Lys Lys Gly Thr Asp Leu Lys Ile
            20                  25                  30

Thr Cys Gln Thr Pro Gly Thr Ser Val Asn Gly Asp Asn Leu Trp Asp
        35                  40                  45

Lys Thr Ser Asp Gly Cys Tyr Val Ala Asp Tyr Tyr Val Lys Thr Gly
    50                  55                  60

Thr Ser Gly Tyr Val Thr Ala His Cys
65                  70

<210> SEQ ID NO 132
<211> LENGTH: 73
<212> TYPE: PRT
<213> ORGANISM: Thielavia terrestris

<400> SEQUENCE: 132

Tyr Pro Ile Lys Gly Asp Gly Val Asn Cys Arg Thr Gly Pro Gly Thr
1               5                   10                  15

Ser Tyr Lys Val Val Lys Ser Tyr Ala Lys Gly Val Asp Val Lys Ile
            20                  25                  30

Thr Cys Gln Thr His Gly Glu Ser Ile Asn Gly Asp Thr Leu Trp Asp
        35                  40                  45

Lys Thr Ser Asp Gly Cys Tyr Val Ala Asp Tyr Tyr Val Lys Thr Gly
    50                  55                  60

Thr Thr Asn Met Val Thr Gly Gln Cys
65                  70

<210> SEQ ID NO 133
<211> LENGTH: 73
<212> TYPE: PRT
<213> ORGANISM: Trichosporon asahii

<400> SEQUENCE: 133

Tyr Pro Ile Lys Thr Asp Gly Val Arg Cys Arg Ser Gly Pro Gly Thr
1               5                   10                  15

Ser Tyr Asp Ile Lys Lys Thr Tyr Ser Ala Gly Asp Lys Val Thr Leu
            20                  25                  30

Ser Cys Tyr Lys Thr Gly Thr Ser Val Glu Gly Asn Thr Tyr Trp Asp
        35                  40                  45

Lys Thr Gly Asp Gly Cys Tyr Val Ser Asp Tyr Tyr Val Lys Thr Gly
    50                  55                  60

Ser Thr Thr Pro Val Val Ser Lys Cys
65                  70

<210> SEQ ID NO 134
<211> LENGTH: 72
<212> TYPE: PRT

<213> ORGANISM: Trichosporon asahii

<400> SEQUENCE: 134

Tyr Pro Val Lys Glu Thr Leu His Cys Arg Ser Ser Pro Ser Thr Ser
1               5                   10                  15

Gly Lys Ile Val Lys Asp Tyr Pro Lys Gly Thr Lys Ile Lys Leu Ser
            20                  25                  30

Cys Tyr Ser Arg Gly Gln Ser Ile Gly Gly Asn Thr Ile Trp Asp Lys
        35                  40                  45

Thr Thr Asp Gly Cys Phe Val Ala Asp Tyr Tyr Val Thr Thr Gly Thr
    50                  55                  60

Thr Asn Pro Val Val Ala Ala Cys
65                  70

<210> SEQ ID NO 135
<211> LENGTH: 73
<212> TYPE: PRT
<213> ORGANISM: Fusarium oxysporum

<400> SEQUENCE: 135

Tyr Pro Ile Thr Gly Asn Asn Val Asn Cys Arg Glu Gly Pro Ser Thr
1               5                   10                  15

Gly Tyr Glu Val Val Lys Thr Tyr His Lys Gly Asp Asp Val Lys Leu
            20                  25                  30

Thr Cys Gln Thr Ser Gly Glu Gly Val Leu Gly Asn Ser Leu Trp Asp
        35                  40                  45

Lys Thr Ser Asp Gly Cys Tyr Val Ala Asp Tyr Tyr Val Lys Thr Gly
    50                  55                  60

Thr Ser Gly Met Val Thr Lys Asp Cys
65                  70

<210> SEQ ID NO 136
<211> LENGTH: 73
<212> TYPE: PRT
<213> ORGANISM: Fusarium oxysporum

<400> SEQUENCE: 136

Tyr Pro Val Thr Ser Asp Asn Leu Asn Cys Arg Ser Gly Pro Gly Thr
1               5                   10                  15

Ala Phe Ala Ile Lys Lys Ser Tyr Lys Lys Gly Gln Asp Val Thr Ile
            20                  25                  30

Thr Cys Gln Thr Gln Gly Asp Lys Val Glu Gly Asn Ser Ile Trp Asp
        35                  40                  45

Lys Thr Ser Asp Gly Cys Tyr Val Ala Asp Lys Tyr Val Lys Thr Gly
    50                  55                  60

Lys Asp Gly Tyr Val Lys Gly Lys Cys
65                  70

<210> SEQ ID NO 137
<211> LENGTH: 72
<212> TYPE: PRT
<213> ORGANISM: Trichosporon asahii

<400> SEQUENCE: 137

Tyr Pro Val Lys Glu Gly Leu Asn Cys Arg Ser Glu Pro Asn Thr Gly
1               5                   10                  15

Gly Gly Ile Val Thr Ser Tyr Ala Ala Gly Thr Gln Val Thr Ile Thr
            20                  25                  30

```
Cys Ala Thr His Gly Glu Ala Val Asn Gly His Asp Val Trp Asp Lys
            35                  40                  45

Thr Thr Asp Gly Cys Phe Val Ser Asp Trp Tyr Val Ser Thr Gly Thr
    50                  55                  60

Ala Glu Phe Val Ala Ser Glu Cys
65                  70

<210> SEQ ID NO 138
<211> LENGTH: 73
<212> TYPE: PRT
<213> ORGANISM: Trichosporon asahii

<400> SEQUENCE: 138

Tyr Pro Ile Lys Thr Asp Gly Val Arg Cys Arg Ser Gly Pro Gly Thr
1               5                   10                  15

Ser Tyr Asp Ile Lys Lys Thr Tyr Ser Ala Gly Asp Lys Val Thr Leu
            20                  25                  30

Ser Cys Tyr Lys Thr Gly Thr Ser Val Glu Gly Asn Thr Tyr Trp Asp
            35                  40                  45

Lys Thr Gly Asp Gly Cys Tyr Val Ser Asp Tyr Tyr Val Lys Thr Gly
    50                  55                  60

Ser Thr Pro Val Val Ser Lys Cys
65                  70

<210> SEQ ID NO 139
<211> LENGTH: 73
<212> TYPE: PRT
<213> ORGANISM: Fusarium oxysporum

<400> SEQUENCE: 139

Tyr Pro Val Thr Ser Asp Asn Leu Asn Cys Arg Ser Gly Pro Gly Thr
1               5                   10                  15

Ala Phe Ala Ile Lys Lys Ser Tyr Lys Gly Gln Asp Val Thr Ile
            20                  25                  30

Asn Cys Gln Thr Gln Gly Asp Asn Val Glu Gly Asn Ser Ile Trp Asp
            35                  40                  45

Lys Thr Ser Asp Gly Cys Tyr Val Ala Asp Lys Tyr Val Lys Thr Gly
    50                  55                  60

Lys Asp Gly Tyr Val Lys Gly Lys Cys
65                  70

<210> SEQ ID NO 140
<211> LENGTH: 69
<212> TYPE: PRT
<213> ORGANISM: Fusarium oxysporum

<400> SEQUENCE: 140

Asp Glu Gly Val Arg Cys Arg Ser Gly Pro Thr Thr Ser Asn Ala Ile
1               5                   10                  15

Gln Arg Gln Phe Ala Lys Gly Thr Asp Val Ala Ile Thr Cys Gln Thr
            20                  25                  30

Glu Gly Thr His Ile Lys Gly Asn Ala Leu Trp Asp Lys Thr Thr Phe
            35                  40                  45

Gly Cys Tyr Val Ser Asp Cys Tyr Val Ala Thr Gly Ser Ser Gly Tyr
            50                  55                  60

Val Thr Ser Lys Cys
65
```

<210> SEQ ID NO 141
<211> LENGTH: 73
<212> TYPE: PRT
<213> ORGANISM: Fusarium oxysporum

<400> SEQUENCE: 141

Tyr Pro Val Thr Ser Asp Asn Leu Asn Cys Arg Ser Gly Pro Gly Thr
1               5                   10                  15

Ala Phe Ala Ile Lys Lys Ser Tyr Lys Lys Gly Gln Asp Val Thr Ile
            20                  25                  30

Thr Cys Gln Thr Gln Gly Asp Asn Val Glu Gly Asn Ser Ile Trp Asp
        35                  40                  45

Lys Thr Ser Asp Gly Cys Tyr Val Ala Asp Lys Tyr Val Lys Thr Gly
    50                  55                  60

Lys Asp Gly Tyr Val Lys Gly Lys Cys
65                  70

<210> SEQ ID NO 142
<211> LENGTH: 69
<212> TYPE: PRT
<213> ORGANISM: Fusarium oxysporum

<400> SEQUENCE: 142

Asp Glu Gly Val Arg Cys Arg Ser Gly Pro Thr Thr Ser His Ala Ile
1 5 10 15

Gln Arg Gln Phe Thr Lys Gly Thr Asp Val Thr Ile Thr Cys Gln Ile
20 25 30

Glu Gly Thr Asn Ile Glu Gly Asn Ala Leu Trp Asp Lys Thr Thr Phe
35 40 45

Gly Cys Tyr Val Ser Asp Tyr Tyr Val Ala Thr Gly Ser Ser Gly Tyr
50 55 60

Val Thr Ser Lys Cys
65

<210> SEQ ID NO 143
<211> LENGTH: 73
<212> TYPE: PRT
<213> ORGANISM: Fusarium oxysporum

<400> SEQUENCE: 143

Tyr Pro Val Thr Ser Asp Asn Leu Asn Cys Arg Ser Gly Pro Gly Thr
1 5 10 15

Ala Phe Ala Ile Lys Lys Ser Tyr Lys Lys Gly Gln Asp Val Thr Ile
20 25 30

Thr Cys Gln Thr Gln Gly Asp Asn Val Glu Gly Asn Ser Ile Trp Asp
35 40 45

Lys Thr Ser Asp Gly Cys Tyr Val Ala Asp Lys Tyr Val Lys Thr Gly
50 55 60

Lys Asp Gly Tyr Val Lys Gly Lys Cys
65 70

<210> SEQ ID NO 144
<211> LENGTH: 73
<212> TYPE: PRT
<213> ORGANISM: Fusarium oxysporum

<400> SEQUENCE: 144

Tyr Pro Val Thr Ser Asp Asn Leu Asn Cys Arg Ser Gly Pro Gly Thr
1 5 10 15

```
Ala Phe Ala Ile Lys Lys Ser Tyr Lys Lys Gly Gln Asp Val Thr Ile
            20                  25                  30

Thr Cys Gln Thr Gln Gly Asp Lys Val Glu Gly Asn Ser Ile Trp Asp
            35                  40                  45

Lys Thr Ser Asp Gly Cys Tyr Val Ala Asp Lys Tyr Val Lys Thr Gly
            50                  55                  60

Lys Asp Gly Tyr Val Lys Gly Lys Cys
65                  70

<210> SEQ ID NO 145
<211> LENGTH: 69
<212> TYPE: PRT
<213> ORGANISM: Fusarium oxysporum

<400> SEQUENCE: 145

Asp Glu Gly Val Arg Cys Arg Ser Gly Pro Thr Thr Ser Asn Ala Ile
1               5                   10                  15

Gln Arg Gln Phe Ala Lys Gly Thr Asp Val Ala Ile Thr Cys Gln Thr
            20                  25                  30

Glu Gly Thr His Ile Lys Gly Asn Val Pro Trp Asp Lys Thr Thr Phe
            35                  40                  45

Gly Cys Tyr Val Ser Asp Tyr Tyr Val Ala Thr Gly Ser Ser Gly Tyr
            50                  55                  60

Val Thr Ser Lys Cys
65

<210> SEQ ID NO 146
<211> LENGTH: 69
<212> TYPE: PRT
<213> ORGANISM: Gibberella moniliformis

<400> SEQUENCE: 146

Asp Glu Gly Val Arg Cys Arg Ser Gly Pro Thr Thr Ser His Ala Ile
1               5                   10                  15

Gln Arg Gln Phe Thr Lys Gly Thr Asp Gly Thr Ile Thr Tyr Gln Thr
            20                  25                  30

Glu Gly Thr Asn Ile Glu Gly Asn Thr Leu Trp Asp Lys Thr Thr Phe
            35                  40                  45

Gly Cys Phe Val Ser Asp Tyr Tyr Val Ala Thr Gly Ser Ser Gly Tyr
            50                  55                  60

Val Thr Ser Lys Cys
65

<210> SEQ ID NO 147
<211> LENGTH: 73
<212> TYPE: PRT
<213> ORGANISM: Fusarium oxysporum

<400> SEQUENCE: 147

Tyr Pro Val Thr Ser Asp Asn Leu Asn Cys Arg Ser Gly Pro Gly Thr
1               5                   10                  15

Ala Phe Ala Ile Lys Lys Ser Tyr Lys Lys Gly Gln Asp Val Thr Ile
            20                  25                  30

Thr Cys Gln Thr Gln Gly Asp Asn Val Glu Gly Asn Ser Ile Trp Asp
            35                  40                  45

Lys Thr Ser Asp Gly Cys Tyr Val Ala Asp Lys Tyr Val Lys Thr Gly
            50                  55                  60

Lys Asp Gly Tyr Val Lys Asp Lys Cys
```

65                  70

<210> SEQ ID NO 148
<211> LENGTH: 69
<212> TYPE: PRT
<213> ORGANISM: Fusarium oxysporum

<400> SEQUENCE: 148

Asp Glu Gly Val Arg Cys Arg Ser Gly Pro Thr Thr Ser His Ala Ile
1               5                   10                  15

Gln Arg Gln Phe Thr Lys Gly Thr Asp Val Thr Ile Thr Cys Gln Ile
                20                  25                  30

Glu Gly Thr Asn Ile Glu Gly Asn Ala Leu Trp Asp Lys Thr Thr Phe
            35                  40                  45

Gly Cys Tyr Val Ser Asp Tyr Tyr Val Ala Thr Gly Ser Ser Gly Tyr
        50                  55                  60

Val Thr Ser Lys Cys
65

<210> SEQ ID NO 149
<211> LENGTH: 73
<212> TYPE: PRT
<213> ORGANISM: Fusarium oxysporum

<400> SEQUENCE: 149

Tyr Pro Val Thr Ser Asp Asn Leu Asn Cys Arg Ser Gly Pro Gly Thr
1               5                   10                  15

Ala Phe Ala Ile Lys Lys Ser Tyr Lys Lys Gly Gln Asp Val Thr Ile
                20                  25                  30

Thr Cys Gln Thr Gln Gly Asp Asn Val Glu Gly Asn Ser Ile Trp Asp
            35                  40                  45

Lys Thr Ser Asp Gly Cys Tyr Val Ala Asp Lys Tyr Val Lys Thr Gly
        50                  55                  60

Lys Asp Gly Tyr Val Lys Gly Lys Cys
65                  70

<210> SEQ ID NO 150
<211> LENGTH: 69
<212> TYPE: PRT
<213> ORGANISM: Fusarium oxysporum

<400> SEQUENCE: 150

Asp Glu Gly Val Arg Cys Arg Ser Gly Pro Thr Thr Ser His Ala Ile
1               5                   10                  15

Gln Arg Gln Phe Thr Lys Gly Thr Asp Val Thr Ile Thr Cys Gln Ile
                20                  25                  30

Glu Gly Thr Asn Ile Glu Gly Asn Ala Leu Trp Asp Lys Thr Thr Phe
            35                  40                  45

Gly Cys Tyr Val Ser Asp Tyr Tyr Val Ala Thr Gly Ser Ser Gly Tyr
        50                  55                  60

Val Thr Ser Lys Cys
65

<210> SEQ ID NO 151
<211> LENGTH: 73
<212> TYPE: PRT
<213> ORGANISM: Penicillium oxalicum

<400> SEQUENCE: 151

```
Tyr Pro Val Lys Thr Asp Gly Leu His Cys Arg Ser Gly Pro Gly Thr
1               5                   10                  15

Ser Tyr Ser Ile Val Lys Thr Tyr Asn Thr Gly Thr Asp Leu Thr Ile
            20                  25                  30

Thr Cys Gln Thr Pro Gly Pro Val Ile Asn Gly Asp Glu Leu Trp Asp
        35                  40                  45

Lys Thr Ser Asp Gly Cys Tyr Val Ser Asp Tyr Tyr Val Lys Thr Gly
    50                  55                  60

Thr Ser Gly Tyr Val Ala Pro His Cys
65              70

<210> SEQ ID NO 152
<211> LENGTH: 73
<212> TYPE: PRT
<213> ORGANISM: Penicillium oxalicum

<400> SEQUENCE: 152

Tyr Pro Val Lys Thr Asp Asp Leu His Cys Arg Ser Gly Pro Gly Thr
1               5                   10                  15

Asn Tyr Ala Val Val Lys Ser Tyr Lys Ile Gly Thr Asp Leu Thr Ile
            20                  25                  30

Thr Cys Gln Ala Pro Gly Thr Val Val Ser Gly Asp Glu Leu Trp Asp
        35                  40                  45

Lys Thr Ser Asp Gly Cys Tyr Val Ser Asp Tyr Tyr Val Lys Thr Gly
    50                  55                  60

Thr Ser Gly Tyr Val Thr Lys Gln Cys
65              70

<210> SEQ ID NO 153
<211> LENGTH: 69
<212> TYPE: PRT
<213> ORGANISM: Fusarium oxysporum

<400> SEQUENCE: 153

Asp Glu Gly Val Arg Cys Arg Ser Gly Pro Thr Thr Ser Asn Ala Ile
1               5                   10                  15

Gln Arg Gln Phe Ala Lys Gly Thr Asp Val Ala Ile Thr Cys Gln Thr
            20                  25                  30

Glu Gly Thr His Ile Lys Gly Asn Val Pro Trp Asp Lys Thr Thr Phe
        35                  40                  45

Gly Cys Tyr Ile Ser Asp Tyr Tyr Val Ala Lys Gly Ser Ser Gly Tyr
    50                  55                  60

Val Thr Ser Lys Cys
65

<210> SEQ ID NO 154
<211> LENGTH: 69
<212> TYPE: PRT
<213> ORGANISM: Fusarium oxysporum

<400> SEQUENCE: 154

Asp Glu Gly Val Arg Cys Arg Ser Gly Pro Thr Thr Ser His Ala Ile
1               5                   10                  15

Gln Arg Gln Phe Thr Lys Gly Thr Asp Val Thr Ile Thr Cys Gln Ile
            20                  25                  30

Glu Gly Thr Asn Ile Glu Gly Asn Ala Leu Trp Asp Lys Thr Thr Phe
        35                  40                  45

Gly Cys Tyr Leu Ser Asp Tyr Tyr Val Ala Thr Gly Ser Ser Gly Tyr
```

Val Thr Ser Lys Cys
65

<210> SEQ ID NO 155
<211> LENGTH: 73
<212> TYPE: PRT
<213> ORGANISM: Fusarium oxysporum

<400> SEQUENCE: 155

Tyr Pro Val Thr Ser Asp Asn Leu Asn Cys Arg Ser Gly Pro Gly Thr
1               5                   10                  15

Gly Phe Ala Ile Lys Lys Ser Tyr Lys Lys Gly Gln Asp Ile Thr Ile
            20                  25                  30

Thr Cys Gln Thr Gln Gly Asp Asn Val Glu Gly Asn Ser Ile Trp Asp
        35                  40                  45

Lys Thr Ser Asn Gly Cys Tyr Val Ala Asp Lys Tyr Val Lys Thr Gly
    50                  55                  60

Lys Asp Gly Tyr Val Lys Gly Lys Cys
65                  70

<210> SEQ ID NO 156
<211> LENGTH: 69
<212> TYPE: PRT
<213> ORGANISM: Gibberella fujikuroi

<400> SEQUENCE: 156

Asp Glu Gly Val Arg Cys Arg Ser Gly Pro Thr Thr Ser His Ala Ile
1               5                   10                  15

Gln Thr His Phe Val Lys Gly Thr Asp Val Thr Ile Thr Cys Gln Thr
            20                  25                  30

Glu Gly Thr Tyr Ile Gly Gly Ser Thr Leu Trp Asp Lys Thr Thr Phe
        35                  40                  45

Gly Cys Tyr Val Ser Asp Tyr Tyr Val Ala Thr Gly Ser Ser Gly Tyr
    50                  55                  60

Val Thr Ser Lys Cys
65

<210> SEQ ID NO 157
<211> LENGTH: 59
<212> TYPE: PRT
<213> ORGANISM: Penicillium roqueforti

<400> SEQUENCE: 157

Tyr Pro Val Thr Gly Ser Val Ile Asp Cys His Ser Gly Pro Gly Ala
1               5                   10                  15

Ser His Ser Val Val Lys Thr Tyr Glu Glu Arg Ala Asp Ile Glu Ile
            20                  25                  30

Val Cys Gln Ala Thr Gly Thr Thr Val Asp Gly Ser Asp Ile Trp His
        35                  40                  45

Gln Thr Val Asp Asp Cys Tyr Val Ser Asp Phe
    50                  55

<210> SEQ ID NO 158
<211> LENGTH: 74
<212> TYPE: PRT
<213> ORGANISM: Pyronema omphalodes

<400> SEQUENCE: 158

```
Tyr Pro Leu Val His Thr Asp Thr Leu Asn Cys Arg Ser Ser Pro Ser
1               5                   10                  15

Thr Ser Ser Ser Ile Thr Lys Thr Tyr Lys Ser Asp Ile Lys
            20                  25                  30

Ile Thr Cys Gln Thr Tyr Gly Asp Thr Ile Lys Gly Asn Asn Ile Trp
            35                  40                  45

Asp Lys Thr Pro Asp Gly Cys Tyr Val Ser Tyr Tyr Val Lys Thr
        50                  55                  60

Gly Lys Ser Gly Phe Val Val Gly Lys Cys
65                  70
```

<210> SEQ ID NO 159
<211> LENGTH: 72
<212> TYPE: PRT
<213> ORGANISM: Pyronema omphalodes

<400> SEQUENCE: 159

```
Tyr Pro Ala Lys Glu Thr Leu Arg Cys Arg Thr Ser Pro Ser Thr Ser
1               5                   10                  15

Ala Ser Ile His Lys Thr Tyr Pro Ala Gly Ala Asp Ile Lys Ile Thr
            20                  25                  30

Cys Gln Thr Thr Gly Thr Lys Val Leu Thr Ser Asn Val Trp Asp Lys
            35                  40                  45

Thr Ser Asp Gly Cys Tyr Val Ser Asp Tyr Tyr Val Ser Thr Gly His
        50                  55                  60

Ser Gly Ile Phe Leu Ser Lys Cys
65                  70
```

<210> SEQ ID NO 160
<211> LENGTH: 73
<212> TYPE: PRT
<213> ORGANISM: Pseudogymnoascus pannorum

<400> SEQUENCE: 160

```
Phe Pro Ile Thr Gly Asn Thr Val Asn Cys Arg Ser Gly Pro Gly Thr
1               5                   10                  15

Asp Phe Ser Ile Lys Gln Thr Tyr Ala Lys Gly Glu Ala Val Ala Ile
            20                  25                  30

Thr Cys Gln Thr Ser Gly Thr Lys Ile Asn Gly Asn Asp Ile Trp Asp
            35                  40                  45

Leu Thr Thr Asp Gly Cys Tyr Val Thr Asp Phe Tyr Val Lys Thr Gly
        50                  55                  60

Ser Ile Ser Tyr Val Leu Pro Lys Cys
65                  70
```

<210> SEQ ID NO 161
<211> LENGTH: 68
<212> TYPE: PRT
<213> ORGANISM: Fusarium oxysporum

<400> SEQUENCE: 161

```
Asp Lys Gly Val Arg Cys Arg Ser Gly Pro Thr Thr Ser His Ala Ile
1               5                   10                  15

Gln Arg Gln Phe Thr Lys Gly Thr Asp Val Thr Ile Thr Cys Gln Ile
            20                  25                  30

Glu Gly Thr Asn Ile Glu Gly Asn Ala Leu Trp Asp Lys Thr Thr Phe
            35                  40                  45

Gly Cys Tyr Val Ser Asp Tyr Tyr Val Ala Thr Gly Ser Ser Gly Tyr
```

```
                   50                  55                  60

Val Thr Leu Lys
 65

<210> SEQ ID NO 162
<211> LENGTH: 68
<212> TYPE: PRT
<213> ORGANISM: Fusarium oxysporum

<400> SEQUENCE: 162

Asp Lys Gly Val Arg Cys Arg Ser Gly Pro Thr Thr Ser His Ala Ile
 1               5                  10                  15

Gln Arg Gln Phe Thr Lys Gly Thr Asp Val Thr Ile Thr Cys Gln Ile
                20                  25                  30

Glu Gly Thr Asn Ile Glu Gly Asn Ala Leu Trp Asp Lys Thr Thr Phe
            35                  40                  45

Gly Cys Tyr Val Ser Asp Tyr Tyr Val Ala Thr Gly Ser Ser Gly Tyr
         50                  55                  60

Val Thr Leu Lys
 65

<210> SEQ ID NO 163
<211> LENGTH: 73
<212> TYPE: PRT
<213> ORGANISM: Acremonium chrysogenum

<400> SEQUENCE: 163

Tyr Pro Ile Thr Gly Asn Glu Val Asn Cys Arg Ser Gly Pro Ser Thr
 1               5                  10                  15

Ser Ser Asp Ile Val Thr Ser Tyr Lys Lys Gly Asp Glu Val Gln Val
                20                  25                  30

Thr Cys Gln Ile Asp Gly Glu Asp Ile Phe Gly Asn Thr Ile Trp Asp
            35                  40                  45

Gln Thr Glu Asp Gly Cys Tyr Val Ala Asp Phe Tyr Val Lys Thr Gly
         50                  55                  60

Ser Asn Ala Phe Val Thr Glu Ala Cys
 65                  70

<210> SEQ ID NO 164
<211> LENGTH: 73
<212> TYPE: PRT
<213> ORGANISM: Acremonium chrysogenum

<400> SEQUENCE: 164

Tyr Pro Ile Thr Ala Asp Asp Val Lys Cys Arg Ala Gly Pro Ser Thr
 1               5                  10                  15

Ser His Asp Ile Val Thr Ala Phe Ala Glu Gly His Glu Val Glu Leu
                20                  25                  30

Glu Cys Gln Ile Val Gly Glu Asn Ile Phe Gly Asn Ser Ile Trp Asp
            35                  40                  45

Lys Thr Thr Asp Gly Cys Tyr Val Ser Asp Tyr Tyr Val Arg Thr Gly
         50                  55                  60

Ser Asp Gly Met Val Val Asp Asn Cys
 65                  70

<210> SEQ ID NO 165
<211> LENGTH: 73
<212> TYPE: PRT
<213> ORGANISM: Acremonium chrysogenum
```

```
<400> SEQUENCE: 165

Tyr Pro Val Thr Ala Asp Ser Leu Asn Cys Arg Glu Gly Ala Gly Thr
1               5                   10                  15

Asp Thr Ala Val Val Thr Thr Tyr Thr Ala Gly Thr Asp Val Glu Val
            20                  25                  30

Val Cys Gln Ala Glu Gly Glu Val Ile Glu Gly Ser Ser Ile Trp Asp
        35                  40                  45

Gln Thr Gln Asp Gly Cys Tyr Val Ser Asp Val Tyr Val Asp Thr Gly
    50                  55                  60

Ser Asp Gly Tyr Val Ala Asp Lys Cys
65                  70

<210> SEQ ID NO 166
<211> LENGTH: 73
<212> TYPE: PRT
<213> ORGANISM: Metarhizium anisopliae

<400> SEQUENCE: 166

Tyr Ala Ile Glu Ala Asp Gly Val Asn Cys Arg Ser Gly Pro Ser Thr
1               5                   10                  15

Ser Asp Lys Val Val Arg Thr Tyr Asn Lys Gly Asn Asp Val Lys Leu
            20                  25                  30

Glu Cys Gln Thr Ala Gly Gln Ala Ile His Gly Asp Ser Leu Trp Asp
        35                  40                  45

Lys Thr Thr Asp Gly Cys Tyr Val Ala Asp Tyr Tyr Val Lys Thr Gly
    50                  55                  60

Thr Thr Asn Met Val Thr Gly Gln Cys
65                  70

<210> SEQ ID NO 167
<211> LENGTH: 73
<212> TYPE: PRT
<213> ORGANISM: Metarhizium anisopliae

<400> SEQUENCE: 167

Phe Pro Val Thr Ala Asp Ser Leu Asn Cys Arg Ala Glu Pro Asn Thr
1               5                   10                  15

Ser Ser Ala Val Lys Lys Thr Tyr Lys Lys Thr Asp Asp Val Lys Ile
            20                  25                  30

Ser Cys Gln Thr Glu Gly Pro Ser Ile Asn Gly Asn Ser Ile Trp Asp
        35                  40                  45

Lys Thr Gln Asp Gly Cys Tyr Val Ala Asp Tyr Tyr Ile Lys Thr Gly
    50                  55                  60

Ser Ser Gly Tyr Val Thr Gly Lys Cys
65                  70

<210> SEQ ID NO 168
<211> LENGTH: 73
<212> TYPE: PRT
<213> ORGANISM: Pseudogymnoascus pannorum

<400> SEQUENCE: 168

Tyr Pro Ile Thr Gly Thr Tyr Val Asn Cys Arg Thr Gly Pro Ser Thr
1               5                   10                  15

Ser Phe Asp Ile Val Arg Ser Tyr Glu Leu Gly Asp Glu Val Asp Leu
            20                  25                  30

Thr Cys Gln Ile Ala Gly Glu Thr Val Thr Gly Asp Asn Leu Trp Asp
```

```
                35                  40                  45
Phe Thr Thr Asp Gly Cys Tyr Val Ala Asp Tyr Phe Val Lys Thr Gly
         50                  55                  60

Thr Phe Gly Met Val Val Asp Glu Cys
 65                  70

<210> SEQ ID NO 169
<211> LENGTH: 73
<212> TYPE: PRT
<213> ORGANISM: Pseudogymnoascus pannorum

<400> SEQUENCE: 169

Tyr Pro Ile Thr Gly Thr Tyr Val Asn Cys Arg Ser Gly Pro Ser Thr
  1               5                  10                  15

Ser Phe Asp Ile Val Arg Ser Tyr Glu Leu Gly Asp Glu Val Ser Leu
                 20                  25                  30

Thr Cys Gln Ile Ala Gly Glu Thr Val Glu Gly Asp Tyr Leu Trp Asp
             35                  40                  45

Leu Thr Thr Asp Gly Cys Tyr Val Ala Asp Tyr Phe Val Lys Thr Gly
         50                  55                  60

Thr Val Gly Met Val Ala Glu Glu Cys
 65                  70

<210> SEQ ID NO 170
<211> LENGTH: 74
<212> TYPE: PRT
<213> ORGANISM: Pseudogymnoascus pannorum

<400> SEQUENCE: 170

Tyr Pro Ile Ser Gly Asp Ser Val Asn Cys Arg Ser Gly Pro Ala Thr
  1               5                  10                  15

Ser Tyr Lys Val Ile Lys Thr Tyr Ala Lys Gly His Asp Val Lys Val
                 20                  25                  30

Thr Cys Gln Thr Val Gly Glu Thr Val Lys Gly Asp Asn Leu Trp Asp
             35                  40                  45

Lys Thr Ala Asp Gly Cys Tyr Val Ala Asp Tyr Tyr Val Lys Thr Gly
         50                  55                  60

Thr Thr Gly Arg Val Val Lys Thr Glu Cys
 65                  70

<210> SEQ ID NO 171
<211> LENGTH: 73
<212> TYPE: PRT
<213> ORGANISM: Pseudogymnoascus pannorum

<400> SEQUENCE: 171

Val Thr Ser Pro Thr Thr Val Lys Cys Arg Ser Gly Pro Gly Thr Gln
  1               5                  10                  15

Tyr Lys Ile Val Lys Thr Tyr Pro Ala Ser Gly Arg Glu Cys Tyr Ser
                 20                  25                  30

Cys Tyr Glu Ser Gly Thr Cys Ile Asn Gly Asn Cys Ser Trp Asp Tyr
             35                  40                  45

Asn Tyr Met Asp Asn Cys Tyr Ile Ser Gly Tyr Tyr Thr Gly Ser Ala
         50                  55                  60

Cys Thr Thr Ala Ala Leu Gly Lys Cys
 65                  70

<210> SEQ ID NO 172
```

```
<211> LENGTH: 74
<212> TYPE: PRT
<213> ORGANISM: Pseudogymnoascus pannorum

<400> SEQUENCE: 172

Tyr Pro Ile Ser Gly Thr Ser Val Asn Cys Arg Ser Gly Pro Ala Thr
1               5                   10                  15

Ser Tyr Lys Val Ile Lys Thr Tyr Lys Lys Gly Gln Asp Val Lys Ile
            20                  25                  30

Thr Cys Gln Thr Val Gly Glu Thr Val Ser Gly Asp Asn Leu Trp Asp
        35                  40                  45

Lys Thr Ser Asp Gly Cys Tyr Val Ala Asp Tyr Tyr Val Lys Thr Gly
    50                  55                  60

Thr Thr Gly Arg Val Val Lys Thr Glu Cys
65                  70

<210> SEQ ID NO 173
<211> LENGTH: 73
<212> TYPE: PRT
<213> ORGANISM: Pseudogymnoascus pannorum

<400> SEQUENCE: 173

Tyr Pro Ile Lys Gly Ser Val Val Asn Cys Arg Ala Gly Pro Gly Thr
1               5                   10                  15

Asn Phe Pro Ile Val Lys Thr Phe Lys Lys Gly Asp Thr Val Asp Ile
            20                  25                  30

Thr Cys Gln Thr Pro Gly Thr Ser Ile Ser Gly Asn Ser Ile Trp Asp
        35                  40                  45

Leu Ile Pro Asp Asn Cys Phe Ile Thr Asp Tyr Tyr Val Lys Thr Gly
    50                  55                  60

Thr Gly Lys Tyr Ile Lys Pro Arg Cys
65                  70

<210> SEQ ID NO 174
<211> LENGTH: 64
<212> TYPE: PRT
<213> ORGANISM: Pseudogymnoascus pannorum

<400> SEQUENCE: 174

Val Thr Asn Pro Thr Thr Val Lys Cys Arg Ser Gly Pro Gly Thr Gln
1               5                   10                  15

Tyr Arg Ile Val Lys Thr Tyr Arg Ala Gly Asp Arg Glu Cys Tyr Ser
            20                  25                  30

Cys Tyr Glu Ser Gly Thr Cys Ile Asn Gly Asn Cys Ser Trp Asp Tyr
        35                  40                  45

Asn Tyr Met Asp Asn Cys Tyr Ile Ser Gly Tyr Tyr Thr Asp Ser Gly
    50                  55                  60

<210> SEQ ID NO 175
<211> LENGTH: 73
<212> TYPE: PRT
<213> ORGANISM: Pseudogymnoascus pannorum

<400> SEQUENCE: 175

Val Thr Ser Pro Thr Thr Val Lys Cys Arg Ser Gly Pro Gly Thr Gln
1               5                   10                  15

Tyr Lys Ile Val Lys Thr Tyr Pro Ala Ser Gly Arg Glu Cys Tyr Ser
            20                  25                  30

Cys Tyr Glu Ser Gly Thr Cys Ile Asn Gly Asn Cys Ser Trp Asp Tyr
```

```
                35                  40                  45
Asn Tyr Met Asp Asn Cys Tyr Ile Ser Gly Tyr Tyr Thr Gly Ser Ala
    50                  55                  60

Cys Thr Thr Ala Ala Leu Gly Lys Cys
65                  70

<210> SEQ ID NO 176
<211> LENGTH: 73
<212> TYPE: PRT
<213> ORGANISM: Pseudogymnoascus pannorum

<400> SEQUENCE: 176

Tyr Pro Ile Thr Gly Asn Thr Val Asn Cys Arg Ser Gly Pro Gly Thr
1               5                   10                  15

Asp Phe Pro Ile Lys Lys Thr Phe Ala Lys Gly Ser Ile Val Ser Ile
                20                  25                  30

Thr Cys Gln Thr Pro Gly Thr Lys Ile Asn Gly Asn Glu Ile Trp Asp
            35                  40                  45

Leu Thr Ser Asp Gly Cys Phe Val Ser Asp Phe Tyr Val Lys Thr Gly
    50                  55                  60

Ser Ile Thr Tyr Val Lys Pro Lys Cys
65                  70

<210> SEQ ID NO 177
<211> LENGTH: 73
<212> TYPE: PRT
<213> ORGANISM: Pseudogymnoascus pannorum

<400> SEQUENCE: 177

Tyr Pro Ile Thr Gly Thr Ser Val Asn Cys Arg Ser Gly Pro Ser Thr
1               5                   10                  15

Lys Phe Asp Val Val Arg Ser Tyr Val Leu Gly Asp Glu Val Thr Leu
                20                  25                  30

Thr Cys Gln Ile Ala Gly Glu Thr Val Thr Gly Asp Tyr Leu Trp Asp
            35                  40                  45

Leu Thr Thr Asp Gly Cys Tyr Val Ala Asp Tyr Phe Val Lys Thr Gly
    50                  55                  60

Thr Val Gly Met Val Thr Glu Ala Cys
65                  70

<210> SEQ ID NO 178
<211> LENGTH: 73
<212> TYPE: PRT
<213> ORGANISM: Pseudogymnoascus pannorum

<400> SEQUENCE: 178

Tyr Pro Ile Thr Gly Thr Val Asn Cys Arg Ser Gly Pro Ser Thr
1               5                   10                  15

Ser Tyr Asp Ile Ile Arg Ser Tyr Glu Leu Gly Asp Glu Val Asp Leu
                20                  25                  30

Thr Cys Gln Ile Ala Gly Glu Thr Val Thr Gly Asp Asn Leu Trp Asp
            35                  40                  45

Phe Thr Thr Asp Gly Cys Tyr Val Ala Asp Tyr Phe Val Lys Thr Gly
    50                  55                  60

Thr Phe Gly Met Val Val Asp Glu Cys
65                  70

<210> SEQ ID NO 179
```

```
<211> LENGTH: 74
<212> TYPE: PRT
<213> ORGANISM: Pseudogymnoascus pannorum

<400> SEQUENCE: 179

Tyr Pro Ile Ser Gly Asp Ser Val Asn Cys Arg Ser Gly Pro Ala Thr
1               5                   10                  15

Ser Tyr Lys Val Ile Lys Thr Tyr Ala Lys Gly His Asp Val Lys Val
            20                  25                  30

Thr Cys Gln Thr Val Gly Glu Thr Val Lys Gly Asp Asn Leu Trp Asp
        35                  40                  45

Lys Thr Ala Asp Gly Cys Tyr Val Ala Asp Tyr Tyr Val Lys Thr Gly
    50                  55                  60

Thr Thr Gly Arg Val Val Lys Thr Glu Cys
65                  70

<210> SEQ ID NO 180
<211> LENGTH: 73
<212> TYPE: PRT
<213> ORGANISM: Pseudogymnoascus pannorum

<400> SEQUENCE: 180

Tyr Pro Ile Thr Gly Thr Tyr Val Asn Cys Arg Thr Gly Pro Ser Thr
1               5                   10                  15

Ser Phe Asp Ile Val Arg Ser Tyr Glu Leu Gly Asp Glu Val Asp Leu
            20                  25                  30

Thr Cys Gln Ile Ala Gly Glu Thr Val Thr Gly Asp Asn Leu Trp Asp
        35                  40                  45

Phe Thr Thr Asp Gly Cys Tyr Val Ala Asp Tyr Phe Val Lys Thr Gly
    50                  55                  60

Thr Phe Gly Met Val Val Asp Glu Cys
65                  70

<210> SEQ ID NO 181
<211> LENGTH: 73
<212> TYPE: PRT
<213> ORGANISM: Pseudogymnoascus pannorum

<400> SEQUENCE: 181

Tyr Pro Ile Thr Gly Thr Tyr Val Asn Cys Arg Ser Gly Pro Ser Thr
1               5                   10                  15

Ser Phe Asp Ile Val Arg Ser Tyr Glu Leu Gly Asp Glu Val Ser Leu
            20                  25                  30

Thr Cys Gln Ile Ala Gly Glu Thr Val Glu Gly Asp Tyr Leu Trp Asp
        35                  40                  45

Leu Thr Thr Asp Gly Cys Tyr Val Ala Asp Tyr Phe Val Lys Thr Gly
    50                  55                  60

Thr Val Gly Met Val Ala Glu Glu Cys
65                  70

<210> SEQ ID NO 182
<211> LENGTH: 72
<212> TYPE: PRT
<213> ORGANISM: Pseudogymnoascus pannorum

<400> SEQUENCE: 182

Tyr Pro Ile Ser Gly Asp Ser Val Asn Cys Arg Ser Gly Pro Ala Thr
1               5                   10                  15

Ser Tyr Lys Val Ile Lys Thr Tyr Leu Lys Gly His Asp Val Asp Leu
```

```
            20                  25                  30
Thr Cys Gln Thr Val Gly Glu Thr Val Lys Gly Asp Ser Leu Trp Asp
         35                  40                  45

Lys Thr Thr Asp Gly Cys Tyr Val Ala Asp Tyr Tyr Val Lys Thr Gly
     50                  55                  60

Thr Thr Gly Arg Val Val Lys Lys
 65                  70

<210> SEQ ID NO 183
<211> LENGTH: 73
<212> TYPE: PRT
<213> ORGANISM: Pseudogymnoascus pannorum

<400> SEQUENCE: 183

Tyr Pro Ile Lys Gly Ser Val Val Asn Cys Arg Ser Gly Pro Gly Thr
 1               5                  10                  15

Asn Phe Ala Ile Val Lys Thr Phe Lys Lys Gly Asp Thr Val Asp Ile
             20                  25                  30

Thr Cys Gln Thr Pro Gly Thr Ser Ile Ser Gly Asn Ser Ile Trp Asp
         35                  40                  45

Leu Thr Pro Asp Asn Cys Phe Ile Thr Asp Tyr Tyr Val Lys Thr Gly
     50                  55                  60

Thr Gly Lys Tyr Ile Lys Pro Arg Cys
 65                  70

<210> SEQ ID NO 184
<211> LENGTH: 67
<212> TYPE: PRT
<213> ORGANISM: Pseudogymnoascus pannorum

<400> SEQUENCE: 184

Cys Arg Ser Gly Pro Gly Thr Gly Tyr Ser Val Ile Ala Thr Val Lys
 1               5                  10                  15

Lys Gly Ser Tyr Tyr Ser Phe Gly Cys Tyr Lys Thr Gly Thr Cys Val
             20                  25                  30

Ser Gly Asn Cys Thr Trp Asp Arg Ile Phe Trp Asp Gly Lys Ser Cys
         35                  40                  45

Tyr Val Ser Gly Tyr Tyr Thr Asp Ser Ala Cys Ser Ala Ser Ala Leu
     50                  55                  60

Gly Lys Cys
 65

<210> SEQ ID NO 185
<211> LENGTH: 73
<212> TYPE: PRT
<213> ORGANISM: Pseudogymnoascus pannorum

<400> SEQUENCE: 185

Tyr Pro Ile Thr Gly Thr Phe Val Asn Cys Arg Ser Gly Pro Ser Thr
 1               5                  10                  15

Lys Phe Asp Val Val Arg Ser Tyr Val Leu Gly Asp Glu Val Thr Leu
             20                  25                  30

Thr Cys Gln Ile Ala Gly Glu Thr Val Thr Gly Asp Tyr Leu Trp Asp
         35                  40                  45

Leu Thr Thr Asp Gly Cys Tyr Val Ala Asp Tyr Phe Val Lys Thr Gly
     50                  55                  60

Thr Val Gly Met Val Thr Glu Ala Cys
 65                  70
```

<210> SEQ ID NO 186
<211> LENGTH: 67
<212> TYPE: PRT
<213> ORGANISM: Pseudogymnoascus pannorum

<400> SEQUENCE: 186

Cys Arg Ser Gly Pro Gly Thr Gly Tyr Ser Val Ile Ala Thr Val Lys
1               5                   10                  15

Lys Gly Ser Tyr Tyr Ser Phe Gly Cys Tyr Lys Thr Gly Thr Cys Val
            20                  25                  30

Ser Gly Asn Cys Thr Trp Asp Arg Ile Phe Trp Asp Gly Lys Ser Cys
        35                  40                  45

Tyr Val Ser Gly Tyr Tyr Thr Asp Ser Ala Cys Ser Ala Ser Ala Leu
    50                  55                  60

Gly Lys Cys
65

<210> SEQ ID NO 187
<211> LENGTH: 73
<212> TYPE: PRT
<213> ORGANISM: Pseudogymnoascus pannorum

<400> SEQUENCE: 187

Tyr Pro Ile Thr Gly Thr Lys Val Asn Cys Arg Thr Gly Pro Ser Thr
1               5                   10                  15

Ser Phe Glu Ile Ile Arg Ser Tyr Lys Leu Gly Asp Glu Val Ser Leu
            20                  25                  30

Thr Cys Gln Ile Ala Gly Glu Thr Val Gln Gly Asn Tyr Leu Trp Asp
        35                  40                  45

Leu Thr Thr Asp Gly Cys Tyr Val Ala Asp Tyr Phe Val Lys Thr Gly
    50                  55                  60

Ser Asp Gly Met Val Thr Glu Gly Cys
65                  70

<210> SEQ ID NO 188
<211> LENGTH: 73
<212> TYPE: PRT
<213> ORGANISM: Aspergillus clavatus

<400> SEQUENCE: 188

Tyr Pro Ile Thr Gly Asp Gly Val Asn Cys Arg Ser Gly Pro Gly Thr
1               5                   10                  15

Ser Tyr Lys Val Val Lys Ser Tyr Pro Lys Gly His Gln Val Ser Ile
            20                  25                  30

Val Cys Gln Ala Thr Gly Thr Asp Val Lys Gly Asp Ser Leu Trp Asp
        35                  40                  45

Lys Thr Ser Asp Gly Cys Tyr Val Ala Asp Tyr Tyr Val Lys Thr Gly
    50                  55                  60

Thr Thr Gly Tyr Val Thr Lys His Cys
65                  70

<210> SEQ ID NO 189
<211> LENGTH: 73
<212> TYPE: PRT
<213> ORGANISM: Aspergillus clavatus

<400> SEQUENCE: 189

Tyr Pro Ile Thr Gly Asp Thr Val Asn Cys Arg Ser Gly Pro Gly Thr

```
                1               5                    10                  15
Ser His Ala Val Val Lys Ser Tyr Lys Lys Gly Glu Asp Val Lys Ile
                    20                  25                  30

Val Cys Gln Ala Pro Gly Thr Asp Val Lys Gly Glu Ser Ile Trp Asp
            35                  40                  45

Lys Thr Ser Asp Gly Cys Tyr Val Ala Asp Tyr Tyr Val Lys Thr Gly
        50                  55                  60

Thr Thr Gly Tyr Val Thr Lys Lys Cys
65                  70

<210> SEQ ID NO 190
<211> LENGTH: 73
<212> TYPE: PRT
<213> ORGANISM: Neosartorya fischeri

<400> SEQUENCE: 190

Tyr Pro Ile Thr Gly Asn Glu Val Asn Cys Arg Ala Gly Pro Ser Thr
1               5                   10                  15

Asn Asp Lys Val Val Lys Ser Tyr His Lys Gly Asp Asp Val Lys Leu
                    20                  25                  30

Ser Cys Gln Thr Tyr Gly Glu Asn Val Gln Gly Asn Ser Ile Trp Asp
            35                  40                  45

Lys Thr Thr Asp Gly Cys Tyr Val Ser Asp Phe Tyr Val Lys Thr Gly
        50                  55                  60

Ser Asn Ser Met Val Thr Lys Glu Cys
65                  70

<210> SEQ ID NO 191
<211> LENGTH: 73
<212> TYPE: PRT
<213> ORGANISM: Neosartorya fischeri

<400> SEQUENCE: 191

Tyr Pro Ile Thr Gly Asp Gly Val Asn Cys Arg Ser Gly Pro Gly Thr
1               5                   10                  15

Asn His Pro Val Val Lys Ser Tyr Pro Lys Gly His Asp Val Ser Ile
                    20                  25                  30

Val Cys Gln Ala Pro Gly Thr Asp Val Lys Gly Asp Lys Leu Trp Asp
            35                  40                  45

Lys Thr Ser Asp Gly Cys Tyr Val Ala Asp Tyr Tyr Val Lys Thr Gly
        50                  55                  60

Ser Thr Asp Tyr Val Thr Lys His Cys
65                  70

<210> SEQ ID NO 192
<211> LENGTH: 73
<212> TYPE: PRT
<213> ORGANISM: Neosartorya fischeri

<400> SEQUENCE: 192

Tyr Pro Ile Thr Gly Asp Gly Val Asn Cys Arg Ser Gly Pro Gly Thr
1               5                   10                  15

Asn His Pro Val Val Lys Ser Tyr Pro Lys Gly His Asp Val Ser Ile
                    20                  25                  30

Val Cys Gln Ala Pro Gly Thr Asp Val Lys Gly Asp Lys Leu Trp Asp
            35                  40                  45

Lys Thr Ser Asp Gly Cys Tyr Val Ala Asp Tyr Tyr Val Lys Thr Gly
        50                  55                  60
```

Ser Ser Asp Tyr Val Thr Lys His Cys
65                  70

<210> SEQ ID NO 193
<211> LENGTH: 73
<212> TYPE: PRT
<213> ORGANISM: Aspergillus terreus

<400> SEQUENCE: 193

Tyr Pro Ile Thr Gly Asp Gly Val Asn Cys Arg Ser Gly Pro Gly Thr
1               5                   10                  15

Ser His Ala Val Val Lys Ser Tyr Pro Lys Gly His Glu Ile Ser Ile
            20                  25                  30

Val Cys Gln Ala Ala Gly Thr Asp Val Lys Gly Asp Asn Leu Trp Asp
        35                  40                  45

Lys Thr Ser Asp Gly Cys Tyr Val Ala Asp Tyr Tyr Val Lys Thr Gly
    50                  55                  60

Ser Thr Gly Tyr Val Thr Lys His Cys
65                  70

<210> SEQ ID NO 194
<211> LENGTH: 64
<212> TYPE: PRT
<213> ORGANISM: Aspergillus terreus

<400> SEQUENCE: 194

Cys Arg Thr Gly Pro Ser Thr Asn Asp Gly Ile Thr Lys Thr Tyr Lys
1               5                   10                  15

Lys Gly Asp Asp Val Lys Leu Ser Cys Gln Thr Tyr Gly Glu Ser Ile
            20                  25                  30

Gln Gly Ser Thr Ile Trp Asp Lys Thr Thr Asp Gly Cys Tyr Val Ala
        35                  40                  45

Asp Tyr Tyr Val Lys Thr Gly Thr Ser Gly Met Val Thr Gly Glu Cys
    50                  55                  60

<210> SEQ ID NO 195
<211> LENGTH: 73
<212> TYPE: PRT
<213> ORGANISM: Aspergillus terreus

<400> SEQUENCE: 195

Tyr Thr Ile Thr Ala Asp Gly Val Asn Cys Arg Ser Gly Pro Gly Thr
1               5                   10                  15

Ser Asn Lys Ser Val Lys Thr Tyr Ala Lys Gly Thr Asp Val Lys Ile
            20                  25                  30

Ser Cys Gln Gln Ala Gly Glu Ser Ile Phe Gly Asn Ser Leu Trp Asp
        35                  40                  45

Lys Thr Ser Asp Gly Cys Tyr Val Ser Asp Tyr Tyr Val Lys Thr Gly
    50                  55                  60

Ser Thr Gly Tyr Val Thr Asp Lys Cys
65                  70

<210> SEQ ID NO 196
<211> LENGTH: 73
<212> TYPE: PRT
<213> ORGANISM: Chaetomium globosum

<400> SEQUENCE: 196

Tyr Pro Ile Thr Gly Ser Val Val Asn Cys Arg Ser Gly Pro Gly Thr

```
                1               5                  10                 15
Ser Tyr Ala Val Lys Lys Ser Tyr Ala Lys Gly Ala Asp Val Lys Ile
                20                 25                 30

Ser Cys Gln Thr Ser Gly Thr Ser Val Asn Gly Asn Asn Ile Trp Asp
                35                 40                 45

Lys Thr Gln Asp Gly Cys Tyr Val Ala Asp Tyr Tyr Val Lys Thr Gly
        50                 55                 60

Thr Asn Gly Tyr Val Thr Lys Lys Cys
65                  70
```

<210> SEQ ID NO 197
<211> LENGTH: 73
<212> TYPE: PRT
<213> ORGANISM: Chaetomium globosum

<400> SEQUENCE: 197

```
Tyr Pro Ile Thr Gly Ser Val Val Asn Cys Arg Ser Gly Pro Gly Thr
1               5                  10                 15

Ser Tyr Ala Val Lys Lys Ser Tyr Asn Lys Gly Ala Asp Val Thr Ile
                20                 25                 30

Ser Cys Gln Thr Thr Gly Thr Ser Val Asn Gly Asn Ser Ile Trp Asp
                35                 40                 45

Lys Thr Gln Asp Gly Cys Tyr Val Ala Asp Tyr Tyr Val Lys Thr Gly
        50                 55                 60

Thr Asn Gly Tyr Val Thr Lys Lys Cys
65                  70
```

<210> SEQ ID NO 198
<211> LENGTH: 73
<212> TYPE: PRT
<213> ORGANISM: Chaetomium globosum

<400> SEQUENCE: 198

```
Tyr Pro Ile Thr Gly Asn Asp Val Asn Cys Arg Ser Gly Pro Asp Thr
1               5                  10                 15

Ser Tyr Lys Ser Val Lys Thr Tyr Lys Lys Gly Ala Asp Val Lys Leu
                20                 25                 30

Thr Cys Gln Thr Tyr Gly Glu Ser Ile Asn Gly Asn Ala Ile Trp Asp
                35                 40                 45

Lys Thr Ser Asp Gly Cys Tyr Val Ser Asp Tyr Tyr Val Lys Thr Gly
        50                 55                 60

Ser Asn Ser Met Val Thr Lys Glu Cys
65                  70
```

<210> SEQ ID NO 199
<211> LENGTH: 73
<212> TYPE: PRT
<213> ORGANISM: Neosartorya fumigata

<400> SEQUENCE: 199

```
Tyr Pro Ile Thr Gly Asn Gly Val Asn Cys Arg Ala Gly Pro Ser Thr
1               5                  10                 15

Asn Asp Lys Val Ile Lys Ser Tyr Ala Lys Gly Thr Asp Val Lys Leu
                20                 25                 30

Ser Cys Gln Thr Tyr Gly Glu Asn Ile Asn Gly Asn Ser Ile Trp Asp
                35                 40                 45

Lys Thr Thr Asp Gly Cys Tyr Val Ala Asp Tyr Tyr Val Lys Thr Gly
        50                 55                 60
```

Ser Asn Ser Met Val Thr Lys Glu Cys
65                  70

<210> SEQ ID NO 200
<211> LENGTH: 73
<212> TYPE: PRT
<213> ORGANISM: Neosartorya fumigata

<400> SEQUENCE: 200

Tyr Pro Ile Thr Gly Asn Gly Val Asn Cys Arg Ser Gly Pro Gly Thr
1               5                   10                  15

Asn Tyr Pro Val Val Lys Ser Tyr Pro Lys Gly His Glu Val Ser Ile
            20                  25                  30

Val Cys Gln Ala Pro Gly Thr Asp Ile Lys Gly Asp Lys Leu Trp Asp
        35                  40                  45

Lys Thr Ser Asp Gly Cys Tyr Val Ala Asp Tyr Tyr Val Lys Thr Gly
    50                  55                  60

Thr Thr Gly Tyr Val Thr Lys His Cys
65                  70

<210> SEQ ID NO 201
<211> LENGTH: 73
<212> TYPE: PRT
<213> ORGANISM: Neosartorya fumigata

<400> SEQUENCE: 201

Tyr Pro Ile Thr Gly Asp Gly Val Asn Cys Arg Ser Gly Pro Gly Thr
1               5                   10                  15

Asn Tyr Pro Val Val Lys Ser Tyr Pro Lys Gly His Glu Val Ser Ile
            20                  25                  30

Val Cys Gln Ala Pro Gly Thr Asp Ile Lys Gly Asp Lys Leu Trp Asp
        35                  40                  45

Lys Thr Ser Asp Gly Cys Tyr Val Ala Asp Tyr Tyr Val Lys Thr Gly
    50                  55                  60

Thr Thr Asn Tyr Val Ala Lys His Cys
65                  70

<210> SEQ ID NO 202
<211> LENGTH: 73
<212> TYPE: PRT
<213> ORGANISM: Penicillium chrysogenum

<400> SEQUENCE: 202

Tyr Pro Ile Thr Gly Asp Ser Val Asn Cys Arg Ser Gly Pro Gly Thr
1               5                   10                  15

Thr His Ala Val Val Lys Ser Tyr Lys Lys Ala Gln Asp Val Thr Val
            20                  25                  30

Thr Cys Gln Thr Ala Gly Glu Ser Ile Phe Gly Asp Asn Leu Trp Asp
        35                  40                  45

Lys Thr Ser Asp Gly Cys Tyr Val Ala Asp Tyr Tyr Val Gln Thr Gly
    50                  55                  60

Thr Ser Asn Tyr Val Thr Thr Lys Cys
65                  70

<210> SEQ ID NO 203
<211> LENGTH: 73
<212> TYPE: PRT
<213> ORGANISM: Penicillium chrysogenum

<400> SEQUENCE: 203

Tyr Pro Ile Thr Ser Asp Gln Leu Asn Cys Arg Ser Gly Pro Ser Thr
1               5                   10                  15

Ser Asp Ser Val Val Lys Thr Tyr Lys Ser Gly Ala Asp Val Lys Val
                20                  25                  30

Ser Cys Gln Thr Tyr Gly Glu Ser Ile Asn Gly Asn Thr Ile Trp Asp
            35                  40                  45

Lys Thr Ser Asp Asn Cys Tyr Val Ala Asp Tyr Tyr Val Lys Thr Gly
        50                  55                  60

Ser Asp Ser Met Val Thr Glu Ser Cys
65                  70

<210> SEQ ID NO 204
<211> LENGTH: 73
<212> TYPE: PRT
<213> ORGANISM: Nectria haematococca

<400> SEQUENCE: 204

Tyr Pro Ile Thr Gly Asp Asp Val Arg Cys Arg Ser Gly Pro Gly Thr
1               5                   10                  15

Ser Tyr Ala Ile Lys Lys Thr Phe Lys Lys Gly Thr Asn Val Lys Ile
                20                  25                  30

Thr Cys Gln Thr Thr Gly Thr Asn Ile Lys Gly Asn Asn Ile Trp Asp
            35                  40                  45

Lys Val Ser Glu Gly Cys Tyr Val Ser Asp Tyr Tyr Val Lys Thr Gly
        50                  55                  60

Ser Ser Gly Phe Val Thr Lys Lys Cys
65                  70

<210> SEQ ID NO 205
<211> LENGTH: 73
<212> TYPE: PRT
<213> ORGANISM: Nectria haematococca

<400> SEQUENCE: 205

Tyr Pro Ile Thr Gly Asp Asp Val Lys Cys Arg Ser Gly Pro Gly Thr
1               5                   10                  15

Ser Tyr Ala Val Lys Lys Val Leu Lys Lys Gly Thr Asp Val Thr Ile
                20                  25                  30

Thr Cys Gln Thr Glu Gly Thr Asn Ile Ser Gly Asn Thr Ile Trp Asp
            35                  40                  45

Lys Ile Ser Asp Gly Cys Tyr Val Ser Asp Tyr Tyr Val Lys Thr Gly
        50                  55                  60

Ser Asn Gly Tyr Val Lys Pro Lys Cys
65                  70

<210> SEQ ID NO 206
<211> LENGTH: 73
<212> TYPE: PRT
<213> ORGANISM: Hypocrea jecorina

<400> SEQUENCE: 206

Tyr Pro Ile Thr Gly Asp Val Val Asn Cys Arg Thr Gly Pro Gly Thr
1               5                   10                  15

Ser Tyr Ala Ile Lys Thr Ser Tyr Lys Lys Ser His Asp Ile Ser Ile
                20                  25                  30

Ser Cys Gln Thr Thr Gly Thr Ser Val Asn Gly Asn Asn Ile Trp Asp
            35                  40                  45

```
Lys Thr Ala Asp Gly Cys Tyr Val Ala Asp Tyr Tyr Val Lys Thr Gly
        50                  55                  60

Ser Ser Gly Phe Val Thr Lys Lys Cys
65                  70

<210> SEQ ID NO 207
<211> LENGTH: 73
<212> TYPE: PRT
<213> ORGANISM: Thielavia terrestris

<400> SEQUENCE: 207

Tyr Ala Ile Thr Gly Asp Thr Val Asn Cys Arg Ser Gly Pro Gly Thr
1               5                   10                  15

Asn Tyr Ala Val Lys Lys Thr Tyr Ala Lys Gly His Asp Val Thr Leu
                20                  25                  30

Ser Cys Gln Thr Ser Gly Thr Val Asn Gly Asn Ser Ile Trp Asp
            35                  40                  45

Lys Thr Ser Asp Gly Cys Tyr Val Ser Asp Tyr Tyr Val Lys Thr Gly
        50                  55                  60

Ser Asn Ser Tyr Val Thr Lys Lys Cys
65                  70

<210> SEQ ID NO 208
<211> LENGTH: 74
<212> TYPE: PRT
<213> ORGANISM: Thielavia heterothallica

<400> SEQUENCE: 208

Tyr Pro Val Thr Ala Asn Gly Gly Leu Ser Cys Arg Ser Gly Pro Gly
1               5                   10                  15

Thr Ser Tyr Pro Val Lys Lys Thr Tyr Lys Lys Gly Phe Asp Ile Lys
                20                  25                  30

Ile Ser Cys Gln Thr Thr Gly Thr Ser Val Asn Gly Tyr Asn Ile Trp
            35                  40                  45

Asp Lys Thr Gln Asp Gly Cys Tyr Val Ser Asp Tyr Tyr Val Lys Thr
        50                  55                  60

Gly Lys Ser Gly Phe Val Thr Thr Lys Cys
65                  70

<210> SEQ ID NO 209
<211> LENGTH: 73
<212> TYPE: PRT
<213> ORGANISM: Hypocrea jecorina

<400> SEQUENCE: 209

Tyr Pro Ile Thr Gly Asp Thr Val Asn Cys Arg Ser Gly Pro Gly Thr
1               5                   10                  15

Ser Phe Ala Ile Lys Lys Thr Tyr Lys Lys Ser Gln Asp Val Ser Val
                20                  25                  30

Thr Cys Gln Thr Ser Gly Thr Ser Val Asn Gly Asn Ser Ile Trp Asp
            35                  40                  45

Lys Thr Ser Asp Gly Cys Tyr Val Ala Asp Tyr Tyr Val Lys Thr Gly
        50                  55                  60

Ser Ser Ser Tyr Val Thr Lys Lys Cys
65                  70

<210> SEQ ID NO 210
<211> LENGTH: 73
```

```
<212> TYPE: PRT
<213> ORGANISM: Chaetomium thermophilum

<400> SEQUENCE: 210

Tyr Pro Ile Thr Gly Glu Gly Val Asn Cys Arg Ser Gly Pro Gly Thr
1               5                   10                  15

Ser Tyr Lys Val Ile Lys Ser Tyr Lys Lys Gly Thr Asp Val Lys Ile
            20                  25                  30

Ser Cys Gln Ile Lys Gly Glu Ser Ile Asn Gly Asn Asn Leu Trp Asp
        35                  40                  45

Lys Thr Gln Asp Gly Cys Tyr Val Ser Asp Tyr Tyr Val Lys Thr Gly
    50                  55                  60

Ser Asn Ser Met Val Thr Lys Gln Cys
65                  70

<210> SEQ ID NO 211
<211> LENGTH: 73
<212> TYPE: PRT
<213> ORGANISM: Chaetomium thermophilum

<400> SEQUENCE: 211

Tyr Lys Ile Thr Gly Asn Asn Val Asn Cys Arg Ser Gly Pro Gly Thr
1               5                   10                  15

Ser Tyr Ser Val Lys Lys Thr Tyr Ala Lys Gly Thr Asp Val Lys Ile
            20                  25                  30

Thr Cys Gln Thr Thr Gly Thr Asn Ile Asn Gly Asn Asn Ile Trp Asp
        35                  40                  45

Lys Thr Ser Asp Gly Cys Tyr Val Ser Asp Tyr Tyr Val Lys Thr Gly
    50                  55                  60

Thr Asn Gly Tyr Val Thr Thr Lys Cys
65                  70

<210> SEQ ID NO 212
<211> LENGTH: 73
<212> TYPE: PRT
<213> ORGANISM: Fusarium oxysporum

<400> SEQUENCE: 212

Tyr Pro Ile Thr Gly Asn Asp Val Lys Cys Arg Ser Gly Pro Gly Thr
1               5                   10                  15

Ser Tyr Ala Val Lys Lys Val Leu Lys Gly Thr Asp Val Lys Ile
            20                  25                  30

Thr Cys Gln Thr Glu Gly Thr Asn Ile Ser Gly Asn Thr Ile Trp Asp
        35                  40                  45

Lys Ile Ser Asp Gly Cys Tyr Val Ser Asp Tyr Tyr Val Lys Thr Gly
    50                  55                  60

Ser Ser Gly Tyr Ile Lys Pro Lys Cys
65                  70

<210> SEQ ID NO 213
<211> LENGTH: 73
<212> TYPE: PRT
<213> ORGANISM: Thielavia heterothallica

<400> SEQUENCE: 213

Tyr Pro Ile Thr Gly Asp Asp Val Asn Cys Arg Thr Gly Pro Gly Thr
1               5                   10                  15

Ser Phe Lys Ser Val Lys Thr Tyr Pro Lys Gly Thr Asp Val Lys Leu
            20                  25                  30
```

```
Ser Cys Gln Thr Tyr Gly Glu Val Ile Phe Gly Asn Ser Ile Trp Asp
        35                  40                  45

Lys Thr Gln Asp Gly Cys Tyr Val Ser Asp Tyr Tyr Val Lys Thr Gly
 50                  55                  60

Ser Asn Asn Met Val Thr Gly Glu Cys
 65                  70

<210> SEQ ID NO 214
<211> LENGTH: 74
<212> TYPE: PRT
<213> ORGANISM: Thielavia heterothallica

<400> SEQUENCE: 214

Tyr Pro Val Thr Ala Asn Gly Gly Leu Ser Cys Arg Ser Gly Pro Gly
 1               5                  10                  15

Thr Ser Tyr Ala Val Lys Lys Thr Tyr Lys Lys Gly Phe Asp Val Lys
                 20                  25                  30

Ile Ser Cys Gln Thr Thr Gly Thr Ser Val Asn Gly Asn Asn Ile Trp
        35                  40                  45

Asp Lys Thr Gln Asp Gly Cys Tyr Val Ala Asp Tyr Tyr Val Lys Thr
 50                  55                  60

Gly Lys Asn Gly Phe Val Thr Ser Lys Cys
 65                  70

<210> SEQ ID NO 215
<211> LENGTH: 73
<212> TYPE: PRT
<213> ORGANISM: Hypocrea virens

<400> SEQUENCE: 215

Tyr Pro Ile Thr Gly Glu Ala Val Asn Cys Arg Thr Gly Pro Gly Thr
 1               5                  10                  15

Ser Phe Ala Ile Lys Lys Thr Tyr Lys Lys Ser Gln Asp Val Ser Val
                 20                  25                  30

Thr Cys Gln Thr Ser Gly Thr Ser Val Asn Gly Asn Ser Ile Trp Asp
        35                  40                  45

Lys Thr Ser Asp Gly Cys Tyr Val Ala Asp Tyr Tyr Val Lys Thr Gly
 50                  55                  60

Ser Ser Ser Tyr Val Thr Lys Lys Cys
 65                  70

<210> SEQ ID NO 216
<211> LENGTH: 73
<212> TYPE: PRT
<213> ORGANISM: Metarhizium robertsii

<400> SEQUENCE: 216

Tyr Pro Ile Thr Gly Thr Thr Val Asn Cys Arg Ser Gly Pro Ser Thr
 1               5                  10                  15

His Asp Lys Val Ile Lys Thr Tyr Asn Lys Gly Asn Asp Ile Lys Ile
                 20                  25                  30

Ser Cys Gln Val Ala Gly Glu Thr Val Ser Gly Asn Asn Leu Trp Asp
        35                  40                  45

Lys Thr Gln Asp Gly Cys Phe Val Ser Asp Tyr Tyr Val Lys Thr Gly
 50                  55                  60

Ser Asn Gly Met Val Thr Gly Gln Cys
 65                  70
```

<210> SEQ ID NO 217
<211> LENGTH: 73
<212> TYPE: PRT
<213> ORGANISM: Fusarium oxysporum

<400> SEQUENCE: 217

Tyr Pro Ile Thr Gly Asn Asp Val Lys Cys Arg Ser Gly Pro Gly Thr
1               5                   10                  15

Ser Tyr Ala Val Lys Lys Val Leu Lys Lys Gly Thr Asp Val Lys Ile
            20                  25                  30

Thr Cys Gln Thr Glu Gly Thr Asn Ile Ser Gly Asn Thr Ile Trp Asp
        35                  40                  45

Lys Ile Ser Asp Gly Cys Tyr Val Ser Asp Tyr Tyr Val Lys Thr Gly
    50                  55                  60

Ser Ser Gly Tyr Ile Lys Pro Lys Cys
65                  70

<210> SEQ ID NO 218
<211> LENGTH: 73
<212> TYPE: PRT
<213> ORGANISM: Chaetomium thermophilum

<400> SEQUENCE: 218

Tyr Ala Ile Thr Gly Asp Asn Val Asn Cys Arg Ser Gly Pro Gly Thr
1               5                   10                  15

Ser Tyr Ala Val Lys Lys Val Tyr Lys Lys Gly Thr Asp Val Lys Ile
            20                  25                  30

Ser Cys Gln Thr Thr Gly Thr Asn Ile Asn Gly Asn Asn Leu Trp Asp
        35                  40                  45

Lys Thr Ser Asp Gly Cys Tyr Val Ser Asp Tyr Tyr Val Lys Thr Gly
    50                  55                  60

Ser Asn Gly Tyr Val Thr Ser Lys Cys
65                  70

<210> SEQ ID NO 219
<211> LENGTH: 73
<212> TYPE: PRT
<213> ORGANISM: Thielavia terrestris

<400> SEQUENCE: 219

Tyr Pro Ile Thr Gly Asn Gly Val Asn Cys Arg Ser Gly Pro Gly Thr
1               5                   10                  15

Ser His Ala Val Lys Lys Val Tyr Ala Lys Gly Thr Asp Ile Lys Val
            20                  25                  30

Thr Cys Gln Thr Glu Gly Thr Ser Ile Asn Gly Asn Ser Ile Trp Asp
        35                  40                  45

Lys Thr Ser Asp Gly Cys Tyr Val Ala Asp Tyr Tyr Val Lys Thr Gly
    50                  55                  60

Ser Asn Ser Tyr Val Thr Lys Lys Cys
65                  70

<210> SEQ ID NO 220
<211> LENGTH: 73
<212> TYPE: PRT
<213> ORGANISM: Fusarium oxysporum

<400> SEQUENCE: 220

Tyr Pro Ile Thr Gly Asn Asp Val Lys Cys Arg Ser Gly Pro Gly Thr
1               5                   10                  15

Ser Tyr Ala Val Lys Lys Val Leu Lys Lys Gly Thr Asp Val Lys Ile
            20                  25                  30

Thr Cys Gln Thr Glu Gly Thr Asn Ile Ser Gly Asn Thr Ile Trp Asp
            35                  40                  45

Lys Thr Ser Asp Gly Cys Tyr Val Ser Asp Tyr Tyr Val Lys Thr Gly
    50                  55                  60

Ser Ser Gly Tyr Ile Lys Pro Lys Cys
65                  70

<210> SEQ ID NO 221
<211> LENGTH: 73
<212> TYPE: PRT
<213> ORGANISM: Fusarium oxysporum

<400> SEQUENCE: 221

Tyr Pro Ile Thr Gly Asn Asp Val Lys Cys Arg Ser Gly Pro Gly Thr
1               5                   10                  15

Ser Tyr Ala Val Lys Glu Val Leu Lys Lys Gly Thr Asp Val Lys Ile
            20                  25                  30

Thr Cys Gln Thr Glu Gly Thr Asn Ile Ser Gly Asn Thr Ile Trp Asp
            35                  40                  45

Lys Ile Ser Asp Gly Cys Tyr Val Ser Asp Tyr Tyr Val Lys Thr Gly
    50                  55                  60

Ser Ser Gly Tyr Ile Lys Pro Lys Cys
65                  70

<210> SEQ ID NO 222
<211> LENGTH: 73
<212> TYPE: PRT
<213> ORGANISM: Fusarium oxysporum

<400> SEQUENCE: 222

Phe Pro Ile Thr Gly Asn Thr Val Asn Cys Arg Ser Gly Pro Gly Thr
1               5                   10                  15

Ser Tyr Ser Val Lys Arg Thr Tyr Lys Lys Gly Gln Asp Val Ser Ile
            20                  25                  30

Thr Cys Gln Thr Tyr Gly Thr Asn Val Asn Gly Asn Ser Ile Trp Asp
            35                  40                  45

Lys Thr Ser Asp Gly Cys Tyr Val Ala Asp Tyr Tyr Val Lys Thr Gly
    50                  55                  60

Ser Asp Glu Phe Val Thr Lys Lys Cys
65                  70

<210> SEQ ID NO 223
<211> LENGTH: 73
<212> TYPE: PRT
<213> ORGANISM: Fusarium oxysporum

<400> SEQUENCE: 223

Tyr Pro Ile Thr Gly Asn Asp Val Lys Cys Arg Ser Gly Pro Gly Thr
1               5                   10                  15

Ser Tyr Ala Val Lys Lys Val Leu Lys Lys Gly Thr Asp Val Lys Ile
            20                  25                  30

Thr Cys Gln Thr Glu Gly Thr Asn Ile Ser Gly Asn Thr Ile Trp Asp
            35                  40                  45

Lys Ile Ser Asp Gly Cys Tyr Val Ser Asp Tyr Tyr Val Lys Thr Gly
    50                  55                  60

-continued

Ser Asn Gly Tyr Ile Lys Pro Lys Cys
65                  70

<210> SEQ ID NO 224
<211> LENGTH: 73
<212> TYPE: PRT
<213> ORGANISM: Fusarium oxysporum

<400> SEQUENCE: 224

Tyr Pro Ile Thr Gly Asn Asp Val Lys Cys Arg Ser Gly Pro Gly Thr
1               5                   10                  15

Ser Tyr Ala Val Lys Lys Val Leu Lys Lys Gly Thr Asp Val Lys Ile
                20                  25                  30

Thr Cys Gln Thr Glu Gly Thr Asn Ile Ser Gly Asn Thr Ile Trp Asp
            35                  40                  45

Lys Ile Ser Asp Gly Cys Tyr Val Ser Asp Tyr Tyr Val Lys Thr Gly
        50                  55                  60

Ser Ser Gly Tyr Ile Lys Pro Lys Cys
65                  70

<210> SEQ ID NO 225
<211> LENGTH: 73
<212> TYPE: PRT
<213> ORGANISM: Fusarium oxysporum

<400> SEQUENCE: 225

Tyr Pro Ile Thr Gly Asn Asp Val Lys Cys Arg Ser Gly Pro Gly Thr
1               5                   10                  15

Ser Tyr Ala Val Lys Lys Val Leu Lys Lys Gly Thr Asp Val Lys Ile
                20                  25                  30

Thr Cys Gln Thr Glu Gly Thr Asn Ile Ser Gly Asn Thr Ile Trp Asp
            35                  40                  45

Lys Ile Ser Asp Gly Cys Tyr Val Ser Asp Tyr Tyr Val Lys Thr Gly
        50                  55                  60

Ser Ser Gly Tyr Ile Lys Pro Lys Cys
65                  70

<210> SEQ ID NO 226
<211> LENGTH: 73
<212> TYPE: PRT
<213> ORGANISM: Fusarium oxysporum

<400> SEQUENCE: 226

Tyr Pro Ile Thr Gly Asn Asp Val Lys Cys Arg Ser Gly Pro Gly Thr
1               5                   10                  15

Ser Tyr Ala Val Lys Lys Val Leu Lys Lys Gly Thr Asp Val Lys Ile
                20                  25                  30

Thr Cys Gln Thr Glu Gly Thr Asn Ile Ser Gly Asn Thr Ile Trp Asp
            35                  40                  45

Lys Ile Ser Asp Gly Cys Tyr Val Ser Asp Tyr Tyr Val Lys Thr Gly
        50                  55                  60

Ser Ser Gly Tyr Ile Lys Pro Lys Cys
65                  70

<210> SEQ ID NO 227
<211> LENGTH: 73
<212> TYPE: PRT
<213> ORGANISM: Penicillium roqueforti

<400> SEQUENCE: 227

```
Tyr Pro Ile Thr Gly Asp Thr Val Asn Cys Arg Ser Gly Pro Gly Thr
1               5                   10                  15

Ser His Thr Val Val Lys Thr Tyr Lys Lys Ala His Asp Val Lys Ile
            20                  25                  30

Thr Cys Gln Thr Thr Gly Asp Ser Ile Ser Gly Asn Asn Ile Trp Asp
            35                  40                  45

Lys Thr Ser Asp Gly Cys Tyr Val Ala Asp Tyr Tyr Val Lys Thr Gly
        50                  55                  60

Ser Asn Ser Tyr Val Thr Ala Lys Cys
65              70

<210> SEQ ID NO 228
<211> LENGTH: 73
<212> TYPE: PRT
<213> ORGANISM: Penicillium roqueforti

<400> SEQUENCE: 228

Tyr Ala Ile Thr Ala Ser Val Ala Asn Cys Arg Thr Gly Pro Ser Thr
1               5                   10                  15

Ser Asn Ala Val Val Thr Thr Tyr Lys Lys Gly Ala Asp Val Lys Ile
            20                  25                  30

Thr Cys Gln Thr Tyr Gly Glu Asn Ile Gln Gly Asn Ser Ile Trp Asp
            35                  40                  45

Lys Thr Ser Asp Gly Cys Tyr Val Ala Asp Tyr Tyr Val Lys Thr Gly
        50                  55                  60

Ser Asn Ser Met Val Thr Lys Asp Cys
65              70

<210> SEQ ID NO 229
<211> LENGTH: 73
<212> TYPE: PRT
<213> ORGANISM: Trichoderma reesei

<400> SEQUENCE: 229

Tyr Pro Ile Thr Gly Asp Thr Val Asn Cys Arg Ser Gly Pro Gly Thr
1               5                   10                  15

Ser Phe Ala Ile Lys Lys Thr Tyr Lys Lys Ser Gln Asp Val Ser Val
            20                  25                  30

Thr Cys Gln Thr Ser Gly Thr Ser Val Asn Gly Asn Ser Ile Trp Asp
            35                  40                  45

Lys Thr Ser Asp Gly Cys Tyr Val Ala Asp Tyr Tyr Val Lys Thr Gly
        50                  55                  60

Ser Ser Ser Tyr Val Thr Lys Lys Cys
65              70

<210> SEQ ID NO 230
<211> LENGTH: 73
<212> TYPE: PRT
<213> ORGANISM: Metarhizium anisopliae

<400> SEQUENCE: 230

Tyr Pro Ile Thr Gly Thr Thr Val Asn Cys Arg Ser Gly Pro Ser Thr
1               5                   10                  15

His Asp Lys Val Ile Lys Thr Tyr Asn Lys Gly Asn Asp Ile Lys Ile
            20                  25                  30

Ser Cys Gln Val Ala Gly Glu Asn Val Ser Gly Asn Asn Leu Trp Asp
            35                  40                  45
```

```
Lys Thr Arg Asp Gly Cys Tyr Val Ser Asp Tyr Tyr Val Lys Thr Gly
 50                  55                  60

Ser Asn Gly Met Val Thr Gly Gln Cys
 65                  70

<210> SEQ ID NO 231
<211> LENGTH: 73
<212> TYPE: PRT
<213> ORGANISM: Pseudogymnoascus pannorum

<400> SEQUENCE: 231

Tyr Pro Ile Thr Gly Ser Thr Val Asn Cys Arg Ser Gly Pro Gly Thr
 1               5                  10                  15

Ser Tyr Ala Val Lys Lys Thr Tyr Lys Lys Gly Asp Ala Val Thr Ile
                20                  25                  30

Thr Cys Gln Lys Glu Gly Pro Val Val Ser Gly Asn Ser Ile Trp Asp
            35                  40                  45

Lys Thr Ser Asp Gly Cys Tyr Val Ala Asp Tyr Tyr Val Lys Thr Gly
 50                  55                  60

Ser Asn Gly Tyr Val Lys Pro Lys Cys
 65                  70

<210> SEQ ID NO 232
<211> LENGTH: 72
<212> TYPE: PRT
<213> ORGANISM: Pseudogymnoascus pannorum

<400> SEQUENCE: 232

Tyr Pro Ile Ser Gly Asp Ser Val Asn Cys Arg Ser Gly Pro Ala Thr
 1               5                  10                  15

Ser Tyr Lys Val Ile Lys Thr Tyr Lys Lys Gly His Asp Val Lys Ile
                20                  25                  30

Thr Cys Gln Thr Val Gly Glu Thr Ile Lys Gly Gly Asn Leu Trp Asp
            35                  40                  45

Lys Thr Ser Asp Gly Cys Tyr Val Thr Asp Tyr Tyr Val Lys Thr Gly
 50                  55                  60

Thr Thr Gly Arg Val Val Lys Lys
 65                  70

<210> SEQ ID NO 233
<211> LENGTH: 72
<212> TYPE: PRT
<213> ORGANISM: Pseudogymnoascus pannorum

<400> SEQUENCE: 233

Phe Pro Val Thr Ala Thr Val Asn Cys Arg Ser Gly Pro Gly Thr Gly
 1               5                  10                  15

Phe Ala Val Lys Lys Ser Tyr Thr Lys Gly His Ala Val Thr Ile Ser
                20                  25                  30

Cys Gln Thr Gly Gly Thr Ser Val Gln Gly Asn Ser Ile Trp Asp Lys
            35                  40                  45

Thr Ser Asp Gly Cys Tyr Val Ala Asp Tyr Tyr Val Lys Thr Gly Ser
 50                  55                  60

Ser Gly Tyr Val Lys Pro Lys Cys
 65                  70

<210> SEQ ID NO 234
<211> LENGTH: 73
<212> TYPE: PRT
```

<213> ORGANISM: Pseudogymnoascus pannorum

<400> SEQUENCE: 234

Phe Pro Ile Thr Gly Asp Thr Val Asn Cys Arg Ser Gly Pro Gly Thr
1               5                   10                  15

Ser Tyr Ala Val Lys Lys Ser Tyr Asn Lys Gly His Ser Val Thr Ile
            20                  25                  30

Thr Cys Gln Thr Gly Gly Thr Ser Val Lys Gly Asn Ser Ile Trp Asp
        35                  40                  45

Lys Thr Ser Asp Gly Cys Tyr Val Ala Asp Tyr Tyr Val Lys Thr Gly
    50                  55                  60

Ser Ser Gly Tyr Val Lys Pro Lys Cys
65                  70

<210> SEQ ID NO 235
<211> LENGTH: 73
<212> TYPE: PRT
<213> ORGANISM: Pseudogymnoascus pannorum

<400> SEQUENCE: 235

Phe Pro Ile Thr Gly Asp Ser Val Asn Cys Arg Ser Gly Pro Gly Thr
1               5                   10                  15

Ser Tyr Ala Val Lys Lys Ser Tyr Ala Lys Gly His Ser Val Thr Ile
            20                  25                  30

Thr Cys Gln Thr Gly Gly Thr Ser Val Asn Gly Asn Ser Ile Trp Asp
        35                  40                  45

Lys Thr Ser Asp Gly Cys Tyr Val Ala Asp Tyr Tyr Val Lys Thr Gly
    50                  55                  60

Ser Ser Gly Tyr Val Lys Pro Lys Cys
65                  70

<210> SEQ ID NO 236
<211> LENGTH: 73
<212> TYPE: PRT
<213> ORGANISM: Pseudogymnoascus pannorum

<400> SEQUENCE: 236

Tyr Pro Ile Asn Ala Ala Gly Val Asn Cys Arg Ser Gly Pro Gly Thr
1               5                   10                  15

Ser Tyr Ala Val Lys Lys Ser Tyr Ala Lys Asp His Ala Val Thr Val
            20                  25                  30

Thr Cys Gln Thr Ala Gly Thr Ser Val Asn Gly Asn Ser Ile Trp Asp
        35                  40                  45

Lys Thr Ser Asp Gly Cys Tyr Val Ala Asp Tyr Tyr Val Asn Thr Gly
    50                  55                  60

Ser Ser Gly Tyr Val Lys Pro Lys Cys
65                  70

<210> SEQ ID NO 237
<211> LENGTH: 73
<212> TYPE: PRT
<213> ORGANISM: Pseudogymnoascus pannorum

<400> SEQUENCE: 237

Tyr Pro Ile Asn Ala Ala Gly Val Asn Cys Arg Ser Gly Pro Gly Thr
1               5                   10                  15

Gly Tyr Ala Val Lys Lys Ser Tyr Ala Lys Asp His Ala Val Thr Val
            20                  25                  30

```
Thr Cys Gln Thr Ala Gly Thr Val Asn Gly Asn Ser Ile Trp Asp
            35                  40                  45

Lys Thr Ser Asp Gly Cys Tyr Val Ala Asp Tyr Val Asn Thr Gly
 50                  55                  60

Ser Ser Gly Tyr Val Lys Pro Lys Cys
 65                  70

<210> SEQ ID NO 238
<211> LENGTH: 73
<212> TYPE: PRT
<213> ORGANISM: Pseudogymnoascus pannorum

<400> SEQUENCE: 238

Tyr Pro Ile Thr Gly Thr Thr Val Asn Cys Arg Ser Gly Pro Gly Thr
 1               5                  10                  15

Ser Tyr Ala Val Lys Lys Thr Tyr Lys Lys Gly Asp Ala Val Thr Ile
                20                  25                  30

Thr Cys Gln Lys Glu Gly Pro Val Ile Ser Gly Asn Ser Ile Trp Asp
            35                  40                  45

Lys Thr Ser Asp Gly Cys Tyr Val Ala Asp Tyr Val Lys Thr Gly
 50                  55                  60

Ser Asn Gly Tyr Val Lys Pro Lys Cys
 65                  70

<210> SEQ ID NO 239
<211> LENGTH: 73
<212> TYPE: PRT
<213> ORGANISM: Pseudogymnoascus pannorum

<400> SEQUENCE: 239

Tyr Pro Ile Thr Gly Lys Thr Val Asn Cys Arg Ala Gly Pro Gly Thr
 1               5                  10                  15

Ser Tyr Pro Val Lys Lys Thr Tyr Ser Lys Gly Asp Thr Val Thr Ile
                20                  25                  30

Thr Cys Gln Thr Ser Gly Thr Lys Val

```
<210> SEQ ID NO 241
<211> LENGTH: 73
<212> TYPE: PRT
<213> ORGANISM: Pseudogymnoascus pannorum

<400> SEQUENCE: 241

Tyr Pro Ile Asn Thr Ala Gly Val Asn Cys Arg Ser Gly Pro Gly Thr
1               5                   10                  15

Ser Tyr Ala Val Lys Lys Ser Tyr Ala Lys Asp His Ala Val Thr Val
                20                  25                  30

Thr Cys Gln Thr Ala Gly Thr Ser Val Asn Gly Asn Ala Ile Trp Asp
            35                  40                  45

Lys Thr Ser Asp Gly Cys Tyr Val Ala Asp Tyr Tyr Val Asn Thr Gly
        50                  55                  60

Ser Asn Gly Tyr Val Lys Pro Lys Cys
65                  70

<210> SEQ ID NO 242
<211> LENGTH: 73
<212> TYPE: PRT
<213> ORGANISM: Pseudogymnoascus pannorum

<400> SEQUENCE: 242

Tyr Pro Ile Asn Ala Ala Gly Val Asn Cys Arg Ser Gly Pro Gly Thr
1               5                   10                  15

Gly Tyr Ala Val Lys Lys Ser Tyr Ala Lys Asp His Ala Val Thr Val
                20                  25                  30

Thr Cys Gln Thr Ala Gly Thr Ser Val Asn Gly Asn Ser Ile Trp Asp
            35                  40                  45

Lys Thr Ser Asp Gly Cys Tyr Val Ala Asp Tyr Tyr Val Asn Thr Gly
        50                  55                  60

Ser Ser Gly Tyr Val Lys Pro Lys Cys
65                  70

<210> SEQ ID NO 243
<211> LENGTH: 74
<212> TYPE: PRT
<213> ORGANISM: Pseudogymnoascus pannorum

<400> SEQUENCE: 243

Tyr Pro Ile Ser Gly Thr Ser Val Asn Cys Arg Ser Gly Pro Ala Thr
1               5                   10                  15

Ser Tyr Lys Val Ile Lys Ala Tyr Lys Lys Gly Gln Asp Val Lys Ile
                20                  25                  30

Thr Cys Gln Thr Val Gly Glu Thr Val Ser Gly Asp Asn

```
Ser Tyr Ala Val Lys Lys Ser Tyr Ala Lys Gly His Ser Val Thr Ile
            20                  25                  30

Thr Cys Gln Thr Gly Gly Thr Ser Val Asn Gly Asn Ser Ile Trp Asp
        35                  40                  45

Lys Thr Ser Asp Gly Cys Tyr Val Ala Asp Tyr Tyr Val Lys Thr Gly
    50                  55                  60

Ser Ser Gly Tyr Val Lys Pro Lys Cys
65                  70

<210> SEQ ID NO 245
<211> LENGTH: 73
<212> TYPE: PRT
<213> ORGANISM: Pseudogymnoascus pannorum

<400> SEQUENCE: 245

Phe Pro Ile Thr Gly Asp Thr Val Asn Cys Arg Ser Gly Pro Gly Thr
1               5                   10                  15

Ser Tyr Ala Val Lys Lys Ser Tyr Ala Lys Gly His Asp Val Thr Ile
            20                  25                  30

Thr Cys Gln Thr Gly Gly Thr Ser Val Ser Gly Asn Ser Ile Trp Asp
        35                  40                  45

Lys Thr Ser Asp Gly Cys Tyr Val Ala Asp Tyr Tyr Val Lys Thr Gly
    50                  55                  60

Ser Ser Gly Tyr Val Lys Pro Lys Cys
65                  70

<210> SEQ ID NO 246
<211> LENGTH: 64
<212> TYPE: PRT
<213> ORGANISM: Pseudogymnoascus pannorum

<400> SEQUENCE: 246

Tyr Pro Ile Thr Gly Lys Thr Val Asn Cys Arg Ala Gly Pro Gly Thr
1               5                   10                  15

Ser Tyr Pro Val Lys Lys Thr Tyr Ser Lys Gly Asp Thr Val Thr Ile
            20                  25                  30

Thr Cys Gln Thr Ser Gly Thr Lys Val Asn Gly Asn Ala Ile Trp Asp
        35                  40                  45

Leu Thr Ser Asp Gly Cys Tyr Leu Thr Asp Tyr Tyr Val Lys Thr Gly
    50                  55                  60

<210> SEQ ID NO 247
<211> LENGTH: 73
<212> TYPE: PRT
<213> ORGANISM: Pseudogymnoascus pannorum

<400> SEQUENCE: 247

Phe Pro Ile Thr Gly Asp Ser Val Asn Cys Arg Ser Gly Pro Gly Thr
1               5                   10                  15

Ser Tyr Ala Val Lys Lys Ser Tyr Ala Lys Gly His Asp Val Thr Ile
            20                  25                  30

Thr Cys Gln Thr Gly Gly Thr Ser Val Ser Gly Asn Ser Ile Trp Asp
        35                  40                  45

Lys Thr Ser Asp Gly Cys Tyr Val Ala Asp Tyr Tyr Val Lys Thr Gly
    50                  55                  60

Ser Ser Gly Tyr Val Lys Pro Lys Cys
65                  70
```

<210> SEQ ID NO 248
<211> LENGTH: 72
<212> TYPE: PRT
<213> ORGANISM: Pseudogymnoascus pannorum

<400> SEQUENCE: 248

Phe Pro Val Thr Glu Thr Val Asn Cys Arg Ser Gly Pro Gly Thr Ser
1               5                   10                  15

Tyr Gly Val Lys Lys Ser Tyr Thr Lys Gly His Ala Val Thr Ile Ser
            20                  25                  30

Cys Gln Thr Gly Gly Thr Ser Val Lys Gly Asn Ser Ile Trp Asp Lys
        35                  40                  45

Thr Ser Asp Gly Cys Tyr Val Ala Asp Tyr Tyr Val Lys Thr Gly Ser
    50                  55                  60

Asn Gly Tyr Val Lys Pro Lys Cys
65                  70

<210> SEQ ID NO 249
<211> LENGTH: 72
<212> TYPE: PRT
<213> ORGANISM: Pseudogymnoascus pannorum

<400> SEQUENCE: 249

Phe Pro Val Thr Ala Thr Val Asn Cys Arg Ser Gly Pro Gly Thr Gly
1               5                   10                  15

Tyr Ala Val Lys Lys Ser Tyr Thr Lys Gly Asn Ala Val Thr Ile Ser
            20                  25                  30

Cys Gln Thr Gly Gly Thr Ser Val Asn Gly Asn Ser Ile Trp Asp Lys
        35                  40                  45

Thr Ser Asp Gly Cys Tyr Val Ala Asp Tyr Tyr Val Lys Thr Gly Ser
    50                  55                  60

Ser Gly Tyr Val Lys Pro Lys Cys
65                  70

<210> SEQ ID NO 250
<211> LENGTH: 73
<212> TYPE: PRT
<213> ORGANISM: Pseudogymnoascus pannorum

<400> SEQUENCE: 250

Tyr Pro Ile Asn Ala Ala Gly Val Asn Cys Arg Ser Gly Pro Gly Thr
1               5                   10                  15

Ser Tyr Ala Val Lys Lys Ser Tyr Ala Lys Asp His Ala Val Thr Val
            20                  25                  30

Thr Cys Gln Thr Ala Gly Thr Ser Val Asn Gly Asn Ala Ile Trp Asp
        35                  40                  45

Lys Thr Ser Asp Gly Cys Tyr Val Ala Asp Tyr Tyr Val Asn Thr Gly
    50                  55                  60

Ser Asn Gly Tyr Val Lys Pro Lys Cys
65                  70

<210> SEQ ID NO 251
<211> LENGTH: 73
<212> TYPE: PRT
<213> ORGANISM: Pseudogymnoascus pannorum

<400> SEQUENCE: 251

Phe Pro Ile Thr Gly Ala Thr Val Asn Cys Arg Ser Gly Pro Gly Thr
1               5                   10                  15

```
Ser Tyr Ala Val Lys Lys Ser Tyr Ala Lys Gly His Asp Val Thr Ile
            20                  25                  30

Thr Cys Gln Thr Gly Gly Thr Ser Val Asn Gly Asn Ser Ile Trp Asp
        35                  40                  45

Lys Thr Ser Asp Gly Cys Tyr Val Ala Asp Tyr Tyr Val Lys Thr Gly
    50                  55                  60

Ser Ser Gly Tyr Val Lys Pro Lys Cys
65                  70
```

<210> SEQ ID NO 252
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: NON_CONS
<222> LOCATION: (1)..(1)
<223> OTHER INFORMATION: The amino acid in position 1 of the conserved
      motif is alanine, serine or threonine.
<220> FEATURE:
<221> NAME/KEY: NON_CONS
<222> LOCATION: (2)..(2)
<223> OTHER INFORMATION: The amino acid in position 2 of the conserved
      motif is Valine, Isoleucine or Leucine
<220> FEATURE:
<221> NAME/KEY: NON_CONS
<222> LOCATION: (3)..(3)
<223> OTHER INFORMATION: The amino acid in position 3 of the conserved
      motif is alanine, cysteine or glycine.
<220> FEATURE:
<221> NAME/KEY: NON_CONS
<222> LOCATION: (4)..(4)
<223> OTHER INFORMATION: The amino acid in position 4 of the conserved
      motif is isoleucine, phenylalanine or tyrosine.
<220> FEATURE:
<221> NAME/KEY: NON_CONS
<222> LOCATION: (7)..(7)
<223> OTHER INFORMATION: The amino acid in position 7 of the conserved
      motif is any amino acid.
<220> FEATURE:
<221> NAME/KEY: NON_CONS
<222> LOCATION: (8)..(8)
<223> OTHER INFORMATION: The amino acid in position 8 of the conserved
      motif is alanine, cysteine, isoleucine, valine or tyrosine.

<400> SEQUENCE: 252

```
Xaa Xaa Xaa Xaa Gly His Xaa Xaa
1               5
```

<210> SEQ ID NO 253
<211> LENGTH: 15
<212> TYPE: PRT
<213> ORGANISM: Artificial Sequence
<220> FEATURE:
<223> OTHER INFORMATION: Synthetic construct
<220> FEATURE:
<221> NAME/KEY: NON_CONS
<222> LOCATION: (1)..(1)
<223> OTHER INFORMATION: The amino acid in position 1 of the conserved
      motif is leucine or valine.
<220> FEATURE:
<221> NAME/KEY: NON_CONS
<222> LOCATION: (2)..(2)
<223> OTHER INFORMATION: The amino acid in position 2 of the conserved
      motif is asparagine, aspartic acid, serine or threonine.
<220> FEATURE:
<221> NAME/KEY: NON_CONS
<222> LOCATION: (3)..(3)
<223> OTHER INFORMATION: The amino acid in position 3 of the conserved
      motif is any amino acid.
<220> FEATURE:
<221> NAME/KEY: NON_CONS

```
<222> LOCATION: (5)..(5)
<223> OTHER INFORMATION: The amino acid in position 5 of the conserved
      motif is glutamic acid or glutamine.
<220> FEATURE:
<221> NAME/KEY: NON_CONS
<222> LOCATION: (6)..(6)
<223> OTHER INFORMATION: The amino acid in position 6 of the conserved
      motif is phenylalanine, tyrosine or tryptophan.
<220> FEATURE:
<221> NAME/KEY: NON_CONS
<222> LOCATION: (7)..(7)
<223> OTHER INFORMATION: The amino acid in position 7 of the conserved
      motif is alanine, aspartic acid, asparagine, glycine or serine.
<220> FEATURE:
<221> NAME/KEY: NON_CONS
<222> LOCATION: (10)..(10)
<223> OTHER INFORMATION: The amino acid in position 10 of the conserved
      motif is any amino acid.
<220> FEATURE:
<221> NAME/KEY: NON_CONS
<222> LOCATION: (12)..(12)
<223> OTHER INFORMATION: The amino acid in position 12 of the conserved
      motif is leucine, phenylalanine, tyrosine or tryptophan.
<220> FEATURE:
<221> NAME/KEY: NON_CONS
<222> LOCATION: (13)..(13)
<223> OTHER INFORMATION: The amino acid in position 13 of the conserved
      motif is any amino acid.
<220> FEATURE:
<221> NAME/KEY: NON_CONS
<222> LOCATION: (14)..(14)
<223> OTHER INFORMATION: The amino acid in position 14 of the conserved
      motif is phenylalanine or tyrosine.

<400> SEQUENCE: 253

Xaa Xaa Xaa Asn Xaa Xaa Xaa Ala Leu Xaa Ser Xaa Xaa Xaa Asn
1               5                   10                  15

<210> SEQ ID NO 254
<211> LENGTH: 11
<212> TYPE: PRT
<213> ORGANISM: Artificial Sequence
<220> FEATURE:
<223> OTHER INFORMATION: Synthetic construct
<220> FEATURE:
<221> NAME/KEY: NON_CONS
<222> LOCATION: (1)..(1)
<223> OTHER INFORMATION: The amino acid in position 1 of the conserved
      motif is cysteine, glycine or tyrosine.
<220> FEATURE:
<221> NAME/KEY: NON_CONS
<222> LOCATION: (2)..(2)
<223> OTHER INFORMATION: The amino acid in position 2 of the conserved
      motif is phenylalanine or tyrosine.
<220> FEATURE:
<221> NAME/KEY: NON_CONS
<222> LOCATION: (3)..(3)
<223> OTHER INFORMATION: The amino acid in position 3 of the conserved
      motif is valine, isoleucine or leucine.
<220> FEATURE:
<221> NAME/KEY: NON_CONS
<222> LOCATION: (4)..(4)
<223> OTHER INFORMATION: The amino acid in position 4 of the conserved
      motif is alanine, proline, serine or threonine.
<220> FEATURE:
<221> NAME/KEY: NON_CONS
<222> LOCATION: (5)..(5)
<223> OTHER INFORMATION: The amino acid in position 5 of the conserved
      motif is aspartic acid or glycine.
<220> FEATURE:
<221> NAME/KEY: NON_CONS
<222> LOCATION: (6)..(6)
<223> OTHER INFORMATION: The amino acid in position 6 of the conserved
      motif is any amino acid.
<220> FEATURE:
<221> NAME/KEY: NON_CONS
<222> LOCATION: (7)..(7)
```

<223> OTHER INFORMATION: The amino acid in position 7 of the conserved
motif is phenylalanine or tyrosine.
<220> FEATURE:
<221> NAME/KEY: NON_CONS
<222> LOCATION: (8)..(8)
<223> OTHER INFORMATION: The amino acid in position 8 of the conserved
motif is isoleucine, threonine or valine..
<220> FEATURE:
<221> NAME/KEY: NON_CONS
<222> LOCATION: (9)..(9)
<223> OTHER INFORMATION: The amino acid in position 9 of the conserved
motif is any amino acid.
<220> FEATURE:
<221> NAME/KEY: NON_CONS
<222> LOCATION: (10)..(10)
<223> OTHER INFORMATION: The amino acid in position 10 of the conserved
motif is serine or threonine.
<220> FEATURE:
<221> NAME/KEY: NON_CONS
<222> LOCATION: (11)..(11)
<223> OTHER INFORMATION: The amino acid in position 11 of the conserved
motif is alanine, glycine or asparagine.

<400> SEQUENCE: 254

Xaa Xaa Xaa Xaa Xaa Xaa Xaa Xaa Xaa Xaa Xaa
1               5                   10

<210> SEQ ID NO 255
<211> LENGTH: 946
<212> TYPE: DNA
<213> ORGANISM: Trichophaea saccata
<220> FEATURE:
<221> NAME/KEY: CDS
<222> LOCATION: (1)..(347)
<220> FEATURE:
<221> NAME/KEY: sig_peptide
<222> LOCATION: (1)..(51)
<220> FEATURE:
<221> NAME/KEY: mat_peptide
<222> LOCATION: (52)..(943)
<220> FEATURE:
<221> NAME/KEY: CDS
<222> LOCATION: (401)..(615)
<220> FEATURE:
<221> NAME/KEY: CDS
<222> LOCATION: (668)..(772)
<220> FEATURE:
<221> NAME/KEY: CDS
<222> LOCATION: (825)..(943)

<400> SEQUENCE: 255

| | | |
|---|---|---|
| atg cac gct ctc acc ctt ctc acc gca acc ctc ttc ggt ctc gca gcg<br>Met His Ala Leu Thr Leu Leu Thr Ala Thr Leu Phe Gly Leu Ala Ala<br>     -15            -10              -5 | | 48 |
| gcc tac cca gtg aag acc gac ctt cac tgc cgc tcc tct ccc agc act<br>Ala Tyr Pro Val Lys Thr Asp Leu His Cys Arg Ser Ser Pro Ser Thr<br>-1  1           5                 10             15 | | 96 |
| tcc gcc agc atc gtc cgc acc tac tcc agt gga acg gaa gtc cag atc<br>Ser Ala Ser Ile Val Arg Thr Tyr Ser Ser Gly Thr Glu Val Gln Ile<br>            20                25               30 | | 144 |
| cag tgc cag acc acg ggc act tcg gtc caa gga tcc aat gtc tgg gac<br>Gln Cys Gln Thr Thr Gly Thr Ser Val Gln Gly Ser Asn Val Trp Asp<br>        35                40               45 | | 192 |
| aag acc cag cac ggt tgc tac gtc gca gac tac tac gtc aag acc ggg<br>Lys Thr Gln His Gly Cys Tyr Val Ala Asp Tyr Tyr Val Lys Thr Gly<br>    50                55               60 | | 240 |
| cat tct ggg att ttc acc acc aag tgc ggt agc agc tcg ggt gga ggt<br>His Ser Gly Ile Phe Thr Thr Lys Cys Gly Ser Ser Ser Gly Gly Gly<br>65                  70               75 | | 288 |
| tcc tgc aag cct ccc ccg atc aat gct gct act gtc gca ttg atc aag | | 336 |

```
Ser Cys Lys Pro Pro Pro Ile Asn Ala Ala Thr Val Ala Leu Ile Lys
 80                  85                  90                  95 gag ttt gag gg  gtaagtgaca gctctgagtg aggtggtatg aggattaaga            387
Glu Phe Glu Gly ctgacgagga tag a ttc gtt cct aag ccc gcc ccg gat cct att gga ttg       437
                 Phe Val Pro Lys Pro Ala Pro Asp Pro Ile Gly Leu
                             100                 105                 110 ccg acc gtg gga tac ggg cat ctt tgc aag act aag ggc tgc aaa gaa        485
Pro Thr Val Gly Tyr Gly His Leu Cys Lys Thr Lys Gly Cys Lys Glu
                115                 120                 125 gtg cct tac agc ttc cct ctc acc cag gag act gcc acc aag ttg ctt        533
Val Pro Tyr Ser Phe Pro Leu Thr Gln Glu Thr Ala Thr Lys Leu Leu
    130                 135                 140 cag agc gat atc aag act ttc acc tct tgc gtt agc aac tac gtc aag        581
Gln Ser Asp Ile Lys Thr Phe Thr Ser Cys Val Ser Asn Tyr Val Lys
145                 150                 155 gac tct gtt aag ctc aac gat aac cag tac gga g gtgagttcca               625
Asp Ser Val Lys Leu Asn Asp Asn Gln Tyr Gly
160                 165                 170 gtgtaacagt gaatttattg atgatattct aagtaatttt ag ct  ctg gcg tct         678
                                                  Ala Leu Ala Ser tgg gct ttc aac gtc ggc tgc gga aac gtc cag act tct tcg ctg atc        726
Trp Ala Phe Asn Val Gly Cys Gly Asn Val Gln Thr Ser Ser Leu Ile
175                 180                 185                 190 aag aga ttg aac gct ggg gag aac cct aac act gtc gct gct cag g          772
Lys Arg Leu Asn Ala Gly Glu Asn Pro Asn Thr Val Ala Ala Gln
                195                 200                 205 gtaagatatt tatcccggat ttgctcttga cacatggctg aaaaagttgc ag aa  ctc      829
                                                             Glu Leu ccc aag tgg aag tac gct ggt gga aag gtt atg cct ggc ttg gtc cgc        877
Pro Lys Trp Lys Tyr Ala Gly Gly Lys Val Met Pro Gly Leu Val Arg
        210                 215                 220 cgc cgc aat gct gag gtc gcg ctc ttc aag aag ccc agc agc gtt cag        925
Arg Arg Asn Ala Glu Val Ala Leu Phe Lys Lys Pro Ser Ser Val Gln
    225                 230                 235 gcc cac cct ccc aag tgc taa                                            946
Ala His Pro Pro Lys Cys
240                 245

<210> SEQ ID NO 256
<211> LENGTH: 262
<212> TYPE: PRT
<213> ORGANISM: Trichophaea saccata

<400> SEQUENCE: 256

Met His Ala Leu Thr Leu Leu Thr Ala Thr Leu Phe Gly Leu Ala Ala
        -15                 -10                 -5

Ala Tyr Pro Val Lys Thr Asp Leu His Cys Arg Ser Ser Pro Ser Thr
 -1  1               5                  10                  15

Ser Ala Ser Ile Val Arg Thr Tyr Ser Ser Gly Thr Glu Val Gln Ile
                20                  25                  30

Gln Cys Gln Thr Thr Gly Thr Ser Val Gln Gly Ser Asn Val Trp Asp
            35                  40                  45

Lys Thr Gln His Gly Cys Tyr Val Ala Asp Tyr Tyr Val Lys Thr Gly
        50                  55                  60

His Ser Gly Ile Phe Thr Thr Lys Cys Gly Ser Ser Gly Gly Gly
    65                  70                  75

Ser Cys Lys Pro Pro Pro Ile Asn Ala Ala Thr Val Ala Leu Ile Lys
```

```
                80                  85                  90                  95

Glu Phe Glu Gly Phe Val Pro Lys Pro Ala Pro Asp Pro Ile Gly Leu
                        100                 105                 110

Pro Thr Val Gly Tyr Gly His Leu Cys Lys Thr Lys Gly Cys Lys Glu
                        115                 120                 125

Val Pro Tyr Ser Phe Pro Leu Thr Gln Glu Thr Ala Thr Lys Leu Leu
                        130                 135                 140

Gln Ser Asp Ile Lys Thr Phe Thr Ser Cys Val Ser Asn Tyr Val Lys
                        145                 150                 155

Asp Ser Val Lys Leu Asn Asp Asn Gln Tyr Gly Ala Leu Ala Ser Trp
        160                 165                 170                 175

Ala Phe Asn Val Gly Cys Gly Asn Val Gln Thr Ser Ser Leu Ile Lys
                        180                 185                 190

Arg Leu Asn Ala Gly Glu Asn Pro Asn Thr Val Ala Ala Gln Glu Leu
                        195                 200                 205

Pro Lys Trp Lys Tyr Ala Gly Gly Lys Val Met Pro Gly Leu Val Arg
                        210                 215                 220

Arg Arg Asn Ala Glu Val Ala Leu Phe Lys Lys Pro Ser Ser Val Gln
                        225                 230                 235

Ala His Pro Pro Lys Cys
        240                 245

<210> SEQ ID NO 257
<211> LENGTH: 245
<212> TYPE: PRT
<213> ORGANISM: Trichophaea saccata
<220> FEATURE:
<221> NAME/KEY: mat_peptide
<222> LOCATION: (1)..(245)

<400> SEQUENCE: 257

Tyr Pro Val Lys Thr Asp Leu His Cys Arg Ser Ser Pro Ser Thr Ser
        1               5                   10                  15

Ala Ser Ile Val Arg Thr Tyr Ser Ser Gly Thr Glu Val Gln Ile Gln
                        20                  25                  30

Cys Gln Thr Thr Gly Thr Ser Val Gln Gly Ser Asn Val Trp Asp Lys
                        35                  40                  45

Thr Gln His Gly Cys Tyr Val Ala Asp Tyr Tyr Val Lys Thr Gly His
                        50                  55                  60

Ser Gly Ile Phe Thr Thr Lys Cys Gly Ser Ser Gly Gly Gly Ser
        65                  70                  75                  80

Cys Lys Pro Pro Ile Asn Ala Ala Thr Val Ala Leu Ile Lys Glu
                        85                  90                  95

Phe Glu Gly Phe Val Pro Lys Pro Ala Pro Asp Pro Ile Gly Leu Pro
                        100                 105                 110

Thr Val Gly Tyr Gly His Leu Cys Lys Thr Lys Gly Cys Lys Glu Val
                        115                 120                 125

Pro Tyr Ser Phe Pro Leu Thr Gln Glu Thr Ala Thr Lys Leu Leu Gln
                        130                 135                 140

Ser Asp Ile Lys Thr Phe Thr Ser Cys Val Ser Asn Tyr Val Lys Asp
        145                 150                 155                 160

Ser Val Lys Leu Asn Asp Asn Gln Tyr Gly Ala Leu Ala Ser Trp Ala
                        165                 170                 175

Phe Asn Val Gly Cys Gly Asn Val Gln Thr Ser Ser Leu Ile Lys Arg
                        180                 185                 190
```

Leu Asn Ala Gly Glu Asn Pro Asn Thr Val Ala Ala Gln Glu Leu Pro
            195                 200                 205

Lys Trp Lys Tyr Ala Gly Gly Lys Val Met Pro Gly Leu Val Arg Arg
210                 215                 220

Arg Asn Ala Glu Val Ala Leu Phe Lys Lys Pro Ser Ser Val Gln Ala
225                 230                 235                 240

His Pro Pro Lys Cys
                245

<210> SEQ ID NO 258
<211> LENGTH: 39
<212> TYPE: DNA
<213> ORGANISM: Artificial Sequence
<220> FEATURE:
<223> OTHER INFORMATION: Synthetic construct

<400> SEQUENCE: 258
acacaactgg ggatccacca tgcacgctct cacccttct                          39

<210> SEQ ID NO 259
<211> LENGTH: 38
<212> TYPE: DNA
<213> ORGANISM: Artificial Sequence
<220> FEATURE:
<223> OTHER INFORMATION: Synthetic construct

<400> SEQUENCE: 259
ctagatctcg agaagctttt agcacttggg agggtggg                           38

<210> SEQ ID NO 260
<211> LENGTH: 20
<212> TYPE: DNA
<213> ORGANISM: Artificial Sequence
<220> FEATURE:
<223> OTHER INFORMATION: Synthetic construct

<400> SEQUENCE: 260
gcaagggatg ccatgcttgg                                               20

<210> SEQ ID NO 261
<211> LENGTH: 19
<212> TYPE: DNA
<213> ORGANISM: Artificial Sequence
<220> FEATURE:
<223> OTHER INFORMATION: Synthetic construct

<400> SEQUENCE: 261
catataacca attgccctc                                                19

<210> SEQ ID NO 262
<211> LENGTH: 923
<212> TYPE: DNA
<213> ORGANISM: Chaetomium thermophilum
<220> FEATURE:
<221> NAME/KEY: CDS
<222> LOCATION: (1)..(367)
<220> FEATURE:
<221> NAME/KEY: sig_peptide
<222> LOCATION: (1)..(54)
<220> FEATURE:
<221> NAME/KEY: mat_peptide
<222> LOCATION: (55)..(920)
<220> FEATURE:
<221> NAME/KEY: CDS
<222> LOCATION: (425)..(555)
<220> FEATURE:
<221> NAME/KEY: CDS -continued

<222> LOCATION: (630)..(920)

<400> SEQUENCE: 262

```
atg aag ttc gcc atc ctc gcc gcc gtt gcc tcc ttc ctt gct ccc gcc      48
Met Lys Phe Ala Ile Leu Ala Ala Val Ala Ser Phe Leu Ala Pro Ala
        -15                 -10                 -5 agc gcc tat gcc att acc ggc gac aac gtc aac tgt cgc agc ggc cca      96
Ser Ala Tyr Ala Ile Thr Gly Asp Asn Val Asn Cys Arg Ser Gly Pro
    -1  1               5                   10 ggc act agc tac gcg gtc aag aag gtc tac aag aag ggc acc gac gtc     144
Gly Thr Ser Tyr Ala Val Lys Lys Val Tyr Lys Lys Gly Thr Asp Val
15                  20                  25                  30 aag atc agc tgc cag act act ggc acc aat atc aac ggc aac aat ctt     192
Lys Ile Ser Cys Gln Thr Thr Gly Thr Asn Ile Asn Gly Asn Asn Leu
                35                  40                  45 tgg gac aag acc tct gac ggc tgc tat gtt tcg gac tat tac gtc aag     240
Trp Asp Lys Thr Ser Asp Gly Cys Tyr Val Ser Asp Tyr Tyr Val Lys
            50                  55                  60 act ggc agc aac ggc tat gtg acc agc aag tgc agc tct agt gga ggc     288
Thr Gly Ser Asn Gly Tyr Val Thr Ser Lys Cys Ser Ser Ser Gly Gly
        65                  70                  75 agc acc tgc gct gcg cca aag tct aac caa gcc act gtc gat ctc atc     336
Ser Thr Cys Ala Ala Pro Lys Ser Asn Gln Ala Thr Val Asp Leu Ile
    80                  85                  90 gct gag ttt gag ggc ttc cgc gcc aat atc t gtatgtgata tcaacctcgc     387
Ala Glu Phe Glu Gly Phe Arg Ala Asn Ile
95                  100 attgtactta agaacaaggc tctaactcgt gaacaag ac  acc gat gca gct gga    441
                                            Thr Asp Ala Ala Gly
                                                105             110 tac gcc act gtc gga tac ggc cac aag tgc cag aag gct aag tgc gct     489
Tyr Ala Thr Val Gly Tyr Gly His Lys Cys Gln Lys Ala Lys Cys Ala
                    115                 120                 125 gag gtc aag tac aag att ccc ctt tcc aag gcc gat ggc aag aag ctt     537
Glu Val Lys Tyr Lys Ile Pro Leu Ser Lys Ala Asp Gly Lys Lys Leu
            130                 135                 140 ctg gcc gat gat atg agg gtatgttcct cccttcataa aaaccatacc            585
Leu Ala Asp Asp Met Arg
                145 atctctggaa gcctcatcaa tttcgactaa ccccaaatct acag agc ttc gaa gtc    641
                                                Ser Phe Glu Val
                                                            150 tgc att acg aac atg ctc aat agc aag gcc aag ctg aac tac aac cag     689
Cys Ile Thr Asn Met Leu Asn Ser Lys Ala Lys Leu Asn Tyr Asn Gln
            155                 160                 165 ttc ggt gca ctg gtc agt tgg tcc ttc aat gtc ggc tgc ggc gct gcc     737
Phe Gly Ala Leu Val Ser Trp Ser Phe Asn Val Gly Cys Gly Ala Ala
        170                 175                 180 aag tcg tcg act ctc atc aag cgc cta aac aac ggc gag aat gtc aac     785
Lys Ser Ser Thr Leu Ile Lys Arg Leu Asn Asn Gly Glu Asn Val Asn
185                 190                 195                 200 aag gtt ctt tcc gag gag ctg ccc aag tgg aac aag gct ggt ggc aag     833
Lys Val Leu Ser Glu Glu Leu Pro Lys Trp Asn Lys Ala Gly Gly Lys
                205                 210                 215 gtt ctt caa ggc ctt gtc cgc cgc cgt gct gct gag gtc gct ctg gct     881
Val Leu Gln Gly Leu Val Arg Arg Arg Ala Ala Glu Val Ala Leu Ala
            220                 225                 230 aag aag tct ggc agc tct cag gct ctt cct gtt aag tgc tga             923
Lys Lys Ser Gly Ser Ser Gln Ala Leu Pro Val Lys Cys
        235                 240                 245
```

<210> SEQ ID NO 263
<211> LENGTH: 263
<212> TYPE: PRT
<213> ORGANISM: Chaetomium thermophilum

<400> SEQUENCE: 263

```
Met Lys Phe Ala Ile Leu Ala Ala Val Ala Ser Phe Leu Ala Pro Ala
            -15                 -10                  -5

Ser Ala Tyr Ala Ile Thr Gly Asp Asn Val Asn Cys Arg Ser Gly Pro
 -1   1               5                  10

Gly Thr Ser Tyr Ala Val Lys Lys Val Tyr Lys Lys Gly Thr Asp Val
 15                  20                  25                  30

Lys Ile Ser Cys Gln Thr Thr Gly Thr Asn Ile Asn Gly Asn Asn Leu
                     35                  40                  45

Trp Asp Lys Thr Ser Asp Gly Cys Tyr Val Ser Asp Tyr Tyr Val Lys
                 50                  55                  60

Thr Gly Ser Asn Gly Tyr Val Thr Ser Lys Cys Ser Ser Gly Gly
             65                  70                  75

Ser Thr Cys Ala Ala Pro Lys Ser Asn Gln Ala Thr Val Asp Leu Ile
 80                  85                  90

Ala Glu Phe Glu Gly Phe Arg Ala Asn Ile Tyr Thr Asp Ala Ala Gly
 95                 100                 105                 110

Tyr Ala Thr Val Gly Tyr Gly His Lys Cys Gln Lys Ala Lys Cys Ala
                    115                 120                 125

Glu Val Lys Tyr Lys Ile Pro Leu Ser Lys Ala Asp Gly Lys Lys Leu
                130                 135                 140

Leu Ala Asp Asp Met Arg Ser Phe Glu Val Cys Ile Thr Asn Met Leu
            145                 150                 155

Asn Ser Lys Ala Lys Leu Asn Tyr Asn Gln Phe Gly Ala Leu Val Ser
        160                 165                 170

Trp Ser Phe Asn Val Gly Cys Gly Ala Ala Lys Ser Ser Thr Leu Ile
175                 180                 185                 190

Lys Arg Leu Asn Asn Gly Glu Asn Val Asn Lys Val Leu Ser Glu Glu
                195                 200                 205

Leu Pro Lys Trp Asn Lys Ala Gly Gly Lys Val Leu Gln Gly Leu Val
            210                 215                 220

Arg Arg Arg Ala Ala Glu Val Ala Leu Ala Lys Lys Ser Gly Ser Ser
                225                 230                 235

Gln Ala Leu Pro Val Lys Cys
    240                 245
```

<210> SEQ ID NO 264
<211> LENGTH: 249
<212> TYPE: PRT
<213> ORGANISM: Chaetomium thermophilum
<220> FEATURE:
<221> NAME/KEY: mat_peptide
<222> LOCATION: (1)..(249)

<400> SEQUENCE: 264

```
Pro Ala Ser Ala Tyr Ala Ile Thr Gly Asp Asn Val Asn Cys Arg Ser
 1               5                  10                  15

Gly Pro Gly Thr Ser Tyr Ala Val Lys Lys Val Tyr Lys Lys Gly Thr
             20                  25                  30

Asp Val Lys Ile Ser Cys Gln Thr Thr Gly Thr Asn Ile Asn Gly Asn
                 35                  40                  45
```

```
Asn Leu Trp Asp Lys Thr Ser Asp Gly Cys Tyr Val Ser Asp Tyr Tyr
     50                  55                  60

Val Lys Thr Gly Ser Asn Gly Tyr Val Thr Ser Lys Cys Ser Ser Ser
 65                  70                  75                  80

Gly Gly Ser Thr Cys Ala Ala Pro Lys Ser Asn Gln Ala Thr Val Asp
                 85                  90                  95

Leu Ile Ala Glu Phe Glu Gly Phe Arg Ala Asn Ile Tyr Thr Asp Ala
            100                 105                 110

Ala Gly Tyr Ala Thr Val Gly Tyr Gly His Lys Cys Gln Lys Ala Lys
            115                 120                 125

Cys Ala Glu Val Lys Tyr Lys Ile Pro Leu Ser Lys Ala Asp Gly Lys
            130                 135                 140

Lys Leu Leu Ala Asp Asp Met Arg Ser Phe Glu Val Cys Ile Thr Asn
145                 150                 155                 160

Met Leu Asn Ser Lys Ala Lys Leu Asn Tyr Asn Gln Phe Gly Ala Leu
                165                 170                 175

Val Ser Trp Ser Phe Asn Val Gly Cys Gly Ala Ala Lys Ser Ser Thr
            180                 185                 190

Leu Ile Lys Arg Leu Asn Asn Gly Glu Asn Val Asn Lys Val Leu Ser
            195                 200                 205

Glu Glu Leu Pro Lys Trp Asn Lys Ala Gly Gly Lys Val Leu Gln Gly
210                 215                 220

Leu Val Arg Arg Arg Ala Ala Glu Val Ala Leu Ala Lys Lys Ser Gly
225                 230                 235                 240

Ser Ser Gln Ala Leu Pro Val Lys Cys
                245

<210> SEQ ID NO 265
<211> LENGTH: 801
<212> TYPE: DNA
<213> ORGANISM: Trichoderma harzianum
<220> FEATURE:
<221> NAME/KEY: CDS
<222> LOCATION: (1)..(798)
<220> FEATURE:
<221> NAME/KEY: sig_peptide
<222> LOCATION: (1)..(54)
<220> FEATURE:
<221> NAME/KEY: mat_peptide
<222> LOCATION: (55)..(798)

<400> SEQUENCE: 265 atg aag act gcc ttt gct gct ctc gtt ttc tcc ctg gca tcc atc gtc      48
Met Lys Thr Ala Phe Ala Ala Leu Val Phe Ser Leu Ala Ser Ile Val
            -15                 -10                  -5 agc gcc tac ccc atc act ggc gat gtt gtc aac tgc cgc acc gga cct      96
Ser Ala Tyr Pro Ile Thr Gly Asp Val Val Asn Cys Arg Thr Gly Pro
 -1  1               5                  10 ggc acc agc tac gcc atc aag aag tcc tac aag aag aac caa gac atc     144
Gly Thr Ser Tyr Ala Ile Lys Lys Ser Tyr Lys Lys Asn Gln Asp Ile
 15                  20                  25                  30 tcc ata agc tgt cag aca gcg gga acc agc gtc aat ggc aac agc att     192
Ser Ile Ser Cys Gln Thr Ala Gly Thr Ser Val Asn Gly Asn Ser Ile
             35                  40                  45 tgg gat aag acc gcc gac ggc tgc tac gtc gcc gac tac tac gtc aag     240
Trp Asp Lys Thr Ala Asp Gly Cys Tyr Val Ala Asp Tyr Tyr Val Lys
             50                  55                  60 acg ggc tcc agc ggc tac gtg acc aag aag tgc act gct tcc tcc ggc     288
Thr Gly Ser Ser Gly Tyr Val Thr Lys Lys Cys Thr Ala Ser Ser Gly
```

```
              65                  70                  75
ggc ggc tcc tcg tcc agc tac tgc aag acc atc aac agc gcc ggc gtc      336
Gly Gly Ser Ser Ser Ser Tyr Cys Lys Thr Ile Asn Ser Ala Gly Val
 80                  85                  90 gat ctc atc gcc aag tgg gag ggc ttc gtc gcc agc cca aag ccc gac      384
Asp Leu Ile Ala Lys Trp Glu Gly Phe Val Ala Ser Pro Lys Pro Asp
 95                 100                 105                 110 ccc att ggc ctg ccc acg gtt ggc tac ggc cat ctc tgc cag cag aag      432
Pro Ile Gly Leu Pro Thr Val Gly Tyr Gly His Leu Cys Gln Gln Lys
                115                 120                 125 aac tgc aga gag gtc aag tac aag ttc ccc ctg acc aag acc acc gcc      480
Asn Cys Arg Glu Val Lys Tyr Lys Phe Pro Leu Thr Lys Thr Thr Ala
            130                 135                 140 aag gag ctg ctg ctg gac gac ctg ccc aag tac aca aag tgc ctc gcc      528
Lys Glu Leu Leu Leu Asp Asp Leu Pro Lys Tyr Thr Lys Cys Leu Ala
        145                 150                 155 gac tac ctc aac gac aag ccc aag ctc aat gcc aac cag tgg gcg gcc      576
Asp Tyr Leu Asn Asp Lys Pro Lys Leu Asn Ala Asn Gln Trp Ala Ala
    160                 165                 170 ctg acg tcc tgg gtc ttc aac gtc ggc tgc ggc aac gca aag aca tcg      624
Leu Thr Ser Trp Val Phe Asn Val Gly Cys Gly Asn Ala Lys Thr Ser
175                 180                 185                 190 act ctc gtg aag cgc ctc aac aac ggc gag gct gcc aac act gtt gct      672
Thr Leu Val Lys Arg Leu Asn Asn Gly Glu Ala Ala Asn Thr Val Ala
                195                 200                 205 gca gag gaa ctc ccc aag tgg cgc atg gca gga gga aaa gtc ctg cca      720
Ala Glu Glu Leu Pro Lys Trp Arg Met Ala Gly Gly Lys Val Leu Pro
            210                 215                 220 ggc ctc gag gct cgc cga aag gac gag gtc aag ctg ttc aag acg gcg      768
Gly Leu Glu Ala Arg Arg Lys Asp Glu Val Lys Leu Phe Lys Thr Ala
        225                 230                 235 tca tcg aag cag gcc tat cca aag tgc cag tga                          801
Ser Ser Lys Gln Ala Tyr Pro Lys Cys Gln
    240                 245

<210> SEQ ID NO 266
<211> LENGTH: 266
<212> TYPE: PRT
<213> ORGANISM: Trichoderma harzianum

<400> SEQUENCE: 266

Met Lys Thr Ala Phe Ala Ala Leu Val Phe Ser Leu Ala Ser Ile Val
            -15                 -10                  -5

Ser Ala Tyr Pro Ile Thr Gly Asp Val Val Asn Cys Arg Thr Gly Pro
 -1   1                   5                  10

Gly Thr Ser Tyr Ala Ile Lys Lys Ser Tyr Lys Lys Asn Gln Asp Ile
 15                  20                  25                  30

Ser Ile Ser Cys Gln Thr Ala Gly Thr Ser Val Asn Gly Asn Ser Ile
                 35                  40                  45

Trp Asp Lys Thr Ala Asp Gly Cys Tyr Val Ala Asp Tyr Tyr Val Lys
             50                  55                  60

Thr Gly Ser Ser Gly Tyr Val Thr Lys Lys Cys Thr Ala Ser Ser Gly
         65                  70                  75

Gly Gly Ser Ser Ser Tyr Cys Lys Thr Ile Asn Ser Ala Gly Val
     80                  85                  90

Asp Leu Ile Ala Lys Trp Glu Gly Phe Val Ala Ser Pro Lys Pro Asp
 95                 100                 105                 110

Pro Ile Gly Leu Pro Thr Val Gly Tyr Gly His Leu Cys Gln Gln Lys
```

```
            115                 120                 125
Asn Cys Arg Glu Val Lys Tyr Lys Phe Pro Leu Thr Lys Thr Thr Ala
            130                 135                 140

Lys Glu Leu Leu Leu Asp Asp Leu Pro Lys Tyr Thr Lys Cys Leu Ala
            145                 150                 155

Asp Tyr Leu Asn Asp Lys Pro Lys Leu Asn Ala Asn Gln Trp Ala Ala
160                 165                 170

Leu Thr Ser Trp Val Phe Asn Val Gly Cys Gly Asn Ala Lys Thr Ser
175                 180                 185                 190

Thr Leu Val Lys Arg Leu Asn Asn Gly Glu Ala Ala Asn Thr Val Ala
            195                 200                 205

Ala Glu Glu Leu Pro Lys Trp Arg Met Ala Gly Gly Lys Val Leu Pro
            210                 215                 220

Gly Leu Glu Ala Arg Arg Lys Asp Glu Val Lys Leu Phe Lys Thr Ala
            225                 230                 235

Ser Ser Lys Gln Ala Tyr Pro Lys Cys Gln
            240                 245

<210> SEQ ID NO 267
<211> LENGTH: 248
<212> TYPE: PRT
<213> ORGANISM: Trichoderma harzianum
<220> FEATURE:
<221> NAME/KEY: mat_peptide
<222> LOCATION: (1)..(248)

<400> SEQUENCE: 267

Tyr Pro Ile Thr Gly Asp Val Val Asn Cys Arg Thr Gly Pro Gly Thr
1               5                   10                  15

Ser Tyr Ala Ile Lys Lys Ser Tyr Lys Lys Asn Gln Asp Ile Ser Ile
            20                  25                  30

Ser Cys Gln Thr Ala Gly Thr Ser Val Asn Gly Asn Ser Ile Trp Asp
        35                  40                  45

Lys Thr Ala Asp Gly Cys Tyr Val Ala Asp Tyr Tyr Val Lys Thr Gly
    50                  55                  60

Ser Ser Gly Tyr Val Thr Lys Lys Cys Thr Ala Ser Ser Gly Gly Gly
65                  70                  75                  80

Ser Ser Ser Ser Tyr Cys Lys Thr Ile Asn Ser Ala Gly Val Asp Leu
                85                  90                  95

Ile Ala Lys Trp Glu Gly Phe Val Ala Ser Pro Lys Pro Asp Pro Ile
            100                 105                 110

Gly Leu Pro Thr Val Gly Tyr Gly His Leu Cys Gln Gln Lys Asn Cys
            115                 120                 125

Arg Glu Val Lys Tyr Lys Phe Pro Leu Thr Lys Thr Thr Ala Lys Glu
        130                 135                 140

Leu Leu Leu Asp Asp Leu Pro Lys Tyr Thr Lys Cys Leu Ala Asp Tyr
145                 150                 155                 160

Leu Asn Asp Lys Pro Lys Leu Asn Ala Asn Gln Trp Ala Ala Leu Thr
                165                 170                 175

Ser Trp Val Phe Asn Val Gly Cys Gly Asn Ala Lys Thr Ser Thr Leu
            180                 185                 190

Val Lys Arg Leu Asn Asn Gly Glu Ala Ala Asn Thr Val Ala Ala Glu
        195                 200                 205

Glu Leu Pro Lys Trp Arg Met Ala Gly Gly Lys Val Leu Pro Gly Leu
    210                 215                 220
```

```
Glu Ala Arg Arg Lys Asp Glu Val Lys Leu Phe Lys Thr Ala Ser Ser
225                 230                 235                 240

Lys Gln Ala Tyr Pro Lys Cys Gln
                245

<210> SEQ ID NO 268
<211> LENGTH: 585
<212> TYPE: DNA
<213> ORGANISM: Artificial Sequence
<220> FEATURE:
<223> OTHER INFORMATION: Synthetic construct
<220> FEATURE:
<221> NAME/KEY: CDS
<222> LOCATION: (10)..(576)
<220> FEATURE:
<221> NAME/KEY: sig_peptide
<222> LOCATION: (10)..(69)
<220> FEATURE:
<221> NAME/KEY: mat_peptide
<222> LOCATION: (70)..(576)

<400> SEQUENCE: 268 ggatccacc atg gcg aaa gtc tcc act ctc acc atc gca ttg ctc acg atg       51
          Met Ala Lys Val Ser Thr Leu Thr Ile Ala Leu Leu Thr Met
          -20             -15                 -10 gcg tcg cag gca agg gca cag tgt gtg ggc tgt aaa cct cct ccg atc         99
Ala Ser Gln Ala Arg Ala Gln Cys Val Gly Cys Lys Pro Pro Pro Ile
 -5              -1  1               5                       10 aac gca gcc aca gtg gcg ttg atc aaa gag ttc gaa ggc ttc gtg cct        147
Asn Ala Ala Thr Val Ala Leu Ile Lys Glu Phe Glu Gly Phe Val Pro
                15                  20                  25 aaa cct gca ccc gat ccg atc ggc ctc cct aca gtc ggc tac ggc cat        195
Lys Pro Ala Pro Asp Pro Ile Gly Leu Pro Thr Val Gly Tyr Gly His
            30                  35                  40 ctc tgt aaa act aag gga tgt aaa gag gtc ccc tac tcc ttc cct ttg        243
Leu Cys Lys Thr Lys Gly Cys Lys Glu Val Pro Tyr Ser Phe Pro Leu
        45                  50                  55 acc cag gag act gcc acg aaa ttg ctc cag tcg gat atc aag acc ttc        291
Thr Gln Glu Thr Ala Thr Lys Leu Leu Gln Ser Asp Ile Lys Thr Phe
    60                  65                  70 acc tcc tgt gtc tcc aac tac gtc aaa gac tcg gtc aag ctc aac gac        339
Thr Ser Cys Val Ser Asn Tyr Val Lys Asp Ser Val Lys Leu Asn Asp
75                  80                  85                  90 aac cag tat gga gcc ttg gcc tcg tgg gcc ttc aac gtg gga tgt ggc        387
Asn Gln Tyr Gly Ala Leu Ala Ser Trp Ala Phe Asn Val Gly Cys Gly
                95                  100                 105 aac gtg cag aca tcg tcg ctc att aag cgc ttg aac gca ggc gaa aac        435
Asn Val Gln Thr Ser Ser Leu Ile Lys Arg Leu Asn Ala Gly Glu Asn
            110                 115                 120 ccc aac acc gtc gca gcc cag gag ttg ccg aag tgg aag tat gcg gga        483
Pro Asn Thr Val Ala Ala Gln Glu Leu Pro Lys Trp Lys Tyr Ala Gly
        125                 130                 135 ggc aag gtc atg cct ggt ctc gtc cgt agg agg aac gca gag gtg gcc        531
Gly Lys Val Met Pro Gly Leu Val Arg Arg Arg Asn Ala Glu Val Ala
    140                 145                 150 ctc ttc aag aag cct tcg tcc gtc cag gcg cac cct cct aaa tgt            576
Leu Phe Lys Lys Pro Ser Ser Val Gln Ala His Pro Pro Lys Cys
155                 160                 165 taaaagctt                                                              585

<210> SEQ ID NO 269
<211> LENGTH: 189
<212> TYPE: PRT
```

<213> ORGANISM: Artificial Sequence
<220> FEATURE:
<223> OTHER INFORMATION: Synthetic Construct

<400> SEQUENCE: 269

```
Met Ala Lys Val Ser Thr Leu Thr Ile Ala Leu Leu Thr Met Ala Ser
-20             -15                 -10                  -5

Gln Ala Arg Ala Gln Cys Val Gly Cys Lys Pro Pro Ile Asn Ala
            -1  1               5                  10

Ala Thr Val Ala Leu Ile Lys Glu Phe Glu Gly Phe Val Pro Lys Pro
            15                  20                  25

Ala Pro Asp Pro Ile Gly Leu Pro Thr Val Gly Tyr Gly His Leu Cys
        30                  35                  40

Lys Thr Lys Gly Cys Lys Glu Val Pro Tyr Ser Phe Pro Leu Thr Gln
45                  50                  55                  60

Glu Thr Ala Thr Lys Leu Leu Gln Ser Asp Ile Lys Thr Phe Thr Ser
                65                  70                  75

Cys Val Ser Asn Tyr Val Lys Asp Ser Val Lys Leu Asn Asp Asn Gln
                80                  85                  90

Tyr Gly Ala Leu Ala Ser Trp Ala Phe Asn Val Gly Cys Gly Asn Val
                95                  100                 105

Gln Thr Ser Ser Leu Ile Lys Arg Leu Asn Ala Gly Glu Asn Pro Asn
        110                 115                 120

Thr Val Ala Ala Gln Glu Leu Pro Lys Trp Lys Tyr Ala Gly Gly Lys
125                 130                 135                 140

Val Met Pro Gly Leu Val Arg Arg Arg Asn Ala Glu Val Ala Leu Phe
                145                 150                 155

Lys Lys Pro Ser Ser Val Gln Ala His Pro Pro Lys Cys
                160                 165
```

<210> SEQ ID NO 270
<211> LENGTH: 169
<212> TYPE: PRT
<213> ORGANISM: Artificial Sequence
<220> FEATURE:
<223> OTHER INFORMATION: Synthetic construct

<400> SEQUENCE: 270

```
Gln Cys Val Gly Cys Lys Pro Pro Ile Asn Ala Ala Thr Val Ala
1               5                   10                  15

Leu Ile Lys Glu Phe Glu Gly Phe Val Pro Lys Pro Ala Pro Asp Pro
                20                  25                  30

Ile Gly Leu Pro Thr Val Gly Tyr Gly His Leu Cys Lys Thr Lys Gly
            35                  40                  45

Cys Lys Glu Val Pro Tyr Ser Phe Pro Leu Thr Gln Glu Thr Ala Thr
50                  55                  60

Lys Leu Leu Gln Ser Asp Ile Lys Thr Phe Thr Ser Cys Val Ser Asn
65                  70                  75                  80

Tyr Val Lys Asp Ser Val Lys Leu Asn Asp Asn Gln Tyr Gly Ala Leu
                85                  90                  95

Ala Ser Trp Ala Phe Asn Val Gly Cys Gly Asn Val Gln Thr Ser Ser
            100                 105                 110

Leu Ile Lys Arg Leu Asn Ala Gly Glu Asn Pro Asn Thr Val Ala Ala
        115                 120                 125

Gln Glu Leu Pro Lys Trp Lys Tyr Ala Gly Gly Lys Val Met Pro Gly
130                 135                 140
```

Leu Val Arg Arg Arg Asn Ala Glu Val Ala Leu Phe Lys Lys Pro Ser
145                 150                 155                 160

Ser Val Gln Ala His Pro Pro Lys Cys
            165

<210> SEQ ID NO 271
<211> LENGTH: 270
<212> TYPE: DNA
<213> ORGANISM: Artificial Sequence
<220> FEATURE:
<223> OTHER INFORMATION: Synthetic construct
<220> FEATURE:
<221> NAME/KEY: CDS
<222> LOCATION: (1)..(270)
<220> FEATURE:
<221> NAME/KEY: sig_peptide
<222> LOCATION: (1)..(51)
<220> FEATURE:
<221> NAME/KEY: mat_peptide
<222> LOCATION: (52)..(270)

<400> SEQUENCE: 271 atg cac gct ctc acc ctt ctc acc gca acc ctc ttc ggt ctc gca gcg      48
Met His Ala Leu Thr Leu Leu Thr Ala Thr Leu Phe Gly Leu Ala Ala
        -15                 -10                 -5 gcc tac cca gtg aag acc gac ctt cac tgc cgc tcc tct ccc agc act      96
Ala Tyr Pro Val Lys Thr Asp Leu His Cys Arg Ser Ser Pro Ser Thr
-1  1               5                   10                  15 tcc gcc agc atc gtc cgc acc tac tcc agt gga acg gaa gtc cag atc     144
Ser Ala Ser Ile Val Arg Thr Tyr Ser Ser Gly Thr Glu Val Gln Ile
                20                  25                  30 cag tgc cag acc acg ggc act tcg gtc caa gga tcc aat gtc tgg gac     192
Gln Cys Gln Thr Thr Gly Thr Ser Val Gln Gly Ser Asn Val Trp Asp
            35                  40                  45 aag acc cag cac ggt tgc tac gtc gca gac tac tac gtc aag acc ggg     240
Lys Thr Gln His Gly Cys Tyr Val Ala Asp Tyr Tyr Val Lys Thr Gly
        50                  55                  60 cat tct ggg att ttc acc acc aag tgc ggt                              270
His Ser Gly Ile Phe Thr Thr Lys Cys Gly
    65                  70

<210> SEQ ID NO 272
<211> LENGTH: 90
<212> TYPE: PRT
<213> ORGANISM: Artificial Sequence
<220> FEATURE:
<223> OTHER INFORMATION: Synthetic Construct

<400> SEQUENCE: 272

Met His Ala Leu Thr Leu Leu Thr Ala Thr Leu Phe Gly Leu Ala Ala
        -15                 -10                 -5

Ala Tyr Pro Val Lys Thr Asp Leu His Cys Arg Ser Ser Pro Ser Thr
-1  1               5                   10                  15

Ser Ala Ser Ile Val Arg Thr Tyr Ser Ser Gly Thr Glu Val Gln Ile
                20                  25                  30

Gln Cys Gln Thr Thr Gly Thr Ser Val Gln Gly Ser Asn Val Trp Asp
            35                  40                  45

Lys Thr Gln His Gly Cys Tyr Val Ala Asp Tyr Tyr Val Lys Thr Gly
        50                  55                  60

His Ser Gly Ile Phe Thr Thr Lys Cys Gly
    65                  70

<210> SEQ ID NO 273

<211> LENGTH: 73
<212> TYPE: PRT
<213> ORGANISM: Artificial Sequence
<220> FEATURE:
<223> OTHER INFORMATION: Synthetic construct
<220> FEATURE:
<221> NAME/KEY: mat_peptide
<222> LOCATION: (1)..(73)

<400> SEQUENCE: 273

Tyr Pro Val Lys Thr Asp Leu His Cys Arg Ser Ser Pro Ser Thr Ser
1               5                   10                  15

Ala Ser Ile Val Arg Thr Tyr Ser Ser Gly Thr Glu Val Gln Ile Gln
            20                  25                  30

Cys Gln Thr Thr Gly Thr Ser Val Gln Gly Ser Asn Val Trp Asp Lys
        35                  40                  45

Thr Gln His Gly Cys Tyr Val Ala Asp Tyr Tyr Val Lys Thr Gly His
    50                  55                  60

Ser Gly Ile Phe Thr Thr Lys Cys Gly
65                  70

<210> SEQ ID NO 274
<211> LENGTH: 37
<212> TYPE: DNA
<213> ORGANISM: Artificial Sequence
<220> FEATURE:
<223> OTHER INFORMATION: Synthetic construct

<400> SEQUENCE: 274
agatctcgag aagcttatac cgcacttggt ggtgaaa                            37

<210> SEQ ID NO 275
<211> LENGTH: 39
<212> TYPE: DNA
<213> ORGANISM: Artificial Sequence
<220> FEATURE:
<223> OTHER INFORMATION: Synthetic construct

<400> SEQUENCE: 275
acacaactgg ggatccacca tgaagactgc ctttgctgc                          39

<210> SEQ ID NO 276
<211> LENGTH: 38
<212> TYPE: DNA
<213> ORGANISM: Artificial Sequence
<220> FEATURE:
<223> OTHER INFORMATION: Synthetic construct

<400> SEQUENCE: 276
agatctcgag aagcttatca ctggcacttt ggataggc                           38

<210> SEQ ID NO 277
<211> LENGTH: 39
<212> TYPE: DNA
<213> ORGANISM: Artificial Sequence
<220> FEATURE:
<223> OTHER INFORMATION: Synthetic construct

<400> SEQUENCE: 277
acacaactgg ggatccacca tgaagttcgc catcctcgc                          39

<210> SEQ ID NO 278
<211> LENGTH: 39
<212> TYPE: DNA
<213> ORGANISM: Artificial Sequence
<220> FEATURE:
<223> OTHER INFORMATION: Synthetic construct

<400> SEQUENCE: 278
agatctcgag aagcttatca gcacttaaca ggaagagcc                                 39

<210> SEQ ID NO 279
<211> LENGTH: 166
<212> TYPE: PRT
<213> ORGANISM: Acremonium alcalophilum
<220> FEATURE:
<221> NAME/KEY: mat_peptide
<222> LOCATION: (1)..(166)

<400> SEQUENCE: 279

Gln Cys Val Gly Pro Glu Val Asn Ser Ala Ser Ile Asn Leu Ile Lys
1               5                   10                  15

Glu Phe Glu Gly Trp Tyr Pro Asp Ile Tyr Val Asp Pro Ala Gly Tyr
                20                  25                  30

Pro Thr Val Gly Tyr Gly His Leu Cys Ser Asp Ser Cys Ser Asp
            35                  40                  45

Val Ser Tyr Ser Ile Pro Leu Ser Glu Ala Asp Gly Glu Asn Leu Leu
50                  55                  60

Arg Asp Asp Ile Thr Asn Phe Gln Asn Cys Ile Thr Trp Gln Thr Ala
65                  70                  75                  80

Ser Ser Val Val Leu Asn Ala Asn Gln Tyr Gly Ala Leu Val Ser Trp
                85                  90                  95

Ala Phe Asn Val Gly Cys Gly Ser Glu Ser Ser Leu Ile Ala
                100                 105                 110

Arg Leu Asn Ala Gly Glu Asp Pro Asn Thr Val Ala Glu Glu Leu
            115                 120                 125

Pro Arg Trp Asn Gln Gly Gly Gln Val Leu Pro Gly Leu Val Arg
130                 135                 140

Arg Arg Ala Ala Glu Val Glu Leu His Gln Ile Pro Thr Asp Val Ala
145                 150                 155                 160

Ala Leu Pro Ala Cys Ser
                165

<210> SEQ ID NO 280
<211> LENGTH: 157
<212> TYPE: PRT
<213> ORGANISM: Acremonium alcalophilum
<220> FEATURE:
<221> NAME/KEY: mat_peptide
<222> LOCATION: (1)..(157)

<400> SEQUENCE: 280

Gln Cys Val Gly Pro Ala Ile Asn Ser Ala Ala Leu Asn Leu Ile Lys
1               5                   10                  15

Glu Phe Glu Gly Trp Arg Pro Asn Ile Tyr Arg Asp Pro Val Gly Leu
                20                  25                  30

Pro Thr Val Gly Tyr Gly His Leu Cys Arg Asp Ser Ser Cys Ser Asp
            35                  40                  45

Val Pro Tyr Pro Ile Pro Leu Ser Val Ala Asn Gly Glu Arg Leu Leu
50                  55                  60

Arg Ser Asp Leu Ala Thr Ala Ser Ser Val Val Leu Asn Ala Asn Gln
65                  70                  75                  80

Tyr Gly Ala Leu Val Ser Trp Ala Phe Asn Val Gly Cys Gly Ala Thr
                85                  90                  95

```
Ser Thr Ser Thr Leu Ile Arg Arg Leu Asn Ala Gly Glu Ser Pro Asn
            100                 105                 110

Thr Val Ala Ala Gln Glu Leu Pro Arg Trp Asn Lys Ala Gly Gly Gln
        115                 120                 125

Val Leu Pro Gly Leu Val Arg Arg Ala Ala Glu Val Glu Leu His
    130                 135                 140

Arg Thr Ser Thr Ser Val Arg Ala Leu Pro Ala Cys Ser
145                 150                 155

<210> SEQ ID NO 281
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: NON_CONS
<222> LOCATION: (1)..(1)
<223> OTHER INFORMATION: The amino acid in position 1 of the conserved
      motif is alanine, serine or threonine.
<220> FEATURE:
<221> NAME/KEY: NON_CONS
<222> LOCATION: (2)..(2)
<223> OTHER INFORMATION: The amino acid in position 2 of the conserved
      motif is valine, isoleucine or leucine.
<220> FEATURE:
<221> NAME/KEY: NON_CONS
<222> LOCATION: (3)..(3)
<223> OTHER INFORMATION: The amino acid in position 3 of the conserved
      motif is alanine, cysteine or glycine.
<220> FEATURE:
<221> NAME/KEY: NON_CONS
<222> LOCATION: (4)..(4)
<223> OTHER INFORMATION: The amino acid in position 4 of the conserved
      motif is isoleucine, phenylalanine or tyrosine.
<220> FEATURE:
<221> NAME/KEY: NON_CONS
<222> LOCATION: (7)..(7)
<223> OTHER INFORMATION: The amino acid in position 7 of the conserved
      motif is any amino acid.
<220> FEATURE:
<221> NAME/KEY: NON_CONS
<222> LOCATION: (8)..(8)
<223> OTHER INFORMATION: The amino acid in position 8 of the conserved
      motif is alanine, cysteine, isoleucine, phenylalanine or valine.

<400> SEQUENCE: 281

Xaa Xaa Xaa Xaa Gly His Xaa Xaa
1               5

<210> SEQ ID NO 282
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: NON_CONS
<222> LOCATION: (2)..(2)
<223> OTHER INFORMATION: The amino acid in position 2 of the conserved
      motif is valine or isoleucine.
<220> FEATURE:
<221> NAME/KEY: NON_CONS
<222> LOCATION: (7)..(7)
<223> OTHER INFORMATION: The amino acid in position 7 of the conserved
      motif is any amino acid.

<400> SEQUENCE: 282

Thr Xaa Gly Tyr Gly His Xaa Cys
1               5
```

```
<210> SEQ ID NO 283
<211> LENGTH: 15
<212> TYPE: PRT
<213> ORGANISM: Artificial Sequence
<220> FEATURE:
<223> OTHER INFORMATION: Synthetic construct
<220> FEATURE:
<221> NAME/KEY: NON_CONS
<222> LOCATION: (3)..(3)
<223> OTHER INFORMATION: The amino acid in position 3 of the conserved
      motif is any amino acid.
<220> FEATURE:
<221> NAME/KEY: NON_CONS
<222> LOCATION: (5)..(5)
<223> OTHER INFORMATION: The amino acid in position 5 of the conserved
      motif is glutamic acid or glutamine.
<220> FEATURE:
<221> NAME/KEY: NON_CONS
<222> LOCATION: (6)..(6)
<223> OTHER INFORMATION: The amino acid in position 6 of the conserved
      motif is phenylalanine, tryptophan or tyrosine.
<220> FEATURE:
<221> NAME/KEY: NON_CONS
<222> LOCATION: (7)..(7)
<223> OTHER INFORMATION: The amino acid in position 7 of the conserved
      motif is alanine or glycine.
<220> FEATURE:
<221> NAME/KEY: NON_CONS
<222> LOCATION: (10)..(10)
<223> OTHER INFORMATION: The amino acid in position 10 of the conserved
      motif is any amino acid.
<220> FEATURE:
<221> NAME/KEY: NON_CONS
<222> LOCATION: (12)..(12)
<223> OTHER INFORMATION: The amino acid in position 12 of the conserved
      motif is leucine, phenylalanine or tryptophan.
<220> FEATURE:
<221> NAME/KEY: NON_CONS
<222> LOCATION: (13)..(13)
<223> OTHER INFORMATION: The amino acid in position 13 of the conserved
      motif is any amino acid.
<220> FEATURE:
<221> NAME/KEY: NON_CONS
<222> LOCATION: (14)..(14)
<223> OTHER INFORMATION: The amino acid in position 14 of the conserved
      motif is phenylalanine or tyrosine.

<400> SEQUENCE: 283

Leu Asn Xaa Asn Xaa Xaa Xaa Ala Leu Xaa Ser Xaa Xaa Xaa Asn
1               5                   10                  15

<210> SEQ ID NO 284
<211> LENGTH: 11
<212> TYPE: PRT
<213> ORGANISM: Artificial Sequence
<220> FEATURE:
<223> OTHER INFORMATION: Synthetic construct
<220> FEATURE:
<221> NAME/KEY: NON_CONS
<222> LOCATION: (2)..(2)
<223> OTHER INFORMATION: The amino acid in position 2 of the conserved
      motif is phenylalanine or tyrosine.
<220> FEATURE:
<221> NAME/KEY: NON_CONS
<222> LOCATION: (3)..(3)
<223> OTHER INFORMATION: The amino acid in position 3 of the conserved
      motif is isoleucine or valine.
<220> FEATURE:
<221> NAME/KEY: NON_CONS
<222> LOCATION: (4)..(4)
<223> OTHER INFORMATION: The amino acid in position 4 of the conserved
      motif is alanine, serine or threonine.
<220> FEATURE:
<221> NAME/KEY: NON_CONS
<222> LOCATION: (6)..(6)
<223> OTHER INFORMATION: The amino acid in position 6 of the conserved
```

```
      motif is lysine, phenylalanine or tyrosine.
<220> FEATURE:
<221> NAME/KEY: NON_CONS
<222> LOCATION: (7)..(7)
<223> OTHER INFORMATION: The amino acid in position 7 of the conserved
      motif is phenylalanine or tyrosine.
<220> FEATURE:
<221> NAME/KEY: NON_CONS
<222> LOCATION: (8)..(8)
<223> OTHER INFORMATION: The amino acid in position 8 of the conserved
      motif is isoleucine or valine.
<220> FEATURE:
<221> NAME/KEY: NON_CONS
<222> LOCATION: (9)..(9)
<223> OTHER INFORMATION: The amino acid in position 9 of the conserved
      motif is any amino acid.

<400> SEQUENCE: 284

Cys Xaa Xaa Xaa Asp Xaa Xaa Xaa Xaa Thr Gly
1               5                   10

<210> SEQ ID NO 285
<211> LENGTH: 9
<212> TYPE: PRT
<213> ORGANISM: Artificial Sequence
<220> FEATURE:
<223> OTHER INFORMATION: Synthetic construct
<220> FEATURE:
<221> NAME/KEY: NON_CONS
<222> LOCATION: (1)..(1)
<223> OTHER INFORMATION: The amino acid in position 1 of the conserved
      motif is glutamic acid, glycine or valine.
<220> FEATURE:
<221> NAME/KEY: NON_CONS
<222> LOCATION: (3)..(3)
<223> OTHER INFORMATION: The amino acid in position 3 of the conserved
      motif is any amino acid.
<220> FEATURE:
<221> NAME/KEY: NON_CONS
<222> LOCATION: (4)..(4)
<223> OTHER INFORMATION: The amino acid in position 4 of the conserved
      motif is any amino acid.
<220> FEATURE:
<221> NAME/KEY: NON_CONS
<222> LOCATION: (7)..(7)
<223> OTHER INFORMATION: The amino acid in position 7 of the conserved
      motif is any amino acid.
<220> FEATURE:
<221> NAME/KEY: NON_CONS
<222> LOCATION: (8)..(8)
<223> OTHER INFORMATION: The amino acid in position 8 of the conserved
      motif is any amino acid.

<400> SEQUENCE: 285

Xaa Leu Xaa Xaa Arg Arg Xaa Xaa Glu
1               5

<210> SEQ ID NO 286
<211> LENGTH: 9
<212> TYPE: PRT
<213> ORGANISM: Artificial Sequence
<220> FEATURE:
<223> OTHER INFORMATION: Synthetic construct
<220> FEATURE:
<221> NAME/KEY: NON_CONS
<222> LOCATION: (3)..(3)
<223> OTHER INFORMATION: The amino acid in position 3 of the conserved
      motif is any amino acid.
<220> FEATURE:
<221> NAME/KEY: NON_CONS
<222> LOCATION: (4)..(4)
<223> OTHER INFORMATION: The amino acid in position 4 of the conserved
      motif is any amino acid.
<220> FEATURE:
<221> NAME/KEY: NON_CONS
```

```
<222> LOCATION: (7)..(7)
<223> OTHER INFORMATION: The amino acid in position 7 of the conserved
      motif is any amino acid.
<220> FEATURE:
<221> NAME/KEY: NON_CONS
<222> LOCATION: (8)..(8)
<223> OTHER INFORMATION: The amino acid in position 8 of the conserved
      motif is any amino acid.

<400> SEQUENCE: 286

Gly Leu Xaa Xaa Arg Arg Xaa Xaa Glu
1               5

<210> SEQ ID NO 287
<211> LENGTH: 961
<212> TYPE: DNA
<213> ORGANISM: Trichophaea minuta
<220> FEATURE:
<221> NAME/KEY: CDS
<222> LOCATION: (1)..(347)
<220> FEATURE:
<221> NAME/KEY: sig_peptide
<222> LOCATION: (1)..(51)
<220> FEATURE:
<221> NAME/KEY: mat_peptide
<222> LOCATION: (52)..(958)
<220> FEATURE:
<221> NAME/KEY: CDS
<222> LOCATION: (410)..(624)
<220> FEATURE:
<221> NAME/KEY: CDS
<222> LOCATION: (683)..(787)
<220> FEATURE:
<221> NAME/KEY: CDS
<222> LOCATION: (840)..(958)

<400> SEQUENCE: 287
```

| | | | | | | | | | | | | | | | | |
|---|---|---|---|---|---|---|---|---|---|---|---|---|---|---|---|---|
| atg | cac | gcc | ctc | gcc | ctc | ctc | gca | gca | acc | ctc | ttc | ggt | ctc | gca | gcg | 48 |
| Met | His | Ala | Leu | Ala | Leu | Leu | Ala | Ala | Thr | Leu | Phe | Gly | Leu | Ala | Ala | |
| | | -15 | | | | -10 | | | | | -5 | | | | | |

| | | | | | | | | | | | | | | | | |
|---|---|---|---|---|---|---|---|---|---|---|---|---|---|---|---|---|
| gcc | tac | cca | gcg | aaa | gtt | gac | ctc | cgc | tgc | cgt | tcc | tct | ccc | agc | acc | 96 |
| Ala | Tyr | Pro | Ala | Lys | Val | Asp | Leu | Arg | Cys | Arg | Ser | Ser | Pro | Ser | Thr | |
| -1 | 1 | | | 5 | | | | | 10 | | | | | 15 | | |

| | | | | | | | | | | | | | | | | |
|---|---|---|---|---|---|---|---|---|---|---|---|---|---|---|---|---|
| tcc | gcg | agc | gta | gtc | cgc | acc | tac | tcc | aaa | ggc | tcc | gaa | atc | cag | atc | 144 |
| Ser | Ala | Ser | Val | Val | Arg | Thr | Tyr | Ser | Lys | Gly | Ser | Glu | Ile | Gln | Ile | |
| | | | 20 | | | | | 25 | | | | | 30 | | | |

| | | | | | | | | | | | | | | | | |
|---|---|---|---|---|---|---|---|---|---|---|---|---|---|---|---|---|
| tct | tgc | cag | acc | acg | ggc | act | tcc | gtc | gaa | ggc | tcc | aat | gtc | tgg | gac | 192 |
| Ser | Cys | Gln | Thr | Thr | Gly | Thr | Ser | Val | Glu | Gly | Ser | Asn | Val | Trp | Asp | |
| | | 35 | | | | | 40 | | | | | 45 | | | | |

| | | | | | | | | | | | | | | | | |
|---|---|---|---|---|---|---|---|---|---|---|---|---|---|---|---|---|
| aag | acc | cag | cat | ggc | tgc | tac | gtc | gcc | gac | tac | tac | gtc | aag | acc | ggg | 240 |
| Lys | Thr | Gln | His | Gly | Cys | Tyr | Val | Ala | Asp | Tyr | Tyr | Val | Lys | Thr | Gly | |
| | | 50 | | | | | 55 | | | | | 60 | | | | |

| | | | | | | | | | | | | | | | | |
|---|---|---|---|---|---|---|---|---|---|---|---|---|---|---|---|---|
| cat | tct | gga | atc | ttc | aca | acc | aag | tgc | ggc | agc | agc | tct | ggt | ggt | ggt | 288 |
| His | Ser | Gly | Ile | Phe | Thr | Thr | Lys | Cys | Gly | Ser | Ser | Ser | Gly | Gly | Gly | |
| | 65 | | | | | 70 | | | | | 75 | | | | | |

| | | | | | | | | | | | | | | | | |
|---|---|---|---|---|---|---|---|---|---|---|---|---|---|---|---|---|
| tct | tgc | aag | ccg | ccc | ccg | atc | aat | gcg | gct | act | gtg | gcg | ttg | att | aag | 336 |
| Ser | Cys | Lys | Pro | Pro | Pro | Ile | Asn | Ala | Ala | Thr | Val | Ala | Leu | Ile | Lys | |
| 80 | | | | | 85 | | | | | 90 | | | | | 95 | |

| | | | | | | | | | | | | | | |
|---|---|---|---|---|---|---|---|---|---|---|---|---|---|---|
| gag | ttt | gag | gg | gtaagtggcc | ggcggacttg | gggagtgaga | gctatggagc | | | | | | | 387 |
| Glu | Phe | Glu | Gly | | | | | | | | | | | |

| | | | | | | | | | | |
|---|---|---|---|---|---|---|---|---|---|---|
| tggatgctga cgggactact ag | a | ttt | gtt | gct | aag | ccc | gca | ccg | gat | cct | 437 |
| | | Phe | Val | Ala | Lys | Pro | Ala | Pro | Asp | Pro | |
| | | | | | 100 | | | | | 105 | |

| | | | | | | | | | | | | | | | | |
|---|---|---|---|---|---|---|---|---|---|---|---|---|---|---|---|---|
| att | gga | ttg | ccg | act | gtg | gga | tat | ggt | cat | ctt | tgc | aag | act | aag | ggc | 485 |
| Ile | Gly | Leu | Pro | Thr | Val | Gly | Tyr | Gly | His | Leu | Cys | Lys | Thr | Lys | Gly | |
| | 110 | | | | | 115 | | | | | 120 | | | | | |

```
tgc aag gag gtg cct tac agt ttc ccg ctc acc cag act acc gcc acc      533
Cys Lys Glu Val Pro Tyr Ser Phe Pro Leu Thr Gln Thr Thr Ala Thr
125             130                 135                 140 aag ttg ctg cag agc gat atc aag act ttc acc tcc tgt gtt agc aac      581
Lys Leu Leu Gln Ser Asp Ile Lys Thr Phe Thr Ser Cys Val Ser Asn
                145                 150                 155 tac gtc aag gac tct gtt aag ctt aac gat aac cag ttc gga g            624
Tyr Val Lys Asp Ser Val Lys Leu Asn Asp Asn Gln Phe Gly
            160                 165                 170 gtaatttcca gtattccccg ttgatcagtg ataatataat gattctgacg aatttttag     682 ct cta tcg tcg tgg gct ttc aac gtt ggt tgc gga aat atc cag act       729
   Ala Leu Ser Ser Trp Ala Phe Asn Val Gly Cys Gly Asn Ile Gln Thr
                   175                 180                 185 tct tcg ctg atc aag aga ctg aat gct gga gag aac cct aac act gtt      777
Ser Ser Leu Ile Lys Arg Leu Asn Ala Gly Glu Asn Pro Asn Thr Val
            190                 195                 200 gcc gct cag g gtaagacctt ctcactggag tgaattttgg ggaggagctg            827
Ala Ala Gln
        205 acaaagttgc ag aa ctc cct aag tgg aaa tat gct ggt gga aag gtt ctt     877
                 Glu Leu Pro Lys Trp Lys Tyr Ala Gly Gly Lys Val Leu
                                 210                 215 ccc ggc ttg gtc cgc cgc cgg aag gct gag gtc gcg ctt ttc aag aag      925
Pro Gly Leu Val Arg Arg Arg Lys Ala Glu Val Ala Leu Phe Lys Lys
220                 225                 230 ccc agc agc gtc cag gcc cac cct ccc aag tgc tag                      961
Pro Ser Ser Val Gln Ala His Pro Pro Lys Cys
235                 240                 245

<210> SEQ ID NO 288
<211> LENGTH: 262
<212> TYPE: PRT
<213> ORGANISM: Trichophaea minuta

<400> SEQUENCE: 288

Met His Ala Leu Ala Leu Leu Ala Ala Thr Leu Phe Gly Leu Ala Ala
        -15                 -10                 -5

Ala Tyr Pro Ala Lys Val Asp Leu Arg Cys Arg Ser Ser Pro Ser Thr
-1  1               5                   10                  15

Ser Ala Ser Val Val Arg Thr Tyr Ser Lys Gly Ser Glu Ile Gln Ile
                20                  25                  30

Ser Cys Gln Thr Thr Gly Thr Ser Val Glu Gly Ser Asn Val Trp Asp
            35                  40                  45

Lys Thr Gln His Gly Cys Tyr Val Ala Asp Tyr Tyr Val Lys Thr Gly
        50                  55                  60

His Ser Gly Ile Phe Thr Thr Lys Cys Gly Ser Ser Gly Gly Gly
    65                  70                  75

Ser Cys Lys Pro Pro Ile Asn Ala Ala Thr Val Ala Leu Ile Lys
80                  85                  90                  95

Glu Phe Glu Gly Phe Val Ala Lys Pro Ala Pro Asp Pro Ile Gly Leu
                100                 105                 110

Pro Thr Val Gly Tyr Gly His Leu Cys Lys Thr Lys Gly Cys Lys Glu
            115                 120                 125

Val Pro Tyr Ser Phe Pro Leu Thr Gln Thr Thr Ala Thr Lys Leu Leu
        130                 135                 140

Gln Ser Asp Ile Lys Thr Phe Thr Ser Cys Val Ser Asn Tyr Val Lys
    145                 150                 155
```

```
Asp Ser Val Lys Leu Asn Asp Asn Gln Phe Gly Ala Leu Ser Ser Trp
160                 165                 170                 175

Ala Phe Asn Val Gly Cys Gly Asn Ile Gln Thr Ser Ser Leu Ile Lys
                180                 185                 190

Arg Leu Asn Ala Gly Glu Asn Pro Asn Thr Val Ala Ala Gln Glu Leu
            195                 200                 205

Pro Lys Trp Lys Tyr Ala Gly Lys Val Leu Pro Gly Leu Val Arg
        210                 215                 220

Arg Arg Lys Ala Glu Val Ala Leu Phe Lys Lys Pro Ser Ser Val Gln
225                 230                 235

Ala His Pro Pro Lys Cys
240                 245

<210> SEQ ID NO 289
<211> LENGTH: 789
<212> TYPE: DNA
<213> ORGANISM: Artificial Sequence
<220> FEATURE:
<223> OTHER INFORMATION: Synthetic construct
<220> FEATURE:
<221> NAME/KEY: CDS
<222> LOCATION: (1)..(786)
<220> FEATURE:
<221> NAME/KEY: sig_peptide
<222> LOCATION: (1)..(51)
<220> FEATURE:
<221> NAME/KEY: mat_peptide
<222> LOCATION: (52)..(796)

<400> SEQUENCE: 289 atg cac gca ctc gcg ctc ttg gca gcc act ctc ttc ggc ctc gca gca       48
Met His Ala Leu Ala Leu Leu Ala Ala Thr Leu Phe Gly Leu Ala Ala
            -15                 -10                 -5 gcc tat ccc gca aag gtg gac ctc cga tgt cgt tcg tcc cct tcc aca       96
Ala Tyr Pro Ala Lys Val Asp Leu Arg Cys Arg Ser Ser Pro Ser Thr
-1  1               5                   10                  15 tcc gcc tcc gtc gtc agg act tat tcc aag ggc tcc gag atc cag att      144
Ser Ala Ser Val Val Arg Thr Tyr Ser Lys Gly Ser Glu Ile Gln Ile
                20                  25                  30 tcg tgt cag acc acg ggc aca tcg gtg gaa ggc tcc aac gtg tgg gac      192
Ser Cys Gln Thr Thr Gly Thr Ser Val Glu Gly Ser Asn Val Trp Asp
            35                  40                  45 aag acg cag cac ggc tgt tac gtc gcc gat tac tac gtc aag acc ggt      240
Lys Thr Gln His Gly Cys Tyr Val Ala Asp Tyr Tyr Val Lys Thr Gly
                50                  55                  60 cat tcg ggc atc ttc aca acc aag tgt ggt tcc tcg tcg gga gga ggc      288
His Ser Gly Ile Phe Thr Thr Lys Cys Gly Ser Ser Ser Gly Gly Gly
65                  70                  75 tcc tgt aaa cct cct ccg atc aac gca gca aca gtc gcc ctc atc aag      336
Ser Cys Lys Pro Pro Pro Ile Asn Ala Ala Thr Val Ala Leu Ile Lys
80                  85                  90                  95 gag ttc gaa ggc ttc gtg gca aaa cct gca ccc gat ccc atc ggt ttg      384
Glu Phe Glu Gly Phe Val Ala Lys Pro Ala Pro Asp Pro Ile Gly Leu
                100                 105                 110 ccc act gtg gga tac ggc cac ttg tgt aag acg aaa ggc tgt aag gag      432
Pro Thr Val Gly Tyr Gly His Leu Cys Lys Thr Lys Gly Cys Lys Glu
            115                 120                 125 gtg ccc tac tcc ttc ccg ttg act cag aca acg gcg acg aaa ttg ttg      480
Val Pro Tyr Ser Phe Pro Leu Thr Gln Thr Thr Ala Thr Lys Leu Leu
                130                 135                 140 cag tcg gac atc aaa act ttc aca tcc tgt gtg tcc aac tac gtc aag      528
Gln Ser Asp Ile Lys Thr Phe Thr Ser Cys Val Ser Asn Tyr Val Lys
```

```
                    145                 150                 155
gat tcg gtc aaa ctc aac gat aac cag ttc gga gcg ttg tcg tcg tgg        576
Asp Ser Val Lys Leu Asn Asp Asn Gln Phe Gly Ala Leu Ser Ser Trp
160                 165                 170                 175 gcc ttc aac gtc gga tgt ggc aac atc cag acg tcg tcg ctc atc aag        624
Ala Phe Asn Val Gly Cys Gly Asn Ile Gln Thr Ser Ser Leu Ile Lys
                180                 185                 190 cgt ctc aac gca gga gag aac ccg aac act gtc gca gcc cag gaa ctc        672
Arg Leu Asn Ala Gly Glu Asn Pro Asn Thr Val Ala Ala Gln Glu Leu
            195                 200                 205 ccg aaa tgg aag tat gcg ggt ggc aag gtc ctc cct ggt ttg gtc cga        720
Pro Lys Trp Lys Tyr Ala Gly Gly Lys Val Leu Pro Gly Leu Val Arg
        210                 215                 220 agg cgg aag gca gaa gtc gcg ttg ttc aag aag ccg tcg tcg gtc cag        768
Arg Arg Lys Ala Glu Val Ala Leu Phe Lys Lys Pro Ser Ser Val Gln
    225                 230                 235 gca cat cct ccg aag tgt taa                                            789
Ala His Pro Pro Lys Cys
240                 245

<210> SEQ ID NO 290
<211> LENGTH: 262
<212> TYPE: PRT
<213> ORGANISM: Artificial Sequence
<220> FEATURE:
<223> OTHER INFORMATION: Synthetic Construct

<400> SEQUENCE: 290

Met His Ala Leu Ala Leu Leu Ala Ala Thr Leu Phe Gly Leu Ala Ala
        -15                 -10                 -5

Ala Tyr Pro Ala Lys Val Asp Leu Arg Cys Arg Ser Ser Pro Ser Thr
-1  1                   5                   10                  15

Ser Ala Ser Val Val Arg Thr Tyr Ser Lys Gly Ser Glu Ile Gln Ile
                20                  25                  30

Ser Cys Gln Thr Thr Gly Thr Ser Val Glu Gly Ser Asn Val Trp Asp
            35                  40                  45

Lys Thr Gln His Gly Cys Tyr Val Ala Asp Tyr Tyr Val Lys Thr Gly
        50                  55                  60

His Ser Gly Ile Phe Thr Thr Lys Cys Gly Ser Ser Gly Gly Gly
    65                  70                  75

Ser Cys Lys Pro Pro Ile Asn Ala Ala Thr Val Ala Leu Ile Lys
80                  85                  90                  95

Glu Phe Glu Gly Phe Val Ala Lys Pro Ala Pro Asp Pro Ile Gly Leu
                100                 105                 110

Pro Thr Val Gly Tyr Gly His Leu Cys Lys Thr Lys Gly Cys Lys Glu
            115                 120                 125

Val Pro Tyr Ser Phe Pro Leu Thr Gln Thr Thr Ala Thr Lys Leu Leu
        130                 135                 140

Gln Ser Asp Ile Lys Thr Phe Thr Ser Cys Val Ser Asn Tyr Val Lys
    145                 150                 155

Asp Ser Val Lys Leu Asn Asp Asn Gln Phe Gly Ala Leu Ser Ser Trp
160                 165                 170                 175

Ala Phe Asn Val Gly Cys Gly Asn Ile Gln Thr Ser Ser Leu Ile Lys
                180                 185                 190

Arg Leu Asn Ala Gly Glu Asn Pro Asn Thr Val Ala Ala Gln Glu Leu
            195                 200                 205

Pro Lys Trp Lys Tyr Ala Gly Gly Lys Val Leu Pro Gly Leu Val Arg
```

```
                   210                 215                 220
Arg Arg Lys Ala Glu Val Ala Leu Phe Lys Lys Pro Ser Ser Val Gln
    225                 230                 235

Ala His Pro Pro Lys Cys
240                 245

<210> SEQ ID NO 291
<211> LENGTH: 245
<212> TYPE: PRT
<213> ORGANISM: Trichophaea minuta
<220> FEATURE:
<221> NAME/KEY: mat_peptide
<222> LOCATION: (1)..(245)

<400> SEQUENCE: 291

Tyr Pro Ala Lys Val Asp Leu Arg Cys Arg Ser Ser Pro Ser Thr Ser
1               5                   10                  15

Ala Ser Val Val Arg Thr Tyr Ser Lys Gly Ser Glu Ile Gln Ile Ser
                20                  25                  30

Cys Gln Thr Thr Gly Thr Ser Val Glu Gly Ser Asn Val Trp Asp Lys
            35                  40                  45

Thr Gln His Gly Cys Tyr Val Ala Asp Tyr Tyr Val Lys Thr Gly His
        50                  55                  60

Ser Gly Ile Phe Thr Thr Lys Cys Gly Ser Ser Gly Gly Gly Ser
65                  70                  75                  80

Cys Lys Pro Pro Ile Asn Ala Ala Thr Val Ala Leu Ile Lys Glu
                85                  90                  95

Phe Glu Gly Phe Val Ala Lys Pro Ala Pro Asp Pro Ile Gly Leu Pro
                100                 105                 110

Thr Val Gly Tyr Gly His Leu Cys Lys Thr Lys Gly Cys Lys Glu Val
                115                 120                 125

Pro Tyr Ser Phe Pro Leu Thr Gln Thr Thr Ala Thr Lys Leu Leu Gln
            130                 135                 140

Ser Asp Ile Lys Thr Phe Thr Ser Cys Val Ser Asn Tyr Val Lys Asp
145                 150                 155                 160

Ser Val Lys Leu Asn Asp Asn Gln Phe Gly Ala Leu Ser Ser Trp Ala
                165                 170                 175

Phe Asn Val Gly Cys Gly Asn Ile Gln Thr Ser Ser Leu Ile Lys Arg
                180                 185                 190

Leu Asn Ala Gly Glu Asn Pro Asn Thr Val Ala Ala Gln Glu Leu Pro
            195                 200                 205

Lys Trp Lys Tyr Ala Gly Gly Lys Val Leu Pro Gly Leu Val Arg Arg
    210                 215                 220

Arg Lys Ala Glu Val Ala Leu Phe Lys Lys Pro Ser Ser Val Gln Ala
225                 230                 235                 240

His Pro Pro Lys Cys
                245

<210> SEQ ID NO 292
<211> LENGTH: 935
<212> TYPE: DNA
<213> ORGANISM: Chaetomium sp.
<220> FEATURE:
<221> NAME/KEY: CDS
<222> LOCATION: (1)..(379)
<220> FEATURE:
<221> NAME/KEY: sig_peptide
<222> LOCATION: (1)..(54)
<220> FEATURE:
```

```
<221> NAME/KEY: mat_peptide
<222> LOCATION: (55)..(932)
<220> FEATURE:
<221> NAME/KEY: CDS
<222> LOCATION: (448)..(578)
<220> FEATURE:
<221> NAME/KEY: CDS
<222> LOCATION: (642)..(932)

<400> SEQUENCE: 292
```

| | | | | | | | | | | | | | | | | |
|---|---|---|---|---|---|---|---|---|---|---|---|---|---|---|---|---|
| atg | aag | ttc | gct | atc | atc | gcc | gcc | gtc | gtt | ccc | ttc | ctg | gcc | ccc | gcc | 48 |
| Met | Lys | Phe | Ala | Ile | Ile | Ala | Ala | Val | Val | Pro | Phe | Leu | Ala | Pro | Ala | |
| | | | -15 | | | | -10 | | | | | -5 | | | | |
| tcg | gcc | tac | aag | atc | tcg | ggc | agc | tcc | gtc | aac | tgc | cgc | tcc | ggg | ccc | 96 |
| Ser | Ala | Tyr | Lys | Ile | Ser | Gly | Ser | Ser | Val | Asn | Cys | Arg | Ser | Gly | Pro | |
| | -1 | 1 | | | 5 | | | | | 10 | | | | | | |
| ggc | acc | aac | tac | ccc | gtc | aag | aag | acc | tac | gcc | aac | ggt | gac | gag | gtc | 144 |
| Gly | Thr | Asn | Tyr | Pro | Val | Lys | Lys | Thr | Tyr | Ala | Asn | Gly | Asp | Glu | Val | |
| 15 | | | | 20 | | | | | 25 | | | | | 30 | | |
| acc | att | agc | tgc | cag | acc | acc | ggc | acg | aac | gtg | gag | ggc | aac | aac | atc | 192 |
| Thr | Ile | Ser | Cys | Gln | Thr | Thr | Gly | Thr | Asn | Val | Glu | Gly | Asn | Asn | Ile | |
| | | | 35 | | | | | 40 | | | | | 45 | | | |
| tgg | gac | aag | acc | cag | cac | ggc | tgc | tac | gtc | gcc | gac | aag | tat | gtc | aag | 240 |
| Trp | Asp | Lys | Thr | Gln | His | Gly | Cys | Tyr | Val | Ala | Asp | Lys | Tyr | Val | Lys | |
| | | 50 | | | | | 55 | | | | | 60 | | | | |
| acc | ggc | aag | gac | ggc | ttc | gtc | acc | aag | aag | tgc | ggc | agc | tcc | ggt | ggt | 288 |
| Thr | Gly | Lys | Asp | Gly | Phe | Val | Thr | Lys | Lys | Cys | Gly | Ser | Ser | Gly | Gly | |
| | 65 | | | | | 70 | | | | | 75 | | | | | |
| ggt | ggt | ggt | ggc | aag | acc | tgc | aag | gcc | ccc | aag | tcc | aac | gcc | gct | acc | 336 |
| Gly | Gly | Gly | Gly | Lys | Thr | Cys | Lys | Ala | Pro | Lys | Ser | Asn | Ala | Ala | Thr | |
| 80 | | | | | 85 | | | | | 90 | | | | | | |
| gtt | gat | ttg | att | gct | tcg | ttc | gag | ggc | ttc | cgg | gcc | aat | atc | t | | 379 |
| Val | Asp | Leu | Ile | Ala | Ser | Phe | Glu | Gly | Phe | Arg | Ala | Asn | Ile | | | |
| 95 | | | | | 100 | | | | | 105 | | | | | | |

| | |
|---|---|
| gtgagtagac ccccgaaagg gaaagtggca taagctgtgc agactcctaa cgagtgcacc | 439 |
| cctttcag ac acg gat gcc act ggc cac ccc acc gtt ggc tac ggc cac | 488 |

| | | | | | | | | | | | |
|---|---|---|---|---|---|---|---|---|---|---|---|
| | Tyr | Thr | Asp | Ala | Thr | Gly | His | Pro | Thr | Val | Gly | Tyr | Gly | His |
| | | 110 | | | | | 115 | | | | | 120 | | |

| | | | | | | | | | | | | | | | | |
|---|---|---|---|---|---|---|---|---|---|---|---|---|---|---|---|---|
| atg | tgc | acc | aag | tcc | agg | tgc | gcc | gag | gtc | aag | tac | aag | atc | ccg | ctc | 536 |
| Met | Cys | Thr | Lys | Ser | Arg | Cys | Ala | Glu | Val | Lys | Tyr | Lys | Ile | Pro | Leu | |
| | 125 | | | | | 130 | | | | | 135 | | | | | |
| tcc | aag | gcc | gac | ggc | aag | aag | ctg | ctc | gcc | gat | gac | atg | gcg | | | 578 |
| Ser | Lys | Ala | Asp | Gly | Lys | Lys | Leu | Leu | Ala | Asp | Asp | Met | Ala | | | |
| | 140 | | | | | 145 | | | | | 150 | | | | | |

| | |
|---|---|
| gtgagtccca tccattccct ccttcacaga ctaacttact gacgcgccct ctccaatttc | 638 |

| | | | | | | | | | | | | | | | | |
|---|---|---|---|---|---|---|---|---|---|---|---|---|---|---|---|---|
| aag | aaa | ttc | gag | aag | tgc | atc | aag | gag | atg | ctc | aac | tcc | aag | gcc | aag | 686 |
| Lys | Phe | Glu | Lys | Cys | Ile | Lys | Glu | Met | Leu | Asn | Ser | Lys | Ala | Lys | | |
| | 155 | | | | | 160 | | | | | 165 | | | | | |
| ctc | aac | ctg | aac | cag | tac | ggc | gcc | ctc | gtc | agc | tgg | tcc | ttc | aac | gtc | 734 |
| Leu | Asn | Leu | Asn | Gln | Tyr | Gly | Ala | Leu | Val | Ser | Trp | Ser | Phe | Asn | Val | |
| | 170 | | | | | 175 | | | | | 180 | | | | | |
| ggc | tgc | ggc | gcc | gcc | aag | ggc | tcc | cag | ctc | gtc | agc | cgc | ctc | aac | aag | 782 |
| Gly | Cys | Gly | Ala | Ala | Lys | Gly | Ser | Gln | Leu | Val | Ser | Arg | Leu | Asn | Lys | |
| 185 | | | | | 190 | | | | | 195 | | | | | | |
| ggc | gag | aac | ccc | aac | acg | gtc | ctc | tcc | aac | gag | ctc | ccc | aag | tgg | gtc | 830 |
| Gly | Glu | Asn | Pro | Asn | Thr | Val | Leu | Ser | Asn | Glu | Leu | Pro | Lys | Trp | Val | |
| 200 | | | | 205 | | | | | 210 | | | | | 215 | | |
| cac | ggc | aac | ggc | aag | gtg | ctg | ccc | ggt | ctc | gtc | cgc | cgc | cgc | aac | gcc | 878 |
| His | Gly | Asn | Gly | Lys | Val | Leu | Pro | Gly | Leu | Val | Arg | Arg | Arg | Asn | Ala | |
| | | | 220 | | | | | 225 | | | | | 230 | | | |

```
gag att gcc ctc gcc aag aag agc ggc agc ggc gcc gcc ctg ccc gtc      926
Glu Ile Ala Leu Ala Lys Lys Ser Gly Ser Gly Ala Ala Leu Pro Val
        235             240             245 aag tgc tag                                                          935
Lys Cys
```

<210> SEQ ID NO 293
<211> LENGTH: 267
<212> TYPE: PRT
<213> ORGANISM: Chaetomium sp.

<400> SEQUENCE: 293

```
Met Lys Phe Ala Ile Ile Ala Ala Val Val Pro Phe Leu Ala Pro Ala
            -15                 -10                  -5

Ser Ala Tyr Lys Ile Ser Gly Ser Ser Val Asn Cys Arg Ser Gly Pro
     -1  1               5                  10

Gly Thr Asn Tyr Pro Val Lys Lys Thr Tyr Ala Asn Gly Asp Glu Val
 15                 20              25                  30

Thr Ile Ser Cys Gln Thr Thr Gly Thr Asn Val Glu Gly Asn Asn Ile
                 35                  40                  45

Trp Asp Lys Thr Gln His Gly Cys Tyr Val Ala Asp Lys Tyr Val Lys
             50                  55                  60

Thr Gly Lys Asp Gly Phe Val Thr Lys Lys Cys Gly Ser Ser Gly Gly
 65                  70                  75

Gly Gly Gly Gly Lys Thr Cys Lys Ala Pro Lys Ser Asn Ala Ala Thr
 80                  85                  90

Val Asp Leu Ile Ala Ser Phe Glu Gly Phe Arg Ala Asn Ile Tyr Thr
 95                 100                 105                 110

Asp Ala Thr Gly His Pro Thr Val Gly Tyr Gly His Met Cys Thr Lys
                115                 120                 125

Ser Arg Cys Ala Glu Val Lys Tyr Lys Ile Pro Leu Ser Lys Ala Asp
            130                 135                 140

Gly Lys Lys Leu Leu Ala Asp Asp Met Ala Lys Phe Glu Lys Cys Ile
            145                 150                 155

Lys Glu Met Leu Asn Ser Lys Ala Lys Leu Asn Leu Asn Gln Tyr Gly
160                 165                 170

Ala Leu Val Ser Trp Ser Phe Asn Val Gly Cys Gly Ala Ala Lys Gly
175                 180                 185                 190

Ser Gln Leu Val Ser Arg Leu Asn Lys Gly Glu Asn Pro Asn Thr Val
                195                 200                 205

Leu Ser Asn Glu Leu Pro Lys Trp Val His Gly Asn Gly Lys Val Leu
            210                 215                 220

Pro Gly Leu Val Arg Arg Asn Ala Glu Ile Ala Leu Ala Lys Lys
            225                 230                 235

Ser Gly Ser Gly Ala Ala Leu Pro Val Lys Cys
240                 245
```

<210> SEQ ID NO 294
<211> LENGTH: 249
<212> TYPE: PRT
<213> ORGANISM: Chaetomium sp.
<220> FEATURE:
<221> NAME/KEY: mat_peptide
<222> LOCATION: (1)..(249)

<400> SEQUENCE: 294

```
Tyr Lys Ile Ser Gly Ser Ser Val Asn Cys Arg Ser Gly Pro Gly Thr
 1               5                  10                  15
```

```
Asn Tyr Pro Val Lys Lys Thr Tyr Ala Asn Gly Asp Glu Val Thr Ile
            20                  25                  30

Ser Cys Gln Thr Thr Gly Thr Asn Val Glu Gly Asn Asn Ile Trp Asp
        35                  40                  45

Lys Thr Gln His Gly Cys Tyr Val Ala Asp Lys Tyr Val Lys Thr Gly
    50                  55                  60

Lys Asp Gly Phe Val Thr Lys Cys Gly Ser Ser Gly Gly Gly Gly Gly
65                  70                  75                  80

Gly Gly Lys Thr Cys Lys Ala Pro Lys Ser Asn Ala Ala Thr Val Asp
                85                  90                  95

Leu Ile Ala Ser Phe Glu Gly Phe Arg Ala Asn Ile Tyr Thr Asp Ala
                100                 105                 110

Thr Gly His Pro Thr Val Gly Tyr Gly His Met Cys Thr Lys Ser Arg
            115                 120                 125

Cys Ala Glu Val Lys Tyr Lys Ile Pro Leu Ser Lys Ala Asp Gly Lys
        130                 135                 140

Lys Leu Leu Ala Asp Asp Met Ala Lys Phe Glu Lys Cys Ile Lys Glu
145                 150                 155                 160

Met Leu Asn Ser Lys Ala Lys Leu Asn Leu Asn Gln Tyr Gly Ala Leu
                165                 170                 175

Val Ser Trp Ser Phe Asn Val Gly Cys Gly Ala Ala Lys Gly Ser Gln
            180                 185                 190

Leu Val Ser Arg Leu Asn Lys Gly Glu Asn Pro Asn Thr Val Leu Ser
        195                 200                 205

Asn Glu Leu Pro Lys Trp Val His Gly Asn Gly Lys Val Leu Pro Gly
    210                 215                 220

Leu Val Arg Arg Asn Ala Glu Ile Ala Leu Ala Lys Lys Ser Gly
225                 230                 235                 240

Ser Gly Ala Ala Leu Pro Val Lys Cys
                245

<210> SEQ ID NO 295
<211> LENGTH: 795
<212> TYPE: DNA
<213> ORGANISM: Mortierella sp.
<220> FEATURE:
<221> NAME/KEY: CDS
<222> LOCATION: (1)..(792)
<220> FEATURE:
<221> NAME/KEY: sig_peptide
<222> LOCATION: (1)..(57)
<220> FEATURE:
<221> NAME/KEY: mat_peptide
<222> LOCATION: (58)..(792)

<400> SEQUENCE: 295 atg aag ttc acg ctc gcc ctt gct gcc ttg gct gcc tct atc ccc gcc      48
Met Lys Phe Thr Leu Ala Leu Ala Ala Leu Ala Ala Ser Ile Pro Ala
            -15                 -10                  -5 acg ctg gcc tat ccc atc acg ggt gcc gat gct ctg cat tgc cgt tcc      96
Thr Leu Ala Tyr Pro Ile Thr Gly Ala Asp Ala Leu His Cys Arg Ser
    -1   1               5                   10 ggt cct ggt act tcg tac ccc atc caa aag acg ctg cgt cct cct cag     144
Gly Pro Gly Thr Ser Tyr Pro Ile Gln Lys Thr Leu Arg Pro Pro Gln
    15                  20                  25 gat atc aag atc caa tgc cag gag cct ggt acg gtc gtc aac ggc gtt     192
Asp Ile Lys Ile Gln Cys Gln Glu Pro Gly Thr Val Val Asn Gly Val
30                  35                  40                  45
```

| | | |
|---|---|---|
| agc ctg tgg gac aag acc cag ttt ggc tgc tac gtg tcc gat tat tat<br>Ser Leu Trp Asp Lys Thr Gln Phe Gly Cys Tyr Val Ser Asp Tyr Tyr<br>              50                    55                    60 | | 240 |
| gtc aag act ggt acc ggc aac tac gtc gcc cct cgc tgc aac agc ggt<br>Val Lys Thr Gly Thr Gly Asn Tyr Val Ala Pro Arg Cys Asn Ser Gly<br> 65                         70                    75 | | 288 |
| ggc agc tct agc gct tgc act ggc ctg aac gat gct ggc atc aac ttg<br>Gly Ser Ser Ser Ala Cys Thr Gly Leu Asn Asp Ala Gly Ile Asn Leu<br>        80                    85                    90 | | 336 |
| atc aag gag ttt gaa ggc ttc gtc cct cgc cct gcg ccg gat ccc att<br>Ile Lys Glu Phe Glu Gly Phe Val Pro Arg Pro Ala Pro Asp Pro Ile<br> 95                         100                 105 | | 384 |
| ggc ttg ccc acc gtt ggc tac ggt cat ttg tgc cag acc aag ggt tgc<br>Gly Leu Pro Thr Val Gly Tyr Gly His Leu Cys Gln Thr Lys Gly Cys<br>110                    115                 120                 125 | | 432 |
| ggc gag gtc aag tac tca ttc cct ctt acc acc gcg acc gcc acc gct<br>Gly Glu Val Lys Tyr Ser Phe Pro Leu Thr Thr Ala Thr Ala Thr Ala<br>              130                 135                 140 | | 480 |
| ttg ctc aag gac gac ctc ccc aag tac aca tcg tgc ttg gcc aag gcc<br>Leu Leu Lys Asp Asp Leu Pro Lys Tyr Thr Ser Cys Leu Ala Lys Ala<br>                 145                 150                 155 | | 528 |
| ttg aat ggc aaa cca aaa ctg aac aag aac cag tgg gcc gcc ctt gcc<br>Leu Asn Gly Lys Pro Lys Leu Asn Lys Asn Gln Trp Ala Ala Leu Ala<br>        160                    165                 170 | | 576 |
| tcg tgg acg ttt aat gtg ggc tgt ggc aac atg aaa tcc tcg agc ctt<br>Ser Trp Thr Phe Asn Val Gly Cys Gly Asn Met Lys Ser Ser Ser Leu<br>175                    180                 185 | | 624 |
| atc acc cgc ctc aat gca ggt cag aac ccc aac act gtc gcc acc gag<br>Ile Thr Arg Leu Asn Ala Gly Gln Asn Pro Asn Thr Val Ala Thr Glu<br>190                    195                 200                 205 | | 672 |
| gag ctc ccc aag tgg aaa ctg gct ggt ggc aag gtc ctc ccc ggt ctg<br>Glu Leu Pro Lys Trp Lys Leu Ala Gly Gly Lys Val Leu Pro Gly Leu<br>                 210                 215                 220 | | 720 |
| gtc cgt cgt cgt gct gcc gag gtc aag ctg ttc aag acg gcc aac tct<br>Val Arg Arg Arg Ala Ala Glu Val Lys Leu Phe Lys Thr Ala Asn Ser<br>225                    230                 235 | | 768 |
| tcc cag ggt tat cct aag tgt gct taa<br>Ser Gln Gly Tyr Pro Lys Cys Ala<br>        240                    245 | | 795 |

<210> SEQ ID NO 296
<211> LENGTH: 264
<212> TYPE: PRT
<213> ORGANISM: Mortierella sp.

<400> SEQUENCE: 296

Met Lys Phe Thr Leu Ala Leu Ala Ala Leu Ala Ala Ser Ile Pro Ala
                  -15                     -10                        -5

Thr Leu Ala Tyr Pro Ile Thr Gly Ala Asp Ala Leu His Cys Arg Ser
       -1  1                5                        10

Gly Pro Gly Thr Ser Tyr Pro Ile Gln Lys Thr Leu Arg Pro Gln
        15                    20                 25

Asp Ile Lys Ile Gln Cys Gln Glu Pro Gly Thr Val Val Asn Gly Val
30                    35                 40                    45

Ser Leu Trp Asp Lys Thr Gln Phe Gly Cys Tyr Val Ser Asp Tyr Tyr
              50                    55                    60

Val Lys Thr Gly Thr Gly Asn Tyr Val Ala Pro Arg Cys Asn Ser Gly
 65                        70                    75

Gly Ser Ser Ser Ala Cys Thr Gly Leu Asn Asp Ala Gly Ile Asn Leu

-continued

```
            80                  85                  90
Ile Lys Glu Phe Glu Gly Phe Val Pro Arg Pro Ala Pro Asp Pro Ile
 95                 100                 105
Gly Leu Pro Thr Val Gly Tyr Gly His Leu Cys Gln Thr Lys Gly Cys
110                 115                 120                 125
Gly Glu Val Lys Tyr Ser Phe Pro Leu Thr Thr Ala Thr Ala Thr Ala
                    130                 135                 140
Leu Leu Lys Asp Asp Leu Pro Lys Tyr Thr Ser Cys Leu Ala Lys Ala
                145                 150                 155
Leu Asn Gly Lys Pro Lys Leu Asn Lys Asn Gln Trp Ala Ala Leu Ala
            160                 165                 170
Ser Trp Thr Phe Asn Val Gly Cys Gly Asn Met Lys Ser Ser Ser Leu
        175                 180                 185
Ile Thr Arg Leu Asn Ala Gly Gln Asn Pro Asn Thr Val Ala Thr Glu
190                 195                 200                 205
Glu Leu Pro Lys Trp Lys Leu Ala Gly Gly Lys Val Leu Pro Gly Leu
                210                 215                 220
Val Arg Arg Ala Ala Glu Val Lys Leu Phe Lys Thr Ala Asn Ser
            225                 230                 235
Ser Gln Gly Tyr Pro Lys Cys Ala
        240                 245

<210> SEQ ID NO 297
<211> LENGTH: 245
<212> TYPE: PRT
<213> ORGANISM: Mortierella sp.
<220> FEATURE:
<221> NAME/KEY: mat_peptide
<222> LOCATION: (1)..(245)

<400> SEQUENCE: 297

Tyr Pro Ile Thr Gly Ala Asp Ala Leu His Cys Arg Ser Gly Pro Gly
  1               5                  10                  15
Thr Ser Tyr Pro Ile Gln Lys Thr Leu Arg Pro Pro Gln Asp Ile Lys
             20                  25                  30
Ile Gln Cys Gln Glu Pro Gly Thr Val Val Asn Gly Val Ser Leu Trp
         35                  40                  45
Asp Lys Thr Gln Phe Gly Cys Tyr Val Ser Asp Tyr Tyr Val Lys Thr
     50                  55                  60
Gly Thr Gly Asn Tyr Val Ala Pro Arg Cys Asn Ser Gly Gly Ser Ser
 65                  70                  75                  80
Ser Ala Cys Thr Gly Leu Asn Asp Ala Gly Ile Asn Leu Ile Lys Glu
                 85                  90                  95
Phe Glu Gly Phe Val Pro Arg Pro Ala Pro Asp Pro Ile Gly Leu Pro
            100                 105                 110
Thr Val Gly Tyr Gly His Leu Cys Gln Thr Lys Gly Cys Gly Glu Val
        115                 120                 125
Lys Tyr Ser Phe Pro Leu Thr Thr Ala Thr Ala Thr Ala Leu Leu Lys
    130                 135                 140
Asp Asp Leu Pro Lys Tyr Thr Ser Cys Leu Ala Lys Ala Leu Asn Gly
145                 150                 155                 160
Lys Pro Lys Leu Asn Lys Asn Gln Trp Ala Ala Leu Ala Ser Trp Thr
                165                 170                 175
Phe Asn Val Gly Cys Gly Asn Met Lys Ser Ser Ser Leu Ile Thr Arg
            180                 185                 190
```

-continued

```
Leu Asn Ala Gly Gln Asn Pro Asn Thr Val Ala Thr Glu Glu Leu Pro
            195                 200                 205

Lys Trp Lys Leu Ala Gly Gly Lys Val Leu Pro Gly Leu Val Arg Arg
210                 215                 220

Arg Ala Ala Glu Val Lys Leu Phe Lys Thr Ala Asn Ser Ser Gln Gly
225                 230                 235                 240

Tyr Pro Lys Cys Ala
            245

<210> SEQ ID NO 298
<211> LENGTH: 801
<212> TYPE: DNA
<213> ORGANISM: Metarhizium sp.
<220> FEATURE:
<221> NAME/KEY: CDS
<222> LOCATION: (1)..(798)
<220> FEATURE:
<221> NAME/KEY: sig_peptide
<222> LOCATION: (1)..(57)
<220> FEATURE:
<221> NAME/KEY: mat_peptide
<222> LOCATION: (58)..(798)

<400> SEQUENCE: 298 atg aag ttt ctc gct gtt gca aat gtc ttg gca atg aca tcc act gtg      48
Met Lys Phe Leu Ala Val Ala Asn Val Leu Ala Met Thr Ser Thr Val
                -15                 -10                  -5 gta gtt gcc tac cca gtt tct gct gat agt ctc aac tgc cga gcc gag      96
Val Val Ala Tyr Pro Val Ser Ala Asp Ser Leu Asn Cys Arg Ala Glu
     -1   1                   5                  10 ccc aac acc agc tcc gcc atc aaa aca acc tac aag aag ggt gaa gat     144
Pro Asn Thr Ser Ser Ala Ile Lys Thr Thr Tyr Lys Lys Gly Glu Asp
         15                  20                  25 gtc aaa att tcc tgc cag acc gag ggt ccc tcc atc aac ggc aac acc     192
Val Lys Ile Ser Cys Gln Thr Glu Gly Pro Ser Ile Asn Gly Asn Thr
 30                  35                  40                  45 atc tgg gac aag acc caa gat ggt tgc tac gtc gcc gac tac tac gtc     240
Ile Trp Asp Lys Thr Gln Asp Gly Cys Tyr Val Ala Asp Tyr Tyr Val
                 50                  55                  60 aaa acc gga tcc tct ggc tac gtc act ggc aaa tgc ggc ggt agc agt     288
Lys Thr Gly Ser Ser Gly Tyr Val Thr Gly Lys Cys Gly Gly Ser Ser
             65                  70                  75 ccc cca agc ggt tcc ggc ttt tgc aag acg gta aac aag gcg ggc ctc     336
Pro Pro Ser Gly Ser Gly Phe Cys Lys Thr Val Asn Lys Ala Gly Leu
         80                  85                  90 gat ctc atc acc aag tgg gaa ggc ttt gtt tcc agc ccc agg ggc gac     384
Asp Leu Ile Thr Lys Trp Glu Gly Phe Val Ser Ser Pro Arg Gly Asp
     95                 100                 105 ccc atc ggc ctg cct act gtt ggc tat ggc cat ctc tgc cag aag aag     432
Pro Ile Gly Leu Pro Thr Val Gly Tyr Gly His Leu Cys Gln Lys Lys
110                 115                 120                 125 ggc tgc gcc gaa gtc aag tac aag ttc cct ttg acc aag gcc act gcc     480
Gly Cys Ala Glu Val Lys Tyr Lys Phe Pro Leu Thr Lys Ala Thr Ala
                130                 135                 140 ctg cag ctc ctc aac gac gat ctc ccc aag tat acc ggc tgc ctc ggc     528
Leu Gln Leu Leu Asn Asp Asp Leu Pro Lys Tyr Thr Gly Cys Leu Gly
            145                 150                 155 aag ctc ctc aac agc aag gtc aag ctt aat gac aat cag tgg gcg gct     576
Lys Leu Leu Asn Ser Lys Val Lys Leu Asn Asp Asn Gln Trp Ala Ala
        160                 165                 170 ctg acc tcc tgg gtt ttc aac gtt gga tgt ggc aac gct cag tct tcc     624
Leu Thr Ser Trp Val Phe Asn Val Gly Cys Gly Asn Ala Gln Ser Ser
```

```
                175                 180                 185
tct ctt gtc aga cgt ctc aac aat ggc gag aac ccc aac aca gtt gct       672
Ser Leu Val Arg Arg Leu Asn Asn Gly Glu Asn Pro Asn Thr Val Ala
190                 195                 200                 205 ccc agt gag ctt ccc aag tgg aaa atg gcc ggt ggt aag gtg ttg gag       720
Pro Ser Glu Leu Pro Lys Trp Lys Met Ala Gly Gly Lys Val Leu Glu
            210                 215                 220 ggc ttg gtc aaa cgc cgt gct gac gag gtc aga ctc ttc aag gtt tct       768
Gly Leu Val Lys Arg Arg Ala Asp Glu Val Arg Leu Phe Lys Val Ser
            225                 230                 235 tct tcc aag ggc gca ttc ccc aaa tgc cag tag                           801
Ser Ser Lys Gly Ala Phe Pro Lys Cys Gln
            240                 245

<210> SEQ ID NO 299
<211> LENGTH: 266
<212> TYPE: PRT
<213> ORGANISM: Metarhizium sp.

<400> SEQUENCE: 299

Met Lys Phe Leu Ala Val Ala Asn Val Leu Ala Met Thr Ser Thr Val
                -15                 -10                 -5

Val Val Ala Tyr Pro Val Ser Ala Asp Ser Leu Asn Cys Arg Ala Glu
        -1  1               5                   10

Pro Asn Thr Ser Ser Ala Ile Lys Thr Thr Tyr Lys Lys Gly Glu Asp
 15                  20                  25

Val Lys Ile Ser Cys Gln Thr Glu Gly Pro Ser Ile Asn Gly Asn Thr
30                  35                  40                  45

Ile Trp Asp Lys Thr Gln Asp Gly Cys Tyr Val Ala Asp Tyr Tyr Val
                50                  55                  60

Lys Thr Gly Ser Ser Gly Tyr Val Thr Gly Lys Cys Gly Gly Ser Ser
                65                  70                  75

Pro Pro Ser Gly Ser Gly Phe Cys Lys Thr Val Asn Lys Ala Gly Leu
            80                  85                  90

Asp Leu Ile Thr Lys Trp Glu Gly Phe Val Ser Ser Pro Arg Gly Asp
 95                 100                 105

Pro Ile Gly Leu Pro Thr Val Gly Tyr Gly His Leu Cys Gln Lys Lys
110                 115                 120                 125

Gly Cys Ala Glu Val Lys Tyr Lys Phe Pro Leu Thr Lys Ala Thr Ala
                130                 135                 140

Leu Gln Leu Leu Asn Asp Asp Leu Pro Lys Tyr Thr Gly Cys Leu Gly
                145                 150                 155

Lys Leu Leu Asn Ser Lys Val Lys Leu Asn Asp Asn Gln Trp Ala Ala
            160                 165                 170

Leu Thr Ser Trp Val Phe Asn Val Gly Cys Gly Asn Ala Gln Ser Ser
            175                 180                 185

Ser Leu Val Arg Arg Leu Asn Asn Gly Glu Asn Pro Asn Thr Val Ala
190                 195                 200                 205

Pro Ser Glu Leu Pro Lys Trp Lys Met Ala Gly Gly Lys Val Leu Glu
            210                 215                 220

Gly Leu Val Lys Arg Arg Ala Asp Glu Val Arg Leu Phe Lys Val Ser
            225                 230                 235

Ser Ser Lys Gly Ala Phe Pro Lys Cys Gln
            240                 245

<210> SEQ ID NO 300
```

```
<211> LENGTH: 247
<212> TYPE: PRT
<213> ORGANISM: Metarhizium sp.
<220> FEATURE:
<221> NAME/KEY: mat_peptide
<222> LOCATION: (1)..(247)

<400> SEQUENCE: 300

Tyr Pro Val Ser Ala Asp Ser Leu Asn Cys Arg Ala Glu Pro Asn Thr
1               5                   10                  15

Ser Ser Ala Ile Lys Thr Thr Tyr Lys Lys Gly Glu Asp Val Lys Ile
            20                  25                  30

Ser Cys Gln Thr Glu Gly Pro Ser Ile Asn Gly Asn Thr Ile Trp Asp
        35                  40                  45

Lys Thr Gln Asp Gly Cys Tyr Val Ala Asp Tyr Tyr Val Lys Thr Gly
    50                  55                  60

Ser Ser Gly Tyr Val Thr Gly Lys Cys Gly Gly Ser Ser Pro Pro Ser
65                  70                  75                  80

Gly Ser Gly Phe Cys Lys Thr Val Asn Lys Ala Gly Leu Asp Leu Ile
                85                  90                  95

Thr Lys Trp Glu Gly Phe Val Ser Ser Pro Arg Gly Asp Pro Ile Gly
            100                 105                 110

Leu Pro Thr Val Gly Tyr Gly His Leu Cys Gln Lys Lys Gly Cys Ala
        115                 120                 125

Glu Val Lys Tyr Lys Phe Pro Leu Thr Lys Ala Thr Ala Leu Gln Leu
    130                 135                 140

Leu Asn Asp Asp Leu Pro Lys Tyr Thr Gly Cys Leu Gly Lys Leu Leu
145                 150                 155                 160

Asn Ser Lys Val Lys Leu Asn Asp Asn Gln Trp Ala Ala Leu Thr Ser
                165                 170                 175

Trp Val Phe Asn Val Gly Cys Gly Asn Ala Gln Ser Ser Ser Leu Val
            180                 185                 190

Arg Arg Leu Asn Asn Gly Glu Asn Pro Asn Thr Val Ala Pro Ser Glu
        195                 200                 205

Leu Pro Lys Trp Lys Met Ala Gly Gly Lys Val Leu Glu Gly Leu Val
    210                 215                 220

Lys Arg Arg Ala Asp Glu Val Arg Leu Phe Lys Val Ser Ser Ser Lys
225                 230                 235                 240

Gly Ala Phe Pro Lys Cys Gln
                245

<210> SEQ ID NO 301
<211> LENGTH: 921
<212> TYPE: DNA
<213> ORGANISM: Geomyces auratus
<220> FEATURE:
<221> NAME/KEY: CDS
<222> LOCATION: (1)..(382)
<220> FEATURE:
<221> NAME/KEY: sig_peptide
<222> LOCATION: (1)..(54)
<220> FEATURE:
<221> NAME/KEY: mat_peptide
<222> LOCATION: (55)..(918)
<220> FEATURE:
<221> NAME/KEY: CDS
<222> LOCATION: (440)..(570)
<220> FEATURE:
<221> NAME/KEY: CDS
<222> LOCATION: (628)..(918)

<400> SEQUENCE: 301
```

```
atg aag ctt tct ctt ctc gcc gtt ggc gcc gtg gca tgc tct ttc gtg         48
Met Lys Leu Ser Leu Leu Ala Val Gly Ala Val Ala Cys Ser Phe Val
        -15                 -10                 -5 agc gcc gct ttc ccc att acc ggc agt act gtc aac tgc cgc act ggg         96
Ser Ala Ala Phe Pro Ile Thr Gly Ser Thr Val Asn Cys Arg Thr Gly
    -1  1               5                   10 cca gga acg agc cat ggc gtg aag aca tca tac aag aag ggc cac gaa        144
Pro Gly Thr Ser His Gly Val Lys Thr Ser Tyr Lys Lys Gly His Glu
15                  20                  25                  30 gta acg gta tcc tgc cag acc gga gga acc agt gtg aac ggc aat tca        192
Val Thr Val Ser Cys Gln Thr Gly Gly Thr Ser Val Asn Gly Asn Ser
                35                  40                  45 atc tgg gat aag aca tcc gat ggc tgt tat gtt gcc gat tac tat gtt        240
Ile Trp Asp Lys Thr Ser Asp Gly Cys Tyr Val Ala Asp Tyr Tyr Val
            50                  55                  60 aag act ggt tca agc ggc tac gtg aag ccc aag tgc ggc tcc tct tcc        288
Lys Thr Gly Ser Ser Gly Tyr Val Lys Pro Lys Cys Gly Ser Ser Ser
65                  70                  75 gga ggt gga ggc gga agc agt tgt ggt gca cct aaa tct aac gct gct        336
Gly Gly Gly Gly Gly Ser Ser Cys Gly Ala Pro Lys Ser Asn Ala Ala
        80                  85                  90 act gtc aac ctg att gcc gaa ttt gag ggt ttc gtt agc cac gtt t          382
Thr Val Asn Leu Ile Ala Glu Phe Glu Gly Phe Val Ser His Val
95                  100                 105 gtaagtgacc ctttgtctgg atgcgggctg tcggggatac tgaccaactt gtgatag          439 at  acc gac gct act ggt cac cct act gtc ggc tat ggc cat ctc tgc        486
    Tyr Thr Asp Ala Thr Gly His Pro Thr Val Gly Tyr Gly His Leu Cys
    110                 115                 120                 125 agc aac tcg aag tgc tct ggc atc gga tac tca att cct atc tcc aag        534
Ser Asn Ser Lys Cys Ser Gly Ile Gly Tyr Ser Ile Pro Ile Ser Lys
                130                 135                 140 gcc aat gct aag aag ctt ctc gcc aag gac atg gct gtaagtagtc             580
Ala Asn Ala Lys Lys Leu Leu Ala Lys Asp Met Ala
            145                 150 accgatgctt gaagatccca agtattctaa ccattctcta tgtatag atc gcc gag        636
                                                    Ile Ala Glu
                                                            155 aag tgc att act gca atg atc aac aag agc cgt aca ctc aat ctg aac        684
Lys Cys Ile Thr Ala Met Ile Asn Lys Ser Arg Thr Leu Asn Leu Asn
                160                 165                 170 caa tac ggt gct ctg gtt agc tgg gct ttc aac gaa gga tgt ggc gcg        732
Gln Tyr Gly Ala Leu Val Ser Trp Ala Phe Asn Glu Gly Cys Gly Ala
            175                 180                 185 gcc aaa tca tcc acc ctc atc aaa cgc atc aac aat ggc gaa aag ccc        780
Ala Lys Ser Ser Thr Leu Ile Lys Arg Ile Asn Asn Gly Glu Lys Pro
190                 195                 200 agc act gtc att cct caa gag ctt cca aag tgg gta tat ggt ggg agc        828
Ser Thr Val Ile Pro Gln Glu Leu Pro Lys Trp Val Tyr Gly Gly Ser
205                 210                 215                 220 agc gtc ctt cct ggt ctt gtt cgc cgt cgt aac gct gag att gcg ctt        876
Ser Val Leu Pro Gly Leu Val Arg Arg Arg Asn Ala Glu Ile Ala Leu
                225                 230                 235 gct aaa aag gct aca tcg agc aag gca ctg ccg gct cac tgc taa            921
Ala Lys Lys Ala Thr Ser Ser Lys Ala Leu Pro Ala His Cys
            240                 245                 250

<210> SEQ ID NO 302
<211> LENGTH: 268
<212> TYPE: PRT
```

<213> ORGANISM: Geomyces auratus

<400> SEQUENCE: 302

Met Lys Leu Ser Leu Leu Ala Val Gly Ala Val Ala Cys Ser Phe Val
        -15                 -10                  -5

Ser Ala Ala Phe Pro Ile Thr Gly Ser Thr Val Asn Cys Arg Thr Gly
    -1   1               5                  10

Pro Gly Thr Ser His Gly Val Lys Thr Ser Tyr Lys Lys Gly His Glu
 15              20                  25                      30

Val Thr Val Ser Cys Gln Thr Gly Gly Thr Ser Val Asn Gly Asn Ser
                 35                  40                  45

Ile Trp Asp Lys Thr Ser Asp Gly Cys Tyr Val Ala Asp Tyr Tyr Val
             50                  55                  60

Lys Thr Gly Ser Ser Gly Tyr Val Lys Pro Lys Cys Gly Ser Ser Ser
             65                  70                  75

Gly Gly Gly Gly Gly Ser Ser Cys Gly Ala Pro Lys Ser Asn Ala Ala
 80                  85                  90

Thr Val Asn Leu Ile Ala Glu Phe Glu Gly Phe Val Ser His Val Tyr
 95              100                 105                     110

Thr Asp Ala Thr Gly His Pro Thr Val Gly Tyr Gly His Leu Cys Ser
                 115                 120                 125

Asn Ser Lys Cys Ser Gly Ile Gly Tyr Ser Ile Pro Ile Ser Lys Ala
             130                 135                 140

Asn Ala Lys Lys Leu Leu Ala Lys Asp Met Ala Ile Ala Glu Lys Cys
             145                 150                 155

Ile Thr Ala Met Ile Asn Lys Ser Arg Thr Leu Asn Leu Asn Gln Tyr
             160                 165                 170

Gly Ala Leu Val Ser Trp Ala Phe Asn Glu Gly Cys Gly Ala Ala Lys
 175                 180                 185                 190

Ser Ser Thr Leu Ile Lys Arg Ile Asn Asn Gly Glu Lys Pro Ser Thr
                 195                 200                 205

Val Ile Pro Gln Glu Leu Pro Lys Trp Val Tyr Gly Gly Ser Ser Val
                 210                 215                 220

Leu Pro Gly Leu Val Arg Arg Asn Ala Glu Ile Ala Leu Ala Lys
             225                 230                 235

Lys Ala Thr Ser Ser Lys Ala Leu Pro Ala His Cys
 240                 245                 250

<210> SEQ ID NO 303
<211> LENGTH: 250
<212> TYPE: PRT
<213> ORGANISM: Geomyces auratus
<220> FEATURE:
<221> NAME/KEY: mat_peptide
<222> LOCATION: (1)..(250)

<400> SEQUENCE: 303

Ala Phe Pro Ile Thr Gly Ser Thr Val Asn Cys Arg Thr Gly Pro Gly
 1               5                  10                  15

Thr Ser His Gly Val Lys Thr Ser Tyr Lys Lys Gly His Glu Val Thr
             20                  25                  30

Val Ser Cys Gln Thr Gly Gly Thr Ser Val Asn Gly Asn Ser Ile Trp
             35                  40                  45

Asp Lys Thr Ser Asp Gly Cys Tyr Val Ala Asp Tyr Tyr Val Lys Thr
         50                  55                  60

Gly Ser Ser Gly Tyr Val Lys Pro Lys Cys Gly Ser Ser Ser Gly Gly

```
                65                  70                  75                  80
Gly Gly Gly Ser Ser Cys Gly Ala Pro Lys Ser Asn Ala Ala Thr Val
                85                  90                  95

Asn Leu Ile Ala Glu Phe Glu Gly Phe Val Ser His Val Tyr Thr Asp
            100                 105                 110

Ala Thr Gly His Pro Thr Val Gly Tyr Gly His Leu Cys Ser Asn Ser
            115                 120                 125

Lys Cys Ser Gly Ile Gly Tyr Ser Ile Pro Ile Ser Lys Ala Asn Ala
        130                 135                 140

Lys Lys Leu Leu Ala Lys Asp Met Ala Ile Ala Glu Lys Cys Ile Thr
145                 150                 155                 160

Ala Met Ile Asn Lys Ser Arg Thr Leu Asn Leu Asn Gln Tyr Gly Ala
                165                 170                 175

Leu Val Ser Trp Ala Phe Asn Glu Gly Cys Gly Ala Ala Lys Ser Ser
            180                 185                 190

Thr Leu Ile Lys Arg Ile Asn Asn Gly Glu Lys Pro Ser Thr Val Ile
        195                 200                 205

Pro Gln Glu Leu Pro Lys Trp Val Tyr Gly Gly Ser Ser Val Leu Pro
    210                 215                 220

Gly Leu Val Arg Arg Asn Ala Glu Ile Ala Leu Ala Lys Lys Ala
225                 230                 235                 240

Thr Ser Ser Lys Ala Leu Pro Ala His Cys
                245                 250
```

<210> SEQ ID NO 304
<211> LENGTH: 902
<212> TYPE: DNA
<213> ORGANISM: Ilyonectria rufa
<220> FEATURE:
<221> NAME/KEY: CDS
<222> LOCATION: (1)..(352)
<220> FEATURE:
<221> NAME/KEY: sig_peptide
<222> LOCATION: (1)..(54)
<220> FEATURE:
<221> NAME/KEY: mat_peptide
<222> LOCATION: (55)..(899)
<220> FEATURE:
<221> NAME/KEY: CDS
<222> LOCATION: (418)..(548)
<220> FEATURE:
<221> NAME/KEY: CDS
<222> LOCATION: (609)..(899)

<400> SEQUENCE: 304

```
atg aag ttc tct ctc ttt gct gtc tat gct ctt gca gca tcc ctg act      48
Met Lys Phe Ser Leu Phe Ala Val Tyr Ala Leu Ala Ala Ser Leu Thr
            -15                 -10                  -5 agc gcc tat aag atc acc ggt gac aat gtc aac tgc cga agt ggt cca      96
Ser Ala Tyr Lys Ile Thr Gly Asp Asn Val Asn Cys Arg Ser Gly Pro
 -1   1               5                  10 ggc act agc tac tcc gta aag agg tcc ttc aag aag gga act gat gtt     144
Gly Thr Ser Tyr Ser Val Lys Arg Ser Phe Lys Lys Gly Thr Asp Val
 15                  20                  25                  30 acc cta tct tgt caa acc acc gga gaa aat gtt ttg ggt act agt atc     192
Thr Leu Ser Cys Gln Thr Thr Gly Glu Asn Val Leu Gly Thr Ser Ile
                 35                  40                  45 tgg gac aag acc tca tat ggc tgc tat gtc tcg gac tac tat gtc aag     240
Trp Asp Lys Thr Ser Tyr Gly Cys Tyr Val Ser Asp Tyr Tyr Val Lys
             50                  55                  60 aca ggc tcc agc gga ttt gtc gtg aag aag tgc ggt act tgc ggt gcg     288
```

```
Thr Gly Ser Ser Gly Phe Val Val Lys Lys Cys Gly Thr Cys Gly Ala
            65                  70                  75 ccg aag tcg aac gcg gct acc gtg aat ctc atc tcc gat ttc gag gga       336
Pro Lys Ser Asn Ala Ala Thr Val Asn Leu Ile Ser Asp Phe Glu Gly
        80                  85                  90 ttc agg gcg aat atc t gtaagtgttc tttgttcttt gaagacaata ccggaagatt    392
Phe Arg Ala Asn Ile
95 aggtatgcta atacgctggc attag ac  aag gat gct gct ggc tat ccc act       443
                                Tyr Lys Asp Ala Ala Gly Tyr Pro Thr
                                            100                 105 gtc gga tat ggg cac ctc tgc agc aac tcg aga tgc acc gac gtc ccg       491
Val Gly Tyr Gly His Leu Cys Ser Asn Ser Arg Cys Thr Asp Val Pro
            110                 115                 120 tac tct atc cca ctg tct aag gcc aat ggc aaa aac ctc ctc gca act       539
Tyr Ser Ile Pro Leu Ser Lys Ala Asn Gly Lys Asn Leu Leu Ala Thr
    125                 130                 135                 140 gac atg aca gtaagtattc tcctctagca ttcactttc acgcactcat               588
Asp Met Thr tgacacctcc tcttttacag aaa ttc gag aag tgc atc aca gcc atg gtc agc    641
                      Lys Phe Glu Lys Cys Ile Thr Ala Met Val Ser
                                145                 150 agc tcc gtg act ctc aac aag aac cag tat ggc gcc ttg gtc agc tgg       689
Ser Ser Val Thr Leu Asn Lys Asn Gln Tyr Gly Ala Leu Val Ser Trp
    155                 160                 165                 170 gct ttc aac atg ggt tgc gga gcc act aag acg tct acc ctg atc aag       737
Ala Phe Asn Met Gly Cys Gly Ala Thr Lys Thr Ser Thr Leu Ile Lys
                175                 180                 185 cgc ctc aac cag ggc cag aac gtg aac acg gtc ttg tct act gag ctc       785
Arg Leu Asn Gln Gly Gln Asn Val Asn Thr Val Leu Ser Thr Glu Leu
            190                 195                 200 ccg aag tgg gtg tac gca ggt ggc aag aag ctc aat ggt ctt gtt cgc       833
Pro Lys Trp Val Tyr Ala Gly Gly Lys Lys Leu Asn Gly Leu Val Arg
        205                 210                 215 cga cgc aac gcc gag att gct ttg gct aag aag aag acc acc gaa aag       881
Arg Arg Asn Ala Glu Ile Ala Leu Ala Lys Lys Lys Thr Thr Glu Lys
    220                 225                 230 gct ctt ccg aac aag tgc tag                                          902
Ala Leu Pro Asn Lys Cys
235                 240

<210> SEQ ID NO 305
<211> LENGTH: 258
<212> TYPE: PRT
<213> ORGANISM: Ilyonectria rufa

<400> SEQUENCE: 305

Met Lys Phe Ser Leu Phe Ala Val Tyr Ala Leu Ala Ala Ser Leu Thr
            -15                 -10                 -5

Ser Ala Tyr Lys Ile Thr Gly Asp Asn Val Asn Cys Arg Ser Gly Pro
        -1  1                   5                   10

Gly Thr Ser Tyr Ser Val Lys Arg Ser Phe Lys Lys Gly Thr Asp Val
15                  20                  25                  30

Thr Leu Ser Cys Gln Thr Thr Gly Glu Asn Val Leu Gly Thr Ser Ile
                35                  40                  45

Trp Asp Lys Thr Ser Tyr Gly Cys Tyr Val Ser Asp Tyr Tyr Val Lys
            50                  55                  60

Thr Gly Ser Ser Gly Phe Val Val Lys Lys Cys Gly Thr Cys Gly Ala
            65                  70                  75
```

```
Pro Lys Ser Asn Ala Ala Thr Val Asn Leu Ile Ser Asp Phe Glu Gly
     80                  85                  90

Phe Arg Ala Asn Ile Tyr Lys Asp Ala Ala Gly Tyr Pro Thr Val Gly
 95                 100                 105                 110

Tyr Gly His Leu Cys Ser Asn Ser Arg Cys Thr Asp Val Pro Tyr Ser
            115                 120                 125

Ile Pro Leu Ser Lys Ala Asn Gly Lys Asn Leu Leu Ala Thr Asp Met
            130                 135                 140

Thr Lys Phe Glu Lys Cys Ile Thr Ala Met Val Ser Ser Val Thr
            145                 150                 155

Leu Asn Lys Asn Gln Tyr Gly Ala Leu Val Ser Trp Ala Phe Asn Met
160                 165                 170

Gly Cys Gly Ala Thr Lys Thr Ser Thr Leu Ile Lys Arg Leu Asn Gln
175                 180                 185                 190

Gly Gln Asn Val Asn Thr Val Leu Ser Thr Glu Leu Pro Lys Trp Val
                195                 200                 205

Tyr Ala Gly Gly Lys Lys Leu Asn Gly Leu Val Arg Arg Asn Ala
            210                 215                 220

Glu Ile Ala Leu Ala Lys Lys Lys Thr Thr Glu Lys Ala Leu Pro Asn
            225                 230                 235

Lys Cys
    240

<210> SEQ ID NO 306
<211> LENGTH: 240
<212> TYPE: PRT
<213> ORGANISM: Ilyonectria rufa
<220> FEATURE:
<221> NAME/KEY: mat_peptide
<222> LOCATION: (1)..(240)

<400> SEQUENCE: 306

Tyr Lys Ile Thr Gly Asp Asn Val Asn Cys Arg Ser Gly Pro Gly Thr
  1               5                  10                  15

Ser Tyr Ser Val Lys Arg Ser Phe Lys Lys Gly Thr Asp Val Thr Leu
             20                  25                  30

Ser Cys Gln Thr Thr Gly Glu Asn Val Leu Gly Thr Ser Ile Trp Asp
         35                  40                  45

Lys Thr Ser Tyr Gly Cys Tyr Val Ser Asp Tyr Tyr Val Lys Thr Gly
     50                  55                  60

Ser Ser Gly Phe Val Val Lys Lys Cys Gly Thr Cys Gly Ala Pro Lys
 65                  70                  75                  80

Ser Asn Ala Ala Thr Val Asn Leu Ile Ser Asp Phe Glu Gly Phe Arg
                 85                  90                  95

Ala Asn Ile Tyr Lys Asp Ala Ala Gly Tyr Pro Thr Val Gly Tyr Gly
            100                 105                 110

His Leu Cys Ser Asn Ser Arg Cys Thr Asp Val Pro Tyr Ser Ile Pro
        115                 120                 125

Leu Ser Lys Ala Asn Gly Lys Asn Leu Leu Ala Thr Asp Met Thr Lys
    130                 135                 140

Phe Glu Lys Cys Ile Thr Ala Met Val Ser Ser Val Thr Leu Asn
145                 150                 155                 160

Lys Asn Gln Tyr Gly Ala Leu Val Ser Trp Ala Phe Asn Met Gly Cys
                165                 170                 175

Gly Ala Thr Lys Thr Ser Thr Leu Ile Lys Arg Leu Asn Gln Gly Gln
```

```
                180                 185                 190
Asn Val Asn Thr Val Leu Ser Thr Glu Leu Pro Lys Trp Val Tyr Ala
            195                 200                 205

Gly Gly Lys Lys Leu Asn Gly Leu Val Arg Arg Asn Ala Glu Ile
        210                 215                 220

Ala Leu Ala Lys Lys Lys Thr Thr Glu Lys Ala Leu Pro Asn Lys Cys
225                 230                 235                 240
```

ANIMAL FEED COMPOSITIONS AND USES THEREOF

CROSS-REFERENCE TO RELATED APPLICATIONS

This application is a divisional of U.S. application Ser. No. 15/579,769 filed Dec. 5, 2017, now pending, which is a 35 U.S.C. 371 national application of international application no. PCT/CN2016/088362 filed Jul. 4, 2016, which claims priority or the benefit under 35 U.S.C. 119 of European application no. 15175030.4 filed Jul. 2, 2015. The content of each application is fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates animal feed or animal feed additives comprising one or more polypeptides having lysozyme activity. The invention also relates to polypeptides having lysozyme activity, polynucleotides encoding the polypeptides nucleic acid constructs, vectors, and host cells comprising the polynucleotides as well as methods of producing and using the polypeptides.

Description of the Related Art

Lysozyme is an O-glycosyl hydrolase produced as a defensive mechanism against bacteria by many organisms. The enzyme causes the hydrolysis of bacterial cell walls by cleaving the glycosidic bonds of peptidoglycan; an important structural molecule in bacteria. After having their cell walls weakened by lysozyme action, bacterial cells lyse as a result of unbalanced osmotic pressure.

Lysozyme naturally occurs in many organisms such as viruses, plants, insects, birds, reptiles and mammals. In mammals, Lysozyme has been isolated from nasal secretions, saliva, tears, intestinal content, urine and milk. The enzyme cleaves the glycosidic bond between carbon number 1 of N-acetylmuramic acid and carbon number 4 of N-acetyl-D-glucosamine. In vivo, these two carbohydrates are polymerized to form the cell wall polysaccharide of many microorganisms.

Lysozyme has been classified into five different glycoside hydrolase (GH) families (CAZy, cazy.org): hen egg-white lysozyme (GH22), goose egg-white lysozyme (GH23), bacteriophage T4 lysozyme (GH24), *Sphingomonas* flagellar protein (GH73) and *Chalaropsis* lysozymes (GH25). Lysozymes from the families GH23 and GH24 are primarily known from bacteriophages and have only recently been identified in fungi. The lysozyme family GH25 has been found to be structurally unrelated to the other lysozyme families.

Lysozyme extracted from hen egg white is the primary product available on the commercial market, but does not cleave N,6-O-diacetylmuramic acid in, e.g., *Staphylococcus aureus* cell walls and is thus unable to lyse this important human pathogen among others (Masschalck B, Deckers D, Michiels C W (2002), "Lytic and nonlytic mechanism of inactivation of gram-positive bacteria by lysozyme under atmospheric and high hydrostatic pressure", *J Food Prot.* 65(12): 1916-23).

WO 2012/035103 discloses variants of a GH22 lysozyme from the bird *Opisthocomus hoazin*. WO 2013/076253 and WO 2013/076259 disclose single domain GH24 and GH25 lysozymes for use in animal feed. GB 2002780 discloses the use of a lysozyme in the prophylaxis treatment of chickens. The lysozyme used was the same as isolated by Flemming in 1922 which is a GH22 lysozyme from hen egg white.

CN 101912048 discloses the use of a bacteriophage T4 lysozyme in animal feed. Bacteriophage T4 lysozymes do not comprise the same domain structure as the lysozymes of the present invention. CN 103385366 discloses the use of a lysozyme (unknown type, but based on the activity assay most likely the GH22 lysozyme from hen egg white) for use in animal feed.

Antimicrobial growth promoters (AGP's) have traditionally been used for growth promotion in animals, and probably work by preventing low level infections by pathogens such as *Clostridium perfringens*. However, AGP's are increasingly being banned worldwide and therefore new solutions to promote animal growth but which are not AGP's are of interest. The object of the present invention is to provide new and effective solutions to this problem.

SUMMARY OF THE INVENTION

The present invention relates to an animal feed or animal feed additive comprising one or more polypeptides having lysozyme activity, wherein the polypeptide comprises one or more GH24 catalytic domains and one or more lysozyme enhancing domains and wherein:
  (a) GH24 catalytic domain gives a domT score of at least 200 when queried using a Profile Hidden Markov Model prepared using SEQ ID NOs: 1 to 122 and hmmbuild software program, and wherein the query is carried out using hmmscan software program with default settings; and
  (b) the polypeptide comprises one or more lysozyme enhancing domains, wherein the lysozyme enhancing domain gives a domT score of at least 100 when queried using a Profile Hidden Markov Model prepared using SEQ ID NOs: 123 to 251 and hmmbuild software program, and wherein the query is carried out using the hmmscan software program with default settings.

The invention also relates to a polypeptide having lysozyme activity, selected from the group consisting of:
  (a) a polypeptide having at least 80% sequence identity to SEQ ID NO: 257;
  (b) a polypeptide having at least 95% sequence identity to SEQ ID NO: 267;
  (c) a polypeptide having at least 80% sequence identity to SEQ ID NO: 291;
  (d) a polypeptide having at least 80% sequence identity to SEQ ID NO: 294;
  (e) a polypeptide having at least 82% sequence identity to SEQ ID NO: 297;
  (f) a polypeptide having at least 80% sequence identity to SEQ ID NO: 300;
  (g) a polypeptide having at least 80% sequence identity to SEQ ID NO: 303;
  (h) a polypeptide having at least 80% sequence identity to SEQ ID NO: 306;

(i) a polypeptide encoded by a polynucleotide that hybridizes under medium-high stringency conditions, high stringency conditions or very-high stringency conditions with:
  (i) the mature polypeptide coding sequence of SEQ ID NO: 255;
  (ii) the mature polypeptide coding sequence of SEQ ID NO: 287;
  (iii) the mature polypeptide coding sequence of SEQ ID NO: 292;
  (iv) the mature polypeptide coding sequence of SEQ ID NO: 295;
  (v) the mature polypeptide coding sequence of SEQ ID NO: 298;
  (vi) the mature polypeptide coding sequence of SEQ ID NO: 301;
  (vii) the mature polypeptide coding sequence of SEQ ID NO: 304;
  (viii) the cDNA sequence thereof; or
  (ix) the full-length complement of (i), (ii), (iii), (iv) (v), (vi), (vii) or (viii);
(j) a polypeptide encoded by a polynucleotide that hybridizes under very-high stringency conditions with:
  (i) the mature polypeptide coding sequence of SEQ ID NO: 265;
  (ii) the full-length complement of (i);
(k) a polypeptide encoded by a polynucleotide having at least 80% sequence identity to the mature polypeptide coding sequence of SEQ ID NO: 255;
(l) a polypeptide encoded by a polynucleotide having at least 95% sequence identity to the mature polypeptide coding sequence of SEQ ID NO: 265;
(m) a polypeptide encoded by a polynucleotide having at least 80% sequence identity to the mature polypeptide coding sequence of SEQ ID NO: 287;
(n) a polypeptide encoded by a polynucleotide having at least 80% sequence identity to the mature polypeptide coding sequence of SEQ ID NO: 292;
(o) a polypeptide encoded by a polynucleotide having at least 80% sequence identity to the mature polypeptide coding sequence of SEQ ID NO: 295;
(p) a polypeptide encoded by a polynucleotide having at least 82% sequence identity to the mature polypeptide coding sequence of SEQ ID NO: 298;
(q) a polypeptide encoded by a polynucleotide having at least 80% sequence identity to the mature polypeptide coding sequence of SEQ ID NO: 301;
(r) a polypeptide encoded by a polynucleotide having at least 80% sequence identity to the mature polypeptide coding sequence of SEQ ID NO: 304;
(s) a variant of SEQ ID NO: 257, wherein the variant has lysozyme activity and comprises one or more substitutions and/or one or more deletions and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 positions; and
(t) a variant of SEQ ID NO: 267, wherein the variant has lysozyme activity and comprises one or more substitutions and/or one or more deletions and/or one or more insertions or any combination thereof in 1, 2, 3, 4, 5, 6, 7, 8, 9, 10, 11 or 12 positions; and
(u) a variant of SEQ ID NO: 291, wherein the variant has lysozyme activity and comprises one or more substitutions and/or one or more deletions and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 positions;
(v) a variant of SEQ ID NO: 294, wherein the variant has lysozyme activity and comprises one or more substitutions and/or one or more deletions and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 positions;
(w) a variant of SEQ ID NO: 297, wherein the variant has lysozyme activity and comprises one or more substitutions and/or one or more deletions and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 positions;
(x) a variant of SEQ ID NO: 300, wherein the variant has lysozyme activity and comprises one or more substitutions and/or one or more deletions and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 positions;
(y) a variant of SEQ ID NO: 303, wherein the variant has lysozyme activity and comprises one or more substitutions and/or one or more deletions and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 positions;
(z) a variant of SEQ ID NO: 306, wherein the variant has lysozyme activity and comprises one or more substitutions and/or one or more deletions and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 positions; and
(aa) a fragment of the polypeptide of (a), (b), (c), (d), (e), (f), (g), (h), (i), (j), (k), (l), (m), (n), (o), (p), (q), (r), (s), (t), (u), (v), (w), (x), (y) or (z) that has lysozyme activity wherein the fragment comprises at least 200 amino acids, such as at least 210 amino acids, at least 215 amino acids, at least 220 amino acids, at least 225 amino acids, at least 230 amino acids, at least 235 amino acids or at least 240 amino acids.

The invention further relates to compositions comprising the lysozyme of the invention; use of the lysozyme of the invention in animal feed, in animal feed additives, in the preparation of a composition for use in animal feed, for improving one or more performance parameters in an animal, for the treatment of *Clostridium perfringens* infection in an animal; for the treatment of necrotic enteritis, and as a medicament; methods of treatment of a *Clostridium perfringens* infection and/or necrotic enteritis in an animal; method of improving the performance of an animal; and isolated polynucleotides encoding the polypeptides of the invention.

Overview of Sequence Listing

SEQ ID NO: 1 is the amino acid sequence of the GH24 catalytic domain of SWISSPROT:A6R5W4 from *Ajellomyces capsulatus*.

SEQ ID NO: 2 is the amino acid sequence of the GH24 catalytic domain of SWISSPROT:A8PEU5 from *Coprinopsis cinerea*.

SEQ ID NO: 3 is the amino acid sequence of the GH24 catalytic domain of SWISSPROT:Q0CMX2 from *Aspergillus terreus*.

SEQ ID NO: 4 is the amino acid sequence of the GH24 catalytic domain of SWISSPROT:Q0D1K1 from *Aspergillus terreus*.

SEQ ID NO: 5 is the amino acid sequence of the GH24 catalytic domain of SWISSPROT:Q2TXN3 from *Aspergillus oryzae*.

SEQ ID NO: 6 is the amino acid sequence of the GH24 catalytic domain of SWISSPROT:Q2UFQ2 from *Aspergillus oryzae*.

SEQ ID NO: 7 is the amino acid sequence of the GH24 catalytic domain of SWISSPROT:Q5B9R1 from *Emericella nidulans*.

SEQ ID NO: 8 is the amino acid sequence of the GH24 catalytic domain of SWISSPROT:B0DQF7 from *Laccaria bicolor*.

SEQ ID NO: 9 is the amino acid sequence of the GH24 catalytic domain of SWISSPROT:B8NGV0 from *Aspergillus flavus*.

SEQ ID NO: 10 is the amino acid sequence of the GH24 catalytic domain of SWISSPROT:B8NVG8 from *Aspergillus flavus*.

SEQ ID NO: 11 is the amino acid sequence of the GH24 catalytic domain of SWISSPROT:C0NHY3 from *Ajellomyces capsulatus*.

SEQ ID NO: 12 is the amino acid sequence of the GH24 catalytic domain of SWISSPROT:C5FQ03 from *Arthroderma otae*.

SEQ ID NO: 13 is the amino acid sequence of the GH24 catalytic domain of SWISSPROT:C5FZ72 from *Arthroderma otae*.

SEQ ID NO: 14 is the amino acid sequence of the GH24 catalytic domain of SWISSPROT:C5GQK2 from *Ajellomyces dermatitidis*.

SEQ ID NO: 15 is the amino acid sequence of the GH24 catalytic domain of SWISSPROT:C6H5Y9 from *Ajellomyces capsulatus*.

SEQ ID NO: 16 is the amino acid sequence of the GH24 catalytic domain of SWISSPROT:D4AT26 from *Arthroderma benhamiae*.

SEQ ID NO: 17 is the amino acid sequence of the GH24 catalytic domain of SWISSPROT:D4CZH0 from *Trichophyton verrucosum*.

SEQ ID NO: 18 is the amino acid sequence of the GH24 catalytic domain of SWISSPROT:D4DKV0 from *Trichophyton verrucosum*.

SEQ ID NO: 19 is the amino acid sequence of the GH24 catalytic domain of SWISSPROT:E4UVW7 from *Arthroderma gypseum*.

SEQ ID NO: 20 is the amino acid sequence of the GH24 catalytic domain of SWISSPROT:E4V546 from *Arthroderma gypseum*.

SEQ ID NO: 21 is the amino acid sequence of the GH24 catalytic domain of SWISSPROT:G9N4L5 from *Hypocrea virens*.

SEQ ID NO: 22 is the amino acid sequence of the GH24 catalytic domain of SWISSPROT:E9F1Z9 from *Metarhizium robertsii*.

SEQ ID NO: 23 is the amino acid sequence of the GH24 catalytic domain of SWISSPROT:F0UVK8 from *Ajellomyces capsulatus*.

SEQ ID NO: 24 is the amino acid sequence of the GH24 catalytic domain of SWISSPROT:F2RV71 from *Trichophyton tonsurans*.

SEQ ID NO: 25 is the amino acid sequence of the GH24 catalytic domain of SWISSPROT:F2PV65 from *Trichophyton equinum*.

SEQ ID NO: 26 is the amino acid sequence of the GH24 catalytic domain of SWISSPROT:F2SGL6 from *Trichophyton rubrum*.

SEQ ID NO: 27 is the amino acid sequence of the GH24 catalytic domain of SWISSPROT:F2SJH3 from *Trichophyton rubrum*.

SEQ ID NO: 28 is the amino acid sequence of the GH24 catalytic domain of SWISSPROT:L7ZJC4 from *Serratia marcescens*.

SEQ ID NO: 29 is the amino acid sequence of the GH24 catalytic domain of SWISSPROT:J5TH48 from *Trichosporon asahii*.

SEQ ID NO: 30 is the amino acid sequence of the GH24 catalytic domain of SWISSPROT:J4UH35 from *Trichosporon asahii*.

SEQ ID NO: 31 is the amino acid sequence of the GH24 catalytic domain of SWISSPROT:K1VMN5 from *Trichosporon asahii*.

SEQ ID NO: 32 is the amino acid sequence of the GH24 catalytic domain of SWISSPROT:K1WL46 from *Trichosporon asahii*.

SEQ ID NO: 33 is the amino acid sequence of the GH24 catalytic domain of SWISSPROT:U9T5J9 from *Rhizophagus irregularis*.

SEQ ID NO: 34 is the amino acid sequence of the GH24 catalytic domain of SWISSPROT:U9TCU3 from *Rhizophagus irregularis*.

SEQ ID NO: 35 is the amino acid sequence of the GH24 catalytic domain of SWISSPROT:U9UUS9 from *Rhizophagus irregularis*.

SEQ ID NO: 36 is the amino acid sequence of the GH24 catalytic domain of SWISSPROT:R7Z482 from *Coniosporium apollinis*.

SEQ ID NO: 37 is the amino acid sequence of the GH24 catalytic domain of SWISSPROT:A0A015K1S5 from *Rhizophagus irregularis*.

SEQ ID NO: 38 is the amino acid sequence of the GH24 catalytic domain of SWISSPROT:W6PQ31 from *Penicillium roqueforti*.

SEQ ID NO: 39 is the amino acid sequence of the GH24 catalytic domain of SWISSPROT:A0A017SCH5 from *Aspergillus ruber*.

SEQ ID NO: 40 is the amino acid sequence of the GH24 catalytic domain of SWISSPROT:A0A022UIH6 from *Trichophyton interdigitale*.

SEQ ID NO: 41 is the amino acid sequence of the GH24 catalytic domain of SWISSPROT:A0A015LDX8 from *Rhizophagus irregularis*.

SEQ ID NO: 42 is the amino acid sequence of the GH24 catalytic domain of SWISSPROT:A0A015L2T0 from *Rhizophagus irregularis*.

SEQ ID NO: 43 is the amino acid sequence of the GH24 catalytic domain of SWISSPROT:A0A086NFK5 from *Metarhizium anisopliae*.

SEQ ID NO: 44 is the amino acid sequence of the GH24 catalytic domain of SWISSPROT:A0A0A2V9H7 from *Beauveria bassiana*.

SEQ ID NO: 45 is the amino acid sequence of the GH24 catalytic domain of SWISSPROT:A0A0A2W0Z0 from *Beauveria bassiana*.

SEQ ID NO: 46 is the amino acid sequence of the GH24 catalytic domain of SWISSPROT:A0A0A2W518 from *Beauveria bassiana*.

SEQ ID NO: 47 is the amino acid sequence of the GH24 catalytic domain of SWISSPROT:A0A0B4HPE0 from *Metarhizium guizhouense*.

SEQ ID NO: 48 is the amino acid sequence of the GH24 catalytic domain of SWISSPROT:A0A0B4HHE7 from *Metarhizium majus*.

SEQ ID NO: 49 is the amino acid sequence of the GH24 catalytic domain of SWISSPROT:A0A0B4FYT8 from *Metarhizium brunneum*.

SEQ ID NO: 50 is the amino acid sequence of the GH24 catalytic domain of SWISSPROT:A8PEP0 from *Coprinopsis cinerea*.

SEQ ID NO: 51 is the amino acid sequence of the GH24 catalytic domain of SWISSPROT:A8PEP4 from *Coprinopsis cinerea*.

SEQ ID NO: 52 is the amino acid sequence of the GH24 catalytic domain of SWISSPROT:A8PEQ3 from *Coprinopsis cinerea*.

SEQ ID NO: 53 is the amino acid sequence of the GH24 catalytic domain of SWISSPROT:B0DQ1 from *Laccaria bicolor*.

SEQ ID NO: 54 is the amino acid sequence of the GH24 catalytic domain of SWISSPROT:B0DUH4 from *Laccaria bicolor*.

SEQ ID NO: 55 is the amino acid sequence of the GH24 catalytic domain of SWISSPROT:C7Z8W0 from *Nectria haematococca*.

SEQ ID NO: 56 is the amino acid sequence of the GH24 catalytic domain of SWISSPROT:C7ZQ20 from *Nectria haematococca*.

SEQ ID NO: 57 is the amino acid sequence of the GH24 catalytic domain of SWISSPROT:G0RP87 from *Hypocrea jecorina*.

SEQ ID NO: 58 is the amino acid sequence of the GH24 catalytic domain of SWISSPROT:A8PEQ1 from *Coprinopsis cinerea*.

SEQ ID NO: 59 is the amino acid sequence of the GH24 catalytic domain of SWISSPROT:D6RMD2 from *Coprinopsis cinerea*.

SEQ ID NO: 60 is the amino acid sequence of the GH24 catalytic domain of SWISSPROT:K91708 from *Agaricus bisporus*.

SEQ ID NO: 61 is the amino acid sequence of the GH24 catalytic domain of SWISSPROT:E9DUC1 from *Metarhizium acridum*.

SEQ ID NO: 62 is the amino acid sequence of the GH24 catalytic domain of SWISSPROT:E9FAC9 from *Metarhizium robertsii*.

SEQ ID NO: 63 is the amino acid sequence of the GH24 catalytic domain of SWISSPROT:F9GF09 from *Fusarium oxysporum*.

SEQ ID NO: 64 is the amino acid sequence of the GH24 catalytic domain of SWISSPROT:A0A067NV59 from *Pleurotus ostreatus*.

SEQ ID NO: 65 is the amino acid sequence of the GH24 catalytic domain of SWISSPROT:A0A067NBT7 from *Pleurotus ostreatus*.

SEQ ID NO: 66 is the amino acid sequence of the GH24 catalytic domain of SWISSPROT:A0A067NLC3 from *Pleurotus ostreatus*.

SEQ ID NO: 67 is the amino acid sequence of the GH24 catalytic domain of SWISSPROT:A0A067TC70 from *Galerina marginata*.

SEQ ID NO: 68 is the amino acid sequence of the GH24 catalytic domain of SWISSPROT:A0A067T7N7 from *Galerina marginata*.

SEQ ID NO: 69 is the amino acid sequence of the GH24 catalytic domain of SWISSPROT:K5VNL0 from *Agaricus bisporus*.

SEQ ID NO: 70 is the amino acid sequence of the GH24 catalytic domain of SWISSPROT:W9Z992 from *Fusarium oxysporum*.

SEQ ID NO: 71 is the amino acid sequence of the GH24 catalytic domain of SWISSPROT:W9ZZW9 from *Fusarium oxysporum*.

SEQ ID NO: 72 is the amino acid sequence of the GH24 catalytic domain of SWISSPROT:X0A5V9 from *Fusarium oxysporum*.

SEQ ID NO: 73 is the amino acid sequence of the GH24 catalytic domain of SWISSPROT:N4UD22 from *Fusarium oxysporum*.

SEQ ID NO: 74 is the amino acid sequence of the GH24 catalytic domain of SWISSPROT:N4UKT7 from *Fusarium oxysporum*.

SEQ ID NO: 75 is the amino acid sequence of the GH24 catalytic domain of SWISSPROT:W9KX02 from *Fusarium oxysporum*.

SEQ ID NO: 76 is the amino acid sequence of the GH24 catalytic domain of SWISSPROT:X0MM97 from *Fusarium oxysporum*.

SEQ ID NO: 77 is the amino acid sequence of the GH24 catalytic domain of SWISSPROT:W7N5Q6 from *Gibberella moniliformis*.

SEQ ID NO: 78 is the amino acid sequence of the GH24 catalytic domain of SWISSPROT:X0BII8 from *Fusarium oxysporum*.

SEQ ID NO: 79 is the amino acid sequence of the GH24 catalytic domain of SWISSPROT:W9NXR4 from *Fusarium oxysporum*.

SEQ ID NO: 80 is the amino acid sequence of the GH24 catalytic domain of SWISSPROT:W9LDD0 from *Fusarium oxysporum*.

SEQ ID NO: 81 is the amino acid sequence of the GH24 catalytic domain of SWISSPROT:W9HEM8 from *Fusarium oxysporum*.

SEQ ID NO: 82 is the amino acid sequence of the GH24 catalytic domain of SWISSPROT:S0EP16 from *Gibberella fujikuroi*.

SEQ ID NO: 83 is the amino acid sequence of the GH24 catalytic domain of SWISSPROT:S3D2D9 from *Glarea lozoyensis*.

SEQ ID NO: 84 is the amino acid sequence of the GH24 catalytic domain of SWISSPROT:R7Z235 from *Coniosporium apollinis*.

SEQ ID NO: 85 is the amino acid sequence of the GH24 catalytic domain of SWISSPROT:U4LG64 from *Pyronema omphalodes*.

SEQ ID NO: 86 is the amino acid sequence of the GH24 catalytic domain of SWISSPROT:U1HSJ9 from *Endocarpon pusillum*.

SEQ ID NO: 87 is the amino acid sequence of the GH24 catalytic domain of SWISSPROT:U4LQS4 from *Pyronema omphalodes*.

SEQ ID NO: 88 is the amino acid sequence of the GH24 catalytic domain of SWISSPROT:X0IVL1 from *Fusarium oxysporum*.

SEQ ID NO: 89 is the amino acid sequence of the GH24 catalytic domain of SWISSPROT:A0A086T9F0 from *Acremonium chrysogenum*.

SEQ ID NO: 90 is the amino acid sequence of the GH24 catalytic domain of SWISSPROT:A0A086NUM9 from *Metarhizium anisopliae*.

SEQ ID NO: 91 is the amino acid sequence of the GH24 catalytic domain of SWISSPROT:A0A0A1TCW0 from *Torrubiella hemipterigena*.

SEQ ID NO: 92 is the amino acid sequence of the GH24 catalytic domain of SWISSPROT:A0A093ZCQ3 from *Pseudogymnoascus pannorum*.

SEQ ID NO: 93 is the amino acid sequence of the GH24 catalytic domain of SWISSPROT:A0A0B4HLN8 from *Metarhizium majus*.

SEQ ID NO: 94 is the amino acid sequence of the GH24 catalytic domain of SWISSPROT:A0A0B4H8G1 from *Metarhizium guizhouense*.

SEQ ID NO: 95 is the amino acid sequence of the GH24 catalytic domain of SWISSPROT:A4UCC9 from *Magnaporthe oryzae*.

SEQ ID NO: 96 is the amino acid sequence of the GH24 catalytic domain of SWISSPROT:Q2GND9 from *Chaetomium globosum*.

SEQ ID NO: 97 is the amino acid sequence of the GH24 catalytic domain of SWISSPROT:C7Z967 from *Nectria haematococca*.

SEQ ID NO: 98 is the amino acid sequence of the GH24 catalytic domain of SWISSPROT:C9SY46 from *Verticillium alfalfae*.

SEQ ID NO: 99 is the amino acid sequence of the GH24 catalytic domain of SWISSPROT:G2RG69 from *Thielavia terrestris*.

SEQ ID NO: 100 is the amino acid sequence of the GH24 catalytic domain of SWISSPROT:G2QNE9 from *Thielavia heterothallica*.

SEQ ID NO: 101 is the amino acid sequence of the GH24 catalytic domain of SWISSPROT:J9NQV9 from *Fusarium oxysporum*.

SEQ ID NO: 102 is the amino acid sequence of the GH24 catalytic domain of SWISSPROT:F9F2K4 from *Fusarium oxysporum*.

SEQ ID NO: 103 is the amino acid sequence of the GH24 catalytic domain of SWISSPROT:G0RZV2 from *Chaetomium thermophilum*.

SEQ ID NO: 104 is the amino acid sequence of the GH24 catalytic domain of SWISSPROT:G2XHC2 from *Verticillium dahliae*.

SEQ ID NO: 105 is the amino acid sequence of the GH24 catalytic domain of SWISSPROT:N1RWA4 from *Fusarium oxysporum*.

SEQ ID NO: 106 is the amino acid sequence of the GH24 catalytic domain of SWISSPROT:X0B4J3 from *Fusarium oxysporum*.

SEQ ID NO: 107 is the amino acid sequence of the GH24 catalytic domain of SWISSPROT:A0A084PYR3 from *Stachybotrys chartarum*.

SEQ ID NO: 108 is the amino acid sequence of the GH24 catalytic domain of SWISSPROT:A0A086TBZ4 from *Acremonium chrysogenum*.

SEQ ID NO: 109 is the amino acid sequence of the GH24 catalytic domain of SWISSPROT:A0A086SUF8 from *Acremonium chrysogenum*.

SEQ ID NO: 110 is the amino acid sequence of the GH24 catalytic domain of SWISSPROT:A0A084R326 from *Stachybotrys chlorohalonata*.

SEQ ID NO: 111 is the amino acid sequence of the GH24 catalytic domain of SWISSPROT:A0A093Z6Z8 from *Pseudogymnoascus pannorum*.

SEQ ID NO: 112 is the amino acid sequence of the GH24 catalytic domain of SWISSPROT:A0A0941ML3 from *Pseudogymnoascus pannorum*.

SEQ ID NO: 113 is the amino acid sequence of the GH24 catalytic domain of SWISSPROT:A0A094GY79 from *Pseudogymnoascus pannorum*.

SEQ ID NO: 114 is the amino acid sequence of the GH24 catalytic domain of SWISSPROT:A0A093XPZ7 from *Pseudogymnoascus pannorum*.

SEQ ID NO: 115 is the amino acid sequence of the GH24 catalytic domain of SWISSPROT:A0A093XAS9 from *Pseudogymnoascus pannorum*.

SEQ ID NO: 116 is the amino acid sequence of the GH24 catalytic domain of SWISSPROT:A0A0A1TNV6 from *Torrubiella hemipterigena*.

SEQ ID NO: 117 is the amino acid sequence of the GH24 catalytic domain of SWISSPROT:A0A094DVF4 from *Pseudogymnoascus pannorum*.

SEQ ID NO: 118 is the amino acid sequence of the GH24 catalytic domain of SWISSPROT:A0A0941E25 from *Pseudogymnoascus pannorum*.

SEQ ID NO: 119 is the amino acid sequence of the GH24 catalytic domain of SWISSPROT:A0A094HNM8 from *Pseudogymnoascus pannorum*.

SEQ ID NO: 120 is the amino acid sequence of the GH24 catalytic domain of SWISSPROT:A0A094EPJ7 from *Pseudogymnoascus pannorum*.

SEQ ID NO: 121 is the amino acid sequence of the GH24 catalytic domain of SWISSPROT:A0A094BWD6 from *Pseudogymnoascus pannorum*.

SEQ ID NO: 122 is the amino acid sequence of the GH24 catalytic domain of SWISSPROT:A0A093ZTZ8 from *Pseudogymnoascus pannorum*.

SEQ ID NO: 123 is the amino acid sequence of the lysozyme enhancing domain of SWISSPROT:B2ASY2 from *Podospora anserina*.

SEQ ID NO: 124 is the amino acid sequence of the lysozyme enhancing domain of SWISSPROT:B6GZX8 from *Penicillium chrysogenum*.

SEQ ID NO: 125 is the amino acid sequence of the lysozyme enhancing domain of SWISSPROT:C7ZQ22 from *Nectria haematococca*.

SEQ ID NO: 126 is the amino acid sequence of the lysozyme enhancing domain of SWISSPROT:E9DSA6 from *Metarhizium acridum*.

SEQ ID NO: 127 is the amino acid sequence of the lysozyme enhancing domain of SWISSPROT:E9F1Z9 from *Metarhizium robertsii*.

SEQ ID NO: 128 is the amino acid sequence of the lysozyme enhancing domain of SWISSPROT:E9FC42 from *Metarhizium robertsii*.

SEQ ID NO: 129 is the amino acid sequence of the lysozyme enhancing domain of SWISSPROT:F9F2K5 from *Fusarium oxysporum*.

SEQ ID NO: 130 is the amino acid sequence of the lysozyme enhancing domain of SWISSPROT:F9GF09 from *Fusarium oxysporum*.

SEQ ID NO: 131 is the amino acid sequence of the lysozyme enhancing domain of SWISSPROT:G2QV10 from *Thielavia terrestris*.

SEQ ID NO: 132 is the amino acid sequence of the lysozyme enhancing domain of SWISSPROT:G2QV26 from *Thielavia terrestris*.

SEQ ID NO: 133 is the amino acid sequence of the lysozyme enhancing domain of SWISSPROT:J5TH48 from *Trichosporon asahii* var. *Asahii*.

SEQ ID NO: 134 is the amino acid sequence of the lysozyme enhancing domain of SWISSPROT:J4UH35 from *Trichosporon asahii* var. *Asahii.*

SEQ ID NO: 135 is the amino acid sequence of the lysozyme enhancing domain of SWISSPROT:J9NQ28 from *Fusarium oxysporum* f. sp. *Lycopersici.*

SEQ ID NO: 136 is the amino acid sequence of the lysozyme enhancing domain of SWISSPROT:J9NQW0 from *Fusarium oxysporum* f. sp. *Lycopersici.*

SEQ ID NO: 137 is the amino acid sequence of the lysozyme enhancing domain of SWISSPROT:K1VMN5 from *Trichosporon asahii* var. *Asahii.*

SEQ ID NO: 138 is the amino acid sequence of the lysozyme enhancing domain of SWISSPROT:K1WL46 from *Trichosporon asahii* var. *Asahii.*

SEQ ID NO: 139 is the amino acid sequence of the lysozyme enhancing domain of SWISSPROT:W9Z45 from *Fusarium oxysporum* f. sp. *Melonis.*

SEQ ID NO: 140 is the amino acid sequence of the lysozyme enhancing domain of SWISSPROT:X0A5V9 from *Fusarium oxysporum* f. sp. *Melonis.*

SEQ ID NO: 141 is the amino acid sequence of the lysozyme enhancing domain of SWISSPROT:N1S551 from *Fusarium oxysporum* f. sp. *Cubense.*

SEQ ID NO: 142 is the amino acid sequence of the lysozyme enhancing domain of SWISSPROT:N4UD22 from *Fusarium oxysporum* f. sp. *Cubense.*

SEQ ID NO: 143 is the amino acid sequence of the lysozyme enhancing domain of SWISSPROT:N4UT47 from *Fusarium oxysporum* f. sp. *Cubense.*

SEQ ID NO: 144 is the amino acid sequence of the lysozyme enhancing domain of SWISSPROT:W9KWW4 from *Fusarium oxysporum.*

SEQ ID NO: 145 is the amino acid sequence of the lysozyme enhancing domain of SWISSPROT:X0MM97 from *Fusarium oxysporum* f. sp. *Vasinfectum.*

SEQ ID NO: 146 is the amino acid sequence of the lysozyme enhancing domain of SWISSPROT:W7N5Q6 from *Gibberella moniliformis.*

SEQ ID NO: 147 is the amino acid sequence of the lysozyme enhancing domain of SWISSPROT:X0BE07 from *Fusarium oxysporum* f. sp. *Raphani.*

SEQ ID NO: 148 is the amino acid sequence of the lysozyme enhancing domain of SWISSPROT:X0BII8 from *Fusarium oxysporum.*

SEQ ID NO: 149 is the amino acid sequence of the lysozyme enhancing domain of SWISSPROT:W9NW59 from *Fusarium oxysporum* f. sp. *Pisi.*

SEQ ID NO: 150 is the amino acid sequence of the lysozyme enhancing domain of SWISSPROT:W9NXR4 from *Fusarium oxysporum* f. sp. *Pisi.*

SEQ ID NO: 151 is the amino acid sequence of the lysozyme enhancing domain of SWISSPROT:S7ZNE7 from *Penicillium oxalicum.*

SEQ ID NO: 152 is the amino acid sequence of the lysozyme enhancing domain of SWISSPROT:S7Z5Z6 from *Penicillium oxalicum.*

SEQ ID NO: 153 is the amino acid sequence of the lysozyme enhancing domain of SWISSPROT:W9LDD0 from *Fusarium oxysporum* f. sp. *Lycopersici.*

SEQ ID NO: 154 is the amino acid sequence of the lysozyme enhancing domain of SWISSPROT:W9HEM8 from *Fusarium oxysporum.*

SEQ ID NO: 155 is the amino acid sequence of the lysozyme enhancing domain of SWISSPROT:W9JDH4 from *Fusarium oxysporum.*

SEQ ID NO: 156 is the amino acid sequence of the lysozyme enhancing domain of SWISSPROT:S0EPI6 from *Gibberella fujikuroi.*

SEQ ID NO: 157 is the amino acid sequence of the lysozyme enhancing domain of SWISSPROT:W6QNL2 from *Penicillium roqueforti.*

SEQ ID NO: 158 is the amino acid sequence of the lysozyme enhancing domain of SWISSPROT:U4LJD9 from *Pyronema omphalodes.*

SEQ ID NO: 159 is the amino acid sequence of the lysozyme enhancing domain of SWISSPROT:U4LG64 from *Pyronema omphalodes.*

SEQ ID NO: 160 is the amino acid sequence of the lysozyme enhancing domain of SWISSPROT:A0A094AK50 from *Pseudogymnoascus pannorum.*

SEQ ID NO: 161 is the amino acid sequence of the lysozyme enhancing domain of SWISSPROT:W9JIH2 from *Fusarium oxysporum.*

SEQ ID NO: 162 is the amino acid sequence of the lysozyme enhancing domain of SWISSPROT:X0FW82 from *Fusarium oxysporum* f. sp. *radicis-lycopersici.*

SEQ ID NO: 163 is the amino acid sequence of the lysozyme enhancing domain of SWISSPROT:A0A086TBY7 from *Acremonium chrysogenum.*

SEQ ID NO: 164 is the amino acid sequence of the lysozyme enhancing domain of SWISSPROT:A0A086T755 from *Acremonium chrysogenum.*

SEQ ID NO: 165 is the amino acid sequence of the lysozyme enhancing domain of SWISSPROT:A0A086T4C8 from *Acremonium chrysogenum.*

SEQ ID NO: 166 is the amino acid sequence of the lysozyme enhancing domain of SWISSPROT:A0A086NNR4 from *Metarhizium anisopliae.*

SEQ ID NO: 167 is the amino acid sequence of the lysozyme enhancing domain of SWISSPROT:A0A086NFK5 from *Metarhizium anisopliae.*

SEQ ID NO: 168 is the amino acid sequence of the lysozyme enhancing domain of SWISSPROT:A0A094FY19 from *Pseudogymnoascus pannorum.*

SEQ ID NO: 169 is the amino acid sequence of the lysozyme enhancing domain of SWISSPROT:A0A094G1N0 from *Pseudogymnoascus pannorum.*

SEQ ID NO: 170 is the amino acid sequence of the lysozyme enhancing domain of SWISSPROT:A0A094GEA0 from *Pseudogymnoascus pannorum.*

SEQ ID NO: 171 is the amino acid sequence of the lysozyme enhancing domain of SWISSPROT:A0A094GJR5 from *Pseudogymnoascus pannorum.*

SEQ ID NO: 172 is the amino acid sequence of the lysozyme enhancing domain of SWISSPROT:A0A094G660 from *Pseudogymnoascus pannorum.*

SEQ ID NO: 173 is the amino acid sequence of the lysozyme enhancing domain of SWISSPROT:A0A093YBN4 from *Pseudogymnoascus pannorum.*

SEQ ID NO: 174 is the amino acid sequence of the lysozyme enhancing domain of SWISSPROT:A0A094FSZ5 from *Pseudogymnoascus pannorum.*

SEQ ID NO: 175 is the amino acid sequence of the lysozyme enhancing domain of SWISSPROT:A0A094FBW1 from *Pseudogymnoascus pannorum.*

SEQ ID NO: 176 is the amino acid sequence of the lysozyme enhancing domain of SWISSPROT:A0A094HOG2 from *Pseudogymnoascus pannorum.*

SEQ ID NO: 177 is the amino acid sequence of the lysozyme enhancing domain of SWISSPROT:A0A094H7M1 from *Pseudogymnoascus pannorum.*

SEQ ID NO: 178 is the amino acid sequence of the lysozyme enhancing domain of SWISSPROT: A0A093Y8W3 from *Pseudogymnoascus pannorum*.

SEQ ID NO: 179 is the amino acid sequence of the lysozyme enhancing domain of SWISSPROT: A0A094GYN9 from *Pseudogymnoascus pannorum*.

SEQ ID NO: 180 is the amino acid sequence of the lysozyme enhancing domain of SWISSPROT: A0A093XAD4 from *Pseudogymnoascus pannorum*.

SEQ ID NO: 181 is the amino acid sequence of the lysozyme enhancing domain of SWISSPROT:A0A094H7J6 from *Pseudogymnoascus pannorum*.

SEQ ID NO: 182 is the amino acid sequence of the lysozyme enhancing domain of SWISSPROT:A0A094E0I1 from *Pseudogymnoascus pannorum*.

SEQ ID NO: 183 is the amino acid sequence of the lysozyme enhancing domain of SWISSPROT: A0A094CC50 from *Pseudogymnoascus pannorum*.

SEQ ID NO: 184 is the amino acid sequence of the lysozyme enhancing domain of SWISSPROT:A0A094I95 from *Pseudogymnoascus pannorum*.

SEQ ID NO: 185 is the amino acid sequence of the lysozyme enhancing domain of SWISSPROT:A0A094AA0 from *Pseudogymnoascus pannorum*.

SEQ ID NO: 186 is the amino acid sequence of the lysozyme enhancing domain of SWISSPROT: A0A094IBC0 from *Pseudogymnoascus pannorum*.

SEQ ID NO: 187 is the amino acid sequence of the lysozyme enhancing domain of SWISSPROT:A0A094E946 from *Pseudogymnoascus pannorum*.

SEQ ID NO: 188 is the amino acid sequence of the lysozyme enhancing domain of SWISSPROT: A0A094A3A0 from *Pseudogymnoascus pannorum*.

SEQ ID NO: 189 is the amino acid sequence of the lysozyme enhancing domain of SWISSPROT:A1C4L9 from *Aspergillus clavatus*.

SEQ ID NO: 190 is the amino acid sequence of the lysozyme enhancing domain of SWISSPROT:A1CBV9 from *Aspergillus clavatus*.

SEQ ID NO: 191 is the amino acid sequence of the lysozyme enhancing domain of SWISSPROT:A1DA80 from *Neosartorya fischeri*.

SEQ ID NO: 192 is the amino acid sequence of the lysozyme enhancing domain of SWISSPROT:A1DBW2 from *Neosartorya fischeri*.

SEQ ID NO: 193 is the amino acid sequence of the lysozyme enhancing domain of SWISSPROT:A1DDF2 from *Neosartorya fischeri*.

SEQ ID NO: 194 is the amino acid sequence of the lysozyme enhancing domain of SWISSPROT:Q0CED1 from *Aspergillus terreus*.

SEQ ID NO: 195 is the amino acid sequence of the lysozyme enhancing domain of SWISSPROT:Q0CED2 from *Aspergillus terreus*.

SEQ ID NO: 196 is the amino acid sequence of the lysozyme enhancing domain of SWISSPROT:Q0CV85 from *Aspergillus terreus*.

SEQ ID NO: 197 is the amino acid sequence of the lysozyme enhancing domain of SWISSPROT:Q2GND8 from *Chaetomium globosum*.

SEQ ID NO: 198 is the amino acid sequence of the lysozyme enhancing domain of SWISSPROT:Q2GND9 from *Chaetomium globosum*.

SEQ ID NO: 199 is the amino acid sequence of the lysozyme enhancing domain of SWISSPROT:Q2H6W7 from *Chaetomium globosum*.

SEQ ID NO: 200 is the amino acid sequence of the lysozyme enhancing domain of SWISSPROT:Q4WAY2 from *Neosartorya fumigata*.

SEQ ID NO: 201 is the amino acid sequence of the lysozyme enhancing domain of SWISSPROT:Q4WBR4 from *Neosartorya fumigata*.

SEQ ID NO: 202 is the amino acid sequence of the lysozyme enhancing domain of SWISSPROT:Q4WVY3 from *Neosartorya fumigata*.

SEQ ID NO: 203 is the amino acid sequence of the lysozyme enhancing domain of SWISSPROT:B6H9X5 from *Penicillium chrysogenum*.

SEQ ID NO: 204 is the amino acid sequence of the lysozyme enhancing domain of SWISSPROT:B6HR38 from *Penicillium chrysogenum*.

SEQ ID NO: 205 is the amino acid sequence of the lysozyme enhancing domain of SWISSPROT:C7Z8W0 from *Nectria haematococca*.

SEQ ID NO: 206 is the amino acid sequence of the lysozyme enhancing domain of SWISSPROT:C7ZQ20 from *Nectria haematococca*.

SEQ ID NO: 207 is the amino acid sequence of the lysozyme enhancing domain of SWISSPROT:G0RP87 from *Hypocrea jecorina*.

SEQ ID NO: 208 is the amino acid sequence of the lysozyme enhancing domain of SWISSPROT:G2RG69 from *Thielavia terrestris*.

SEQ ID NO: 209 is the amino acid sequence of the lysozyme enhancing domain of SWISSPROT:G2QNE9 from *Thielavia heterothallica*.

SEQ ID NO: 210 is the amino acid sequence of the lysozyme enhancing domain of SWISSPROT:G0RM22 from *Hypocrea jecorina*.

SEQ ID NO: 211 is the amino acid sequence of the lysozyme enhancing domain of SWISSPROT:G0SG36 from *Chaetomium thermophilum* var. *Thermophilum*.

SEQ ID NO: 212 is the amino acid sequence of the lysozyme enhancing domain of SWISSPROT:G0RZV3 from *Chaetomium thermophilum* var. *Thermophilum*.

SEQ ID NO: 213 is the amino acid sequence of the lysozyme enhancing domain of SWISSPROT:J9NQV9 from *Fusarium oxysporum* f. sp. *Lycopersici*.

SEQ ID NO: 214 is the amino acid sequence of the lysozyme enhancing domain of SWISSPROT:G2QD02 from *Thielavia heterothallica*.

SEQ ID NO: 215 is the amino acid sequence of the lysozyme enhancing domain of SWISSPROT:G2QNF0 from *Thielavia heterothallica*.

SEQ ID NO: 216 is the amino acid sequence of the lysozyme enhancing domain of SWISSPROT:G9MHR1 from *Hypocrea virens*.

SEQ ID NO: 217 is the amino acid sequence of the lysozyme enhancing domain of SWISSPROT:E9ELX9 from *Metarhizium robertsii*.

SEQ ID NO: 218 is the amino acid sequence of the lysozyme enhancing domain of SWISSPROT:F9F2K4 from *Fusarium oxysporum*.

SEQ ID NO: 219 is the amino acid sequence of the lysozyme enhancing domain of SWISSPROT:G0RZV2 from *Chaetomium thermophilum* var. *Thermophilum*.

SEQ ID NO: 220 is the amino acid sequence of the lysozyme enhancing domain of SWISSPROT:G2RG70 from *Thielavia terrestris*.

SEQ ID NO: 221 is the amino acid sequence of the lysozyme enhancing domain of SWISSPROT:W9Z992 from *Fusarium oxysporum* f. sp. *Melonis*.

SEQ ID NO: 222 is the amino acid sequence of the lysozyme enhancing domain of SWISSPROT:W9ZZW9 from *Fusarium oxysporum* f. sp. *Melonis*.

SEQ ID NO: 223 is the amino acid sequence of the lysozyme enhancing domain of SWISSPROT:W9ZAE8 from *Fusarium oxysporum* f. sp. *Melonis*.

SEQ ID NO: 224 is the amino acid sequence of the lysozyme enhancing domain of SWISSPROT:N1RWA4 from *Fusarium oxysporum* f. sp. *Cubense*.

SEQ ID NO: 225 is the amino acid sequence of the lysozyme enhancing domain of SWISSPROT:N4UKT7 from *Fusarium oxysporum* f. sp. *Cubense*.

SEQ ID NO: 226 is the amino acid sequence of the lysozyme enhancing domain of SWISSPROT:W9KXO2 from *Fusarium oxysporum*.

SEQ ID NO: 227 is the amino acid sequence of the lysozyme enhancing domain of SWISSPROT:X0B4J3 from *Fusarium oxysporum* f. sp. *Raphani*.

SEQ ID NO: 228 is the amino acid sequence of the lysozyme enhancing domain of SWISSPROT:W6QE02 from *Penicillium roqueforti*.

SEQ ID NO: 229 is the amino acid sequence of the lysozyme enhancing domain of SWISSPROT:W6R4X8 from *Penicillium roqueforti*.

SEQ ID NO: 230 is the amino acid sequence of the lysozyme enhancing domain of SWISSPROT:A0A024S9B8 from *Trichoderma reesei*.

SEQ ID NO: 231 is the amino acid sequence of the lysozyme enhancing domain of SWISSPROT: A0A086NN36 from *Metarhizium anisopliae*.

SEQ ID NO: 232 is the amino acid sequence of the lysozyme enhancing domain of SWISSPROT: A0A094GA03 from *Pseudogymnoascus pannorum*.

SEQ ID NO: 233 is the amino acid sequence of the lysozyme enhancing domain of SWISSPROT: A0A094C8U1 from *Pseudogymnoascus pannorum*.

SEQ ID NO: 234 is the amino acid sequence of the lysozyme enhancing domain of SWISSPROT:A0A093Z6Z8 from *Pseudogymnoascus pannorum*.

SEQ ID NO: 235 is the amino acid sequence of the lysozyme enhancing domain of SWISSPROT: A0A0941ML3 from *Pseudogymnoascus pannorum*.

SEQ ID NO: 236 is the amino acid sequence of the lysozyme enhancing domain of SWISSPROT: A0A094GY79 from *Pseudogymnoascus pannorum*.

SEQ ID NO: 237 is the amino acid sequence of the lysozyme enhancing domain of SWISSPROT: A0A093XPZ7 from *Pseudogymnoascus pannorum*.

SEQ ID NO: 238 is the amino acid sequence of the lysozyme enhancing domain of SWISSPROT: A0A093XAS9 from *Pseudogymnoascus pannorum*.

SEQ ID NO: 239 is the amino acid sequence of the lysozyme enhancing domain of SWISSPROT:A0A0948J6 from *Pseudogymnoascus pannorum*.

SEQ ID NO: 240 is the amino acid sequence of the lysozyme enhancing domain of SWISSPROT: A0A094FTL0 from *Pseudogymnoascus pannorum*.

SEQ ID NO: 241 is the amino acid sequence of the lysozyme enhancing domain of SWISSPROT:A0A094AT39 from *Pseudogymnoascus pannorum*.

SEQ ID NO: 242 is the amino acid sequence of the lysozyme enhancing domain of SWISSPROT: A0A093XSP5 from *Pseudogymnoascus pannorum*.

SEQ ID NO: 243 is the amino acid sequence of the lysozyme enhancing domain of SWISSPROT: A0A094BAE6 from *Pseudogymnoascus pannorum*.

SEQ ID NO: 244 is the amino acid sequence of the lysozyme enhancing domain of SWISSPROT:A0A0941E25 from *Pseudogymnoascus pannorum*.

SEQ ID NO: 245 is the amino acid sequence of the lysozyme enhancing domain of SWISSPROT: A0A094HNM8 from *Pseudogymnoascus pannorum*.

SEQ ID NO: 246 is the amino acid sequence of the lysozyme enhancing domain of SWISSPROT:A0A094ETJ5 from *Pseudogymnoascus pannorum*.

SEQ ID NO: 247 is the amino acid sequence of the lysozyme enhancing domain of SWISSPROT:A0A094EPJ7 from *Pseudogymnoascus pannorum*.

SEQ ID NO: 248 is the amino acid sequence of the lysozyme enhancing domain of SWISSPROT: A0A094E9W0 from *Pseudogymnoascus pannorum*.

SEQ ID NO: 249 is the amino acid sequence of the lysozyme enhancing domain of SWISSPROT: A0A094BWD6 from *Pseudogymnoascus pannorum*.

SEQ ID NO: 250 is the amino acid sequence of the lysozyme enhancing domain of SWISSPROT: A0A094BTS1 from *Pseudogymnoascus pannorum*.

SEQ ID NO: 251 is the amino acid sequence of the lysozyme enhancing domain of SWISSPROT: A0A093ZTZ8 from *Pseudogymnoascus pannorum*.

SEQ ID NO: 252 is conserved motif I [TAS][VIL][GAC][YF]GHX[CAYIV]. SEQ ID NO: 253 is conserved motif II [LV][NDST]XN[QE][YFW][GASND]ALXS[WFLY]X[FY]N.

SEQ ID NO: 254 is conserved motif III [CGY][YF][VIL][ASTP][DG]X[YF][VIT]X[TS][GAN].

SEQ ID NO: 255 is the cDNA sequence of the GH24 lysozyme as isolated from *Trichophaea saccata*.

SEQ ID NO: 256 is the amino acid sequence as deduced from SEQ ID NO: 255.

SEQ ID NO: 257 is the amino acid sequence of the mature GH24 lysozyme from *Trichophaea saccata*.

SEQ ID NO: 258 is primer F-80470.

SEQ ID NO: 259 is primer R-80470.

SEQ ID NO: 260 is primer 8643.

SEQ ID NO: 261 is primer 8654.

SEQ ID NO: 262 is the cDNA sequence of the GH24 lysozyme as isolated from *Chaetomium thermophilum*.

SEQ ID NO: 263 is the amino acid sequence as deduced from SEQ ID NO: 262.

SEQ ID NO: 264 is the amino acid sequence of the mature GH24 lysozyme from *Chaetomium thermophilum*.

SEQ ID NO: 265 is the DNA sequence of the GH24 lysozyme as isolated from 10 *Trichoderma harzianum*.

SEQ ID NO: 266 is the amino acid sequence as deduced from SEQ ID NO: 265.

SEQ ID NO: 267 is the amino acid sequence of the mature GH24 lysozyme from *Trichoderma harzianum*.

SEQ ID NO: 268 is the codon optimised DNA sequence of the GH24 catalytic domain from SEQ ID NO: 255 with QCVG-linker and Savinase signal peptide.

SEQ ID NO: 269 is the amino acid sequence as deduced from SEQ ID NO: 268.

SEQ ID NO: 270 is the amino acid sequence of the mature GH24 catalytic domain from *Trichophaea saccata* with QCVG-linker.

SEQ ID NO: 271 is the DNA sequence of the lysozyme enhancing domain from SEQ ID NO: 255.

SEQ ID NO: 272 is the amino acid sequence as deduced from SEQ ID NO: 271.

SEQ ID NO: 273 is the amino acid sequence of the mature LED from *Trichophaea saccata*.

SEQ ID NO: 274 is primer P348F9-R.

SEQ ID NO: 275 is primer A00611-F.
SEQ ID NO: 276 is primer A00611-R.
SEQ ID NO: 277 is primer CBS14450-F.
SEQ ID NO: 278 is primer CBS14450-R.
SEQ ID NO: 279 is the amino acid sequence of the mature GH24 lysozyme from *Acremonium alcalophilum* corresponding to the mature sequence of SEQ ID NO: 4 of WO 2013/076259.
SEQ ID NO: 280 is the amino acid sequence of the mature GH24 lysozyme from *Acremonium alcalophilum* corresponding to the mature sequence of SEQ ID NO: 6 of WO 2013/076259.
SEQ ID NO: 281 is conserved motif I-B [TAS][VIL][GAC][YF]GHX[CAYIV].
SEQ ID NO: 282 is conserved motif I-C T[VI]GYGHXC.
SEQ ID NO: 283 is conserved motif II-B LNXN[QE][YFW][GA]ALXS[WFL]X[YF]N.
SEQ ID NO: 284 is conserved motif I-B C[YF][V][AST]D[YKF][YF][VI]XTG.
SEQ ID NO: 285 is conserved motif IV [GEV]LXXRRXXE.
SEQ ID NO: 286 is conserved motif IV-B GLXXRRXXE.
SEQ ID NO: 287 is the gene sequence of the GH24 lysozyme as isolated from *Trichophaea minuta*.
SEQ ID NO: 288 is the amino acid sequence as deduced from SEQ ID NO: 287.
SEQ ID NO: 289 is the codon optimised DNA sequence of SEQ ID NO: 287.
SEQ ID NO: 290 is the amino acid sequence as deduced from SEQ ID NO: 287.
SEQ ID NO: 291 is the amino acid sequence of the mature GH24 lysozyme from *Trichophaea minuta*.
SEQ ID NO: 292 is the gene sequence of the GH24 lysozyme as isolated from *Chaetomium* sp. ZY287.
SEQ ID NO: 293 is the amino acid sequence as deduced from SEQ ID NO: 292.
SEQ ID NO: 294 is the amino acid sequence of the mature GH24 lysozyme from *Chaetomium* sp. ZY287.
SEQ ID NO: 295 is the gene sequence of the GH24 lysozyme as isolated from *Mortierella* sp. ZY002.
SEQ ID NO: 296 is the amino acid sequence as deduced from SEQ ID NO: 295.
SEQ ID NO: 297 is the amino acid sequence of the mature GH24 lysozyme from *Mortierella* sp. ZY002.
SEQ ID NO: 298 is the gene sequence of the GH24 lysozyme as isolated from *Metarhizium* sp. XZ2431.
SEQ ID NO: 299 is the amino acid sequence as deduced from SEQ ID NO: 298.
SEQ ID NO: 300 is the amino acid sequence of the mature GH24 lysozyme from *Metarhizium* sp. XZ2431.
SEQ ID NO: 301 is the gene sequence of the GH24 lysozyme as isolated from *Geomyces auratus*.
SEQ ID NO: 302 is the amino acid sequence as deduced from SEQ ID NO: 301.
SEQ ID NO: 303 is the amino acid sequence of the mature GH24 lysozyme from *Geomyces auratus*.
SEQ ID NO: 304 is the gene sequence of the GH24 lysozyme as isolated from *Ilyonectria rufa*.
SEQ ID NO: 305 is the amino acid sequence as deduced from SEQ ID NO: 304.
SEQ ID NO: 306 is the amino acid sequence of the mature GH24 lysozyme from *Ilyonectria rufa*.

Definitions

50% MHB, pH 6: The term "50% MHB, pH 6" means that the antimicrobial activity of the lysozyme was tested using an RDA plate wherein the media used was ½ Mueller-Hinton broth (MHB) (Sigma/Fluka, 90922) (i.e., adjusted to pH 6 with 4 M HCl and diluted 1:1 with water) with 1.5% agarose.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Animal: The term "animal" refers to any animal except humans. Examples of animals are non-ruminants and ruminants. Ruminant animals include, for example, animals such as sheep, goats, cattle, e.g., beef cattle, cows, and young calves, deer, yank, camel, llama and kangaroo. Non-ruminant animals include monogastric animals, including but not limited to pigs or swine (including, but not limited to, piglets, growing pigs, and sows); poultry such as turkeys, ducks, quail, guinea fowl, geese, pigeons (including squabs) and chicken (including but not limited to broiler chickens (referred to herein as broiles), chicks, layer hens (referred to herein as layers)); horses (including but not limited to hotbloods, coldbloods and warm bloods) crustaceans (including but not limited to shrimps and prawns) and fish (including but not limited to amberjack, arapaima, barb, bass, bluefish, bocachico, bream, bullhead, cachama, carp, catfish, catla, chanos, char, cichlid, cobia, cod, crappie, dorada, drum, eel, goby, goldfish, gourami, grouper, guapote, halibut, java, labeo, lai, loach, mackerel, milkfish, mojarra, mudfish, mullet, paco, pearlspot, pejerrey, perch, pike, pompano, roach, salmon, sampa, sauger, sea bass, seabream, shiner, sleeper, snakehead, snapper, snook, sole, spinefoot, sturgeon, sunfish, sweetfish, tench, terror, tilapia, trout, tuna, turbot, vendace, walleye and whitefish).

Animal feed: The term "animal feed" refers to any compound, preparation, or mixture suitable for, or intended for intake by an animal. Animal feed for a monogastric animal typically comprises concentrates as well as vitamins, minerals, enzymes, direct fed microbial, amino acids and/or other feed ingredients (such as in a premix) whereas animal feed for ruminants generally comprises forage (including roughage and silage) and may further comprise concentrates as well as vitamins, minerals, enzymes direct fed microbial, amino acid and/or other feed ingredients (such as in a premix).

Antimicrobial activity: The term "antimicrobial activity" is defined herein as an activity that kills or inhibits the growth of microorganisms, such as, algae, archea, bacteria, fungi and/or protozoans. The antimicrobial activity can, for example, be bactericidal meaning the killing of bacteria or bacteriostatic meaning the prevention of bacterial growth. The antimicrobial activity can include catalyzing the hydrolysis of 1,4-beta-linkages between N-acetylmuramic acid and N-acetyl-D-glucosamine residues in a peptidoglycan and between N-acetyl-D-glucosamine residues in chitodextrins. Antimicrobial activity can also include the lysozyme binding to the surface of the microorganism and inhibiting its growth. The antimicrobial effect can also include the use of the lysozymes of the present invention for activation of bacterial autolysins, as an immunostimulator, by inhibiting or reducing bacterial toxins and by an opsonin effect.

For the purpose of the present invention, antimicrobial activity is determined according to the antimicrobial assay described in Example 12 ("Determination of antimicrobial activity"). Antimicrobial activity is determined if there is a clearing zone when using 50% Mueller-Hinton broth, pH 6. Preferably the diameter of the clearing zone is 4 mm or more.

Thus, the term "antimicrobial activity of SEQ ID NO: x against *Clostridium perfringens* using the conditions 50% MHB, pH 6" mean that the polypeptide shows antimicrobial activity (i.e., clearing zone) against *Clostridium perfringens* DSM756 when the conditions 50% Mueller-Hinton broth, pH 6 are used, when the experiment is performed as described in example 12.

Body Weight Gain: The term "body weight gain" means an increase in live weight of an animal during a given period of time, e.g., the increase in weight from day 1 to day 21.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Concentrates: The term "concentrates" means feed with high protein and energy concentrations, such as fish meal, molasses, oligosaccharides, sorghum, seeds and grains (either whole or prepared by crushing, milling, etc. from, e.g., corn, oats, rye, barley, wheat), oilseed press cake (e.g., from cottonseed, safflower, sunflower, soybean (such as soybean meal), rapeseed/canola, peanut or groundnut), palm kernel cake, yeast derived material and distillers grains (such as wet distillers grains (WDS) and dried distillers grains with solubles (DDGS)).

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

domT score: The term "domT score" or domain score means the score for the best scoring domain when aligning the query sequence to the HMM.

European Production Efficacy Factor (EPEF): The "European Production Efficacy Factor" is a way of comparing the performance of animals. This single-figure facilitates comparison of performance within and among farms and can be used to assess environmental, climatic and managemental variables. The EPEF is calculated as [(liveability (%)× Liveweight (kg))/(Age at depletion (days)×FCR)]×100, wherein livability is the percentage of animals alive at slaughter, Liveweight is the average weight of the animals at slaughter, age of depletion is the age of the animals at slaughter and FCR is the feed conversion ratio at slaughter.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Feed Conversion Ratio (FCR): FCR is a measure of an animal's efficiency in converting feed mass into increases of the desired output. Animals raised for meat—such as swine, poultry and fish—the output is the mass gained by the animal. Specifically FCR is calculated as feed intake divided by weight gain, all over a specified period. Improvement in FCR means reduction of the FCR value. A FCR improvement of 2% means that the FCR was reduced by 2%.

Feed efficiency: The term "feed efficiency" means the amount of weight gain per unit of feed when the animal is fed ad-libitum or a specified amount of food during a period of time. By "increased feed efficiency" it is meant that the use of a feed additive composition according the present invention in feed results in an increased weight gain per unit of feed intake compared with an animal fed without said feed additive composition being present.

Forage: The term "forage" as defined herein also includes roughage. Forage is fresh plant material such as hay and silage from forage plants, grass and other forage plants, seaweed, sprouted grains and legumes, or any combination thereof. Examples of forage plants are Alfalfa (lucerne), birdsfoot trefoil, brassica (e.g., kale, rapeseed (canola), rutabaga (swede), turnip), clover (e.g., alsike clover, red clover, subterranean clover, white clover), grass (e.g., Bermuda grass, brome, false oat grass, fescue, heath grass, meadow grasses, orchard grass, ryegrass, Timothy-grass), corn (maize), millet, barley, oats, rye, sorghum, soybeans and wheat and vegetables such as beets. Forage further includes crop residues from grain production (such as corn stover; straw from wheat, barley, oat, rye and other grains); residues from vegetables like beet tops; residues from oilseed production like stems and leaves form soy beans, rapeseed and other legumes; and fractions from the refining of grains for animal or human consumption or from fuel production or other industries.

Fragment: The term "fragment" means a polypeptide having one or more (e.g., several) amino acids absent from the amino and/or carboxyl terminus of a mature polypeptide or domain; wherein the fragment has lysozyme activity. In one aspect, a fragment contains at least 215 amino acid residues (e.g., amino acids 16 to 230 of SEQ ID NO: 257), at least 225 amino acid residues (e.g., amino acids 11 to 235 of SEQ ID NO: 257), or at least 235 amino acid residues (e.g., amino acids 6 to 240 of SEQ ID NO: 257). In another aspect, a fragment contains at least 215 amino acid residues (e.g., amino acids 16 to 230 of SEQ ID NO: 264), at least 225 amino acid residues (e.g., amino acids 11 to 235 of SEQ ID NO: 264), or at least 235 amino acid residues (e.g., amino acids 6 to 240 of SEQ ID NO: 264). In another aspect, a fragment contains at least 218 amino acid residues (e.g., amino acids 16 to 233 of SEQ ID NO: 267), at least 228 amino acid residues (e.g., amino acids 11 to 238 of SEQ ID NO: 267), or at least 238 amino acid residues (e.g., amino acids 6 to 243 of SEQ ID NO: 267).

In one aspect, the fragment comprises at least 90% of the length of the mature polypeptide, such as at least 220 amino acids of SEQ ID NO: 288, at least 220 amino acids of SEQ ID NO: 290, at least 220 amino acids of SEQ ID NO: 291, at least 224 amino acids of SEQ ID NO: 293, at least 224 amino acids of SEQ ID NO: 294, at least 220 amino acids of SEQ ID NO: 296, at least 220 amino acids of SEQ ID NO: 297, at least 222 amino acids of SEQ ID NO: 299, at least 222 amino acids of SEQ ID NO: 300, at least 225 amino acids of SEQ ID NO: 302, at least 225 amino acids of SEQ ID NO: 303, at least 216 amino acids of SEQ ID NO: 305 or at least 216 amino acids of SEQ ID NO: 306.

In another aspect, the fragment comprises at least 92% of the length of the mature polypeptide, such as at least 225 amino acids of SEQ ID NO: 288, at least 225 amino acids of SEQ ID NO: 290, at least 225 amino acids of SEQ ID NO: 291, at least 229 amino acids of SEQ ID NO: 293, at least 229 amino acids of SEQ ID NO: 294, at least 225 amino acids of SEQ ID NO: 296, at least 225 amino acids of SEQ ID NO: 297, at least 227 amino acids of SEQ ID NO: 299, at least 227 amino acids of SEQ ID NO: 300, at least 230 amino acids of SEQ ID NO: 302, at least 230 amino acids of SEQ ID NO: 303, at least 220 amino acids of SEQ ID NO: 305 or at least 220 amino acids of SEQ ID NO: 306.

In another aspect, the fragment comprises at least 94% of the length of the mature polypeptide, such as at least 230 amino acids of SEQ ID NO: 288, at least 230 amino acids of SEQ ID NO: 290, at least 230 amino acids of SEQ ID NO: 291, at least 234 amino acids of SEQ ID NO: 293, at least 234 amino acids of SEQ ID NO: 294, at least 230 amino acids of SEQ ID NO: 296, at least 230 amino acids of SEQ ID NO: 297, at least 232 amino acids of SEQ ID NO: 299, at least 232 amino acids of SEQ ID NO: 300, at least 235 amino acids of SEQ ID NO: 302, at least 235 amino acids of SEQ ID NO: 303, at least 225 amino acids of SEQ ID NO: 305 or at least 225 amino acids of SEQ ID NO: 306.

In another aspect, the fragment comprises at least 96% of the length of the mature polypeptide, such as at least 235 amino acids of SEQ ID NO: 288, at least 235 amino acids of SEQ ID NO: 290, at least 235 amino acids of SEQ ID NO: 291, at least 239 amino acids of SEQ ID NO: 293, at least 239 amino acids of SEQ ID NO: 294, at least 235 amino acids of SEQ ID NO: 296, at least 235 amino acids of SEQ ID NO: 297, at least 237 amino acids of SEQ ID NO: 299, at least 237 amino acids of SEQ ID NO: 300, at least 240 amino acids of SEQ ID NO: 302, at least 240 amino acids of SEQ ID NO: 303, at least 230 amino acids of SEQ ID NO: 305 or at least 230 amino acids of SEQ ID NO: 306.

In another aspect, the fragment comprises at least 98% of the length of the mature polypeptide, such as at least 240 amino acids of SEQ ID NO: 288, at least 240 amino acids of SEQ ID NO: 290, at least 240 amino acids of SEQ ID NO: 291, at least 244 amino acids of SEQ ID NO: 293, at least 244 amino acids of SEQ ID NO: 294, at least 240 amino acids of SEQ ID NO: 296, at least 240 amino acids of SEQ ID NO: 297, at least 242 amino acids of SEQ ID NO: 299, at least 242 amino acids of SEQ ID NO: 300, at least 245 amino acids of SEQ ID NO: 302, at least 245 amino acids of SEQ ID NO: 303, at least 235 amino acids of SEQ ID NO: 305 or at least 235 amino acids of SEQ ID NO: 306.

In another aspect, the fragment comprises at least 99% of the length of the mature polypeptide, such as at least 242 amino acids of SEQ ID NO: 288, at least 242 amino acids of SEQ ID NO: 290, at least 242 amino acids of SEQ ID NO: 291, at least 246 amino acids of SEQ ID NO: 293, at least 246 amino acids of SEQ ID NO: 294, at least 242 amino acids of SEQ ID NO: 296, at least 242 amino acids of SEQ ID NO: 297, at least 244 amino acids of SEQ ID NO: 299, at least 244 amino acids of SEQ ID NO: 300, at least 247 amino acids of SEQ ID NO: 302, at least 247 amino acids of SEQ ID NO: 303, at least 237 amino acids of SEQ ID NO: 305 or at least 237 amino acids of SEQ ID NO: 306.

hmmbuild: The term "hmmbuild" is a program from the package HMMER 3.0 (March 2010) (hmmer.org/) that builds a profile HMM from an input multiple alignment.

hmmscan: The term "hmmscan" is a program from the package HMMER 3.0 (March 2010) (hmmer.org/) that searches a protein sequence against a protein profile HMM database.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance).

Lysozyme activity: The term "lysozyme activity" means the hydrolysis of the 1,4-beta-linkages between N-acetyl-muramic acid and N-acetyl-D-glucosamine residues in a peptidoglycan or between N-acetyl-D-glucosamine residues in chitodextrins, resulting in bacteriolysis. Lysozyme belongs to the enzyme class EC 3.2.1.17. Lysozyme activity is typically measured by turbidimetric determination, such as the changes in turbidity of a suspension of *Micrococcus luteus* ATCC 4698 or *Exiguobacterium undea* (DSM14481) induced by the lytic action of the lysozyme. In appropriate experimental conditions these changes are proportional to the amount of lysozyme in the medium (c.f. INS 1105 of the Combined Compendium of Food Additive Specifications of the Food and Agriculture Organisation of the UN (fao.org)). For the purpose of the present invention, lysozyme activity is determined according to the turbidity assay described in example 11 ("Determination of Lysozyme Activity") and the polypeptidehas lysozyme activity if it shows activity against one or more bacteria, such as *Micrococcus luteus* ATCC 4698 and/or *Exiguobacterium undea* (DSM14481). In one aspect, the polypeptides of the present invention have at least 20%, e.g., at least 40%, at least 50%, at least 60%, at least 70%, at least 80%, at least 90%, at least 95%, or at least 100% of the lysozyme activity of SEQ ID NO: 257. In another aspect, the polypeptides of the present invention have at least 20%, e.g., at least 40%, at least 50%, at least 60%, at least 70%, at least 80%, at least 90%, at least 95%, or at least 100% of the lysozyme activity of SEQ ID NO: 264. In another aspect, the polypeptides of the present invention have at least 20%, e.g., at least 40%, at least 50%, at least 60%, at least 70%, at least 80%, at least 90%, at least 95%, or at least 100% of the lysozyme activity of SEQ ID NO: 267.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide amino acids 1 to 245 of SEQ ID NO: 257 based on EDMAN N-terminal sequencing data, intact molecular weight analysis and proteomic analysis. In another aspect, the mature polypeptide amino acids 1 to 245 of SEQ ID NO: 264. In another aspect, the mature polypeptide amino acids 1 to 248 of SEQ ID NO: 267.

In one aspect, the mature polypeptide is amino acids 1 to 245 of SEQ ID NO: 288 and amino acids −17 to −1 of SEQ ID NO: 288 are a signal peptide. In another aspect, the mature polypeptide is amino acids 1 to 245 of SEQ ID NO: 290. In an alternative aspect, the mature polypeptide is amino acids 1 to 245 of SEQ ID NO: 291.

In one aspect, the mature polypeptide is amino acids 1 to 249 of SEQ ID NO: 293 and amino acids −18 to −1 of SEQ ID NO: 293 are a signal peptide. In an alternative aspect, the mature polypeptide is amino acids 1 to 249 of SEQ ID NO: 294.

In one aspect, the mature polypeptide is amino acids 1 to 245 of SEQ ID NO: 296 and amino acids −19 to −1 of SEQ ID NO: 296 are a signal peptide. In an alternative aspect, the mature polypeptide is amino acids 1 to 245 of SEQ ID NO: 297.

In one aspect, the mature polypeptide is amino acids 1 to 247 of SEQ ID NO: 299 and amino acids −19 to −1 of SEQ ID NO: 299 are a signal peptide. In an alternative aspect, the mature polypeptide is amino acids 1 to 247 of SEQ ID NO: 300.

In one aspect, the mature polypeptide is amino acids 1 to 250 of SEQ ID NO: 302 and amino acids −18 to −1 of SEQ ID NO: 302 are a signal peptide. In an alternative aspect, the mature polypeptide is amino acids 1 to 250 of SEQ ID NO: 303.

In one aspect, the mature polypeptide is amino acids 1 to 240 of SEQ ID NO: 305 and amino acids −18 to −1 of SEQ ID NO: 305 are a signal peptide. In an alternative aspect, the mature polypeptide is amino acids 1 to 240 of SEQ ID NO: 306.

It is known in the art that a host cell may produce a mixture of two of more different mature polypeptides (i.e., with a different C-terminal and/or N-terminal amino acid) expressed by the same polynucleotide. It is also known in the art that different host cells process polypeptides differently, and thus, one host cell expressing a polynucleotide may produce a different mature polypeptide (e.g., having a different C-terminal and/or N-terminal amino acid) as compared to another host cell expressing the same polynucleotide.

Mature polypeptide coding sequence: The term "mature polypeptide coding sequence" means a polynucleotide that encodes a mature polypeptide having lysozyme activity. In one aspect, the mature polypeptide coding sequence is the joined sequence of nucleotides 52 to 347, nucleotides 401 to 615, nucleotides 668 to 772 and nucleotides 825 to 943 of SEQ ID NO: 255 or the cDNA sequence thereof and nucleotides 1 to 51 of SEQ ID NO: 255 are the signal peptide. In another aspect, the mature polypeptide coding sequence is the joined sequence of nucleotides 55 to 367, nucleotides 425 to 555 and nucleotides 630 to 920 of SEQ ID NO: 262 or the cDNA sequence thereof and nucleotides 1 to 54 of SEQ ID NO: 262 are the signal peptide. In another aspect, the mature polypeptide coding sequence is nucleotides 55 to 798 of SEQ ID NO: 265 and nucleotides 1 to 54 of SEQ ID NO: 265 are the signal peptide.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Obtained or obtainable from: The term "obtained or obtainable from" means that the polypeptide may be found in an organism from a specific taxonomic rank. In one embodiment, the polypeptide is obtained or obtainable from the kingdom Fungi, wherein the term kingdom is the taxonomic rank. In a preferred embodiment, the polypeptide is obtained or obtainable from the phylum Ascomycota, wherein the term phylum is the taxonomic rank. In another preferred embodiment, the polypeptide is obtained or obtainable from the subphylum Pezizomycotina, wherein the term subphylum is the taxonomic rank.

If the taxonomic rank of a polypeptide is not known, it can easily be determined by a person skilled in the art by performing a BLASTP search of the polypeptide (using, e.g., the National Center for Biotechnology Information (NCIB) website: ncbi.nlm.nih.gov/) and comparing it to the closest homologues. An unknown polypeptide which is a fragment of a known polypeptide is considered to be of the same taxonomic species. An unknown natural polypeptide or artificial variant which comprises a substitution, deletion and/or insertion in up to 10 positions is considered to be from the same taxonomic species as the known polypeptide.

Operably linked: The term "operably linked" means a configuration in which a control sequence is placed at an appropriate position relative to the coding sequence of a polynucleotide such that the control sequence directs expression of the coding sequence.

Profile Hidden Markov Model: "Profile Hidden Markov Model" are statistical models of multiple sequence alignments. They capture position-specific information about how conserved each column of the alignment is, and which residues are likely (see ftp://ftp.hgc.jp/pub/mirror/wustl/hmmer3/3.1b1/Userguide.pdf.

Roughage: The term "roughage" means dry plant material with high levels of fiber, such as fiber, bran, husks from seeds and grains and crop residues (such as stover, copra, straw, chaff, sugar beet waste).

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labelled "longest identity" (obtained using the —nobrief option) is used as the percent identity and is calculated as follows:

(Identical Residues×100)/(Length of Alignment−
Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labelled "longest identity" (obtained using the —nobrief option) is used as the percent identity and is calculated as follows:

(Identical Deoxyribonucleotides×100)/(Length of Alignment−Total Number of Gaps in Alignment)

Stringency conditions: The different stringency conditions are defined as follows.

The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 0.8×SSC, 0.2% SDS at 55° C.

The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 0.8×SSC, 0.2% SDS at 60° C.

The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 0.8×SSC, 0.2% SDS at 65° C.

The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 0.8×SSC, 0.2% SDS at 70° C.

The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 0.4×SSC, 0.2% SDS at 70° C.

The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 0.4×SSC, 0.2% SDS at 75° C.

Subsequence: The term "subsequence" means a polynucleotide having one or more (e.g., several) nucleotides absent from the 5' and/or 3' end of a mature polypeptide coding sequence; wherein the subsequence encodes a fragment having lysozyme activity. In one aspect, a subsequence contains at least 645 nucleotides (e.g., the joined sequence of nucleotides 97 to 347, nucleotides 401 to 615, nucleotides 668 to 772 and nucleotides 825 to 898 of SEQ ID NO: 255 or the cDNA sequence thereof), at least 675 nucleotides (e.g., the joined sequence of nucleotides 82 to 347, nucleotides 401 to 615, nucleotides 668 to 772 and nucleotides 825 to 913 of SEQ ID NO: 255 or the cDNA sequence thereof), or at least 705 nucleotides (e.g., the joined sequence of nucleotides 67 to 347, nucleotides 401 to 615, nucleotides 668 to 772 and nucleotides 825 to 928 of SEQ ID NO: 255 or the cDNA sequence thereof).

Substantially pure polypeptide: The term "substantially pure polypeptide" means a preparation that contains at most 10%, at most 8%, at most 6%, at most 5%, at most 4%, at most 3%, at most 2%, at most 1%, and at most 0.5% by weight of other polypeptide material with which it is natively or recombinantly associated. Preferably, the polypeptide is at least 92% pure, e.g., at least 94% pure, at least 95% pure, at least 96% pure, at least 97% pure, at least 98% pure, at least 99%, at least 99.5% pure, and 100% pure by weight of the total polypeptide material present in the preparation. The polypeptides of the present invention are preferably in a substantially pure form. This can be accomplished, for example, by preparing the polypeptide by well known recombinant methods or by classical purification methods.

Variant: The term "variant" means a polypeptide having lysozyme activity comprising an alteration, i.e., a substitution, insertion, and/or deletion, of one or more (several) amino acid residues at one or more (e.g., several) positions. A substitution means replacement of the amino acid occupying a position with a different amino acid; a deletion means removal of the amino acid occupying a position; and an insertion means adding 1, 2, or 3 amino acids adjacent to and immediately following the amino acid occupying the position.

In one aspect, a lysozyme variant according to the invention may comprise from 1 to 5; from 1 to 10; from 1 to 15; from 1 to 20; from 1 to 25; from 1 to 30; from 1 to 35; from 1 to 40; from 1 to 45; or from 1-50, i.e., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 alterations and have at least 20%, e.g., at least 40%, at least 50%, at least 60%, at least 70%, at least 80%, at least 90%, at least 95%, or at least 100% of the lysozyme activity of the parent lysozyme, such as SEQ ID NO: 257, SEQ ID NO: 264 or SEQ ID NO: 267.

Nomenclature

For purposes of the present invention, the nomenclature [E/Q] means that the amino acid at this position may be a glutamic acid (Glu, E) or a glutamine (Gln, Q). Likewise the nomenclature [V/G/A/I] means that the amino acid at this position may be a valine (Val, V), glycine (Gly, G), alanine (Ala, A) or isoleucine (Ile, I), and so forth for other combinations as described herein. Unless otherwise limited further, the amino acid X is defined such that it may be any of the 20 natural amino acids.

DETAILED DESCRIPTION OF THE INVENTION

Animal Feed and Animal Feed Additives Comprising Polypeptides Having Lysozyme Activity The inventors have discovered that some polypeptides that comprise one or more Glycosyl Hydrolase family 24

(GH24) catalytic domains also comprise sections of polypeptide which until now has not been known to have any function and have therefore not been annotated. The inventors have herein annotated these sections of polypeptide, which is referred to herein as a lysozyme enhancing domain (LED), and have surprisingly discovered that this lysozyme enhancing domain significantly enhances antimicrobial activity against *Clostridium perfringens*.

For example, the polypeptide of SEQ ID NO: 257 which comprises a GH24 domain and a lysozyme enhancing domain has significant activity against *Clostridium perfringens* (see table 3 of example 12). However, when the polypeptide is expressed without the lysozyme enhancing domain being present (SEQ ID NO: 270), there is no activity against *Clostridium perfringens* using the conditions 50% MHB, pH 6.

Two other polypeptides comprising a GH24 domain and a lysozyme enhancing domain (SEQ ID NO: 264 and 267) also have significant activity against *Clostridium perfringens* (see table 3) using the conditions 50% MHB, pH 6. However, two known GH24 lysozymes (SEQ ID NO: 279 and SEQ ID NO: 280) which do not comprise a lysozyme enhancing domain do not have any activity against *Clostridium perfringens*.

The inventors have also discovered that the LED protein (SEQ ID NO: 273) binds to *M. lysodiektikus* cells under the buffer conditions tested while crystalline cellulose did not bind the LED protein. This demonstrates that the LED protein is an important feature of the lysozymes of the invention and possibly explains why said lysozymes are more active against *Clostridium perfringens* under the tested conditions compared to GH24 lysozymes lacking the LED.

Thus, in one aspect, the invention relates to an animal feed or animal feed additive comprising one or more polypeptides having lysozyme activity, wherein the polypeptide comprises one or more GH24 catalytic domains and one or more lysozyme enhancing domains and wherein:
  (a) GH24 catalytic domain gives a domT score of at least 200 when queried using a Profile Hidden Markov Model prepared using SEQ ID NOs: 1 to 122 and hmmbuild software program, and wherein the query is carried out using hmmscan software program with default settings; and
  (b) the polypeptide comprises one or more lysozyme enhancing domains, wherein the lysozyme enhancing domain gives a domT score of at least 100 when queried using a Profile Hidden Markov Model prepared using SEQ ID NOs: 123 to 251 and hmmbuild software program, and wherein the query is carried out using the hmmscan software program with default settings.

In another aspect, the present invention relates to an animal feed or animal feed additive comprising one or more polypeptides having lysozyme activity, wherein:
  (a) the polypeptide comprises one or more GH24 catalytic domains, wherein the GH24 catalytic domain gives a domT score of 200 or more when queried using a Profile Hidden Markov Model prepared using SEQ ID NOs: 1 to 122 inclusive using the software program hmmbuild, the query being carried out using the hmmscan software program with default settings; and
  (b) the polypeptide comprises one or more lysozyme enhancing domains, wherein the lysozyme enhancing domain gives a domT score of 100 or more when queried using a Profile Hidden Markov Model prepared using SEQ ID NOs: 123 to 251 inclusive using the software program hmmbuild, the query being carried out using the hmmscan software program with default settings.

In another aspect, the present invention relates to an animal feed or animal feed additive comprising one or more vitamins and one or more polypeptides having lysozyme activity, wherein the polypeptide comprises one or more GH24 catalytic domains and one or more lysozyme enhancing domains and wherein:
  (a) GH24 catalytic domain gives a domT score of at least 200 when queried using a Profile Hidden Markov Model prepared using SEQ ID NOs: 1 to 122 and hmmbuild software program, and wherein the query is carried out using hmmscan software program with default settings; and
  (b) the polypeptide comprises one or more lysozyme enhancing domains, wherein the lysozyme enhancing domain gives a domT score of at least 100 when queried using a Profile Hidden Markov Model prepared using SEQ ID NOs: 123 to 251 and hmmbuild software program, and wherein the query is carried out using the hmmscan software program with default settings.

In another aspect, the present invention relates to an animal feed or animal feed additive comprising one or more minerals and one or more polypeptides having lysozyme activity, wherein the polypeptide comprises one or more GH24 catalytic domains and one or more lysozyme enhancing domains and wherein:
  (a) GH24 catalytic domain gives a domT score of at least 200 when queried using a Profile Hidden Markov Model prepared using SEQ ID NOs: 1 to 122 and hmmbuild software program, and wherein the query is carried out using hmmscan software program with default settings; and
  (b) the polypeptide comprises one or more lysozyme enhancing domains, wherein the lysozyme enhancing domain gives a domT score of at least 100 when queried using a Profile Hidden Markov Model prepared using SEQ ID NOs: 123 to 251 and hmmbuild software program, and wherein the query is carried out using the hmmscan software program with default settings.

In another aspect, the present invention relates to an animal feed or animal feed additive comprising one or more amino acids and one or more polypeptides having lysozyme activity, wherein the polypeptide comprises one or more GH24 catalytic domains and one or more lysozyme enhancing domains and wherein:
  (a) GH24 catalytic domain gives a domT score of at least 200 when queried using a Profile Hidden Markov Model prepared using SEQ ID NOs: 1 to 122 and hmmbuild software program, and wherein the query is carried out using hmmscan software program with default settings; and
  (b) the polypeptide comprises one or more lysozyme enhancing domains, wherein the lysozyme enhancing domain gives a domT score of at least 100 when queried using a Profile Hidden Markov Model prepared using SEQ ID NOs: 123 to 251 and hmmbuild software program, and wherein the query is carried out using the hmmscan software program with default settings.

In another aspect, the present invention relates to an animal feed or animal feed additive comprising one or more polypeptides having lysozyme activity, wherein the polypeptide comprises one or more GH24 catalytic domains and one or more lysozyme enhancing domains and wherein:
  (a) GH24 catalytic domain gives a domT score of at least 200 when queried using a Profile Hidden Markov Model prepared using SEQ ID NOs: 1 to 122 and hmmbuild software program, and wherein the query is carried out using hmmscan software program with default settings; and (b) the polypeptide comprises one or more lysozyme enhancing domains, wherein the lysozyme enhancing domain gives a domT score of at least 100 when queried using a Profile Hidden Markov Model prepared using SEQ ID NOs: 123 to 251 and hmmbuild software program, and wherein the query is carried out using the hmmscan software program with default settings; and one or more components selected from the list consisting of:
one or more additional enzymes;
one or more microbes;
one or more vitamins;
one or more minerals;
one or more amino acids; and
one or more other feed ingredients.

In another aspect, the present invention relates to a pelleted animal feed comprising plant based material and one or more polypeptides having lysozyme activity, wherein the polypeptide comprises one or more GH24 catalytic domains and one or more lysozyme enhancing domains and wherein:

(a) GH24 catalytic domain gives a domT score of at least 200 when queried using a Profile Hidden Markov Model prepared using SEQ ID NOs: 1 to 122 and hmmbuild software program, and wherein the query is carried out using hmmscan software program with default settings; and (b) the polypeptide comprises one or more lysozyme enhancing domains, wherein the lysozyme enhancing domain gives a domT score of at least 100 when queried using a Profile Hidden Markov Model prepared using SEQ ID NOs: 123 to 251 and hmmbuild software program, and wherein the query is carried out using the hmmscan software program with default settings.

The theory behind Profile HMMs as described in Durbin et al. (Biological sequence analysis: probabilistic models of proteins and nucleic acids, Cambridge University Press, 1998) and Krogh et al. (*J. Mol. Biol.* 235: 1501-1531 (1994)), both incorporated herein by reference, is characterization of a set of proteins based on the probability of each amino acid occurring at each position in the alignment of the proteins of the set.

Specifically, profile HMMs are statistical models of multiple sequence alignments, or even of single sequences. They capture position-specific information about how conserved each column of the alignment is, and which residues are likely. All profile methods are more or less statistical descriptions of the consensus of a multiple sequence alignment. They use position-specific scores for amino acids or nucleotides (residues) and position specific penalties for opening and extending an insertion or deletion. Traditional pairwise alignment (for example, BLAST, FASTA or the Smith/Waterman algorithm) uses position-independent scoring parameters. This property of profiles captures important information about the degree of conservation at various positions in the multiple alignment, and the varying degree to which gaps and insertions are permitted.

The advantage of using HMMs is that HMMs have a formal probabilistic basis. Probability theory is used to guide how all the scoring parameters should be set. One of the most important aspect is that HMMs have a consistent theory for setting position-specific gap and insertion scores. The methods are consistent and therefore highly automatable, allowing hundreds of profile HMMs to be applied to, e.g., whole genome analysis. An example of a protein domain model database is Pfam (Sonnhammer et al., 1997, 'A comprehensive database of protein families based on seed alignments', *Proteins* 28: 405-420; Finn et al., 2010, 'The Pfam protein families database', *Nucl. Acids Res.* 38: D211-D222), which is a significant part of the Interpro protein domain annotation system. The construction and use of Pfam is tightly tied to the HMMER software package (see en.wikipedia.org/wiki/HMMER).

The GH24 domain is defined in the following manner. SEQ ID NOs: 1 to 122, which are partial sequences of the UniProt entries as explained in the 'overview of sequence listing' section herein, are aligned using the software program MUSCLE v3.8.31 with the default settings. Using this alignment, a hidden Markov model (HMM) is built for the GH24 domain. The HMM is constructed using the software program 'hmmbuild' from the package HMMER 3.0 (March 2010) (hmmer.org/) and the software is invoked using the default settings.

A GH24 domain is defined to match the above mentioned HMM using the software program 'hmmscan' from the package HMMER 3.0 (March 2010) (hmmer.org/) using the default settings if the domT score is at least 200. In a preferred embodiment, the domT score is at least 220, preferably at least 230, more preferably at least 240, even more preferably at least 250, even more preferably at least 255, or most preferably at least 260.

The HMM profile of the GH24 domain as generated using SEQ ID NOs: 1 to 122 according to the procedure above is given in example 15. The HMM profile can be copied into a text file which is subsequently loaded into the software program 'hmmscan' so that other polypeptides can be tested to see whether said polypeptide comprises one or more GH24 catalytic domains.

The Lysozyme Enhancing Domain (LED) is defined in the following manner. SEQ ID NOs: 123 to 251, which are partial sequences of the Uniprot entries as explained in the 'overview of sequence listing' section herein, are aligned using the software program MUSCLE v3.8.31 with the default settings. Using this alignment, a hidden Markov model (HMM) is built for the LED. The HMM is constructed using the software program 'hmmbuild' from the package HMMER 3.0 (March 2010) (hmmer.org/) and the software is invoked using the default settings.

A LED is defined to match the above mentioned HMM using the software program 'hmmscan' from the package HMMER 3.0 (March 2010) (hmmer.org/) using the default settings if the domT score is at least 100. In a preferred embodiment, the domT score is at least 103, preferably at least 106, more preferably at least 109, more preferably at least 112, more preferably at least 115, more preferably at least 118, even more preferably at least 121, or most preferably at least 124.

The HMM profile of the LED as generated using SEQ ID NOs: 123 to 251 according to the procedure above is given in example 16. The HMM profile can be copied into a text file which is subsequently loaded into the software program 'hmmscan' so that other polypeptides can be tested to see whether said polypeptide comprises one or more LED.

In an embodiment, the GH24 catalytic domain gives a domT score of at least 220 and the lysozyme enhancing domain gives a domT score of at least 100. In an embodiment, the GH24 catalytic domain gives a domT score of at least 230 and the lysozyme enhancing domain gives a domT score of at least 100. In an embodiment, the GH24 catalytic domain gives a domT score of at least 240 and the lysozyme enhancing domain gives a domT score of at least 100. In an embodiment, the GH24 catalytic domain gives a domT score of at least 250 and the lysozyme enhancing domain gives a domT score of at least 100.

In an embodiment, the GH24 catalytic domain gives a domT score of at least 220 and the lysozyme enhancing domain gives a domT score of at least 103. In an embodiment, the GH24 catalytic domain gives a domT score of at least 230 and the lysozyme enhancing domain gives a domT score of at least 103. In an embodiment, the GH24 catalytic domain gives a domT score of at least 240 and the lysozyme enhancing domain gives a domT score of at least 103. In an embodiment, the GH24 catalytic domain gives a domT score of at least 250 and the lysozyme enhancing domain gives a domT score of at least 103.

In an embodiment, the GH24 catalytic domain gives a domT score of at least 220 and the lysozyme enhancing domain gives a domT score of at least 106. In an embodiment, the GH24 catalytic domain gives a domT score of at least 230 and the lysozyme enhancing domain gives a domT score of at least 106. In an embodiment, the GH24 catalytic domain gives a domT score of at least 240 and the lysozyme enhancing domain gives a domT score of at least 106. In an embodiment, the GH24 catalytic domain gives a domT score of at least 250 and the lysozyme enhancing domain gives a domT score of at least 106.

In an embodiment, the GH24 catalytic domain gives a domT score of at least 220 and the lysozyme enhancing domain gives a domT score of at least 109. In an embodiment, the GH24 catalytic domain gives a domT score of at least 230 and the lysozyme enhancing domain gives a domT score of at least 109. In an embodiment, the GH24 catalytic domain gives a domT score of at least 240 and the lysozyme enhancing domain gives a domT score of at least 109. In an embodiment, the GH24 catalytic domain gives a domT score of at least 250 and the lysozyme enhancing domain gives a domT score of at least 109.

In an embodiment, the GH24 catalytic domain gives a domT score of at least 220 and the lysozyme enhancing domain gives a domT score of at least 112. In an embodiment, the GH24 catalytic domain gives a domT score of at least 230 and the lysozyme enhancing domain gives a domT score of at least 112. In an embodiment, the GH24 catalytic domain gives a domT score of at least 240 and the lysozyme enhancing domain gives a domT score of at least 112. In an embodiment, the GH24 catalytic domain gives a domT score of at least 250 and the lysozyme enhancing domain gives a domT score of at least 112.

In an embodiment, the GH24 catalytic domain gives a domT score of at least 220 and the lysozyme enhancing domain gives a domT score of at least 115. In an embodiment, the GH24 catalytic domain gives a domT score of at least 230 and the lysozyme enhancing domain gives a domT score of at least 115. In an embodiment, the GH24 catalytic domain gives a domT score of at least 240 and the lysozyme enhancing domain gives a domT score of at least 115. In an embodiment, the GH24 catalytic domain gives a domT score of at least 250 and the lysozyme enhancing domain gives a domT score of at least 115.

In an embodiment, the GH24 catalytic domain gives a domT score of at least 220 and the lysozyme enhancing domain gives a domT score of at least 118. In an embodiment, the GH24 catalytic domain gives a domT score of at least 230 and the lysozyme enhancing domain gives a domT score of at least 118. In an embodiment, the GH24 catalytic domain gives a domT score of at least 240 and the lysozyme enhancing domain gives a domT score of at least 118. In an embodiment, the GH24 catalytic domain gives a domT score of at least 250 and the lysozyme enhancing domain gives a domT score of at least 118.

In an embodiment, the polypeptide having lysozyme activity is obtained or obtainable from the kingdom Fungi, preferably from the phylum Ascomycota.

In an embodiment, the polypeptide having lysozyme activity has at least 30% of the antimicrobial activity of SEQ ID NO: 257 against *Clostridium perfringens* using the conditions 50% MHB, pH 6. In an embodiment, the polypeptide having lysozyme activity has at least 50% of the antimicrobial activity of SEQ ID NO: 257 against *Clostridium perfringens* using the conditions 50% MHB, pH 6. In an embodiment, the polypeptide having lysozyme activity has at least 60% of the antimicrobial activity of SEQ ID NO: 257 against *Clostridium perfringens* using the conditions 50% MHB, pH 6.

In an embodiment, the polypeptide having lysozyme activity has at least 70% of the antimicrobial activity of SEQ ID NO: 257 against *Clostridium perfringens* using the conditions 50% MHB, pH 6. In an embodiment, the polypeptide having lysozyme activity has at least 75% of the antimicrobial activity of SEQ ID NO: 257 against *Clostridium perfringens* using the conditions 50% MHB, pH 6. In an embodiment, the polypeptide having lysozyme activity has at least 80% of the antimicrobial activity of SEQ ID NO: 257 against *Clostridium perfringens* using the conditions 50% MHB, pH 6.

In an embodiment, the polypeptide having lysozyme activity has at least 85% of the antimicrobial activity of SEQ ID NO: 257 against *Clostridium perfringens* using the conditions 50% MHB, pH 6. In an embodiment, the polypeptide having lysozyme activity has at least 90% of the antimicrobial activity of SEQ ID NO: 257 against *Clostridium perfringens* using the conditions 50% MHB, pH 6. In an embodiment, the polypeptide having lysozyme activity has at least 95% of the antimicrobial activity of SEQ ID NO: 257 against *Clostridium perfringens* using the conditions 50% MHB, pH 6. In an embodiment, the polypeptide having lysozyme activity has at least 100% of the antimicrobial activity of SEQ ID NO: 257 against *Clostridium perfringens* using the conditions 50% MHB, pH 6.

In one aspect, the invention relates to an animal feed or animal feed additive comprising one or more polypeptides having lysozyme activity, wherein the polypeptide having lysozyme activity comprises one or more GH24 catalytic domains and one or more lysozyme enhancing domains, wherein:

(a) the GH24 catalytic domain comprises one or more motif I: [TAS][VIL][GAC][YFI]GHX[CAYIV] (SEQ ID NO: 252) and/or one or more motif II [LV][NDST]XN[QE][YFW][GASND]ALXS[WFLY]X[FY]N (SEQ ID NO: 253); and (b) the lysozyme enhancing domain comprises one or more motif III: [CGY][YF][VIL][ASTP][DG]X[YF][VIT]X[TS][GAN] (SEQ ID NO: 254).

In one aspect, the invention relates to an animal feed or animal feed additive comprising one or more polypeptides having lysozyme activity, wherein the polypeptide having lysozyme activity comprises one or more GH24 catalytic domains and one or more lysozyme enhancing domains, wherein:

(a) the GH24 catalytic domain comprises one or more motif I: [TAS][VIL][GAC][YFI]GHX[CAYIV] (SEQ ID NO: 281) and/or one or more motif II LNXN[QE][YFW][GA]ALXS[WFL]X[YF]N (SEQ ID NO: 283); and
(b) the lysozyme enhancing domain comprises one or more motif III: C[YF][V][AST]D[YKF][YF][V]XTG (SEQ ID NO: 284).

In one aspect, the invention relates to an animal feed or animal feed additive comprising one or more polypeptides having lysozyme activity, wherein the polypeptide having lysozyme activity comprises one or more GH24 catalytic domains and one or more lysozyme enhancing domains, wherein:
(a) the GH24 catalytic domain comprises one or more motif: T[VI]GYGHXC (SEQ ID NO: 282) and/or one or more motif II LNXN[QE][YFW][GA]ALXS[WFL]X[YF]N (SEQ ID NO: 283); and
(b) the lysozyme enhancing domain comprises one or more motif III: C[YF][V][AST]D[YKF][YF][V]XTG (SEQ ID NO: 284).

In one aspect, the invention relates to an animal feed or animal feed additive comprising one or more polypeptides having lysozyme activity, wherein the polypeptide having lysozyme activity comprises one or more GH24 catalytic domains and one or more lysozyme enhancing domains, wherein:
(a) the GH24 catalytic domain comprises one or more motif I: [TAS][VIL][GAC][YFI]GHX[CAYIV] (SEQ ID NO: 252), one or more motif II [LV][NDST]XN[QE][YFW][GASND]ALXS[WFLY]X[FY]N (SEQ ID NO: 253) and/or one or more motif IV [GEV]LXXRRXXE (SEQ ID NO: 285); and
(b) the lysozyme enhancing domain comprises one or more motif III: [CGY][YF][VIL][ASTP][DG]X[YF][VIT]X[TS][GAN] (SEQ ID NO: 254).

In one aspect, the invention relates to an animal feed or animal feed additive comprising one or more polypeptides having lysozyme activity, wherein the polypeptide having lysozyme activity comprises one or more GH24 catalytic domains and one or more lysozyme enhancing domains, wherein:
(a) the GH24 catalytic domain comprises one or more motif I: [TAS][VIL][GAC][YFI]GHX[CAYIV] (SEQ ID NO: 281), one or more motif II LNXN[QE][YFW][GA]ALXS[WFL]X[YF]N (SEQ ID NO: 283) and/or one or more motif IV GLXXRRXXE (SEQ ID NO: 286); and
(b) the lysozyme enhancing domain comprises one or more motif III: C[YF][V][AST]D[YKF][YF][V]XTG (SEQ ID NO: 284).

In one aspect, the invention relates to an animal feed or animal feed additive comprising one or more polypeptides having lysozyme activity, wherein the polypeptide having lysozyme activity comprises one or more GH24 catalytic domains and one or more lysozyme enhancing domains, wherein:
(a) the GH24 catalytic domain comprises one or more motif I: [TAS][VIL][GAC][YFI]GHX[CAYIV] (SEQ ID NO: 252) and one or more motif II [LV][NDST]XN[QE][YFW][GASND]ALXS[WFLY]X[FY]N (SEQ ID NO: 253); and
(b) the lysozyme enhancing domain comprises one or more motif III: [CGY][YF][VIL][ASTP][DG]X[YF][VIT]X[TS][GAN] (SEQ ID NO: 254).

In one aspect, the invention relates to an animal feed or animal feed additive comprising one or more polypeptides having lysozyme activity, wherein the polypeptide having lysozyme activity comprises one or more GH24 catalytic domains and one or more lysozyme enhancing domains, wherein:
(a) the GH24 catalytic domain comprises one or more motif I: [TAS][VIL][GAC][YFI]GHX[CAYIV] (SEQ ID NO: 281) and one or more motif II LNXN[QE][YFW][GA]ALXS[WFL]X[YF]N (SEQ ID NO: 283); and
(b) the lysozyme enhancing domain comprises one or more motif III: C[YF][V][AST]D[YKF][YF][V]XTG (SEQ ID NO: 284).

In one aspect, the invention relates to an animal feed or animal feed additive comprising one or more polypeptides having lysozyme activity, wherein the polypeptide having lysozyme activity comprises one or more GH24 catalytic domains and one or more lysozyme enhancing domains, wherein:
(a) the GH24 catalytic domain comprises one or more motif: T[VI]GYGHXC (SEQ ID NO: 282) and one or more motif II LNXN[QE][YFW][GA]ALXS[WFL]X[YF]N (SEQ ID NO: 283); and
(b) the lysozyme enhancing domain comprises one or more motif III: C[YF][V][AST]D[YKF][YF][V]XTG (SEQ ID NO: 284).

In one aspect, the invention relates to an animal feed or animal feed additive comprising one or more polypeptides having lysozyme activity, wherein the polypeptide having lysozyme activity comprises one or more GH24 catalytic domains and one or more lysozyme enhancing domains, wherein:
(a) the GH24 catalytic domain comprises one or more motif I: [TAS][VIL][GAC][YFI]GHX[CAYIV] (SEQ ID NO: 252), one or more motif II [LV][NDST]XN[QE][YFW][GASND]ALXS[WFLY]X[FY]N (SEQ ID NO: 253) and one or more motif IV [GEV]LXXRRXXE (SEQ ID NO: 285); and
(b) the lysozyme enhancing domain comprises one or more motif III: [CGY][YF][VIL][ASTP][DG]X[YF][VIT]X[TS][GAN] (SEQ ID NO: 254).

In one aspect, the invention relates to an animal feed or animal feed additive comprising one or more polypeptides having lysozyme activity, wherein the polypeptide having lysozyme activity comprises one or more GH24 catalytic domains and one or more lysozyme enhancing domains, wherein:
(a) the GH24 catalytic domain comprises one or more motif I: [TAS][VIL][GAC][YFI]GHX[CAYIV] (SEQ ID NO: 281), one or more motif II LNXN[QE][YFW][GA]ALXS[WFL]X[YF]N (SEQ ID NO: 283) and one or more motif IV GLXXRRXXE (SEQ ID NO: 286); and
(b) the lysozyme enhancing domain comprises one or more motif III: C[YF][V][AST]D[YKF][YF][VI]XTG (SEQ ID NO: 284).

In an embodiment, the polypeptide having lysozyme activity is obtained or obtainable from the kingdom Fungi, preferably from the phylum Ascomycota.

In an embodiment, the polypeptide having lysozyme activity has at least 30% of the antimicrobial activity of SEQ ID NO: 257 against *Clostridium perfringens* using the conditions 50% MHB, pH 6. In an embodiment, the polypeptide having lysozyme activity has at least 50% of the antimicrobial activity of SEQ ID NO: 257 against *Clostridium perfringens* using the conditions 50% MHB, pH 6. In an embodiment, the polypeptide having lysozyme activity has at least 60% of the antimicrobial activity of SEQ ID NO: 257 against *Clostridium perfringens* using the conditions 50% MHB, pH 6.

In an embodiment, the polypeptide having lysozyme activity has at least 70% of the antimicrobial activity of SEQ ID NO: 257 against *Clostridium perfringens* using the conditions 50% MHB, pH 6. In an embodiment, the polypeptide having lysozyme activity has at least 75% of the antimicrobial activity of SEQ ID NO: 257 against *Clostridium perfringens* using the conditions 50% MHB, pH 6. In an embodiment, the polypeptide having lysozyme activity has at least 80% of the antimicrobial activity of SEQ ID NO: 257 against *Clostridium perfringens* using the conditions 50% MHB, pH 6.

In an embodiment, the polypeptide having lysozyme activity has at least 85% of the antimicrobial activity of SEQ ID NO: 257 against *Clostridium perfringens* using the conditions 50% MHB, pH 6. In an embodiment, the polypeptide having lysozyme activity has at least 90% of the antimicrobial activity of SEQ ID NO: 257 against *Clostridium perfringens* using the conditions 50% MHB, pH 6. In an embodiment, the polypeptide having lysozyme activity has at least 95% of the antimicrobial activity of SEQ ID NO: 257 against *Clostridium perfringens* using the conditions 50% MHB, pH 6. In an embodiment, the polypeptide having lysozyme activity has at least 100% of the antimicrobial activity of SEQ ID NO: 257 against *Clostridium perfringens* using the conditions 50% MHB, pH 6.

In another aspect, the invention relates to an animal feed or animal feed additive comprising one or more polypeptides having lysozyme activity, wherein the polypeptide having lysozyme activity comprises one or more GH24 catalytic domains and one or more lysozyme enhancing domains, wherein:
(a) the GH24 catalytic domain comprises one or more motif I: [TAS][VIL][GAC][YFI]GHX[CAYIV] (SEQ ID NO: 252), one or more motif II [LV][NDST]XN[QE][YFW][GASND]ALXS[WFLY]X[FY]N (SEQ ID NO: 253) and has at least 50%, e.g., at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 14; and
(b) the GH24 lysozyme enhancing domain comprises one or more motif I: [TAS][VIL][GAC][YFI]GHX[CAYIV] (SEQ ID NO: 252), one or more motif II [LV][NDST]XN[QE][YFW][GASND]ALXS[WFLY]X[FY]N (SEQ ID NO: 253) and has at least 45%, e.g., at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 180.

In an embodiment, the polypeptide having lysozyme activity is obtained or obtainable from the kingdom Fungi, preferably from the phylum Ascomycota.

In an embodiment, the polypeptide having lysozyme activity has at least 30% of the antimicrobial activity of SEQ ID NO: 257 against *Clostridium perfringens* using the conditions 50% MHB, pH 6. In an embodiment, the polypeptide having lysozyme activity has at least 50% of the antimicrobial activity of SEQ ID NO: 257 against *Clostridium perfringens* using the conditions 50% MHB, pH 6. In an embodiment, the polypeptide having lysozyme activity has at least 60% of the antimicrobial activity of SEQ ID NO: 257 against *Clostridium perfringens* using the conditions 50% MHB, pH 6.

In an embodiment, the polypeptide having lysozyme activity has at least 70% of the antimicrobial activity of SEQ ID NO: 257 against *Clostridium perfringens* using the conditions 50% MHB, pH 6. In an embodiment, the polypeptide having lysozyme activity has at least 75% of the antimicrobial activity of SEQ ID NO: 257 against *Clostridium perfringens* using the conditions 50% MHB, pH 6. In an embodiment, the polypeptide having lysozyme activity has at least 80% of the antimicrobial activity of SEQ ID NO: 257 against *Clostridium perfringens* using the conditions 50% MHB, pH 6.

In an embodiment, the polypeptide having lysozyme activity has at least 85% of the antimicrobial activity of SEQ ID NO: 257 against *Clostridium perfringens* using the conditions 50% MHB, pH 6. In an embodiment, the polypeptide having lysozyme activity has at least 90% of the antimicrobial activity of SEQ ID NO: 257 against *Clostridium perfringens* using the conditions 50% MHB, pH 6. In an embodiment, the polypeptide having lysozyme activity has at least 95% of the antimicrobial activity of SEQ ID NO: 257 against *Clostridium perfringens* using the conditions 50% MHB, pH 6. In an embodiment, the polypeptide having lysozyme activity has at least 100% of the antimicrobial activity of SEQ ID NO: 257 against *Clostridium perfringens* using the conditions 50% MHB, pH 6.

In another aspect, the invention relates to an animal feed or animal feed additive comprising one or more polypeptides having lysozyme activity, wherein the polypeptide having lysozyme activity comprises one or more GH24 catalytic domains and one or more lysozyme enhancing domains, wherein:
(b) the GH24 catalytic domain comprises one or more motif I: [TAS][VIL][GAC][YFI]GHX[CAYIV] (SEQ ID NO: 252), one or more motif II [LV][NDST]XN[QE][YFW][GASND]ALXS[WFLY]X[FY]N (SEQ ID NO: 253) and has at least 65%, e.g., at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to one or more of SEQ ID NO: 1 to 122; and
(b) the lysozyme enhancing domain comprises one or more motif I: [TAS][VIL][GAC][YFI]GHX[CAYIV] (SEQ ID NO: 252), one or more motif II [LV][NDST]XN[QE][YFW][GASND]ALXS[WFLY]X[FY]N (SEQ ID NO: 253) and has at least 65%, e.g., at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to one or more of SEQ ID NO: 123 to 251.

In an embodiment, the polypeptide having lysozyme activity is obtained or obtainable from the kingdom Fungi, preferably from the phylum Ascomycota.

In an embodiment, the polypeptide having lysozyme activity has at least 30% of the antimicrobial activity of SEQ ID NO: 257 against *Clostridium perfringens* using the conditions 50% MHB, pH 6. In an embodiment, the polypeptide having lysozyme activity has at least 50% of the antimicrobial activity of SEQ ID NO: 257 against *Clostridium perfringens* using the conditions 50% MHB, pH 6. In an embodiment, the polypeptide having lysozyme activity has at least 60% of the antimicrobial activity of SEQ ID NO: 257 against *Clostridium perfringens* using the conditions 50% MHB, pH 6.

In an embodiment, the polypeptide having lysozyme activity has at least 70% of the antimicrobial activity of SEQ ID NO: 257 against *Clostridium perfringens* using the conditions 50% MHB, pH 6. In an embodiment, the polypeptide having lysozyme activity has at least 75% of the antimicrobial activity of SEQ ID NO: 257 against *Clostridium perfringens* using the conditions 50% MHB, pH 6. In an embodiment, the polypeptide having lysozyme activity has at least 80% of the antimicrobial activity of SEQ ID NO: 257 against *Clostridium perfringens* using the conditions 50% MHB, pH 6.

In an embodiment, the polypeptide having lysozyme activity has at least 85% of the antimicrobial activity of SEQ ID NO: 257 against *Clostridium perfringens* using the conditions 50% MHB, pH 6. In an embodiment, the polypeptide having lysozyme activity has at least 90% of the antimicrobial activity of SEQ ID NO: 257 against *Clostridium perfringens* using the conditions 50% MHB, pH 6. In an embodiment, the polypeptide having lysozyme activity has at least 95% of the antimicrobial activity of SEQ ID NO: 257 against *Clostridium perfringens* using the conditions 50% MHB, pH 6. In an embodiment, the polypeptide having lysozyme activity has at least 100% of the antimicrobial activity of SEQ ID NO: 257 against *Clostridium perfringens* using the conditions 50% MHB, pH 6.

In a further embodiment, the invention relates to an animal feed or animal feed additive comprising one or more polypeptides having lysozyme activity, wherein the polypeptide having lysozyme activity has at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 257.

In a further embodiment, the invention relates to an animal feed or animal feed additive comprising one or more polypeptides having lysozyme activity, wherein the polypeptide having lysozyme activity has at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 257 and at least 70% of the antimicrobial activity of SEQ ID NO: 257 against *Clostridium perfringens* using the conditions 50% MHB, pH 6.

In a further embodiment, the invention relates to an animal feed or animal feed additive comprising one or more polypeptides having lysozyme activity, wherein the polypeptide having lysozyme activity has at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 257 and at least 80% of the antimicrobial activity of SEQ ID NO: 257 against *Clostridium perfringens* using the conditions 50% MHB, pH 6.

In a further embodiment, the invention relates to an animal feed or animal feed additive comprising one or more polypeptides having lysozyme activity, wherein the polypeptide having lysozyme activity has at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 257 and at least 90% of the antimicrobial activity of SEQ ID NO: 257 against *Clostridium perfringens* using the conditions 50% MHB, pH 6.

In a further embodiment, the invention relates to an animal feed or animal feed additive comprising one or more polypeptides having lysozyme activity, wherein the polypeptide having lysozyme activity has at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 257 and at least 95% of the antimicrobial activity of SEQ ID NO: 257 against *Clostridium perfringens* using the conditions 50% MHB, pH 6.

In a further embodiment, the invention relates to an animal feed or animal feed additive comprising one or more polypeptides having lysozyme activity, wherein the polypeptide having lysozyme activity has at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 257 and at least 100% of the antimicrobial activity of SEQ ID NO: 257 against *Clostridium perfringens* using the conditions 50% MHB, pH 6.

In a further embodiment, the animal feed or animal feed additive comprises one or more polypeptides having lysozyme activity, wherein the polypeptide having lysozyme activity differs by up to 49 amino acids, e.g., between 1 and 49 amino acids, such as 1-45, 1-40, 1-35, 1-30, 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 amino acids from SEQ ID NO: 257. In an embodiment, the polypeptide has at least 70%, e.g., at least 80%, at least 90%, at least 95% or at least 100% of the antimicrobial activity of SEQ ID NO: 257 against *Clostridium perfringens* using the conditions 50% MHB, pH 6.

In a preferred embodiment, the animal feed or animal feed additive comprises one or more polypeptides having lysozyme activity, wherein the polypeptide having lysozyme activity comprising or consists of the amino acid sequence of SEQ ID NO: 257 or an allelic variant thereof having lysozyme activity; comprises or consists of the amino acid sequence of SEQ ID NO: 257 and a N-terminal and/or C-terminal His-tag and/or HQ-tag; or is a fragment thereof having lysozyme activity wherein the fragment comprises at least 200 amino acids, such as at least 210 amino acids, at least 215 amino acids, at least 220 amino acids, at least 225 amino acids, at least 230 amino acids, at least 235 amino acids or at least 240 amino acids. In a preferred embodiment, the animal feed or animal feed additive comprises one or more polypeptides having lysozyme activity, wherein the polypeptide having lysozyme activity comprising or consists of amino acids 1 to 245 of SEQ ID NO: 257 and has lysozyme activity.

In a further embodiment, the invention relates to an animal feed or animal feed additive comprising one or more polypeptides having lysozyme activity, wherein the polypeptide having lysozyme activity has at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 264.

In a further embodiment, the invention relates to an animal feed or animal feed additive comprising one or more polypeptides having lysozyme activity, wherein the polypeptide having lysozyme activity has at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 264 and at least 70% of the antimicrobial activity of SEQ ID NO: 264 against *Clostridium perfringens* using the conditions 50% MHB, pH 6.

In a further embodiment, the invention relates to an animal feed or animal feed additive comprising one or more polypeptides having lysozyme activity, wherein the polypeptide having lysozyme activity has at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 264 and at least 80% of the antimicrobial activity of SEQ ID NO: 264 against *Clostridium perfringens* using the conditions 50% MHB, pH 6.

In a further embodiment, the invention relates to an animal feed or animal feed additive comprising one or more polypeptides having lysozyme activity, wherein the polypeptide having lysozyme activity has at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 264 and at least 90% of the antimicrobial activity of SEQ ID NO: 264 against *Clostridium perfringens* using the conditions 50% MHB, pH 6.

In a further embodiment, the invention relates to an animal feed or animal feed additive comprising one or more polypeptides having lysozyme activity, wherein the polypeptide having lysozyme activity has at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 264 and at least 95% of the antimicrobial activity of SEQ ID NO: 264 against *Clostridium perfringens* using the conditions 50% MHB, pH 6.

In a further embodiment, the invention relates to an animal feed or animal feed additive comprising one or more polypeptides having lysozyme activity, wherein the polypeptide having lysozyme activity has at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 264 and at least 100% of the antimicrobial activity of SEQ ID NO: 264 against *Clostridium perfringens* using the conditions 50% MHB, pH 6.

In a further embodiment, the animal feed or animal feed additive comprises one or more polypeptides having lysozyme activity, wherein the polypeptide having lysozyme activity differs by up to 49 amino acids, e.g., between 1 and 49 amino acids, such as 1-45, 1-40, 1-35, 1-30, 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 amino acids from SEQ ID NO: 264. In an embodiment, the polypeptide has at least 70%, e.g., at least 80%, at least 90%, at least 95% or at least 100% of the antimicrobial activity of SEQ ID NO: 264 against *Clostridium perfringens* using the conditions 50% MHB, pH 6.

In a preferred embodiment, the animal feed or animal feed additive comprises one or more polypeptides having lysozyme activity, wherein the polypeptide having lysozyme activity comprising or consists of the amino acid sequence of SEQ ID NO: 264 or an allelic variant thereof having lysozyme activity; comprises or consists of the amino acid sequence of SEQ ID NO: 264 and a N-terminal and/or C-terminal His-tag and/or HQ-tag; or is a fragment thereof having lysozyme activity wherein the fragment comprises at least 200 amino acids, such as at least 210 amino acids, at least 215 amino acids, at least 220 amino acids, at least 225 amino acids, at least 230 amino acids, at least 235 amino acids or at least 240 amino acids. In a preferred embodiment, the animal feed or animal feed additive comprises one or more polypeptides having lysozyme activity, wherein the polypeptide having lysozyme activity comprising or consists of amino acids 1 to 245 of SEQ ID NO: 264 and has lysozyme activity.

In a further embodiment, the invention relates to an animal feed or animal feed additive comprising one or more polypeptides having lysozyme activity, wherein the polypeptide having lysozyme activity has at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 267.

In a further embodiment, the invention relates to an animal feed or animal feed additive comprising one or more polypeptides having lysozyme activity, wherein the polypeptide having lysozyme activity has at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 267 and at least 70% of the antimicrobial activity of SEQ ID NO: 267 against *Clostridium perfringens* using the conditions 50% MHB, pH 6.

In a further embodiment, the invention relates to an animal feed or animal feed additive comprising one or more polypeptides having lysozyme activity, wherein the polypeptide having lysozyme activity has at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 267 and at least 80% of the antimicrobial activity of SEQ ID NO: 267 against *Clostridium perfringens* using the conditions 50% MHB, pH 6.

In a further embodiment, the invention relates to an animal feed or animal feed additive comprising one or more polypeptides having lysozyme activity, wherein the polypeptide having lysozyme activity has at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 267 and at least 90% of the antimicrobial activity of SEQ ID NO: 267 against *Clostridium perfringens* using the conditions 50% MHB, pH 6.

In a further embodiment, the invention relates to an animal feed or animal feed additive comprising one or more polypeptides having lysozyme activity, wherein the polypeptide having lysozyme activity has at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 267 and at least 95% of the antimicrobial activity of SEQ ID NO: 267 against *Clostridium perfringens* using the conditions 50% MHB, pH 6.

In a further embodiment, the invention relates to an animal feed or animal feed additive comprising one or more polypeptides having lysozyme activity, wherein the polypeptide having lysozyme activity has at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 267 and at least 100% of the antimicrobial activity of SEQ ID NO: 267 against *Clostridium perfringens* using the conditions 50% MHB, pH 6.

In a further embodiment, the animal feed or animal feed additive comprises one or more polypeptides having lysozyme activity, wherein the polypeptide having lysozyme activity differs by up to 49 amino acids, e.g., between 1 and 49 amino acids, such as 1-45, 1-40, 1-35, 1-30, 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 amino acids from SEQ ID NO: 267. In an embodiment, the polypeptide has at least 70%, e.g., at least 80%, at least 90%, at least 95% or at least 100% of the antimicrobial activity of SEQ ID NO: 267 against *Clostridium perfringens* using the conditions 50% MHB, pH 6.

In a preferred embodiment, the animal feed or animal feed additive comprises one or more polypeptides having lysozyme activity, wherein the polypeptide having lysozyme activity comprising or consists of the amino acid sequence of SEQ ID NO: 267 or an allelic variant thereof having lysozyme activity; comprises or consists of the amino acid sequence of SEQ ID NO: 267 and a N-terminal and/or C-terminal His-tag and/or HQ-tag; or is a fragment thereof having lysozyme activity wherein the fragment comprises at least 200 amino acids, such as at least 210 amino acids, at least 215 amino acids, at least 220 amino acids, at least 225 amino acids, at least 230 amino acids, at least 235 amino acids or at least 240 amino acids. In a preferred embodiment, the animal feed or animal feed additive comprises one or more polypeptides having lysozyme activity, wherein the polypeptide having lysozyme activity comprising or consists of amino acids 1 to 248 of SEQ ID NO: 267 and has lysozyme activity.

In a further embodiment, the invention relates to an animal feed or animal feed additive comprising one or more polypeptides having lysozyme activity, wherein the polypeptide having lysozyme activity has at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 291.

In a further embodiment, the invention relates to an animal feed or animal feed additive comprising one or more polypeptides having lysozyme activity, wherein the polypeptide having lysozyme activity has at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 291 and at least 70% of the antimicrobial activity of SEQ ID NO: 291 against *Clostridium perfringens* using the conditions 50% MHB, pH 6.

In a further embodiment, the invention relates to an animal feed or animal feed additive comprising one or more polypeptides having lysozyme activity, wherein the polypeptide having lysozyme activity has at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 291 and at least 80% of the antimicrobial activity of SEQ ID NO: 291 against *Clostridium perfringens* using the conditions 50% MHB, pH 6.

In a further embodiment, the invention relates to an animal feed or animal feed additive comprising one or more polypeptides having lysozyme activity, wherein the polypeptide having lysozyme activity has at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 291 and at least 90% of the antimicrobial activity of SEQ ID NO: 291 against *Clostridium perfringens* using the conditions 50% MHB, pH 6.

In a further embodiment, the invention relates to an animal feed or animal feed additive comprising one or more polypeptides having lysozyme activity, wherein the polypeptide having lysozyme activity has at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 291 and at least 95% of the antimicrobial activity of SEQ ID NO: 291 against *Clostridium perfringens* using the conditions 50% MHB, pH 6.

In a further embodiment, the invention relates to an animal feed or animal feed additive comprising one or more polypeptides having lysozyme activity, wherein the polypeptide having lysozyme activity has at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 291 and at least 100% of the antimicrobial activity of SEQ ID NO: 291 against *Clostridium perfringens* using the conditions 50% MHB, pH 6.

In a further embodiment, the animal feed or animal feed additive comprises one or more polypeptides having lysozyme activity, wherein the polypeptide having lysozyme activity differs by up to 49 amino acids, e.g., between 1 and 49 amino acids, such as 1-45, 1-40, 1-35, 1-30, 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 amino acids from SEQ ID NO: 291. In an embodiment, the polypeptide has at least 70%, e.g., at least 80%, at least 90%, at least 95% or at least 100% of the antimicrobial activity of SEQ ID NO: 291 against *Clostridium perfringens* using the conditions 50% MHB, pH 6.

In a preferred embodiment, the animal feed or animal feed additive comprises one or more polypeptides having lysozyme activity, wherein the polypeptide having lysozyme activity comprising or consists of the amino acid sequence of SEQ ID NO: 291 or an allelic variant thereof having lysozyme activity; comprises or consists of the amino acid sequence of SEQ ID NO: 291 and a N-terminal and/or C-terminal His-tag and/or HQ-tag; or is a fragment thereof having lysozyme activity wherein the fragment comprises at least 200 amino acids, such as at least 210 amino acids, at least 215 amino acids, at least 220 amino acids, at least 225 amino acids, at least 230 amino acids, at least 235 amino acids or at least 240 amino acids. In a preferred embodiment, the animal feed or animal feed additive comprises one or more polypeptides having lysozyme activity, wherein the polypeptide having lysozyme activity comprising or consists of amino acids 1 to 245 of SEQ ID NO: 291 and has lysozyme activity.

In a further embodiment, the invention relates to an animal feed or animal feed additive comprising one or more polypeptides having lysozyme activity, wherein the polypeptide having lysozyme activity has at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 294.

In a further embodiment, the invention relates to an animal feed or animal feed additive comprising one or more polypeptides having lysozyme activity, wherein the polypeptide having lysozyme activity has at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 294 and at least 70% of the antimicrobial activity of SEQ ID NO: 294 against *Clostridium perfringens* using the conditions 50% MHB, pH 6.

In a further embodiment, the invention relates to an animal feed or animal feed additive comprising one or more polypeptides having lysozyme activity, wherein the polypeptide having lysozyme activity has at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 294 and at least 80% of the antimicrobial activity of SEQ ID NO: 294 against *Clostridium perfringens* using the conditions 50% MHB, pH 6.

In a further embodiment, the invention relates to an animal feed or animal feed additive comprising one or more polypeptides having lysozyme activity, wherein the polypeptide having lysozyme activity has at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 294 and at least 90% of the antimicrobial activity of SEQ ID NO: 294 against *Clostridium perfringens* using the conditions 50% MHB, pH 6.

In a further embodiment, the invention relates to an animal feed or animal feed additive comprising one or more polypeptides having lysozyme activity, wherein the polypeptide having lysozyme activity has at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 294 and at least 95% of the antimicrobial activity of SEQ ID NO: 294 against *Clostridium perfringens* using the conditions 50% MHB, pH 6.

In a further embodiment, the invention relates to an animal feed or animal feed additive comprising one or more polypeptides having lysozyme activity, wherein the polypeptide having lysozyme activity has at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 294 and at least 100% of the antimicrobial activity of SEQ ID NO: 294 against *Clostridium perfringens* using the conditions 50% MHB, pH 6.

In a further embodiment, the animal feed or animal feed additive comprises one or more polypeptides having lysozyme activity, wherein the polypeptide having lysozyme activity differs by up to 49 amino acids, e.g., between 1 and 49 amino acids, such as 1-45, 1-40, 1-35, 1-30, 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 amino acids from SEQ ID NO: 294. In an embodiment, the polypeptide has at least 70%, e.g., at least 80%, at least 90%, at least 95% or at least 100% of the antimicrobial activity of SEQ ID NO: 294 against *Clostridium perfringens* using the conditions 50% MHB, pH 6.

In a preferred embodiment, the animal feed or animal feed additive comprises one or more polypeptides having lysozyme activity, wherein the polypeptide having lysozyme activity comprising or consists of the amino acid sequence of SEQ ID NO: 294 or an allelic variant thereof having lysozyme activity; comprises or consists of the amino acid sequence of SEQ ID NO: 294 and a N-terminal and/or C-terminal His-tag and/or HQ-tag; or is a fragment thereof having lysozyme activity wherein the fragment comprises at least 200 amino acids, such as at least 210 amino acids, at least 215 amino acids, at least 220 amino acids, at least 225 amino acids, at least 230 amino acids, at least 235 amino acids or at least 240 amino acids. In a preferred embodiment, the animal feed or animal feed additive comprises one or more polypeptides having lysozyme activity, wherein the polypeptide having lysozyme activity comprising or consists of amino acids 1 to 245 of SEQ ID NO: 294 and has lysozyme activity.

In a further embodiment, the invention relates to an animal feed or animal feed additive comprising one or more polypeptides having lysozyme activity, wherein the polypeptide having lysozyme activity has at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 297.

In a further embodiment, the invention relates to an animal feed or animal feed additive comprising one or more polypeptides having lysozyme activity, wherein the polypeptide having lysozyme activity has at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 297 and at least 70% of the antimicrobial activity of SEQ ID NO: 297 against *Clostridium perfringens* using the conditions 50% MHB, pH 6.

In a further embodiment, the invention relates to an animal feed or animal feed additive comprising one or more polypeptides having lysozyme activity, wherein the polypeptide having lysozyme activity has at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 297 and at least 80% of the antimicrobial activity of SEQ ID NO: 297 against *Clostridium perfringens* using the conditions 50% MHB, pH 6.

In a further embodiment, the invention relates to an animal feed or animal feed additive comprising one or more polypeptides having lysozyme activity, wherein the polypeptide having lysozyme activity has at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 297 and at least 90% of the antimicrobial activity of SEQ ID NO: 297 against *Clostridium perfringens* using the conditions 50% MHB, pH 6.

In a further embodiment, the invention relates to an animal feed or animal feed additive comprising one or more polypeptides having lysozyme activity, wherein the polypeptide having lysozyme activity has at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 297 and at least 95% of the antimicrobial activity of SEQ ID NO: 297 against *Clostridium perfringens* using the conditions 50% MHB, pH 6.

In a further embodiment, the invention relates to an animal feed or animal feed additive comprising one or more polypeptides having lysozyme activity, wherein the polypeptide having lysozyme activity has at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 297 and at least 100% of the antimicrobial activity of SEQ ID NO: 297 against *Clostridium perfringens* using the conditions 50% MHB, pH 6.

In a further embodiment, the animal feed or animal feed additive comprises one or more polypeptides having lysozyme activity, wherein the polypeptide having lysozyme activity differs by up to 49 amino acids, e.g., between 1 and 49 amino acids, such as 1-45, 1-40, 1-35, 1-30, 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 amino acids from SEQ ID NO: 297. In an embodiment, the polypeptide has at least 70%, e.g., at least 80%, at least 90%, at least 95% or at least 100% of the antimicrobial activity of SEQ ID NO: 297 against *Clostridium perfringens* using the conditions 50% MHB, pH 6.

In a preferred embodiment, the animal feed or animal feed additive comprises one or more polypeptides having lysozyme activity, wherein the polypeptide having lysozyme activity comprising or consists of the amino acid sequence of SEQ ID NO: 297 or an allelic variant thereof having lysozyme activity; comprises or consists of the amino acid sequence of SEQ ID NO: 297 and a N-terminal and/or C-terminal His-tag and/or HQ-tag; or is a fragment thereof having lysozyme activity wherein the fragment comprises at least 200 amino acids, such as at least 210 amino acids, at least 215 amino acids, at least 220 amino acids, at least 225 amino acids, at least 230 amino acids, at least 235 amino acids or at least 240 amino acids. In a preferred embodiment, the animal feed or animal feed additive comprises one or more polypeptides having lysozyme activity, wherein the polypeptide having lysozyme activity comprising or consists of amino acids 1 to 249 of SEQ ID NO: 297 and has lysozyme activity.

In a further embodiment, the invention relates to an animal feed or animal feed additive comprising one or more polypeptides having lysozyme activity, wherein the polypeptide having lysozyme activity has at least 82%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 300.

In a further embodiment, the invention relates to an animal feed or animal feed additive comprising one or more polypeptides having lysozyme activity, wherein the polypeptide having lysozyme activity has at least 82%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 300 and at least 70% of the antimicrobial activity of SEQ ID NO: 300 against *Clostridium perfringens* using the conditions 50% MHB, pH 6.

In a further embodiment, the invention relates to an animal feed or animal feed additive comprising one or more polypeptides having lysozyme activity, wherein the polypeptide having lysozyme activity has at least 82%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 300 and at least 80% of the antimicrobial activity of SEQ ID NO: 300 against *Clostridium perfringens* using the conditions 50% MHB, pH 6.

In a further embodiment, the invention relates to an animal feed or animal feed additive comprising one or more polypeptides having lysozyme activity, wherein the polypeptide having lysozyme activity has at least 82%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 300 and at least 90% of the antimicrobial activity of SEQ ID NO: 300 against *Clostridium perfringens* using the conditions 50% MHB, pH 6.

In a further embodiment, the invention relates to an animal feed or animal feed additive comprising one or more polypeptides having lysozyme activity, wherein the polypeptide having lysozyme activity has at least 82%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 300 and at least 95% of the antimicrobial activity of SEQ ID NO: 300 against *Clostridium perfringens* using the conditions 50% MHB, pH 6.

In a further embodiment, the invention relates to an animal feed or animal feed additive comprising one or more polypeptides having lysozyme activity, wherein the polypeptide having lysozyme activity has at least 82%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 300 and at least 100% of the antimicrobial activity of SEQ ID NO: 300 against *Clostridium perfringens* using the conditions 50% MHB, pH 6.

In a further embodiment, the animal feed or animal feed additive comprises one or more polypeptides having lysozyme activity, wherein the polypeptide having lysozyme activity differs by up to 49 amino acids, e.g., between 1 and 49 amino acids, such as 1-45, 1-40, 1-35, 1-30, 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 amino acids from SEQ ID NO: 300. In an embodiment, the polypeptide has at least 70%, e.g., at least 80%, at least 90%, at least 95% or at least 100% of the antimicrobial activity of SEQ ID NO: 300 against *Clostridium perfringens* using the conditions 50% MHB, pH 6.

In a preferred embodiment, the animal feed or animal feed additive comprises one or more polypeptides having lysozyme activity, wherein the polypeptide having lysozyme activity comprising or consists of the amino acid sequence of SEQ ID NO: 300 or an allelic variant thereof having lysozyme activity; comprises or consists of the amino acid sequence of SEQ ID NO: 300 and a N-terminal and/or C-terminal His-tag and/or HQ-tag; or is a fragment thereof having lysozyme activity wherein the fragment comprises at least 200 amino acids, such as at least 210 amino acids, at least 215 amino acids, at least 220 amino acids, at least 225 amino acids, at least 230 amino acids, at least 235 amino acids or at least 240 amino acids. In a preferred embodiment, the animal feed or animal feed additive comprises one or more polypeptides having lysozyme activity, wherein the polypeptide having lysozyme activity comprising or consists of amino acids 1 to 247 of SEQ ID NO: 300 and has lysozyme activity.

In a further embodiment, the invention relates to an animal feed or animal feed additive comprising one or more polypeptides having lysozyme activity, wherein the polypeptide having lysozyme activity has at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 303.

In a further embodiment, the invention relates to an animal feed or animal feed additive comprising one or more polypeptides having lysozyme activity, wherein the polypeptide having lysozyme activity has at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 303 and at least 70% of the antimicrobial activity of SEQ ID NO: 303 against *Clostridium perfringens* using the conditions 50% MHB, pH 6.

In a further embodiment, the invention relates to an animal feed or animal feed additive comprising one or more polypeptides having lysozyme activity, wherein the polypeptide having lysozyme activity has at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 303 and at least 80% of the antimicrobial activity of SEQ ID NO: 303 against *Clostridium perfringens* using the conditions 50% MHB, pH 6.

In a further embodiment, the invention relates to an animal feed or animal feed additive comprising one or more polypeptides having lysozyme activity, wherein the polypeptide having lysozyme activity has at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 303 and at least 90% of the antimicrobial activity of SEQ ID NO: 303 against *Clostridium perfringens* using the conditions 50% MHB, pH 6.

In a further embodiment, the invention relates to an animal feed or animal feed additive comprising one or more polypeptides having lysozyme activity, wherein the polypeptide having lysozyme activity has at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 303 and at least 95% of the antimicrobial activity of SEQ ID NO: 303 against *Clostridium perfringens* using the conditions 50% MHB, pH 6.

In a further embodiment, the invention relates to an animal feed or animal feed additive comprising one or more polypeptides having lysozyme activity, wherein the polypeptide having lysozyme activity has at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 303 and at least 100% of the antimicrobial activity of SEQ ID NO: 303 against *Clostridium perfringens* using the conditions 50% MHB, pH 6.

In a further embodiment, the animal feed or animal feed additive comprises one or more polypeptides having lysozyme activity, wherein the polypeptide having lysozyme activity differs by up to 49 amino acids, e.g., between 1 and 49 amino acids, such as 1-45, 1-40, 1-35, 1-30, 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 amino acids from SEQ ID NO: 303. In an embodiment, the polypeptide has at least 70%, e.g., at least 80%, at least 90%, at least 95% or at least 100% of the antimicrobial activity of SEQ ID NO: 303 against *Clostridium perfringens* using the conditions 50% MHB, pH 6.

In a preferred embodiment, the animal feed or animal feed additive comprises one or more polypeptides having lysozyme activity, wherein the polypeptide having lysozyme activity comprising or consists of the amino acid sequence of SEQ ID NO: 303 or an allelic variant thereof having lysozyme activity; comprises or consists of the amino acid sequence of SEQ ID NO: 303 and a N-terminal and/or C-terminal His-tag and/or HQ-tag; or is a fragment thereof having lysozyme activity wherein the fragment comprises at least 200 amino acids, such as at least 210 amino acids, at least 215 amino acids, at least 220 amino acids, at least 225 amino acids, at least 230 amino acids, at least 235 amino acids or at least 240 amino acids. In a preferred embodiment, the animal feed or animal feed additive comprises one or more polypeptides having lysozyme activity, wherein the polypeptide having lysozyme activity comprising or consists of amino acids 1 to 250 of SEQ ID NO: 303 and has lysozyme activity.

In a further embodiment, the invention relates to an animal feed or animal feed additive comprising one or more polypeptides having lysozyme activity, wherein the polypeptide having lysozyme activity has at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 306.

In a further embodiment, the invention relates to an animal feed or animal feed additive comprising one or more polypeptides having lysozyme activity, wherein the polypeptide having lysozyme activity has at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 306 and at least 70% of the antimicrobial activity of SEQ ID NO: 306 against *Clostridium perfringens* using the conditions 50% MHB, pH 6.

In a further embodiment, the invention relates to an animal feed or animal feed additive comprising one or more polypeptides having lysozyme activity, wherein the polypeptide having lysozyme activity has at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 306 and at least 80% of the antimicrobial activity of SEQ ID NO: 306 against *Clostridium perfringens* using the conditions 50% MHB, pH 6.

In a further embodiment, the invention relates to an animal feed or animal feed additive comprising one or more polypeptides having lysozyme activity, wherein the polypeptide having lysozyme activity has at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 306 and at least 90% of the antimicrobial activity of SEQ ID NO: 306 against *Clostridium perfringens* using the conditions 50% MHB, pH 6.

In a further embodiment, the invention relates to an animal feed or animal feed additive comprising one or more polypeptides having lysozyme activity, wherein the polypeptide having lysozyme activity has at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 306 and at least 95% of the antimicrobial activity of SEQ ID NO: 306 against *Clostridium perfringens* using the conditions 50% MHB, pH 6.

In a further embodiment, the invention relates to an animal feed or animal feed additive comprising one or more polypeptides having lysozyme activity, wherein the polypeptide having lysozyme activity has at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 306 and at least 100% of the antimicrobial activity of SEQ ID NO: 306 against *Clostridium perfringens* using the conditions 50% MHB, pH 6.

In a further embodiment, the animal feed or animal feed additive comprises one or more polypeptides having lysozyme activity, wherein the polypeptide having lysozyme activity differs by up to 49 amino acids, e.g., between 1 and 49 amino acids, such as 1-45, 1-40, 1-35, 1-30, 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 amino acids from SEQ ID NO: 306. In an embodiment, the polypeptide has at least 70%, e.g., at least 80%, at least 90%, at least 95% or at least 100% of the antimicrobial activity of SEQ ID NO: 306 against *Clostridium perfringens* using the conditions 50% MHB, pH 6.

In a preferred embodiment, the animal feed or animal feed additive comprises one or more polypeptides having lysozyme activity, wherein the polypeptide having lysozyme activity comprising or consists of the amino acid sequence of SEQ ID NO: 306 or an allelic variant thereof having lysozyme activity; comprises or consists of the amino acid sequence of SEQ ID NO: 306 and a N-terminal and/or C-terminal His-tag and/or HQ-tag; or is a fragment thereof having lysozyme activity wherein the fragment comprises at least 200 amino acids, such as at least 210 amino acids, at least 215 amino acids, at least 220 amino acids, at least 225 amino acids, at least 230 amino acids, at least 235 amino acids or at least 240 amino acids. In a preferred embodiment, the animal feed or animal feed additive comprises one or more polypeptides having lysozyme activity, wherein the polypeptide having lysozyme activity comprising or consists of amino acids 1 to 240 of SEQ ID NO: 306 and has lysozyme activity.

Novel Lysozymes of the Invention

The invention further relates to polypeptides having a sequence identity to the mature polypeptide of SEQ ID NO: 256 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which have lysozyme activity. In one aspect, the polypeptides differ by up to 49 amino acids, e.g., between 1 and 49 amino acids, such as 1-45, 1-40, 1-35, 1-30, 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 amino acids from the mature polypeptide of SEQ ID NO: 256. In an embodiment, the polypeptide has been isolated. In an embodiment, the polypeptide has at least at least 70%, e.g., at least 80%, at least 90%, at least 95% or at least 100% of the lysozyme activity of the mature polypeptide of SEQ ID NO: 256.

A polypeptide of the present invention preferably comprises or consists of the amino acid sequence of SEQ ID NO: 256 or an allelic variant thereof; comprises or consists of the amino acid sequence of SEQ ID NO: 256 and a N-terminal and/or C-terminal His-tag and/or HQ-tag; or is a fragment thereof having lysozyme activity wherein the fragment comprises at least 200 amino acids, such as at least 210 amino acids, at least 215 amino acids, at least 220 amino acids, at least 225 amino acids, at least 230 amino acids, at least 235 amino acids or at least 240 amino acids. In another aspect, the polypeptide comprises or consists of the mature polypeptide of SEQ ID NO: 256. In another aspect, the polypeptide comprises or consists of amino acids 1 to 245 of SEQ ID NO: 256.

The present invention further relates to polypeptides having a sequence identity to SEQ ID NO: 257 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, and wherein the polypeptide has at least at least 70% of the lysozyme activity of SEQ ID NO: 257.

In a particular embodiment, the invention relates to polypeptides having a sequence identity to SEQ ID NO: 257 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, and wherein the polypeptide has at least at least 80% of the lysozyme activity of SEQ ID NO: 257.

In a particular embodiment, the invention relates to polypeptides having a sequence identity to SEQ ID NO: 257 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, and wherein the polypeptide has at least at least 90% of the lysozyme activity of SEQ ID NO: 257.

In a particular embodiment, the invention relates to polypeptides having a sequence identity to SEQ ID NO: 257 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, and wherein the polypeptide has at least at least 95% of the lysozyme activity of SEQ ID NO: 257.

In a particular embodiment, the invention relates to polypeptides having a sequence identity to SEQ ID NO: 257 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, and wherein the polypeptide has at least at least 100% of the lysozyme activity of SEQ ID NO: 257.

In one aspect, the polypeptides differ by up to 49 amino acids, e.g., between 1 and 49 amino acids, such as 1-45, 1-40, 1-35, 1-30, 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 amino acids from SEQ ID NO: 257. In an embodiment, the polypeptide has at least at least 70%, e.g., at least 80%, at least 90%, at least 95% or at least 100% of the lysozyme activity of SEQ ID NO: 257.

A polypeptide of the present invention preferably comprises or consists of the amino acid sequence of SEQ ID NO: 257 or an allelic variant thereof having lysozyme activity; comprises or consists of the amino acid sequence of SEQ ID NO: 257 and a N-terminal and/or C-terminal His-tag and/or HQ-tag; or is a fragment thereof having lysozyme activity wherein the fragment comprises at least 200 amino acids, such as at least 210 amino acids, at least 215 amino acids, at least 220 amino acids, at least 225 amino acids, at least 230 amino acids, at least 235 amino acids or at least 240 amino acids. In another aspect, the polypeptide comprises or consists of amino acids 1 to 245 of SEQ ID NO: 257 and has lysozyme activity.

In another aspect, the present invention relates to a polypeptide having lysozyme activity encoded by a polynucleotide that hybridizes under medium-high stringency conditions, high stringency conditions, or very high stringency conditions with (i) the mature polypeptide coding sequence of SEQ ID NO: 255, (ii) the cDNA sequence thereof; or (iii) the full-length complement of (i) or (ii) (Sambrook et al., 1989, *Molecular Cloning, A Laboratory Manual*, 2d edition, Cold Spring Harbor, New York). In an embodiment, the polypeptide has been isolated.

In another embodiment, the present invention relates to a polypeptide having lysozyme activity encoded by a polynucleotide having a sequence identity to the mature polypeptide coding sequence of SEQ ID NO: 255 or the cDNA sequence thereof of at least 80%, e.g., at least 85%, at least 90%, at least 91%, at least 92%, at least 93%, at least 94%, at least 95%, at least 96%, at least 97%, at least 98%, at least 99%, or 100%. In a further embodiment, the polypeptide has been isolated.

In another embodiment, the present invention relates to variants of the mature polypeptide of SEQ ID NO: 257 comprising a substitution, and/or deletion, and/or insertion at one or more (e.g., several) positions. In an embodiment, the number of positions comprising one or more amino acid substitutions, and/or one or more amino acid deletions, and/or one or more amino acid insertions or any combination thereof in SEQ ID NO: 257 is not more than 49, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49. In another embodiment, the number of positions comprising one or more amino acid substitutions, and/or one or more amino acid deletions, and/or one or more amino acid insertions or any combination thereof in SEQ ID NO: 257 is between 1 and 45, such as 1-40, 1-35, 1-30, 1-25, 1-20, 1-15, 1-10 or 1-5 positions. In an embodiment, the number of positions comprising one or more amino acid substitutions, and/or one or more amino acid deletions, and/or one or more amino acid insertions or any combination thereof in SEQ ID NO: 257 is not more than 10, e.g., 1, 2, 3, 4, 5, 6, 7, 8, 9 or 10. In another embodiment, the number of substitutions and/or deletions and/or insertions in SEQ ID NO: 257 is not more than 10, e.g., 1, 2, 3, 4, 5, 6, 7, 8, 9 or 10. In a further embodiment, the number of substitutions in SEQ ID NO: 257 is not more than 10, e.g., 1, 2, 3, 4, 5, 6, 7, 8, 9 or 10. In a further embodiment, the number of conservative substitutions in SEQ ID NO: 257 is not more than 10, e.g., 1, 2, 3, 4, 5, 6, 7, 8, 9 or 10. In an embodiment, the variant has at least at least 70%, e.g., at least 80%, at least 90%, at least 95% or at least 100% of the lysozyme activity of SEQ ID NO: 257.

The invention further relates to polypeptides having a sequence identity to the mature polypeptide of SEQ ID NO: 266 of at least 95%, e.g., at least 96%, at least 97%, at least 98%, at least 99%, or 100%, which have lysozyme activity. In one aspect, the polypeptides differ by up to 12 amino acids, e.g., between 1 and 12 amino acids, such as 1-10 or 1-5 amino acids, or 1, 2, 3, 4, 5, 6, 7, 8, 9, 10, 11 or 12 amino acids from the mature polypeptide of SEQ ID NO: 266. In an embodiment, the polypeptide has been isolated. In an embodiment, the polypeptide has at least at least 70%, e.g., at least 80%, at least 90%, at least 95% or at least 100% of the lysozyme activity of the mature polypeptide of SEQ ID NO: 266.

A polypeptide of the present invention preferably comprises or consists of the amino acid sequence of SEQ ID NO: 266 or an allelic variant thereof; comprises or consists of the amino acid sequence of SEQ ID NO: 266 and a N-terminal and/or C-terminal His-tag and/or HQ-tag; or is a fragment thereof having lysozyme activity wherein the fragment comprises at least 200 amino acids, such as at least 210 amino acids, at least 215 amino acids, at least 220 amino acids, at least 225 amino acids, at least 230 amino acids, at least 235 amino acids, at least 240 amino acids or at least 245 amino acids. In another aspect, the polypeptide comprises or consists of the mature polypeptide of SEQ ID NO: 266. In another aspect, the polypeptide comprises or consists of amino acids 1 to 248 of SEQ ID NO: 266.

The present invention further relates to polypeptides having a sequence identity to SEQ ID NO: 267 of at least 95%, e.g., at least 96%, at least 97%, at least 98%, at least 99%, or 100%, and wherein the polypeptide has at least at least 70% of the lysozyme activity of SEQ ID NO: 267.

The present invention further relates to polypeptides having a sequence identity to SEQ ID NO: 267 of at least 95%, e.g., at least 96%, at least 97%, at least 98%, at least 99%, or 100%, and wherein the polypeptide has at least at least 80% of the lysozyme activity of SEQ ID NO: 267.

The present invention further relates to polypeptides having a sequence identity to SEQ ID NO: 267 of at least 95%, e.g., at least 96%, at least 97%, at least 98%, at least 99%, or 100%, and wherein the polypeptide has at least at least 90% of the lysozyme activity of SEQ ID NO: 267.

The present invention further relates to polypeptides having a sequence identity to SEQ ID NO: 267 of at least 95%, e.g., at least 96%, at least 97%, at least 98%, at least 99%, or 100%, and wherein the polypeptide has at least at least 95% of the lysozyme activity of SEQ ID NO: 267.

The present invention further relates to polypeptides having a sequence identity to SEQ ID NO: 267 of at least 95%, e.g., at least 96%, at least 97%, at least 98%, at least 99%, or 100%, and wherein the polypeptide has at least at least 100% of the lysozyme activity of SEQ ID NO: 267.

In one aspect, the polypeptides differ by up to 49 amino acids, e.g., between 1 and 12 amino acids, such as 1-10 or 1-5 amino acids, or 1, 2, 3, 4, 5, 6, 7, 8, 9, 10, 11 or 12 amino acids from SEQ ID NO: 267. In an embodiment, the polypeptide has at least at least 70%, e.g., at least 80%, at least 90%, at least 95% or at least 100% of the lysozyme activity of SEQ ID NO: 267.

A polypeptide of the present invention preferably comprises or consists of the amino acid sequence of SEQ ID NO: 267 or an allelic variant thereof having lysozyme activity; comprises or consists of the amino acid sequence of SEQ ID NO: 267 and a N-terminal and/or C-terminal His-tag and/or HQ-tag; or is a fragment thereof having lysozyme activity wherein the fragment comprises at least 200 amino acids, such as at least 210 amino acids, at least 215 amino acids, at least 220 amino acids, at least 225 amino acids, at least 230 amino acids, at least 235 amino acids, at least 240 amino acids or at least 245 amino acids. In another aspect, the polypeptide comprises or consists of amino acids 1 to 248 of SEQ ID NO: 267 and has lysozyme activity.

In another aspect, the present invention relates to a polypeptide having lysozyme activity encoded by a polynucleotide that hybridizes under very high stringency conditions with (i) the mature polypeptide coding sequence of SEQ ID NO: 265, (ii) the cDNA sequence thereof; or (iii) the full-length complement of (i) or (ii) (Sambrook et al., 1989, *Molecular Cloning, A Laboratory Manual*, 2d edition, Cold Spring Harbor, New York). In an embodiment, the polypeptide has been isolated.

In another embodiment, the present invention relates to a polypeptide having lysozyme activity encoded by a polynucleotide having a sequence identity to the mature polypeptide coding sequence of SEQ ID NO: 265 or the cDNA sequence thereof of at least 95%, e.g., at least 96%, at least 97%, at least 98%, at least 99%, or 100%. In a further embodiment, the polypeptide has been isolated.

In another embodiment, the present invention relates to variants of the mature polypeptide of SEQ ID NO: 267 comprising a substitution, and/or deletion, and/or insertion at one or more (e.g., several) positions. In an embodiment, the number of positions comprising one or more amino acid substitutions, and/or one or more amino acid deletions, and/or one or more amino acid insertions or any combination thereof in SEQ ID NO: 267 is not more than 12, e.g., 1, 2, 3, 4, 5, 6, 7, 8, 9, 10, 11 or 12. In another embodiment, the number of positions comprising one or more amino acid substitutions, and/or one or more amino acid deletions, and/or one or more amino acid insertions or any combination thereof in SEQ ID NO: 267 is between 1 and 12, such as 1-10 or 1-5 positions. In an embodiment, the number of positions comprising one or more amino acid substitutions, and/or one or more amino acid deletions, and/or one or more amino acid insertions or any combination thereof in SEQ ID NO: 267 is not more than 10, e.g., 1, 2, 3, 4, 5, 6, 7, 8, 9 or 10. In another embodiment, the number of substitutions and/or deletions and/or insertions in SEQ ID NO: 267 is not more than 10, e.g., 1, 2, 3, 4, 5, 6, 7, 8, 9 or 10. In a further embodiment, the number of substitutions in SEQ ID NO: 267 is not more than 10, e.g., 1, 2, 3, 4, 5, 6, 7, 8, 9 or 10. In a further embodiment, the number of conservative substitutions in SEQ ID NO: 267 is not more than 10, e.g., 1, 2, 3, 4, 5, 6, 7, 8, 9 or 10. In an embodiment, the variant has at least at least 70%, e.g., at least 80%, at least 90%, at least 95% or at least 100% of the lysozyme activity of SEQ ID NO: 267.

The amino acid changes in the mature polypeptide of SEQ ID NO: 256, SEQ ID NO: 257, the mature polypeptide of SEQ ID NO: 266 or the mature polypeptide of SEQ ID NO: 267 described above may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, *In, The Proteins*, Academic Press, New York. Common substitutions are Ala/Ser, Val/Ile, Asp/Gu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for lysozyme activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labelling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be a hybrid polypeptide in which a region of one polypeptide is fused at the N-terminus or the C-terminus of a region of another polypeptide.

The polypeptide may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

The invention further relates to polypeptides having a sequence identity to the mature polypeptide of SEQ ID NO: 288 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which have lysozyme activity. In one aspect, the polypeptides differ by up to 49 amino acids, e.g., between 1 and 49 amino acids, such as 1-45, 1-40, 1-35, 1-30, 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 amino acids from the mature polypeptide of SEQ ID NO: 288. In an embodiment, the polypeptide has been isolated. In an embodiment, the polypeptide has at least at least 70%, e.g., at least 80%, at least 90%, at least 95% or at least 100% of the lysozyme activity of the mature polypeptide of SEQ ID NO: 288.

A polypeptide of the present invention preferably comprises or consists of the amino acid sequence of SEQ ID NO: 288 or an allelic variant thereof; comprises or consists of the amino acid sequence of SEQ ID NO: 288 and a N-terminal and/or C-terminal His-tag and/or HQ-tag; or is a fragment thereof having lysozyme activity wherein the fragment comprises at least 200 amino acids, such as at least 210 amino acids, at least 215 amino acids, at least 220 amino acids, at least 225 amino acids, at least 230 amino acids, at least 235 amino acids or at least 240 amino acids. In another aspect, the polypeptide comprises or consists of the mature polypeptide of SEQ ID NO: 288. In another aspect, the polypeptide comprises or consists of amino acids 1 to 245 of SEQ ID NO: 288.

The present invention further relates to polypeptides having a sequence identity to SEQ ID NO: 291 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, and wherein the polypeptide has at least at least 70% of the lysozyme activity of SEQ ID NO: 291.

In a particular embodiment, the invention relates to polypeptides having a sequence identity to SEQ ID NO: 291 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, and wherein the polypeptide has at least at least 80% of the lysozyme activity of SEQ ID NO: 291.

In a particular embodiment, the invention relates to polypeptides having a sequence identity to SEQ ID NO: 291 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, and wherein the polypeptide has at least at least 90% of the lysozyme activity of SEQ ID NO: 291.

In a particular embodiment, the invention relates to polypeptides having a sequence identity to SEQ ID NO: 291 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, and wherein the polypeptide has at least at least 95% of the lysozyme activity of SEQ ID NO: 291.

In a particular embodiment, the invention relates to polypeptides having a sequence identity to SEQ ID NO: 291 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, and wherein the polypeptide has at least at least 100% of the lysozyme activity of SEQ ID NO: 291.

In one aspect, the polypeptides differ by up to 49 amino acids, e.g., between 1 and 49 amino acids, such as 1-45, 1-40, 1-35, 1-30, 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 amino acids from SEQ ID NO: 291. In an embodiment, the polypeptide has at least at least 70%, e.g., at least 80%, at least 90%, at least 95% or at least 100% of the lysozyme activity of SEQ ID NO: 291.

A polypeptide of the present invention preferably comprises or consists of the amino acid sequence of SEQ ID NO: 291 or an allelic variant thereof having lysozyme activity; comprises or consists of the amino acid sequence of SEQ ID NO: 291 and a N-terminal and/or C-terminal His-tag and/or HQ-tag; or is a fragment thereof having lysozyme activity wherein the fragment comprises at least 200 amino acids, such as at least 210 amino acids, at least 215 amino acids, at least 220 amino acids, at least 225 amino acids, at least 230 amino acids, at least 235 amino acids or at least 240 amino acids. In another aspect, the polypeptide comprises or consists of amino acids 1 to 245 of SEQ ID NO: 291 and has lysozyme activity.

In another aspect, the present invention relates to a polypeptide having lysozyme activity encoded by a polynucleotide that hybridizes under medium-high stringency conditions, high stringency conditions, or very high stringency conditions with (i) the mature polypeptide coding sequence of SEQ ID NO: 287, (ii) the cDNA sequence thereof; or (iii) the full-length complement of (i) or (ii) (Sambrook et al., 1989, *Molecular Cloning, A Laboratory Manual*, 2d edition, Cold Spring Harbor, New York). In an embodiment, the polypeptide has been isolated.

In another embodiment, the present invention relates to a polypeptide having lysozyme activity encoded by a polynucleotide having a sequence identity to the mature polypeptide coding sequence of SEQ ID NO: 287 or the cDNA sequence thereof of at least 80%, e.g., at least 85%, at least 90%, at least 91%, at least 92%, at least 93%, at least 94%, at least 95%, at least 96%, at least 97%, at least 98%, at least 99%, or 100%. In a further embodiment, the polypeptide has been isolated.

In another embodiment, the present invention relates to variants of the mature polypeptide of SEQ ID NO: 291 comprising a substitution, and/or deletion, and/or insertion at one or more (e.g., several) positions. In an embodiment, the number of positions comprising one or more amino acid substitutions, and/or one or more amino acid deletions, and/or one or more amino acid insertions or any combination thereof in SEQ ID NO: 291 is not more than 49, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49. In another embodiment, the number of positions comprising one or more amino acid substitutions, and/or one or more amino acid deletions, and/or one or more amino acid insertions or any combination thereof in SEQ ID NO: 291 is between 1 and 45, such as 1-40, 1-35, 1-30, 1-25, 1-20, 1-15, 1-10 or 1-5 positions. In an embodiment, the number of positions comprising one or more amino acid substitutions, and/or one or more amino acid deletions, and/or one or more amino acid insertions or any combination thereof in SEQ ID NO: 291 is not more than 10, e.g., 1, 2, 3, 4, 5, 6, 7, 8, 9 or 10. In another embodiment, the number of substitutions and/or deletions and/or insertions in SEQ ID NO: 291 is not more than 10, e.g., 1, 2, 3, 4, 5, 6, 7, 8, 9 or 10. In a further embodiment, the number of substitutions in SEQ ID NO: 291 is not more than 10, e.g., 1, 2, 3, 4, 5, 6, 7, 8, 9 or 10. In a further embodiment, the number of conservative substitutions in SEQ ID NO: 291 is not more than 10, e.g., 1, 2, 3, 4, 5, 6, 7, 8, 9 or 10. In an embodiment, the variant has at least at least 70%, e.g., at least 80%, at least 90%, at least 95% or at least 100% of the lysozyme activity of SEQ ID NO: 291.

The invention further relates to polypeptides having a sequence identity to the mature polypeptide of SEQ ID NO: 293 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which have lysozyme activity. In one aspect, the polypeptides differ by up to 49 amino acids, e.g., between 1 and 49 amino acids, such as 1-45, 1-40, 1-35, 1-30, 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 amino acids from the mature polypeptide of SEQ ID NO: 293. In an embodiment, the polypeptide has been isolated. In an embodiment, the polypeptide has at least at least 70%, e.g., at least 80%, at least 90%, at least 95% or at least 100% of the lysozyme activity of the mature polypeptide of SEQ ID NO: 293.

A polypeptide of the present invention preferably comprises or consists of the amino acid sequence of SEQ ID NO: 293 or an allelic variant thereof; comprises or consists of the amino acid sequence of SEQ ID NO: 293 and a N-terminal and/or C-terminal His-tag and/or HQ-tag; or is a fragment thereof having lysozyme activity wherein the fragment comprises at least 200 amino acids, such as at least 210 amino acids, at least 215 amino acids, at least 220 amino acids, at least 225 amino acids, at least 230 amino acids, at least 235 amino acids or at least 240 amino acids. In another aspect, the polypeptide comprises or consists of the mature polypeptide of SEQ ID NO: 293. In another aspect, the polypeptide comprises or consists of amino acids 1 to 249 of SEQ ID NO: 293.

The present invention further relates to polypeptides having a sequence identity to SEQ ID NO: 294 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, and wherein the polypeptide has at least at least 70% of the lysozyme activity of SEQ ID NO: 294.

In a particular embodiment, the invention relates to polypeptides having a sequence identity to SEQ ID NO: 294 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, and wherein the polypeptide has at least at least 80% of the lysozyme activity of SEQ ID NO: 294.

In a particular embodiment, the invention relates to polypeptides having a sequence identity to SEQ ID NO: 294 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, and wherein the polypeptide has at least at least 90% of the lysozyme activity of SEQ ID NO: 294.

In a particular embodiment, the invention relates to polypeptides having a sequence identity to SEQ ID NO: 294 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, and wherein the polypeptide has at least at least 95% of the lysozyme activity of SEQ ID NO: 294.

In a particular embodiment, the invention relates to polypeptides having a sequence identity to SEQ ID NO: 294 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, and wherein the polypeptide has at least at least 100% of the lysozyme activity of SEQ ID NO: 294.

In one aspect, the polypeptides differ by up to 49 amino acids, e.g., between 1 and 49 amino acids, such as 1-45, 1-40, 1-35, 1-30, 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 amino acids from SEQ ID NO: 294. In an embodiment, the polypeptide has at least at least 70%, e.g., at least 80%, at least 90%, at least 95% or at least 100% of the lysozyme activity of SEQ ID NO: 294.

A polypeptide of the present invention preferably comprises or consists of the amino acid sequence of SEQ ID NO: 294 or an allelic variant thereof having lysozyme activity; comprises or consists of the amino acid sequence of SEQ ID NO: 294 and a N-terminal and/or C-terminal His-tag and/or HQ-tag; or is a fragment thereof having lysozyme activity wherein the fragment comprises at least 200 amino acids, such as at least 210 amino acids, at least 215 amino acids, at least 220 amino acids, at least 225 amino acids, at least 230 amino acids, at least 235 amino acids or at least 240 amino acids. In another aspect, the polypeptide comprises or consists of amino acids 1 to 249 of SEQ ID NO: 294 and has lysozyme activity.

In another aspect, the present invention relates to a polypeptide having lysozyme activity encoded by a polynucleotide that hybridizes under medium-high stringency conditions, high stringency conditions, or very high stringency conditions with (i) the mature polypeptide coding sequence of SEQ ID NO: 292, (ii) the cDNA sequence thereof; or (iii) the full-length complement of (i) or (ii) (Sambrook et al., 1989, *Molecular Cloning, A Laboratory Manual*, 2d edition, Cold Spring Harbor, New York). In an embodiment, the polypeptide has been isolated.

In another embodiment, the present invention relates to a polypeptide having lysozyme activity encoded by a polynucleotide having a sequence identity to the mature polypeptide coding sequence of SEQ ID NO: 292 or the cDNA sequence thereof of at least 80%, e.g., at least 85%, at least 90%, at least 91%, at least 92%, at least 93%, at least 94%, at least 95%, at least 96%, at least 97%, at least 98%, at least 99%, or 100%. In a further embodiment, the polypeptide has been isolated.

In another embodiment, the present invention relates to variants of the mature polypeptide of SEQ ID NO: 294 comprising a substitution, and/or deletion, and/or insertion at one or more (e.g., several) positions. In an embodiment, the number of positions comprising one or more amino acid substitutions, and/or one or more amino acid deletions, and/or one or more amino acid insertions or any combination thereof in SEQ ID NO: 294 is not more than 49, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49. In another embodiment, the number of positions comprising one or more amino acid substitutions, and/or one or more amino acid deletions, and/or one or more amino acid insertions or any combination thereof in SEQ ID NO: 294 is between 1 and 45, such as 1-40, 1-35, 1-30, 1-25, 1-20, 1-15, 1-10 or 1-5 positions. In an embodiment, the number of positions comprising one or more amino acid substitutions, and/or one or more amino acid deletions, and/or one or more amino acid insertions or any combination thereof in SEQ ID NO: 294 is not more than 10, e.g., 1, 2, 3, 4, 5, 6, 7, 8, 9 or 10. In another embodiment, the number of substitutions and/or deletions and/or insertions in SEQ ID NO: 294 is not more than 10, e.g., 1, 2, 3, 4, 5, 6, 7, 8, 9 or 10. In a further embodiment, the number of substitutions in SEQ ID NO: 294 is not more than 10, e.g., 1, 2, 3, 4, 5, 6, 7, 8, 9 or 10. In a further embodiment, the number of conservative substitutions in SEQ ID NO: 294 is not more than 10, e.g., 1, 2, 3, 4, 5, 6, 7, 8, 9 or 10. In an embodiment, the variant has at least at least 70%, e.g., at least 80%, at least 90%, at least 95% or at least 100% of the lysozyme activity of SEQ ID NO: 294.

The invention further relates to polypeptides having a sequence identity to the mature polypeptide of SEQ ID NO: 296 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which have lysozyme activity. In one aspect, the polypeptides differ by up to 49 amino acids, e.g., between 1 and 49 amino acids, such as 1-45, 1-40, 1-35, 1-30, 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 amino acids from the mature polypeptide of SEQ ID NO: 296. In an embodiment, the polypeptide has been isolated. In an embodiment, the polypeptide has at least at least 70%, e.g., at least 80%, at least 90%, at least 95% or at least 100% of the lysozyme activity of the mature polypeptide of SEQ ID NO: 296.

A polypeptide of the present invention preferably comprises or consists of the amino acid sequence of SEQ ID NO: 296 or an allelic variant thereof; comprises or consists of the amino acid sequence of SEQ ID NO: 296 and a N-terminal and/or C-terminal His-tag and/or HQ-tag; or is a fragment thereof having lysozyme activity wherein the fragment comprises at least 200 amino acids, such as at least 210 amino acids, at least 215 amino acids, at least 220 amino acids, at least 225 amino acids, at least 230 amino acids, at least 235 amino acids or at least 240 amino acids. In another aspect, the polypeptide comprises or consists of the mature polypeptide of SEQ ID NO: 296. In another aspect, the polypeptide comprises or consists of amino acids 1 to 245 of SEQ ID NO: 296.

The present invention further relates to polypeptides having a sequence identity to SEQ ID NO: 297 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, and wherein the polypeptide has at least at least 70% of the lysozyme activity of SEQ ID NO: 297.

In a particular embodiment, the invention relates to polypeptides having a sequence identity to SEQ ID NO: 297 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, and wherein the polypeptide has at least at least 80% of the lysozyme activity of SEQ ID NO: 297.

In a particular embodiment, the invention relates to polypeptides having a sequence identity to SEQ ID NO: 297 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, and wherein the polypeptide has at least at least 90% of the lysozyme activity of SEQ ID NO: 297.

In a particular embodiment, the invention relates to polypeptides having a sequence identity to SEQ ID NO: 297 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, and wherein the polypeptide has at least at least 95% of the lysozyme activity of SEQ ID NO: 297.

In a particular embodiment, the invention relates to polypeptides having a sequence identity to SEQ ID NO: 297 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, and wherein the polypeptide has at least at least 100% of the lysozyme activity of SEQ ID NO: 297.

In one aspect, the polypeptides differ by up to 49 amino acids, e.g., between 1 and 49 amino acids, such as 1-45, 1-40, 1-35, 1-30, 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 amino acids from SEQ ID NO: 297. In an embodiment, the polypeptide has at least at least 70%, e.g., at least 80%, at least 90%, at least 95% or at least 100% of the lysozyme activity of SEQ ID NO: 297.

A polypeptide of the present invention preferably comprises or consists of the amino acid sequence of SEQ ID NO: 297 or an allelic variant thereof having lysozyme activity; comprises or consists of the amino acid sequence of SEQ ID NO: 297 and a N-terminal and/or C-terminal His-tag and/or HQ-tag; or is a fragment thereof having lysozyme activity wherein the fragment comprises at least 200 amino acids, such as at least 210 amino acids, at least 215 amino acids, at least 220 amino acids, at least 225 amino acids, at least 230 amino acids, at least 235 amino acids or at least 240 amino acids. In another aspect, the polypeptide comprises or consists of amino acids 1 to 245 of SEQ ID NO: 297 and has lysozyme activity.

In another aspect, the present invention relates to a polypeptide having lysozyme activity encoded by a polynucleotide that hybridizes under medium-high stringency conditions, high stringency conditions, or very high stringency conditions with (i) the mature polypeptide coding sequence of SEQ ID NO: 295, (ii) the cDNA sequence thereof; or (iii) the full-length complement of (i) or (ii) (Sambrook et al., 1989, *Molecular Cloning, A Laboratory Manual,* 2d edition, Cold Spring Harbor, New York). In an embodiment, the polypeptide has been isolated.

In another embodiment, the present invention relates to a polypeptide having lysozyme activity encoded by a polynucleotide having a sequence identity to the mature polypeptide coding sequence of SEQ ID NO: 295 or the cDNA sequence thereof of at least 80%, e.g., at least 85%, at least 90%, at least 91%, at least 92%, at least 93%, at least 94%, at least 95%, at least 96%, at least 97%, at least 98%, at least 99%, or 100%. In a further embodiment, the polypeptide has been isolated.

In another embodiment, the present invention relates to variants of the mature polypeptide of SEQ ID NO: 297 comprising a substitution, and/or deletion, and/or insertion at one or more (e.g., several) positions. In an embodiment, the number of positions comprising one or more amino acid substitutions, and/or one or more amino acid deletions, and/or one or more amino acid insertions or any combination thereof in SEQ ID NO: 297 is not more than 49, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49. In another embodiment, the number of positions comprising one or more amino acid substitutions, and/or one or more amino acid deletions, and/or one or more amino acid insertions or any combination thereof in SEQ ID NO: 297 is between 1 and 45, such as 1-40, 1-35, 1-30, 1-25, 1-20, 1-15, 1-10 or 1-5 positions. In an embodiment, the number of positions comprising one or more amino acid substitutions, and/or one or more amino acid deletions, and/or one or more amino acid insertions or any combination thereof in SEQ ID NO: 297 is not more than 10, e.g., 1, 2, 3, 4, 5, 6, 7, 8, 9 or 10. In another embodiment, the number of substitutions and/or deletions and/or insertions in SEQ ID NO: 297 is not more than 10, e.g., 1, 2, 3, 4, 5, 6, 7, 8, 9 or 10. In a further embodiment, the number of substitutions in SEQ ID NO: 297 is not more than 10, e.g., 1, 2, 3, 4, 5, 6, 7, 8, 9 or 10. In a further embodiment, the number of conservative substitutions in SEQ ID NO: 297 is not more than 10, e.g., 1, 2, 3, 4, 5, 6, 7, 8, 9 or 10. In an embodiment, the variant has at least at least 70%, e.g., at least 80%, at least 90%, at least 95% or at least 100% of the lysozyme activity of SEQ ID NO: 297.

The invention further relates to polypeptides having a sequence identity to the mature polypeptide of SEQ ID NO: 299 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which have lysozyme activity. In one aspect, the polypeptides differ by up to 49 amino acids, e.g., between 1 and 49 amino acids, such as 1-45, 1-40, 1-35, 1-30, 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 amino acids from the mature polypeptide of SEQ ID NO: 299. In an embodiment, the polypeptide has been isolated. In an embodiment, the polypeptide has at least at least 70%, e.g., at least 80%, at least 90%, at least 95% or at least 100% of the lysozyme activity of the mature polypeptide of SEQ ID NO: 299.

A polypeptide of the present invention preferably comprises or consists of the amino acid sequence of SEQ ID NO: 299 or an allelic variant thereof; comprises or consists of the amino acid sequence of SEQ ID NO: 299 and a N-terminal and/or C-terminal His-tag and/or HQ-tag; or is a fragment thereof having lysozyme activity wherein the fragment comprises at least 200 amino acids, such as at least 210 amino acids, at least 215 amino acids, at least 220 amino acids, at least 225 amino acids, at least 230 amino acids, at least 235 amino acids or at least 240 amino acids. In another aspect, the polypeptide comprises or consists of the mature polypeptide of SEQ ID NO: 299. In another aspect, the polypeptide comprises or consists of amino acids 1 to 247 of SEQ ID NO: 299.

The present invention further relates to polypeptides having a sequence identity to SEQ ID NO: 300 of at least 82%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, and wherein the polypeptide has at least at least 70% of the lysozyme activity of SEQ ID NO: 300.

In a particular embodiment, the invention relates to polypeptides having a sequence identity to SEQ ID NO: 300 of at least 82%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, and wherein the polypeptide has at least at least 80% of the lysozyme activity of SEQ ID NO: 300.

In a particular embodiment, the invention relates to polypeptides having a sequence identity to SEQ ID NO: 300 of at least 82%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, and wherein the polypeptide has at least at least 90% of the lysozyme activity of SEQ ID NO: 300.

In a particular embodiment, the invention relates to polypeptides having a sequence identity to SEQ ID NO: 300 of at least 82%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, and wherein the polypeptide has at least at least 95% of the lysozyme activity of SEQ ID NO: 300.

In a particular embodiment, the invention relates to polypeptides having a sequence identity to SEQ ID NO: 300 of at least 82%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, and wherein the polypeptide has at least at least 100% of the lysozyme activity of SEQ ID NO: 300.

In one aspect, the polypeptides differ by up to 49 amino acids, e.g., between 1 and 49 amino acids, such as 1-45, 1-40, 1-35, 1-30, 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 amino acids from SEQ ID NO: 300. In an embodiment, the polypeptide has at least at least 70%, e.g., at least 80%, at least 90%, at least 95% or at least 100% of the lysozyme activity of SEQ ID NO: 300.

A polypeptide of the present invention preferably comprises or consists of the amino acid sequence of SEQ ID NO: 300 or an allelic variant thereof having lysozyme activity; comprises or consists of the amino acid sequence of SEQ ID NO: 300 and a N-terminal and/or C-terminal His-tag and/or HQ-tag; or is a fragment thereof having lysozyme activity wherein the fragment comprises at least 200 amino acids, such as at least 210 amino acids, at least 215 amino acids, at least 220 amino acids, at least 225 amino acids, at least 230 amino acids, at least 235 amino acids or at least 240 amino acids. In another aspect, the polypeptide comprises or consists of amino acids 1 to 247 of SEQ ID NO: 300 and has lysozyme activity.

In another aspect, the present invention relates to a polypeptide having lysozyme activity encoded by a polynucleotide that hybridizes under medium-high stringency conditions, high stringency conditions, or very high stringency conditions with (i) the mature polypeptide coding sequence of SEQ ID NO: 298, (ii) the cDNA sequence thereof; or (iii) the full-length complement of (i) or (ii) (Sambrook et al., 1989, *Molecular Cloning, A Laboratory Manual*, 2d edition, Cold Spring Harbor, New York). In an embodiment, the polypeptide has been isolated.

In another embodiment, the present invention relates to a polypeptide having lysozyme activity encoded by a polynucleotide having a sequence identity to the mature polypeptide coding sequence of SEQ ID NO: 298 or the cDNA sequence thereof of at least 80%, e.g., at least 85%, at least 90%, at least 91%, at least 92%, at least 93%, at least 94%, at least 95%, at least 96%, at least 97%, at least 98%, at least 99%, or 100%. In a further embodiment, the polypeptide has been isolated.

In another embodiment, the present invention relates to variants of the mature polypeptide of SEQ ID NO: 300 comprising a substitution, and/or deletion, and/or insertion at one or more (e.g., several) positions. In an embodiment, the number of positions comprising one or more amino acid substitutions, and/or one or more amino acid deletions, and/or one or more amino acid insertions or any combination thereof in SEQ ID NO: 300 is not more than 49, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49. In another embodiment, the number of positions comprising one or more amino acid substitutions, and/or one or more amino acid deletions, and/or one or more amino acid insertions or any combination thereof in SEQ ID NO: 300 is between 1 and 45, such as 1-40, 1-35, 1-30, 1-25, 1-20, 1-15, 1-10 or 1-5 positions. In an embodiment, the number of positions comprising one or more amino acid substitutions, and/or one or more amino acid deletions, and/or one or more amino acid insertions or any combination thereof in SEQ ID NO: 300 is not more than 10, e.g., 1, 2, 3, 4, 5, 6, 7, 8, 9 or 10. In another embodiment, the number of substitutions and/or deletions and/or insertions in SEQ ID NO: 300 is not more than 10, e.g., 1, 2, 3, 4, 5, 6, 7, 8, 9 or 10. In a further embodiment, the number of substitutions in SEQ ID NO: 300 is not more than 10, e.g., 1, 2, 3, 4, 5, 6, 7, 8, 9 or 10. In a further embodiment, the number of conservative substitutions in SEQ ID NO: 300 is not more than 10, e.g., 1, 2, 3, 4, 5, 6, 7, 8, 9 or 10. In an embodiment, the variant has at least at least 70%, e.g., at least 80%, at least 90%, at least 95% or at least 100% of the lysozyme activity of SEQ ID NO: 300.

The invention further relates to polypeptides having a sequence identity to the mature polypeptide of SEQ ID NO: 302 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which have lysozyme activity. In one aspect, the polypeptides differ by up to 49 amino acids, e.g., between 1 and 49 amino acids, such as 1-45, 1-40, 1-35, 1-30, 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 amino acids from the mature polypeptide of SEQ ID NO: 302. In an embodiment, the polypeptide has been isolated. In an embodiment, the polypeptide has at least at least 70%, e.g., at least 80%, at least 90%, at least 95% or at least 100% of the lysozyme activity of the mature polypeptide of SEQ ID NO: 302.

A polypeptide of the present invention preferably comprises or consists of the amino acid sequence of SEQ ID NO: 302 or an allelic variant thereof; comprises or consists of the amino acid sequence of SEQ ID NO: 302 and a N-terminal and/or C-terminal His-tag and/or HQ-tag; or is a fragment thereof having lysozyme activity wherein the fragment comprises at least 200 amino acids, such as at least 210 amino acids, at least 215 amino acids, at least 220 amino acids, at least 225 amino acids, at least 230 amino acids, at least 235 amino acids or at least 240 amino acids. In another aspect, the polypeptide comprises or consists of the mature polypeptide of SEQ ID NO: 302. In another aspect, the polypeptide comprises or consists of amino acids 1 to 250 of SEQ ID NO: 302.

The present invention further relates to polypeptides having a sequence identity to SEQ ID NO: 303 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, and wherein the polypeptide has at least at least 70% of the lysozyme activity of SEQ ID NO: 303.

In a particular embodiment, the invention relates to polypeptides having a sequence identity to SEQ ID NO: 303 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, and wherein the polypeptide has at least at least 80% of the lysozyme activity of SEQ ID NO: 303.

In a particular embodiment, the invention relates to polypeptides having a sequence identity to SEQ ID NO: 303 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, and wherein the polypeptide has at least at least 90% of the lysozyme activity of SEQ ID NO: 303.

In a particular embodiment, the invention relates to polypeptides having a sequence identity to SEQ ID NO: 303 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, and wherein the polypeptide has at least at least 95% of the lysozyme activity of SEQ ID NO: 303.

In a particular embodiment, the invention relates to polypeptides having a sequence identity to SEQ ID NO: 303 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, and wherein the polypeptide has at least at least 100% of the lysozyme activity of SEQ ID NO: 303.

In one aspect, the polypeptides differ by up to 49 amino acids, e.g., between 1 and 49 amino acids, such as 1-45, 1-40, 1-35, 1-30, 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 amino acids from SEQ ID NO: 303. In an embodiment, the polypeptide has at least at least 70%, e.g., at least 80%, at least 90%, at least 95% or at least 100% of the lysozyme activity of SEQ ID NO: 303.

A polypeptide of the present invention preferably comprises or consists of the amino acid sequence of SEQ ID NO: 303 or an allelic variant thereof having lysozyme activity; comprises or consists of the amino acid sequence of SEQ ID NO: 303 and a N-terminal and/or C-terminal His-tag and/or HQ-tag; or is a fragment thereof having lysozyme activity wherein the fragment comprises at least 200 amino acids, such as at least 210 amino acids, at least 215 amino acids, at least 220 amino acids, at least 225 amino acids, at least 230 amino acids, at least 235 amino acids or at least 240 amino acids. In another aspect, the polypeptide comprises or consists of amino acids 1 to 250 of SEQ ID NO: 303 and has lysozyme activity.

In another aspect, the present invention relates to a polypeptide having lysozyme activity encoded by a polynucleotide that hybridizes under medium-high stringency conditions, high stringency conditions, or very high stringency conditions with (i) the mature polypeptide coding sequence of SEQ ID NO: 301, (ii) the cDNA sequence thereof; or (iii) the full-length complement of (i) or (ii) (Sambrook et al., 1989, *Molecular Cloning, A Laboratory Manual,* 2d edition, Cold Spring Harbor, New York). In an embodiment, the polypeptide has been isolated.

In another embodiment, the present invention relates to a polypeptide having lysozyme activity encoded by a polynucleotide having a sequence identity to the mature polypeptide coding sequence of SEQ ID NO: 301 or the cDNA sequence thereof of at least 80%, e.g., at least 85%, at least 90%, at least 91%, at least 92%, at least 93%, at least 94%, at least 95%, at least 96%, at least 97%, at least 98%, at least 99%, or 100%. In a further embodiment, the polypeptide has been isolated.

In another embodiment, the present invention relates to variants of the mature polypeptide of SEQ ID NO: 303 comprising a substitution, and/or deletion, and/or insertion at one or more (e.g., several) positions. In an embodiment, the number of positions comprising one or more amino acid substitutions, and/or one or more amino acid deletions, and/or one or more amino acid insertions or any combination thereof in SEQ ID NO: 303 is not more than 49, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49. In another embodiment, the number of positions comprising one or more amino acid substitutions, and/or one or more amino acid deletions, and/or one or more amino acid insertions or any combination thereof in SEQ ID NO: 303 is between 1 and 45, such as 1-40, 1-35, 1-30, 1-25, 1-20, 1-15, 1-10 or 1-5 positions. In an embodiment, the number of positions comprising one or more amino acid substitutions, and/or one or more amino acid deletions, and/or one or more amino acid insertions or any combination thereof in SEQ ID NO: 303 is not more than 10, e.g., 1, 2, 3, 4, 5, 6, 7, 8, 9 or 10. In another embodiment, the number of substitutions and/or deletions and/or insertions in SEQ ID NO: 303 is not more than 10, e.g., 1, 2, 3, 4, 5, 6, 7, 8, 9 or 10. In a further embodiment, the number of substitutions in SEQ ID NO: 303 is not more than 10, e.g., 1, 2, 3, 4, 5, 6, 7, 8, 9 or 10. In a further embodiment, the number of conservative substitutions in SEQ ID NO: 303 is not more than 10, e.g., 1, 2, 3, 4, 5, 6, 7, 8, 9 or 10. In an embodiment, the variant has at least at least 70%, e.g., at least 80%, at least 90%, at least 95% or at least 100% of the lysozyme activity of SEQ ID NO: 303.

The invention further relates to polypeptides having a sequence identity to the mature polypeptide of SEQ ID NO: 305 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which have lysozyme activity. In one aspect, the polypeptides differ by up to 49 amino acids, e.g., between 1 and 49 amino acids, such as 1-45, 1-40, 1-35, 1-30, 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 amino acids from the mature polypeptide of SEQ ID NO: 305. In an embodiment, the polypeptide has been isolated. In an embodiment, the polypeptide has at least at least 70%, e.g., at least 80%, at least 90%, at least 95% or at least 100% of the lysozyme activity of the mature polypeptide of SEQ ID NO: 305.

A polypeptide of the present invention preferably comprises or consists of the amino acid sequence of SEQ ID NO: 305 or an allelic variant thereof; comprises or consists of the amino acid sequence of SEQ ID NO: 305 and a N-terminal and/or C-terminal His-tag and/or HQ-tag; or is a fragment thereof having lysozyme activity wherein the fragment comprises at least 200 amino acids, such as at least 210 amino acids, at least 215 amino acids, at least 220 amino acids, at least 225 amino acids, at least 230 amino acids, at least 235 amino acids or at least 240 amino acids. In another aspect, the polypeptide comprises or consists of the mature polypeptide of SEQ ID NO: 305. In another aspect, the polypeptide comprises or consists of amino acids 1 to 240 of SEQ ID NO: 305.

The present invention further relates to polypeptides having a sequence identity to SEQ ID NO: 306 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, and wherein the polypeptide has at least at least 70% of the lysozyme activity of SEQ ID NO: 306.

In a particular embodiment, the invention relates to polypeptides having a sequence identity to SEQ ID NO: 306 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, and wherein the polypeptide has at least at least 80% of the lysozyme activity of SEQ ID NO: 306.

In a particular embodiment, the invention relates to polypeptides having a sequence identity to SEQ ID NO: 306 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, and wherein the polypeptide has at least at least 90% of the lysozyme activity of SEQ ID NO: 306.

In a particular embodiment, the invention relates to polypeptides having a sequence identity to SEQ ID NO: 306 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, and wherein the polypeptide has at least at least 95% of the lysozyme activity of SEQ ID NO: 306.

In a particular embodiment, the invention relates to polypeptides having a sequence identity to SEQ ID NO: 306 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, and wherein the polypeptide has at least at least 100% of the lysozyme activity of SEQ ID NO: 306.

In one aspect, the polypeptides differ by up to 49 amino acids, e.g., between 1 and 49 amino acids, such as 1-45, 1-40, 1-35, 1-30, 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 amino acids from SEQ ID NO: 306. In an embodiment, the polypeptide has at least at least 70%, e.g., at least 80%, at least 90%, at least 95% or at least 100% of the lysozyme activity of SEQ ID NO: 306.

A polypeptide of the present invention preferably comprises or consists of the amino acid sequence of SEQ ID NO: 306 or an allelic variant thereof having lysozyme activity; comprises or consists of the amino acid sequence of SEQ ID NO: 306 and a N-terminal and/or C-terminal His-tag and/or HQ-tag; or is a fragment thereof having lysozyme activity wherein the fragment comprises at least 200 amino acids, such as at least 210 amino acids, at least 215 amino acids, at least 220 amino acids, at least 225 amino acids, at least 230 amino acids, at least 235 amino acids or at least 240 amino acids. In another aspect, the polypeptide comprises or consists of amino acids 1 to 240 of SEQ ID NO: 306 and has lysozyme activity.

In another aspect, the present invention relates to a polypeptide having lysozyme activity encoded by a polynucleotide that hybridizes under medium-high stringency conditions, high stringency conditions, or very high stringency conditions with (i) the mature polypeptide coding sequence of SEQ ID NO: 304, (ii) the cDNA sequence thereof; or (iii) the full-length complement of (i) or (ii) (Sambrook et al., 1989, *Molecular Cloning, A Laboratory Manual,* 2d edition, Cold Spring Harbor, New York). In an embodiment, the polypeptide has been isolated.

In another embodiment, the present invention relates to a polypeptide having lysozyme activity encoded by a polynucleotide having a sequence identity to the mature polypeptide coding sequence of SEQ ID NO: 304 or the cDNA sequence thereof of at least 80%, e.g., at least 85%, at least 90%, at least 91%, at least 92%, at least 93%, at least 94%, at least 95%, at least 96%, at least 97%, at least 98%, at least 99%, or 100%. In a further embodiment, the polypeptide has been isolated.

In another embodiment, the present invention relates to variants of the mature polypeptide of SEQ ID NO: 306 comprising a substitution, and/or deletion, and/or insertion at one or more (e.g., several) positions. In an embodiment, the number of positions comprising one or more amino acid substitutions, and/or one or more amino acid deletions, and/or one or more amino acid insertions or any combination thereof in SEQ ID NO: 306 is not more than 49, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49. In another embodiment, the number of positions comprising one or more amino acid substitutions, and/or one or more amino acid deletions, and/or one or more amino acid insertions or any combination thereof in SEQ ID NO: 306 is between 1 and 45, such as 1-40, 1-35, 1-30, 1-25, 1-20, 1-15, 1-10 or 1-5 positions. In an embodiment, the number of positions comprising one or more amino acid substitutions, and/or one or more amino acid deletions, and/or one or more amino acid insertions or any combination thereof in SEQ ID NO: 306 is not more than 10, e.g., 1, 2, 3, 4, 5, 6, 7, 8, 9 or 10. In another embodiment, the number of substitutions and/or deletions and/or insertions in SEQ ID NO: 306 is not more than 10, e.g., 1, 2, 3, 4, 5, 6, 7, 8, 9 or 10. In a further embodiment, the number of substitutions in SEQ ID NO: 306 is not more than 10, e.g., 1, 2, 3, 4, 5, 6, 7, 8, 9 or 10. In a further embodiment, the number of conservative substitutions in SEQ ID NO: 306 is not more than 10, e.g., 1, 2, 3, 4, 5, 6, 7, 8, 9 or 10. In an embodiment, the variant has at least at least 70%, e.g., at least 80%, at least 90%, at least 95% or at least 100% of the lysozyme activity of SEQ ID NO: 306.

Sources of Polypeptides Having Lysozyme Activity

A polypeptide having lysozyme activity of the present invention may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

The polypeptide may be a fungal polypeptide. In one aspect, the polypeptide is a polypeptide having lysozyme activity from a fungus of the class Pezizomycetes, such as from the order Pezizales, or from the family Pyronemataceae, or from the genus *Trichophaea* or from the species *Trichophaea saccata* or *Trichophaea minuta*. In another aspect, the polypeptide is a polypeptide having lysozyme activity from a fungus of the class Sordariomycetes, such as from the order Hypocreales, or from the family Hypocreaceae, or from the genus *Trichoderma* or from the species *Trichoderma harzianum*.

In another aspect, the polypeptide is a polypeptide having lysozyme activity from a fungus of the class Sordariomycetes, such as from the order Sordariales, or from the family Chaetomiaceae, or from the genus *Chaetomium* or from the species *Chaetomium* sp. ZY287.

In another aspect, the polypeptide is a polypeptide having lysozyme activity from a fungus of the order Mortierellales, or from the family Mortierellaceae, or from the genus *Mortierella* or from the species *Mortierella* sp. ZY002.

In another aspect, the polypeptide is a polypeptide having lysozyme activity from a fungus of the class Sordariomycetes, such as from the order Hypocreales, or from the family Clavicipitaceae, or from the genus *Metarhizium* or from the species *Metarhizium* sp. XZ2431.

In another aspect, the polypeptide is a polypeptide having lysozyme activity from a fungus of the class Leotiomycetes, such as from the family Pseudeurotiaceae, or from the genus *Geomyces* or from the species *Geomyces auratus*.

In another aspect, the polypeptide is a polypeptide having lysozyme activity from a fungus of the class Sordariomycetes, such as from the order Hypocreales, or from the family Nectriaceae, or from the genus *Ilyonectria* or from the species *Ilyonectria rufa*.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen und Zellkulturen GmbH (DSMZ), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).

Polynucleotides

The present invention also relates to polynucleotides encoding a polypeptide of the present invention, as described herein. In an embodiment, the polynucleotide encoding the polypeptide of the present invention has been isolated.

The techniques used to isolate or clone a polynucleotide are known in the art and include isolation from genomic DNA or cDNA, or a combination thereof. The cloning of the polynucleotides from genomic DNA can be effected, e.g., by using the well-known polymerase chain reaction (PCR) or antibody screening of expression libraries to detect cloned DNA fragments with shared structural features. See, e.g., Innis et al., 1990, *PCR: A Guide to Methods and Applications*, Academic Press, New York. Other nucleic acid amplification procedures such as ligase chain reaction (LCR), ligation activated transcription (LAT) and polynucleotide-based amplification (NASBA) may be used. The polynucleotides may be cloned from a strain of *Trichophaea* or a strain of *Trichoderma*, or a related organism and thus, for example, may be an allelic or species variant of the polypeptide encoding region of the polynucleotide.

Modification of a polynucleotide encoding a polypeptide of the present invention may be necessary for synthesizing polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variants may be constructed on the basis of the polynucleotide presented as the mature polypeptide coding sequence of SEQ ID NO: 255, SEQ ID NO: 265, SEQ ID NO: 287, SEQ ID NO: 292, SEQ ID NO: 295, SEQ ID NO: 298, SEQ ID NO: 301, SEQ ID NO: 304, or the cDNA sequence thereof, e.g., a subsequence thereof, and/or by introduction of nucleotide substitutions that do not result in a change in the amino acid sequence of the polypeptide, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences.

The polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xyA and xyB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof. Other promoters are described in U.S. Pat. No. 6,011,147.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* acetamidase, *Aspergillus nidulans* anthranilate synthase, *Aspergillus niger* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NClB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory sequences are those that cause expression of the gene to be turned on or off in response to a chemical or physical stimulus, including the presence of a regulatory compound. Regulatory sequences in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked to the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, adeA (phosphoribosylaminoimidazole-succinocarboxamide synthase), adeB (phosphoribosyl-aminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes.

The selectable marker may be a dual selectable marker system as described in WO 2010/039889. In one aspect, the dual selectable marker is an hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMß1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol.* (Praha) 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397) or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804), or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, Passmore, and Davenport, editors, *Soc. App. Bacteriol. Symposium Series No. 9*, 1980).

The yeast host cell may be a *Candida, Hansenula, Kluyveromyces, Pichia, Saccharomyces, Schizosaccharomyces*, or *Yarrowia* cell, such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide of the present invention, comprising (a) cultivating a cell, which in its wild-type form produces the polypeptide, under conditions conducive for production of the polypeptide; and optionally, (b) recovering the polypeptide. In one aspect, the cell is a *Trichophaea* cell. In another aspect, the cell is a *Trichophaea saccata* cell. In another aspect, the cell is a *Trichoderma* cell. In another aspect, the cell is a *Trichoderma harzianum* cell. In another aspect, the cell is a *Trichoderma minuta* cell. In another aspect, the cell is a *Chaetomium* cell. In another aspect, the cell is a *Chaetomium* sp. ZY287 cell. In another aspect, the cell is a Mortierellaceae cell. In another aspect, the cell is a *Mortierella* sp. ZY002 cell. In another aspect, the cell is a *Metarhizium* cell. In another aspect, the cell is a *Metarhizium* sp. XZ2431 cell. In another aspect, the cell is a *Geomyces* cell. In another aspect, the cell is a *Geomyces auratus* cell. In another aspect, the cell is a *Ilyonectria* cell. In another aspect, the cell is a *Ilyonectria rufa* cell.

The present invention also relates to methods of producing a polypeptide of the present invention, comprising (a) cultivating a recombinant host cell of the present invention under conditions conducive for production of the polypeptide; and optionally, (b) recovering the polypeptide.

The host cells are cultivated in a nutrient medium suitable for production of the polypeptide using methods known in the art. For example, the cells may be cultivated by shake flask cultivation, or small-scale or large-scale fermentation (including continuous, batch, fed-batch, or solid state fermentations) in laboratory or industrial fermenters in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation. In one aspect, a fermentation broth comprising the polypeptide is recovered.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

In an alternative aspect, the polypeptide is not recovered, but rather a host cell of the present invention expressing the polypeptide is used as a source of the polypeptide.

Production in Plants

The present invention also relates to isolated plants, e.g., a transgenic plant, plant part, or plant cell, comprising a polynucleotide of the present invention so as to express and produce a polypeptide or domain in recoverable quantities. The polypeptide or domain may be recovered from the plant or plant part. Alternatively, the plant or plant part containing the polypeptide or domain may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, *Poa*), forage grass such as *Festuca, Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems.

Plant cells and specific plant cell compartments, such as chloroplasts, apoplasts, mitochondria, vacuoles, peroxisomes and cytoplasm are also considered to be a plant part.

Also included within the scope of the present invention are the progeny of such plants, plant parts, and plant cells.

The transgenic plant or plant cell expressing the polypeptide or domain may be constructed in accordance with methods known in the art.

The present invention also relates to methods of producing a polypeptide or domain of the present invention comprising (a) cultivating a transgenic plant or a plant cell comprising a polynucleotide encoding the polypeptide or domain under conditions conducive for production of the polypeptide or domain; and (b) recovering the polypeptide or domain.

Fermentation Broth Formulations or Cell Compositions

The present invention also relates to a fermentation broth formulation or a cell composition comprising a polypeptide of the present invention. The fermentation broth product further comprises additional ingredients used in the fermentation process, such as, for example, cells (including, the host cells containing the gene encoding the polypeptide of the present invention which are used to produce the polypeptide of interest), cell debris, biomass, fermentation media and/or fermentation products. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In an embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid (s), and optionally further contains killed cells and/or cell debris. In one embodiment, the killed cells and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis. In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

Enzyme Compositions

The present invention also relates to compositions comprising a lysozyme of the present invention. Preferably, the compositions are enriched in the lysozyme of the invention. The term "enriched" indicates that the lysozyme activity of the composition has been increased, e.g., with an enrichment factor of at least 1.1, such as at least 1.2, at least 1.3, at least 1.4, at least 1.5, at least 2.0, at least 3.0, at least 4.0, at least 5.0, at least 10.

The compositions may comprise a polypeptide of the present invention as the major enzymatic component, e.g., a mono-component composition. Such a composition may further comprise a formulating agent, as described below. Alternatively, the compositions may comprise multiple enzymatic activities.

In an embodiment, the composition comprises the polypeptide of the invention and one or more formulating agents as described below.

Formulating Agent

The enzyme of the invention may be formulated as a liquid or a solid. For a liquid formulation, the formulating agent may comprise a polyol (such as, e.g., glycerol, ethylene glycol or propylene glycol), a salt (such as, e.g., sodium chloride, sodium benzoate, potassium sorbate) or a sugar or sugar derivative (such as, e.g., dextrin, glucose, sucrose, and sorbitol). Thus in one embodiment, the composition is a liquid composition comprising the polypeptide of the invention and one or more formulating agents selected from the list consisting of glycerol, ethylene glycol, 1,2-propylene glycol, 1,3-propylene glycol, sodium chloride, sodium benzoate, potassium sorbate, dextrin, glucose, sucrose, and sorbitol. The liquid formulation may be sprayed onto the feed after it has been pelleted or may be added to drinking water given to the animals.

For a solid formulation, the formulation may be for example as a granule, spray dried powder or agglomerate. The formulating agent may comprise a salt (organic or inorganic zinc, sodium, potassium or calcium salts such as, e.g., calcium acetate, calcium benzoate, calcium carbonate, calcium chloride, calcium citrate, calcium sorbate, calcium sulfate, potassium acetate, potassium benzoate, potassium carbonate, potassium chloride, potassium citrate, potassium sorbate, potassium sulfate, sodium acetate, sodium benzoate, sodium carbonate, sodium chloride, sodium citrate, sodium sulfate, zinc acetate, zinc benzoate, zinc carbonate, zinc chloride, zinc citrate, zinc sorbate, zinc sulfate), starch or a sugar or sugar derivative (such as, e.g., sucrose, dextrin, glucose, lactose, sorbitol).

In an embodiment, the solid composition is in granulated form. The granule may have a matrix structure where the components are mixed homogeneously. However, the granule typically comprises a core particle and one or more coatings, which typically are salt and/or wax coatings. Examples of waxes are polyethylene glycols; polypropylenes; Carnauba wax; Candelilla wax; bees wax; hydrogenated plant oil or animal tallow such as hydrogenated ox tallow, hydrogenated palm oil, hydrogenated cotton seeds and/or hydrogenated soy bean oil; fatty acid alcohols; mono-glycerides and/or di-glycerides, such as glyceryl stearate, wherein stearate is a mixture of stearic and palmitic acid; micro-crystalline wax; paraffin's; and fatty acids, such as hydrogenated linear long chained fatty acids and derivatives thereof. A preferred wax is palm oil or hydrogenated palm oil. The core particle can either be a homogeneous blend of lysozyme of the invention optionally combined with one or more additional enzymes and optionally together with one or more salts or an inert particle with the lysozyme of the invention optionally combined with one or more additional enzymes applied onto it.

In an embodiment, the material of the core particles are selected from the group consisting of inorganic salts (such as calcium acetate, calcium benzoate, calcium carbonate, calcium chloride, calcium citrate, calcium sorbate, calcium sulfate, potassium acetate, potassium benzoate, potassium carbonate, potassium chloride, potassium citrate, potassium sorbate, potassium sulfate, sodium acetate, sodium benzoate, sodium carbonate, sodium chloride, sodium citrate, sodium sulfate, zinc acetate, zinc benzoate, zinc carbonate, zinc chloride, zinc citrate, zinc sorbate, zinc sulfate), starch or a sugar or sugar derivative (such as, e.g., sucrose, dextrin, glucose, lactose, sorbitol), sugar or sugar derivative (such as, e.g., sucrose, dextrin, glucose, lactose, sorbitol), small organic molecules, starch, flour, cellulose and minerals and clay minerals (also known as hydrous aluminium phyllosilicates). In a preferred embodiment, the core comprises a clay mineral such as kaolinite or kaolin.

The salt coating is typically at least 1 μm thick and can either be one particular salt or a mixture of salts, such as $Na_2SO_4$, $K_2SO_4$, $MgSO_4$ and/or sodium citrate. Other examples are those described in, e.g., WO 2008/017659, WO 2006/034710, WO 97/05245, WO 98/54980, WO 98/55599, WO 00/70034 or polymer coating such as described in WO 01/00042.

In another embodiment, the composition is a solid composition comprising the lysozyme of the invention and one or more formulating agents selected from the list consisting of sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch and cellulose. In a preferred embodiment, the formulating agent is selected from one or more of the following compounds: sodium sulfate, dextrin, cellulose, sodium thiosulfate and calcium carbonate. In a preferred embodiment, the solid composition is in granulated form. In an embodiment, the solid composition is in granulated form and comprises a core particle, an enzyme layer comprising the lysozyme of the invention and a salt coating.

In a further embodiment, the formulating agent is selected from one or more of the following compounds: glycerol, ethylene glycol, 1,2-propylene glycol or 1,3-propylene glycol, sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch, kaolin and cellulose. In a preferred embodiment, the formulating agent is selected from one or more of the following compounds: 1,2-propylene glycol, 1,3-propylene glycol, sodium sulfate, dextrin, cellulose, sodium thiosulfate, kaolin and calcium carbonate.

Animal Feed and Animal Feed Additives

The present invention also relates to animal feed compositions and animal feed additives. Animal feed compositions or diets have a relatively high content of protein. Poultry and pig diets can be characterised as indicated in Table B of WO 01/58275, columns 2-3. Fish diets can be characterised as indicated in column 4 of this Table B. Furthermore, such fish diets usually have a crude fat content of 200-310 g/kg.

An animal feed composition according to the invention has a crude protein content of 50-800 g/kg, and furthermore comprises at least one lysozyme as described herein or more than one lysozyme as described herein.

Furthermore, or in the alternative (to the crude protein content indicated above), the animal feed composition of the invention has a content of metabolisable energy of 10-30 MJ/kg; and/or a content of calcium of 0.1-200 g/kg; and/or a content of available phosphorus of 0.1-200 g/kg; and/or a content of methionine of 0.1-100 g/kg; and/or a content of methionine plus cysteine of 0.1-150 g/kg; and/or a content of lysine of 0.5-50 g/kg.

In particular embodiments, the content of metabolisable energy, crude protein, calcium, phosphorus, methionine, methionine plus cysteine, and/or lysine is within any one of ranges 2, 3, 4 or 5 in Table B of WO 01/58275 (R. 2-5).

Crude protein is calculated as nitrogen (N) multiplied by a factor 6.25, i.e., Crude protein (g/kg)=N (g/kg)×6.25. The nitrogen content is determined by the Kjeldahl method (A.O.A.C., 1984, Official Methods of Analysis 14th ed., Association of Official Analytical Chemists, Washington DC).

Metabolisable energy can be calculated on the basis of the NRC publication Nutrient requirements in swine, ninth revised edition 1988, subcommittee on swine nutrition, committee on animal nutrition, board of agriculture, national research council. National Academy Press, Washington, D.C., pp. 2-6, and the European Table of Energy Values for Poultry Feed-stuffs, Spelderholt centre for poultry research and extension, 7361 DA Beekbergen, The Netherlands. Grafisch bedrijf Ponsen & looijen bv, Wageningen. ISBN 90-71463-12-5.

The dietary content of calcium, available phosphorus and amino acids in complete animal diets is calculated on the basis of feed tables such as Veevoedertabel 1997, gegevens over chemische samenstelling, verteerbaarheid en voederwaarde van voedermiddelen, Central Veevoederbureau, Runderweg 6, 8219 pk Lelystad. ISBN 90-72839-13-7.

In a particular embodiment, the animal feed composition of the invention contains at least one vegetable protein as defined above.

The animal feed composition of the invention may also contain animal protein, such as Meat and Bone Meal, Feather meal, and/or Fish Meal, typically in an amount of 0-25%. The animal feed composition of the invention may also comprise Dried Distillers Grains with Solubles (DDGS), typically in amounts of 0-30%.

In still further particular embodiments, the animal feed composition of the invention contains 0-80% maize; and/or 0-80% sorghum; and/or 0-70% wheat; and/or 0-70% Barley; and/or 0-30% oats; and/or 0-40% soybean meal; and/or 0-25% fish meal; and/or 0-25% meat and bone meal; and/or 0-20% whey.

The animal feed may comprise vegetable proteins. In particular embodiments, the protein content of the vegetable proteins is at least 10, 20, 30, 40, 50, 60, 70, 80, or 90% (w/w).

Vegetable proteins may be derived from vegetable protein sources, such as legumes and cereals, for example, materials from plants of the families Fabaceae (Leguminosae), Cruciferaceae, Chenopodiaceae, and Poaceae, such as soy bean meal, lupin meal, rapeseed meal, and combinations thereof.

In a particular embodiment, the vegetable protein source is material from one or more plants of the family Fabaceae, e.g., soybean, lupine, pea, or bean. In another particular embodiment, the vegetable protein source is material from one or more plants of the family Chenopodiaceae, e.g., beet, sugar beet, spinach or *quinoa*. Other examples of vegetable protein sources are rapeseed, and cabbage. In another particular embodiment, soybean is a preferred vegetable protein source. Other examples of vegetable protein sources are cereals such as barley, wheat, rye, oat, maize (corn), rice, and sorghum.

Animal diets can, e.g., be manufactured as mash feed (non-pelleted) or pelleted feed. Typically, the milled feed-stuffs are mixed and sufficient amounts of essential vitamins and minerals are added according to the specifications for the species in question. Enzymes can be added as solid or liquid enzyme formulations. For example, for mash feed a solid or liquid enzyme formulation may be added before or during the ingredient mixing step. For pelleted feed the (liquid or solid) lysozyme/enzyme preparation may also be added before or during the feed ingredient step. Typically, a liquid lysozyme/enzyme preparation comprises the lysozyme of the invention optionally with a polyol, such as glycerol, ethylene glycol or propylene glycol, and is added after the pelleting step, such as by spraying the liquid formulation onto the pellets. The enzyme may also be incorporated in a feed additive or premix.

Alternatively, the lysozyme can be prepared by freezing a mixture of liquid enzyme solution with a bulking agent such as ground soybean meal, and then lyophilizing the mixture.

In an embodiment, the composition comprises one or more additional enzymes. In an embodiment, the composition comprises one or more microbes. In an embodiment, the composition comprises one or more vitamins. In an embodiment, the composition comprises one or more minerals. In an embodiment, the composition comprises one or more amino acids. In an embodiment, the composition comprises one or more other feed ingredients.

In another embodiment, the composition comprises one or more of the polypeptides of the invention, one or more formulating agents and one or more additional enzymes. In an embodiment, the composition comprises one or more of the polypeptides of the invention, one or more formulating agents and one or more microbes. In an embodiment, the composition comprises one or more of the polypeptides of the invention, one or more formulating agents and one or more vitamins. In an embodiment, the composition comprises one or more of the polypeptides of the invention and one or more minerals. In an embodiment, the composition comprises the polypeptide of the invention, one or more formulating agents and one or more amino acids. In an embodiment, the composition comprises one or more of the polypeptides of the invention, one or more formulating agents and one or more other feed ingredients.

In a further embodiment, the composition comprises one or more of the polypeptides of the invention, one or more formulating agents and one or more components selected from the list consisting of: one or more additional enzymes; one or more microbes; one or more vitamins; one or more minerals; one or more amino acids; and one or more other feed ingredients.

The final lysozyme concentration in the diet is within the range of 0.01-200 ppm enzyme protein per kg animal feed, such as 0.1 to 150 ppm, 0.5 to 100 ppm, 1 to 75 ppm, 2 to 50 ppm, 3 to 25 ppm, 2 to 80 ppm, 5 to 60 ppm, 8 to 40 ppm or 10 to 30 ppm enzyme protein per kg animal feed, or any combination of these intervals.

It is at present contemplated that the lysozyme is administered in one or more of the following amounts (dosage ranges): 0.01-200; 0.01-100; 0.5-100; 1-50; 5-100; 5-50;

10-100; 0.05-50; 5-25; or 0.10-10—all these ranges being in mg lysozyme per kg feed (ppm).

For determining mg lysozyme protein per kg feed, the lysozyme is purified from the feed composition, and the specific activity of the purified lysozyme is determined using a relevant assay (see under lysozyme activity). The lysozyme activity of the feed composition as such is also determined using the same assay, and on the basis of these two determinations, the dosage in mg lysozyme protein per kg feed is calculated.

In a particular embodiment, the animal feed additive of the invention is intended for being included (or prescribed as having to be included) in animal diets or feed at levels of 0.01 to 10.0%; more particularly 0.05 to 5.0%; or 0.2 to 1.0% (% meaning g additive per 100 g feed).

This is so in particular for premixes.

The same principles apply for determining mg lysozyme protein in feed additives. Of course, if a sample is available of the lysozyme used for preparing the feed additive or the feed, the specific activity is determined from this sample (no need to purify the lysozyme from the feed composition or the additive).

Additional Enzymes

In another embodiment, the compositions described herein optionally include one or more enzymes. Enzymes can be classified on the basis of the handbook Enzyme Nomenclature from NC-IUBMB, 1992), see also the ENZYME site at the internet: expasy.ch/enzyme/. ENZYME is a repository of information relative to the nomenclature of enzymes. It is primarily based on the recommendations of the Nomenclature Committee of the International Union of Biochemistry and Molecular Biology (IUB-MB), Academic Press, Inc., 1992, and it describes each type of characterized enzyme for which an EC (Enzyme Commission) number has been provided (Bairoch, 2000, "The ENZYME Database", *Nucleic Acids Res.* 28: 304-305). This IUB-MB Enzyme nomenclature is based on their substrate specificity and occasionally on their molecular mechanism; such a classification does not reflect the structural features of these enzymes.

Another classification of certain glycoside hydrolase enzymes, such as endoglucanase, xylanase, galactanase, mannanase, dextranase, lysozyme and galactosidase is described in Henrissat et al, "The carbohydrate-active enzymes database (CAZy) in 2013", *Nucl. Acids Res.* (1 Jan. 2014) 42(D1): D490-D495; see also cazy.org.

Thus the composition of the invention may also comprise at least one other enzyme selected from the group comprising of phytase (EC 3.1.3.8 or 3.1.3.26); xylanase (EC 3.2.1.8); galactanase (EC 3.2.1.89); alpha-galactosidase (EC 3.2.1.22); protease (EC 3.4); phospholipase A1 (EC 3.1.1.32); phospholipase A2 (EC 3.1.1.4); lysophospholipase (EC 3.1.1.5); phospholipase C (3.1.4.3); phospholipase D (EC 3.1.4.4); amylase such as, for example, alpha-amylase (EC 3.2.1.1); arabinofuranosidase (EC 3.2.1.55); beta-xylosidase (EC 3.2.1.37); acetyl xylan esterase (EC 3.1.1.72); feruloyl esterase (EC 3.1.1.73); cellulase (EC 3.2.1.4); cellobiohydrolases (EC 3.2.1.91); beta-glucosidase (EC 3.2.1.21); pullulanase (EC 3.2.1.41); alpha-mannosidase (EC 3.2.1.24), mannanase (EC 3.2.1.25) and beta-glucanase (EC 3.2.1.4 or EC 3.2.1.6), or any mixture thereof.

In a particular embodiment, the composition of the invention comprises a phytase (EC 3.1.3.8 or 3.1.3.26). Examples of commercially available phytases include Bio-Feed™ Phytase (Novozymes), Ronozyme® P, Ronozyme® NP and Ronozyme® HiPhos (DSM Nutritional Products), Natu-phos™ (BASF), Finase® and Quantum® Blue (AB Enzymes), OptiPhos® (Huvepharma) Phyzyme® XP (Verenium/DuPont) and Axtra® PHY (DuPont). Other preferred phytases include those described in, e.g., WO 98/28408, WO 00/43503, and WO 03/066847.

In a particular embodiment, the composition of the invention comprises a xylanase (EC 3.2.1.8). Examples of commercially available xylanases include Ronozyme® WX and Ronozyme® G2 (DSM Nutritional Products), Econase® XT and Barley (AB Vista), Xylathin® (Verenium), Hostazym® X (Huvepharma) and Axtra® XB (Xylanase/beta-glucanase, DuPont).

In a particular embodiment, the composition of the invention comprises a protease (EC 3.4). Examples of commercially available proteases include Ronozyme® ProAct (DSM NutritionalProducts).

Microbes

In an embodiment, the animal feed composition further comprises one or more additional microbes. In a particular embodiment, the animal feed composition further comprises a bacterium from one or more of the following genera: *Lactobacillus, Lactococcus, Streptococcus, Bacillus, Pediococcus, Enterococcus, Leuconostoc, Carnobacterium, Propionibacterium, Bifidobacterium, Clostridium* and *Megasphaera* or any combination thereof.

In a preferred embodiment, animal feed composition further comprises a bacterium from one or more of the following strains: *Bacillus subtilis, Bacillus licheniformis, Bacillus amyloliquefaciens, Bacillus cereus, Bacillus pumilus, Bacillus polymyxa, Bacillus megaterium, Bacillus coagulans, Bacillus circulans, Enterococcus faecium, Enterococcus* spp, and *Pediococcus* spp, *Lactobacillus* spp, *Bifidobacterium* spp, *Lactobacillus acidophilus, Pediococsus acidilactici, Lactococcus lactis, Bifidobacterium bifidum, Propionibacterium thoenii, Lactobacillus farciminus, Lactobacillus rhamnosus, Clostridium butyricum, Bifidobacterium animalis* ssp. *animalis, Lactobacillus reuteri, Lactobacillus salivarius* ssp. *salivarius, Megasphaera elsdenii, Propionibacteria* sp.

In a more preferred embodiment, composition, animal feed additive or animal feed further comprises a bacterium from one or more of the following strains of *Bacillus subtilis*: 3A-P4 (PTA-6506), 15A-P4 (PTA-6507), 22C-P1 (PTA-6508), 2084 (NRRL B-500130), LSSA01 (NRRL-B-50104), BS27 (NRRL B-501 05), BS 18 (NRRL B-50633), BS 278 (NRRL B-50634), DSM 29870, DSM 29871, NRRL B-50136, NRRL B-50605, NRRL B-50606, NRRL B-50622 and PTA-7547.

In a more preferred embodiment, composition, animal feed additive or animal feed further comprises a bacterium from one or more of the following strains of *Bacillus pumilus*: NRRL B-50016, ATCC 700385, NRRL B-50885 or NRRL B-50886.

In a more preferred embodiment, composition, animal feed additive or animal feed further comprises a bacterium from one or more of the following strains of *Bacillus lichenformis*: NRRL B 50015, NRRL B-50621 or NRRL B-50623.

In a more preferred embodiment, composition, animal feed additive or animal feed further comprises a bacterium from one or more of the following strains of *Bacillus amyloliquefaciens*: DSM 29869, DSM 29869, NRRL B 50607, PTA-7543, PTA-7549, NRRL B-50349, NRRL B-50606, NRRL B-50013, NRRL B-50151, NRRL B-50141, NRRL B-50147 or NRRL B-50888.

The bacterial count of each of the bacterial strains in the animal feed composition is between $1 \times 10^4$ and $1 \times 10^{14}$ CFU/kg of dry matter, preferably between $1\times10^6$ and $1\times10^{12}$ CFU/kg of dry matter, and more preferably between $1\times10^7$ and $1\times10^{11}$ CFU/kg of dry matter. In a more preferred embodiment the bacterial count of each of the bacterial strains in the animal feed composition is between $1\times10^8$ and $1\times10^{10}$ CFU/kg of dry matter.

The bacterial count of each of the bacterial strains in the animal feed composition is between $1\times10^5$ and $1\times10^{15}$ CFU/animal/day, preferably between $1\times10^7$ and $1\times10^{13}$ CFU/animal/day, and more preferably between $1\times10^8$ and $1\times10^{12}$ CFU/animal/day. In a more preferred embodiment the bacterial count of each of the bacterial strains in the animal feed composition is between $1\times10^9$ and $1\times10^{11}$ CFU/animal/day.

In another embodiment, the one or more bacterial strains are present in the form of a stable spore.

Premix

In an embodiment, the animal feed may include a premix, comprising, e.g., vitamins, minerals, enzymes, amino acids, preservatives, antibiotics, other feed ingredients or any combination thereof which are mixed into the animal feed.

Amino Acids

The composition of the invention may further comprise one or more amino acids. Examples of amino acids which are used in animal feed are lysine, alanine, beta-alanine, threonine, methionine and tryptophan.

Vitamins and Minerals

In another embodiment, the animal feed may include one or more vitamins, such as one or more fat-soluble vitamins and/or one or more water-soluble vitamins. In another embodiment, the animal feed may optionally include one or more minerals, such as one or more trace minerals and/or one or more macro minerals.

Usually fat- and water-soluble vitamins, as well as trace minerals form part of a so-called premix intended for addition to the feed, whereas macro minerals are usually separately added to the feed.

Non-limiting examples of fat-soluble vitamins include vitamin A, vitamin D3, vitamin E, and vitamin K, e.g., vitamin K3.

Non-limiting examples of water-soluble vitamins include vitamin B12, biotin and choline, vitamin 1, vitamin B2, vitamin B6, niacin, folic acid and panthothenate, e.g., Ca-D-panthothenate.

Non-limiting examples of trace minerals include boron, cobalt, chloride, chromium, copper, fluoride, iodine, iron, manganese, molybdenum, selenium and zinc.

Non-limiting examples of macro minerals include calcium, magnesium, potassium and sodium.

The nutritional requirements of these components (exemplified with poultry and piglets/pigs) are listed in Table A of WO 01/58275. Nutritional requirement means that these components should be provided in the diet in the concentrations indicated.

In the alternative, the animal feed additive of the invention comprises at least one of the individual components specified in Table A of WO 01/58275. At least one means either of, one or more of, one, or two, or three, or four and so forth up to all thirteen, or up to all fifteen individual components. More specifically, this at least one individual component is included in the additive of the invention in such an amount as to provide an in-feed-concentration within the range indicated in column four, or column five, or column six of Table A.

In a still further embodiment, the animal feed additive of the invention comprises at least one of the below vitamins, preferably to provide an in-feed-concentration within the ranges specified in the below Table 1 (for piglet diets, and broiler diets, respectively).

TABLE 1

Typical vitamin recommendations

| Vitamin | Piglet diet | Broiler diet |
| --- | --- | --- |
| Vitamin A | 10,000-15,000 IU/kg feed | 8-12,500 IU/kg feed |
| Vitamin D3 | 1800-2000 IU/kg feed | 3000-5000 IU/kg feed |
| Vitamin E | 60-100 mg/kg feed | 150-240 mg/kg feed |
| Vitamin K3 | 2-4 mg/kg feed | 2-4 mg/kg feed |
| Vitamin B1 | 2-4 mg/kg feed | 2-3 mg/kg feed |
| Vitamin B2 | 6-10 mg/kg feed | 7-9 mg/kg feed |
| Vitamin B6 | 4-8 mg/kg feed | 3-6 mg/kg feed |
| Vitamin B12 | 0.03-0.05 mg/kg feed | 0.015-0.04 mg/kg feed |
| Niacin (Vitamin B3) | 30-50 mg/kg feed | 50-80 mg/kg feed |
| Pantothenic acid | 20-40 mg/kg feed | 10-18 mg/kg feed |
| Folic acid | 1-2 mg/kg feed | 1-2 mg/kg feed |
| Biotin | 0.15-0.4 mg/kg feed | 0.15-0.3 mg/kg feed |
| Choline chloride | 200-400 mg/kg feed | 300-600 mg/kg feed |

Other Feed Ingredients

The composition of the invention may further comprise colouring agents, stabilisers, growth improving additives and aroma compounds/flavourings, polyunsaturated fatty acids (PUFAs); reactive oxygen generating species, antimicrobial peptides and anti-fungal polypeptides.

Examples of colouring agents are carotenoids such as beta-carotene, astaxanthin, and lutein.

Examples of aroma compounds/flavourings are creosol, anethol, deca-, undeca- and/or dodeca-lactones, ionones, irone, gingerol, piperidine, propylidene phatalide, butylidene phatalide, capsaicin and tannin.

Examples of stabilizing agents (e.g., acidifiers) are organic acids. Examples of these are benzoic acid (VevoVitall, DSM Nutritional Products), formic acid, butyric acid, fumaric acid and propionic acid.

Examples of antimicrobial peptides (AMP's) are CAP18, Leucocin A, Tritrpticin, Protegrin-1, Thanatin, Defensin, Lactoferrin, Lactoferricin, and Ovispirin such as Novispirin (Robert Lehrer, 2000), Plectasins, and Statins, including the compounds and polypeptides disclosed in WO 03/044049 and WO 03/048148, as well as variants or fragments of the above that retain antimicrobial activity.

Examples of antifungal polypeptides (AFP's) are the *Aspergillus giganteus*, and *Aspergillus niger* peptides, as well as variants and fragments thereof which retain antifungal activity, as disclosed in WO 94/01459 and WO 02/090384.

Examples of polyunsaturated fatty acids are C18, C20 and C22 polyunsaturated fatty acids, such as arachidonic acid, docosohexaenoic acid, eicosapentaenoic acid and gamma-linoleic acid.

Examples of reactive oxygen generating species are chemicals such as perborate, persulphate, or percarbonate; and enzymes such as an oxidase, an oxygenase or a syntethase.

The composition of the invention may further comprise at least one amino acid.

Examples of amino acids which are used in animal feed are lysine, alanine, beta-alanine, threonine, methionine and tryptophan.

Uses

Use in Animal Feed

A lysozyme of the invention may also be used in animal feed, wherein the term "animal" refers to all animals except humans. Examples of animals are non-ruminants, and ruminants. Ruminant animals include, for example, animals such as sheep, goats, cattle, e.g., beef cattle, cows, and young calves, deer, yank, camel, llama and kangaroo. Non-ruminant animals include mono-gastric animals, e.g., pigs or swine (including, but not limited to, piglets, growing pigs, and sows); poultry such as turkeys, ducks and chicken (including but not limited to broiler chicks, layers); horses (including but not limited to hotbloods, coldbloods and warm bloods), young calves; fish (including but not limited to amberjack, arapaima, barb, bass, bluefish, bocachico, bream, bullhead, cachama, carp, catfish, catla, chanos, char, cichlid, cobia, cod, crappie, dorada, drum, eel, goby, goldfish, gourami, grouper, guapote, halibut, java, labeo, lai, loach, mackerel, milkfish, mojarra, mudfish, mullet, paco, pearlspot, pejerrey, perch, pike, pompano, roach, salmon, sampa, sauger, sea bass, seabream, shiner, sleeper, snakehead, snapper, snook, sole, spinefoot, sturgeon, sunfish, sweetfish, tench, terror, tilapia, trout, tuna, turbot, vendace, walleye and whitefish); and crustaceans (including but not limited to shrimps and prawns).

In the use according to the invention the lysozymes can be fed to the animal before, after, or simultaneously with the diet. The latter is preferred.

In a particular embodiment, the lysozyme, in the form in which it is added to the feed, or when being included in a feed additive, is well-defined. Well-defined means that the lysozyme preparation is at least 50% pure as determined by Size-exclusion chromatography (see Example 12 of WO 01/58275). In other particular embodiments the lysozyme preparation is at least 60, 70, 80, 85, 88, 90, 92, 94, or at least 95% pure as determined by this method.

A well-defined lysozyme preparation is advantageous. For instance, it is much easier to dose correctly to the feed a lysozyme that is essentially free from interfering or contaminating other lysozymes. The term dose correctly refers in particular to the objective of obtaining consistent and constant results, and the capability of optimizing dosage based upon the desired effect.

For the use in animal feed, however, the lysozyme need not be pure; it may, e.g., include other enzymes, in which case it could be termed a lysozyme preparation.

The lysozyme preparation can be (a) added directly to the feed, or (b) it can be used in the production of one or more intermediate compositions such as feed additives or pre-mixes that is subsequently added to the feed (or used in a treatment process). The degree of purity described above refers to the purity of the original lysozyme preparation, whether used according to (a) or (b) above.

Methods of Improving Animal Performance

In an embodiment, the present invention also relates to a method of improving the performance of an animal comprising administering to the animal the animal feed or an animal feed additive of the invention.

In a preferred embodiment, the method of improving the performance of an animal comprises administering to the animal an animal feed or an animal feed additive comprising the lysozyme of SEQ ID NO: 257, SEQ ID NO: 264, SEQ ID NO: 267, SEQ ID NO: 291, SEQ ID NO: 294, SEQ ID NO: 297, SEQ ID NO: 300, SEQ ID NO: 303 and/or SEQ ID NO: 306.

In an embodiment, the present invention also relates to the use of the animal feed or an animal feed additive of the invention for improving the performance of an animal. In another embodiment, the invention relates to the use of one or more lysozymes of the invention for improving the performance of an animal.

In one embodiment, 'improving the performance of an animal' means that there is an increase in body weight gain. In another embodiment, 'improving the performance of an animal' means that there is an improved feed conversion ratio. In a further embodiment, 'improving the performance of an animal' means that there is an increased feed efficiency. In a further embodiment, 'improving the performance of an animal' means that there is an increase in body weight gain and/or an improved feed conversion ratio and/or an increased feed efficiency.

Methods of Preparing an Animal Feed

In an embodiment, the present invention provides a method for preparing an animal feed comprising adding one or more lysozymes of the present invention to one or more animal feed ingredients. Animal feed ingredients include, but are not limited to, concentrates (as defined herein), forage (as defined herein), enzymes, microbe, vitamins, minerals and amino acids.

In a preferred embodiment, the method of preparing an animal feed comprises mixing the lysozyme of SEQ ID NO: 257, SEQ ID NO: 264, SEQ ID NO: 267, SEQ ID NO: 291, SEQ ID NO: 294, SEQ ID NO: 297, SEQ ID NO: 300, SEQ ID NO: 303 and/or SEQ ID NO: 306 with concentrate and/or forage.

Methods of Treatment of *Clostridium perfringens* and/or Necrotic Enteritis

In another aspect, the present invention provides a method of treatment of necrotic enteritis comprising the steps of administering the animal feed or animal feed additive to one or more animals with necrotic enteritis. In an embodiment, the present invention provides a method of treatment of a *Clostridium perfringens* infection comprising the steps of administering the animal feed or animal feed additive to one or more animals with a *Clostridium perfringens* infection.

In another aspect, the present invention provides a method of treatment of necrotic enteritis comprising the steps of administering one or more lysozymes of the invention to one or more animals with necrotic enteritis. In an embodiment, the present invention provides a method of treatment of a *Clostridium perfringens* infection comprising the steps of administering one or more lysozymes of the invention to one or more animals with a *Clostridium perfringens* infection.

In a further aspect, the invention relates to the animal feed or animal feed additive of the invention for the treatment of necrotic enteritis in an animal. In an embodiment, the invention relates to composition comprising the lysozyme of SEQ ID NO: 257, SEQ ID NO: 264, SEQ ID NO: 267, SEQ ID NO: 291, SEQ ID NO: 294, SEQ ID NO: 297, SEQ ID NO: 300, SEQ ID NO: 303 and/or SEQ ID NO: 306 for the treatment of necrotic enteritis in an animal.

In a further aspect, the invention relates to the animal feed or animal feed additive of the invention for the treatment of a *Clostridium perfringens* infection in an animal. In an embodiment, the invention relates to composition comprising the lysozyme of SEQ ID NO: 257, SEQ ID NO: 264, SEQ ID NO: 267, SEQ ID NO: 291, SEQ ID NO: 294, SEQ ID NO: 297, SEQ ID NO: 300, SEQ ID NO: 303 and/or SEQ ID NO: 306 for the treatment of a *Clostridium perfringens* infection in an animal.

Antimicrobial activity towards *Clostridium perfringens* can be determined according to the antimicrobial assay described in Example 12.

Preferred Embodiments

Herein follows a list if preferred embodiments of the invention.

1. An animal feed or animal feed additive comprising one or more polypeptides having lysozyme activity, wherein the polypeptide comprises one or more GH24 catalytic domains and one or more lysozyme enhancing domains and wherein:
   (a) GH24 catalytic domain gives a domT score of at least 200 when queried using a Profile Hidden Markov Model prepared using SEQ ID NOs: 1 to 122 and hmmbuild software program, and wherein the query is carried out using hmmscan software program with default settings; and
   (b) the polypeptide comprises one or more lysozyme enhancing domains, wherein the lysozyme enhancing domain gives a domT score of at least 100 when queried using a Profile Hidden Markov Model prepared using SEQ ID NOs: 123 to 251 and hmmbuild software program, and wherein the query is carried out using the hmmscan software program with default settings.
2. The animal feed or animal feed additive of item 1, wherein the GH24 catalytic domain gives a domT score of 220 or more and the lysozyme enhancing domain gives a domT score of 100 or more.
3. The animal feed or animal feed additive of item 1, wherein the GH24 catalytic domain gives a domT score of 230 or more and the lysozyme enhancing domain gives a domT score of 100 or more.
4. The animal feed or animal feed additive of item 1, wherein the GH24 catalytic domain gives a domT score of 240 or more and the lysozyme enhancing domain gives a domT score of 100 or more.
5. The animal feed or animal feed additive of item 1, wherein the GH24 catalytic domain gives a domT score of 250 or more and the lysozyme enhancing domain gives a domT score of 103 or more.
6. An animal feed or animal feed additive comprising one or more polypeptides having lysozyme activity, wherein:
   (a) the polypeptide comprises one or more GH24 catalytic domain comprising one or more motif I: [TAS][VIL][GAC][YF]GHX[CAYIV] (SEQ ID NO: 252) and/or one or more motif II [LV][NDST]XN[QE][YFW][GASND]ALXS[WFLY]X[FY]N (SEQ ID NO: 253); and
   (b) the polypeptide comprises one or more lysozyme enhancing domain comprising one or more motif III: [CGY][YF][VIL][ASTP][DG]X[YF][VIT]X[TS][GAN] (SEQ ID NO: 254).
7. An animal feed or animal feed additive comprising one or more polypeptides having lysozyme activity, wherein:
   (a) the polypeptide comprises one or more GH24 catalytic domain comprising one or more motif I: [TAS][VIL][GAC][YF]GHX[CAYIV] (SEQ ID NO: 252) and one or more motif II [LV][NDST]XN[QE][YFW][GASND]ALXS[WFLY]X[FY]N (SEQ ID NO: 253); and
   (b) the polypeptide comprises one or more lysozyme enhancing domain comprising one or more motif III: [CGY][YF][VIL][ASTP][DG]X[YF][VIT]X[TS][GAN] (SEQ ID NO: 254).
8. The animal feed or animal feed additive of item 6 or 7, wherein the one or more motif I is [TAS][VIL][GAC][YFI]GHX[CAYIV] (SEQ ID NO: 281).
9. The animal feed or animal feed additive of item 6 or 7, wherein the one or more motif I is T[VI]GYGHXC (SEQ ID NO: 282).
10. The animal feed or animal feed additive of any of items 6 to 9, wherein the one or more motif II LNXN[QE][YFW][GA]ALXS[WFL]X[YF]N (SEQ ID NO: 283).
11. The animal feed or animal feed additive of any of items 6 to 10, wherein the one or more motif III C[YF][VI][AST]D[YKF][YF][V]XTG (SEQ ID NO: 284).
12. The animal feed or animal feed additive of any of items 6 to 11, wherein the GH24 catalytic domain further comprises one or more motif IV: [GEV]LXXRRXXE (SEQ ID NO: 285).
13. The animal feed or animal feed additive of any of items 6 to 12, wherein the GH24 catalytic domain further comprises one or more motif IV: GLXXRRXXE (SEQ ID NO: 286).
14. The animal feed or animal feed additive of any of items 1 to 13, wherein the lysozyme enhancing domain has at least 45% sequence identity to SEQ ID NO: 180.
15. The animal feed or animal feed additive of any of items 1 to 14, wherein the lysozyme enhancing domain has at least 65% sequence identity to one or more of SEQ ID NO: 123 to 251.
16. The animal feed or animal feed additive of any of items 1 to 15, wherein the GH24 catalytic domain has at least 55% sequence identity to SEQ ID NO: 14.
17. The animal feed or animal feed additive of any of items 1 to 16, wherein the GH24 catalytic domain has at least 65% sequence identity to one or more of SEQ ID NO: 1 to 122.
18. The animal feed or animal feed additive of any of items 1 to 17, wherein the polypeptide is obtained or obtainable from the kingdom Fungi.
19. The animal feed or animal feed additive of any of items 1 to 18, wherein the polypeptide is obtained or obtainable from the phylum Ascomycota.
20. The animal feed or animal feed additive of any of items 1 to 19, wherein the polypeptide is selected from the group consisting of:
   (a) a polypeptide having at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 257;
   (b) a polypeptide having at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 264;
   (c) a polypeptide having at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 267;
   (d) a polypeptide having at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 291;
   (e) a polypeptide having at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 294;
(f) a polypeptide having at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 297;
(g) a polypeptide having at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 300;
(h) a polypeptide having at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 303;
(i) a polypeptide having at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 306;
(j) a variant of SEQ ID NO: 257, wherein the variant has lysozyme activity and comprises one or more substitutions and/or one or more deletions and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 positions;
(k) a variant of SEQ ID NO: 264, wherein the variant has lysozyme activity and comprises one or more substitutions and/or one or more deletions and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 positions;
(l) a variant of SEQ ID NO: 267, wherein the variant has lysozyme activity and comprises one or more substitutions and/or one or more deletions and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 positions;
(m) a variant of SEQ ID NO: 291, wherein the variant has lysozyme activity and comprises one or more substitutions and/or one or more deletions and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 positions;
(n) a variant of SEQ ID NO: 294, wherein the variant has lysozyme activity and comprises one or more substitutions and/or one or more deletions and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 positions;
(o) a variant of SEQ ID NO: 297, wherein the variant has lysozyme activity and comprises one or more substitutions and/or one or more deletions and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 positions;
(p) a variant of SEQ ID NO: 300, wherein the variant has lysozyme activity and comprises one or more substitutions and/or one or more deletions and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 positions;
(q) a variant of SEQ ID NO: 303, wherein the variant has lysozyme activity and comprises one or more substitutions and/or one or more deletions and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 positions;
(r) a variant of SEQ ID NO: 306, wherein the variant has lysozyme activity and comprises one or more substitutions and/or one or more deletions and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 positions;
(s) a fragment of the polypeptide of (a), (b), (c), (d), (e), (f), (g), (h), (i), (j), (k), (l), (m), (n), (o), (p), (q) or (r) that has lysozyme activity wherein the fragment comprises at least 200 amino acids, such as at least 210 amino acids, at least 215 amino acids, at least 220 amino acids, at least 225 amino acids, at least 230 amino acids, at least 235 amino acids or at least 240 amino acids.

21. The animal feed or animal feed additive of any of items 1 to 20, wherein the polypeptide having lysozyme activity has at least 30% of the antimicrobial activity of SEQ ID NO: 257 against *Clostridium perfringens* using the conditions 50% MHB, pH 6.

22. The animal feed or animal feed additive of any of items 1 to 20, wherein the polypeptide having lysozyme activity has at least 30%, e.g., at least 50%, at least 60%, at least 70%, at least 80%, at least 90%, at least 95%, or at least 100% of the antimicrobial activity of SEQ ID NO: 257 against *Clostridium perfringens* using the conditions 50% MHB, pH 6.

23. The animal feed or animal feed additive of any of items 1 to 20, wherein the polypeptide having lysozyme activity has at least 30%, e.g., at least 50%, at least 60%, at least 70%, at least 80%, at least 90%, at least 95%, or at least 100% of the antimicrobial activity of SEQ ID NO: 264 against *Clostridium perfringens* using the conditions 50% MHB, pH 6.

24. The animal feed or animal feed additive of any of items 1 to 20, wherein the polypeptide having lysozyme activity has at least 30%, e.g., at least 50%, at least 60%, at least 70%, at least 80%, at least 90%, at least 95%, or at least 100% of the antimicrobial activity of SEQ ID NO: 267 against *Clostridium perfringens* using the conditions 50% MHB, pH 6.

25. The animal feed or animal feed additive of any of items 1 to 24 further comprising one or more components selected from the list consisting of:
one or more additional enzymes;
one or more microbes;

one or more vitamins;
one or more minerals;
one or more amino acids; and
one or more other feed ingredients.

26. The animal feed or animal feed additive of item 25, wherein the one or more additional enzymes is selected from the group consisting of phytase, xylanase, galactanase, alpha-galactosidase, protease, phospholipase A1, phospholipase A2, lysophospholipase, phospholipase C, phospholipase D, amylase, lysozyme, arabinofuranosidase, beta-xylosidase, acetyl xylan esterase, feruloyl esterase, cellulase, cellobiohydrolases, beta-glucosidase, pullulanase, and beta-glucanase or any combination thereof.

27. The animal feed or animal feed additive of item 25, wherein the one or more microbes is selected from the group consisting of *Bacillus subtilis, Bacillus licheniformis, Bacillus amyloliquefaciens, Bacillus cereus, Bacillus pumilus, Bacillus polymyxa, Bacillus megaterium, Bacillus coagulans, Bacillus circulans, Bifidobacterium bifidum, Bifidobacterium animalis, Bifidobacterium* sp., *Carnobacterium* sp., *Clostridium butyricum, Clostridium* sp., *Enterococcus faecium, Enterococcus* sp., *Lactobacillus* sp., *Lactobacillus acidophilus, Lactobacillus farciminus, Lactobacillus rhamnosus, Lactobacillus reuteri, Lactobacillus salivarius, Lactococcus lactis, Lactococcus* sp., *Leuconostoc* sp., *Megasphaera elsdenii, Megasphaera* sp., *Pediococcus acidilactici, Pediococcus* sp., *Propionibacterium thoenii, Propionibacterium* sp. and *Streptococcus* sp. or any combination thereof.

28. A pelleted animal feed comprising plant based material and the animal feed or animal feed additive of any of items 1 to 27.

29. The pelleted animal feed of item 28, wherein the plant based material comprises oats, rye, barley, wheat, maize, corn, sorghum, switchgrass, millet, pearl millet, foxtail millet, soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape) or pea, in a processed form thereof or any combination thereof.

30. A polypeptide having lysozyme activity, selected from the group consisting of:
(a) a polypeptide having at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 257;
(b) a polypeptide having at least 95%, e.g., at least 96%, at least 97%, at least 98%, at least 99%, or 100% sequence identity to SEQ ID NO: 267;
(c) a polypeptide having at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 291;
(d) a polypeptide having at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 294;
(e) a polypeptide having at least 82%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 297;
(f) a polypeptide having at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 300;
(g) a polypeptide having at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 303;
(h) a polypeptide having at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 306;
(i) a polypeptide encoded by a polynucleotide that hybridizes under medium-high stringency conditions, high stringency conditions or very-high stringency conditions with:
  (i) the mature polypeptide coding sequence of SEQ ID NO: 255;
  (ii) the mature polypeptide coding sequence of SEQ ID NO: 287;
  (iii) the mature polypeptide coding sequence of SEQ ID NO: 292;
  (iv) the mature polypeptide coding sequence of SEQ ID NO: 295;
  (v) the mature polypeptide coding sequence of SEQ ID NO: 298;
  (vi) the mature polypeptide coding sequence of SEQ ID NO: 301;
  (vii) the mature polypeptide coding sequence of SEQ ID NO: 304;
  (viii) the cDNA sequence thereof; or
  (ix) the full-length complement of (i), (ii), (iii), (iv) (v), (vi), (vii) or (viii);
(j) a polypeptide encoded by a polynucleotide that hybridizes under very-high stringency conditions with:
  (i) the mature polypeptide coding sequence of SEQ ID NO: 265;
  (ii) the full-length complement of (i);
(k) a polypeptide encoded by a polynucleotide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 255;
(l) a polypeptide encoded by a polynucleotide having at least 95%, e.g., at least 96%, at least 97%, at least 98%, at least 99%, or 100% sequence identity to the mature polypeptide coding sequence of SEQ ID NO: 265;
(m) a polypeptide encoded by a polynucleotide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 287;

(n) a polypeptide encoded by a polynucleotide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 292;

(o) a polypeptide encoded by a polynucleotide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 295;

(p) a polypeptide encoded by a polynucleotide having at least 82%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 298;

(q) a polypeptide encoded by a polynucleotide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 301;

(r) a polypeptide encoded by a polynucleotide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 304;

(s) a variant of SEQ ID NO: 257, wherein the variant has lysozyme activity and comprises one or more substitutions and/or one or more deletions and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 positions; and (t) a variant of SEQ ID NO: 267, wherein the variant has lysozyme activity and comprises one or more substitutions and/or one or more deletions and/or one or more insertions or any combination thereof in 1, 2, 3, 4, 5, 6, 7, 8, 9, 10, 11 or 12 positions; and (u) a variant of SEQ ID NO: 291, wherein the variant has lysozyme activity and comprises one or more substitutions and/or one or more deletions and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 positions;

(v) a variant of SEQ ID NO: 294, wherein the variant has lysozyme activity and comprises one or more substitutions and/or one or more deletions and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 positions;

(w) a variant of SEQ ID NO: 297, wherein the variant has lysozyme activity and comprises one or more substitutions and/or one or more deletions and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 positions;

(x) a variant of SEQ ID NO: 300, wherein the variant has lysozyme activity and comprises one or more substitutions and/or one or more deletions and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 positions;

(y) a variant of SEQ ID NO: 303, wherein the variant has lysozyme activity and comprises one or more substitutions and/or one or more deletions and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 positions;

(z) a variant of SEQ ID NO: 306, wherein the variant has lysozyme activity and comprises one or more substitutions and/or one or more deletions and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 positions; and (aa) a fragment of the polypeptide of (a), (b), (c), (d), (e), (f), (g), (h), (i), (j), (k), (l), (m), (n), (o), (p), (q), (r), (s), (t), (u), (v), (w), (x), (y) or (z) that has lysozyme activity wherein the fragment comprises at least 200 amino acids, such as at least 210 amino acids, at least 215 amino acids, at least 220 amino acids, at least 225 amino acids, at least 230 amino acids, at least 235 amino acids or at least 240 amino acids.

31. The polypeptide according to item 30, wherein the polypeptide comprises or consists of amino acids 1 to 245 of SEQ ID NO: 257, amino acids 1 to 248 of SEQ ID NO: 267, amino acids 1 to 245 of SEQ ID NO: 291, amino acids 1 to 249 of SEQ ID NO: 294, amino acids 1 to 245 of SEQ ID NO: 297, amino acids 1 to 247 of SEQ ID NO: 300, amino acids 1 to 250 of SEQ ID NO:303 or amino acids 1 to 240 of SEQ ID NO: 306.

32. A composition comprising one or more polypeptides of any of items 30 to 31 and one or more formulating agents.

33. The composition of item 32 wherein the formulating agent comprises one or more of the following compounds: glycerol, ethylene glycol, 1, 2-propylene glycol or 1, 3-propylene glycol, sodium chloride, sodium benzoate, potassium sorbate, sodium sulfate, potassium sulfate, magnesium sulfate, sodium thiosulfate, calcium carbonate, sodium citrate, dextrin, maltodextrin, glucose, sucrose, sorbitol, lactose, wheat flour, wheat bran, corn gluten meal, starch, kaolin and cellulose or any combination thereof.

34. A granule comprising one or more polypeptides of item 30 or 31 or the composition of item 32 or 33.

35. The granule of item 34 wherein the granule is coated.

36. The granule of item 35 wherein the coating comprises a salt and/or wax and/or a flour.

37. Use of the polypeptide of item 30 or 31, the animal feed or animal feed additive of any of items 1 to 27, the pelleted animal feed of item 28 or 29, the composition of item 32 or 33 or the granule of any of items 34 to 36:
in animal feed;
in animal feed additives;
in the preparation of a composition for use in animal feed;

for improving one or more performance parameters in an animal;

for the treatment of *Clostridium perfringens* infection in an animal; and/or for the treatment of necrotic enteritis in an animal.

38. A method of treatment of a *Clostridium perfringens* infection and/or necrotic enteritis in an animal comprising the steps of administering the polypeptide of item 30 or 31, the animal feed or animal feed additive of any of items 1 to 27, the pelleted animal feed of item 28 or 29, the composition of item 32 or 33 or the granule of any of items 34 to 36 to one or more animals.

39. The polypeptide of item 30 or 31, the animal feed or animal feed additive of any of items 1 to 27, the pelleted animal feed of item 28 or 29, the composition of item 32 or 33 or the granule of any of items 34 to 36 for use as a medicament.

40. The polypeptide of item 30 or 31, the animal feed or animal feed additive of any of items 1 to 27, the pelleted animal feed of item 28 or 29, the composition of item 32 or 33 or the granule of any of items 34 to 36 for use in treatment of a *Clostridium perfringens* infection and/or necrotic enteritis in an animal.

41. A method of improving the performance of an animal comprising administering to the animal the polypeptide of item 30 or 31, the animal feed or animal feed additive of any of items 1 to 27, the pelleted animal feed of item 28 or 29, the composition of item 32 or 33 or the granule of any of items 34 to 36.

42. An isolated polynucleotide encoding the polypeptide of item 30 or 31.

43. A nucleic acid construct or expression vector comprising the polynucleotide of item 42 operably linked to one or more control sequences that direct the production of the polypeptide in an expression host cell.

44. A recombinant expression host cell comprising the polynucleotide of item 42 operably linked to one or more control sequences that direct the production of the polypeptide.

45. A method of producing the polypeptide of item 30 or 31, comprising:
   (a) cultivating a cell, which in its wild-type form produces the polypeptide, under conditions conductive for production of the polypeptide; and
   (b) recovering the polypeptide.

46. A method of producing the polypeptide of item 30 or 31, comprising:
   (a) cultivating a host cell of item 44 under conditions conducive for production of the polypeptide; and
   (b) recovering the polypeptide.

47. A transgenic plant, plant part or plant cell transformed with a polynucleotide encoding the polypeptide of item 30 or 31.

48. A whole broth formulation or cell culture composition comprising a polypeptide of item 30 or 31.

The present invention is further described by the following examples that should not be construed as limiting the scope of the invention.

EXAMPLES

Strains

*Trichophaea saccata* CBS804.70 was purchased from the Centraalbureau voor Schimmelcultures (Utrecht, the Netherlands). According to CBS, the strain was obtained from coal spoil tip soil, with high surface temperatures from Staffordshire, England in May 1968.

*Trichoderma harzianum*, originally named A00611 was deposited at the Centraalbureau voor Schimmelcultures, Ultrecht, Netherlands under the code: CBS223.93.

*Chaetomium thermophilum* var. *thermophilum* was purchased from Centraalbureau voor Schimmelcultures, Ultrecht, Netherlands under the code CBS144.50. According to CBS, the strain was obtained from decaying wheat straw from Leeds, England on or before 1950.

*Chaetomium* sp. ZY287 was obtained from a soil sample from Beijing, China in August 2013. *Mortierella* sp. ZY002 were obtained from a soil sample from Shanxi province, China in December 2012. *Metarhizium* sp. XZ2431 and *Geomyces auratus* were obtained from soil samples from Guizhou province, China in July 2014. *Ilyonectria rufa* was obtained from Tibet in August 2011.

Media and Solutions

YP+2% glucose medium was composed of 1% yeast extract, 2% peptone and 2% glucose.

YP+2% maltodextrin medium was composed of 1% yeast extract, 2% peptone and 2% maltodextrin.

PDA agar plates were composed of potato infusion (potato infusion was made by boiling 300 g of sliced (washed but unpeeled) potatoes in water for 30 minutes and then decanting or straining the broth through cheesecloth. Distilled water was then added until the total volume of the suspension was one liter, followed by 20 g of dextrose and 20 g of agar powder. The medium was sterilized by autoclaving at 15 psi for 15 minutes (Bacteriological Analytical Manual, 8th Edition, Revision A, 1998).

LB plates were composed of 10 g of Bacto-Tryptone, 5 g of yeast extract, 10 g of sodium chloride, 15 g of Bacto-agar, and deionized water to 1 liter.

LB medium was composed of 10 g of Bacto-Tryptone, 5 g of yeast extract, 10 g of sodium chloride, and deionized water to 1 liter.

COVE sucrose plates were composed of 342 g of sucrose, 20 g of agar powder, 20 ml of COVE salts solution, and deionized water to 1 liter. The medium was sterilized by autoclaving at 15 psi for 15 minutes (Bacteriological Analytical Manual, 8th Edition, Revision A, 1998). The medium was cooled to 60° C. and 10 mM acetamide, 15 mM CsCl, TRITON® X-100 (50 µl/500 ml) were added.

COVE salts solution was composed of 26 g of MgSO4·7H2O, 26 g of KCL, 26 g of KH2PO4, 50 ml of COVE trace metals solution, and deionized water to 1 liter.

COVE trace metals solution was composed of 0.04 g of $Na_2B_4O_7 \cdot 10H_2O$, 0.4 g of $CuSO_4 \cdot 5H_2O$, 1.2 g of $FeSO_4 \cdot 7H_2O$, 0.7 g of $MnSO_4 \cdot H_2O$, 0.8 g of $Na_2MoO_4 \cdot 2H_2O$, 10 g of $ZnSO_4 \cdot 7H_2O$, and deionized water to 1 liter.

Dap-4C medium was composed of 20 g Dextrose, 10 g Maltose, 11 g $MgSO_4 \cdot 7H_2O$, 1 g $KH_2PO_4$, 2 g Citric Acid, 5.2 g $K_3PO_4 \cdot H_2O$, 0.5 g Yeast Extract (Difco), 1 ml Dowfax 63N10 (Dow Chemical Company), 0.5 ml KU6 trace metals solution, 2.5 g $CaCO_3$, and deionized water to 1 liter. The medium was sterilized by autoclaving at 15 psi for 15 minutes (Bacteriological Analytical Manual, 8th Edition, Revision A, 1998). Before use, Dap-4C medium was added 3.5 ml sterile 50% $(NH_4)_2HPO_4$ and 5 ml sterile 20% Lactic Acid per 150 ml medium.

Dap-2C medium was composed of 20 g maltodextrin, 11 g $MgSO_4 \cdot 7H_2O$, 1 g $KH_2PO_4$, 2 g Citric Acid, 5.2 g $K_3PO_4 \cdot H_2O$, 0.5 g Yeast Extract (Difco), 1 ml Dowfax 63N10 (Dow Chemical Company), 0.5 ml KU6 trace metals solution, 2.5 g $CaCO_3$, and deionized water to 1 liter. The medium was sterilized by autoclaving at 15 psi for 15 minutes (Bacteriological Analytical Manual, 8th Edition, Revision A, 1998). Before use, Dap-4C medium was added 3.5 ml sterile 50% (NH$_4$)$_2$HPO$_4$ and 5 ml sterile 20% Lactic Acid per 150 ml medium.

KU6 trace metals solution was composed of 0.13 g NiCl$_2$, 2.5 g CuSO$_4$·5H$_2$O, 13.9 g FeSO$_4$·7H$_2$O, 8.45 g MnSO$_4$·H$_2$O, 6.8 g ZnCl$_2$, 3 g Citric Acid, and deionized water to 1 liter.

PDA medium was composed of 39 g of potato dextrose agar and deionized water to 1 liter.

Horikoshi medium contained 10 g of glucose, 5 g of peptone, 5 g of yeast extract, 1 g of K$_2$HPO$_4$, 0.2 g of MgSO$_4$ 7H$_2$O, 15 g of agar in 900 ml of distilled water. Autoclave at 121° C. for 15 minutes. After autoclaving, aseptically add 100.0 ml of sterile 10% Na$_2$CO$_3$ to the medium. Adjust for final pH of 10.0.

YPM medium contained 1% of Yeast extract, 2% of Peptone and 2% of Maltose.

Selective medium was composed of 342 g of sucrose, 20 ml of salt solution, 20 g of agar.

Salt solution was composed of 26 g of KCl, 26 g of MgSO$_4$ 7H$_2$O, 76 g of KH$_2$PO$_4$, 50 ml of trace element solution, in water with final volume of 1 L.

Trace element solution was composed of 400 mg of Na$_2$B$_4$O$_7$ 10H$_2$O, 400 mg of CuSO$_4$ 5H$_2$O, 800 mg of FeSO$_4$ 7H$_2$O, 800 mg of MnSO$_4$ 2H$_2$O, 800 mg of Na$_2$MoO$_4$ 2H$_2$O, 8 g of ZnSO$_4$ 7H$_2$O in water with final volume of 1 L.

Slant medium was composed of 30 g of sucrose, 20 ml of salt solution, 20 g of agar.

Example 1: Expression of the GH24 Lysozyme from *Trichophaea saccata*

The fungal strain was cultivated in 100 ml of YP+2% glucose medium in 1000 ml Erlenmeyer shake flasks for 5 days at 20° C. Mycelia were harvested from the flasks by filtration of the medium through a Buchner vacuum funnel lined with MIRACLOTH® (EMD Millipore, Billerica, MA, USA). Mycelia were frozen in liquid nitrogen and stored at −80° C. until further use. Genomic DNA was isolated using a DNEASY® Plant Maxi Kit (QIAGEN GMBH, Hilden Germany) according to the manufacturer's instructions.

Genomic sequence information was generated by Illumina MySeq (Illumina Inc., San Diego, CA). The polypeptide coding sequence for the entire coding region was cloned from *Trichophaea saccata* CBS804.70 genomic DNA by PCR using the primers F-80470 and R-80470 (SEQ ID NO: 258 and SEQ ID NO: 259 respectively) as described below.

```
                                         (SEQ ID NO: 258)
5'- ACACAACTGGGGATCCACCATGCACGCTCTCACCCTTCT -3'

(SEQ ID NO: 259)
5'- CTAGATCTCGAGAAGCTTTTAGCACTTGGGAGGGTGGG -3'
```

Bold letters represent *Trichophaea saccata* enzyme coding sequence. Restriction sites are underlined. The sequence to the left of the restriction sites is homologous to the insertion sites of pDau109 (WO 2005/042735).

Extensor HIFI PCR mix, 2× concentration (Thermo Scientific cat no AB-0795) was used for experiment.

The amplification reaction (25 µl) was performed according to the manufacturer's instructions (Thermo Scientific cat no AB-0795) with the following final concentrations:

PCR Mix:
    0.5 µM Primer F-80470
    0.5 µM Primer R-80470
    12.5 µl Extensor HIFI PCR mix, 2× conc.
    11.0 µl H$_2$O
    10 ng of *Trichophaea saccata* CBS804.70 genomic DNA.

The PCR reaction was incubated in a DYAD® Dual-Block Thermal Cycler (BioRad, USA) programmed for 1 cycle at 94° C. for 30 seconds; 30 cycles each at 94° C. for 30 seconds, 52° C. for 30 seconds and 68° C. for 60 seconds followed by 1 cycle at 68° C. for 6 minutes. Samples were cooled to 10° C. before removal and further processing.

Three µl of the PCR reaction were analyzed by 1% agarose gel electrophoresis using 40 mM Tris base, 20 mM sodium acetate, 1 mM disodium EDTA (TAE) buffer. A major band of about 946 bp was observed. The remaining PCR reaction was purified directly with an ILLUSTRA™ GFX™ PCR DNA and Gel Band Purification Kit (GE Healthcare, Piscataway, NJ, USA) according to the manufacturer's instructions.

Two µg of plasmid pDau109 was digested with Bam HI and Hind III and the digested plasmid was run on a 1% agarose gel using 50 mM Tris base-50 mM boric acid-1 mM disodium EDTA (TBE) buffer in order to remove the stuffer fragment from the restricted plasmid. The bands were visualized by the addition of SYBR® Safe DNA gel stain (Life Technologies Corporation, Grand Island, NY, USA) and use of a 470 nm wavelength transilluminator. The band corresponding to the restricted plasmid was excised and purified using an ILLUSTRA™ GFX™ PCR DNA and Gel Band Purification Kit. The plasmid was eluted into 10 mM Tris pH 8.0 and its concentration adjusted to 20 ng per µl. An IN-FUSION® PCR Cloning Kit (Clontech Laboratories, Inc., Mountain View, CA, USA) was used to clone the 983 bp PCR fragment into pDau109 digested with Bam HI and Hind III (20 ng). The IN-FUSION® total reaction volume was 10 µl. The IN-FUSION® total reaction volume was 10 µl. The IN-FUSION® reaction was transformed into FUSION-BLUE™ *E. coli* cells (Clontech Laboratories, Inc., Mountain View, CA, USA) according to the manufacturer's protocol and plated onto LB agar plates supplemented with 50 µg of ampicillin per ml. After incubation overnight at 37° C., transformant colonies were observed growing under selection on the LB plates supplemented with 50 µg of ampicillin per ml.

Several colonies were selected for analysis by colony PCR using the pDau109 vector primers described below. Four colonies were transferred from the LB plates supplemented with 50 µg of ampicillin per ml with a yellow inoculation pin (Nunc A/S, Denmark) to new LB plates supplemented with 50 of ampicillin per ml and incubated overnight at 37° C.

```
Primer 8653:
                                         (SEQ ID NO: 260)
5'-GCAAGGGATGCCATGCTTGG-3'

Primer 8654:
                                         (SEQ ID NO: 261)
5'-CATATAACCAATTGCCCTC-3'
```

Each of the three colonies were transferred directly into 200 µl PCR tubes composed of 5 µl of 2× Extensor HIFI PCR mix, (Thermo Fisher Scientific, Rockford, IL, USA), 0.5 µl of primer 8653 (10 pm/µl), 0.5 µl of primer 8654 (10 pm/µl), and 4 µl of deionized water. Each colony PCR was incubated in a DYAD® Dual-Block Thermal Cycler programmed for 1 cycle at 94° C. for 60 seconds; 30 cycles each at 95° C. for 30 seconds, 60° C. for 45 seconds, 72° C. for 60 seconds, 68° C. for 10 minutes, and 10° C. for 10 minutes.

Three μl of each completed PCR reaction were submitted to 1% agarose gel electrophoresis using TAE buffer. All four *E. coli* transformants showed a PCR band of about 980 bp. Plasmid DNA was isolated from each of the four colonies using a QIAprep Spin Miniprep Kit (QIAGEN GMBH, Hilden Germany). The resulting plasmid DNA was sequenced with primers 8653 and 8654 (SEQ ID NO: 260 and 261) using an Applied Biosystems Model 3730 Automated DNA Sequencer using version 3.1 BIG-DYE™ terminator chemistry (Applied Biosystems, Inc., Foster City, CA, USA). One plasmid, designated pKKSC0312-2, was chosen for transforming *Aspergillus oryzae* MT3568. *A. oryzae* MT3568 is an amdS (acetamidase) disrupted gene derivative of *Aspergillus oryzae* JaL355 (WO 2002/40694) in which pyrG auxotrophy was restored by inactivating the *A. oryzae* amdS gene. Protoplasts of *A. oryzae* MT3568 were prepared according to the method described in EP 0238023, pages 14-15.

*E. coli* 3701 containing pKKSC0312-2 was grown overnight according to the manufacturer's instructions (Genomed) and plasmid DNA of pKKSC0312-2 was isolated using a Plasmid Midi Kit (Genomed JETquick kit, cat.nr. 400250, GENOMED GmbH, Germany) according to the manufacturer's instructions. The purified plasmid DNA was transformed into *Aspergillus oryzae* MT3568. *A. oryzae* MT3568 protoplasts were prepared according to the method of Christensen et al., 1988, *Bio/Technology* 6: 1419-1422. The selection plates consisted of COVE sucrose with +10 mM acetamide+15 mM CsCl+TRITON® X-100 (50 μl/500 ml). The plates were incubated at 37° C. Briefly, 8 μl of plasmid DNA representing 3 ugs of DNA was added to 100 μl MT3568 protoplasts. 250 μl of 60% PEG solution was added and the tubes were gently mixed and incubate at 37° for 30 minutes. The mix was added to 10 ml of pre melted Cove top agarose (The top agarose melted and then the temperature equilibrated to 40 C in a warm water bath before being added to the protoplast mixture). The combined mixture was then plated on two Cove-sucrose selection petri plates with 10 mM Acetamide. The plates were incubated at 37° C. for 4 days. Single *Aspergillus* transformed colonies were identified by growth on plates using the selection Acetimide as a carbon source. Each of the four *A. oryzae* transformants were inoculated into 750 μl of YP medium supplemented with 2% glucose and also 750 μl of 2% maltodextrin and also DAP4C in 96 well deep plates and incubated at 37° C. stationary for 4 days. At the same time the four transformants were restreaked on COVE-2 sucrose agar medium.

Culture broth from the *Aspergillus oryzae* transformants were then analyzed for production of the GH24 polypeptide by SDS-PAGE using NUPAGE® 10% Bis-Tris SDS gels (Invitrogen, Carlsbad, CA, USA) according to the manufacturer's recommendations. A protein band at approximately 27 kDa was observed for each of the *Aspergillus oryzae* transformants. One *A. oryzae* transformant was cultivated in 1000 ml Erlenmeyer shake flasks containing 100 ml of DAP4C medium at 26° C. for 4 days with agitation at 85 rpm and purified as described in example 2.

Example 2: Purification of the GH24 Lysozyme from *Trichophaea saccata*

The fermentation supernatant with the GH24 lysozyme was filtered through a Fast PES Bottle top filter with a 0.22 μm cut-off. The resulting solution was diafiltrated with 5 mM Na-acetate, pH 4.5 and concentrated (volume reduced by a factor of 10) on an Ultra Filtration Unit (Sartorius) with a 10 kDa cut-off membrane.

After pretreatment about 275 mL of the lysozyme containing solution was purified by chromatography on SP Sepharose (approximately 60 mL) in a XK26 column eluting the bound lysozyme with 0 to 100% gradient of buffer A (50 mM Na-acetate pH 4.5) and buffer B (50 mM Na-acetate+1 M NaCl pH 4.5) over 10 column volumes. The fractions from the column were pooled based on the chromatogram (absorption at 280 and 254 nm) and SDS-PAGE analysis.

The molecular weight, as estimated from SDS-PAGE, was approximately 27 kDa and the purity was >90%.
Characteristics for the GH24 Lysozyme from *Trichophaea saccata*

Determination of the N-terminal sequence was: YPVKTDL.

The calculated molecular weight from this mature sequence is 26205.5 Da $(M+H)^+$.

The molecular weight determined by intact molecular weight analysis was 26205.3 Da. $(M+H)^+$.

The mature sequence (from EDMAN N-terminal sequencing data, intact molecular weight analysis and proteomic analysis with 92% amino acid coverage):

(SEQ ID NO: 257)
YPVKTDLHCRSSPSTSASIVRTYSSGTEVQIQCQTTGTSVQGSNVWDKTQH

GCYVADYYVKTGHSGIFTTKCGSSSGGGSCKPPPINAATVALIKEFEGFVP

KPAPDPIGLPTVGYGHLCKTKGCKEVPYSFPLTQETATKLLQSDIKTFTSC

VSNYVKDSVKLNDNQYGALASWAFNVGCGNVQTSSLIKRLNAGENPNTVAA

QELPKWKYAGGKVMPGLVRRRNAEVALFKKPSSVQAHPPKC.

Example 3: Expression of the LED Alone from *Trichophaea saccata*

In order to establish the properties of the newly defined lysozyme enhancing domain, an expression construct in which the N-terminal portion of the GH24 polypeptide coding sequence from example 1 was expressed.

The amino acid sequence shown below represents the signal peptide and the NZ4 domain. The signal peptide is underlined.

(SEQ ID NO: 272)
<u>MHALTLLTATLFGLAAA</u>YPVKTDLHCRSSPSTSASIVRTYSSGTEVQIQCQ

TTGTSVQGSNVWDKTQHGCYVADYYVKTGHSGIFTTKCG

The DNA representing SEQ ID NO: 272 is shown below as SEQ ID NO: 271 wherein the signal peptide is underlined.

(SEQ ID NO: 271)
<u>ATGCACGCTCTCACCCTTCTCACCGCAACCCTCTTCGGTCTCGCAGCGGCC</u>

<u>TACCCAGTGAAGACCGACCTTCACTGCCGCTCCTCTCCCAGCACTTCCGCC</u>

AGCATCGTCCGCACCTACTCCAGTGGAACGGAAGTCCAGATCCAGTGCCAG

ACCACGGGCACTTCGGTCCAAGGATCCAATGTCTGGGACAAGACCCAGCAC

GGTTGCTACGTCGCAGACTACTACGTCAAGACCGGGCATTCTGGGATTTTC

ACCACCAAGTGCGGT

PCR primers were designed in order to amplify the DNA fragment SEQ ID NO: 271 from pKKSC0312-2 of example 1. The forward primer from example 1 (SEQ ID NO: 258) could be reused. For the reverse primer, a TAA stop codon was added to the DNA sequence of the above and then the Infusion cloning site for the HindIII site was added to create the primer below:

(SEQ ID NO: 274)
AGATCTCGAGAAGCTTATACCGCACTTGGTGGTGAAA.

The amplification reaction (25 µl) was performed according example 1. The 270 base pair PCR product was cloned into vector pDau222 also as described in example 1.

Culture broth from the *Aspergillus oryzae* transformants were then analyzed for production of the LED polypeptide by SDS-PAGE using NUPAGE® 8% Bis-Tris SDS gels (Invitrogen, Carlsbad, CA, USA) according to the manufacturer. A band at approximately 14 kDa was observed for each of the *Aspergillus oryzae* transformants. The actual size appears larger than the predicted size of 8.4 kDa possibly because of post translational modification. One *A. oryzae* transformant producing the LED polypeptide was cultivated in 1000 ml Erlenmeyer shake flasks containing 100 ml of DAP4C medium at 30° C. for 4 days with agitation at 150 rpm and purified as described in example 4.

Example 4: Expression of the LED Alone from *Trichophaea saccata*

The fermentation supernatant with the LED alone from *Trichophaea saccata* was filtered through a Fast PES Bottle top filter with a 0.22 µm cut-off. The resulting solution was desalted on a G25 Sephadex column (approximately 500 mL) into 50 mM Na-acetate, pH 4.5. Following this the protein containing solution (approximately 125 ml) was purified by chromatography on SP Sepharose (approximately 50 mL) in a XK26 column eluting the bound lysozyme with 0 to 100% gradient of buffer A (50 mM Na-acetate pH 4.5) and buffer B (50 mM Na-acetate+1 M NaCl pH 4.5) over 10 column volumes. The fractions from the column were pooled based on the chromatogram (absorption at 280 and 254 nm) and SDS-PAGE analysis.

The molecular weight, as estimated from SDS-PAGE, was 6-10 kDa and the purity was >95%. The calculated molecular weight from this mature sequence is 7906.64 Da.

The mature sequence (from proteomic analysis with 97% amino acid coverage) was determined to be:

(SEQ ID NO: 273)
YPVKTDLHCRSSPSTSASIVRTYSSGTEVQIQCQTTGTSVQGSNVWDKTQH

GCYVADYYVKTGHSGIFTTKCG.

Example 5: Expression of the GH24 Domain of *Trichophaea saccata* CBS804.70

In order to determine if the lysozyme enhancing domain has functional or enhancing properties for the associated GH24 lysozyme, a construct was cloned and protein expressed in which the LED had been removed from the GH24 lysozyme. The construct was made as follows:

A synthetic gene was created as described below.

Based on multiple sequence alignments, QCVG or similar appears to be fairly well conserved in the GH24 fungal lysozymes without the LED domain. Therefor the signal and the sequence downstream QCVG sequence from SEQ ID NO: 279 (GH24 from *Acremonium acalophilum*) was used in part of the construct. This peptide sequence was then added directly to the mature peptide fragment containing only the GH24 lysozyme region of SEQ ID NO: 257 resulting in the amino acid sequence below:

(SEQ ID NO: 269)
MAKVSTLTIALLTMASQARAQCVGCKPPPINAATVALIKEFEGFVPKPAPD

PIGLPTVGYGHLCKTKGCKEVPYSFPLTQETATKLLQSDIKTFTSCVSNYV

KDSVKLNDNQYGALASWAFNVGCGNVQTSSLIKRLNAGENPNTVAAQELPK

WKYAGGKVMPGLVRRRNAEVALFKKPSSVQAHPPKC.

A synthetic DNA (SEQ ID NO: 268) that had been codon optimised for expression in *Aspergillus oryzae* was ordered from GeneArt® Gene Synthesis, Life Technologies. The synthetic DNA conveniently had BamHI and HindIII restriction sites added to the ends so as to make a BamHI-HindIII restricted fragment compatible with the cloning vector pDau109 used in example 1.

The fragment was received from GeneArt in kanamycin resistant vector pMK and the plasmid was dissolved DNA in 50 uls in 10 mM Tris, pH7.5. 20 uls of the mixture with BamHI-HindIII according to the protocol below:

| | |
|---|---|
| Plasmid | 20 µl |
| Cut smart buffer: 10x #B7204S | 4.0 µl |
| Milli-Q H₂O: | 14.0 µl |
| Hind III HF: NEB #R3104S | 1 µl |
| BamH HF: NEB #R3136S | 1 µl |
| Total volume | 40 µl |

The reaction was incubated for 3 hours at 37° C. The restriction digest was purified with the GFX PCR DNA and Gel Band purification Kit (Cat.no 28-9034-71) from GE Healthcare and eluted in 40 uls 10 mM Tris, pH 7.5. The purified restriction digest was then used in a simple ligation with BamHI-HindIII restricted pDau109 (example 1) according to the T4 DNA ligase manufacturer's instructions (New England Biolabs., neb.com).

2.5 µl of the 10 µl ligation was used to transform 25 µl Stelar (Life Technologies) Competent cells according to the manufacturer's instructions and the treated cells plated on LB agar plates with 50 mg/ml ampicillin. Colony PCR of select tranformants was performed according to example 1 and the PCR fragments sequenced. A single plasmid, selected as being PCR error free, was transformed into *Aspergillus oryzae* MT3568 according to example 1. Among the several transformants that produced the secreted product of about 20 kDa, one was chosen and cultivated in 1000 ml Erlenmeyer shake flasks containing 100 ml of DAP4C medium at 30° C. for 4 days with agitation at 150 rpm and purified as described in example 6.

Example 6: Purification of the GH24 Domain of *Trichophaea saccata* CBS804.70

The fermentation supernatant with the GH24 domain was filtered through a Fast PES Bottle top filter with a 0.22 µm cut-off. The resulting solution was diafiltrated with 50 mM Na-acetate, pH 4.5 on an Ultra Filtration Unit (Sartorius) with a 10 kDa cut-off membrane.

After pretreatment about 500 mL of the lysozyme containing solution was purified by chromatography on SP Sepharose (approximately 50 mL) in a XK26 column eluting the bound protein with 0 to 100% gradient of buffer A (50 mM Na-acetate pH 4.5) and buffer B (50 mM Na-acetate+1 M NaCl pH 4.5) over 10 column volumes. The fractions from the column were pooled based on the chromatogram (absorption at 280 and 254 nm) and SDS-PAGE analysis.

The molecular weight, as estimated from SDS-PAGE, was approximately 20 kDa and the purity was >90%.

The calculated molecular weight from this mature sequence is 18182.86 Da.

The mature sequence (from proteomic analysis with 72% amino acid coverage) was determined to be:

(SEQ ID NO: 270)
QCVGCKPPPINAATVALIKEFEGFVPKPAPDPIGLPTVGYGHLCKTKGCKE

VPYSFPLTQETATKLLQSDIKTFTSCVSNYVKDSVKLNDNQYGALASWAFN

VGCGNVQTSSLIKRLNAGENPNTVAAQELPKWKYAGGKVMPGLVRRRNAEV

ALFKKPSSVQAHPPKC.

Example 7: Cloning and Expression of GH24 Lysozyme from *Trichoderma harzianum* A00611

*Trichoderma harzianum*, originally named A00611 was deposited at the Centraalbureau voor Schimmelcultures, Ultrecht, Netherlands under the code: CBS223.93. *Trichoderma harzianum* A00611 was grown on Potato Dextrose Agar at 26° C. for several days. Mycelia was harvested directly from the inoculated PDA agar plate and the DNA prepared as in example 1.

The polypeptide coding sequence for the entire coding region was cloned from *Trichoderma harzianum* A00611 genomic DNA by PCR using primers SEQ ID NO: 275 and SEQ ID NO: 276 as given below.

F
SEQ ID NO: 275
5'-ACACAACTGGGGATCCACCATGAAGACTGCCTTTGCTGC-3'

R
SEQ ID NO: 276
5'-AGATCTCGAGAAGCTTATCACTGGCACTTTGGATAGGC-3'

Bold letters represent *Trichoderma harzianum* enzyme coding sequence. Restriction sites are underlined. The sequence to the left of the restriction sites is homologous to the insertion sites of pDau109 (WO 2005/042735).

Cloning of the 800 bp PCR fragment, transformation into *Aspergillus oryzae* and production of culture fluid for purification of the GH24 lysozyme was performed according to example 1.

A band at approximately 27 kDa was observed for each of the *Aspergillus oryzae* transformants. One *A. oryzae* transformant producing the polypeptide was chosen and cultivated in 1000 ml Erlenmeyer shake flasks containing 100 ml of DAP4C medium at 30° C. for 4 days with agitation at 150 rpm and purified as described in example 8.

Example 8: Purification of the GH24 Lysozyme from *Trichoderma harzianum* A00611

The fermentation supernatant with the GH24 lysozyme from *Trichoderma harzianum* A00611 was filtered through a Fast PES Bottle top filter with a 0.22 μm cut-off. About one liter was obtained and the pH was adjusted to 4.5 with diluted acetic acid. The sample was diluted to two liters with Milli-Q water.

After pretreatment about 1000 mL of the lysozyme containing solution was purified by chromatography on SP Sepharose (approximately 30 mL) in a XK26 column eluting the bound lysozyme with 0 to 100% gradient of buffer A (50 mM Na-acetate pH 4.5) and buffer B (50 mM Na-acetate+1 M NaCl pH 4.5) over 10 column volumes. The fractions from the column were pooled based on the chromatogram (absorption at 280 and 254 nm) and SDS-PAGE analysis.

The molecular weight, as estimated from SDS-PAGE, was approximately 27 kDa and the purity was >90%.

Example 9: Cloning and Expression of the GH24 Lysozyme from *Chaetomium thermophilum* var. *thermophilum*

*Chaetomium thermophilum* var. *thermophilum* was purchased from Centraalbureau voor Schimmelcultures, Ultrecht, Netherlands under the code CBS144.50. The strain was grown on Potato Dextrose Agar at 37° C. for several days. Mycelia was harvested directly from the inoculated PDA agar plate and the DNA prepared as in example 1.

The polypeptide coding sequence for the entire coding region was cloned from *Chaetomium thermophilum* CBS144.50 genomic DNA by PCR using primers SEQ ID NO: 277 and SEQ ID NO: 278 as given below.

F
SEQ ID NO: 277
5'- ACACAACTGGGGATCCACCATGAAGTTCGCCATCCTCGC-3'

R
SEQ ID NO: 278
5'- AGATCTCGAGAAGCTTATCAGCACTTAACAGGAAGAGCC-3'

Bold letters represent GH24 enzyme coding sequence. Restriction sites are underlined. The sequence to the left of the restriction sites is homologous to the insertion sites of pDau109 (WO 2005/042735).

Cloning of the 960 bp PCR fragment, transformation into *Aspergillus oryzae* and production of culture fluid for purification of the GH24 lysozyme was performed according to example 1. A band at approximately 26 kDa was observed for each of the *Aspergillus oryzae* transformants. One *A. oryzae* transformant producing the polypeptide was chosen and cultivated in 1000 ml Erlenmeyer shake flasks containing 100 ml of DAP4C medium at 30° C. for 4 days with agitation at 150 rpm and purified as described in example 10.

Example 10: Purification of the GH24 Lysozyme from *Chaetomium thermophilum* Var. *thermophilum*

The fermentation supernatant with the GH24 lysozyme from *Chaetomium thermophilum* var. *thermophilum* was filtered through a Fast PES Bottle top filter with a 0.22 μm cut-off. The resulting solution was diafiltrated with 50 mM Na-acetate, pH 4.5 and concentrated (volume reduced by a factor of 10) on an Ultra Filtration Unit (Sartorius) with a 10 kDa cut-off membrane.

After pretreatment about 300 mL of the lysozyme containing solution was purified by chromatography on SP Sepharose (approximately 60 mL) in a XK26 column eluting the bound lysozyme with 0 to 100% gradient of buffer A (50 mM Na-acetate pH 4.5) and buffer B (50 mM Na-acetate+1 M NaCl pH 4.5) over 10 column volumes. The fractions from the column were pooled based on the chromatogram (absorption at 280 and 254 nm) and SDS-PAGE analysis.

The molecular weight, as estimated from SDS-PAGE, was approximately 27 kDa and the purity was >90%.

Example 11: Determination of Lysozyme Activity

Lysozyme activity was determined by measuring the decrease (drop) in absorbance/optical density of a solution of resuspended *Micrococcus* lysodeikticus ATTC No. 4698 (Sigma-Aldrich M3770) or *Exiguobacterium undea* (DSM14481) measured in a spectrophotometer at 540 nm.
Preparation of *Micrococcus lysodeikticus* Substrate Before use, the cells were resuspended in citric acid—phosphate buffer pH 6.5 to a concentration of 0.5 mg cells/mL and the optical density (OD) at 540 nm was measured. The cell suspension was then adjusted so that the cell concentration equalled an OD540=1.0. The adjusted cell suspension was then stored cold before use. Resuspended cells were used within 4 hours.
Preparation of Dried Cells of *Exiquobacterium undae* Substrate A culture of *E. undae* (DSM14481) was grown in 100 mL LB medium (Fluka 51208, 25 g/L) in a 500 mL shake-flask at 30° C., 250 rpm overnight. The overnight culture was then centrifuged at 20° C. and 5000 g for 10 minutes, and the pellet was then washed twice with sterile milliQ water, and resuspended in Milli-Q water. The washed cells were centrifuged for 1 minute at 13000 rpm and as much as possible of the supernatant was decanted. The washed cells were dried in a vacuum centrifuge for 1 hour. The cell pellet was resuspended in citric acid—phosphate buffer pH 4, 5 or 6 so that the optical density (OD) at 540 nm=1.
Measurement of Lysozyme Antimicrobial Activity in the Turbidity Assay The lysozyme sample to be measured was diluted to a concentration of 100-200 mg enzyme protein/L in citric acid—phosphate buffer pH 4, 5 or 6, and kept on ice until use. In a 96 well microtiterplate (Nunc) 200 μL of the substrate was added to each well, and the plate was incubated at 37° C. for 5 minutes in a VERSAmax microplate reader (Molecular Devices). Following incubation, the absorbance of each well was measured at 540 nm (start value). To start the activity measurement, 20 μL of the diluted lysozyme sample was added to each substrate (200 μL) and kinetic measurement of absorbance at 540 nm was initiated for minimum 30 minutes up to 24 hours at 37° C. The measured absorbance at 540 nm was monitored for each well and over time a drop in absorbance is seen if the lysozyme has lysozyme activity. The results are presented in table 2 below.

TABLE 2

Lysozyme Activity against *Micrococcus lysodeikticus* and *Exiguobacterium undea* as measured by Optical Density Drop

| GH24 Lysozyme | *Micrococcus lysodeikticus*[1] | *Exiguobacterium undae*[1] |
|---|---|---|
| GH24 Lysozyme from *Trichophaea saccata* (SEQ ID NO: 257) | ++ (pH 6) | ++ (pH 6) |
| GH24 lysozyme from *Chaetomium thermophilum* (SEQ ID NO: 264) | ++++ (pH 5) | ++++ (pH 6) |
| GH24 lysozyme from *Trichophaea saccata* | − (pH 6) | Not tested |

TABLE 2-continued

Lysozyme Activity against *Micrococcus lysodeikticus* and *Exiguobacterium undea* as measured by Optical Density Drop

| GH24 Lysozyme | *Micrococcus lysodeikticus*[1] | *Exiguobacterium undae*[1] |
|---|---|---|
| lacking LED (SEQ ID NO: 270) | | |
| GH24 lysozyme from *Acremonium alcalophilum* (SEQ ID NO: 280) | + (pH 4.5) | − (pH 3-7) |

[1]Means no significant effect;
+ means small effect;
++ means medium effect;
+++ means large effect;
++++ means very large effect.
The pH value in the brackets lists the assay pH based on lysozyme-substrate combination.

The data shows that the two GH24 lysozymes that naturally comprise the lysozyme enhancing domain (LED) (SEQ ID NO: 257 and 264) showed good activity against both substrates. In comparison, SEQ ID NO: 270 (which is SEQ ID NO: 257 but lacking the LED) demonstrated no lysozyme activity against *Micrococcus lysodeikticus* and the GH24 lysozyme which does not natively comprise a LED (SEQ ID NO: 280) showed a small amount of activity.

Example 12: Determination of Antimicrobial Activity

The antimicrobial activity of 3 GH24 lysozymes also comprising the lysozyme enhancing domain (LED) (SEQ ID NO: 257, 264 and 267), two GH24 lysozymes which natively do not comprise the LED (SEQ ID NO: 279 and 280) and the GH24 lysozyme of SEQ ID NO. 257 for which the LED was removed (resulting in SEQ ID NO: 269) against *Clostridium perfringens* DSM756 was tested using an RDA as described previously by Lehrer et al. ("Ultrasensitive assays for endogenous antimicrobial polypeptides", *J. Immunol. Methods* 137:167-73 (1991)), but with several modifications.

Briefly, RDA bacteria were prepared by streaking *C. perfringens* DSM756 from freeze stocks on Luria-Bertani agar plates (Sigma L3027) and the plates were incubated overnight at 37° C. under anaerobic conditions (Anaerogen, Oxoid) in a jar. The following day colonies were suspended in 0.9% NaCl and the suspensions were adjusted to McFarland std. 1. 87% sterile glycerol was added to give a final glycerol concentration of 20% and the cells were frozen at −80° C. until use. For estimation of colony forming units (CFU) per milliliter of the RDA bacteria 10-fold dilution series were prepared of the freeze stock in 0.9% NaCl and 100 μl of the dilutions were plated on Luria-Bertani agar plates (Sigma L3027) and incubated overnight at 37° C. under anaerobic conditions (Anaerogen, Oxoid) in a jar.

When preparing the RDA plates broth media with agar was melted and cooled to 42° C. Two media were tested in the experiment:
  a) ½ Mueller-Hinton broth (MHB) (Sigma/Fluka, 90922) (i.e., adjusted to pH 6 with 4 M HCl and diluted 1:1 with water) with 1.5% agarose, and
  b) ¹/₁₀ Mueller-Hinton broth (MHB) (Sigma/Fluka, 90922) (i.e., diluted 1:9 with water) with 1% agarose.

For each assay plate 30 ml of melted media was added to achieve around $5.0 \times 10^5$ cfu/mL *C. perfringens* DSM756 and this was poured into a single-well omnitray (Nunc) plate. The omnitray plate was overlaid with a TSP plate (Nunc) and left to solidify (at room temperature or below). Afterwards, the TSP plate was removed; leaving 96 wells, in which 10 μL of the compound of interest could be tested.

10 μl of the test solutions were spotted pr. well and the plates were incubated over night at 37° C. in a jar under anaerobic condition (Anaerogen, Oxoid). The following day a clearing zone indicated inhibition of growth of test bacteria and thereby antimicrobial activity. For the RDA plates with ½ MHB, the clearing zones were visualized by coloring with MTT (3-(4,5-dimethylthiazol-2-yl)-2,5-diphenyltetrazolium bromide, a yellow tertrazole), that is reduced to purple formazan in living cells (Mosmann, 1983, "Rapid colorimetric assay for cellular growth and survival: application to proliferation and cytotoxicity assays", *Journal of Immunological Methods* 65(1-2): 55-63). This coloring provides for a dark coloring of living cells and no coloring of the clearing zones without living cells.

Bacitracin zinc salt (Sigma B-8800) (50 μg/ml) was included as a positive control and lysozymes were tested using a solution of 100 μg/ml. The results are presented in table 3 below.

TABLE 3

Antimicrobial Activity against *Clostridium perfringens* as measured by RDA

| | Diameter of clearing zone (mm) | | |
|---|---|---|---|
| Experiment | 1 | 2 | 1 |
| Lysozyme | 1/10 MHB pH 7 | 1/10 MHB pH 7 | 1/2 MHB pH 6 |
| GH24 Lysozyme from *Trichophaea saccata* (SEQ ID NO: 257) | 9 | 8 | 11 |
| GH24 lysozyme from *Chaetomium thermophilum* (SEQ ID NO: 264) | 9 | 7 | 10 |
| GH24 lysozyme from *Trichoderma harzianum* (SEQ ID NO: 267) | 10 | 8 | 12 |
| GH24 lysozyme from *Trichophaea saccata* lacking LED (SEQ ID NO: 270) | (8)* | (5)* | 0 |
| GH24 lysozyme from *Acremonium alcalophilum* (SEQ ID NO: 279) | 0 | 0 | 0 |
| GH24 lysozyme from *Acremonium alcalophilum* (SEQ ID NO: 280) | 0 | 0 | 0 |
| Bacitracin zinc salt | 22 | 18 | 11 |

*Incomplete inhibition of growth visible after MTT colouring

The 3GH24 lysozymes also comprising the lysozyme enhancing domain (LED) (SEQ ID NO: 257, 264 and 267) all showed antimicrobial activity against viable cells of *C. perfringens* DSM756 under both tested conditions. In comparison, the two GH24 lysozymes which natively do not comprise the LED (SEQ ID NO: 279 and 280) did not inhibit growth under the test conditions. Furthermore, the GH24 lysozyme for which the LED was removed (SEQ ID NO: 269) also showed no inhibition of growth in ½ MHB, pH 6, although incomplete inhibition of growth was observed when using 1/10 MBH, pH 7.

Thus, the results show that GH24 lysozymes tested which comprise a LED show significant activity *Clostridium perfringens* using the conditions 50% MHB, pH 6 whereas the GH24 lysozymes without the LED (either naturally or when the LED has been removed) do not show activity *Clostridium perfringens* using the conditions 50% MHB, pH 6.

Example 13: Temperature Stability

Temperature stability was determined for the GH24 lysozyme from *Trichophaea saccata* (SEQ ID NO: 257) by incubating the lysozyme at different temperatures (60-99° C.) for a short period of time (30, 60 and 90 seconds) after which the residual activity was measured for 1 h at 37° C. using *M. lysodeikticus* substrate prepared as described in Example 11.

Heat Treatment

The samples to be evaluated were diluted to a lysozyme concentration of 0.05 mg enzyme protein/mL in milliQ water. Initially 40 μL of each lysozyme sample was pipetted into PCR tubes (3 replicates) and the closed tubes were then kept on ice. The PCR tubes were placed in a preheated PCR machine for 30, 60 or 90 seconds at 60, 65, 70, 75, 80, 85, 90, 95 or 99° C. and then put back on ice for instant cooling. Non heated control samples corresponding to the heated samples were prepared and kept on ice.

Activity Measurement

The OD drop assay using *M. lysodeikticus* as substrate was used to determine lysozyme activity in heated and non-heated samples. Initially 20 μL of each sample (control and heat treated) was transferred to a 96-well microtiter plate, then 180 μL assay buffer (pH 6) and 20 μL *M. lysodeikticus* substrate was added to each well. The plate was immediately placed in an absorbance reader preheated to 37° C. and $OD_{540}$ recorded for 1 hour. The difference between the absorbance at T=0 and the time points was calculated as the ΔOD. The percentage residual activity was calculated by comparing the ΔOD of the heat treated sample with the corresponding ΔOD of the sample which was not heat treated (Table 5).

TABLE 5

Residual activity (%) of the GH24 lysozyme from *Trichophaea saccata* (SEQ ID NO: 257) measured by OD drop after heat treatment at different temperatures

| | Temperature (° C.) | | | | | | | | |
|---|---|---|---|---|---|---|---|---|---|
| Time (Sec) | 60 | 65 | 70 | 75 | 80 | 85 | 90 | 95 | 99 |
| 30 | 93 | 99 | 94 | 101 | 94 | 98 | 94 | 98 | 93 |
| 60 | 99 | 97 | 93 | 96 | 98 | 94 | 99 | 94 | 97 |
| 90 | 96 | 99 | 98 | 98 | 97 | 100 | 97 | 102 | 89 |

The results show that the GH24 lysozyme from *Trichophaea saccata* (SEQ ID NO: 257) is stable for at least 90 seconds at temperatures as high as 99° C.

Example 13: Thermostability Determined Using DSC

The thermostability of GH24 lysozyme from *Trichophaea saccata* (SEQ ID NO: 257) at different pH values was determined by Differential Scanning Calorimetry (DSC) using a VP-capillary DSC instrument (MicroCal Inc., Piscataway, NJ, USA) equipped with an auto sampler. Aliquots of the GH24 lysozyme, purified as described in Example 2, were buffer-changed (see buffer in table 6 below) using prepacked NAP-5 columns. The samples were diluted with the corresponding buffer to approximately 0.5 mg/ml and the buffer was used as reference solution. Sample and reference solutions (approx. 0.5 ml) were thermally pre-equilibrated for 10 minutes at 20° C. and the DSC scan was performed from 20 to 100° C. at a scan rate of 200 K/hour. Data-handling was performed using the MicroCal Origin software (version 7.0383). The thermal denaturation temperature, Td (° C.), was taken as the top of denaturation peak (major endothermic peak) in thermograms (Cp vs. T) obtained after heating the lysozyme solution in the buffer at a constant programmed heating rate. Denaturation temperatures were determined at an accuracy of approximately +/−0.5° C. and are given in table 6 below.

TABLE 6

Denaturation Temperature of the GH24 lysozyme from Trichophaea saccata (SEQ ID NO: 257) at various pH's

| Buffer | Td (° C.) |
| --- | --- |
| 50 mM Na-acetate, pH 4.5 | 70.0 |
| 50 mM Na-acetate, pH 5.5 | 70.8 |
| 50 mM Na-acetate, pH 6.5 | 69.7 |

Example 14: Lysozyme Enhancing Domain Binds to Bacterial Cells 250 mg Micrococcus lysodeiktikus ATCC No. 4698 (Sigma M3770) cells were resuspended in 2.5 mL distilled $H_2O$ with 0.1% Tween 80. Cells were soaked at 4° C. overnight.

Avicel® PH-101 is a microcrystalline cellulose powder trademarked by FMC Corporation (Philadelphia, Pennsylvania) and sold by Sigma Aldrich (cat no. 11365). 250 mg Avicel was suspended in $H_2O$ with 0.1% Tween 80. This was also left hydrating overnight.

After overnight hydrations, 50 µl of each suspension was taken out and this was washed once in 50 µl $H_2O$ with 0.1% Tween 80. The purified LED (SEQ ID NO: 273) had a concentration of 0.23 mg/ml in a buffer consisting of 50 mM Na-Acetate, pH 4.5+50 mM NaCl. For the experiment, 50 µl of Avicel suspension or 50 µl of M. lysodeiktikus suspension were aliquoted into 1.5 ml Eppendorf tubes. 50 µl (11.5 mgs) of purified LED protein were then added to each tube, mixed by vortexing and then incubated at room temperature for 30 minutes. The samples were then centrifuged, and the liquid decanted to a 1.5 ml Eppendorf tube.

For each sample, 8 µl 4× E-PAGE Loading Buffer (EP-BUF-01, Life Technologies), 1 µl (10×) NuPAGE® Sample Reducing Agent (Life Technologies), were added to 24 µl supernatant. The two samples were then vortex mixed and heated in a heating block at 70° C. for 10 minutes. 20 µl of each prepared sample were then loaded on to a Criterion XT 8-16% gradient BIS-Tris SDS gel and run in Criterion XT MOPS buffer according to the manufacturer's instructions (BioRad Laboratories). A Rainbow recombinant molecular weight marker was also run in the gel (RPN800, GE Healthcare). The SDS gel was stained with Simply Blue Coomassie stain (Life Technologies) and the results visualized as shown in table 7.

TABLE 7

Binding of LED to Avicel or M. lysodeiktikus suspension

| Sample | Lysozyme enhancing domain | Suspension | Result |
| --- | --- | --- | --- |
| 1 | SEQ ID NO: 273 | Avicel | +++ |
| 2 | SEQ ID NO: 273 | M. lysodeiktikus | + |
| 3 | SEQ ID NO: 273 | None | +++ |

+ represents band intensity on an SDS gel.

The results show that the LED protein migrates on the SDS gel at about 8 kDa as expected. The LED protein SDS band intensity is approximately equal in the Avicel and the untreated samples (samples 1 and 3) while the SDS band intensity was substantially reduced in the M. lysodiektikus cells treated sample (sample 2). This means that the M. lysodiektikus cells were able to bind the LED protein under the buffer conditions tested (25 mM Na-Acetate, pH 4.5, 25 mM NaCl) while crystalline cellulose could not bind LED protein. It should be noted that it is unknown which component of the Micrococcus cells that LED binds to.

Example 15: The Lysozyme Enhancing Domain HMM

SEQ ID NOs: 123 to 251 were aligned using the software program MUSCLE v3.8.31 with the default settings. Using this alignment, the HMM was constructed using the software program 'hmmbuild' from the package HMMER 3.0 (March 2010) (hmmer.org/) and the software was invoked using the default settings. The lysozyme enhancing domain HMM profile thereby generated for subsequent loading into the software program 'hmmscan' is given below.

```
HMMER3/b [3.0 | March 2010]
NAME  lysozyme_enhancing_domain
LENG  73
ALPH  amino
RF    no
CS    no
MAP   yes
DATE  Tue Feb 3 15:29:15 2015
NSEQ  129
EFFN  1.263702
CKSUM 3302514446
STATS LOCAL MSV    -9.1036  0.71868
STATS LOCAL VITERBI -9.7357 0.71868
STATS LOCAL FORWARD -3.7686 0.71868
HMM       A    C    D    E    F    G    H    I    K    L    M    N
          P    Q    R    S    T    V    W    Y
          m->m   m->i   m->d   i->m   i->i   d->m   d->d
  COMPO  2.64236 3.16005 2.87141 2.79417 3.60706 2.63596 3.86157 2.94229
         2.65279 2.95816 3.97690 3.11757 3.46392 3.12498 3.11011 2.56828 2.58627 2.58086
         4.17029 3.04296
         2.68618 4.42225 2.77519 2.73123 3.46354 2.40513 3.72494 3.29354 2.67741
         2.69355 4.24690 2.90347 2.73739 3.18146 2.89801 2.37887 2.77519 2.98518 4.58477
         3.61503
         0.17958 4.32413 1.88959 0.61958 0.77255 0.00000  *
```

-continued

```
   1    3.80107 5.04040 4.67499 4.39045 1.81828 4.48873 3.56285 3.50991
4.23379 2.82560 4.11380 4.16131 4.81340 4.22617 4.28030 3.87997 4.03091
3.43577 3.70270 0.73371   1 - -
        2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
        0.02327 4.16783 4.89017 0.61958 0.77255 0.67437 0.71228
   2    2.33952 4.44593 3.23890 3.02979 4.35083 3.16321 4.20776 3.67603
3.02584 3.40031 4.31198 3.32021 1.10553 3.46227 3.39562 2.64660 2.86963
3.24503 5.70138 4.44714   2 - -
        2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
        0.02327 4.16783 4.89017 0.61958 0.77255 0.58149 0.81886
   3    2.99224 4.47028 5.00531 4.50059 3.72470 4.59877 5.18674 1.10701
4.40105 2.19903 3.51509 4.69439 4.89181 4.65354 4.58483 3.98375 3.44715
1.21838 5.67709 4.47722   3 - -
        2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
        0.02218 4.21548 4.93783 0.61958 0.77255 0.62351 0.76800
   4    2.67119 4.76820 3.04982 2.54195 4.12069 3.43519 3.75916 3.51149
2.19874 3.13703 3.97428 2.96845 3.89558 2.93360 2.89915 2.57877 1.61288
3.10281 5.38435 4.08520   4 - -
        2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
        0.02491 4.21548 4.62159 0.61958 0.77255 0.52151 0.90048
   5    2.37234 5.08464 2.49824 2.21575 4.41120 1.99198 3.58111 3.86677
2.52882 3.41126 4.20120 2.81325 3.86140 2.84200 3.02691 2.42476 2.83819
3.48001 5.60144 4.21122   5 - -
        2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
        0.02114 4.26301 4.98536 0.61958 0.77255 0.56183 0.84436
   6    2.63301 5.17310 2.09015 2.17272 4.49463 3.27178 3.65545 3.97097
2.38584 3.47241 4.23433 2.52660 3.34330 2.76874 2.94084 2.41690 2.44683
3.55393 5.62559 4.21427   6 - -
        2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
        0.07099 4.26555 2.90975 0.61958 0.77255 0.56422 0.84119
   7    2.61111 4.85146 2.70126 2.41033 4.02944 2.66646 3.65077 3.52514
2.43178 3.11934 3.92649 2.77281 3.83428 2.77300 2.91547 2.42718 2.41739 2.79685
5.35415 3.75427   7 - -
        2.68619 4.42226 2.77521 2.73124 3.46355 2.40511 3.72496 3.29355
2.67742 2.69356 4.24691 2.90348 2.73741 3.18147 2.89802 2.37888 2.77504 2.98519
4.58478 3.61504
        0.09494 2.48394 4.93906 0.38374 1.14353 0.52245 0.89910
   8    3.16563 4.52406 5.00410 4.47860 3.59477 4.61318 5.11093 1.75130
4.36399 1.66390 3.39589 4.68330 4.88103 4.58179 4.52924 3.98371 3.48258 0.98654
5.56065 4.39116   9 - -
        2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
        0.02108 4.26555 4.98790 0.61958 0.77255 0.56422 0.84119
   9    2.74568 5.18103 2.62071 2.37499 4.50785 3.44148 3.43386 3.97009
2.14487 3.46738 4.24084 1.77122 3.86903 2.77625 2.44752 2.65464 2.97757 3.56615
5.60976 4.22640  10 - -
        2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
        0.02108 4.26555 4.98790 0.61958 0.77255 0.43965 1.03356
  10    3.21633 0.35479 4.79708 4.65548 4.57914 3.72194 5.20787 3.82938
4.49870 3.70850 4.85167 4.53077 4.45916 4.82584 4.53365 3.48556 3.72159 3.53505
5.86530 4.85631  11 - -
        2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
        0.01987 4.32413 5.04648 0.61958 0.77255 0.48576 0.95510
  11    3.30119 5.31389 3.73668 3.09114 4.51121 3.86969 3.13217 4.16018
2.10415 3.58751 4.49408 3.45992 4.26052 2.99924 0.83233 3.31264 3.47550 3.85705
5.50391 4.26079  12 - -
        2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
        0.01987 4.32413 5.04648 0.61958 0.77255 0.48576 0.95510
  12    2.24421 4.51545 3.30473 2.81428 4.39051 3.23670 4.14928 3.77491
3.04692 3.44962 4.27960 3.30747 3.89875 3.36729 3.42822 1.05895 2.51437 3.31859
```

-continued 5.70279 4.43964  13 - -
         2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
         0.01987 4.32413 5.04648 0.61958 0.77255 0.48576 0.95510
    13  2.69468 4.75034 2.89429 2.56341 4.66767 0.94912 4.20148 4.12822
3.15097 3.75743 4.60332 3.20872 3.96757 3.42394 3.55601 2.47312 3.12631 3.62410
5.94365 4.63448  14 - -
         2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
         0.01987 4.32413 5.04648 0.61958 0.77255 0.48576 0.95510
    14  2.67424 4.69741 3.65691 3.53445 4.63811 3.40395 4.65858 4.09486
3.63150 3.77181 4.76683 3.75211 0.59051 3.99224 3.88152 2.99980 3.31792 3.64480
5.92609 4.77080  15 - -
         2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
         0.01987 4.32413 5.04648 0.61958 0.77255 0.48576 0.95510
    15  2.26323 4.51933 3.21961 2.94036 4.47411 1.38422 4.14822 3.91245
3.06085 3.54037 4.34588 2.97288 3.87499 3.35219 3.46854 1.96711 2.52323 3.40350
5.76384 4.49002  16 - -
         2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
         0.01987 4.32413 5.04648 0.61958 0.77255 0.48576 0.95510
    16  2.20668 4.36145 3.82003 3.56662 4.41076 3.20360 4.55272 3.51597
3.53768 3.41304 4.35967 3.64187 3.96341 3.86648 3.78744 2.68079 0.81042 3.10831
5.83931 4.64399  17 - -
         2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
         0.01987 4.32413 5.04648 0.61958 0.77255 0.48576 0.95510
    17  2.61570 5.10849 2.62653 2.38205 4.43252 2.78078 3.60811 3.89018
2.47426 3.42628 4.20945 2.71231 3.87390 2.61734 2.99949 1.64993 2.94705 3.49936
5.60799 4.21799  18 - -
         2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
         0.01987 4.32413 5.04648 0.61958 0.77255 0.48576 0.95510
    18  2.58292 4.58689 3.02231 2.68583 3.00245 3.32285 2.97170 3.14564
2.67302 2.81683 3.67939 2.99852 3.79428 3.00246 3.09283 2.65865 2.82740 2.88473
5.11794 2.25478  19 - -
         2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
         0.01987 4.32413 5.04648 0.61958 0.77255 0.48576 0.95510
    19  2.02971 5.05961 2.68453 2.36019 4.37471 3.26819 3.65420 3.83090
2.10672 3.36092 4.13132 2.92980 3.45060 2.77060 2.82369 2.16905 2.88648 3.43886
5.53518 4.15201  20 - -
         2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
         0.01987 4.32413 5.04648 0.61958 0.77255 0.48576 0.95510
    20  3.16684 4.47509 4.98151 4.48359 3.78153 4.52597 5.13073 1.23357
4.37208 2.38350 3.60515 4.64947 4.86068 4.63385 4.54770 3.62858 3.43521 1.03896
5.65865 4.43929  21 - -
         2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
         0.01987 4.32413 5.04648 0.61958 0.77255 0.48576 0.95510
    21  2.67985 4.50015 3.40866 2.83947 3.66095 3.60615 3.61051 2.50038
2.12953 2.71143 3.59755 3.27678 3.98763 2.81347 3.06211 2.85030 2.83675 1.92294
5.06195 3.81377  22 - -
         2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
         0.01987 4.32413 5.04648 0.61958 0.77255 0.48576 0.95510
    22  2.57540 5.16214 3.25351 2.63376 4.54584 3.62294 3.69980 3.93939
1.30635 3.43432 4.24813 3.13299 4.00544 2.78831 2.11440 2.89381 2.74985 3.58326
5.55169 4.27942  23 - -
         2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
         0.01987 4.32413 5.04648 0.61958 0.77255 0.48576 0.95510
    23  2.54455 4.73655 3.02733 2.59505 4.05985 3.44683 3.70095 3.46466
2.60056 3.09418 3.92399 3.08417 3.89235 2.67009 3.04116 2.11836 1.78482 2.95974
5.35882 4.04770  24 - -
         2.68618 4.42225 2.77519 2.73123 3.46354 2.40513 3.72494 3.29354

2.67741 2.69355 4.24690 2.90347 2.73739 3.18146 2.89801 2.37887 2.77519 2.98518
4.58477 3.61503
    0.01987 4.32413 5.04648 0.61958 0.77255 0.48576 0.95510
  24  3.40982 4.75103 4.67192 4.22624 1.97308 4.35966 3.81417 3.04888
4.07862 2.38151 3.72579 4.16721 4.67838 4.14717 4.17038 3.68839 3.63576 2.47365
4.02768 0.99393  25 - -
    2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
    0.01987 4.32413 5.04648 0.61958 0.77255 0.48576 0.95510
  25  2.33607 5.05721 2.94517 2.24042 4.36369 3.44673 3.55543 3.81754
1.82729 3.31948 4.11325 2.80831 3.17764 2.75227 2.78214 2.58400 2.65726 3.32087
5.51479 4.13659  26 - -
    2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
    0.01987 4.32413 5.04648 0.61958 0.77255 0.48576 0.95510
  26  2.36555 5.04925 3.04993 2.35049 4.35720 3.51989 3.68369 3.71551
1.45376 3.06828 4.12214 3.00561 3.91721 2.74243 2.72409 2.73518 2.95391 3.42066
5.49677 4.16815  27 - -
    2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
    0.01987 4.32413 5.04648 0.61958 0.77255 0.48576 0.95510
  27  2.61202 4.80098 2.75023 2.62858 4.42906 1.32629 3.93435 3.86483
2.78346 3.46292 4.27988 3.09911 3.91159 3.10786 2.85440 2.43819 2.91018 3.44468
5.68001 4.35178  28 - -
    2.68618 4.42225 2.77519 2.73123 3.46354 2.40513 3.72494 3.29354
2.67741 2.69355 4.24690 2.90347 2.73739 3.18146 2.89801 2.37887 2.77519
2.98518 4.58477 3.61503
    0.01987 4.32413 5.04648 0.61958 0.77255 0.48576 0.95510
  28  2.39518 5.06692 2.42469 2.35324 4.15968 3.22653 3.04826 3.83188
2.39351 3.35617 4.12096 2.82671 3.83411 2.52507 2.87979 2.43622 2.35726 3.41027
5.52582 4.13893  29 - -
    2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
    0.01987 4.32413 5.04648 0.61958 0.77255 0.48576 0.95510
  29  2.56098 5.10975 1.84700 2.22610 4.41970 3.43432 3.64564 3.82090
2.31577 3.39892 4.16246 2.88269 3.84241 2.68525 2.69153 2.62766 2.81515 3.48193
5.56120 3.47482  30 - -
    2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
    0.01987 4.32413 5.04648 0.61958 0.77255 0.48576 0.95510
  30  2.71289 4.20867 4.05384 3.08944 3.32534 3.70711 4.11635 2.10460
3.37170 2.31376 3.31881 3.74286 4.18005 3.62760 3.59433 3.09939 2.94743 1.40821
4.85949 3.10435  31 - -
    2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
    0.01987 4.32413 5.04648 0.61958 0.77255 0.48576 0.95510
  31  2.56066 3.98356 2.83917 2.26935 4.26245 3.45019 3.65582 3.70207
1.96206 3.26063 4.04582 2.95679 3.84786 2.75603 2.89654 2.30158 2.29348 3.33728
5.46026 4.09624  32 - -
    2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
    0.01987 4.32413 5.04648 0.61958 0.77255 0.48576 0.95510
  32  2.98261 4.34033 4.74407 4.16222 2.74015 4.19374 4.48870 1.33722
4.00888 1.70186 3.16247 4.27271 4.50036 4.14592 4.09048 3.51345 3.21313 1.97755
4.93581 3.15765  33 - -
    2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
    0.01987 4.32413 5.04648 0.61958 0.77255 0.48576 0.95510
  33  2.50714 4.52249 3.32761 2.73441 3.99413 2.87824 3.93263 3.37611
2.83014 3.05077 3.89907 3.20556 3.90546 3.15647 3.23473 2.09891 1.66153 2.58887
5.34950 4.08041  34 - -
    2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
    0.01987 4.32413 5.04648 0.61958 0.77255 0.48576 0.95510
  34  2.73372 0.86170 4.21080 3.82223 3.72250 3.51687 4.43487 3.14732
3.50989 2.93675 3.97687 3.88251 4.17078 3.93344 3.44432 2.99564 3.14856 2.89652
5.25169 3.70577  35 - -
    2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503

```
          0.01987 4.32413 5.04648 0.61958 0.77255 0.48576 0.95510
     35 2.78221 4.93521 3.15849 2.72873 3.66991 3.61431 3.78500 3.57206
2.57323 3.13265 4.05241 3.20038 4.05162 1.36867 2.92156 2.93601 3.12692 3.29834
5.09768 2.57435   36 - -
          2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
          0.01987 4.32413 5.04648 0.61958 0.77255 0.48576 0.95510
     36 2.39232 4.68655 3.16574 2.46000 3.89951 3.51768 3.74742 2.86223
2.34831 2.93724 3.78511 3.11031 3.91433 2.90991 3.00803 2.69966 1.85059 2.95170
5.23226 3.93826   37 - -
          2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
          0.01987 4.32413 5.04648 0.61958 0.77255 0.48576 0.95510
     37 2.38712 4.95526 2.95139 2.14292 4.22581 3.30071 3.48757 3.66208
2.41922 3.22834 4.01725 2.96015 3.42523 2.64575 2.85382 2.40915 2.33462 3.08668
5.43599 3.59495   38 - -
          2.68618 4.42225 2.77519 2.73123 3.46354 2.40513 3.72494 3.29354
2.67741 2.69355 4.24690 2.90347 2.73739 3.18146 2.89801 2.37887 2.77519
2.98518 4.58477   3.61503
          0.01987 4.32413 5.04648 0.61958 0.77255 0.48576 0.95510
     38 3.32493 5.03100 4.08842 4.05521 5.14287 0.28143 5.12256 4.87721
4.29611 4.46333 5.45951 4.25516 4.43330 4.58529 4.45932 3.51325 3.84001 4.31766
6.09414 5.26815   39 - -
          2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
          0.01987 4.32413 5.04648 0.61958 0.77255 0.48576 0.95510
     39 2.77845 5.16916 2.50798 1.90461 4.47239 3.42576 3.73520 3.92893
2.55535 3.46812 4.26082 2.91770 3.47218 2.74953 3.05304 2.74879 1.68968 3.54385
5.65411 4.25701   40 - -
          2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
          0.01987 4.32413 5.04648 0.61958 0.77255 0.48576 0.95510
     40 2.55637 3.36322 2.86419 2.49420 4.07854 3.43147 3.53651 3.49427
2.36324 3.10007 3.91410 2.51497 3.86778 2.83786 2.95074 2.24490 2.43049 3.00556
5.34651 3.93774   41 - -
          2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
          0.01987 4.32413 5.04648 0.61958 0.77255 0.48576 0.95510
     41 3.32262 4.56891 5.24679 4.77118 3.84175 4.81012 5.48421 1.14831
4.68143 2.30177 3.60891 4.94823 5.08094 4.93596 4.85577 4.22682 3.58792 0.99460
5.88795 4.67682   42 - -
          2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
          0.01987 4.32413 5.04648 0.61958 0.77255 0.48576 0.95510
     42 2.65825 5.10541 2.72992 2.15627 3.98363 3.31023 3.53625 3.89170
2.18852 3.23731 4.15424 2.23857 3.82936 2.65748 2.86654 2.25743 2.79796 3.48165
5.55380 4.15800   43 - -
          2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
          0.01987 4.32413 5.04648 0.61958 0.77255 0.48576 0.95510
     43 2.61182 4.52680 3.60621 3.51889 4.78008 0.61583 4.68006 4.23876
3.72062 3.95294 4.83622 3.66170 4.02536 4.00392 3.97409 2.79132 2.85714 3.64017
6.05621 4.90618   44 - -
          2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
          0.01987 4.32413 5.04648 0.61958 0.77255 0.48576 0.95510
     44 2.79049 5.22667 2.25221 2.33027 4.53369 3.27947 3.53614 4.00930
2.56097 3.52971 4.31450 1.59788 3.89352 2.86397 3.06987 2.39242 3.03945 3.49407
5.69864 4.13140   45 - -
          2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
          0.01987 4.32413 5.04648 0.61958 0.77255 0.48576 0.95510
     45 2.49378 3.36932 2.74714 2.42229 4.10830 3.46961 3.68039 3.52770
2.44255 3.12654 3.93602 2.51463 3.86384 2.82770 2.94369 2.19290 2.51568 3.13211
5.36588 3.76024   46 - -
          2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
          0.01987 4.32413 5.04648 0.61958 0.77255 0.48576 0.95510
     46 2.69732 4.16858 4.15640 3.57668 3.28068 3.80998 4.13366 1.64485
```

-continued 3.45403 1.84904 3.26899 3.79253 3.96991 3.68559 3.64246 2.81777 2.62992 2.15853
4.82146 3.52063   47 - -
          2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
          0.01987 4.32413 5.04648 0.61958 0.77255 0.48576 0.95510
     47   4.19233 5.38393 4.84605 4.67977 3.27817 4.29458 4.57157 4.26819
4.41284 3.57367 4.87507 4.74845 4.85287 4.77414 4.45256 4.39169 4.52083 4.16862
0.32020 3.26075   48 - -
          2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
          0.01987 4.32413 5.04648 0.61958 0.77255 0.48576 0.95510
     48   3.20149 5.67973 0.78816 2.34486 4.76934 3.43076 3.17601 4.55895
3.07436 4.04716 4.94146 2.92732 4.07402 3.21129 3.65781 3.08955 3.50632 4.14006
6.03658 4.51417   49 - -
          2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
          0.01987 4.32413 5.04648 0.61958 0.77255 0.48576 0.95510
     49   2.76346 4.98544 3.15831 2.56957 4.01057 3.55403 3.68400 3.67589
1.47331 2.89158 4.05158 3.07047 3.93382 2.56322 2.45400 2.78078 2.98070 3.34485
5.41794 3.49426   50 - -
          2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
          0.01987 4.32413 5.04648 0.61958 0.77255 0.48576 0.95510
     50   2.64257 4.43619 3.56736 3.08202 3.77537 3.52079 4.05811 2.42620
3.00927 2.79176 3.72810 2.99222 4.03030 3.35753 3.34645 2.85418 1.35329 2.62966
5.23131 3.98292   51 - -
          2.68619 4.42226 2.77521 2.73124 3.46340 2.40514 3.72496 3.29355
2.67742 2.69356 4.24691 2.90348 2.73741 3.18148 2.89802 2.37888 2.77521 2.98520
4.58478 3.61472
          0.08832 2.54971 5.04648 0.37639 1.15942 0.48576 0.95510
     51   2.52068 4.47414 3.35565 2.74391 3.33968 3.48613 3.81115 3.00228
2.76056 2.69538 3.20591 3.24034 3.68619 2.82417 3.12828 2.08694 2.32290 2.59916
4.31681 3.78415   53 - -
          2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
          0.01987 4.32413 5.04648 0.61958 0.77255 0.48576 0.95510
     52   2.77860 4.87789 1.42239 2.56155 3.13731 3.54366 3.74371 3.49507
2.67769 3.09585 3.97167 3.06454 3.97169 2.99708 3.12924 2.82286 3.01884 3.20614
4.04928 3.59798   54 - -
          2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
          0.01987 4.32413 5.04648 0.61958 0.77255 0.48576 0.95510
     53   2.94931 5.28328 2.08563 2.39481 4.84632 1.16425 4.00151 4.36230
3.01231 3.90219 4.74326 2.45548 3.99074 3.18038 3.56729 2.91382 3.29175 3.89959
6.06470 4.62009   55 - -
          2.68621 4.42228 2.77522 2.73126 3.46357 2.40509 3.72497 3.29357
2.67727 2.69358 4.24693 2.90346 2.73742 3.18149 2.89804 2.37878 2.77522 2.98521
4.58480 3.61506
          0.08509 2.58845 5.04648 0.73284 0.65497 0.48576 0.95510
     54   3.21633 0.35479 4.79708 4.65548 4.57914 3.72194 5.20787 3.82938
4.49870 3.70850 4.85167 4.53077 4.45916 4.82584 4.53365 3.48556 3.72159 3.53505
5.86530 4.85631   59 - -
          2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
          0.01987 4.32413 5.04648 0.61958 0.77255 0.48576 0.95510
     55   4.07603 5.22780 4.94333 4.71701 1.81696 4.70604 3.64405 3.73694
4.54415 3.00155 4.31962 4.34626 5.01267 4.44587 4.52415 4.10863 4.29875 3.67538
3.75731 0.60600   60 - -
          2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
          0.01987 4.32413 5.04648 0.61958 0.77255 0.48576 0.95510
     56   3.29932 4.57114 5.13914 4.65306 3.79025 4.73170 5.36042 1.62171
4.54191 2.21256 3.57888 4.84627 5.01963 4.80796 4.72647 4.13701 3.56571 0.76183
5.80720 4.58938   61 - -
          2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
          0.01987 4.32413 5.04648 0.61958 0.77255 0.48576 0.95510
     57   1.40302 4.31490 3.77731 3.44350 4.52474 3.10962 4.46137 3.90675
3.45708 3.61908 4.43729 3.53676 3.86941 3.73557 3.76041 1.18441 2.55005 3.34107
5.86901 4.67381   62 - -

-continued

```
     2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
     0.01987 4.32413 5.04648 0.61958 0.77255 0.48576 0.95510
 58  3.16638 5.52729 0.80512 2.42994 5.07620 2.30005 4.12607 4.65042
3.22647 4.16769 5.05164 2.99972 4.08759 3.32219 3.82773 3.09290 3.51563 4.17606
6.23444 4.80691   63 - -
     2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
     0.01987 4.32413 5.04648 0.61958 0.77255 0.48576 0.95510
 59  3.11990 4.36544 4.32127 3.81191 2.17745 4.09367 3.78203 3.04592
3.23806 2.64903 3.67717 3.91110 4.44159 3.85035 3.84946 3.39383 3.34718 2.77912
3.74216 1.06936   64 - -
     2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
     0.01987 4.32413 5.04648 0.61958 0.77255 0.48576 0.95510
 60  3.51146 4.91649 4.45325 4.08004 2.02567 4.31163 3.69403 3.46524
3.96389 2.92976 4.07889 4.05659 4.68281 4.07537 4.10672 2.99801 3.75887 3.31559
3.91189 0.78971   65 - -
     2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
     0.01987 4.32413 5.04648 0.61958 0.77255 0.48576 0.95510
 61  2.72553 4.31253 4.16671 3.66674 3.67680 3.72642 4.41126 2.29394
3.56150 2.58708 3.60951 3.86666 4.24179 3.84789 3.80334 2.76599 2.38224 1.10833
5.25833 4.04936   66 - -
     2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
     0.02985 4.32413 4.12501 0.61958 0.77255 0.48576 0.95510
 62  2.51216 5.16569 2.33791 2.35923 4.49437 3.19374 3.66109 3.96480
1.64210 3.46558 4.22781 2.83561 3.85394 2.71011 2.84192 2.54559 2.88860 3.55105
5.61534 4.21583   67 - -
     2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
     0.02007 4.31435 5.03670 0.61958 0.77255 0.49963 0.93333
 63  2.49188 4.38955 3.59551 3.16295 4.09719 3.28177 4.17679 3.38911
3.04040 3.15453 4.02841 3.43067 3.92288 3.44894 3.44644 2.11805 1.20176 2.68117
5.48692 4.25411   68 - -
     2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
     0.02007 4.31435 5.03670 0.61958 0.77255 0.49963 0.93333
 64  1.89508 4.31720 3.70048 3.48388 4.63634 0.95179 4.55159 4.00807
3.58485 3.73760 4.55934 3.55250 3.87506 3.84242 3.86415 2.56592 2.50453 3.40204
5.97883 4.79808   69 - -
     2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
     0.03953 4.31435 3.67355 0.61958 0.77255 0.49963 0.93333
 65  2.63597 3.39258 3.14566 2.45530 3.91792 3.49097 3.54341 3.31288
2.40023 2.95698 3.79792 3.08785 3.89316 2.92081 3.00148 1.97899 2.29007 2.96915
5.24220 3.94276   70 - -
     2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
     0.02046 4.29528 5.01763 0.61958 0.77255 0.52575 0.89432
 66  2.59137 4.97540 2.68695 2.29850 4.05453 3.34590 3.64946 3.59380
2.42308 3.26160 4.04572 2.57932 3.83844 2.77492 2.90216 1.98570 2.44689 3.22530
5.46068 4.09334   71 - -
     2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
     0.02046 4.29528 5.01763 0.61958 0.77255 0.52575 0.89432
 67  2.36239 3.82492 3.07537 2.52645 4.05085 1.94430 3.77137 3.45853
2.53920 3.08721 3.91418 2.86394 3.87403 2.94691 3.05153 2.46988 2.65768 3.12923
5.35184 4.04208   72 - -
     2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
     0.02046 4.29528 5.01763 0.61958 0.77255 0.52575 0.89432
 68  2.51473 4.23017 3.73065 3.15738 2.96324 3.66009 3.93184 2.62617
3.08387 2.43082 2.74387 3.49391 3.33993 3.35931 3.14679 2.64784 2.86016 2.49302
4.81896 2.22311   73 - -
     2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
```

```
4.58477 3.61503
        0.02046 4.29528 5.01763 0.61958 0.77255 0.52575 0.89432
    69  2.33893 4.26290 4.21737 3.66773 3.27773 3.87203 4.32579 2.12233
3.56960 2.41061 3.43058 3.89614 4.28394 3.82133 3.79298 2.87144 3.03565 1.21453
5.06701 3.86005   74 - -
        2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
        0.02293 4.29528 4.70670 0.61958 0.77255 0.52575 0.89432
    70  2.49593 4.60476 3.23381 2.52485 3.79749 3.53767 3.76569 3.14297
2.26081 2.40764 3.70182 3.15412 3.92810 2.98301 3.03430 2.76728 2.09050 2.55846
5.16115 3.88294   75 - -
        2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
        0.02051 4.29287 5.01521 0.61958 0.77255 0.52898 0.88967
    71  2.60687 5.12624 2.52016 2.23382 4.44833 2.55208 3.64005 3.91884
2.12896 3.37075 4.18386 2.86694 3.03933 2.74997 2.89501 2.33562 2.83629 3.50672
5.58015 4.17955   76 - -
        2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
        0.02051 4.29287 5.01521 0.61958 0.77255 0.52898 0.88967
    72  2.57816 5.12677 2.87095 2.24649 4.45454 3.41210 3.40077 3.91086
1.59193 3.41242 4.17909 2.90547 3.85681 2.60853 2.68264 2.65653 2.67555 3.50960
5.55782 4.18309   77 - -
        2.68618 4.42225 2.77520 2.73117 3.46354 2.40513 3.72495 3.29354
2.67741 2.69355 4.24690 2.90347 2.73740 3.18147 2.89801 2.37887 2.77520 2.98519
4.58477 3.61503
        0.09497 3.41028 2.85473 0.52137 0.90068 0.52898 0.88967
    73  3.08258 0.42515 4.66004 4.49479 4.42412 3.61311 5.06351 3.64868
4.33208 3.53771 4.67608 4.38809 4.34603 4.66309 4.38494 3.35266 3.58099 3.36315
5.74041 4.70439   79 - -
        2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
        0.01461 4.23357   *   0.61958 0.77255 0.00000   *
//
```

Example 16: The GH24 Catalytic Domain HMM

SEQ ID NOs: 1 to 122 were aligned using the software program MUSCLE v3.8.31 with the default settings. Using this alignment, the HMM was constructed using the software program 'hmmbuild' from the package HMMER 3.0 (March 2010) (hmmer.org/) and the software was invoked using the default settings. The GH24 catalytic domain HMM profile thereby generated for subsequent loading into the software program 'hmmscan' is given below.

```
HMMER3/b [3.0 | March 2010]
NAME  GH24_catalytic_domain
LENG  161
ALPH  amino
RF    no
CS    no
MAP   yes
DATE  Tue Apr 14 10:23:27 2015
NSEQ  122
EFFN  1.567444
CKSUM 3253961472
STATS LOCAL MSV       -10.1203 0.70833
STATS LOCAL VITERBI   -10.9320 0.70833
STATS LOCAL FORWARD    -4.4787 0.70833
HMM          A        C        D        E        F        G        H        I        K        L        M        N
             P        Q        R        S        T        V        W        Y
            m->m     m->i     m->d     i->m     i->i     d->m     d->d
  COMPO   2.44048 3.93467 3.01702 2.62301 3.43295 2.77445 3.69252 3.04117
2.65511 2.46463 3.77377 2.92042 3.46380 3.02561 2.94926 2.63867 2.77262 2.69908
4.58415 3.55522
        2.68613 4.42197 2.77528 2.73121 3.46362 2.40507 3.72503 3.29362
2.67741 2.69347 4.24698 2.90355 2.73748 3.18155 2.89786 2.37893 2.77517 2.98499
4.58485 3.61511
        0.42529 2.02566 1.53938 0.94684 0.49097 0.00000   *
    1   2.72350 4.81830 3.16936 2.62649 4.11581 3.51252 3.71942 3.50389
2.24998 2.85999 3.95362 3.10351 1.86600 2.88649 2.42995 2.74652 2.82871 3.19574
5.34619 4.06251    6 - -
        2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
```

|   |   |
|---|---|
|   | 0.02197 4.22496 4.94731 0.61958 0.77255 0.75070 0.63873 |
| 2 | 2.54350 5.09272 2.65636 2.29098 4.41602 2.99758 3.47346 3.88723 2.05017 3.38851 4.14035 2.65877 3.36878 2.57545 2.80210 2.49808 2.60450 3.36099 5.53830 4.14000   7 - - |
|   | 2.68618 4.42225 2.77519 2.73123 3.46354 2.40513 3.72494 3.29354 2.67741 2.69355 4.24690 2.90347 2.73739 3.18146 2.89801 2.37887 2.77519 2.98518 4.58477 3.61503 |
|   | 0.02165 4.23928 4.96162 0.61958 0.77255 0.55400 0.85483 |
| 3 | 2.29319 4.21840 3.95914 3.39016 3.37768 3.73291 4.08404 2.12760 3.30131 2.30451 3.36148 3.66722 3.96097 3.55864 3.55098 2.44506 2.67959 1.73447 4.88856 3.68459   8 - - |
|   | 2.68618 4.42225 2.77519 2.73123 3.46354 2.40513 3.72494 3.29354 2.67741 2.69355 4.24690 2.90347 2.73739 3.18146 2.89801 2.37887 2.77519 2.98518 4.58477 3.61503 |
|   | 0.01947 4.34420 5.06654 0.61958 0.77255 0.61386 0.77927 |
| 4 | 2.74772 4.85695 2.87194 2.73668 4.63295 3.30941 4.14345 4.20984 3.05642 3.80763 4.64806 1.00956 3.98834 3.35260 3.47426 2.10780 3.15897 3.70197 5.91048 4.53618   9 - - |
|   | 2.68618 4.42225 2.77519 2.73123 3.46354 2.40513 3.72494 3.29354 2.67741 2.69355 4.24690 2.90347 2.73739 3.18146 2.89801 2.37887 2.77519 2.98518 4.58477 3.61503 |
|   | 0.01917 4.35956 5.08190 0.61958 0.77255 0.63061 0.75986 |
| 5 | 2.12850 5.12616 2.51993 2.17045 4.44916 3.31679 3.63665 3.80796 2.17180 3.42224 4.17456 2.91475 3.69539 2.47321 2.87406 2.49141 2.67432 3.46760 5.57266 4.17399   10 - - |
|   | 2.68618 4.42225 2.77519 2.73123 3.46354 2.40513 3.72494 3.29354 2.67741 2.69355 4.24690 2.90347 2.73739 3.18146 2.89801 2.37887 2.77519 2.98518 4.58477 3.61503 |
|   | 0.01917 4.35956 5.08190 0.61958 0.77255 0.63061 0.75986 |
| 6 | 1.46486 5.07291 2.62203 2.24830 4.37269 3.31665 3.74063 3.81552 2.50756 3.37686 4.17647 2.86466 3.60033 2.87945 2.92672 2.74276 2.99812 3.44901 5.58151 4.20704   11 - - |
|   | 2.68618 4.42225 2.77519 2.73123 3.46354 2.40513 3.72494 3.29354 2.67741 2.69355 4.24690 2.90347 2.73739 3.18146 2.89801 2.37887 2.77519 2.98518 4.58477 3.61503 |
|   | 0.01917 4.35956 5.08190 0.61958 0.77255 0.59794 0.79839 |
| 7 | 2.17549 4.36144 3.73727 3.42594 4.53253 1.83798 4.46965 3.92664 3.46881 3.62766 4.44736 3.54831 3.90736 3.74497 3.77756 2.51903 1.12529 3.37293 5.87792 4.67921   12 - - |
|   | 2.68618 4.42225 2.77519 2.73123 3.46354 2.40513 3.72494 3.29354 2.67741 2.69355 4.24690 2.90347 2.73739 3.18146 2.89801 2.37887 2.77519 2.98518 4.58477 3.61503 |
|   | 0.01891 4.37321 5.09556 0.61958 0.77255 0.61277 0.78055 |
| 8 | 3.21972 4.50196 5.08099 4.54710 3.67073 4.61619 5.10917 1.48214 4.43636 1.72834 3.48636 4.70971 4.89148 4.64075 4.57635 3.97953 3.10048 1.11742 5.56354 4.38821   13 - - |
|   | 2.68618 4.42225 2.77519 2.73123 3.46354 2.40513 3.72494 3.29354 2.67741 2.69355 4.24690 2.90347 2.73739 3.18146 2.89801 2.37887 2.77519 2.98518 4.58477 3.61503 |
|   | 0.01891 4.37321 5.09556 0.61958 0.77255 0.61277 0.78055 |
| 9 | 2.35795 5.16270 2.30078 2.19496 4.49371 3.33251 3.64118 3.79980 2.21875 3.46186 4.20895 2.47286 3.84197 2.71978 2.70252 2.33251 2.91273 3.54614 5.60290 4.19720   14 - - |
|   | 2.68618 4.42225 2.77519 2.73123 3.46354 2.40513 3.72494 3.29354 2.67741 2.69355 4.24690 2.90347 2.73739 3.18146 2.89801 2.37887 2.77519 2.98518 4.58477 3.61503 |
|   | 0.01891 4.37321 5.09556 0.61958 0.77255 0.47193 0.97763 |
| 10 | 3.10702 4.52363 4.59128 3.76793 2.82202 4.24456 4.31533 2.53549 3.86137 0.84608 2.77098 4.22984 4.53874 4.04360 4.00636 3.55360 3.33165 2.56243 4.98174 3.78454   15 - - |
|   | 2.68618 4.42225 2.77519 2.73123 3.46354 2.40513 3.72494 3.29354 2.67741 2.69355 4.24690 2.90347 2.73739 3.18146 2.89801 2.37887 2.77519 2.98518 4.58477 3.61503 |
|   | 0.01780 4.43314 5.15549 0.61958 0.77255 0.52727 0.89212 |
| 11 | 3.43901 4.67793 5.35556 4.83217 3.64816 4.91195 5.41930 0.86797 4.72910 1.79405 3.18234 5.01743 5.11165 4.88087 4.84705 4.30046 3.68194 1.65293 5.72096 4.59690   16 - - |
|   | 2.68618 4.42225 2.77519 2.73123 3.46354 2.40513 3.72494 3.29354 2.67741 2.69355 4.24690 2.90347 2.73739 3.18146 2.89801 2.37887 2.77519 2.98518 4.58477 3.61503 |
|   | 0.01780 4.43314 5.15549 0.61958 0.77255 0.52727 0.89212 |
| 12 | 2.25468 5.11708 2.95136 2.31419 4.43742 2.93886 3.67050 3.89862 1.79270 3.41419 4.17655 2.95628 3.57244 2.54460 2.89046 2.49672 2.70342 3.49694 5.57506 4.18857   17 - - |
|   | 2.68618 4.42225 2.77519 2.73123 3.46354 2.40513 3.72494 3.29354 2.67741 2.69355 4.24690 2.90347 2.73739 3.18146 2.89801 2.37887 2.77519 2.98518 4.58477 3.61503 |
|   | 0.01780 4.43314 5.15549 0.61958 0.77255 0.52727 0.89212 |
| 13 | 2.67371 5.19058 2.65415 1.77278 4.52357 2.97916 3.37968 4.00320 |

-continued 2.29480 3.45227 4.23628 2.89789 3.86090 2.69304 2.74143 2.20291 2.82697 3.57508
5.62881 4.22137    18 - -
             2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
             0.01780 4.43314 5.15549 0.61958 0.77255 0.49458 0.94117
    14       2.81579 4.22364 4.47018 3.89188 1.48290 3.93522 4.09383 2.62540
3.73020 1.92295 3.15573 3.97226 4.29103 3.88937 3.82500 2.90865 3.04647 2.32749
3.69273 3.08017    19 - -
             2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
             0.01758 4.44584 5.16819 0.61958 0.77255 0.50746 0.92136
    15       3.18472 5.59003 2.51116 0.73356 4.97137 3.49635 4.05433 4.46680
2.91869 4.01079 4.89285 3.02135 4.12423 3.23170 3.44861 2.94448 3.49165 4.05785
6.14660 4.69845    20 - -
             2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
             0.01758 4.44584 5.16819 0.61958 0.77255 0.50746 0.92136
    16       2.63285 4.65582 3.05809 2.95774 4.52790 0.99566 4.22427 3.96361
3.15170 3.35882 4.43654 3.32975 3.98358 3.44306 3.48471 2.26849 2.95946 3.48867
5.83543 4.54966    21 - -
             2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
             0.01758 4.44584 5.16819 0.61958 0.77255 0.50746 0.92136
    17       2.85632 3.37564 4.60322 4.02460 1.39485 3.99023 4.14489 2.59011
3.84632 2.15449 3.18679 4.06005 4.34070 3.98159 3.90687 3.30078 3.08762 2.25178
3.05451 3.20082    22 - -
             2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
             0.01758 4.44584 5.16819 0.61958 0.77255 0.50746 0.92136
    18       2.66729 4.65691 3.26612 2.63248 3.59907 3.57768 3.79390 3.22463
2.58508 2.88889 3.74552 3.18306 3.96288 2.76398 2.21227 2.49586 2.92028 2.02229
5.19804 3.45436    23 - -
             2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
             0.01758 4.44584 5.16819 0.61958 0.77255 0.50746 0.92136
    19       2.15329 4.93377 2.72392 2.45038 4.18602 3.46029 3.70858 3.61065
2.39726 2.85937 4.00284 3.02169 2.29781 2.84985 2.92083 2.61534 2.92011 3.27400
5.42832 3.51133    24 - -
             2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
             0.01758 4.44584 5.16819 0.61958 0.77255 0.50746 0.92136
    20       2.60039 5.14177 2.40424 2.39661 4.46473 3.46452 3.22687 3.82146
2.34703 3.43742 4.18905 2.53509 3.85931 2.76069 2.48112 2.15943 2.56736 3.52065
5.58781 3.98848    25 - -
             2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
             0.01758 4.44584 5.16819 0.61958 0.77255 0.50746 0.92136
    21       2.67842 4.25530 3.93960 3.30296 2.65434 3.76986 4.06743 2.34859
3.16231 2.41816 3.35928 3.66250 1.99709 3.53911 3.53118 3.04669 2.94335 1.99782
4.87521 3.66773    26 - -
             2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
             0.01758 4.44584 5.16819 0.61958 0.77255 0.50746 0.92136
    22       2.35693 4.72401 3.20434 2.57805 3.89878 3.59542 3.83415 3.30513
2.45060 2.96490 3.82939 3.20409 4.00721 3.02410 3.01463 2.73830 2.99846 3.03825
5.25060 1.65974    27 - -
             2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
             0.04783 4.44584 3.35315 0.61958 0.77255 0.50746 0.92136
    23       2.67429 5.03904 2.71552 2.42815 4.32871 3.47139 3.66503 3.56736
2.12738 3.11366 4.09499 2.80474 2.49274 2.58565 2.81632 2.65515 2.70589 3.31018
5.50599 3.32956    28 - -
             2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
             0.01811 4.41613 5.13847 0.61958 0.77255 0.46783 0.98447
    24       2.80258 3.80314 1.07544 2.73853 4.22664 3.51752 4.00892 3.12191
2.89547 3.24952 4.16749 3.22350 4.04459 3.20256 3.34582 2.88238 3.10901 3.14052
5.59573 4.24511    29 - -

-continued

|   | |
|---|---|
|   | 2.68618 4.42225 2.77519 2.73123 3.46354 2.40513 3.72494 3.29354 2.67741 2.69355 4.24690 2.90347 2.73739 3.18146 2.89801 2.37887 2.77519 2.98518 4.58477 3.61503 |
|   | 0.02905 4.45025 4.07730 0.61958 0.77255 0.50044 0.93208 |
| 25 | 2.25512 4.65074 3.26511 2.72356 3.93527 3.14982 3.83757 3.32426 2.65175 2.98376 3.43732 3.00233 1.89086 3.04409 3.13107 2.60570 2.91688 2.73040 5.28256 3.99674   30 - - |
|   | 2.68618 4.42225 2.77520 2.73123 3.46354 2.40510 3.72495 3.29354 2.67741 2.69355 4.24690 2.90347 2.73740 3.18146 2.89801 2.37887 2.77520 2.98518 4.58477 3.61503 |
|   | 0.09269 3.75476 2.73149 0.54795 0.86306 0.48896 0.95001 |
| 26 | 2.20760 4.20273 3.79874 3.31128 3.16594 3.51238 4.00110 2.04422 3.04865 2.40223 3.06460 3.46501 4.08831 3.47948 3.47692 2.91568 2.45698 2.12142 4.80701 3.37658   32 - - |
|   | 2.68618 4.42225 2.77519 2.73123 3.46354 2.40513 3.72494 3.29354 2.67741 2.69355 4.24690 2.90347 2.73739 3.18146 2.89801 2.37887 2.77519 2.98518 4.58477 3.61503 |
|   | 0.01860 4.38973 5.11208 0.61958 0.77255 0.44606 1.02206 |
| 27 | 2.89429 4.80561 3.58134 3.54304 4.97183 0.46686 4.80272 4.62849 3.86637 4.26878 5.14633 3.40192 4.22316 4.13479 4.14184 3.05434 3.41253 3.99006 6.18155 5.02899   33 - - |
|   | 2.68620 4.42227 2.77521 2.73125 3.46355 2.40514 3.72472 3.29356 2.67742 2.69356 4.24691 2.90348 2.73732 3.18134 2.89802 2.37888 2.77521 2.98520 4.58478 3.61505 |
|   | 0.04293 3.31454 5.17259 0.77558 0.61699 0.50044 0.93208 |
| 28 | 2.68018 4.37382 3.60152 3.03271 3.37749 3.67013 2.87447 2.64539 2.70815 1.83610 3.47768 2.80710 4.04839 3.27708 3.31669 2.91878 2.91175 2.35117 4.95200 3.30164   37 - - |
|   | 2.68618 4.42225 2.77519 2.73123 3.46354 2.40513 3.72494 3.29354 2.67741 2.69355 4.24690 2.90347 2.73739 3.18146 2.89801 2.37887 2.77519 2.98518 4.58477 3.61503 |
|   | 0.01750 4.45025 5.17259 0.61958 0.77255 0.50044 0.93208 |
| 29 | 2.59450 4.66219 3.27040 2.59506 3.84655 3.58175 3.79708 3.14848 2.36788 2.60330 3.75125 3.18753 2.01907 2.93847 3.06156 2.80580 2.85294 2.96388 3.37709 3.92228   38 - - |
|   | 2.68618 4.42225 2.77519 2.73123 3.46354 2.40513 3.72494 3.29354 2.67741 2.69355 4.24690 2.90347 2.73739 3.18146 2.89801 2.37887 2.77519 2.98518 4.58477 3.61503 |
|   | 0.01750 4.45025 5.17259 0.61958 0.77255 0.47669 0.96978 |
| 30 | 2.38332 4.46240 3.96391 3.74958 4.56460 3.29443 4.72276 3.67520 3.71927 3.57098 4.53007 3.78193 4.07155 4.04991 3.94677 2.78605 0.65157 3.25220 5.99515 4.80793   39 - - |
|   | 2.68618 4.42225 2.77519 2.73123 3.46354 2.40513 3.72494 3.29354 2.67741 2.69355 4.24690 2.90347 2.73739 3.18146 2.89801 2.37887 2.77519 2.98518 4.58477 3.61503 |
|   | 0.01734 4.45929 5.18164 0.61958 0.77255 0.48576 0.95510 |
| 31 | 2.99096 4.42944 4.70942 4.15218 3.57105 4.31482 4.71076 1.65507 4.01113 2.14494 3.46003 4.34534 4.64055 4.17763 3.56162 4.17763 3.64279 3.30622 1.03756 5.29753 4.10999   40 - - |
|   | 2.68618 4.42225 2.77519 2.73123 3.46354 2.40513 3.72494 3.29354 2.67741 2.69355 4.24690 2.90347 2.73739 3.18146 2.89801 2.37887 2.77519 2.98518 4.58477 3.61503 |
|   | 0.01734 4.45929 5.18164 0.61958 0.77255 0.48576 0.95510 |
| 32 | 2.68716 3.00522 4.44310 4.24828 4.84005 0.50716 5.03457 4.26978 4.19629 4.02594 4.89944 4.06659 4.16496 4.45125 4.33862 2.90519 3.23060 3.67814 6.12241 5.07039   41 - - |
|   | 2.68618 4.42225 2.77519 2.73123 3.46354 2.40513 3.72494 3.29354 2.67741 2.69355 4.24690 2.90347 2.73739 3.18146 2.89801 2.37887 2.77519 2.98518 4.58477 3.61503 |
|   | 0.01734 4.45929 5.18164 0.61958 0.77255 0.48576 0.95510 |
| 33 | 3.88807 5.12914 4.96349 4.62971 2.07646 4.68858 3.80768 2.95192 4.45489 2.84188 4.11936 4.39032 4.99014 4.43288 4.48511 4.04965 4.11066 3.40338 3.94943 0.62936   42 - - |
|   | 2.68618 4.42225 2.77519 2.73123 3.46354 2.40513 3.72494 3.29354 2.67741 2.69355 4.24690 2.90347 2.73739 3.18146 2.89801 2.37887 2.77519 2.98518 4.58477 3.61503 |
|   | 0.01734 4.45929 5.18164 0.61958 0.77255 0.48576 0.95510 |
| 34 | 3.55261 5.22999 4.34030 4.32810 5.38495 0.21258 5.36943 5.16848 4.58491 4.72792 5.73557 4.50771 4.63301 4.86357 4.71836 3.74664 4.07606 4.58314 6.28543 5.51964   43 - - |
|   | 2.68618 4.42225 2.77519 2.73123 3.46354 2.40513 3.72494 3.29354 2.67741 2.69355 4.24690 2.90347 2.73739 3.18146 2.89801 2.37887 2.77519 2.98518 4.58477 3.61503 |
|   | 0.01734 4.45929 5.18164 0.61958 0.77255 0.48576 0.95510 |
| 35 | 3.87327 5.50886 3.92890 3.78212 3.89799 4.10572 0.35257 4.67985 3.62123 4.07577 5.19561 4.15242 4.70480 4.16744 3.83107 3.95140 4.21270 4.40275 5.33871 3.84015   44 - - |
|   | 2.68618 4.42225 2.77519 2.73123 3.46354 2.40513 3.72494 3.29354 2.67741 2.69355 4.24690 2.90347 2.73739 3.18146 2.89801 2.37887 2.77519 2.98518 |

-continued

```
4.58477 3.61503
            0.01734 4.45929 5.18164 0.61958 0.77255 0.48576 0.95510
    36      2.55850 4.67610 2.85436 2.69895 3.86374 3.57559 3.81417 3.24443
2.55253 1.61527 3.72651 3.02186 3.97376 2.93710 3.10915 2.81523 2.56702 2.97733
5.22462 3.94128   45 - -
            2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
            0.01734 4.45929 5.18164 0.61958 0.77255 0.48576 0.95510
    37      2.36682 1.08021 4.17330 3.72135 3.82769 2.87004 4.41678 2.93056
3.59066 2.91000 3.83458 3.78442 4.07632 3.86713 3.80034 2.83912 2.97220 2.78923
5.31748 3.88653   46 - -
            2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
            0.01734 4.45929 5.18164 0.61958 0.77255 0.48576 0.95510
    38      2.44867 5.13209 2.74120 2.37534 4.45129 3.13883 3.37571 3.81639
2.09231 3.25691 4.17977 2.88681 3.86250 2.39570 2.69695 2.32020 2.78438 3.04671
5.58043 4.18603   47 - -
            2.68605 4.42230 2.77519 2.73128 3.46359 2.40494 3.72500 3.29359
2.67735 2.69360 4.24695 2.90338 2.73745 3.18151 2.89806 2.37892 2.77525 2.98523
4.58482 3.61508
            0.20624 2.21113 2.56670 0.73716 0.65099 0.48576 0.95510
    39      2.38824 5.13667 2.46225 2.33995 4.46125 3.44638 3.64321 3.93304
1.96184 3.43315 4.18470 2.59657 3.84499 2.58355 2.85687 2.53095 2.55813 3.25538
5.58195 4.18304   52 - -
            2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
            0.01868 4.38546 5.10781 0.61958 0.77255 0.59629 0.80040
    40      2.52969 5.03587 2.97654 2.42115 4.32785 3.46441 3.53193 3.77619
2.02445 3.31736 4.09206 2.74547 2.84178 2.54513 2.88744 2.19787 2.76245 3.39795
4.74099 3.94803   53 - -
            2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
            0.01868 4.38546 5.10781 0.61958 0.77255 0.52092 0.90134
    41      2.60675 5.16003 2.52146 2.30324 4.48997 2.73454 3.64845 3.96623
2.17370 3.45896 4.20601 2.47959 3.85066 2.56867 2.84590 2.41657 2.61213 3.27322
5.60178 4.19843   54 - -
            2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
            0.01810 4.41655 5.13890 0.61958 0.77255 0.55221 0.85726
    42      2.65287 1.19275 3.40429 3.38996 3.71368 3.53484 4.23292 2.66477
3.32728 2.80149 3.73937 3.41343 4.09824 3.63311 3.60222 2.91375 2.99822 2.67046
5.20557 3.95872   55 - -
            2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
            0.01810 4.41655 5.13890 0.61958 0.77255 0.55221 0.85726
    43      2.11988 4.99095 2.69229 2.46032 4.29867 3.20836 3.70173 3.73910
2.41197 3.30074 4.08762 2.99012 3.49720 2.83041 2.93503 1.83660 2.75199 3.37089
5.50311 3.91158   56 - -
            2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
            0.01810 4.41655 5.13890 0.61958 0.77255 0.44635 1.02155
    44      2.97807 5.54822 1.79883 1.40119 4.86180 2.66411 3.85669 4.37053
2.55019 3.84442 4.63047 2.91417 3.99223 2.98875 3.29382 2.51970 3.23747 3.92819
5.98719 4.51765   57 - -
            2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
            0.03941 4.45929 3.60927 0.61958 0.77255 0.48576 0.95510
    45      2.61240 4.24725 4.16179 3.58472 3.39505 3.87860 4.19991 1.92349
3.14424 2.34125 3.37288 3.82971 4.24684 3.71715 3.49381 3.16925 2.66754 1.39907
4.93254 3.73395   58 - -
            2.68614 4.42226 2.77520 2.73124 3.46355 2.40514 3.72495 3.29355
2.67742 2.69356 4.24691 2.90347 2.73740 3.18139 2.89802 2.37888 2.77515 2.98519
4.58478 3.61504
            0.25671 3.65255 1.60702 0.72234 0.66479 0.46471 0.98972
    46      2.58330 4.92802 2.97235 2.46773 4.31534 2.58226 3.69110 3.75176
1.87863 3.30755 4.09886 2.98123 2.63799 2.82333 2.81087 2.53970 2.76486 3.37093
5.49792 4.14980   62 - -
            2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
            0.02147 4.24787 4.97022 0.61958 0.77255 0.55284 0.85640
```

-continued

| | | | | | | | | | |
|---|---|---|---|---|---|---|---|---|---|
| 47 | 2.77665 | 4.24510 | 4.17142 | 3.60737 | 2.13407 | 3.57711 | 3.73827 | 2.35069 | |
| 3.48227 | 2.34958 | 3.36160 | 3.78414 | 4.21156 | 3.69055 | 3.54299 | 3.02842 | 3.00774 | 2.51180 |
| 4.48419 | 1.75453 | 63 | - | - | | | | | |
| | | 2.68618 | 4.42225 | 2.77519 | 2.73123 | 3.46354 | 2.40513 | 3.72494 | 3.29354 |
| 2.67741 | 2.69355 | 4.24690 | 2.90347 | 2.73739 | 3.18146 | 2.89801 | 2.37887 | 2.77519 | 2.98518 |
| 4.58477 | 3.61503 | | | | | | | | |
| | | 0.03412 | 4.34809 | 3.88173 | 0.61958 | 0.77255 | 0.48868 | 0.95045 | |
| 48 | 2.64793 | 5.13223 | 2.68703 | 2.40086 | 4.44996 | 3.45949 | 3.57898 | 3.91234 | |
| 1.96012 | 3.42866 | 4.19439 | 2.88878 | 2.24549 | 2.73197 | 2.91333 | 2.37138 | 2.77466 | 3.51110 |
| 5.59115 | 4.20105 | 64 | - | - | | | | | |
| | | 2.68618 | 4.42225 | 2.77519 | 2.73123 | 3.46354 | 2.40513 | 3.72494 | 3.29354 |
| 2.67741 | 2.69355 | 4.24690 | 2.90347 | 2.73739 | 3.18146 | 2.89801 | 2.37887 | 2.77519 | 2.98518 |
| 4.58477 | 3.61503 | | | | | | | | |
| | | 0.04971 | 4.40314 | 3.31713 | 0.61958 | 0.77255 | 0.57163 | 0.83150 | |
| 49 | 2.37672 | 4.18835 | 3.56611 | 3.33942 | 2.17161 | 3.71892 | 4.00701 | 2.08833 | |
| 3.02370 | 2.38402 | 3.30016 | 3.62106 | 4.09164 | 3.49901 | 3.49065 | 2.99304 | 2.64183 | 2.38390 |
| 4.79262 | 3.11868 | 65 | - | - | | | | | |
| | | 2.68620 | 4.42227 | 2.77521 | 2.73125 | 3.46356 | 2.40514 | 3.72496 | 3.29356 |
| 2.67728 | 2.69357 | 4.24691 | 2.90348 | 2.73728 | 3.18148 | 2.89802 | 2.37888 | 2.77521 | 2.98520 |
| 4.58479 | 3.61505 | | | | | | | | |
| | | 0.10921 | 2.32965 | 5.09470 | 0.32898 | 1.27175 | 0.41324 | 1.08324 | |
| 50 | 2.36036 | 4.48294 | 3.68434 | 3.32162 | 3.85852 | 3.33505 | 4.35926 | 3.56334 | |
| 3.31819 | 3.31552 | 4.22296 | 3.55561 | 0.98977 | 3.63840 | 3.64294 | 2.75832 | 2.58704 | 3.18303 |
| 5.67820 | 4.43472 | 67 | - | - | | | | | |
| | | 2.68618 | 4.42225 | 2.77519 | 2.73123 | 3.46354 | 2.40513 | 3.72494 | 3.29354 |
| 2.67741 | 2.69355 | 4.24690 | 2.90347 | 2.73739 | 3.18146 | 2.89801 | 2.37887 | 2.77519 | 2.98518 |
| 4.58477 | 3.61503 | | | | | | | | |
| | | 0.01734 | 4.45929 | 5.18164 | 0.61958 | 0.77255 | 0.48576 | 0.95510 | |
| 51 | 3.33618 | 4.66932 | 5.03266 | 4.45397 | 3.21894 | 4.56404 | 4.81904 | 1.85917 | |
| 4.29340 | 0.83078 | 3.04538 | 4.61993 | 4.79371 | 4.38871 | 4.36938 | 3.89649 | 3.55725 | 2.44200 |
| 5.15478 | 3.19773 | 68 | - | - | | | | | |
| | | 2.68618 | 4.42225 | 2.77519 | 2.73123 | 3.46354 | 2.40513 | 3.72494 | 3.29354 |
| 2.67741 | 2.69355 | 4.24690 | 2.90347 | 2.73739 | 3.18146 | 2.89801 | 2.37887 | 2.77519 | 2.98518 |
| 4.58477 | 3.61503 | | | | | | | | |
| | | 0.01734 | 4.45929 | 5.18164 | 0.61958 | 0.77255 | 0.48576 | 0.95510 | |
| 52 | 2.63866 | 4.70838 | 2.85148 | 2.85343 | 4.48197 | 3.34287 | 4.11038 | 3.90212 | |
| 3.00292 | 3.53870 | 4.35671 | 3.26563 | 3.96589 | 3.30138 | 3.43429 | 1.35458 | 1.61544 | 3.45306 |
| 5.76856 | 4.46367 | 69 | - | - | | | | | |
| | | 2.68618 | 4.42225 | 2.77519 | 2.73123 | 3.46354 | 2.40513 | 3.72494 | 3.29354 |
| 2.67741 | 2.69355 | 4.24690 | 2.90347 | 2.73739 | 3.18146 | 2.89801 | 2.37887 | 2.77519 | 2.98518 |
| 4.58477 | 3.61503 | | | | | | | | |
| | | 0.01734 | 4.45929 | 5.18164 | 0.61958 | 0.77255 | 0.48576 | 0.95510 | |
| 53 | 2.60942 | 5.07136 | 2.96029 | 1.86628 | 4.36808 | 3.48244 | 3.67378 | 3.41756 | |
| 2.01165 | 2.96551 | 4.12545 | 2.81630 | 3.87448 | 2.70253 | 2.69783 | 2.64352 | 2.83702 | 3.14160 |
| 5.53327 | 3.97650 | 70 | - | - | | | | | |
| | | 2.68618 | 4.42225 | 2.77519 | 2.73123 | 3.46354 | 2.40513 | 3.72494 | 3.29354 |
| 2.67741 | 2.69355 | 4.24690 | 2.90347 | 2.73739 | 3.18146 | 2.89801 | 2.37887 | 2.77519 | 2.98518 |
| 4.58477 | 3.61503 | | | | | | | | |
| | | 0.01734 | 4.45929 | 5.18164 | 0.61958 | 0.77255 | 0.48576 | 0.95510 | |
| 54 | 1.73678 | 5.05920 | 2.76019 | 2.19606 | 4.34746 | 3.40699 | 3.38009 | 3.79477 | |
| 2.40682 | 3.34131 | 4.11991 | 2.97912 | 3.88458 | 2.75025 | 2.94159 | 2.52476 | 2.67210 | 3.17492 |
| 5.53093 | 4.15658 | 71 | - | - | | | | | |
| | | 2.68618 | 4.42225 | 2.77519 | 2.73123 | 3.46354 | 2.40513 | 3.72494 | 3.29354 |
| 2.67741 | 2.69355 | 4.24690 | 2.90347 | 2.73739 | 3.18146 | 2.89801 | 2.37887 | 2.77519 | 2.98518 |
| 4.58477 | 3.61503 | | | | | | | | |
| | | 0.01734 | 4.45929 | 5.18164 | 0.61958 | 0.77255 | 0.48576 | 0.95510 | |
| 55 | 2.74043 | 5.24631 | 2.40465 | 1.98907 | 4.58049 | 3.38842 | 3.68829 | 4.06538 | |
| 2.30593 | 3.54649 | 4.29373 | 2.38561 | 3.88263 | 2.43061 | 2.89904 | 2.64727 | 2.26054 | 3.63184 |
| 5.68162 | 4.26599 | 72 | - | - | | | | | |
| | | 2.68618 | 4.42225 | 2.77519 | 2.73123 | 3.46354 | 2.40513 | 3.72494 | 3.29354 |
| 2.67741 | 2.69355 | 4.24690 | 2.90347 | 2.73739 | 3.18146 | 2.89801 | 2.37887 | 2.77519 | 2.98518 |
| 4.58477 | 3.61503 | | | | | | | | |
| | | 0.01734 | 4.45929 | 5.18164 | 0.61958 | 0.77255 | 0.48576 | 0.95510 | |
| 56 | 1.08787 | 3.11680 | 4.26466 | 3.92702 | 4.56744 | 1.40507 | 4.74478 | 3.93820 | |
| 3.86529 | 3.68181 | 4.51094 | 3.79343 | 3.96845 | 4.09724 | 4.08049 | 2.63816 | 2.94685 | 3.37322 |
| 5.95490 | 4.80790 | 73 | - | - | | | | | |
| | | 2.68618 | 4.42225 | 2.77519 | 2.73123 | 3.46354 | 2.40513 | 3.72494 | 3.29354 |
| 2.67741 | 2.69355 | 4.24690 | 2.90347 | 2.73739 | 3.18146 | 2.89801 | 2.37887 | 2.77519 | 2.98518 |
| 4.58477 | 3.61503 | | | | | | | | |
| | | 0.01734 | 4.45929 | 5.18164 | 0.61958 | 0.77255 | 0.48576 | 0.95510 | |
| 57 | 2.41449 | 5.12942 | 2.78064 | 2.08572 | 4.44698 | 3.23509 | 3.61872 | 3.91373 | |
| 2.08441 | 3.01887 | 4.17771 | 2.90972 | 3.86400 | 2.67091 | 2.76247 | 2.56463 | 2.37385 | 3.34773 |
| 5.57871 | 4.18533 | 74 | - | - | | | | | |
| | | 2.68618 | 4.42225 | 2.77519 | 2.73123 | 3.46354 | 2.40513 | 3.72494 | 3.29354 |
| 2.67741 | 2.69355 | 4.24690 | 2.90347 | 2.73739 | 3.18146 | 2.89801 | 2.37887 | 2.77519 | 2.98518 |
| 4.58477 | 3.61503 | | | | | | | | |
| | | 0.01734 | 4.45929 | 5.18164 | 0.61958 | 0.77255 | 0.48576 | 0.95510 | |
| 58 | 2.35618 | 5.15466 | 2.90683 | 2.03302 | 4.48230 | 3.47903 | 3.65791 | 3.95381 | |
| 1.95514 | 3.38590 | 3.74147 | 2.87799 | 3.86418 | 2.42507 | 2.64313 | 2.58222 | 2.72135 | 3.53606 |

5.59647 4.19971  75 - -
2.68618 4.42225 2.77519 2.73123 3.46354 2.40513 3.72494 3.29354 2.67741 2.69355 4.24690 2.90347 2.73739 3.18146 2.89801 2.37887 2.77519 2.98518 4.58477 3.61503
0.01734 4.45929 5.18164 0.61958 0.77255 0.48576 0.95510
59    2.82048 4.31441 3.59911 3.58912 3.26417 3.91044 4.18415 2.46874 3.46903 1.09245 3.07229 3.84330 4.26181 3.60727 3.67712 3.19562 3.05032 2.49869 4.07413 3.66480  76 - -
2.68618 4.42225 2.77519 2.73123 3.46354 2.40513 3.72494 3.29354 2.67741 2.69355 4.24690 2.90347 2.73739 3.18146 2.89801 2.37887 2.77519 2.98518 4.58477 3.61503
0.01734 4.45929 5.18164 0.61958 0.77255 0.48576 0.95510
60    3.81742 5.05913 5.53372 4.96642 2.73032 5.13111 5.29889 2.41979 4.82530 0.53749 2.78402 5.19788 5.17474 4.75171 4.83127 4.50985 4.01876 2.71504 5.35596 4.27056  77 - -
2.68618 4.42225 2.77519 2.73123 3.46354 2.40513 3.72494 3.29354 2.67741 2.69355 4.24690 2.90347 2.73739 3.18146 2.89801 2.37887 2.77519 2.98518 4.58477 3.61503
0.01734 4.45929 5.18164 0.61958 0.77255 0.48576 0.95510
61    2.18353 5.08325 2.76302 2.42575 4.38435 3.47806 3.51762 3.56262 2.08507 3.12651 3.85720 2.82327 3.87031 2.36589 2.66671 2.51935 2.91708 3.18798 5.54292 4.16091  78 - -
2.68618 4.42225 2.77519 2.73123 3.46354 2.40513 3.72494 3.29354 2.67741 2.69355 4.24690 2.90347 2.73739 3.18146 2.89801 2.37887 2.77519 2.98518 4.58477 3.61503
0.01734 4.45929 5.18164 0.61958 0.77255 0.48576 0.95510
62    2.69830 5.20991 2.17874 2.32825 4.54673 3.35646 3.67029 4.02682 1.91955 3.50995 4.25567 2.93721 3.87314 2.41655 2.73200 2.29314 2.77110 3.59671 5.64478 4.23801  79 - -
2.68618 4.42225 2.77519 2.73123 3.46354 2.40513 3.72494 3.29354 2.67741 2.69355 4.24690 2.90347 2.73739 3.18146 2.89801 2.37887 2.77519 2.98518 4.58477 3.61503
0.01734 4.45929 5.18164 0.61958 0.77255 0.48576 0.95510
63    3.48091 5.78050 0.48398 2.64029 5.32183 3.22187 4.38302 4.97741 3.56135 4.48508 5.42901 3.21673 4.30207 3.60605 4.17838 3.38965 3.84278 4.50650 6.42296 5.06153  80 - -
2.68618 4.42225 2.77519 2.73123 3.46354 2.40513 3.72494 3.29354 2.67741 2.69355 4.24690 2.90347 2.73739 3.18146 2.89801 2.37887 2.77519 2.98518 4.58477 3.61503
0.01734 4.45929 5.18164 0.61958 0.77255 0.48576 0.95510
64    2.89612 4.42362 4.83116 4.24658 3.32561 4.29064 4.63708 2.02632 4.09588 1.20988 2.20498 4.37598 4.59093 4.23666 4.18320 3.48664 3.29831 1.90263 5.10096 3.96543  81 - -
2.68618 4.42225 2.77519 2.73123 3.46354 2.40513 3.72494 3.29354 2.67741 2.69355 4.24690 2.90347 2.73739 3.18146 2.89801 2.37887 2.77519 2.98518 4.58477 3.61503
0.01734 4.45929 5.18164 0.61958 0.77255 0.48576 0.95510
65    2.20468 5.00834 3.02460 2.46700 4.28538 3.22809 3.68956 3.72332 2.07471 3.22745 4.06994 2.99846 3.13955 2.71422 2.40530 2.55367 2.81763 2.91995 5.48516 3.93946  82 - -
2.68618 4.42225 2.77519 2.73123 3.46354 2.40513 3.72494 3.29354 2.67741 2.69355 4.24690 2.90347 2.73739 3.18146 2.89801 2.37887 2.77519 2.98518 4.58477 3.61503
0.02786 4.45929 4.14114 0.61958 0.77255 0.48576 0.95510
66    2.57606 4.97328 3.01298 2.37658 4.23859 2.99122 3.69147 3.38775 2.24029 3.15189 3.89305 2.89169 3.40567 2.76365 2.64345 2.34850 2.54841 2.73885 5.45700 4.10045  83 - -
2.68618 4.42225 2.77519 2.73123 3.46354 2.40513 3.72494 3.29354 2.67741 2.69355 4.24690 2.90347 2.73739 3.18146 2.89801 2.37887 2.77519 2.98518 4.58477 3.61503
0.01752 4.44895 5.17130 0.61958 0.77255 0.50251 0.92889
67    2.13166 4.25308 3.90762 3.34403 2.05039 3.72688 4.02347 2.73125 3.25999 2.46542 3.38226 3.63057 3.61807 3.51702 3.51516 2.92597 2.67380 2.52551 4.81288 2.35249  84 - -
2.68618 4.42225 2.77519 2.73123 3.46354 2.40513 3.72494 3.29354 2.67741 2.69355 4.24690 2.90347 2.73739 3.18146 2.89801 2.37887 2.77519 2.98518 4.58477 3.61503
0.01752 4.44895 5.17130 0.61958 0.77255 0.50251 0.92889
68    2.51295 5.09054 2.98184 1.72812 4.39612 3.48435 3.67785 3.73881 2.41954 3.37739 4.14803 2.97394 3.88052 2.28202 2.67212 2.68772 2.46700 3.25830 5.55010 4.17304  85 - -
2.68618 4.42225 2.77519 2.73123 3.46354 2.40513 3.72494 3.29354 2.67741 2.69355 4.24690 2.90347 2.73739 3.18146 2.89801 2.37887 2.77519 2.98518 4.58477 3.61503
0.01752 4.44895 5.17130 0.61958 0.77255 0.47543 0.97185
69    2.66132 5.17285 2.66986 2.39540 4.50725 3.46839 3.65551 3.76967 1.96543 3.47208 4.21733 2.37317 3.86241 2.33907 2.51152 2.47816 2.84664 3.35597 5.61061 4.20948  86 - -
2.68618 4.42225 2.77519 2.73123 3.46354 2.40513 3.72494 3.29354

-continued 2.67741 2.69355 4.24690 2.90347 2.73739 3.18146 2.89801 2.37887 2.77519 2.98518 4.58477 3.61503
   0.01734 4.45929 5.18164 0.61958 0.77255 0.48576 0.95510
 70 2.40476 1.44095 3.96481 3.44698 3.67421 2.80450 4.21141 3.02108 3.36628 2.76284 3.66000 3.64693 4.04722 3.63180 3.63000 2.52077 2.78604 2.59026 5.14211 3.50924 87 - -
  2.68618 4.42225 2.77519 2.73123 3.46354 2.40513 3.72494 3.29354 2.67741 2.69355 4.24690 2.90347 2.73739 3.18146 2.89801 2.37887 2.77519 2.98518 4.58477 3.61503
   0.01734 4.45929 5.18164 0.61958 0.77255 0.48576 0.95510
 71 3.14464 4.45336 5.03021 4.46417 3.35819 4.45790 4.86159 1.42980 4.32230 1.69292 2.86587 4.38080 4.74701 4.47359 4.40409 3.79830 3.38213 1.35681 5.29927 4.14289 88 - -
  2.68618 4.42225 2.77519 2.73123 3.46354 2.40513 3.72494 3.29354 2.67741 2.69355 4.24690 2.90347 2.73739 3.18146 2.89801 2.37887 2.77519 2.98518 4.58477 3.61503
   0.01734 4.45929 5.18164 0.61958 0.77255 0.48576 0.95510
 72 2.30011 3.73407 3.03761 2.41231 4.07806 3.34217 3.55224 3.48929 2.54009 3.10364 3.92326 2.86753 3.54726 2.88785 2.87570 2.44080 2.13433 3.07048 5.35921 3.53834 89 - -
  2.68618 4.42225 2.77519 2.73123 3.46354 2.40513 3.72494 3.29354 2.67741 2.69355 4.24690 2.90347 2.73739 3.18146 2.89801 2.37887 2.77519 2.98518 4.58477 3.61503
   0.01734 4.45929 5.18164 0.61958 0.77255 0.48576 0.95510
 73 2.14048 5.14694 2.67449 2.30248 4.47134 3.40113 3.65777 3.94253 2.17125 2.97837 4.13264 2.74458 3.76417 2.57571 2.52099 2.46181 2.82539 3.52649 5.59184 4.19432 90 - -
  2.68618 4.42225 2.77519 2.73123 3.46354 2.40513 3.72494 3.29354 2.67741 2.69355 4.24690 2.90347 2.73739 3.18146 2.89801 2.37887 2.77519 2.98518 4.58477 3.61503
   0.01734 4.45929 5.18164 0.61958 0.77255 0.48576 0.95510
 74 2.33987 3.97918 2.71800 2.68393 3.66274 3.56899 3.79046 3.23575 2.52458 2.58207 2.74593 2.97884 3.95502 2.69024 3.09550 2.49450 2.91310 2.83865 5.20705 3.47237 91 - -
  2.68618 4.42225 2.77519 2.73123 3.46354 2.40513 3.72494 3.29354 2.67741 2.69355 4.24690 2.90347 2.73739 3.18146 2.89801 2.37887 2.77519 2.98518 4.58477 3.61503
   0.01734 4.45929 5.18164 0.61958 0.77255 0.48576 0.95510
 75 2.72508 4.24130 3.63475 3.45984 3.36239 3.81026 4.11532 2.14147 3.36542 1.74492 3.34959 3.73067 3.64897 3.61353 3.59970 3.09084 2.24848 1.97147 4.88118 3.68107 92 - -
  2.68618 4.42225 2.77519 2.73123 3.46354 2.40513 3.72494 3.29354 2.67741 2.69355 4.24690 2.90347 2.73739 3.18146 2.89801 2.37887 2.77519 2.98518 4.58477 3.61503
   0.11347 4.45929 2.34657 0.61958 0.77255 0.48576 0.95510
 76 2.44605 5.08758 2.70732 2.38750 4.40669 3.21874 3.64649 3.86979 2.21274 3.38705 4.14749 2.21702 3.28711 2.75638 2.85771 2.36598 2.63424 3.26702 5.55021 4.16021 93 - -
  2.68618 4.42225 2.77519 2.73123 3.46354 2.40513 3.72494 3.29354 2.67741 2.69355 4.24690 2.90347 2.73739 3.18146 2.89801 2.37887 2.77519 2.98518 4.58477 3.61503
   0.09636 4.36489 2.53639 0.61958 0.77255 0.62371 0.76777
 77 2.52140 5.19229 1.93533 2.18979 4.51146 3.30655 3.67579 3.98696 2.38932 3.49150 4.25802 2.75360 3.76248 2.79221 2.91679 2.09509 2.83845 3.57261 5.64795 4.23568 94 - -
  2.68619 4.42226 2.77512 2.73124 3.46355 2.40511 3.72495 3.29355 2.67742 2.69356 4.24691 2.90347 2.73740 3.18147 2.89802 2.37886 2.77520 2.98519 4.58478 3.61504
   0.13745 2.78775 2.70509 0.42399 1.06256 0.37095 1.17143
 78 2.36341 5.11547 2.88923 2.38557 4.43588 3.12293 3.65240 3.90110 1.86565 3.41125 4.16867 2.81154 3.56873 2.61972 2.78323 2.22914 2.70573 3.49407 5.56793 4.17668 96 - -
  2.68618 4.42225 2.77519 2.73123 3.46354 2.40513 3.72494 3.29354 2.67741 2.69355 4.24690 2.90347 2.73739 3.18146 2.89801 2.37887 2.77519 2.98518 4.58477 3.61503
   0.01833 4.40410 5.12644 0.61958 0.77255 0.56252 0.84344
 79 2.28762 4.29763 3.88020 3.31128 3.45344 3.77121 4.08077 2.37703 2.80959 2.48145 3.28647 3.63489 3.92261 3.50644 3.49947 3.04725 2.88061 1.42058 4.95908 3.74730 97 - -
  2.68618 4.42225 2.77519 2.73123 3.46354 2.40513 3.72494 3.29354 2.67741 2.69355 4.24690 2.90347 2.73739 3.18146 2.89801 2.37887 2.77519 2.98518 4.58477 3.61503
   0.01827 4.40717 5.12952 0.61958 0.77255 0.49049 0.94759
 80 2.49336 4.91866 3.06468 2.50610 4.16905 3.50622 3.47926 3.59090 2.04052 3.18152 3.98708 2.87458 3.40359 2.84700 2.63414 2.70907 2.30092 2.61912 5.41218 3.71728 98 - -
  2.68618 4.42225 2.77519 2.73123 3.46354 2.40513 3.72494 3.29354 2.67741 2.69355 4.24690 2.90347 2.73739 3.18146 2.89801 2.37887 2.77519 2.98518 4.58477 3.61503

|  |  |
|---|---|
|  | 0.01772 4.43760 5.15995 0.61958 0.77255 0.46471 0.98972 |
| 81 | 3.45413 4.80651 5.06351 4.52310 3.14668 4.66315 5.03497 2.37248 4.37178 0.65498 3.13154 4.73925 4.90613 4.49133 4.48329 4.02717 3.33601 2.26220 5.35929 4.25227   99 - - |
|  | 2.68618 4.42225 2.77519 2.73123 3.46354 2.40513 3.72494 3.29354 2.67741 2.69355 4.24690 2.90347 2.73739 3.18146 2.89801 2.37887 2.77519 2.98518 4.58477 3.61503 |
|  | 0.01734 4.45929 5.18164 0.61958 0.77255 0.48576 0.95510 |
| 82 | 2.73939 4.83330 3.00723 2.83344 4.71960 3.34320 4.20357 4.19656 3.09807 3.81073 4.63710 0.93081 4.01975 3.40262 3.51075 2.36222 2.79342 3.68571 5.97881 4.64405   100 - - |
|  | 2.68618 4.42225 2.77519 2.73123 3.46354 2.40513 3.72494 3.29354 2.67741 2.69355 4.24690 2.90347 2.73739 3.18146 2.89801 2.37887 2.77519 2.98518 4.58477 3.61503 |
|  | 0.01734 4.45929 5.18164 0.61958 0.77255 0.48576 0.95510 |
| 83 | 2.04424 5.17228 2.45633 2.07839 4.50311 3.46548 3.65902 3.97943 2.19774 3.32071 4.21748 2.93804 3.60950 2.58020 2.72229 2.50774 2.92631 3.55540 5.61278 4.10566   101 - - |
|  | 2.68618 4.42225 2.77519 2.73123 3.46354 2.40513 3.72494 3.29354 2.67741 2.69355 4.24690 2.90347 2.73739 3.18146 2.89801 2.37887 2.77519 2.98518 4.58477 3.61503 |
|  | 0.01734 4.45929 5.18164 0.61958 0.77255 0.48576 0.95510 |
| 84 | 2.94884 5.24796 2.66241 2.49038 4.31917 3.52589 3.86118 3.97970 2.71091 3.53375 4.37214 1.14648 4.03010 2.78537 3.17219 2.92497 3.20366 3.62731 5.61132 3.34532   102 - - |
|  | 2.68618 4.42225 2.77519 2.73123 3.46354 2.40513 3.72494 3.29354 2.67741 2.69355 4.24690 2.90347 2.73739 3.18146 2.89801 2.37887 2.77519 2.98518 4.58477 3.61503 |
|  | 0.01734 4.45929 5.18164 0.61958 0.77255 0.48576 0.95510 |
| 85 | 3.04248 5.24204 2.96062 2.60820 4.65653 3.59476 3.94929 4.07361 2.56705 3.61817 4.49759 3.18876 4.11995 0.96272 2.89157 3.04418 2.94698 3.72218 5.79098 4.47565   103 - - |
|  | 2.68618 4.42225 2.77519 2.73123 3.46354 2.40513 3.72494 3.29354 2.67741 2.69355 4.24690 2.90347 2.73739 3.18146 2.89801 2.37887 2.77519 2.98518 4.58477 3.61503 |
|  | 0.01734 4.45929 5.18164 0.61958 0.77255 0.48576 0.95510 |
| 86 | 3.15528 4.57797 4.44504 3.93193 1.85137 4.15122 3.86565 3.06977 3.40619 2.70190 3.70726 4.00202 4.49914 3.94620 3.42969 3.27245 3.38207 2.89093 2.96247 1.23585   104 - - |
|  | 2.68618 4.42225 2.77519 2.73123 3.46354 2.40513 3.72494 3.29354 2.67741 2.69355 4.24690 2.90347 2.73739 3.18146 2.89801 2.37887 2.77519 2.98518 4.58477 3.61503 |
|  | 0.01734 4.45929 5.18164 0.61958 0.77255 0.48576 0.95510 |
| 87 | 1.91388 4.74994 2.64175 2.83276 4.65908 1.23026 4.17545 4.11077 3.11125 3.71800 4.52370 3.25060 3.97313 3.36530 3.56454 2.36795 3.06739 3.59931 5.92594 4.60838   105 - - |
|  | 2.68618 4.42225 2.77519 2.73123 3.46354 2.40513 3.72494 3.29354 2.67741 2.69355 4.24690 2.90347 2.73739 3.18146 2.89801 2.37887 2.77519 2.98518 4.58477 3.61503 |
|  | 0.01734 4.45929 5.18164 0.61958 0.77255 0.48576 0.95510 |
| 88 | 0.42105 4.60486 4.18172 4.04773 4.75980 3.40644 4.98013 3.98668 4.08316 3.83537 4.82707 4.00997 4.20267 4.37016 4.26066 2.96393 3.28352 3.52613 6.11697 5.00536   106 - - |
|  | 2.68618 4.42225 2.77519 2.73123 3.46354 2.40513 3.72494 3.29354 2.67741 2.69355 4.24690 2.90347 2.73739 3.18146 2.89801 2.37887 2.77519 2.98518 4.58477 3.61503 |
|  | 0.01734 4.45929 5.18164 0.61958 0.77255 0.48576 0.95510 |
| 89 | 2.94731 4.79718 4.85811 4.40161 3.41462 4.43006 5.01217 2.43392 4.20104 0.64102 3.23863 4.59387 4.80786 4.42809 4.33978 3.84144 3.64619 2.39900 5.44657 4.32673   107 - - |
|  | 2.68618 4.42225 2.77519 2.73123 3.46354 2.40513 3.72494 3.29354 2.67741 2.69355 4.24690 2.90347 2.73739 3.18146 2.89801 2.37887 2.77519 2.98518 4.58477 3.61503 |
|  | 0.01734 4.45929 5.18164 0.61958 0.77255 0.48576 0.95510 |
| 90 | 2.69295 3.98202 4.44440 3.88309 3.49385 3.95542 4.41654 1.88586 3.76101 2.45692 3.45424 4.04259 4.36196 3.98345 3.92955 2.88509 2.53539 1.21450 5.07315 3.87854   108 - - |
|  | 2.68618 4.42225 2.77519 2.73123 3.46354 2.40513 3.72494 3.29354 2.67741 2.69355 4.24690 2.90347 2.73739 3.18146 2.89801 2.37887 2.77519 2.98518 4.58477 3.61503 |
|  | 0.01734 4.45929 5.18164 0.61958 0.77255 0.48576 0.95510 |
| 91 | 2.23020 4.52728 3.33461 3.29998 4.71681 3.23321 4.50469 4.14576 3.50163 3.83741 4.66077 3.52242 3.99178 3.76238 3.84265 0.70612 3.04592 3.56218 6.04302 4.79944   109 - - |
|  | 2.68618 4.42225 2.77519 2.73123 3.46354 2.40513 3.72494 3.29354 2.67741 2.69355 4.24690 2.90347 2.73739 3.18146 2.89801 2.37887 2.77519 2.98518 4.58477 3.61503 |
|  | 0.01734 4.45929 5.18164 0.61958 0.77255 0.48576 0.95510 |
| 92 | 4.05064 5.18728 5.18918 4.93015 1.30934 4.79876 3.74116 3.69305 |

-continued 4.72772 2.64779 4.25890 4.46765 5.07773 4.56292 4.64571 4.16664 4.25926 3.61933
1.17959 1.95218   110 - -
        2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
        0.01734 4.45929 5.18164 0.61958 0.77255 0.48576 0.95510
    93   1.28536 3.49665 3.98287 3.48773 3.94001 3.37174 4.32499 3.24593
3.42157 3.01829 3.90186 3.64596 4.01208 3.68988 3.70737 2.34460 1.97075 2.43625
5.38426 4.18438   111 - -
        2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
        0.01734 4.45929 5.18164 0.61958 0.77255 0.48576 0.95510
    94   4.32746 5.37697 5.24755 5.08968 0.67847 4.92310 3.72282 3.90894
4.89259 3.12203 4.46331 4.52796 5.19934 4.66186 4.77457 4.32624 4.53605 3.86568
3.81270 1.39600   112 - -
        2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
        0.01734 4.45929 5.18164 0.61958 0.77255 0.48576 0.95510
    95   2.96563 5.03414 2.96147 2.89269 4.69467 3.45494 4.31635 4.30858
3.22879 3.95664 4.87223 0.68215 4.15542 3.55820 3.60524 3.03479 3.16772 3.84396
5.99932 4.61384   113 - -
        2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
        0.01734 4.45929 5.18164 0.61958 0.77255 0.48576 0.95510
    96   2.69438 4.19269 4.25987 3.56878 3.31680 3.86774 4.19014 2.37254
3.54681 2.01345 2.82578 3.75808 4.23400 3.76804 3.71685 2.96995 2.77903 1.36393
4.85178 3.66032   114 - -
        2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
        0.01734 4.45929 5.18164 0.61958 0.77255 0.48576 0.95510
    97   2.84079 3.93256 4.40616 4.26397 4.98754 0.39355 5.11403 4.49447
4.25980 4.21665 5.11067 4.15445 4.26046 4.53706 4.40205 3.05226 3.38675 3.87725
6.18922 5.18548   115 - -
        2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
        0.01734 4.45929 5.18164 0.61958 0.77255 0.48576 0.95510
    98   2.56290 1.46178 3.90788 3.37708 3.63161 3.17695 4.15838 2.97148
3.29073 2.63206 3.61432 3.36809 3.48256 3.56931 3.49641 2.86742 2.68116 2.40505
5.09846 3.89390   116 - -
        2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
        0.01734 4.45929 5.18164 0.61958 0.77255 0.48576 0.95510
    99   2.54148 5.04654 2.70539 2.37565 4.49775 1.34409 3.89783 3.94239
2.76174 3.51789 4.32880 2.93324 3.97003 3.05438 3.18788 2.57266 2.88542 3.54943
5.73092 4.36307   117 - -
        2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
        0.01734 4.45929 5.18164 0.61958 0.77255 0.48576 0.95510
   100   1.70557 4.79988 3.14657 2.65009 4.21466 2.82353 3.84500 3.42042
2.59544 3.24327 4.06100 1.96080 3.93084 3.00954 3.10889 2.73130 2.86940 3.18113
5.48983 4.17058   118 - -
        2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
        0.01734 4.45929 5.18164 0.61958 0.77255 0.48576 0.95510
   101   2.00483 4.12604 4.25448 3.66225 2.77296 3.75391 4.11010 2.48130
3.52384 2.03969 2.75516 3.82391 4.16685 3.59884 3.66689 2.88608 2.76467 1.94131
4.74141 3.24653   119 - -
        2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
        0.03303 4.45929 3.86691 0.61958 0.77255 0.48576 0.95510
   102   2.39869 4.21435 2.90223 2.24202 4.43514 2.98780 3.65947 3.89880
2.09993 3.22037 4.16856 2.93058 3.86386 2.09592 2.58555 2.64666 2.91791 3.49428
5.56867 4.17940   120 - -
        2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
        0.03161 4.44387 3.94438 0.61958 0.77255 0.51058 0.91665
   103   2.65435 5.11517 2.88355 2.35449 4.19901 3.13016 3.36182 3.89436
2.23601 3.40681 4.16467 2.87691 3.85914 2.63441 2.47196 1.93702 2.57645 3.48979
5.56559 4.17529   121 - -

-continued

|     | |
| --- | --- |
|     | 2.68618 4.42225 2.77519 2.73123 3.46354 2.40513 3.72494 3.29354 2.67741 2.69355 4.24690 2.90347 2.73739 3.18146 2.89801 2.37887 2.77519 2.98518 4.58477 3.61503 |
|     | 0.01786 4.43012 5.15246 0.61958 0.77255 0.48058 0.96345 |
| 104 | 2.41340 4.51586 3.64272 3.20902 3.96433 3.40133 4.18341 3.53981 3.13494 3.21340 4.09895 3.49607 4.02251 3.49050 3.46406 0.91626 3.00878 3.18189 4.01968 4.06003   122 - - |
|     | 2.68618 4.42225 2.77519 2.73123 3.46354 2.40513 3.72494 3.29354 2.67741 2.69355 4.24690 2.90347 2.73739 3.18146 2.89801 2.37887 2.77519 2.98518 4.58477 3.61503 |
|     | 0.01750 4.45022 5.17257 0.61958 0.77255 0.47667 0.96981 |
| 105 | 2.54090 4.85452 2.71842 2.54794 4.08758 3.52137 3.73124 3.35427 2.53920 3.11249 3.93155 3.06305 3.91306 2.75440 2.85634 2.18869 1.95817 3.18450 3.86953 4.03850   123 - - |
|     | 2.68618 4.42225 2.77519 2.73123 3.46354 2.40513 3.72494 3.29354 2.67741 2.69355 4.24690 2.90347 2.73739 3.18146 2.89801 2.37887 2.77519 2.98518 4.58477 3.61503 |
|     | 0.01734 4.45929 5.18164 0.61958 0.77255 0.48576 0.95510 |
| 106 | 2.89313 4.34581 4.36083 3.78021 3.00250 4.01068 3.73906 2.43845 3.64357 1.03448 3.21890 3.99265 4.35163 3.85444 3.81380 3.30755 2.87425 2.34644 4.89798 3.69665   124 - - |
|     | 2.68618 4.42225 2.77519 2.73123 3.46354 2.40513 3.72494 3.29354 2.67741 2.69355 4.24690 2.90347 2.73739 3.18146 2.89801 2.37887 2.77519 2.98518 4.58477 3.61503 |
|     | 0.01734 4.45929 5.18164 0.61958 0.77255 0.48576 0.95510 |
| 107 | 2.38886 4.16785 4.23962 3.65212 3.27942 3.49631 4.14953 1.93787 3.52117 1.96618 3.08994 3.83908 4.20151 3.73674 3.19737 3.12692 2.88453 1.75092 4.80522 3.61535   125 - - |
|     | 2.68618 4.42225 2.77519 2.73123 3.46354 2.40513 3.72494 3.29354 2.67741 2.69355 4.24690 2.90347 2.73739 3.18146 2.89801 2.37887 2.77519 2.98518 4.58477 3.61503 |
|     | 0.01734 4.45929 5.18164 0.61958 0.77255 0.48576 0.95510 |
| 108 | 2.18860 5.09773 3.01081 2.41645 4.40890 3.02601 3.68034 3.70590 1.98541 3.38487 4.15581 2.98738 3.88981 2.71530 2.19915 2.40384 2.85715 3.47177 5.55249 4.18095   126 - - |
|     | 2.68618 4.42225 2.77519 2.73123 3.46354 2.40513 3.72494 3.29354 2.67741 2.69355 4.24690 2.90347 2.73739 3.18146 2.89801 2.37887 2.77519 2.98518 4.58477 3.61503 |
|     | 0.01734 4.45929 5.18164 0.61958 0.77255 0.48576 0.95510 |
| 109 | 2.88848 5.01007 3.36359 2.70440 4.28892 3.67769 3.76628 3.67046 2.13438 2.83550 3.27792 3.21417 4.04788 2.78880 1.37591 2.92736 2.91052 3.36660 5.44614 4.18169   127 - - |
|     | 2.68618 4.42225 2.77519 2.73123 3.46354 2.40513 3.72494 3.29354 2.67741 2.69355 4.24690 2.90347 2.73739 3.18146 2.89801 2.37887 2.77519 2.98518 4.58477 3.61503 |
|     | 0.01734 4.45929 5.18164 0.61958 0.77255 0.48576 0.95510 |
| 110 | 3.01550 4.50647 4.29320 3.35689 3.38082 4.10807 4.41212 2.46129 3.56171 0.92330 3.04014 4.02324 4.44436 3.85149 3.77877 3.41276 2.95071 2.45376 5.11441 3.95652   128 - - |
|     | 2.68618 4.42225 2.77519 2.73123 3.46354 2.40513 3.72494 3.29354 2.67741 2.69355 4.24690 2.90347 2.73739 3.18146 2.89801 2.37887 2.77519 2.98518 4.58477 3.61503 |
|     | 0.01734 4.45929 5.18164 0.61958 0.77255 0.48576 0.95510 |
| 111 | 2.93246 5.26208 2.83845 2.51972 4.59855 3.53909 3.83421 4.05395 2.41041 3.41162 4.39541 1.22702 4.02054 2.58739 2.94782 2.68984 3.17979 3.67765 5.73531 4.37438   129 - - |
|     | 2.68618 4.42225 2.77519 2.73123 3.46354 2.40513 3.72494 3.29354 2.67741 2.69355 4.24690 2.90347 2.73739 3.18146 2.89801 2.37887 2.77519 2.98518 4.58477 3.61503 |
|     | 0.01734 4.45929 5.18164 0.61958 0.77255 0.48576 0.95510 |
| 112 | 1.88527 5.12970 3.02339 2.46506 4.44856 3.51148 3.58652 3.89850 1.94584 3.41349 3.98691 2.52080 3.90280 2.52008 2.59054 2.68296 2.96264 3.50769 5.57002 4.20272   130 - - |
|     | 2.68618 4.42225 2.77519 2.73123 3.46354 2.40513 3.72494 3.29354 2.67741 2.69355 4.24690 2.90347 2.73739 3.18146 2.89801 2.37887 2.77519 2.98518 4.58477 3.61503 |
|     | 0.02789 4.45929 4.13926 0.61958 0.77255 0.48576 0.95510 |
| 113 | 2.74124 4.71833 3.14766 2.56164 4.15454 1.48155 3.79728 3.56948 2.55233 3.04403 4.01264 2.75713 3.96322 2.96545 2.76272 2.79611 2.99003 3.24999 5.18738 4.10961   131 - - |
|     | 2.68618 4.42225 2.77519 2.73123 3.46354 2.40513 3.72494 3.29354 2.67741 2.69355 4.24690 2.90347 2.73739 3.18146 2.89801 2.37887 2.77519 2.98518 4.58477 3.61503 |
|     | 0.01752 4.44892 5.17127 0.61958 0.77255 0.50256 0.92882 |
| 114 | 2.78829 5.27067 2.39544 1.43884 3.52342 3.39995 3.72836 4.06474 2.49027 3.56292 4.32709 2.73652 3.90878 2.43899 3.02346 2.74367 3.02799 3.64666 5.71376 4.29711   132 - - |
|     | 2.68618 4.42225 2.77519 2.73123 3.46354 2.40513 3.72494 3.29354 2.67741 2.69355 4.24690 2.90347 2.73739 3.18146 2.89801 2.37887 2.77519 2.98518 |

-continued

```
4.58477 3.61503
        0.01752 4.44892 5.17127 0.61958 0.77255 0.50256 0.92882
  115   2.58656 5.08616 1.97465 2.39675 4.38521 3.47529 3.67325 3.84095
2.19218 3.37163 4.14005 2.49894 3.87169 2.78755 2.91440 2.60276 2.70141 3.45224
4.35740 3.44083   133 - -
        2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
        0.01752 4.44892 5.17127 0.61958 0.77255 0.50256 0.92882
  116   2.36408 4.93399 3.05515 2.41820 4.19006 3.28886 3.70715 3.53115
2.35589 3.20126 4.00416 3.02568 2.28335 2.65312 2.79254 2.53358 2.91948 2.72092
5.42832 4.08366   134 - -
        2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
        0.07281 4.44892 2.83821 0.61958 0.77255 0.50256 0.92882
  117   2.47921 5.15398 2.61824 2.37031 4.47665 3.08217 3.69410 3.94314
2.47045 3.45936 4.22669 1.75974 3.87627 2.54232 2.92200 2.53173 2.86250 3.45021
5.62343 4.22533   135 - -
        2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
        0.16248 4.39462 1.98324 0.61958 0.77255 0.58364 0.81613
  118   2.47352 4.43682 3.41083 2.85816 3.65814 3.53539 3.85691 2.85096
2.62235 2.70516 3.52326 3.27951 3.95603 3.10614 3.16295 2.71586 1.69391 2.42145
5.07488 3.82615   136 - -
        2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
        0.02134 4.25348 4.97583 0.61958 0.77255 0.75230 0.63730
  119   3.12393 4.58092 4.64216 4.33325 3.86300 4.10675 5.08066 2.11413
4.20840 2.49287 3.78444 4.45840 4.65799 4.54804 4.38259 3.64748 3.48352 0.64916
5.70632 4.45559   137 - -
        2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
        0.02134 4.25348 4.97583 0.61958 0.77255 0.36777 1.17856
  120   1.52970 4.31242 4.27636 3.70359 3.15057 3.97419 4.29716 1.75553
3.59501 2.15161 3.34066 3.94036 4.33244 3.82618 3.79879 3.27010 3.08534 2.21733
4.97587 3.57672   138 - -
        2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
        0.01752 4.44892 5.17127 0.61958 0.77255 0.50256 0.92882
  121   2.00921 3.05304 3.07103 2.43399 4.07708 3.27326 3.62893 3.48743
2.55372 3.10420 3.92537 3.02189 3.60524 2.90180 2.72153 2.18932 2.85663 3.17238
5.36146 4.03760   139 - -
        2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
        0.01752 4.44892 5.17127 0.61958 0.77255 0.50256 0.92882
  122   2.38800 5.20369 2.45901 1.93151 4.53281 3.41096 3.67622 4.01159
2.41230 3.32407 4.25203 2.80676 3.87283 2.05963 2.92660 2.50851 2.91530 3.52839
5.64462 4.23622   140 - -
        2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
        0.01752 4.44892 5.17127 0.61958 0.77255 0.50256 0.92882
  123   2.80442 5.57008 2.32768 1.01424 4.88079 2.93753 3.89581 4.38320
2.81015 3.87205 4.67758 2.92022 4.01617 2.76513 3.36230 2.93852 3.29333 3.95302
6.02758 4.55781   141 - -
        2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
        0.01752 4.44892 5.17127 0.61958 0.77255 0.50256 0.92882
  124   3.65291 4.92987 5.28841 4.75290 2.09973 4.85851 4.79616 2.49842
4.59706 0.68663 3.08443 4.86508 5.00895 4.57855 4.61939 4.21526 3.86249 2.75251
4.95107 3.43578   142 - -
        2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
        0.01752 4.44892 5.17127 0.61958 0.77255 0.50256 0.92882
  125   2.68163 4.78103 3.25910 2.74134 4.08738 3.29345 3.84411 3.27298
2.47216 3.00438 3.96065 3.20761 1.46271 3.03322 2.77484 2.83542 3.00539 3.16979
5.37921 4.09799   143 - -
        2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
        0.01752 4.44892 5.17127 0.61958 0.77255 0.50256 0.92882
```

-continued

| | | | | | | | | |
|---|---|---|---|---|---|---|---|---|
| 126 | 2.97837 | 5.31590 | 3.32617 | 2.68999 | 4.72425 | 3.69304 | 3.27951 | 4.12761 |
| 1.41978 | 3.15207 | 4.36950 | 2.95852 | 4.05870 | 2.29333 | 1.88668 | 2.95013 | 3.17244 | 3.74769 |
| 5.64414 | 4.36966 | 144 - - | | | | | | |
| | | 2.68618 | 4.42225 | 2.77519 | 2.73123 | 3.46354 | 2.40513 | 3.72494 | 3.29354 |
| 2.67741 | 2.69355 | 4.24690 | 2.90347 | 2.73739 | 3.18146 | 2.89801 | 2.37887 | 2.77519 | 2.98518 |
| 4.58477 | 3.61503 | | | | | | | |
| | | 0.02051 | 4.44892 | 4.75533 | 0.61958 | 0.77255 | 0.50256 | 0.92882 |
| 127 | 3.24053 | 4.68626 | 4.42354 | 3.93390 | 2.40064 | 4.19011 | 3.87268 | 3.13732 |
| 3.77092 | 2.69167 | 3.77020 | 4.01866 | 4.54932 | 3.96154 | 3.93737 | 3.50591 | 2.78389 | 2.98596 |
| 1.09473 | 2.38377 | 145 - - | | | | | | |
| | | 2.68618 | 4.42225 | 2.77519 | 2.73123 | 3.46354 | 2.40513 | 3.72494 | 3.29354 |
| 2.67741 | 2.69355 | 4.24690 | 2.90347 | 2.73739 | 3.18146 | 2.89801 | 2.37887 | 2.77519 | 2.98518 |
| 4.58477 | 3.61503 | | | | | | | |
| | | 0.01757 | 4.44599 | 5.16833 | 0.61958 | 0.77255 | 0.50723 | 0.92171 |
| 128 | 2.69906 | 4.81576 | 3.08565 | 2.57557 | 4.04005 | 3.53963 | 3.74869 | 3.22744 |
| 2.40032 | 3.06681 | 3.89789 | 1.97993 | 3.93159 | 2.91813 | 2.73517 | 2.75677 | 2.74275 | 2.22386 |
| 5.33397 | 4.02105 | 146 - - | | | | | | |
| | | 2.68618 | 4.42225 | 2.77519 | 2.73123 | 3.46354 | 2.40513 | 3.72494 | 3.29354 |
| 2.67741 | 2.69355 | 4.24690 | 2.90347 | 2.73739 | 3.18146 | 2.89801 | 2.37887 | 2.77519 | 2.98518 |
| 4.58477 | 3.61503 | | | | | | | |
| | | 0.02207 | 4.44599 | 4.59455 | 0.61958 | 0.77255 | 0.50723 | 0.92171 |
| 129 | 2.67905 | 4.57309 | 3.32994 | 2.76622 | 3.73883 | 3.59300 | 3.19938 | 3.01028 |
| 2.15094 | 2.56209 | 3.22488 | 3.09606 | 3.97668 | 3.06418 | 2.85128 | 2.81906 | 2.63816 | 2.82377 |
| 4.30953 | 2.58633 | 147 - - | | | | | | |
| | | 2.68618 | 4.42225 | 2.77515 | 2.73123 | 3.46354 | 2.40513 | 3.72495 | 3.29354 |
| 2.67741 | 2.69355 | 4.24690 | 2.90347 | 2.73740 | 3.18146 | 2.89801 | 2.37887 | 2.77520 | 2.98518 |
| 4.58477 | 3.61503 | | | | | | | |
| | | 0.02949 | 3.75743 | 5.16391 | 0.54795 | 0.86306 | 0.51420 | 0.91124 |
| 130 | 1.37236 | 4.40095 | 3.68215 | 3.15295 | 3.75592 | 2.52271 | 4.08407 | 2.92930 |
| 3.10149 | 2.47905 | 3.70955 | 3.48452 | 4.03143 | 3.40599 | 3.44185 | 2.76304 | 2.93611 | 2.46504 |
| 5.20046 | 3.97096 | 149 - - | | | | | | |
| | | 2.68618 | 4.42225 | 2.77519 | 2.73123 | 3.46354 | 2.40513 | 3.72494 | 3.29354 |
| 2.67741 | 2.69355 | 4.24690 | 2.90347 | 2.73739 | 3.18146 | 2.89801 | 2.37887 | 2.77519 | 2.98518 |
| 4.58477 | 3.61503 | | | | | | | |
| | | 0.01765 | 4.44156 | 5.16391 | 0.61958 | 0.77255 | 0.51420 | 0.91124 |
| 131 | 2.92571 | 5.41476 | 2.40274 | 2.25750 | 4.73426 | 1.59137 | 3.83505 | 4.22032 |
| 2.46966 | 3.72284 | 4.51462 | 2.12442 | 3.97518 | 2.96959 | 3.22426 | 2.64902 | 3.18355 | 3.80226 |
| 5.88395 | 4.44532 | 150 - - | | | | | | |
| | | 2.68618 | 4.42225 | 2.77519 | 2.73123 | 3.46354 | 2.40513 | 3.72494 | 3.29354 |
| 2.67741 | 2.69355 | 4.24690 | 2.90347 | 2.73739 | 3.18146 | 2.89801 | 2.37887 | 2.77519 | 2.98518 |
| 4.58477 | 3.61503 | | | | | | | |
| | | 0.01765 | 4.44156 | 5.16391 | 0.61958 | 0.77255 | 0.51420 | 0.91124 |
| 132 | 2.91871 | 5.13022 | 2.71064 | 2.58530 | 4.61395 | 1.08952 | 3.96281 | 4.05904 |
| 2.60237 | 3.62616 | 4.46295 | 2.92155 | 4.04062 | 3.13339 | 2.89835 | 2.92929 | 3.22159 | 3.66933 |
| 5.81419 | 4.46718 | 151 - - | | | | | | |
| | | 2.68618 | 4.42225 | 2.77520 | 2.73124 | 3.46354 | 2.40513 | 3.72495 | 3.29354 |
| 2.67741 | 2.69355 | 4.24690 | 2.90347 | 2.73732 | 3.18147 | 2.89801 | 2.37887 | 2.77520 | 2.98519 |
| 4.58477 | 3.61503 | | | | | | | |
| | | 0.08528 | 3.78188 | 2.83085 | 0.63047 | 0.76001 | 0.51420 | 0.91124 |
| 133 | 2.55415 | 5.12827 | 2.99700 | 2.37401 | 4.45513 | 3.42989 | 3.22630 | 3.91005 |
| 1.66425 | 3.41408 | 4.09517 | 2.82365 | 3.87578 | 2.41406 | 2.56728 | 2.66166 | 2.93780 | 3.15862 |
| 5.56110 | 4.18910 | 154 - - | | | | | | |
| | | 2.68618 | 4.42225 | 2.77519 | 2.73123 | 3.46354 | 2.40513 | 3.72494 | 3.29354 |
| 2.67741 | 2.69355 | 4.24690 | 2.90347 | 2.73739 | 3.18146 | 2.89801 | 2.37887 | 2.77519 | 2.98518 |
| 4.58477 | 3.61503 | | | | | | | |
| | | 0.01865 | 4.38685 | 5.10920 | 0.61958 | 0.77255 | 0.59439 | 0.80274 |
| 134 | 2.68757 | 4.69832 | 3.24582 | 2.59317 | 3.89741 | 3.57072 | 3.77065 | 3.17298 |
| 2.28857 | 2.93278 | 3.78681 | 3.16345 | 3.22761 | 2.80999 | 2.72847 | 2.80064 | 2.93185 | 1.75884 |
| 5.22736 | 3.94700 | 155 - - | | | | | | |
| | | 2.68618 | 4.42225 | 2.77519 | 2.73123 | 3.46354 | 2.40513 | 3.72494 | 3.29354 |
| 2.67741 | 2.69355 | 4.24690 | 2.90347 | 2.73739 | 3.18146 | 2.89801 | 2.37887 | 2.77519 | 2.98518 |
| 4.58477 | 3.61503 | | | | | | | |
| | | 0.01865 | 4.38685 | 5.10920 | 0.61958 | 0.77255 | 0.59439 | 0.80274 |
| 135 | 2.66483 | 4.14616 | 4.10629 | 3.52046 | 3.11519 | 3.76324 | 4.05895 | 2.53934 |
| 3.39922 | 1.42345 | 3.09375 | 3.35986 | 4.13201 | 3.56974 | 3.58549 | 2.72565 | 2.89692 | 2.25748 |
| 3.72072 | 3.54295 | 156 - - | | | | | | |
| | | 2.68618 | 4.42225 | 2.77519 | 2.73123 | 3.46354 | 2.40513 | 3.72494 | 3.29354 |
| 2.67741 | 2.69355 | 4.24690 | 2.90347 | 2.73739 | 3.18146 | 2.89801 | 2.37887 | 2.77519 | 2.98518 |
| 4.58477 | 3.61503 | | | | | | | |
| | | 0.01865 | 4.38685 | 5.10920 | 0.61958 | 0.77255 | 0.59439 | 0.80274 |
| 136 | 2.54947 | 5.15494 | 2.81817 | 2.27071 | 4.47196 | 3.45438 | 3.67320 | 3.93783 |
| 2.18117 | 3.44723 | 4.21076 | 2.61053 | 2.15770 | 2.48927 | 2.90923 | 2.63558 | 2.81969 | 3.53198 |
| 5.60426 | 4.20964 | 157 - - | | | | | | |
| | | 2.68618 | 4.42225 | 2.77519 | 2.73123 | 3.46354 | 2.40513 | 3.72494 | 3.29354 |
| 2.67741 | 2.69355 | 4.24690 | 2.90347 | 2.73739 | 3.18146 | 2.89801 | 2.37887 | 2.77519 | 2.98518 |
| 4.58477 | 3.61503 | | | | | | | |
| | | 0.01865 | 4.38685 | 5.10920 | 0.61958 | 0.77255 | 0.46370 | 0.99143 |
| 137 | 2.48424 | 4.64364 | 3.23983 | 2.74683 | 4.45646 | 0.95630 | 4.24608 | 3.78460 |
| 3.16682 | 3.50936 | 4.37248 | 3.36772 | 4.01139 | 3.48004 | 3.54078 | 2.79397 | 3.07496 | 2.94872 |

|     |     |     |     |     |     |     |     |     |
| --- | --- | --- | --- | --- | --- | --- | --- | --- |
| 5.79263 4.52277 | 158 | - | - | | | | | |

```
            2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
            0.01765 4.44156 5.16391 0.61958 0.77255 0.51420 0.91124
    138     3.30920 4.75420 4.61173 4.11127 3.12041 4.38915 4.69609 2.54917
3.90653 0.68230 3.16405 4.37109 4.69955 3.81654 4.07332 3.74605 3.29083 2.64075
5.18905 3.99579   159 - -
            2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
            0.01765 4.44156 5.16391 0.61958 0.77255 0.51420 0.91124
    139     2.64297 4.51540 3.13915 2.58066 3.67426 3.43890 3.84982 2.79669
2.71873 2.72061 3.40686 3.27646 3.99414 3.11806 3.19182 2.71823 2.35387 1.80992
5.08364 3.82661   160 - -
            2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
            0.02149 4.44156 4.65848 0.61958 0.77255 0.51420 0.91124
    140     2.64854 5.18440 3.10682 2.54595 4.52943 3.57236 3.59991 3.96071
2.19829 3.42661 4.24551 2.43253 3.96199 2.65206 1.54852 2.67222 2.94271 3.57966
5.59352 4.26198   161 - -
            2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
            0.01772 4.43780 5.16014 0.61958 0.77255 0.52008 0.90256
    141     3.44190 5.32458 4.00047 3.46399 4.96977 3.41557 4.22078 4.46813
2.52378 3.92894 4.85429 3.79058 4.42887 3.40774 0.52734 3.51113 3.71233 4.11175
5.83836 4.76025   162 - -
            2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
            0.01772 4.43780 5.16014 0.61958 0.77255 0.52008 0.90256
    142     3.44190 5.32458 4.00047 3.46399 4.96977 3.41557 4.22078 4.46813
2.52378 3.92894 4.85429 3.79058 4.42887 3.40774 0.52734 3.51113 3.71233 4.11175
5.83836 4.76025   163 - -
            2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
            0.02519 4.43780 4.33842 0.61958 0.77255 0.52008 0.90256
    143     1.90653 5.22931 2.62762 2.14830 4.55055 3.46127 3.70649 4.02504
2.07812 3.52458 4.28677 2.20792 3.89414 2.79487 2.97073 2.72114 2.99769 3.55680
5.67510 4.26740   164 - -
            2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
            0.01785 4.43045 5.15280 0.61958 0.77255 0.53138 0.88623
    144     1.66693 4.90314 2.79419 2.43720 4.14970 3.50399 3.70716 3.38051
2.26779 3.16514 3.57851 2.96848 3.89556 2.85254 2.83650 2.70887 2.91240 3.07112
5.40141 4.06201   165 - -
            2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
            0.02074 4.43045 4.75450 0.61958 0.77255 0.53138 0.88623
    145     3.57909 5.69383 2.89268 0.43731 5.13396 3.74413 4.42879 4.71520
3.39551 4.25239 5.24212 3.42136 4.38610 3.65781 3.83675 3.52400 3.90016 4.35367
6.18972 4.96810   166 - -
            2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
            0.02361 4.42762 4.47474 0.61958 0.77255 0.53569 0.88012
    146     2.53815 4.23541 3.89256 3.31415 3.35365 3.43314 4.01926 2.27305
3.13182 2.36020 3.34809 3.61467 4.10930 3.48366 2.78779 3.00792 2.91165 1.57725
4.84488 3.36475   167 - -
            2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
            0.01800 4.42201 5.14436 0.61958 0.77255 0.54412 0.86835
    147     1.80943 5.17035 2.62157 2.07449 4.49100 3.42292 3.67419 3.96118
2.17043 3.46432 4.22212 2.93630 3.87161 2.56527 2.84559 2.64670 2.88453 3.50978
5.61623 4.21716   168 - -
            2.68618 4.42225 2.77519 2.73123 3.46354 2.40513 3.72494 3.29354
2.67741 2.69355 4.24690 2.90347 2.73739 3.18146 2.89801 2.37887 2.77519 2.98518
4.58477 3.61503
            0.01800 4.42201 5.14436 0.61958 0.77255 0.54412 0.86835
    148     3.71568 4.98323 5.39542 4.83916 2.79356 5.00269 5.20401 2.41032
4.69620 0.57295 2.93926 5.06411 5.09914 4.67653 4.73417 4.37793 3.92780 2.46918
5.32073 4.20270   169 - -
            2.68618 4.42225 2.77519 2.73123 3.46354 2.40513 3.72494 3.29354
```

-continued 2.67741 2.69355 4.24690 2.90347 2.73739 3.18146 2.89801 2.37887 2.77519 2.98518 4.58477 3.61503
0.01800 4.42201 5.14436 0.61958 0.77255 0.54412 0.86835
149    1.99327 2.70853 4.08451 3.52864 1.85792 3.42232 3.91516 2.71735 3.41997 2.46283 3.37905 3.72050 4.10390 3.65301 3.62210 2.80539 2.90591 2.50317 4.85301 3.64388   170 - -
2.68618 4.42225 2.77519 2.73123 3.46354 2.40513 3.72494 3.29354 2.67741 2.69355 4.24690 2.90347 2.73739 3.18146 2.89801 2.37887 2.77519 2.98518 4.58477 3.61503
0.03954 4.42201 3.62092 0.61958 0.77255 0.54412 0.86835
150    2.52034 5.07675 2.86686 2.34451 4.38139 3.46473 3.58228 3.83719 1.82596 2.91213 3.78433 2.90755 3.85707 2.33901 2.80894 2.51619 2.74142 3.44564 5.53279 4.15171   171 - -
2.68618 4.42225 2.77519 2.73123 3.46354 2.40513 3.72494 3.29354 2.67741 2.69355 4.24690 2.90347 2.73739 3.18146 2.89801 2.37887 2.77519 2.98518 4.58477 3.61503
0.05269 4.40086 3.24268 0.61958 0.77255 0.57487 0.82732
151    2.56841 4.80930 3.10084 2.47522 4.03593 3.39038 3.70967 3.30280 2.05479 3.06154 3.82459 3.05201 3.89470 2.71798 2.95896 2.58812 1.96719 3.08959 4.39727 4.00056   172 - -
2.68618 4.42225 2.77519 2.73123 3.46354 2.40513 3.72494 3.29354 2.67741 2.69355 4.24690 2.90347 2.73739 3.18146 2.89801 2.37887 2.77519 2.98518 4.58477 3.61503
0.03303 4.36720 3.92179 0.61958 0.77255 0.62070 0.77126
152    2.00712 4.80326 3.04608 2.51290 4.16635 3.12701 3.47637 3.58373 2.58766 3.19402 4.01252 3.03841 2.06845 2.94568 3.05479 2.54694 2.74358 3.23947 5.43985 4.11489   173 - -
2.68621 4.42228 2.77522 2.73117 3.46357 2.40515 3.72476 3.29338 2.67743 2.69358 4.24692 2.90349 2.73734 3.18149 2.89803 2.37884 2.77522 2.98521 4.58480 3.61506
0.11549 2.35531 4.25417 0.54335 0.86941 0.63840 0.75107
153    2.16030 4.62913 3.21138 2.59079 4.25901 2.76297 3.94367 3.67658 2.80049 3.30378 4.12023 3.18454 3.88643 3.12635 3.23166 1.76272 1.88963 3.27351 5.54965 4.25166   176 - -
2.68618 4.42225 2.77519 2.73123 3.46354 2.40513 3.72494 3.29354 2.67741 2.69355 4.24690 2.90347 2.73739 3.18146 2.89801 2.37887 2.77519 2.98518 4.58477 3.61503
0.03127 4.34547 4.02732 0.61958 0.77255 0.64844 0.73995
154    2.66792 5.11177 2.56371 2.33718 4.43052 3.12411 3.63758 3.76704 2.24610 3.40665 4.16392 2.51360 3.83618 2.72460 2.75418 2.00063 2.60055 3.48912 5.56277 4.16722   177 - -
2.68618 4.42225 2.77520 2.73123 3.46354 2.40510 3.72495 3.29354 2.67741 2.69355 4.24690 2.90347 2.73740 3.18146 2.89801 2.37887 2.77520 2.98518 4.58477 3.61503
0.20910 3.75741 1.79972 0.56129 0.84507 0.66269 0.72456
155    2.55143 4.81591 2.81468 2.31661 3.92133 3.34474 3.63569 3.47575 2.37389 3.07571 3.88637 2.95949 3.82254 2.66149 2.66956 2.47706 2.52334 2.53039 5.31632 3.83266   179 - -
2.68618 4.42225 2.77519 2.73123 3.46354 2.40513 3.72494 3.29354 2.67741 2.69355 4.24690 2.90347 2.73739 3.18146 2.89801 2.37887 2.77519 2.98518 4.58477 3.61503
0.03176 4.16074 4.15646 0.61958 0.77255 0.76695 0.62442
156    2.55523 4.93315 2.94860 2.24014 4.20806 3.11633 3.48685 3.19520 2.09238 3.20688 3.99407 2.92490 3.24954 2.58362 2.75119 2.50501 2.80774 3.04779 5.40950 4.04862   180 - -
2.68618 4.42225 2.77519 2.73123 3.46354 2.40513 3.72494 3.29354 2.67741 2.69355 4.24690 2.90347 2.73739 3.18146 2.89801 2.37887 2.77519 2.98518 4.58477 3.61503
0.02276 4.19001 4.91235 0.61958 0.77255 0.81337 0.58584
157    1.20660 4.40759 3.35604 2.93272 3.95893 3.20449 3.52467 3.34303 2.90686 3.04070 3.90878 3.27859 3.58791 3.25408 3.26247 2.65317 2.85764 2.78550 5.33854 4.07865   181 - -
2.68618 4.42225 2.77519 2.73123 3.46354 2.40513 3.72494 3.29354 2.67741 2.69355 4.24690 2.90347 2.73739 3.18146 2.89801 2.37887 2.77519 2.98518 4.58477 3.61503
0.02276 4.19001 4.91235 0.61958 0.77255 0.68268 0.70372
158    2.67140 4.29203 3.70746 3.13942 2.86196 3.68163 2.96310 2.76890 3.05716 1.69286 3.39392 3.48105 3.86490 2.82577 3.35631 2.94264 2.90223 2.56219 3.97407 3.25518   182 - -
2.68618 4.42225 2.77519 2.73123 3.46354 2.40513 3.72494 3.29354 2.67741 2.69355 4.24690 2.90347 2.73739 3.18146 2.89801 2.37887 2.77519 2.98518 4.58477 3.61503
0.02128 4.25624 4.97858 0.61958 0.77255 0.74947 0.63982
159    2.63798 4.48996 3.51982 3.04228 3.81419 3.47372 4.04467 3.03664 2.92137 2.64518 3.23372 3.40240 1.41997 3.31178 3.25344 2.82205 2.74199 2.80698 5.29179 4.03651   183 - -
2.68618 4.42225 2.77519 2.73123 3.46354 2.40513 3.72494 3.29354 2.67741 2.69355 4.24690 2.90347 2.73739 3.18146 2.89801 2.37887 2.77519 2.98518 4.58477 3.61503

-continued

```
        0.14151 4.25624 2.13899 0.61958 0.77255 0.74947 0.63982
160     2.46470 3.83575 3.23523 2.67393 3.66999 3.49642 3.73458 3.04690
2.43613 2.64675 3.59308 3.01880 3.25014 2.84868 2.98138 2.59083 2.70116 2.25801
5.05478 3.78583   184 - -
        2.68617 4.42231 2.77511 2.73129 3.46360 2.40503 3.72497 3.29360
2.67725 2.69361 4.24696 2.90353 2.73733 3.18150 2.89795 2.37891 2.77523 2.98525
4.58483 3.61509
        0.49613 0.96883 4.45773 0.15588 1.93562 0.80876 0.58953
161     2.60601 0.74299 4.28430 4.02298 4.16889 3.28957 4.69398 3.40236
3.85046 3.26155 4.28085 3.92541 3.45640 4.17512 3.98128 2.85611 3.09926 3.06230
5.57309 4.44623   186 - -
        2.68617 4.42226 2.77521 2.73125 3.46355 2.40514 3.72496 3.29355
2.67738 2.69356 4.24691 2.90348 2.73741 3.18131 2.89802 2.37887 2.77517 2.98520
4.58478 3.61504
        0.09408 2.41030   * 0.42020 1.06978 0.00000   *
//
```

Example 17: In Vivo Broiler Trial

Materials and Methods

The trial was performed at the Research Center for Animal Nutrition (DSM Nutritional Products France, F-68305 Village-Neuf) according to the official French guidelines for experiments with live animals. Day-old male broiler chickens ("ROSS PM3"), were supplied by a commercial hatchery (Joseph Grelier S. A., Elevage avicole de la Bohadiere, F-49290 Saint-Laurent de la Plaine, France).

Animals and Housing

On the day of arrival (day 1), the chickens were divided by weight into groups of 20 birds. Each group was placed in one floor-pen littered with wood shavings and allocated to one of the different treatments.

Each treatment was replicated with 8 groups. The chickens were housed in an environmentally controlled room. The room temperature was adapted to the age of the birds. In the first few days an additional infra-red electric heating lamp was placed in each pen. Moreover, in the first week feed was offered to the birds as crumbled pellets, afterwards as pelleted feed. The birds had free access to feed and water.

Feeding and Treatments

The experimental diets (Starter, Grower and Finisher) were based on soybean meal, wheat and rye (12%) as main ingredients (Table 8). The diets were formulated to contain 225 g crude protein and 12.5 MJ/kg $ME_N$ for the starter period, 215 g crude protein and 12.8 MJ/kg $ME_N$ for the grower period and 205 g crude protein and 13.0 MJ/kg $ME_N$ for the finisher period.

TABLE 8

Composition and nutrient contents of the basal experimental diets

|  | Starter (d 1-22) | Grower (d 22-36) | Finisher (d 36-42) |
|---|---|---|---|
| Ingredients (%) |  |  |  |
| Soybean meal | 38.00 | 35.40 | 33.00 |
| Corn | 22.55 | 20.20 | 21.40 |
| Wheat | 20.00 | 24.50 | 25.00 |
| Rye | 12.00 | 12.00 | 12.00 |
| Soya oil | 3.80 | 4.30 | 4.85 |
| DL-Methionine | 0.20 | 0.15 | 0.15 |
| NaCl | 0.15 | 0.15 | 0.15 |
| DCP | 1.70 | 1.85 | 1.95 |
| CaCO3 | 0.54 | 0.39 | 0.34 |
| Premix[1] | 1.00 | 1.00 | 1.00 |
| Coccidiostat | 0.06 | — | — |

TABLE 8-continued

Composition and nutrient contents of the basal experimental diets

|  | Starter (d 1-22) | Grower (d 22-36) | Finisher (d 36-42) |
|---|---|---|---|
| Calculated content |  |  |  |
| Crude protein (%) | 22.5 | 21.5 | 20.5 |
| Metabolizable energy (MJ/kg)[2] | 12.6 | 12.8 | 13.0 |
| Analyzed content |  |  |  |
| Crude protein (%) | 21.9 | 21.5 | 20.8 |
| Metabolizable energy (MJ/kg)[3] | 12.5 | 12.6 | 12.9 |

[1]Vitamin-mineral premix provided per kilogram of diet: Vitamin A: 10'000 I.U.; vitamin E: 40 I.U.; vitamin K3: 3.0 mg; vitamin C: 100 mg; vitamin B1: 2.50 mg; vitamin B2: 8.00 mg; vitamin B6: 5.00 mg; vitamin B12: 0.03 mg; niacin: 50.0 mg; pantothenate calcium: 12.0 mg; folic acid: 1.50 mg; biotin 0.15 mg; cholin: 450 mg; ethoxyquine: 54 mg; Na: 1.17 g; Mg: 0.8 g; Mn: 80 mg; Fe: 60 mg; Cu: 30 mg; Zn: 54 mg; I: 1.24 mg; Co: 0.6 mg; Se: 0.3 mg.
[1]Without coccidiostat;
[2]Calculated with EC-equation;
[3]Calculated with EC-equation based on analysed crude nutrients.

The diets were fed either unsupplemented (negative control, C), supplemented with the GH24 lysozyme (SEQ ID NO: 257) at 25 mg per kg feed or with Avilamycin at an inclusion level of 10 mg/kg. No additional enzymes (e.g., phytase) were added to the feed.

Appropriate amounts of the solid product (Avilamycin) was mixed with a small quantity of the basal feed as a premix which was then added to the feed to get the final concentration, according to the treatment. After mixing the feed was pelleted (3×25 mm) at about 70° C.

Appropriate amount of the liquid preparations of Lysozyme was diluted in water and sprayed onto the respective pelleted feed to get the final concentrations in the feed corresponding to the different treatments. For procedural balance of all treatments the same volume of water were also sprayed onto the pellets of the control diets.

Experimental Parameters and Analyses

For the two experiments, the birds were weighed (as replicate group) on days 1, 22 and 36. The feed consumption for the intermediate periods was determined. Body weight gain and feed conversion ratio (feed/gain) were calculated.

The analyses of the nutrient content in the feed samples were performed according to standard methods (VDLUFA 1976). Nitrogen analysis was carried out with a Leco N analyzer (CP=N*6.25).

Statistical Analysis

For the statistical evaluation of performance data, a one-factorial analysis of variance (factor: treatment) was carried out. The software 'Stat Box Pro Agri', version 7.1.9 (Grimmer soft, 1985-2011) was used. Where significant treatment effects (p<0.05) were indicated, the differences among treatment means were subsequently determined with the Newman-Keuls test.

Results and Discussion

Based on the analyzed chemical compositions of the diets, the content of crude protein was close to the calculated content but the metabolizable energy was higher than expected in all the three diets (starter-grower and finisher) (Table 8).

The results of the growth performance are summarized in table 9 for the two periods (starter period, day 1-22; grower period, day 22-36, finisher period, day 36-42) and for the whole experimental period from day 1 to day 42 (table 10).

TABLE 9

Growth performance data of male broiler chickens fed graded inclusion levels of microbial lysozyme

| Treatment/Product | Starter (d 1-22) | | | Grower (d 22-36) | | | Finisher (d 36-42) | | |
|---|---|---|---|---|---|---|---|---|---|
| | Weight gain (g/b) | Feed intake (g/b) | FCR | Weight gain (g/b) | Feed intake (g/b) | FCR | Weight gain (g/b) | Feed intake (g/b) | FCR |
| Control (C) | 1096 | 1578 | 1.440 | 1328 | 2285 | 1.723 | 761 | 1487 | 1.960 |
| Avilamycin (10 mg/kg) | 1102 | 1593 | 1.452 | 1334 | 2242 | 1.683 | 738 | 1460 | 1.982 |
| Relative to C (%) | 100.6 | 101.0 | 100.8 | 100.4 | 98.1 | 97.7 | 97.0 | 98.2 | 101.1 |
| SEQ ID NO: 257 (25 mg/kg) | 1133 | 1603 | 1.414 | 1364 | 2336 | 1.714 | 800 | 1524 | 1.919 |
| Relative to C (%) | 103.4 | 101.6 | 98.1 | 102.7 | 102.2 | 99.5 | 105.1 | 102.5 | 97.9 |

TABLE 10

Growth performance summary of male broiler chickens fed graded inclusion levels of microbial lysozyme

| Treatment/Product | Whole period | | | | |
|---|---|---|---|---|---|
| | Weight gain (g/b) | Feed intake (g/b) | FCR | Motality | EPEF |
| Control (C) | 3186 | 5351 | 1.680 | 7.5 | 418 |
| Avilamycin (10 mg/kg) | 3184 | 5312 | 1.669 | 12.5 | 397 |
| Relative to C (%) | 99.9 | 99.3 | 99.3 | | 95.0 |
| SEQ ID NO: 257 (25 mg/kg) | 3290 | 5450 | 1.657 | 10.0 | 425 |
| Relative to C (%) | 103.3 | 101.9 | 98.6 | | 101.7 |

Over the whole period, the GH24 supplemented at 25 mg/kg resulted in a FCR improvement of 1.4% compared to NC diet. Furthermore, the GH24 lysozyme supplemented at 25 mg/kg resulted in an EPEF improvements of 1.7% compared to NC diet. Whilst the positive control Avilamycin showed a slight FCR improvement of 0.7%, the EPEF was worse by 5.0%.

Conclusion

The results obtained in the study showed that the inclusion of a microbial lysozyme at 25 mg/kg was effective in improving the FCR and the EPEF of broilers fed diets formulated with coccidiostat in the starter period and based on soybean meal, corn, wheat and rye. In addition, the microbial lysozyme at 25 mg/kg was markedly better in improving the EPEF over the positive control (Avilamycin).

Example 18: In Vivo Piglet Trial

Materials and Methods

The trial was performed from Oct. 23 to Dec. 4, 2014 at the Research Center for Animal Nutrition (DSM Nutritional Products France, F-68305 Village-Neuf) according to the official French guidelines for experiments with live animals.

Animals and Housing

One hundred and four castrated male crossbred (Large-White (female)×Redon (male)) weaned piglets having 28 days of age supplied by the commercial farm "Elevage de la Plaine du Rhin" located in Balgau (France), were used in a 42-day experiment. The initial bodyweight of the piglets was 7.88±0.675 kg. They were sorted by body weight into 32 groups of 3 or 4 piglets and randomly allotted to each dietary treatment. Each group of animals was placed in one flat-deck cages and allocated to one of the different treatments.

Each treatment was replicated with 8 cages using a total of 26 animals (6 cages of 3 animals/treatment and 2 cages of 4 animals/treatment) per treatment. Each cage had a plastic-coated welded wire floor and was equipped with two water nipples and two stainless-steel individualised feeders. Animals were housed in an environmentally controlled room. Room temperature was initially 27° C. and was lowered weekly by about 2° C. until 21-22° C. and relative humidity percentage was 50%.

Feeding and Treatments

The experimental diets (Pre-Starter and Starter) were fed ad libitum in two feeding phases from day 0 to 14 (phase 1, Pre-starter) and day 14 to 42 (phase 2, Starter). The ingredient composition and the calculated nutrient levels of the experimental diets for phases 1 and 2 are presented in table 11. The analysed content is presented in table 12. Both diets were formulated to meet the animals' requirements according NRC (2012) and were fed in pelleted form. Pelleting conditions were at 70° C. for 30 seconds.

TABLE 11

Composition and nutrient contents of the basal experimental diets

| | Pre-starter (%) | Starter (%) |
|---|---|---|
| Ingredients | | |
| Barley | 38.00 | 38.00 |
| Wheat | 22.10 | 17.50 |
| Soybean meal 48% | 24.00 | 22.00 |
| Maize | 6.00 | 16.20 |
| Soybean oil | 1.00 | 2.00 |

TABLE 11-continued

Composition and nutrient contents of the basal experimental diets

|  | Pre-starter (%) | Starter (%) |
| --- | --- | --- |
| Dried whey | 5.00 | — |
| Vermiculite | — | 1.00 |
| Calcium carbonate | 0.30 | 0.30 |
| L-Lysine HCl | 0.10 | — |
| Vitamin-mineral Premix 3136[1] | 3.50 | 3.00 |
| Estimated nutrient content | | |
| Crude protein (%) | 19.47 | 17.95 |
| Lysine (%) | 1.24 | 1.03 |
| Threonine (%) | 0.67 | 0.61 |
| Methionine + cysteine (%) | 0.70 | 0.66 |
| Total P (%) | 0.71 | 0.64 |
| Total Ca (%) | 0.84 | 0.71 |
| Estimated digestible energy (MJ/kg) | 13.62 | 13.87 |

[1]Vitamin-mineral premix 3136 provided per kilogram of diet: Vitamin A: 20'000 I.U.; Vitamin E: 100 mg.; Vitamin K: 4.0 mg; Vitamin C: 200 mg; Vitamin B1: 5.00 mg; Vitamin B2: 10.00 mg; Vitamin B6: 8.00 mg; Vitamin B12: 0.07 mg; Niacin: 60.0 mg; Pantothenic acid: 40.0 mg; Folic acid: 3.00 mg; Biotin 0.4 mg; Choline: 800 mg; Mn: 60.5 mg; Fe: 162 mg; Cu: 9.5 mg; Zn: 100 mg; I: 0.9 mg; Se: 0.3 mg

TABLE 12

Analysed nutrient contents of the basal diets

| Analyzed nutrient content | Pre-starter | Starter |
| --- | --- | --- |
| Dry matter (%) | 87.89 | 87.42 |
| Crude protein (% DM) | 21.69 | 19.63 |
| Crude Ash (% DM) | 6.41 | 6.37 |
| Fat (% DM) | 4.15 | 5.42 |
| Starch (% DM) | 44.63 | 49.54 |
| Total P (mg/g DM) | 8.24 | 7.50 |
| Total Ca (mg/g DM) | 9.01 | 7.69 |
| Total Zn (mg/g DM) | 0.28 | 0.25 |
| Gross energy (MJ/kg DM) | 18.42 | 18.67 |

The diets were fed either unsupplemented (negative control) or supplemented with the GH24 lysozyme (SEQ ID NO: 257) at 50 mg per kg feed or VevoVital at 5000 mg per kg feed. No additional enzymes (e.g., phytase) were added to the feed.

| Treatment | Product | Inclusion level (mg/kg) |
| --- | --- | --- |
| A | Negative control | — |
| B | VevoVital | 5000 |
| C | SEQ ID NO: 257 | 50 |

VevoVital was mixed to the premixed mash diet before pelleting the diet.

Appropriate amount of the liquid preparations of lysozyme was diluted in water and sprayed onto the respective pelleted feed to get the final concentrations in the feed corresponding to the different treatments. For procedural balance of all treatments the same volume of water were also sprayed onto the pellets of the control diets.

Experimental Parameters and Analyses

The health status of the animals was controlled daily.

Body weight of the individual animals and feed consumption per pen were recorded on days 14 and 42 of the study. Performance, average daily weight gain (ADWG), average daily feed intake (ADFI) and feed conversion ratio (FCR) was calculated for phases 1 and 2, and the whole experimental period.

Statistical Analysis

The experimental unit was the piglet, except for ADFI and FCR which were measured by cage, and in both cases, treatment was used as class variable.

Statistical analyses were performed using the StatGraphics Centurion XVI statistical software package (Manugistics, Rockville, MD).

One-factorial ANOVA and Student-Newman-Keuls test was used to assess differences among means in treatment groups.

Variability in the data was expressed as the pooled standard error. In all instances, differences were reported as significant at $P<0.05$.

Results and Discussion

Based on the analyzed chemical compositions of the diets, the content of crude protein (19.07% and 17.16% as is, in pre-starter and starter periods, respectively) was close to the calculated content (19.47% and 17.95% as is, in pre-starter and starter periods, respectively) (Table 12).

All piglets remained healthy throughout the study. During the enzyme supplementation, none of the animals showed any symptoms of illness or toxicosis due to the test compounds. Mortality rate was equal to zero.

Results of the growth performance are summarized for the two periods (pre-starter period, days 0-14, and starter period, days 14-42) and for the whole experimental periods from day 0 to day 42 (Table 12).

In general, excellent animal growth performance was obtained for all treatments.

No significant difference among the supplemented treatments was recorded in terms of body weight. However, the supplementation the GH24 lysozyme (SEQ ID NO: 257) at 50 mg/kg resulted in numerical improvement of the ADWG by 11.8% during the starter period, and 7.8% during the whole period, compared to the negative control diet.

Over the pre-starter, starter and whole periods the supplementation of VevoVital resulted in an improvement of ADWG by 4.8, 5.8 and 5.4% compared to NC.

The results of FCR showed a statistically significant effect ($p<0.05$) of treatment in the pre-starter, starter and overall periods.

Over the starter period, from day 15 to day 42, piglets, which received VevoVital (PC) or the GH24 lysozyme (SEQ ID NO: 257) included at 50 mg/kg showed an improvement to FCR by 9.5% and 9.1% compared to NC.

As presented in Table 13, during the overall period (day 0 to day 42) piglets receiving feed added with VevoVital (PC) at 5000 mg/kg, the GH24 lysozyme (SEQ ID NO: 4) included at 50 mg/kg showed an improvement on FCR by 9.6% and 7.1% respectively compared to the negative control.

TABLE 13

Growth performance data of piglets fed graded inclusion levels of microbial lysozyme

| Treatment | | day 0-14 | | | day 14-42 | | | day 0-42 | | |
|---|---|---|---|---|---|---|---|---|---|---|
| | | ADFI (g/d) (2) | ADWG (g/d) (1) | FCR (2) | ADFI (g/d) (2) | ADWG (g/d) (1) | FCR (2) | ADFI (g/d) (2) | ADWG (g/d) (1) | FCR (2) |
| Negative control (NC) | Mean | 360 | 290 | $1.240^{ab}$ | $930^{bc}$ | 603 | $1.544^b$ | $734^b$ | 499 | $1.484^b$ |
| | SD | 20 | 66 | 0.053 | 34 | 79 | 0.096 | 23 | 69 | 0.072 |
| | % | 100 | 100 | 100 | 100 | 100 | 100 | 100 | 100 | 100 |
| VevoVital (PC) | Mean | 355 | 304 | $1.168^a$ | $886^{ab}$ | 638 | $1.398^a$ | $709^{ab}$ | 526 | $1.342^a$ |
| | SD | 26 | 56 | 0.041 | 33 | 62 | 0.103 | 30 | 52 | 0.079 |
| | % relative NC | 98.6 | 104.8 | 94.2 | 95.3 | 105.8 | 90.5 | 96.6 | 105.4 | 90.4 |
| NC + SEQ ID NO: 257 (50 ppm) | Mean | 333 | 265 | $1.272^b$ | $944^c$ | 674 | $1.404^a$ | $740^b$ | 538 | $1.379^a$ |
| | SD | 42 | 53 | 0.049 | 62 | 89 | 0.044 | 49 | 69 | 0.040 |
| | % relative NC | 92.5 | 91.4 | 102.6 | 101.5 | 111.8 | 90.9 | 100.8 | 107.8 | 92.9 |
| | P value | 0.317 | 0.346 | 0.014 | 0.013 | 0.068 | 0.009 | 0.034 | 0.341 | 0.004 |

(1) Mean ± mean deviation of 18 determinations;
(2) Mean ± mean deviation of 6 determinations;
$^{a,b,c}$Different superscripts in the same column indicate a significant difference ($p < 0.05$);
ADFI: average daily feed intake;
ADWG: average daily weight gain.

Conclusion

It can be concluded that in the present study and at the tested dosages and conditions, the GH24 lysozyme supplemented at 50 mg per kg feed to soybean meal, maize, wheat and barley based diet had a numerically improvement on growth performance of piglets although this effect was not statistically significant. Improvement of BWG with the GH24 lysozyme (SEQ ID NO: 257) at 50 mg/kg feed was even higher than the positive control. Of importance, nevertheless, was to observe a statistically significant effect of the GH24 lysozyme (SEQ ID NO: 257) included at 50 mg/kg feed treatment on ADFI and FCR in the starter and overall periods.

Example 19: Expression of the GH24 Lysozyme from *Trichophaea minuta*

The gene from *Trichophaea minuta* was codon optimized using Gene designer and synthesized by Geneart. The gene of interest was cut out using BamHI and XhoI from NEB and the gel purified using Sigma Agarose gel purification Kit. An expression vector pDAU222 was also made, digested with BamHI and XhoI from NEB, and the larger fragment gel purified.

Finally, the construct of interest was made using Clontech In-Fusion® HD PCR Cloning Kit. In the construct, the gene of interest was under the influence of NA2TPI promoter of the vector pDAU222 and it had its native signal for secretion. The gene of interest was having its own terminator codon TAA made to it. The positive clone grown on LB-ampicillin plate in *E. coli* was re-confirmed by colony PCR and then one positive clone was picked to put into *Aspergillus oryzae* MT3568 strain. The positive clone in *Aspergillus* was selected through AMDS selection by plating the transformants on sucrose agar with 1 M acetamide. One positive transformant was then grown in 300 ml DAP-4C media in 1 liter baffled flask at 30° C. for 4 days and then purified as described in example 20.

Example 20: Purification of the GH24 Lysozyme from *Trichophaea minuta* (SEQ ID NO: 291)

The target molecule was purified using a Phenyl Toyo column. The purification was carried out at pH 8 using HEPES (50 mM)+1.5 M ammonium sulphate for equilibration, HEPES (50 mM)+1 M ammonium sulphate to wash and HEPES, pH8 to elute. The purity of the purified enzymes was checked by SDS-PAGE and the concentration of the enzyme determined by Abs 280 nm after a buffer exchange. The purified protein was also MS verified.

Example 21: Genomic DNA Extraction from Strains of *Chaetomium* sp., *Mortierella* sp., *Metarhizium* sp., *Geomyces auratus* and *Ilyonectria rufa*

Strain *Chaetomium* sp. and *Mortierella* sp. were inoculated onto a PDA plate and incubated for 7 days at 37° C. in the darkness. Several mycelia-PDA plugs were inoculated into 500 ml shake flasks containing 100 ml of YPG medium. The flasks were incubated for 4-5 days at 37° C. with shaking at 160 rpm.

Strain *Metarhizium* sp. and *Geomyces auratus* were inoculated onto a PDA plate and incubated for 7 days at 25° C. in the darkness. Several mycelia-PDA plugs were inoculated into 500 ml shake flasks containing 100 ml of YPG medium. The flasks were incubated for 3 days at 25° C. with shaking at 160 rpm.

Strain *Ilyonectria rufa* were inoculated onto a PDA plate and incubated for 7 days at 25° C. in the darkness. Several mycelia-PDA plugs were inoculated into 500 ml shake flasks containing 100 ml of YPG medium. The flasks were incubated for 11 days at 25° C. with shaking at 160 rpm.

The mycelia were collected by filtration through MIRACLOTH® (Calbiochem, La Jolla, CA, USA) and frozen under liquid nitrogen. Frozen mycelia were ground, by a mortar and a pestle, to a fine powder, and genomic DNA was isolated using DNeasy® Plant Maxi Kit (24) (QIAGEN GmbH, Hilden, Germany) following the manufacturer's instruction.

Example 22: Genome Sequencing, Assembly and Annotation

The extracted genomic DNA samples were genome sequenced using an ILLUMINA® HiSeq 2000 System (Illumina, Inc., San Diego, CA, USA).

The raw reads of *Mortierella* sp. and *Ilyonectria rufa* were assembled using program Idba (Peng Yu et al., 2010, *Research in Computational Molecular Biology* 6044: 426-440. Springer Berlin Heidelberg). The raw reads of *Chaetomium* sp., *Metarhizium* sp. and *Geomyces auratus* were assembled using program Spades (Bankevich et al., 2012, *Journal of Computational Biology* 19(5): 455-477). The assembled sequences were analyzed using standard bioinformatics methods for gene identification and function prediction. GeneMark-ES fungal version (Ter-Hovhannisyan et al., 2008, *Genome Research* 18(12): 1979-1990) was used for gene prediction. Blastall version 2.2.10 (Altschul et al., 1990, *Journal of Molecular Biology* 215(3): 403-410, ncbi.nlm.nih.gov/blast/executables/release/2.2.10/) and HMMER version 2.1.1 (National Center for Biotechnology Information (NCBI), Bethesda, MD, USA) were used to predict function based on structural homology. The GH24 family lysozyme polypeptides were identified directly by analysis of the Blast results. The Agene program (Munch and Krogh, 2006, *BMC Bioinformatics* 7: 263) and SignalP program (Nielsen et al., 1997, *Protein Engineering* 10: 1-6) were used to identify start codons. SignalP program was further used to predict signal peptides. Pepstats (Rice et al., 2000, *Trends in Genetics* 16(6): 276-277) was used to predict isoelectric points and molecular weights.

Example 23: Cloning of GH24 Lysozymes (SEQ ID NO: 292, 295, 298, 301, 304)

Five fungal GH24 lysozyme wild type sequences were cloned from *Chaetomium* sp. (SEQ ID NO: 292), *Mortierella* sp. (SEQ ID NO: 295), *Metarhizium* sp. (SEQ ID NO: 298), *Geomyces auratus* (SEQ ID NO: 301) and *Ilyonectria rufa* (SEQ ID NO: 304).

The fungal GH24 lysozymes were cloned into an *Aspergillus oryzae* expression vector pCaHj505 as described in WO 2013/029496. The transcription of the GH24 lysozyme coding sequence with the native secretion signal was under the control of an *Aspergillus oryzae* alpha-amylase gene promoter.

The final expression plasmids, p505-GH24_Chaet287, p505-GH24_Mort, p505-GH24_Metar, p505-GH24_Geau, and p505-GH24_Ilyru (SEQ ID NO: 292, 295, 298, 301, 304), were individually transformed into an *Aspergillus oryzae* expression host. The GH24 lysozyme genes were integrated by homologous recombination into the *Aspergillus oryzae* host genome upon transformation. Four transformants of each transformation were selected from the selective media agar plate and inoculated to 3 ml of YPM medium in 24-well plate and incubated at 30° C., 150 rpm. After 3 days incubation, 20 µl of supernatant from each transformant were analyzed on NuPAGE Novex 4-12% Bis-Tris Gel w/MES according to the manufacturer's instructions. The resulting gel was stained with Instant Blue. SDS-PAGE profiles of the cultures showed that all 5 genes were expressed with 1 or 2 protein bands each detected at 30 KD, 28 KD & 30 KD, 28 KD, 25 KD & 28KD and 28 KD respectively. The recombinant *Aspergillus oryzae* strain with the strongest protein band were selected for shaking flask culturing and were inoculated on slant made of slant medium and incubated at 37° C. for 6-7 days. When strains were well grown to fully sporulated, they were inoculated to 2 L shaking flasks each containing 400 ml of YPM and 4-8 flasks for each strain. Flasks were shaking at 80 rpm, 30° C. Cultures were harvested on day 3 and filtered using a 0.45 µm DURAPORE Membrane and were purified as described in example 24 to 28.

Example 24: Purification of the GH24 Lysozyme from *Chaetomium* sp. ZY287 (SEQ ID NO: 294)

The culture supernatant was firstly precipitated with ammonium sulfate (80% saturation), then dialyzed with 20 mM PBS at pH 6.5. The solution was filtered with 0.45 um filter and then loaded into SP Fast Flow column (GE Healthcare) equilibrated with 20 mM PBS at pH 6.5. A gradient of NaCl concentration was applied as elution buffer from zero to 1 M, and then elution fractions and flow-through fraction were collected to detect lysozyme activity. The fractions with lysozyme activity were pooled and analyzed by SDS-PAGE, and then concentrated for further evaluation. The protein concentration was determined by Qubit® Protein Assay Kit (Invitrogen, cat Q33212).

Example 25: Purification of the GH24 Lysozyme from *Mortierella* sp. ZY002 (SEQ ID NO: 297)

The culture supernatant was firstly precipitated with ammonium sulfate (80% saturation), then dialyzed with 20 mM PBS at pH 7.0. The solution was filtered with 0.45 um filter and then loaded into SP Fast Flow column (GE Healthcare) equilibrated with 20 mM PBS at pH 7.0. A gradient of NaCl concentration was applied as elution buffer from zero to 1 M, and then elution fractions and flow-through fraction were collected to detect lysozyme activity. The fractions with lysozyme activity were pooled and analyzed by SDS-PAGE, and then concentrated for further evaluation. The protein concentration was determined by Qubit® Protein Assay Kit (Invitrogen, cat Q33212).

Example 26: Purification of the GH24 Lysozyme from *Metarhizium* sp. XZ2431 (SEQ ID NO: 300)

The culture supernatant was firstly precipitated with ammonium sulfate (80% saturation), then dialyzed with 20 mM PBS at pH 7.0. The solution was filtered with 0.45 um filter and then loaded into SP Fast Flow column (GE Healthcare) equilibrated with 20 mM PBS at pH 7.0. A gradient of NaCl concentration was applied as elution buffer from zero to 1 M, and then elution fractions and flow-through fraction were collected to detect lysozyme activity. The fractions with lysozyme activity were pooled and analyzed by SDS-PAGE, and then concentrated for further evaluation. The protein concentration was determined by Qubit® Protein Assay Kit (Invitrogen, cat Q33212).

Example 27: Purification of the GH24 Lysozyme from *Geomyces auratus* (SEQ ID NO: 303)

The culture supernatant was firstly precipitated with ammonium sulfate (80% saturation), then dialyzed with 20 mM PBS at pH 7.0. The solution was filtered with 0.45 um filter and then loaded into SP Fast Flow column (GE Healthcare) equilibrated with 20 mM PBS at pH 7.0. A gradient of NaCl concentration was applied as elution buffer from zero to 1 M, and then elution fractions and flow-through fraction were collected to detect lysozyme activity. The fractions with lysozyme activity were pooled and analyzed by SDS-PAGE, and then concentrated for further evaluation.

Since the purified sample has two bands, the collected sample was added ammonium sulfate with a final conductivity with 180 mS/cm, and then loaded into a Phenyl Sepharose 6 Fast Flow column (GE Healthcare) equilibrated with 20 mM PBS at pH 7.0 with 1.8 M $(NH_4)_2SO_4$. A concentration gradient of $(NH_4)_2SO_4$ was applied as elution buffer from 1.8 M to zero. The fractions with lysozyme activity were collected and carried out for SDS-PAGE. The sample also contains two bands, but MS data showed both bands are target proteins. The protein concentration was determined by Qubit® Protein Assay Kit (Invitrogen, cat Q33212).

Example 28: Purification of the GH24 Lysozyme from *Ilyonectria rufa* (SEQ ID NO: 306)

The culture supernatant was firstly precipitated with ammonium sulfate (80% saturation), then dialyzed with 20 mM PBS at pH 7.5. The solution was filtered with 0.45 um filter and then loaded into SP Fast Flow column (GE Healthcare) equilibrated with 20 mM PBS at pH 7.5. A gradient of NaCl concentration was applied as elution buffer from zero to 1 M, and then elution fractions and flow-through fraction were collected to detect lysozyme activity. The fractions with lysozyme activity were pooled and analyzed by SDS-PAGE, and then concentrated for further evaluation. The protein concentration was determined by Qubit® Protein Assay Kit (Invitrogen, cat Q33212).

Example 29: Determination of Lysozyme Activity

Lysozyme activity was determined as described in example 11 herein and is presented in table 14.

TABLE 14

Lysozyme Activity against *Micrococcus lysodeikticus* and *Exiguobacterium undea* as measured by Optical Density Drop

| GH24 Lysozyme | *Micrococcus lysodeikticus*[1] | *Exiguobacterium undae*[1] |
|---|---|---|
| GH24 lysozyme from *Trichoderma harzianum* (SEQ ID NO: 267) | +++ (pH 6) | ++++ (pH 6) |
| GH24 lysozyme from *Trichophaea minuta* (SEQ ID NO: 291) | ++++ (pH 6) | ++++ (pH 6) |
| GH24 lysozyme from *Chaetomium* sp. ZY287 (SEQ ID NO: 294) | +++ (pH 7) | +++ (pH 7) |
| GH24 lysozyme from *Mortierella* sp. ZY002 (SEQ ID NO: 297) | ++++ (pH 6) | +++ (pH 6) |
| GH24 lysozyme from *Metarhizium* sp. XZ2431 (SEQ ID NO: 300) | +++ (pH 6) | +++ (pH 6) |
| GH24 lysozyme from *Geomyces auratus* (SEQ ID NO: 303) | +++ (pH 6) | ++++ (pH 6) |
| GH24 lysozyme from *Ilyonectria rufa* (SEQ ID NO: 306) | ++ (pH 6) | ++++ (pH 6) |

[1]Means no significant effect;
+ means small effect;
++ means medium effect;
+++ means large effect;
++++ means very large effect.
The pH value in the brackets lists the assay pH based on lysozyme-substrate combination.

The data shows that all of the GH24 lysozymes that naturally comprise the lysozyme enhancing domain (LED) (SEQ ID NO: 267, 291, 294, 297, 300, 303 and 306) showed good activity against both substrates.

Example 30: Determination of DomT Scores

The DomT scores for the GH24 domain and the LED domain of the lysozymes of the invention were determined using the Lysozyme Enhancing Domain HMM from example 15 and the GH24 catalytic domain HMM from example 16 as described herein. The DomT scores for other prior art lysozyme sequences were also calculated and are presented in table 15 below.

TABLE 15

DomT scores for GH24 catalytic and Lysozyme Enhancing Domains

| Sequence | Domains | DomT score of LED[1] | DomT score for GH24 domain |
|---|---|---|---|
| SEQ ID NO: 257 | LED + GH24 | 103.0 | 265.9 |
| SEQ ID NO: 264 | LED + GH24 | 127.0 | 257.2 |
| SEQ ID NO: 267 | LED + GH24 | 125.0 | 249.6 |
| SEQ ID NO: 279 | GH24 | — | 251.9 |
| SEQ ID NO: 280 | GH24 | — | 229.8 |
| SEQ ID NO: 291 | LED + GH24 | 103.1 | 263.2 |
| SEQ ID NO: 294 | LED + GH24 | 113.1 | 254.0 |
| SEQ ID NO: 297 | LED + GH24 | 103.1 | 246.3 |
| SEQ ID NO: 300 | LED + GH24 | 117.8 | 242.2 |
| SEQ ID NO: 303 | LED + GH24 | 119.8 | 246.9 |
| SEQ ID NO: 306 | LED + GH24 | 116.7 | 257.5 |
| *Lactococcus* c2 phage from WO 95/31562 (GENESEQP: AAR85295) | GH24 phage | — | 74.5 |
| Enterobacteria phage T4 lysozyme, SEQ ID NO: 24 of WO 2013/021206 (BAK49017) | GH24 phage | — | 34.9 |

[1]No score means that there was no alignment to the HMM and thus no score could be generated No DomT scores could be generated for the lysozyme enhancing domain or the GH24 domain (i.e., there was no sequence alignment) for the other lysozymes tested, including GH25 lysozymes disclosed in WO 2005/080559, WO 2009/102755, WO 2013/076253, WO 2013/076259, GH22 lysozyme such ashen egg white lysozyme and a GH23 lysozyme disclosed in WO2013/076259 demonstrating that the HMMs are selective for the GH24 catalytic domain and the lysozyme enhancing domain respectively.

Unsurprisingly the prior art GH24 phage lysozymes did not align very well with the HMM of the GH24 catalytic domain as disclosed herein. These phage lysozymes are structurally and taxonomically very different from the fungal GH24 lysozymes of the invention and furthermore do not comprise a LED. In comparison, all of the GH24 lysozymes of the invention gave a domT score of at least 200 for the GH24 catalytic domain and a domT score of at least 100 for the lysozyme enhancing domain indicating good alignment to the HMMs.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

What is claimed is:

1. An animal feed additive comprising at least one polypeptide having lysozyme activity, wherein the polypeptide having lysozyme activity comprises amino acids 1 to 245 of SEQ ID NO: 257.

2. An animal feed additive comprising at least one polypeptide having lysozyme activity, said polypeptide comprising (a) a Glycoside Hydrolase Family 24 (GH24) catalytic domain comprising motif I: [TAS][VIL][GAC][YFI]GHX[CAYIV] (SEQ ID NO: 252) and (b) a lysozyme enhancing domain comprising motif III: [CGY][YF][VIL][ASTP][DG]X[YF][VIT]X[TS][GAN] (SEQ ID NO: 254), wherein the polypeptide having lysozyme activity has at least 85% sequence identity to SEQ ID NO: 257.

3. The animal feed additive of claim 2, wherein the polypeptide having lysozyme activity has at least 90% sequence identity to SEQ ID NO: 257.

4. The animal feed additive of claim 2, wherein the polypeptide having lysozyme activity has at least 95% sequence identity to SEQ ID NO: 257.

5. The animal feed additive of claim 2, wherein the polypeptide having lysozyme activity has at least 97% sequence identity to SEQ ID NO: 257.

6. The animal feed additive of claim 2, wherein the polypeptide having lysozyme activity has at least 99% sequence identity to SEQ ID NO: 257.

7. A method comprising administering the animal feed additive of claim 1 to an animal.

* * * * *